(12) United States Patent
Fukatsu et al.

(10) Patent No.: US 7,960,369 B2
(45) Date of Patent: Jun. 14, 2011

(54) RECEPTOR FUNCTION REGULATOR

(75) Inventors: Kohji Fukatsu, Osaka (JP); Shinobu Sasaki, Osaka (JP); Shuji Hinuma, Tsukuba (JP); Yasuaki Ito, Tsukuba (JP); Nobuhiro Suzuki, Tsukuba (JP); Masataka Harada, Tsukuba (JP); Tsuneo Yasuma, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1766 days.

(21) Appl. No.: 10/534,081

(22) PCT Filed: Nov. 6, 2003

(86) PCT No.: PCT/JP03/14139
§ 371 (c)(1),
(2), (4) Date: Jun. 13, 2005

(87) PCT Pub. No.: WO2004/041266
PCT Pub. Date: May 21, 2004

(65) Prior Publication Data
US 2009/0012093 A1    Jan. 8, 2009

(30) Foreign Application Priority Data

Nov. 8, 2002  (JP) ................. 2002-324632
Jan. 27, 2003 (JP) ................. 2003-016889
May 30, 2003 (JP) ................. 2003-153986

(51) Int. Cl.
*A61K 31/535*   (2006.01)
(52) U.S. Cl. ........ 514/183; 544/236; 544/281; 544/400; 546/121; 546/156; 546/205; 546/340; 548/171; 548/236; 548/253; 548/304.4; 548/537; 549/23; 549/57; 549/76; 549/467; 549/496
(58) Field of Classification Search ............. 435/107; 548/339.1, 171, 236, 253, 304.4, 318.5, 537; 544/236, 281, 400; 546/121, 156, 205, 340; 549/23, 57, 76, 467, 496
See application file for complete search history.

(56) References Cited

U.S. PATENT DOCUMENTS

| | | |
|---|---|---|
| 6,294,580 B1 | 9/2001 | Wilson et al. |
| 6,555,577 B1 | 4/2003 | Mogensen et al. |
| 6,710,063 B1 | 3/2004 | Chao et al. |
| 6,723,740 B2 | 4/2004 | Chao et al. |
| 6,867,218 B2 | 3/2005 | Mogensen et al. |
| 6,867,320 B2 | 3/2005 | Shoda et al. |
| 2004/0058965 A1 | 3/2004 | Momose et al. |
| 2004/0137517 A1 | 7/2004 | Andrews et al. |
| 2004/0157890 A1 | 8/2004 | Beswick et al. |
| 2005/0089866 A1 | 4/2005 | Hinuma et al. |

FOREIGN PATENT DOCUMENTS

| | | |
|---|---|---|
| EP | 1 431 267 | 6/2004 |
| WO | WO 97/31907 | 9/1997 |
| WO | WO 99/11255 | 3/1999 |
| WO | WO 00/64876 | 11/2000 |
| WO | WO 01/00603 | 1/2001 |
| WO | WO-01/47859 | 7/2001 |
| WO | WO 01/55085 | 8/2001 |
| WO | WO-01/66098 | 9/2001 |
| WO | WO 02/053547 | 7/2002 |
| WO | WO 02/057783 | 7/2002 |
| WO | WO 02053547 A1 * | 7/2002 |
| WO | WO 02/083616 | 10/2002 |
| WO | WO 02/092590 | 11/2002 |
| WO | WO 03/016254 | 2/2003 |
| WO | WO 03/068959 | 8/2003 |
| WO | WO 03/070686 | 8/2003 |
| WO | WO 03/099793 | 12/2003 |
| WO | WO-2004/019869 | 3/2004 |
| WO | WO-2005/009104 | 2/2005 |

OTHER PUBLICATIONS

Patini et al., (Bioisosterism: A rational Approach in Drug Design, Chem. Rev. 1998, vol. 96, Issue 8, pp. 3147-3176).*
Supplementary European Search Report dated Jan. 22, 2010, from corresponding European Patent Application No. 03810621.7.

* cited by examiner

*Primary Examiner* — Timothy P Thomas
*Assistant Examiner* — Jean Cornet
(74) *Attorney, Agent, or Firm* — Edwards Angell Palmer & Dodge LLP; David G. Conlin; Mark D. Russett

(57) ABSTRACT

The GPR40 receptor function regulator of the present invention, which comprises a compound having an aromatic ring and a group capable of releasing cation is useful as an insulin secretagogue or an agent for the prophylaxis or treatment of diabetes and the like.

12 Claims, 3 Drawing Sheets

RECEPTOR FUNCTION REGULATOR

This application is the National Phase filing of International Patent Application No. PCT/JP2003/014139, filed Nov. 2003.

TECHNICAL FIELD

The present invention relates to a GPR40 receptor function regulator comprising carboxylic acid having an aromatic ring or a derivative thereof and a novel compound having a GPR40 receptor function regulating action.

BACKGROUND ART

An amino acid sequence of GPR40 derived from human and DNA encoding same are described (WO2000/22129 and *Biochem. Biophys. Res. Commun.* 1997, October 20; 239 (2)).

It is known that carboxylic acid having an aromatic ring and a derivative thereof have various physiological activities.

Alkanoic acid derivatives are known (JP-A-2002-265457).

Isoxazole derivatives having an insulin secretagogue action and a hypoglycemic action, which are useful for the prophylaxis or treatment of diabetes and the like, are known (JP-A-2002-212171).

Nitrogen-containing 5-membered heterocyclic compounds having a hypoglycemic action or a hypolipidemic action, which are useful for the prophylaxis or treatment of diabetes and the like, are known (JP-A-2001-226350).

Alkoxyiminoalkanoic acid derivatives having a hypoglycemic action or a hypolipidemic action, which are useful for the prophylaxis or treatment of diabetes and the like, are known (JP-A-2001-199971).

Oxyiminoalkanoic acid derivatives having a hypoglycemic action or a hypolipidemic action, which are useful for the prophylaxis or treatment of diabetes and the like, are known (JP-A-2000-198772)

1,3-Azole derivatives having a retinoid-related receptor function regulating action, which are useful for the prophylaxis or treatment of diabetic complications and the like, are known (JP-A-2000-80086).

Oxyiminoalkanoic acid derivatives having a hypoglycemic action or a hypolipidemic action, which are useful for the prophylaxis or treatment of diabetes and the like, are known (JP-A-2000-34266).

Oxazole derivatives having an insulin secretagogue action or a hypoglycemic action, which are useful for the prophylaxis or treatment of diabetes and the like, are known (JP-A-09-323983).

Benzofuran derivatives having a hypoglycemic and hypolipidemic action are known (JP-A-08-311065).

Fatty acids have been reported to bind with GPR40 (WO02/057783).

Heretofore, non-peptidic low-molecular agonist or antagonist to GPR40 receptor has not been known. Thus, there is a demand on the development of a superior GRP40 receptor function regulator.

DISCLOSURE OF THE INVENTION

The present invention aims at providing a GPR40 receptor function regulator useful as an insulin secretagogue or agent for the prophylaxis or treatment of diabetes and the like and a novel compound having a GPR40 receptor function regulating action.

The present inventors have conducted various studies and found that, a carboxylic acid having an aromatic ring and a derivative thereof unexpectedly have a superior GPR40 receptor agonist activity based on a specific chemical structure thereof, and further have superior properties as pharmaceutical products such as stability and the like, and provide safe and useful pharmaceutical agents as agents for the prophylaxis or treatment of GPR40 receptor-related pathology or diseases in mammal, based on which findings completed the present invention.

Accordingly, the present invention relates to

[1] a GPR40 receptor function regulator comprising a compound having an aromatic ring and a group capable of releasing cation,

[2] the regulator of the above-mentioned [1] which comprises a carboxylic acid having an aromatic ring, or a derivative thereof,

[3] the regulator of the above-mentioned [1], which comprises a carboxylic acid having two or more aromatic rings, or a derivative thereof,

[4] the regulator of the above-mentioned [1], which comprises a compound represented by the formula

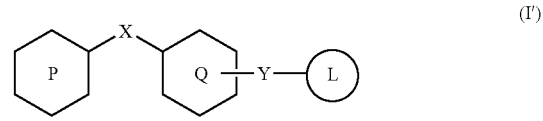

wherein ring P is an aromatic ring optionally having substituent(s), ring Q is an aromatic ring optionally further having substituent(s) besides

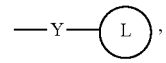

X and Y are each a spacer, and

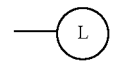

is a group capable of releasing cation, or a salt thereof or a prodrug thereof,

[5] the regulator of the above-mentioned [2], which comprises a compound represented by the formula

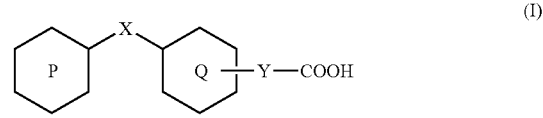

wherein ring P is an aromatic ring optionally having substituent(s), ring Q is an aromatic ring optionally further having substituent(s) besides —Y—COOH, X and Y are each a spacer, and —Y—COOH is substituted at any position on ring Q, or a salt thereof or a prodrug thereof,

[6] the regulator of the above-mentioned [1], wherein the group capable of releasing cation is (1) a 5-membered heterocyclic group capable of releasing cation, (2) a carboxyl group, (3) a sulfonic acid group, (4) a sulfamoyl group optionally mono-substituted by a $C_{1-4}$ alkyl group, (5) a phosphonic acid group, (6) a carbamoyl group optionally mono-substituted by a $C_{1-4}$ alkyl group, (7) a $C_{2-7}$ alkylsulfonylthiocarbamoyl group or (8) a trifluoromethanesulfonic acid amido group (—$NHSO_2CF_3$),

[7] the regulator of the above-mentioned [1], wherein the group capable of releasing cation is

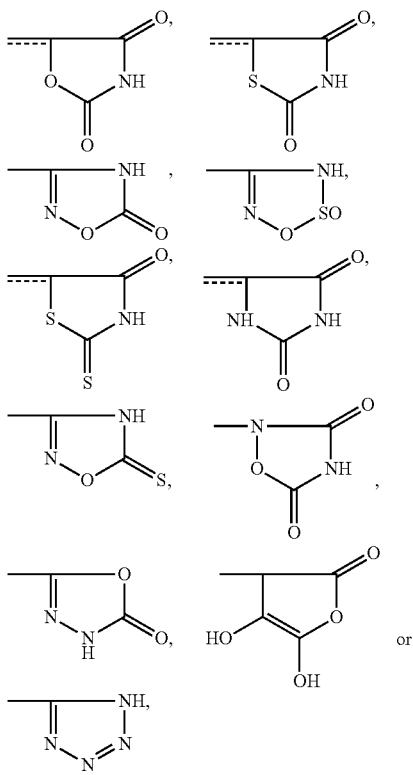

[8] the regulator of the above-mentioned [1], which is an insulin secretion modulator, a hypoglycemic agent or a pancreatic β cell protector,

[9] the regulator of the above-mentioned [1], which is an agent for the prophylaxis or treatment of diabetes, impaired glucose tolerance, ketosis, acidosis, diabetic neuropathy, diabetic nephropathy, diabetic retinopathy, hyperlipidemia, genital disorder, skin disease, arthropathy, osteopenia, arteriosclerosis, thrombotic disease, dyspepsia, memory and learning disorder, obesity, hypoglycemia, hypertension, edema, insulin resistance syndrome, unstable diabetes, fatty atrophy, insulin allergy, insulinoma, lipotoxicity, hyperinsulinemia, or cancers,

[10] a compound represented by the formula

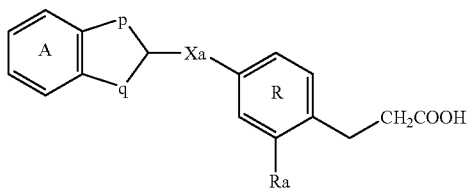

(I-1)

wherein ring A is a benzene ring optionally having substituent(s), ring R is a phenylene group optionally having substituent(s), Xa is a spacer other than an alkylene group, p and q are each a $C_{0-4}$ carbon chain optionally having substituent(s), and Ra is a hydrogen atom or a substituent, or a salt thereof,

[11] a prodrug of the compound of the above-mentioned [10] or a salt thereof,

[12] the compound of the above-mentioned [10], wherein the partial structural formula

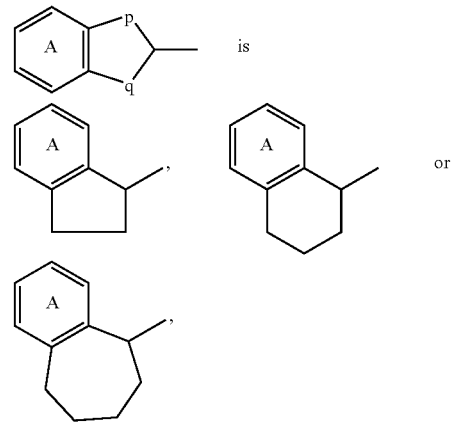

the substituent that ring A optionally has is (1) a halogen atom, (2) a $C_{1-6}$ alkyl group, (3) a $C_{1-6}$ alkoxy group, (4) a $C_{6-14}$ aryl group optionally substituted by a halogen atom, a $C_{1-6}$ alkyl or a $C_{1-6}$ alkoxy, (5) a $C_{6-14}$ aryloxy group or (6) a $C_{7-16}$ aralkyloxy group, the substituent that ring R optionally has is a halogen atom or a $C_{1-6}$ alkyl group, Ra is a hydrogen atom, and the spacer represented by Xa is an oxygen atom,

[13] a compound represented by the formula

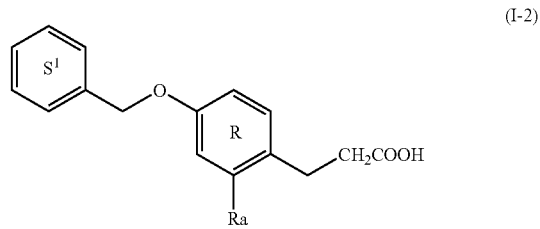

(I-2)

wherein ring $S^1$ is a benzene ring having substituent(s) having a benzene ring, ring R is a phenylene group optionally having substituent(s), and Ra is a hydrogen atom or a substituent, or a salt thereof, except (i) 2-ethoxy-4-[[2-[(5-methyl-2-phenyl-4-oxazolyl)methoxy]phenyl]methoxy] benzenepropanoic acid, (ii) 2-ethoxy-4-[[3-[(5-methyl-2-phenyl-4-oxazolyl)methoxy]phenyl]methoxy] benzenepropanoic acid, (iii) 2-ethoxy-4-[[4-[(5-methyl-2-phenyl-4-oxazolyl)methoxy]phenyl]methoxy] benzenepropanoic acid, and (iv) 4-[[4-[(5-methyl-2-phenyl-4-oxazolyl)methoxy]phenyl]methoxy] benzenepropanoic acid,

[14] a prodrug of the compound of the above-mentioned [13] or a salt thereof,

[15] the compound of the above-mentioned [13], wherein the substituent(s) having a benzene ring is a substituent represented by the formula: $R^{11}$-$E^2$- ($R^{11}$ is a phenyl group, an indanyl group or a naphthyl group, each optionally having substituent(s), and $E^2$ is a bond or a spacer), and the spacer represented by $E^2$ is —$(CH_2)m^1$-$W^1$—$(CH_2)m^2$- ($m^1$ and $m^2$ are each an integer of 0 to 3, $W^1$ is —O—, —N($R^2$)—, —S—, —CO— or —CO—N($R^3$)—, and $R^2$ and $R^3$ are each a hydrogen atom or a $C_{1-6}$ alkyl group),

[16] the compound of the above-mentioned [13], which is represented by the formula

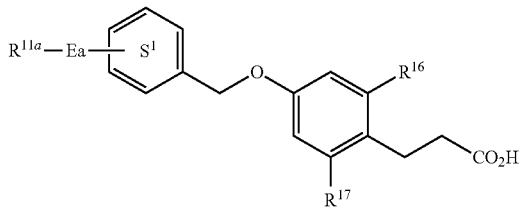

(I-2A)

wherein $R^{11a}$ is a phenyl group having 1 or 2 substituents, Ea is a bond, an oxygen atom or an optionally substituted methylene, ring $S^{1a}$ is a benzene ring optionally further having substituent(s) selected from an optionally substituted $C_{1-6}$ alkyl group, an optionally substituted $C_{1-6}$ alkoxy group and a halogen atom, and $R^{16}$ and $R^{17}$ are the same or different and each is a hydrogen atom, a halogen atom, a $C_{1-6}$ alkyl group or a $C_{1-6}$ alkoxy group,

[17] the compound of the above-mentioned [16], wherein $R^{11a}$ is a phenyl group having two substituents selected from an optionally substituted $C_{1-6}$ alkyl group, an optionally substituted $C_{1-6}$ alkoxy group and a halogen atom; Ea is a bond, an oxygen atom or a methylene; and $R^{16}$ and $R^{17}$ are the same or different and each is a hydrogen atom or a halogen atom,

[18] the compound of the above-mentioned [17], wherein Ea is a bond,

[19] the compound of the above-mentioned [17], wherein $R^{16}$ is a hydrogen atom, and $R^{17}$ is a fluorine atom,

[20] the compound of the above-mentioned [16], wherein the partial structural formula

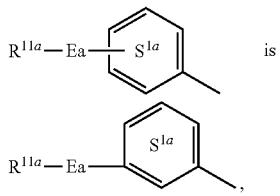

is

[21] the compound of the above-mentioned [20], wherein $R^{11a}$ is a phenyl group having two substituents selected from an optionally substituted $C_{1-6}$ alkyl group, an optionally substituted $C_{1-6}$ alkoxy group and a halogen atom; Ea is a bond; and ring $S^{1a}$ is a benzene ring without additional substituent,

[22] the compound of the above-mentioned [13], wherein the substituent(s) having a benzene ring is a substituent represented by the formula: $R^{11}$-$E^2$- ($R^{11}$ is a phenyl group, an indanyl group or a naphthyl group, each optionally having substituent(s)), and $E^2$ is a bond or a spacer), ring $S^1$ is optionally further substituted by a $C_{1-6}$ alkyl group, and $R^{11}$ optionally forms a ring together with $E^2$ and ring $S^1$,

[23] the compound of the above-mentioned [22], wherein $R^{11}$ is a phenyl group or an indanyl group, each optionally having substituent(s) selected from the group consisting of a halogen atom, a nitro, a carboxy, an optionally halogenated $C_{1-6}$ alkyl, a hydroxy-$C_{1-6}$ alkyl, a carboxy-$C_{1-6}$ alkyl-carbonylamino-$C_{1-6}$ alkyl, an optionally halogenated $C_{1-6}$ alkoxy, a $C_{6-14}$ aryl, a $C_{6-14}$ aryloxy and a $C_{7-16}$ aralkyloxy, $E^2$ is a bond, —O—, —$CH_2$—O—, —CO—, —CONH—, —N($CH_3$)$CH_2$—, —S—$CH_2$— or —C≡C—, ring $S^1$ is optionally further substituted by a $C_{1-6}$ alkyl group, the ring formed by $R^{11}$ together with $E^2$ and ring $S^1$ is

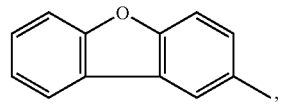

the substituent that ring R optionally has is a $C_{1-6}$ alkyl group, and Ra is a hydrogen atom,

[24] a compound represented by the formula

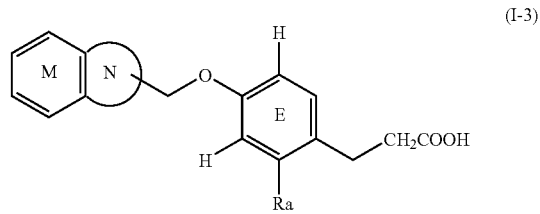

(I-3)

wherein ring M is a benzene ring optionally having substituent(s), ring N is a 5-membered heterocycle optionally having substituent(s), ring E is a phenylene group optionally having substituent(s), and Ra is a hydrogen atom or a substituent, or a salt thereof, except 4-(1H-benzotriazol-1-ylmethoxy)benzenepropanoic acid and 4-(1H-indol-3-ylmethoxy)benzenepropanoic acid,

[25] a prodrug of the compound of the above-mentioned [24] or a salt thereof,

[26] the compound of the above-mentioned [24], wherein the partial structural formula

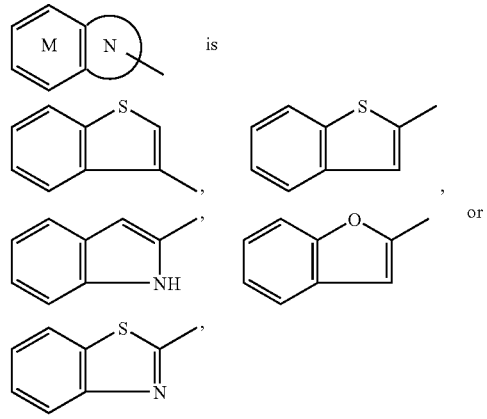

each optionally having substituent(s) selected from a halogen atom, an optionally substituted $C_{1-6}$ alkyl group, an optionally substituted $C_{1-6}$ alkoxy, a $C_{1-6}$ alkoxy-carbonyl and an optionally substituted $C_{7-16}$ aralkyloxy,

[27] the compound of the above-mentioned [24], wherein the partial structural formula

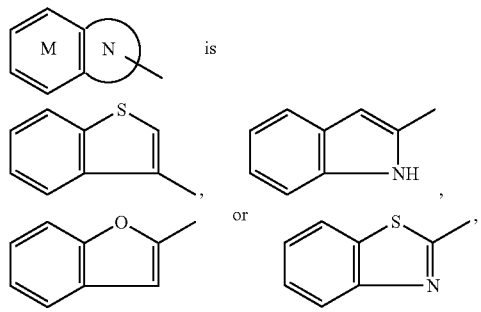

is each optionally having substituent(s) selected from a halogen atom and an optionally substituted $C_{1-6}$ alkyl group, ring E is an unsubstituted phenylene group, and Ra is a hydrogen atom,

[28] a compound represented by the formula

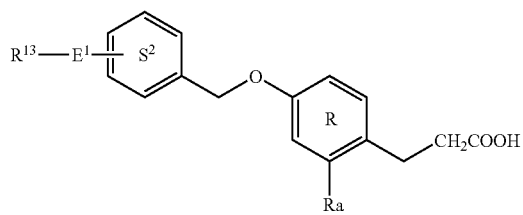

(I-4)

wherein ring $S^2$ is a benzene ring optionally having substituent(s), ring R is a phenylene group optionally having substituent(s), $E^1$ is a bond or a spacer, $R^{13}$ is a thiazolyl group optionally having substituent(s), and Ra is a hydrogen atom or a substituent, or a salt thereof,

[29] a prodrug of the compound of the above-mentioned [28] or a salt thereof,

[30] the compound of the above-mentioned [28], wherein ring $S^2$ is a benzene ring, ring R is an unsubstituted phenylene group, $R^{13}$ is a thiazolyl group optionally having substituent(s) selected from a $C_{6-14}$ aryl and a $C_{1-6}$ alkyl, $E^1$ is —N($R^{14}$)—$(CH_2)m^2$- or —S—$(CH_2)m^2$- ($R^{14}$ is a hydrogen atom or a $C_{1-6}$ alkyl group, and $m^2$ is an integer of 0 to 3), and Ra is a hydrogen atom,

[31] the compound of the above-mentioned [28], wherein $R^{13}$ is a 2-thiazolyl group optionally having substituent(s),

[32] the compound of the above-mentioned [28], which is represented by the formula

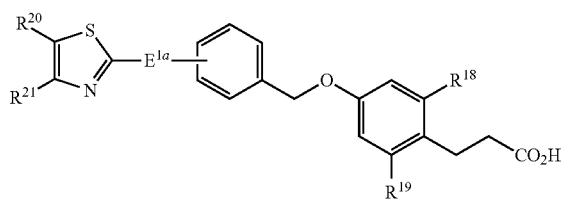

(I-4A)

wherein $E^{1a}$ is —N($R^{14}$)—$CH_2$—, —CH($R^{22}$)—O— or —CH($R^{22}$)—$CH_2$— ($R^{14}$ and $R^{22}$ are a hydrogen atom or a $C_{1-6}$ alkyl group), $R^{18}$ and $R^{19}$ are the same or different and each is a hydrogen atom, a halogen atom, a $C_{1-6}$ alkyl group or a $C_{1-6}$ alkoxy group, and $R^{20}$ and $R^{21}$ are the same or different and each is a hydrogen atom, an optionally substituted $C_{6-14}$ aryl group or an optionally substituted $C_{1-6}$ alkyl group, or $R^{20}$ and $R^{21}$ are bonded to form a ring,

[33] the compound of the above-mentioned [32], wherein $E^{1a}$ is —N($R^{14}$)—$CH_2$— ($R^{14}$ is a hydrogen atom or a $C_{1-6}$ alkyl group), and $R^{18}$ and $R^{19}$ are the same or different and each is a hydrogen atom or a halogen atom,

[34] a pharmaceutical agent comprising the compound of the above-mentioned [10], [13], [24] or [28], or a salt thereof or a prodrug thereof,

[35] a method of regulating a GPR40 receptor function, which comprises administering an effective amount of a compound having an aromatic ring and a group capable of releasing cation to a mammal,

[36] use of a compound having an aromatic ring and a group capable of releasing cation for the production of a GPR40 receptor function regulator,

[37] a screening method for a ligand, agonist or antagonist to GPR40, which comprises using GPR40 or a partial peptide thereof or a salt thereof, and a compound having an aromatic ring and a group capable of releasing cation, and

[38] a kit for screening a ligand, agonist or antagonist to GPR40, which comprises GPR40 or a partial peptide thereof or a salt thereof, and a compound having an aromatic ring and a group capable of releasing cation.

Furthermore, the present invention provides

[39] the regulator of the above-mentioned [2], which comprises a compound represented by the formula

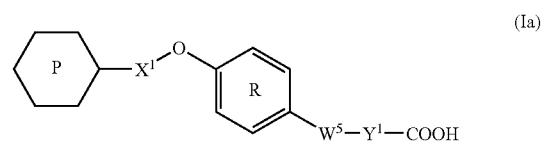

(Ia)

wherein ring P is an aromatic ring optionally having substituent(s), ring R is a phenylene group optionally having substituent(s), $X^1$ is a bond or a $C_{1-6}$ alkylene group optionally having substituent(s), $W^5$ is a bond, —O—, —N($R^6$)—, —CO—N($R^7$)— or —S—, $R^6$ and $R^7$ are each a hydrogen atom or a $C_{1-6}$ alkyl group, and $Y^1$ is a $C_{1-6}$ alkylene group optionally having substituent(s), or a salt thereof or a prodrug thereof,

[40] the regulator of the above-mentioned [2], which comprises a compound represented by the formula

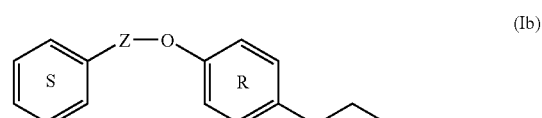

(Ib)

wherein ring S is a benzene ring optionally having substituent(s), ring R is a phenylene group optionally having substituent(s), and Z is a chain formed by 4 linkages, or a salt thereof or a prodrug thereof,

[41] the regulator of the above-mentioned [2], which comprises a compound represented by the formula

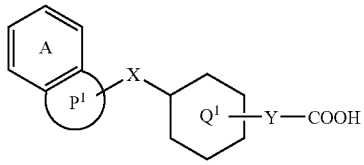
(II)

wherein ring A is a benzene ring optionally having substituent(s), ring $P^1$ is a ring optionally having substituent(s), ring $Q^1$ is an aromatic ring optionally further having substituent(s) besides —Y—COOH, X and Y are each a spacer, and —Y—COOH is substituted at any position on ring $Q^1$, or a salt thereof or a prodrug thereof,

[42] the regulator of the above-mentioned [41], which comprises a compound represented by the formula

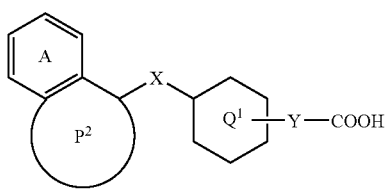
(IIa)

wherein ring $P^2$ is a ring optionally having substituent(s), and other symbols are as defined in the above-mentioned [30], or a salt thereof or a prodrug thereof,

[43] the regulator of the above-mentioned [41], which comprises a compound represented by the formula

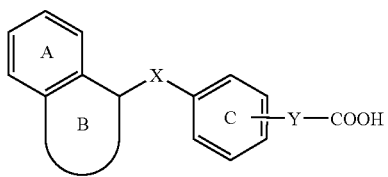
(IIb)

wherein ring A is a benzene ring optionally having substituent(s), ring B is a 5- to 7-membered ring optionally having substituent(s), ring C is a benzene ring optionally further having substituent(s) besides a —Y—COOH group, X and Y are each a spacer, and —Y—COOH is substituted at any position on ring C, or a salt thereof or a prodrug thereof,

[44] the regulator of the above-mentioned [4], [5] or [39], wherein ring P is a benzene ring optionally having substituent(s) or a non-basic aromatic heterocycle optionally having substituent(s),

[45] the regulator of the above-mentioned [4], [5] or [39], wherein ring P is a benzene ring optionally having substituent(s),

[46] the regulator of the above-mentioned [4], [5] or [39], wherein ring P is a benzene ring optionally having substituent(s) at the meta-position,

[47] the regulator of the above-mentioned [4], [5] or [39], wherein the substituent of ring P is a substituent having an aromatic ring,

[48] the regulator of the above-mentioned [47], wherein the substituent having an aromatic ring is a substituent represented by the formula: $R^1$-E- ($R^1$ is an aromatic group optionally having substituent(s), and E is a bond or a spacer),

[49] the regulator of the above-mentioned [48], wherein -E- is a bond, —O—, —$CH_2$—O—, —CO—, —CONH—, —N($R^2$)—$CH_2$— ($R^2$ is a hydrogen atom or a $C_{1-6}$ alkyl group), —S—$CH_2$— or —CH=CH—,

[50] the regulator of the above-mentioned [48], wherein -E- is a bond, —O— or —$CH_2$—O—,

[51] the regulator of the above-mentioned [48], wherein $R^1$ is (i) a phenyl group optionally having substituent(s) selected from the group consisting of a halogen atom, a nitro, a carboxy, an optionally halogenated $C_{1-6}$ alkyl, a hydroxy-$C_{1-16}$ alkyl, a carboxy-$C_{1-6}$ alkyl-carbonylamino-$C_{1-6}$ alkyl, an optionally halogenated $C_{1-6}$ alkoxy, a $C_{6-14}$ aryl, a $C_{6-14}$ aryloxy and a $C_{7-16}$ aralkyloxy or (ii) a 5- to 14-membered heterocyclic group containing, besides carbon atom, 1 to 4 hetero atoms selected from a nitrogen atom, an oxygen atom and a sulfur atom, which optionally has substituent(s) selected from an optionally halogenated $C_{1-6}$ alkyl, a $C_{6-14}$ aryl and a $C_{6-14}$ aryl-$C_{2-6}$ alkenyl, and E is a bond or a spacer represented by —$(CH_2)m^1$-$W^1$—$(CH_2)m^2$- ($m^1$ and $m^2$ are each an integer of 0 to 3, $W^1$ is —O—, —N($R^2$)—, —CO— or —CO—N($R^3$)—, and $R^2$ and $R^3$ are each a hydrogen atom or a $C_{1-6}$ alkyl group),

[52] the regulator of the above-mentioned [5], wherein ring Q is a benzene ring optionally having substituent(s),

[53] the regulator of the above-mentioned [4], [5], [4], [42] or [43], wherein the spacer represented by X is
(i) —$X^1$—$W^2$—$X^2$— ($X^1$ and $X^2$ are each a bond or a $C_{1-6}$ alkylene group optionally having substituent(s), $W^2$ is —O—, —N($R^4$)—, —CO—N($R^5$)— or —S—, and $R^4$ and $R^5$ are each a hydrogen atom or a $C_{1-6}$ alkyl group), or
(ii) —$W^3$—$X^3$—$W^4$— ($X^3$ is a $C_{1-6}$ alkylene group optionally having substituent(s), $W^3$ and $W^4$ are each —O—, —N($R^4$)—, —CO—N($R^5$)— or —S—, and $R^4$ and $R^5$ are each a hydrogen atom or a $C_{1-6}$ alkyl group),

[54] the regulator of the above-mentioned [4], [5], [41], [42] or [43], wherein the spacer represented by X is —$X^1$—O—$X^2$— ($X^1$ and $X^2$ are each a bond or a $C_{1-6}$ alkylene group optionally having substituent(s)),

[55] the regulator of the above-mentioned [4], [5], [41], [42] or [43], wherein the spacer represented by X is —$X^1$—O— ($X^1$ is a bond or a $C_{1-6}$ alkylene group optionally having substituent(s)),

[56] the regulator of the above-mentioned [55], wherein $X^1$ is (i) a bond or (ii) a $C_{1-6}$ alkylene group optionally having substituent(s) selected from a $C_{1-6}$ alkyl and a $C_{6-14}$ aryl,

[57] the regulator of the above-mentioned [4], [5], [41], [42] or [43], wherein the spacer represented by X is
(i) a bond,
(ii) —$X^1$—O— ($X^1$ is a bond or a $C_{1-6}$ alkylene group optionally having substituent(s)),
(iii) —N($R^4$)—$X^3$—O— ($X^3$ is a $C_{1-6}$ alkylene group optionally having substituent(s) and $R^4$ is a $C_{1-6}$ alkyl group),
(iv) —S—$X^3$—O— ($X^3$ is a $C_{1-6}$ alkylene group optionally having substituent(s)),
(v) —N($R^4$)—$X^3$— ($X^3$ is a $C_{1-6}$ alkylene group optionally having substituent(s) and $R^4$ is a hydrogen atom or a $C_{1-6}$ alkyl group),
(vi) —CO—N($R^5$)— ($R^5$ is a hydrogen atom or a $C_{1-6}$ alkyl group),
(vii) —$X^3$—S— ($X^3$ is a $C_{1-6}$ alkylene group optionally having substituent(s)), or (viii) —S—X³—S— (X³ is a C$_{1-6}$ alkylene group optionally having substituent(s)),

[58] the regulator of the above-mentioned [4], [5], [41], [42] or [43], wherein Y is —W⁵—Y¹— (Y¹ is a C$_{1-6}$ alkylene group optionally having substituent(s), W⁵ is a bond, —O—, —N(R⁶)—, —CO—N(R⁷)— or —S—, and R⁶ and R⁷ are each a hydrogen atom or a C$_{1-6}$ alkyl group),

[59] the regulator of the above-mentioned [4], [5], [41], [42] or [43], wherein Y is a C$_{1-6}$ alkylene group optionally having substituent(s),

[60] the regulator of the above-mentioned [4], [5], [41], [42] or [43], wherein Y is an ethylene group optionally having substituent(s),

[61] the regulator of the above-mentioned [4], [5], [41], [42] or [43], wherein Y is —O—Y¹— (Y¹ is a C$_{1-6}$ alkylene group optionally having substituent(s)),

[62] the regulator of the above-mentioned [4], [5], [41], [42] or [43], wherein —Y—COOH is substituted at para-position on ring Q, ring Q' or ring C,

[63] the regulator of the above-mentioned [40], wherein Z is (1) a chain formed by 4 groups selected from —C(R⁸)(R⁸')—, —O—, —CO—, —N(R⁸")— (R⁸, R⁸' and R⁸" are each a hydrogen atom or a C$_{1-6}$ alkyl group) and —S—, or (2) a chain formed by

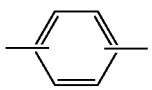

and 2 groups selected from —C(R⁸)(R⁸')—, —O—, —CO—, —N(R⁸")—(R⁸, R⁸' and R⁸" are each a hydrogen atom or a C$_{1-6}$ alkyl group) and —S—,

[64] the regulator of the above-mentioned [40], wherein Z is (1) —(CH$_2$)$_4$—, (2) —O—(CH$_2$)$_3$—, (3)

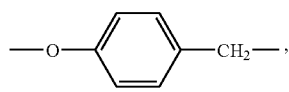

or (4)

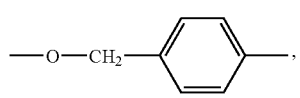

[65] the regulator of the above-mentioned [43], wherein B ring is a 5- to 7-membered ring optionally containing, besides carbon atom, 1 to 3 hetero atoms selected from a nitrogen atom, an oxygen atom and a sulfur atom, which optionally has substituent(s),

[66] the regulator of the above-mentioned [43], wherein the partial structural formula

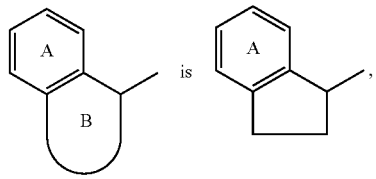

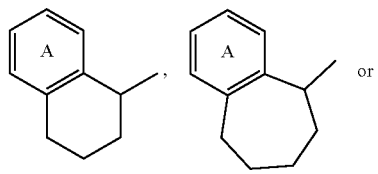

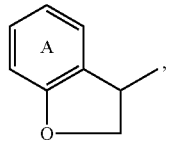

[67] the regulator of the above-mentioned. [43], wherein the partial structural formula

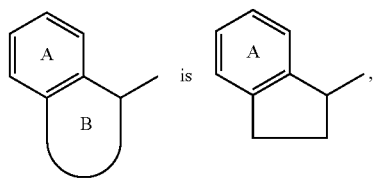

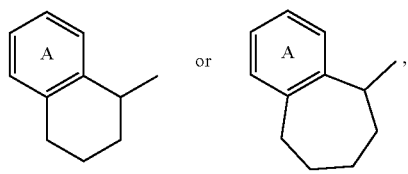

[68] the regulator of the above-mentioned [43], wherein the spacer represented by X is a methylene group optionally having substituent(s), —O— or —S—, and the spacer represented by Y is a C$_{1-6}$ alkylene group optionally having substituent(s), —N(R⁶)—Y¹— (R⁶ is a hydrogen atom or a C$_{1-6}$ alkyl group, and Y¹ is a C$_{1-6}$ alkylene group optionally having substituent(s)), —O—Y¹— (Y¹ is a C$_{1-6}$ alkylene group optionally having substituent(s)) or —S—Y¹— (Y¹ is a C$_{1-6}$ alkylene group optionally having substituent(s)),

[69] the regulator of the above-mentioned [1], which comprises a carboxylic acid having a skeleton represented by the formula

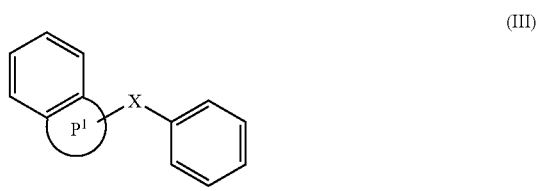

(III)

wherein X is a spacer and ring P¹ is a ring optionally having substituent(s), or a derivative thereof,

[70] the regulator of the above-mentioned [2], which comprises a compound represented by the formula

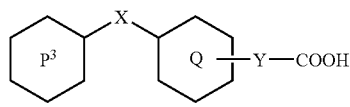
(IV)

wherein ring $P^3$ is an aromatic ring having substituent(s) having a benzene ring, ring Q is an aromatic ring optionally further having substituent(s) besides —Y—COOH, X and Y are each a spacer, and —Y—COOH is substituted at any position on ring Q, or a salt thereof or a prodrug thereof, except (i) 2-ethoxy-4-[[2-[(5-methyl-2-phenyl-4-oxazolyl)methoxy]phenyl]methoxy]benzenepropanoic acid, (ii) 2-ethoxy-4-[[3-[(5-methyl-2-phenyl-4-oxazolyl)methoxy]phenyl]methoxy]benzenepropanoic acid, (iii) 2-ethoxy-4-[[4-[(5-methyl-2-phenyl-4-oxazolyl)methoxy]phenyl]methoxy]benzenepropanoic acid, and (iv) 4-[[4-[(5-methyl-2-phenyl-4-oxazolyl)methoxy]phenyl]methoxy]benzenepropanoic acid,

[71] the regulator of the above-mentioned [2], which comprises a compound represented by the formula

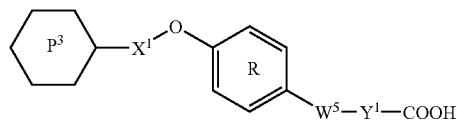
(IVa)

wherein ring $P^3$ is an aromatic ring having substituent(s) having a benzene ring, ring R is a phenylene group optionally having substituent(s), $X^1$ is a bond or a $C_{1-6}$ alkylene group optionally having substituent(s), $W^5$ is a bond, —O—, —N($R^6$)—, —CO—N($R^7$)— or —S—, $R^6$ and $R^7$ are each a hydrogen atom or a $C_{1-6}$ alkyl group, and $Y^1$ is a $C_{1-6}$ alkylene group optionally having substituent(s), or a salt thereof or a prodrug thereof,

[72] the regulator of the above-mentioned [71], wherein $X^1$ is a $C_{1-6}$ alkylene group optionally having substituent(s), $W^5$ is a bond, and $Y^1$ is a $C_{1-6}$ alkylene group optionally having substituent(s),

[73] the regulator of the above-mentioned [71], wherein $X^1$ is a methylene group optionally having substituent(s), $W^5$ is a bond, and $Y^1$ is an ethylene group optionally having substituent(s),

[74] the regulator of the above-mentioned [70], which is represented by the formula

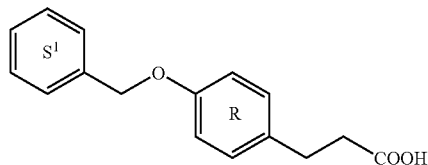
(IVb)

wherein ring $S^1$ is a benzene ring having substituent(s) having a benzene ring, and ring R is a phenylene group optionally having substituent(s),

[75] the regulator of the above-mentioned [70]-[74], wherein the substituent(s) having a benzene ring is a substituent represented by the formula: $R^{11}$-$E^2$- ($R^{11}$ is a phenyl group, an indanyl group or a naphthyl group, each optionally having substituent(s), and $E^2$ is a bond or a spacer),

[76] the regulator of the above-mentioned [75], wherein -$E^2$- is a bond, —O—, —$CH_2$—O—, —CO—, —CONH—, —N($CH_3$)$CH_2$—, —S—$CH_2$— or —C≡C—, preferably a bond, —O— or —$CH_2$—O—,

[77] the regulator of the above-mentioned [75], wherein $R^{11}$ is a phenyl group optionally having substituent(s) selected from the group consisting of a halogen atom, a nitro, a carboxy, an optionally halogenated $C_{1-6}$ alkyl, a hydroxy-$C_{1-6}$ alkyl, a carboxy-$C_{1-6}$ alkyl-carbonylamino-$C_{1-6}$ alkyl, an optionally halogenated $C_{1-6}$ alkoxy, a $C_{6-14}$ aryl, a $C_{6-14}$ aryloxy and a $C_{7-16}$ aralkyloxy,

[78] the regulator of the above-mentioned [2], which comprises a compound represented by the formula

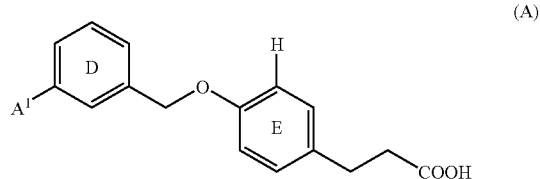
(A)

wherein $A^1$ is a substituent (except a hydrogen atom and a chlorine atom), ring D is a benzene ring optionally further having, besides $A^1$, substituent(s) (except a nitro group and a hydroxy group), and ring E is a phenylene group optionally having substituent(s), or a salt thereof or a prodrug thereof, except 2-ethoxy-4-[[3-[(5-methyl-2-phenyl-4-oxazolyl)methoxy]phenyl]methoxy]benzenepropanoic acid,

[79] the regulator of the above-mentioned [78], wherein $A^1$ is a bromine atom,

[80] the regulator of the above-mentioned [2], which comprises a compound represented by the formula

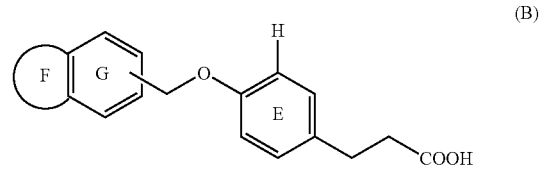
(B)

wherein ring F is a ring optionally having substituent(s),
ring G is a benzene ring optionally having substituent(s), and
ring E is a phenylene group optionally having substituent(s),
provided that the partial structural formula

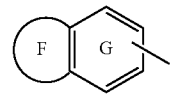

is not an unsubstituted naphthyl group, an unsubstituted 1H-indazolyl group and a quinolyl group optionally having substituent(s), or a salt thereof or a prodrug thereof,

[81] the regulator of the above-mentioned [2], which comprises a compound represented by the formula

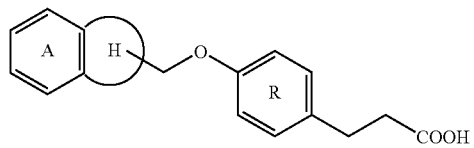
(C)

wherein ring A is a benzene ring optionally having substituent(s), ring H is a 5-membered ring optionally having substituent(s), and ring R is a phenylene group optionally having substituent(s), or a salt thereof or a prodrug thereof, except 3,5-dibromo-4-[(5-chlorobenzo[b]thiophen-3-yl)methoxy]benzenepropanoic acid, 4-(1H-benzotriazol-1-ylmethoxy)benzenepropanoic acid and 4-(1H-indol-3-yl-methoxy)benzenepropanoic acid,

[82] the regulator of the above-mentioned [81], wherein the partial structural formula

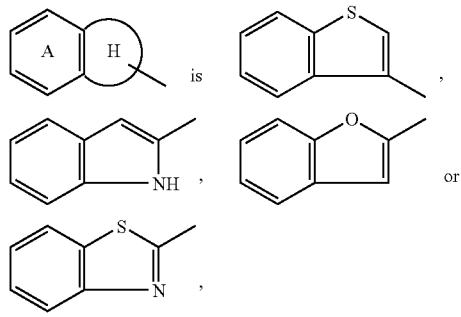

each optionally having substituent(s) selected from a halogen atom and an optionally halogenated $C_{1-6}$ alkyl group,

[83] the regulator of the above-mentioned [2], which comprises a compound represented by the formula

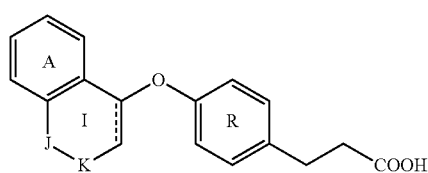
(D)

wherein ring A is a benzene ring optionally having substituent(s), J is —O—, —S—, —CH$_2$— or —NR$^{12}$— (R$^{12}$ is a hydrogen atom or a $C_{1-6}$ alkyl group), K is a bond or a $C_{1-3}$ alkylene group,

------ is a single bond or a double bond, ring R is a phenylene group optionally having substituent(s), and ring I optionally has substituent(s), or a salt thereof or a prodrug thereof,

[84] the regulator of the above-mentioned [83], wherein the partial structural formula

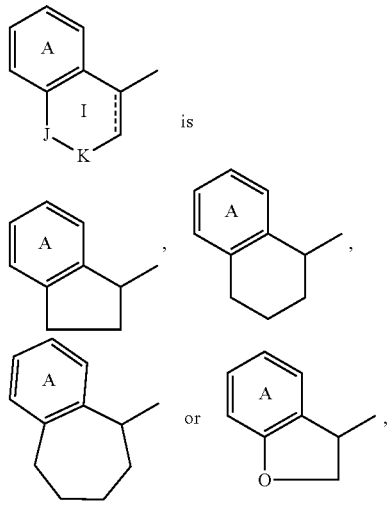

the substituent of ring A is (i) a halogen atom, (ii) a $C_{1-6}$ alkyl group, (iii) a $C_{1-6}$ alkoxy group, (iv) a $C_{6-14}$ aryl group optionally having substituent(s) selected from a halogen atom and a $C_{1-6}$ alkyl, (v) a $C_{6-14}$ aryloxy group or (vi) a $C_{7-15}$ aralkyloxy group, and the substituent of ring R is a halogen atom, and

[85] the regulator of the above-mentioned [1], which comprises the compound of the above-mentioned [10], [13], [24] or [28] or a salt thereof or a prodrug thereof.

BEST MODE FOR CARRYING OUT THE INVENTION

Figure 1:
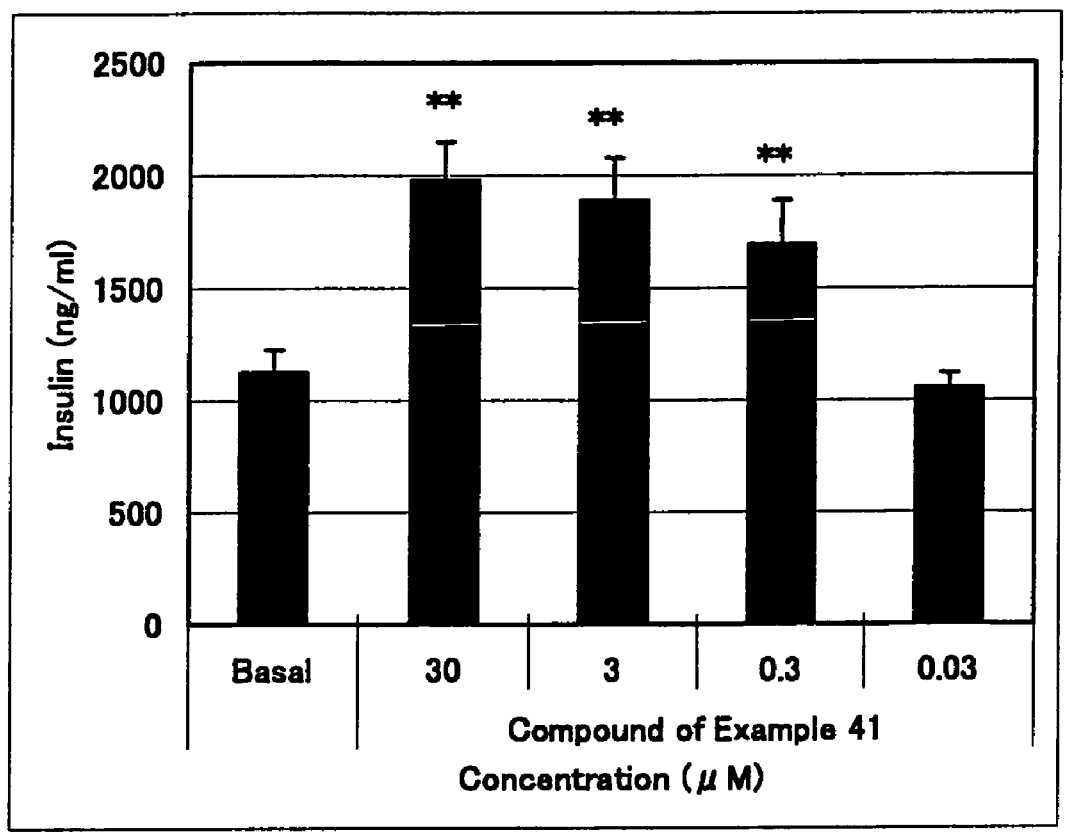
FIG. 1 shows the results of the insulin secretagogue action from MIN6 of compound of Example 41, wherein the concentration on the axis of abscissas shows the concentration (μM) of the added compound of Example 41, **, $p<0.01$ (Student's t test).

The compound to be used in the present invention is a compound having an aromatic ring and a group capable of releasing cation, which is preferably a carboxylic acid having an aromatic ring or a derivative thereof, more preferably a carboxylic acid having 2 or more aromatic rings or a derivative thereof, specifically, the above-mentioned compound (I'), compound (I), compound (I-1), compound (I-2), compound (I-2A), compound (I-3), compound (I-4), compound (I-4A), compound (Ia), compound (Ib), compound (II), compound (IIa), compound (IIb), compound (III), compound (IV), compound (IVa), compound (IVb), compound (A), compound (B), compound (C) and compound (D). The compound (I-1), compound (I-2), compound (I-2A), compound (I-3), compound (I-4) and compound (I-4A) are novel compounds.

In the present specification, the aromatic ring means an aromatic hydrocarbon ring or an aromatic heterocycle.

As the aromatic hydrocarbon ring, a hydrocarbon ring having 6 to 14 carbon atoms, such as a benzene ring, a naphthalene ring and the like, can be used, with preference given to a benzene ring.

As the aromatic heterocycle, for example, a 5- to 14-membered (monocyclic, bicyclic or tricyclic), preferably 5- to 10-membered, more preferably 5- or 6-membered aromatic heterocycle containing, besides carbon atom, 1 or 2 kinds of 1 to 4 hetero atoms selected from a nitrogen atom, a sulfur atom and an oxygen atom can be used. As the above-mentioned "5- to 14-membered (preferably 5- to 10-membered) aromatic heterocycle", for example, aromatic heterocycles such as thiophene, furan, oxazole, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine and the like, rings formed by condensation of these rings (preferably monocycle) with one or plural (preferably 1 or 2) aromatic rings (e.g., benzene ring etc.) and the like can be used. Of these, a non-basic aromatic heterocycle is preferable, for example, aromatic heterocycles such as thiophene, benzo[b]thiophene, benzo[b]furan, benzoxazole, benzothiazole, benzisothiazole, naphtho[2,3-b]thiophene, furan, indole, carbazole, thiazole, isothiazole, isoxazole and the like, rings formed by condensation of these rings (preferably monocycle) with one or plural (preferably 1 or 2) non-basic aromatic rings (e.g., benzene ring etc.) and the like can be used.

In the present specification, the group capable of releasing cation may be a group capable of releasing cation chemically (e.g., by chemical reactions such as oxidation, reduction, hydrolysis and the like, and the like) or biologically, namely under physiological conditions (e.g., in vivo reactions such as oxidation, reduction, hydrolysis and the like due to biological enzymes, and the like), or a group capable of converting to such group.

As the group capable of releasing cation, for example, (1) a 5-membered heterocyclic group capable of releasing cation, (2) a carboxyl group, (3) a sulfonic acid group, (4) a sulfamoyl group optionally mono-substituted by a $C_{1-4}$ alkyl group, (5) a phosphonic acid group, (6) a carbamoyl group optionally mono-substituted by a $C_{1-4}$ alkyl group (e.g., methyl, ethyl, propyl, butyl, isobutyl, tert-butyl and the like), (7) a $C_{2-7}$ alkylsulfonylthiocarbamoyl group (e.g., methylsulfonylthiocarbamoyl, ethylsulfonylthiocarbamoyl etc.), (8) a trifluoromethanesulfonic acid amido group (—$NHSO_2CF_3$) and the like can be used.

As the above-mentioned 5-membered heterocyclic group capable of releasing cation, a 5-membered heterocyclic group comprising 1 to 4 selected from N, O and S as ring-constituting atom(s) and the like can be used. For example,

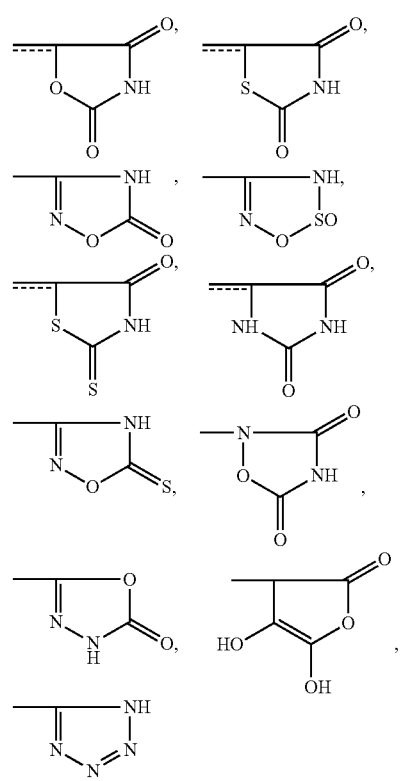

and the like can be mentioned.

Of these,

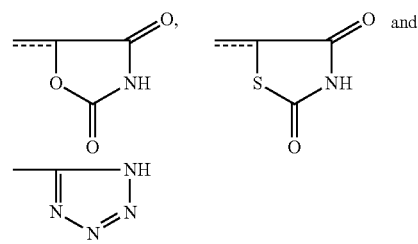

are preferable, and

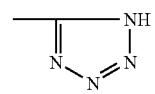

is particularly preferable.

The group capable of releasing cation is particularly preferably a carboxyl group.

In compounds (I'), (I) and (Ia), ring P is an aromatic ring optionally having substituent(s).

As the aromatic ring represented by ring P, a benzene ring, and non-basic aromatic heterocycles such as thiophene, benzo[b]thiophene, benzo[b]furan, benzoxazole, benzothiazole, benzisothiazole, naphtho[2,3-b]thiophene, furan, indole, carbazole, thiazole, isothiazole, isoxazole and the like are preferable, and a benzene ring is particularly preferable.

In compound (I'), (I) and (IV), ring Q is an aromatic ring optionally further having substituent(s) besides

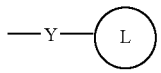

or —Y—COOH.

As the aromatic ring represented by ring Q, a benzene ring, and non-basic aromatic heterocycles such as thiophene, benzo[b]thiophene, benzo[b]furan, benzoxazole, benzothiazole, benzisothiazole, naphtho[2,3-b]thiophene, furan, indole, carbazole, thiazole, isothiazole, isoxazole and the like are preferable, and a benzene ring is particularly preferable.

As the aforementioned substituent that the ring P may have, and as the aforementioned substituent that the ring Q may further have besides

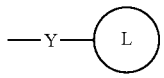

or —Y—COOH, for example, a substituent selected from a substituent selected from a oxo; a halogen atom (e.g., fluorine, chlorine, bromine, iodine etc.); a $C_{1-3}$ alkylenedioxy (e.g., methylenedioxy, ethylenedioxy etc.); a nitro; a cyano; an optionally esterified carboxyl; an optionally substituted lower($C_{1-6}$) alkyl; an optionally substituted lower ($C_{2-6}$) alkenyl; an optionally substituted lower($C_{2-6}$) alkynyl; an optionally substituted $C_{3-8}$ cycloalkyl; an optionally substituted lower($C_{1-6}$) alkoxy; a hydroxy; a mercapto; an optionally substituted lower($C_{1-6}$) alkylthio; a formyl; an optionally substituted lower($C_{1-6}$) alkyl-carbonyl; an optionally substituted $C_{3-8}$ cycloalkyl-carbonyl; a lower($C_{1-6}$) alkylsulfonyl (e.g., methylsulfonyl, ethylsulfonyl etc.); a lower($C_{1-6}$) alkylsulfinyl (e.g., methylsulfinyl, ethylsulfinyl etc.); a formylamino; an optionally substituted lower($C_{1-6}$) alkyl-carbonylamino; an optionally substituted $C_{3-8}$ cycloalkyl-carbonylamino; an optionally substituted lower($C_{1-6}$) alkoxy-carbonylamino; an optionally substituted lower($C_{1-6}$) alkylsulfonylamino; an optionally substituted lower($C_{1-6}$) alkyl-carbonyloxy; an optionally substituted lower($C_{1-6}$) alkoxy-carbonyloxy; an optionally substituted mono-lower($C_{1-6}$) alkyl-carbamoyloxy; an optionally substituted di-lower($C_{1-6}$) alkyl-carbamoyloxy; a sulfo; a sulfamoyl; a sulfinamoyl; a sulfenamoyl; an optionally substituted 5 to 7-membered heterocyclylcarbonyl containing, besides carbon atom, 1 or 2 kinds of 1 to 4 hetero atoms selected from a nitrogen atom, a sulfur atom and an oxygen atom; an optionally substituted $C_{6-14}$ aryloxy, an optionally substituted $C_{7-16}$ aralkyloxy, an optionally substituted $C_{6-14}$ arylthio, an optionally substituted $C_{7-16}$ aralkylthio, an optionally substituted $C_{6-14}$ aryl-carbonyl, an optionally substituted $C_{7-16}$ aralkyl-carbonyl, an optionally substituted $C_{6-14}$ aryl-carbonylamino, an optionally substituted $C_{6-14}$ aryl-carbonyloxy, an optionally substituted mono- or di-$C_{6-14}$ aryl-carbamoyloxy, an optionally substituted $C_{6-14}$ arylsulfonyl, an optionally substituted $C_{6-14}$ arylsulfinyl, an optionally substituted $C_{6-14}$ arylsulfonylamino, an optionally substituted aromatic heterocyclyloxy, an optionally substituted $C_{6-14}$ aryl, an optionally substituted $C_{7-16}$ aralkyl and an optionally substituted $C_{6-14}$ aryl-$C_{2-6}$ alkenyl, which are concrete examples of the substituent represented by the formula:

$R^1$-E- to be mentioned below; an optionally substituted heterocyclic group; a thiocarbamoyl; an optionally substituted carbamoyl group; and an optionally substituted amino; a group wherein two or more (e.g., 2-3) of these substituents are bonded; and the like (hereinafter to be abbreviated as substituent group A) can be used. Ring P may have 1 to 5, preferably 1 to 3, substituents mentioned above at substitutable position(s), and when the number of the substituents is not less than 2, respective substituents may be the same or different.

As the "optionally esterified carboxyl group" in the substituent group A, for example, a carboxyl, a $C_{1-6}$ alkoxy-carbonyl (e.g., methoxycarbonyl, ethoxycarbonyl, propoxycarbonyl, tert-butoxycarbonyl etc.), a $C_{6-14}$ aryloxy-carbonyl (e.g., phenoxycarbonyl etc.), a $C_{7-16}$ aralkyloxy-carbonyl (e.g., benzyloxycarbonyl, phenethyloxycarbonyl etc.) and the like can be used.

As the "lower($C_{1-6}$) alkyl" of the "optionally substituted lower($C_{1-6}$) alkyl" in the substituent group A, for example, methyl, ethyl, propyl, isopropyl, butyl, isobutyl, sec-butyl, tert-butyl, pentyl, isopentyl, neopentyl, hexyl and the like can be used.

As the "lower($C_{2-6}$) alkenyl" of the "optionally substituted lower($C_{2-6}$) alkenyl" in the substituent group A, for example, vinyl, propenyl, isopropenyl, 2-buten-1-yl, 4-penten-1-yl, 5-hexen-1-yl and the like can be used.

As the "lower($C_{2-6}$) alkynyl" of the "optionally substituted lower($C_{2-6}$) alkynyl" in the substituent group A, for example, 2-butyn-1-yl, 4-pentyn-1-yl, 5-hexyn-1-yl and the like can be used.

As the "lower($C_{1-6}$) alkoxy" of the "optionally substituted lower($C_{1-6}$) alkoxy" in the substituent group A, for example, methoxy, ethoxy, propoxy, isopropoxy, butoxy, isobutoxy, sec-butoxy, pentyloxy, hexyloxy and the like can be used.

As the "lower($C_{1-6}$) alkylthio" of the "optionally substituted lower($C_{1-6}$) alkylthio" in the substituent group A, for example, methylthio, ethylthio, propylthio, isopropylthio, butylthio, sec-butylthio, tert-butylthio and the like can be used.

As the "lower($C_{1-6}$) alkyl-carbonyl" of the "optionally substituted lower($C_{1-6}$) alkyl-carbonyl" in the substituent group A, for example, acetyl, propionyl, pivaloyl and the like can be used.

As the "lower($C_{1-6}$) alkyl-carbonylamino" of the "optionally substituted lower($C_{1-6}$) alkyl-carbonylamino" in the substituent group A, for example, acetylamino, propionylamino, pivaloylamino and the like can be used.

As the "lower($C_{1-6}$) alkoxy-carbonylamino" of the "optionally substituted lower($C_{1-6}$) alkoxy-carbonylamino" in the substituent group A, for example, methoxycarbonylamino, ethoxycarbonylamino, propoxycarbonylamino, butoxycarbonylamino and the like can be used.

As the "lower($C_{1-6}$) alkylsulfonylamino" of the "optionally substituted lower($C_{1-6}$) alkylsulfonylamino" in the substituent group A, for example, methylsulfonylamino, ethylsulfonylamino and the like can be used.

As the "lower($C_{1-6}$) alkyl-carbonyloxy" of the "optionally substituted lower($C_{1-6}$) alkyl-carbonyloxy" in the substituent group A, for example, acetoxy, propionyloxy and the like can be used.

As the "lower($C_{1-6}$) alkoxy-carbonyloxy" of the "optionally substituted lower($C_{1-6}$) alkoxy-carbonyloxy" in the substituent group A, for example, methoxycarbonyloxy, ethoxycarbonyloxy, propoxycarbonyloxy, butoxycarbonyloxy and the like can be used.

As the "mono-lower($C_{1-6}$) alkyl-carbamoyloxy" of the "optionally substituted mono-lower($C_{1-6}$) alkyl-carbamoyloxy" in the substituent group A, for example, methylcarbamoyloxy, ethylcarbamoyloxy and the like can be used.

As the "di-lower($C_{1-6}$) alkyl-carbamoyloxy" of the "optionally substituted di-lower($C_{1-6}$) alkyl-carbamoyloxy" in the substituent group A, for example, dimethylcarbamoyloxy, diethylcarbamoyloxy and the like can be used.

These "lower alkyl group", "lower alkenyl", "lower alkynyl", "lower alkoxy", "lower alkylthio", "lower alkyl- carbonyl", "lower alkyl-carbonylamino", "lower alkoxy- carbonylamino", "lower alkylsulfonylamino", "lower alkyl-carbonyloxy", "lower alkoxy-carbonyloxy", "mono-lower alkyl- carbamoyloxy" and "di-lower alkyl-carbamoyloxy" each optionally have, at substitutable position(s), 1 to 5 substituents selected from, for example, a halogen atom (e.g., fluorine atom, chlorine atom, bromine atom, iodine atom); hydroxy; amino; a 5- to 7-membered heterocyclic group containing, besides carbon atom, 1 or 2 kinds of 1 to 4 hetero atoms selected from a nitrogen atom, a sulfur atom and an oxygen atom (e.g., furyl, pyridyl, thienyl etc.) (said heterocyclic group being optionally substituted by a halogen atom, hydroxy, amino, optionally halogenated lower ($C_{1-6}$) alkyl, mono- or di-lower ($C_{1-6}$) alkylamino, mono- or di-$C_{6-14}$ arylamino, $C_{3-8}$ cycloalkyl, lower ($C_{1-6}$) alkoxy, lower ($C_{1-6}$) alkoxy-carbonyl, lower ($C_{1-6}$)alkylthio, lower ($C_{1-6}$) alkylsulfinyl, lower($C_{1-6}$) alkylsulfonyl, the above-mentioned optionally esterified carboxyl, carbamoyl, thiocarbamoyl, mono- lower ($C_{1-6}$) alkyl-carbamoyl, di-lower ($C_{1-6}$) alkyl-carbamoyl, mono- or di-$C_{6-14}$ aryl-carbamoyl and the like); mono- or di-lower ($C_{1-6}$) alkylamino; mono- or di-$C_{6-14}$ arylamino; $C_{3-8}$ cycloalkyl; optionally halogenated lower ($C_{1-6}$) alkoxy; lower ($C_{1-6}$) alkoxy- carbonyl; lower ($C_{1-6}$) alkylthio; lower ($C_{1-6}$) alkylsulfinyl; lower($C_{1-6}$) alkylsulfonyl; the above-mentioned optionally esterified carboxyl; carbamoyl; thiocarbamoyl; mono-lower($C_{1-6}$) alkyl-carbamoyl (e.g., methylcarbamoyl, ethylcarbamoyl etc.); di-lower($C_{1-6}$) alkyl-carbamoyl (e.g., dimethylcarbamoyl, diethylcarbamoyl, ethylmethylcarbamoyl etc.); mono- or di-$C_{6-14}$ aryl-carbamoyl (e.g., phenylcarbamoyl, 1-naphthylcarbamoyl, 2-naphthylcarbamoyl etc.); mono- or di- 5- to 7-membered heterocyclylcarbamoyl containing, (besides carbon atom), 1 or 2 kinds of 1 to 4 hetero atoms selected from a nitrogen atom, a sulfur atom and an oxygen atom (e.g., 2-pyridylcarbamoyl, 3- pyridylcarbamoyl, 4-pyridylcarbamoyl, 2-thienylcarbamoyl, 3- thienylcarbamoyl etc.); $C_{1-6}$ alkyl-carbonylamino (e.g., acetylamino, propionylamino) optionally substituted by carboxy; and the like.

As the "$C_{3-8}$ cycloalkyl" of the "optionally substituted $C_{3-8}$ cycloalkyl" in the substituent group A, for example, cyclopropyl, cyclobutyl, cyclopentyl, cyclohexyl and the like can be used.

As the "$C_{3-8}$ cycloalkyl-carbonyl" of the "optionally substituted $C_{3-8}$ cycloalkyl-carbonyl" in the substituent group A, for example, cyclopropylcarbonyl, cyclopentylcarbonyl, cyclohexylcarbonyl and the like can be used.

As the "$C_{3-8}$ cycloalkyl-carbonylamino" of the "optionally substituted $C_{3-8}$ cycloalkyl-carbonylamino" in the substituent group A, for example, cyclopropylcarbonylamino, cyclopentylcarbonylamino, cyclohexylcarbonylamino and the like can be used.

As the "5 to 7-membered heterocyclylcarbonyl containing, besides carbon atom, 1 or 2 kinds of 1 to 4 hetero atoms selected from a nitrogen atom, a sulfur atom and an oxygen atom" of the "optionally substituted 5 to 7-membered heterocyclylcarbonyl containing, besides carbon atom, 1 or 2 kinds of 1 to 4 hetero atoms selected from a nitrogen atom, a sulfur atom and an oxygen atom" in the substituent group A, for example, nicotinoyl, isonicotinoyl, thenoyl, furoyl, morpholinocarbonyl, thiomorpholinocarbonyl, piperazin-1-ylcarbonyl, pyrrolidin-1-ylcarbonyl and the like can be used.

As the "$C_{6-14}$ aryloxy" of the "optionally substituted $C_{6-14}$ aryloxy" in the substituent group A, for example, phenyloxy, 1-naphthyloxy, 2-naphthyloxy and the like can be used.

As the "$C_{7-16}$ aralkyloxy" of the "optionally substituted $C_{7-16}$ aralkyloxy" in the substituent group A, for example, benzyloxy, phenethyloxy and the like can be used.

As the "$C_{6-14}$ arylthio" of the "optionally substituted $C_{6-14}$ arylthio" in the substituent group A, for example, phenylthio, 1-naphthylthio, 2-naphthylthio and the like can be used.

As the "$C_{7-16}$ aralkylthio" of the "optionally substituted $C_{7-16}$ aralkylthio" in the substituent group A, for example, benzylthio, phenethylthio and the like can be used.

As the "$C_{6-14}$ aryl-carbonyl" of the "optionally substituted $C_{6-14}$ aryl-carbonyl" in the substituent group A, for example, benzoyl, 1-naphthoyl, 2-naphthoyl and the like can be used.

As the "$C_{7-16}$ aralkyl-carbonyl" of the "optionally substituted $C_{7-16}$ aralkyl-carbonyl" in the substituent group A, for example, phenylacetyl, 3-phenylpropionyl and the like can be used.

As the "$C_{6-14}$ aryl-carbonylamino" of the "optionally substituted $C_{6-14}$ aryl-carbonylamino" in the substituent group A, for example, benzoylamino, naphthoylamino and the like can be used.

As the "$C_{6-14}$ aryl-carbonyloxy" of the "optionally substituted $C_{6-14}$ aryl-carbonyloxy" in the substituent group A, for example, benzoyloxy, naphthylcarbonyloxy and the like can be used.

As the "mono- or di-$C_{6-14}$ aryl-carbamoyloxy" of the "optionally substituted mono- or di-$C_{6-14}$ aryl-carbamoyloxy" in the substituent group A, for example, phenylcarbamoyloxy, naphthylcarbamoyloxy and the like can be used.

As the "$C_{6-14}$ arylsulfonyl" of the "optionally substituted $C_{6-14}$ arylsulfonyl" in the substituent group A, for example, phenylsulfonyl, 1-naphthylsulfonyl, 2-naphthylsulfonyl and the like can be used.

As the "$C_{6-14}$ arylsulfinyl" of the "optionally substituted $C_{6-14}$ arylsulfinyl" in the substituent group A, for example, phenylsulfinyl, 1-naphthylsulfinyl, 2-naphthylsulfinyl and the like can be used.

As the "$C_{6-14}$ arylsulfonylamino" of the "optionally substituted $C_{6-14}$ arylsulfonylamino" in the substituent group A, for example, phenylsulfonylamino and the like can be used.

As the "aromatic heterocyclyloxy" of the "optionally substituted aromatic heterocyclyloxy" in the substituent group A, for example, a 5- to 10-membered aromatic heterocyclyl-oxy containing, besides carbon atom, 1 or 2 kinds of 1 to 4 hetero atoms selected from a nitrogen atom, a sulfur atom and an oxygen atom, specifically, pyrazinyloxy and the like, can be used.

These "$C_{3-8}$ cycloalkyl", "$C_{3-8}$ cycloalkyl-carbonyl", "$C_{3-8}$ cycloalkyl-carbonylamino", "5 to 7-membered heterocyclylcarbonyl containing, besides carbon atom, 1 or 2 kinds of 1 to 4 hetero atoms selected from a nitrogen atom, a sulfur atom and an oxygen atom", "$C_{6-14}$ aryloxy", "$C_{7-16}$ aralkyloxy", "$C_{6-14}$ arylthio", "$C_{7-16}$ aralkylthio", "$C_{6-14}$ aryl-carbonyl", "$C_{7-16}$ aralkyl-carbonyl", "$C_{6-14}$ aryl-carbonylamino", "$C_{6-14}$ aryl-carbonyloxy", "mono- or di-$C_{6-14}$ aryl-carbamoyloxy", "$C_{6-14}$ arylsulfonyl", "$C_{6-14}$ arylsulfinyl", "$C_{6-14}$ arylsulfonylamino" and "aromatic heterocyclyloxy" each optionally have, at substitutable position(s), 1 to 5 substituents selected from, for example, a halogen atom (e.g., fluorine atom, chlorine atom, bromine atom, iodine atom); hydroxy; amino; the above-mentioned optionally substituted lower alkyl; the above-mentioned optionally substituted lower alkenyl; the above-mentioned optionally substituted lower alkynyl; $C_{6-14}$ aryl (said $C_{6-14}$ aryl is optionally substituted by a halogen atom, hydroxy, amino, optionally halogenated lower $(C_{1-6})$ alkyl, mono- or di-lower $(C_{1-6})$ alkylamino, mono- or di-$C_{6-14}$ arylamino, $C_{3-8}$ cycloalkyl, lower$(C_{1-6})$ alkoxy, lower$(C_{1-6})$ alkoxy-carbonyl, lower$(C_{1-6})$ alkylthio, lower $(C_{1-6})$ alkylsulfinyl, lower$(C_{1-6})$ alkylsulfonyl, the above-mentioned optionally esterified carboxyl, carbamoyl, thiocarbamoyl, mono-lower$(C_{1-6})$ alkyl- carbamoyl, di-lower $(C_{1-6})$ alkyl-carbamoyl, mono- or di-$C_{6-14}$ aryl- carbamoyl and the like); $C_{6-14}$ aryloxy (said $C_{6-14}$ aryloxy is optionally substituted by a halogen atom, hydroxy, amino, optionally halogenated lower$(C_{1-6})$ alkyl, mono- or di-lower $(C_{1-6})$ alkylamino, mono- or di-$C_{6-14}$ arylamino, $C_{3-8}$ cycloalkyl, lower$(C_{1-6})$ alkoxy, lower$(C_{1-6})$ alkoxy-carbonyl, lower $(C_{1-6})$alkylthio, lower$(C_{1-6})$ alkylsulfinyl, lower$(C_{1-6})$ alkylsulfonyl, the above- mentioned optionally esterified carboxyl, carbamoyl, thiocarbamoyl, mono-lower $(C_{1-6})$ alkyl-carbamoyl, di-lower $(C_{1-6})$ alkyl-carbamoyl, mono- or di-$C_{6-14}$ aryl-carbamoyl and the like); $C_{7-16}$ aralkyloxy (said $C_{7-16}$ aralkyloxy is optionally substituted by a halogen atom, hydroxy, amino, optionally halogenated lower $(C_{1-6})$ alkyl, mono- or di-lower $(C_{1-6})$ alkylamino, mono- or di-$C_{6-14}$ arylamino, $C_{3-6}$ cycloalkyl, lower $(C_{1-6})$ alkoxy, lower $(C_{1-6})$ alkoxy-carbonyl, lower $(C_{1-6})$ alkylthio, lower $(C_{1-6})$ alkylsulfinyl, lower $(C_{1-6})$ alkylsulfonyl, the above-mentioned optionally esterified carboxyl, carbamoyl, thiocarbamoyl, mono-lower$(C_{1-6})$ alkyl-carbamoyl, di-lower $(C_{1-6})$ alkyl-carbamoyl, mono- or di-$C_{6-14}$ aryl-carbamoyl and the like); a 5- to 7-membered heterocyclic group containing, besides carbon atom, 1 or 2 kinds of 1 to 4 hetero atoms selected from a nitrogen atom, a sulfur atom and an oxygen atom (e.g., furyl, pyridyl, thienyl etc.) (said heterocyclic group is optionally substituted by a halogen atom, hydroxy, amino, mono- or di-lower$(C_{1-6})$ alkylamino, mono- or di-$C_{6-14}$ arylamino, $C_{3-6}$ cycloalkyl, lower $(C_{1-6})$ alkoxy, lower $(C_{1-6})$ alkoxy-carbonyl, lower $(C_{1-6})$ alkylthio, lower $(C_{1-6})$ alkylsulfinyl, lower$(C_{1-6})$ alkylsulfonyl, the above-mentioned optionally esterified carboxyl, carbamoyl, thiocarbamoyl, mono- lower $(C_{1-6})$ alkyl-carbamoyl, di-lower $(C_{1-6})$ alkyl-carbamoyl, mono- or di- $C_{6-14}$ aryl-carbamoyl and the like); mono- or di-lower $(C_{1-6})$ alkylamino; mono- or di-$C_{6-14}$ arylamino; $C_{3-6}$ cycloalkyl; the above-mentioned optionally substituted lower$(C_{1-6})$ alkoxy; lower $(C_{1-6})$ alkoxy-carbonyl; lower $(C_{1-6})$alkylthio; lower $(C_{1-6})$ alkylsulfinyl; lower$(C_{1-6})$ alkylsulfonyl; the above-mentioned optionally esterified carboxyl; carbamoyl; thiocarbamoyl; mono- lower$(C_{1-6})$ alkyl-carbamoyl (e.g., methylcarbamoyl, ethylcarbamoyl etc.); di-lower $(C_{1-6})$ alkyl-carbamoyl (e.g., dimethylcarbamoyl, diethylcarbamoyl, ethylmethylcarbamoyl etc.); mono- or di-$C_{6-14}$ aryl-carbamoyl (e.g., phenylcarbamoyl, 1- naphthylcarbamoyl, 2-naphthylcarbamoyl etc.); mono- or di- 5- to 7-membered heterocyclylcarbamoyl containing, besides carbon atom, 1 or 2 kinds of 1 to 4 hetero atoms selected from a nitrogen atom, a sulfur atom and an oxygen atom (e.g., 2- pyridylcarbamoyl, 3-pyridylcarbamoyl, 4-pyridylcarbamoyl, 2- thienylcarbamoyl, 3-thienylcarbamoyl etc.) and the like.

As the "$C_{6-14}$ aryl" of the "optionally substituted $C_{6-14}$ aryl" in the substituent group A, for example, phenyl, 1-naphthyl, 2-naphthyl, 2-biphenylyl, 3-biphenylyl, 4-biphenylyl, 2-anthryl and the like can be used. The $C_{6-14}$ aryl may be partially saturated and as the partially saturated $C_{6-14}$ aryl, for example, tetrahydronaphthyl and the like can be mentioned.

As the "$C_{7-16}$ aralkyl" of the "optionally substituted $C_{7-16}$ aralkyl" in the substituent group A, for example, benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl and the like can be used.

As the "$C_{6-14}$ aryl-$C_{2-6}$ alkenyl" of the "optionally substituted $C_{6-14}$ aryl-$C_{2-6}$ alkenyl" in the substituent group A, for example, styryl and the like can be used.

These "$C_{6-14}$ aryl", "$C_{7-16}$ aralkyl" and "$C_{6-14}$ aryl-$C_{2-6}$ alkenyl" each may have, at substitutable position(s), 1 to 5 substituents selected from, for example, a halogen atom; hydroxy; nitro; cyano; the above-mentioned optionally substituted lower alkyl; the above-mentioned optionally substituted lower alkenyl; the above-mentioned optionally substituted lower alkynyl; the above-mentioned optionally substituted $C_{3-8}$ cycloalkyl; the above-mentioned optionally substituted lower alkoxy; the above-mentioned optionally substituted lower alkylthio; the above-mentioned optionally substituted lower alkylsulfinyl; the above-mentioned optionally substituted lower alkylsulfonyl; the above-mentioned optionally esterified carboxyl; carbamoyl; thiocarbamoyl; mono-lower$(C_{1-6})$ alkyl-carbamoyl; di-lower$(C_{1-6})$ alkyl-carbamoyl; mono- or di-$C_{6-14}$ aryl-carbamoyl; mono- or di-5- to 7-membered heterocyclylcarbamoyl containing, besides carbon atom, 1 or 2 kinds of 1 to 4 hetero atoms selected from a nitrogen atom, a sulfur atom and an oxygen atom (e.g., 2-pyridylcarbamoyl, 3-pyridylcarbamoyl, 4-pyridylcarbamoyl, 2-thienylcarbamoyl, 3-thienylcarbamoyl etc.); and the like.

As the "heterocyclic group" of the "optionally substituted heterocyclic group" in the substituent group A, for example, a 5- to 14-membered (monocycle, bicyclic or tricyclic) heterocyclic group containing, besides carbon atom, 1 or 2 kinds of 1 to 4 hetero atoms selected from a nitrogen atom, a sulfur atom and an oxygen atom, preferably (i) 5- to 14-membered (preferably 5- to 10-membered) aromatic heterocyclic group, (ii) a 5- to 10-membered non-aromatic heterocyclic group, (iii) a monovalent group obtained by removing any one hydrogen atom from a 7- to 10-membered crosslinked heterocycle, and the like can be used, with preference given to a 5-membered aromatic heterocyclic group. Specifically, for example, aromatic heterocyclic groups such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl), isoxazolyl (e.g., 3-isoxazolyl), indolyl (e.g., 1-indolyl, 2-indolyl, 3-indolyl), 2-benzothiazolyl, benzo[b]thienyl, (e.g., 2-benzo[b]thienyl, 3-benzo[b]thienyl), benzo[b]furanyl (e.g., 2-benzo[b]furanyl, 3-benzo[b]furanyl) and the like; non-aromatic heterocyclic groups such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino and the like; and the like can be used.

The heterocyclic group may have, at substitutable position(s), 1 to 5 substituents selected from, for example, a halogen atom; hydroxy; nitro; cyano; the above-mentioned optionally substituted lower alkyl; the above-mentioned optionally substituted lower alkenyl; the above-mentioned optionally substituted lower alkynyl; the above-mentioned optionally substituted $C_{3-8}$ cycloalkyl; the above-mentioned optionally substituted $C_{6-14}$ aryl; the above-mentioned optionally substituted lower alkoxy; the above-mentioned optionally substituted lower alkylthio; the above-mentioned optionally substituted $C_{6-14}$ arylthio; the above-mentioned optionally substituted $C_{7-16}$ aralkylthio; the above-mentioned optionally substituted lower alkylsulfinyl; the above-mentioned optionally substituted $C_{6-14}$ arylsulfinyl; the above-mentioned optionally substituted $C_{1-6}$ alkylsulfonyl; the above-mentioned optionally substituted $C_{6-14}$ arylsulfonyl; the above-mentioned optionally esterified carboxyl; carbamoyl; thiocarbamoyl; mono-lower($C_{1-6}$) alkyl-carbamoyl; di-lower($C_{1-6}$) alkyl-carbamoyl; mono- or di-$C_{6-14}$ aryl-carbamoyl; mono- or di-5- to 7-membered heterocyclylcarbamoyl containing, besides carbon atom, 1 or 2 kinds of 1 to 4 hetero atoms selected from a nitrogen atom, a sulfur atom and an oxygen atom (e.g., 2-pyridylcarbamoyl, 3-pyridylcarbamoyl, 4-pyridylcarbamoyl, 2-thienylcarbamoyl, 3-thienylcarbamoyl etc.); and the like.

As the "optionally substituted carbamoyl group" in the substituent group A, a carbamoyl group optionally substituted by 1 or 2 substituents selected from the above-mentioned optionally substituted lower alkyl, the above-mentioned optionally substituted lower alkenyl, the above-mentioned optionally substituted lower alkynyl, the above-mentioned optionally substituted $C_{3-8}$ cycloalkyl, the above-mentioned optionally substituted $C_{6-14}$ aryl, the above-mentioned optionally substituted heterocyclic group, the above-mentioned optionally substituted lower alkoxy and the like can be used, and specifically, for example, carbamoyl; mono-$C_{1-6}$ alkyl-carbamoyl (e.g., methylcarbamoyl, ethylcarbamoyl etc.); di-$C_{1-6}$ alkyl-carbamoyl (e.g., dimethylcarbamoyl, diethylcarbamoyl, ethylmethylcarbamoyl etc.); $C_{1-6}$ alkyl($C_{1-6}$ alkoxy)-carbamoyl (e.g., methyl(methoxy)carbamoyl, ethyl(methoxy)carbamoyl); mono- or di-$C_{6-14}$ arylcarbamoyl (e.g., phenylcarbamoyl, 1-naphthylcarbamoyl, 2-naphthylcarbamoyl etc.); mono- or di- 5- to 7-membered heterocyclylcarbamoyl containing, besides carbon atom, 1 or 2 kinds of 1 to 4 hetero atoms selected from a nitrogen atom, a sulfur atom and an oxygen atom (e.g., 2-pyridylcarbamoyl, 3-pyridylcarbamoyl, 4-pyridylcarbamoyl, 2-thienylcarbamoyl, 3-thienylcarbamoyl etc.); and the like can be used. As the "optionally substituted carbamoyl group", moreover, 5 to 7-membered cyclylcarbamoyl (e.g., 1-pyrrolidinylcarbonyl, 1-piperidinylcarbonyl, hexamethyleneiminocarbonyl) and the like can be also used.

As the "optionally substituted amino" in the substituent group A, an amino optionally substituted by 1 or 2 substituents selected from the above-mentioned optionally substituted lower alkyl, the above-mentioned optionally substituted lower alkenyl, the above-mentioned optionally substituted lower alkynyl, the above-mentioned optionally substituted $C_{3-8}$ cycloalkyl, the above-mentioned optionally substituted $C_{6-14}$ aryl, the above-mentioned optionally substituted lower alkoxy and the like can be used.

As the substituent of ring P, a substituent having an aromatic ring is preferable. Specifically, a substituent represented by the formula: $R^1$-E- ($R^1$ is an aromatic group optionally having substituent(s), and E is a bond or a spacer) and the like can be used.

As the "aromatic group" of the "aromatic group optionally having substituent(s)" represented by $R^1$, an aromatic hydrocarbon group and an aromatic heterocyclic group can be used.

As the aromatic hydrocarbon group, a $C_{6-14}$ aryl group such as a phenyl group, a naphthyl group and the like can be used, with preference given to a phenyl group.

As the aromatic heterocyclic group, for example, a 5- to 14-membered (monocycle, bicyclic or tricyclic) aromatic heterocyclic group containing, besides carbon atom, 1 or 2 kinds of 1 to 4 hetero atoms selected from a nitrogen atom, a sulfur atom and an oxygen atom, preferably (i) a 5- to 14-membered (preferably 5- to 10-membered) aromatic heterocyclic group, (ii) a monovalent group obtained by removing any one hydrogen atom from a 7- to 10-membered aromatic crosslinked heterocycle, and the like can be mentioned, with preference given to a monocyclic aromatic heterocyclic group. Specifically, for example, thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl), isoxazolyl (e.g., 3-isoxazolyl), indolyl (e.g., 1-indolyl, 2-indolyl, 3-indolyl), 2-benzothiazolyl, benzo[b]thienyl, (e.g., 2-benzo[b]thienyl, 3-benzo[b]thienyl), benzo[b]furanyl (e.g., 2-benzo[b]furanyl, 3-benzo[b]furanyl) and the like can be used.

As the "substituent" of the "aromatic group" represented by $R^1$, a substituent selected from the aforementioned substituent group A can be used. The number of the substituents is, for example, 1 to 3.

As $R^1$, (i) a phenyl group optionally having substituent(s) selected from the group consisting of a halogen atom, a nitro, a carboxy, an optionally substituted $C_{1-6}$ alkyl exemplified for the aforementioned substituent group A [preferably, an optionally halogenated $C_{1-6}$ alkyl, a hydroxy-$C_{1-6}$ alkyl, a carboxy-$C_{1-6}$ alkyl-carbonylamino-$C_{1-6}$ alkyl], an optionally substituted $C_{1-6}$ alkoxy exemplified for the aforementioned substituent group A [preferably, an optionally halogenated $C_{1-6}$ alkoxy], a $C_{6-14}$ aryl, a $C_{6-14}$ aryloxy, a $C_{7-16}$ aralkyloxy, a formyl, a cyano, a hydroxy, a $C_{1-6}$ alkylthio, a $C_{1-6}$ alkoxy-carbonyl, a carbamoyl, a mono-$C_{1-6}$ alkyl-carbamoyl, a di-$C_{1-6}$ alkyl-carbamoyl and a $C_{3-8}$ cycloalkyl (preferably, a phenyl group optionally having substituent(s) selected from a halogen atom, an optionally halogenated $C_{1-6}$ alkyl, an optionally halogenated $C_{1-6}$ alkoxy, a $C_{6-14}$ aryl, a $C_{6-14}$ aryloxy and a $C_{7-16}$ aralkyloxy), or (ii) a 5- to 14-membered aromatic heterocyclic group containing, besides carbon atom, 1 to 4 hetero atoms selected from a nitrogen atom, an oxygen atom and a sulfur atom (e.g., thiazolyl (e.g., 2-thiazolyl, 4-thiazolyl, 5-thiazolyl), oxazolyl (e.g., 2-oxazolyl, 4-oxazolyl) and the like), which optionally has substituent(s) selected from optionally a halogenated $C_{1-6}$ alkyl, a $C_{6-14}$ aryl and a $C_{6-14}$ aryl-$C_{2-6}$ alkenyl, is preferable.

As the spacer represented by E, an alkylene group optionally having substituent(s) or an alkenylene group optionally having substituent(s), wherein —C— in the alkylene group or alkenylene group is optionally substituted by —O—, —N— or —S—, can be used. The position at which —C— in the alkylene group or alkenylene group is substituted by —O—, —N— or —S— may be the terminal or chain of the alkylene group or alkenylene group.

As the "alkylene group" of the "alkylene group optionally having substituent(s)" for the spacer represented by E, for example, a $C_{1-13}$ alkylene group (e.g., methylene, ethylene, propylene, butylene and the like) can be used, and a $C_{1-6}$ alkylene group is particularly preferable.

As the "alkenylene group" of the "alkenylene group optionally having substituent(s)" for the spacer represented by E, for example, a $C_{2-13}$ alkenylene group (e.g., vinylene, propenylene, isopropenylene, 2-buten-1-ylene, 4-penten-1-ylene, 5-hexen-1-ylene) can be used, and a $C_{2-6}$ alkenylene group (e.g., vinylene, propenylene, isopropenylene, 2-buten-1-ylene, 4-penten-1-ylene, 5-hexen-1-ylene) is particularly preferable.

As the substituent of the "alkylene group" or "alkenylene group", a $C_{1-6}$ alkyl group (e.g., methyl, ethyl, propyl, isopropyl, butyl, isobutyl, sec-butyl, tert-butyl, pentyl, isopentyl, neopentyl, hexyl), an oxo group, a $C_{6-14}$ aryl group (e.g., phenyl) and the like can be preferably used, and an oxo group is particularly preferable. The number of the substituents is, for example, 1 to 3.

Specifically, as E, (i) a bond, or (ii) a spacer represented by —$(CH_2)m^1$-$W^1$—$(CH_2)m^2$- ($m^1$ and $m^2$ are each an integer of 0 to 3, $W^1$ is —O—, —N($R^2$)—, —S—, —CO— or —CO—N($R^3$)—, and $R^2$ and $R^3$ are each a hydrogen atom or a $C_{1-6}$ alkyl group) is preferable, and
(i) a bond,
(ii) a spacer represented by —$(CH_2)m^1$-$W^1$- (each symbol is as defined above),
(iii) a spacer represented by —$W^1$—$(CH_2)m^2$- (each symbol is as defined above) or the like is particularly preferable.

As $m^1$, 0 or 1 is preferable.
As $m^2$, 0 or 1 is preferable.
As a combination of $m^1$ and $m^2$, the both being 0, or one being 0 and the other being 1 is preferable.

As the $C_{1-6}$ alkyl group represented by $R^2$ or $R^3$, methyl, ethyl, propyl, isopropyl, butyl, isobutyl, sec-butyl, tert-butyl, pentyl, isopentyl, neopentyl, hexyl can be used.

Particularly, as E, a bond, —O—, —$CH_2$—O—, —CO—, —CONH—, —N($R^2$)—$CH_2$— ($R^2$ is a hydrogen atom or a $C_{1-6}$ alkyl group, preferably methyl), —S—$CH_2$— or —CH=CH— is preferable, particularly, a bond, —O— or —$CH_2$—O— is preferable.

When ring P is a benzene ring, a compound wherein ring P has a substituent at the meta-position relative to X bonded to ring P, is preferable.

In compound (I'), (I), (II), (IIa), (IIb), (III) and (IV), X and Y are each a spacer, and as the spacer, "an alkylene group optionally having substituent(s) or an alkenylene group optionally having substituent(s), wherein —C— in the alkylene group or alkenylene group is optionally substituted by —O—, —N— or —S—" can be used, like the aforementioned spacer represented by E. Particularly an "alkylene group optionally having substituent(s), wherein —C— in the alkylene group is optionally substituted by —O—, —N— or —S—", is preferable.

In compound (I-1), Xa is a spacer other than an alkylene group, and as the spacer, an "alkylene group optionally having substituent(s), wherein —C— in the alkylene group is substituted by —O—, —N— or —S—" or an "alkenylene group optionally having substituent(s), wherein —C— in the alkenylene group is substituted by —O—, —N— or —S—" can be used. Of these an "alkylene group optionally having substituent(s), wherein —C— in the alkylene group is substituted by —O—, —N— or —S—" is preferable. Specifically, of the aforementioned spacers represented by E, those other than the alkylene group can be used.

As the spacer represented by X or Xa,
(i) —$X^1$—$W^2$—$X^2$— ($X^1$ and $X^2$ are each a bond or a $C_{1-6}$ alkylene group optionally having substituent(s), $W^2$ is —O—, —N($R^4$)—, —CO—N($R^5$)— or —S—, and $R^4$ and $R^5$ are each a hydrogen atom or a $C_{1-6}$ alkyl group), or
(ii) —$W^3$—$X^3$—$W^4$— ($X^3$ is a $C_{1-6}$ alkylene group optionally having substituent(s), $W^3$ and $W^4$ are each —O—, —N($R^4$)—, —CO—N($R^5$)— or —S—, and $R^4$ and $R^5$ are each a hydrogen atom or a $C_{1-6}$ alkyl group) is preferable.

As the "$C_{1-6}$ alkylene group" of the "$C_{1-6}$ alkylene group optionally having substituent(s)" represented by $X^1$, $X^2$ or $X^3$, methylene, ethylene, propylene, butylene, pentylene and hexylene can be used, and particularly, a $C_{1-4}$ alkylene group such as methylene, ethylene, propylene and butylene is preferable.

As the substituents for the "$C_{1-6}$ alkylene group", a $C_{1-6}$ alkyl group (e.g., methyl, ethyl, propyl, isopropyl, butyl, isobutyl, sec-butyl, tert-butyl, pentyl, isopentyl, neopentyl, hexyl), a $C_{6-14}$ aryl group (e.g., phenyl) and the like can be preferably used. The number of the substituents is, for example, 1 to 3.

As the $C_{1-6}$ alkyl group represented by $R^4$ or $R^5$, methyl, ethyl, propyl, isopropyl, butyl, isobutyl, sec-butyl, tert-butyl, pentyl, isopentyl, neopentyl and hexyl can be used.

As $W^2$, —O— or the like is preferable.
As $W^3$ and $W^4$, —S— or the like is preferable.

Particularly, the spacer represented by X or Xa, —$X^1$—O—$X^2$— ($X^1$ and $X^2$ are each a bond or a $C_{1-6}$ alkylene group optionally having substituent(s)) is preferable, and particularly, —$X^1$—O— ($X^1$ is a bond or a $C_{1-6}$ alkylene group optionally having substituent(s)) is preferable.

As $X^1$, a bond or a $C_{1-6}$ alkylene group (particularly, a $C_{1-4}$ alkylene group) optionally having substituent(s) selected from a $C_{1-6}$ alkyl and a $C_{6-14}$ aryl is preferable.

As the combination of $X^1$ and $X^2$, the both being bonds, or one of them being a bond is preferable.

More specifically, as the spacer represented by X or Xa,
(i) a bond,
(ii) —$X^1$—O— ($X^1$ is a bond or a $C_{1-6}$ alkylene group optionally having substituent(s)),
(iii) —N($R^4$)—$X^3$—O— ($X^3$ is a $C_{1-6}$ alkylene group optionally having substituent(s), and $R^4$ is a hydrogen atom or a $C_{1-6}$ alkyl group),
(iv) —S—$X^3$—O— ($X^3$ is a $C_{1-6}$ alkylene group optionally having substituent(s)),
(v) —N($R^4$)—$X^3$— ($X^3$ is a $C_{1-6}$ alkylene group optionally having substituent(s), and $R^4$ is a hydrogen atom or a $C_{1-6}$ alkyl group),
(vi) —CO—N($R^5$)— ($R^5$ is a hydrogen atom or a $C_{1-6}$ alkyl group),
(vii) —$X^3$—S— ($X^3$ is a $C_{1-6}$ alkylene group optionally having substituent(s)), or
(viii) —S—$X^3$—S— ($X^3$ is a $C_{1-6}$ alkylene group optionally having substituent(s)) or the like is preferable.

As Xa, —O— is particularly preferable.
As Y, —$W^5$—$Y^1$— ($Y^1$ is a $C_{1-6}$ alkylene group optionally having substituent(s), $W^5$ is a bond, —O—, —N($R^6$)—, —CO—N($R^6$)— or —S—, and $R^6$ and $R^7$ are each a hydrogen atom or a $C_{1-6}$ alkyl group) or the like is preferable.

As the "$C_{1-6}$ alkylene group" of the "$C_{1-6}$ alkylene group optionally having substituent(s)" represented by $Y^1$, methylene, ethylene, propylene, butylene, pentylene and hexylene can be used, and particularly, a $C_{1-4}$ alkylene group such as methylene, ethylene, propylene and butylene is preferable.

As the $C_{1-6}$ alkyl group represented by $R^6$ or $R^7$, methyl, ethyl, propyl, isopropyl, butyl, isobutyl, sec-butyl, tert-butyl, pentyl, isopentyl, neopentyl and hexyl can be used.

As $W^5$, a bond or —O— is preferable, and a bond is particularly preferable.

Particularly, as Y, (i) a $C_{1-6}$ alkylene group optionally having substituent(s) or (ii) —O—$Y^1$— ($Y^1$ is a $C_{1-6}$ alkylene group optionally having substituent(s)) is preferable, and particularly, a $C_{1-6}$ alkylene group (e.g., methylene, ethylene, propylene) optionally having substituent(s) is preferable, and an ethylene group optionally having substituent(s) is particularly preferable. In addition, a $C_{1-6}$ alkylene group represented by Y or $Y^1$ is preferably unsubstituted.

In the compounds (I), (II), (IIa), (IIb) and (IV), —Y—COOH may be bonded at any position on ring Q, ring $Q^1$ or ring C. When ring Q, ring $Q^1$ or ring C is a benzene ring (phenyl group), these rings are preferably bonded at the para-position relative to X bonded to these rings.

In compounds (I-1), (1-2), (1-4), (Ia), (Ib), (IVa), (IVb), (C) and (D), ring R is a phenylene group optionally having substituent (s). As the substituent that a phenylene group represented by ring R may have, a substituent selected from the aforementioned substituent group A can be used, and particularly, a halogen atom, a hydroxy group, a $C_{1-6}$ alkyl, a $C_{1-6}$ alkoxy and the like can be preferably used. The number of the substituents is, for example, 1 to 3, preferably 1 or 2.

In compounds (I-1), (1-2), (1-3) and (1-4), as the substituent represented by Ra, a substituent selected from the aforementioned substituent group A can be used. As the substituent, a halogen atom (e.g., fluorine, chlorine, bromine, iodine), a $C_{1-6}$ alkyl group (e.g., methyl, ethyl, propyl), a $C_{1-6}$ alkoxy group (e.g., methoxy, ethoxy, propoxy) and the like are preferable.

In compound (Ib), ring S is a benzene ring optionally having substituent (s). As the substituent that the benzene ring represented by ring S may have, a substituent selected from the aforementioned substituent group A can be used, and particularly, a $C_{1-6}$ alkyl and the like can be preferably used. The number of the substituents is, for example, 1 to 3.

In compound (Ib), Z is a chain formed by 4 linkages. As the chain represented by Z,
(1) a chain formed by 4 groups selected from —C($R^8$)($R^{8'}$)—, —O—, —CO—, —N($R^{8''}$)— ($R^8$, $R^{8'}$ and $R^{8''}$ are each a hydrogen atom or a $C_{1-6}$ alkyl group) and —S—,
(2) a chain formed by

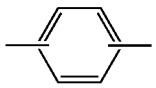

and 2 groups selected from —C($R^8$)($R^{8'}$)—, —O—, —CO—, —N($R^{8''}$)—($R^8$, $R^{8'}$ and $R^{8''}$ are each a hydrogen atom or a $C_{1-6}$ alkyl group) and —S—, or the like can be used, and specifically,
(1) —(CH$_2$)$_4$—,
(2) —O—(CH$_2$)$_3$—,
(3)

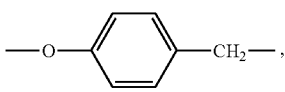

(4)

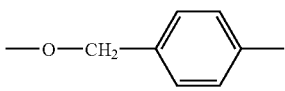

or the like can be used.

As the $C_{1-6}$ alkyl group represented by $R^8$, $R^{8'}$ or $R^{8''}$, those exemplified for the aforementioned $R^6$ can be used.

In compounds (I-1), (IIa), (IIb), (C) and (D), ring A is a benzene ring optionally having substituent(s). As the substituent that the benzene ring represented by ring A may have, a substituent selected from the aforementioned substituent group A can be used. The number of the substituents is, for example, 1 to 3.

Ring $P^1$ in compounds (II) and (III) and ring $P^2$ in compound (IIa) are rings optionally having substituent(s).

As the ring represented by ring $P^1$ or ring $P^2$, a carbon ring or a heterocycle can be used.

As the carbon ring, (1) a cycloalkane having 5 to 7 carbon atoms such as cyclopentane, cyclohexane and the like, (2) an aromatic hydrocarbon ring having 6 to 14 carbon atoms such as a benzene ring, a naphthalene ring and the like can be used, and particularly, a cycloalkane having 5 to 7 carbon atoms such as cyclohexane and the like can be preferably used.

As the heterocycle, for example, a 5- to 14-membered (monocycle, bicyclic or tricyclic) heterocycle containing, besides carbon atom, 1 or 2 kinds of 1 to 4 hetero atoms selected from a nitrogen atom, a sulfur atom and an oxygen atom, (i) a 5- to 14-membered, preferably 5- to 10-membered, more preferably 5- or 6-membered, aromatic heterocycle, (ii) a 5- to 10-membered non-aromatic heterocycle, (iii) a 7- to 10-membered crosslinked heterocycle and the like can be used.

As the above-mentioned "5- to 14-membered (preferably 5- to 10-membered) aromatic heterocycle", for example, aromatic heterocycles such as thiophene, furan, oxazole, benzo[b]thiophene, benzo[b]furan, benzimidazole, benzoxazole, benzothiazole, benzisothiazole, naphtho[2,3-b]thiophene, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine, oxadiazole, thiadiazole and the like, rings formed by condensation of these rings (preferably monocycle) with one or plural (preferably 1 or 2) aromatic rings (e.g., benzene ring etc.) and the like can be used.

As the above-mentioned "5- to 10-membered non-aromatic heterocycle", for example, pyrrolidine, imidazoline, pyrazolidine, pyrazoline, piperidine, piperazine, morpholine, thiomorpholine, dioxazole, oxadiazoline, thiadiazoline, triazoline, dithiazole and the like can be mentioned.

As the above-mentioned "7- to 10-membered crosslinked heterocycle", for example, quinuclidine, 7-azabicyclo[2.2.1] heptane and the like can be mentioned.

As ring $P^1$ and ring $P^2$, a carbon ring is preferable, and particularly, a cycloalkane having 5 to 7 carbon atoms such as cyclohexane or the like is preferable.

As the substituent that a ring represented by ring $P^1$ or ring $P^2$ may have, a substituent selected from the aforementioned substituent group A can be used. The number of the substituents is, for example, 1 to 3.

In compounds (II) and (IIa), ring $Q^1$ is an aromatic ring optionally further having substituent(s) besides —Y—COOH.

As the aromatic ring represented by ring $Q^1$, those similar to the aforementioned aromatic ring represented by ring Q can be used, and particularly, a benzene ring is preferable.

As the substituent that the ring represented by ring $Q^1$ may have besides —Y—COOH, a substituent selected from the aforementioned substituent group A can be used. The number of the substituents is, for example, 1 to 3.

In compound (IIb), ring B is a 5- to 7-membered ring optionally having substituent(s).

As the 5- to 7-membered ring represented by ring B, a 5- to 7-membered ring optionally containing, besides carbon atom, 1 to 3 hetero atoms selected from a nitrogen atom, an oxygen atom and a sulfur atom and the like can be used. Particularly, a 5 to 7-membered carbon ring is preferable.

Particularly, in compounds (IIa) and (IIb), as

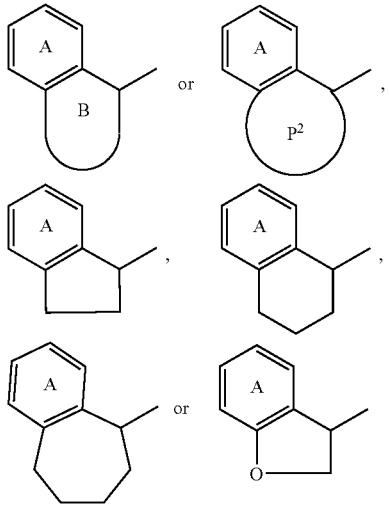

is preferable,

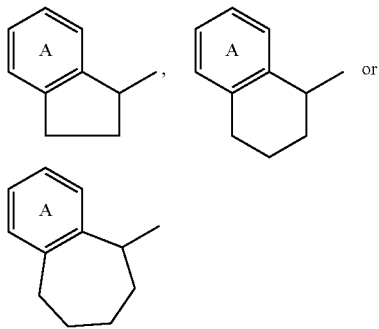

is more preferable, and

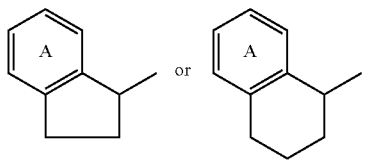

is particularly preferable.

As the substituent that the 5- to 7-membered ring represented by ring B may have, a substituent selected from the aforementioned substituent group A can be used. The number of the substituents is, for example, 1 to 3.

In compounds (IV) and (IVa), ring $P^3$ is an aromatic ring having substituent(s) having a benzene ring.

As the aromatic ring represented by ring $P^3$, those similar to the aromatic ring represented by ring P can be used, and particularly, a benzene ring is preferable.

In compounds (I-2) and (IVb), ring $S^1$ is a benzene ring having substituent(s) having a benzene ring.

Ring $S^1$ optionally further has substituent(s) besides the substituent(s) having a benzene ring. As the substituent, a substituent selected from the aforementioned substituent group A can be used, and particularly, a substituent selected from an optionally substituted $C_{1-6}$ alkyl group, an optionally substituted $C_{1-6}$ alkoxy group, a halogen atom (e.g., fluorine, chlorine, bromine, iodine) and a $C_{7-16}$ aralkyloxy (e.g., benzyloxy) is preferable; and a $C_{1-6}$ alkyl group is more preferable. The number of the substituents is, for example, 1 to 3. Here, as the optionally substituted $C_{1-6}$ alkyl group and the optionally substituted $C_{1-6}$ alkoxy group, a $C_{1-6}$ alkyl group (e.g., methyl) and a $C_{1-6}$ alkoxy group (e.g., methoxy) are preferable, respectively.

As the "substituent(s) having a benzene ring" that the aforementioned aromatic ring represented by ring $P^3$ and the aforementioned benzene ring represented by ring $S^1$ have, for example, a substituent represented by the formula: $R^{11}$-$E^2$- ($R^{11}$ is a phenyl group, an indanyl group or a naphthyl group, each optionally having substituent(s), and $E^2$ is a bond or a spacer) and the like can be used.

As the "substituent" of the "phenyl group", "indanyl group" and "naphthyl group" represented by $R^{11}$, a substituent selected from the aforementioned substituent group A can be used. The number of the substituents is, for example, 1 to 3.

As $R^{11}$, for example, a phenyl group, an indanyl group or a naphthyl group (preferably a phenyl group or an indanyl group), each optionally having 1 to 3 substituents selected from the group consisting of a halogen atom (e.g., fluorine, chlorine), a nitro, a carboxy, an optionally substituted $C_{1-6}$ alkyl exemplified for the aforementioned substituent group A [preferably, an optionally halogenated $C_{1-6}$ alkyl (e.g., methyl, ethyl, propyl, isopropyl, butyl, isobutyl, trifluoromethyl), a hydroxy-$C_{1-6}$ alkyl (e.g., hydroxymethyl, hydroxyethyl), a carboxy-$C_{1-6}$ alkyl-carbonylamino-$C_{1-6}$ alkyl (e.g., carboxyethylcarbonylaminomethyl)], an optionally substituted $C_{1-6}$ alkoxy exemplified for the aforementioned substituent group A [preferably, an optionally halogenated $C_{1-6}$ alkoxy (e.g., methoxy, ethoxy, isopropoxy, trifluoromethoxy)], a $C_{6-14}$ aryl (e.g., phenyl), a $C_{6-14}$ aryloxy (e.g., phenoxy), a $C_{7-16}$ aralkyloxy (e.g., benzyloxy), a formyl, a cyano, a hydroxy, a $C_{1-6}$ alkylthio (e.g., methylthio), a $C_{1-6}$ alkoxy-carbonyl (e.g., methoxycarbonyl, ethoxycarbonyl), a carbamoyl, a mono-$C_{1-6}$ alkyl-carbamoyl (e.g., methylcarbamoyl, ethylcarbamoyl), a di-$C_{1-6}$ alkyl-carbamoyl (e.g., dimethylcarbamoyl, diethylcarbamoyl), a $C_{3-8}$ cycloalkyl (e.g., cyclohexyl) and the like, is preferable, particularly, a phenyl group optionally having substituent(s) selected from the group consisting of a halogen atom, a nitro, a carboxy, an optionally halogenated $C_{1-6}$ alkyl, a hydroxy-$C_{1-6}$ alkyl, a carboxy-$C_{1-6}$ alkyl-carbonylamino-$C_{1-6}$ alkyl, an optionally halogenated $C_{1-6}$ alkoxy, a $C_{6-14}$ aryl, a $C_{6-14}$ aryloxy and a $C_{7-16}$ aralkyloxy is preferable, and a phenyl group optionally having 1 to 3 substituents selected from a halogen atom and an optionally halogenated $C_{1-6}$ alkyl is particularly preferable.

As the spacer represented by $E^2$, those exemplified for the aforementioned E can be mentioned. Particularly,
(i) a bond, or
(ii) a spacer represented by —(CH$_2$)m$^1$-W$^1$—(CH$_2$)m$^2$- (m$^1$ and m$^2$ are each an integer of 0 to 3, W$^1$ is —O—, —N(R$^2$)—, —S—, —CO— or —CO—N(R$^3$)—, and R$^2$ and R$^3$ are each a hydrogen atom or a C$_{1-6}$ alkyl group) is preferable, and (i) a bond,
(ii) a spacer represented by —(CH$_2$)m$^1$-W$^1$- (each symbol is as defined above),
(iii) a spacer represented by —W$^1$—(CH$_2$)m$^2$- (each symbol is as defined above) or the like is more preferable.

Of these, a bond, —O—, —CH$_2$—O—, —CO—, —CONH—, —N(CH$_3$)CH$_2$—, —S—CH$_2$— or —C≡C— is preferable.

Moreover, as the a spacer represented by E$^2$, —SO$_2$—CH$_2$—CH$_2$—N(R$^2$)—CH$_2$—, —O—CH(CH$_3$)—CH$_2$—N(R$^2$)—CH$_2$—, —CH(Ph)-CH$_2$—N(R$^2$)—CH$_2$—, —CH(Pyr)-CH$_2$—N(R$^2$)—CH$_2$—, —CH(CH$_2$-Pyr)-N(R$^2$)—CH$_2$—, —CH$_2$—N(Ph)-CH$_2$—, —CH$_2$—N(CH$_2$-Ph)-CH$_2$—, —N(CH$_2$—CH$_2$—CN)—CH$_2$—, —N(CH$_2$—CH$_2$-Imd)-CH$_2$— (R$^2$ is a hydrogen atom or a C$_{1-6}$ alkyl group, Ph is a phenyl group, Pyr is a pyrrolidinyl group and Imd is imidazopyridinyl) and the like can be also mentioned.

As the spacer represented by E$^2$, a bond, —O—, —CH$_2$—O—, —CO—, —CONH—, —N(R$^2$)CH$_2$—, —S—CH$_2$—, —C≡C—, —(CH$_2$)$_2$—, —(CH$_2$)$_2$O—, —(CH$_2$)$_3$O—, —C(=CH$_2$)—, —N(R$^2$)—, —CH$_2$—N(R$^2$)—, —CH$_2$—N(R$^2$)—CH$_2$—, —SO$_2$—CH$_2$—CH$_2$—N(R$^2$)—CH$_2$—, —O—CH(CH$_3$)—CH$_2$—N(R$^2$)—CH$_2$—, —CH(Ph)-CH$_2$—N(R$^2$)—CH$_2$—, —CH(Pyr)-CH$_2$—N(R$^2$)—CH$_2$—, —CH(CH$_2$-Pyr)-N(R$^2$)—CH$_2$—, —CH$_2$—N(Ph)-CH$_2$—, —CH$_2$—N(CH$_2$-Ph)-CH$_2$—, —N(CH$_2$—CH$_2$—CN)—CH$_2$—, —N(CH$_2$—CH$_2$-Imd)-CH$_2$— (R$^2$ is a hydrogen atom or a C$_{1-6}$ alkyl group, Ph is a phenyl group, Pyr is a pyrrolidinyl group and Imd is imidazopyridinyl) or the like is preferable, and particularly, a bond, —O— or —CH$_2$—O— is preferable.

In compound (I-2), when ring S$^1$ has a substituent represented by the formula: R$^{11}$-E$^2$- (the symbols are as defined above), R$^{11}$ may form a ring together with E$^2$ and ring S$^1$, and as such ring, for example,

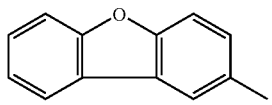

and the like can be used.

In compound (IIb), ring C is a benzene ring optionally further having substituent(s) besides a —Y—COOH group.

As the substituent that the benzene ring represented by ring C may have besides —Y—COOH, a substituent selected from the aforementioned substituent group A can be used. The number of the substituents is, for example, 1 to 3.

In compound (A), A$^1$ is a substituent (except a hydrogen atom and a chlorine atom).

As the substituent (except a hydrogen atom and a chlorine atom) represented by A$^1$, a substituent selected from the aforementioned substituent group A (except a chlorine atom and a C$_{1-3}$ alkylenedioxy) can be used, and particularly, a bromine atom is preferable.

Ring D is a benzene ring further having substituent(s) (except a nitro group and a hydroxy group) besides A$^1$.

As the substituent (except a nitro group and a hydroxy group) that the benzene ring represented by ring D may have besides A$^1$, a substituent selected from the aforementioned substituent group A (except a nitro group and a hydroxy group) can be used. The number of the substituents is, for example, 1 to 3.

In compounds (I-3), (A) and (B), ring E is a phenylene group optionally having substituent(s), and those similar to the "phenylene group optionally having substituent(s)" represented by ring R can be used. However, no substituent is present at the position represented by —H.

In compound (B), ring F is a ring optionally having substituent(s), and those similar to the "ring optionally having substituent(s)" represented by ring P$^1$ can be used.

In compound (B), ring G is a benzene ring optionally having substituent(s), and those similar to the "benzene ring optionally having substituent(s)" represented by ring A can be used.

The partial structural formula:

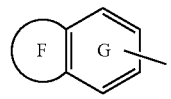

is not an unsubstituted naphthyl group, an unsubstituted 1H-indazolyl group and a quinolyl group optionally having substituent(s).

In compound (C), ring H is a 5-membered ring optionally having substituent(s).

As the 5-membered ring represented by ring H, a 5-membered carbon ring or heterocycle can be used.

As the 5-membered carbon ring, cyclopentane and the like can be used.

As the 5-membered heterocycle, for example, a 5-membered heterocycle containing, besides carbon atom, 1 or 2 kinds of 1 to 4 hetero atoms selected from a nitrogen atom, a sulfur atom and an oxygen atom and the like can be used. Specifically, thiophene, dihydrothiophene, furan, dihydrofuran, thiazole, isothiazole, oxazole, isoxazole, pyrrole, pyrroline, imidazole, imidazoline, pyrazole, pyrrolidine, imidazoline, pyrazolidine, pyrazoline, oxadiazole, thiadiazole and the like can be mentioned.

As the ring H, thiophene, pyrrole and the like are preferable.

As the substituent that the 5-membered ring represented by ring H may have, a substituent selected from the aforementioned substituent group A can be used. The number of the substituents is, for example, 1 to 3.

As the partial structural formula

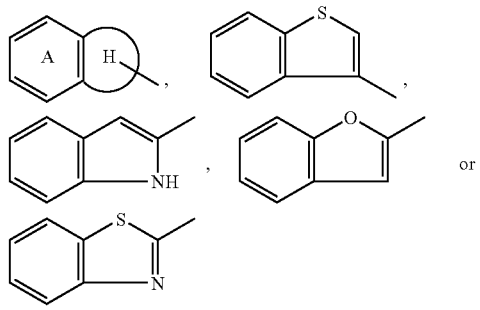

each optionally having substituent(s) selected from a halogen atom (e.g., chlorine atom) and an optionally halogenated C$_{1-6}$ alkyl group (e.g., methyl, trifluoromethyl), and the like can be preferable used.

In compound (D), J is —O—, —S—, —CH$_2$— or NR$^{12}$ (R$^{12}$ is a hydrogen atom or a C$_{1-6}$ alkyl group).

As the C$_{1-6}$ alkyl group represented by R$^{12}$, methyl, ethyl, propyl, isopropyl, butyl, isobutyl, sec-butyl, tert-butyl, pentyl, isopentyl, neopentyl and hexyl can be used.

K is a bond or a $C_{1-3}$ alkylene group.

As the $C_{1-3}$ alkylene group represented by K, methylene, ethylene and propylene can be used.

As K, a bond and methylene are preferable.

------ is a single bond or a double bond.

As the substituent that ring I may have, a substituent selected from the aforementioned substituent group A can be used. The number of the substituents is, for example, 1 to 3.

As the partial structural formula

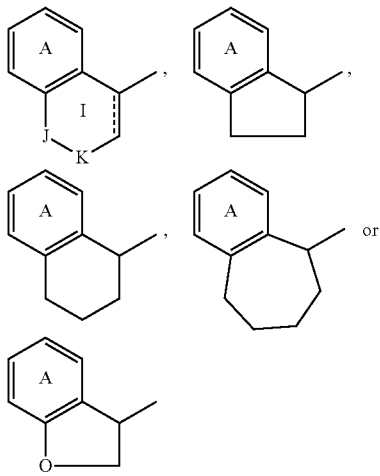

and the like are preferable. As the substituent for ring A in this case, (i) a halogen atom, (ii) a $C_{1-6}$ alkyl group (e.g., methyl, ethyl, propyl), (iii) a $C_{1-6}$ alkoxy group (e.g., methoxy, ethoxy), (iv) a $C_{6-14}$ aryl group (e.g., phenyl, naphthyl) optionally having substituent(s) selected from a halogen atom (e.g., fluorine atom, chlorine atom, bromine atom) and a $C_{1-6}$ alkyl (e.g., methyl, ethyl, propyl), (v) a $C_{6-14}$ aryloxy group (e.g., phenyloxy) and (vi) a $C_{7-15}$ aralkyloxy group (e.g., naphthyloxy), are preferable, and as the substituent of ring R, a halogen atom (e.g., fluorine atom, chlorine atom, bromine atom) is preferable.

A compound (IIb), wherein the spacer represented by X is a methylene group optionally having substituent(s), —O— or —S—; the spacer represented by Y is a $C_{1-6}$ alkylene group optionally having substituent(s), —N($R^6$)—$Y^1$— ($R^6$ is a hydrogen atom or a $C_{1-6}$ alkyl group, and $Y^1$ is a $C_{1-6}$ alkylene group optionally having substituent(s)), —O—$Y^1$— ($Y^1$ is a $C_{1-6}$ alkylene group optionally having substituent(s)) or —S—$Y^1$— ($Y^1$ is a $C_{1-6}$ alkylene group optionally having substituent(s)); and ring B is a 5 to 7-membered carbon ring, is preferable.

A compound (IVa) wherein ring $P^3$ is a benzene ring having "the substituent having a benzene ring" represented by the formula: $R^{11}$-$E^2$- ($R^{11}$ is a phenyl group, an indanyl group or a naphthyl group, each optionally having substituent(s), and $E^2$ is a bond or a spacer) is preferable. As $E^2$, a bond, —O— or —CH$_2$—O— is preferable. As $R^{11}$, a phenyl group optionally having substituent(s) selected from a halogen atom and an optionally halogenated $C_{1-6}$ alkyl is preferable.

As $X^1$, a $C_{1-6}$ alkylene group (particularly, a methylene group) optionally having substituent(s) such as a $C_{1-6}$ alkyl, a $C_{6-14}$ aryl and the like is preferable.

As $W^5$, a bond is preferable.

As $Y^1$, a $C_{1-6}$ alkylene group (particularly, an ethylene group) optionally having substituent(s) is preferable.

As ring R, a phenylene group optionally having a $C_{1-6}$ alkoxy is preferable.

A compound (IVb) wherein ring $S^1$ is a benzene ring having "the substituent having a benzene ring" represented by the formula: $R^{11}$-$E^2$- ($R^{11}$ is a phenyl group, an indanyl group or a naphthyl group, each optionally having substituent(s), and $E^2$ is a bond or a spacer) is preferable. As $E^2$, a bond, —O—, —CH$_2$—O—, —CO—, —CONH—, —N($R^2$)—CH$_2$— ($R^2$ is a hydrogen atom or a $C_{1-6}$ alkyl group), —S—CH$_2$— or —CH=CH— is preferable, and particularly, a bond, —O— or —CH$_2$—O— is preferable. As $R^{11}$, a phenyl group, an indanyl group or a naphthyl group (preferably a phenyl group or an indanyl group), each optionally having substituent(s) selected from the group consisting of a halogen atom, a nitro, a carboxy, an optionally halogenated $C_{1-6}$ alkyl, a hydroxy-$C_{1-6}$ alkyl, a carboxy-$C_{1-6}$ alkyl-carbonylamino-$C_{1-6}$ alkyl, an optionally halogenated $C_{1-6}$ alkoxy, a $C_{6-14}$ aryl, a $C_{6-14}$ aryloxy and a $C_{7-16}$ aralkyloxy is preferable, and particularly, a phenyl group optionally having substituent(s) selected from a halogen atom, an optionally halogenated $C_{1-6}$ alkyl, an optionally halogenated $C_{1-6}$ alkoxy, a $C_{6-14}$ aryl, a $C_{6-14}$ aryloxy and a $C_{7-16}$ aralkyloxy is preferable, and particularly, a phenyl group optionally having substituent(s) selected from a halogen atom and an optionally halogenated $C_{1-6}$ alkyl is preferable.

A compound (A) wherein $A^1$ is a bromine atom is preferable.

A compound (C) wherein the partial structural formula

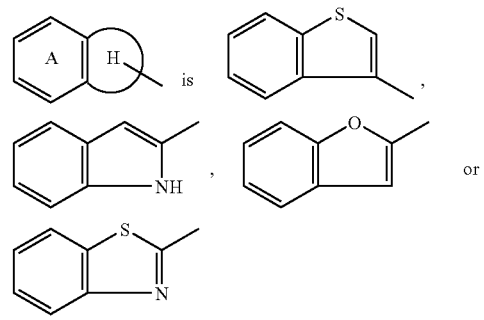

each optionally having a substituent selected from a halogen atom (e.g., chlorine atom) and an optionally halogenated $C_{1-6}$ alkyl group (e.g., methyl, trifluoromethyl) is preferable.

A compound (D) wherein the partial structural formula

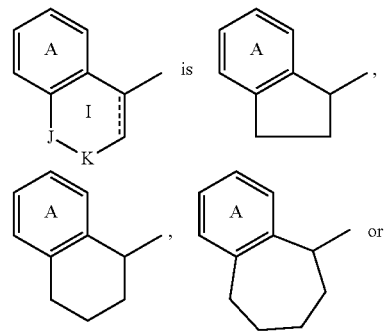

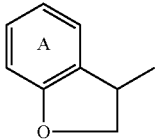

wherein the substituent of ring A is (i) a halogen atom, (ii) a $C_{1-6}$ alkyl group, (iii) a $C_{1-6}$ alkoxy group, (iv) a $C_{6-14}$ aryl group optionally having substituent(s) selected from a halogen atom and a $C_{1-6}$ alkyl, (v) a $C_{6-14}$ aryloxy group or (vi) a $C_{7-15}$ aralkyloxy group, and the substituent of ring R is a halogen atom, is preferable.

In compound (I-1), p and q are each a $C_{0-4}$ carbon chain optionally having substituent(s).

Here, as the $C_{0-4}$ carbon chain, a bond, a $C_{1-4}$ alkylene group (e.g., methylene, ethylene and the like) and the like can be used, and particularly, a $C_{1-4}$ alkylene group (e.g., methylene, ethylene and the like) is preferable, and methylene and ethylene are preferable, and particularly, methylene is preferable.

As the partial structural formula

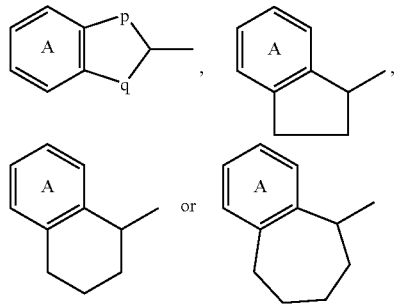

and the like are preferable.

As the substituent that the $C_{0-4}$ carbon chain may have, a substituent selected from the aforementioned substituent group A can be used. The number of the substituents is, for example, 1 to 3.

As the substituent that ring A optionally has, (1) a halogen atom (e.g., fluorine atom, chlorine atom, bromine atom), (2) a $C_{1-6}$ alkyl group (e.g., a $C_{1-3}$ alkyl group such as methyl and the like), (3) a $C_{1-6}$ alkoxy group (e.g., a $C_{1-3}$ alkoxy group such as methoxy and the like), (4) a $C_{6-14}$ aryl group (e.g., phenyl group) optionally substituted by a halogen atom (e.g., fluorine atom, chlorine atom), a $C_{1-6}$ alkyl (e.g., $C_{1-3}$ alkyl such as methyl and the like) or a $C_{1-6}$ alkoxy (e.g., $C_{1-3}$ alkoxy such as methoxy and the like), (5) a $C_{6-14}$ aryloxy group (e.g., phenoxy group) and (6) a $C_{7-16}$ aralkyloxy group (e.g., benzyloxy group, phenylethyloxy group, phenylpropyloxy group, phenylbutyloxy group) are preferable. The number of the substituents is, for example, 1 to 3.

As the substituent that ring R optionally has, a halogen atom (e.g., a fluorine atom, a chlorine atom) and a $C_{1-6}$ alkyl group (e.g., a $C_{1-3}$ alkyl group such as methyl and the like) are preferable, but ring R is more preferably unsubstituted.

As Ra, a hydrogen atom is preferable.

As the spacer represented by Xa, an oxygen atom is preferable.

In compound (I-2), as the substituent(s) having a benzene ring, a substituent represented by the formula: $R^{11}$-$E^2$- ($R^{11}$ is a phenyl group, an indanyl group or a naphthyl group, each optionally having substituent(s), and $E^2$ is a bond or a spacer) is preferable.

Ring $S^1$ may further has substituent(s) selected from an optionally substituted $C_{1-6}$ alkyl group, an optionally substituted $C_{1-6}$ alkoxy group, a halogen atom (e.g., fluorine, chlorine, bromine, iodine) and a $C_{7-16}$ aralkyloxy (e.g., benzyloxy); preferably a $C_{1-6}$ alkyl group. Here, as the optionally substituted $C_{1-6}$ alkyl group and the optionally substituted $C_{1-6}$ alkoxy group, those exemplified for the aforementioned substituent group A can be used, wherein a $C_{1-6}$ alkyl group (e.g., methyl) and a $C_{1-6}$ alkoxy group (e.g., methoxy) are preferable, respectively.

The ring $S^1$ is preferably a benzene ring without additional substituent.

As $R^{11}$, a phenyl group optionally having substituent(s) is preferable.

As $R^{11}$, a phenyl group, an indanyl group or a naphthyl group (preferably phenyl group or indanyl group), each optionally having 1 to 3 substituents selected from the group consisting of a halogen atom (e.g., fluorine, chlorine), a nitro, a carboxy, an optionally substituted $C_{1-6}$ alkyl exemplified for the aforementioned substituent group A [preferably, an optionally halogenated $C_{1-6}$ alkyl (e.g., methyl, ethyl, propyl, isopropyl, butyl, isobutyl, trifluoromethyl), a hydroxy-$C_{1-6}$ alkyl (e.g., hydroxymethyl, hydroxyethyl), a carboxy-$C_{1-6}$ alkyl-carbonylamino-$C_{1-6}$ alkyl (e.g., carboxyethylcarbonylaminomethyl)], an optionally substituted $C_{1-6}$ alkoxy exemplified for the aforementioned substituent group A [preferably, an optionally halogenated $C_{1-6}$ alkoxy (e.g., methoxy, ethoxy, isopropoxy, trifluoromethoxy)], a $C_{6-14}$ aryl (e.g., phenyl), a $C_{6-14}$ aryloxy (e.g., phenoxy), a $C_{7-16}$ aralkyloxy (e.g., benzyloxy), a formyl, a cyano, a hydroxy, a $C_{1-6}$ alkylthio (e.g., methylthio), a $C_{1-6}$ alkoxy-carbonyl (e.g., methoxycarbonyl, ethoxycarbonyl), a carbamoyl, a mono-$C_{1-6}$ alkyl-carbamoyl (e.g., methylcarbamoyl, ethylcarbamoyl), a di-$C_{1-6}$ alkyl-carbamoyl (e.g., dimethylcarbamoyl, diethylcarbamoyl) and a $C_{3-8}$ cycloalkyl (e.g., cyclohexyl) is preferable, particularly, a phenyl group optionally having substituent(s) selected from the group consisting of a halogen atom, a nitro, a carboxy, an optionally halogenated $C_{1-6}$ alkyl, a hydroxy-$C_{1-6}$ alkyl (e.g., hydroxymethyl, hydroxyethyl), a carboxy-$C_{1-6}$ alkyl-carbonylamino-$C_{1-6}$ alkyl (e.g., carboxyethylcarbonylaminomethyl), an optionally halogenated $C_{1-6}$ alkoxy, a $C_{6-14}$ aryl, a $C_{6-14}$ aryloxy and a $C_{7-16}$ aralkyloxy is preferable.

As $E^2$, a bond, —O—, —CH$_2$—O—, —CO—, —CONH—, —N(CH$_3$)CH$_2$—, —S—CH$_2$—, —C=C—, —(CH$_2$)$_2$—, —(CH$_2$)$_2$O—, —(CH$_2$)$_3$O—, —C(=CH$_2$)—, —N(R$^2$)—, —CH$_2$—N(R$^2$)—, —CH$_2$—N(R$^2$)—CH$_2$—, —SO$_2$—CH$_2$—CH$_2$—N(R$^2$)—CH$_2$—, —O—CH(CH$_3$)—CH$_2$—N(R$^2$)—CH$_2$—, —CH(Ph)-CH$_2$—N(R$^2$)—CH$_2$—, —CH(Pyr)-CH$_2$—N(R$^2$)—CH$_2$—, —CH(CH$_2$-Pyr)-N(R$^2$)—CH$_2$—, —CH$_2$—N(Ph)-CH$_2$—, —CH$_2$—N(CH$_2$-Ph)-CH$_2$—, —N(CH$_2$—CH$_2$—CN)—CH$_2$—, —N(CH$_2$—CH$_2$-Imd)-CH$_2$— (R$^2$ is a hydrogen atom or a $C_{1-6}$ alkyl group, Ph is a phenyl group, Pyr is a pyrrolidinyl group and Imd is imidazopyridinyl) or the like is preferable.

$E^2$ is particularly preferably a bond, —O— or —CH$_2$—O—.

When ring $S^1$ has a substituent represented by the formula: $R^{11}$-$E^2$- (the symbols are as defined above), $R^{11}$ may form a ring together with $E^2$ and ring $S^1$.

As the ring formed by $R^{11}$ together with $E^2$ and ring $S^1$,

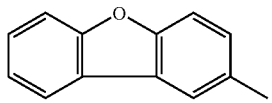

and the like are preferable, but preferably, $R^{11}$ does not form a ring together with $E^2$ and ring $S^1$.

As the substituent that ring R optionally has, a $C_{1-6}$ alkyl group (e.g., a $C_{1-3}$ alkyl group such as methyl and the like), a halogen atom (e.g., fluorine, chlorine, bromine, iodine), a $C_{1-6}$ alkoxy group (e.g., methoxy, ethoxy, propoxy), a hydroxy group and the like are preferable.

As Ra, a hydrogen atom, a halogen atom (e.g., fluorine, chlorine, bromine, iodine), a $C_{1-6}$ alkyl group (e.g., methyl, ethyl, propyl) or a $C_{1-6}$ alkoxy group (e.g., methoxy, ethoxy, propoxy) is preferable; and a halogen atom (preferably fluorine) is more preferable.

Specific examples of compound (I-2) include, a compound wherein the substituent(s) having a benzene ring is a substituent represented by the formula: $R^{11}$-$E^2$- ($R^{11}$ is a phenyl group or an indanyl group each optionally having substituent(s), and $E^2$ is a bond or a spacer), ring $S^1$ is optionally further substituted by a $C_{1-6}$ alkyl group, $R^{11}$ may form a ring together with $E^2$ and ring $S^1$;

preferably, $R^{11}$ is a phenyl group, an indanyl group or a naphthyl group (preferably a phenyl group or an indanyl group), each optionally having substituent(s) selected from the group consisting of a halogen atom, a nitro, a carboxy, an optionally halogenated $C_{1-6}$ alkyl, a hydroxy-$C_{1-6}$ alkyl, a carboxy-$C_{1-6}$ alkyl-carbonylamino-$C_{1-6}$ alkyl, an optionally halogenated $C_{1-6}$ alkoxy, a $C_{6-14}$ aryl, a $C_{6-14}$ aryloxy and a $C_{7-16}$ aralkyloxy, $E^2$ is a bond, —O—, —CH$_2$—O—, —CO—, —CONH—, —N(CH$_3$)CH$_2$—, —S—CH$_2$— or —C=C—, ring $S^1$ is optionally further substituted by a $C_{1-6}$ alkyl group, the ring formed by $R^{11}$ together with $E^2$ and ring $S^1$ is

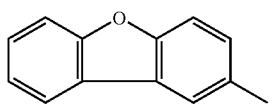

the substituent that ring R optionally has is a $C_{1-6}$ alkyl group, and Ra is a hydrogen atom, and the like, can be mentioned.

A compound (I-2) wherein the substituent(s) having a benzene ring is a substituent represented by the formula: $R^{11}$-$E^2$- ($R^{11}$ is a phenyl group, an indanyl group or a naphthyl group, each optionally having substituent(s), and $E^2$ is a bond or a spacer), the spacer represented by $E^2$ is —(CH$_2$)m$^1$-W$^1$—(CH$_2$)m$^2$- (m$^1$ and m$^2$ are each an integer of 0 to 3, W$^1$ is —O—, —N(R$^2$)—, —S—, —CO— or —CO—N(R$^3$—, and R$^2$ and R$^3$ are each a hydrogen atom or a $C_{1-6}$ alkyl group) is preferable.

The compound (I-2) is preferably a compound represented by the formula

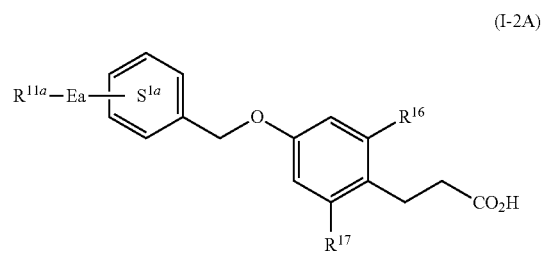

(I-2A)

wherein $R^{11a}$ is a phenyl group having 1 or 2 substituents, Ea is a bond, an oxygen atom or an optionally substituted methylene, ring $S^{1a}$ is a benzene ring optionally further having substituent(s) selected from an optionally substituted $C_{1-6}$ alkyl group, an optionally substituted $C_{1-6}$ alkoxy group and a halogen atom, and $R^{16}$ and $R^{17}$ are the same or different and each is a hydrogen atom, a halogen atom, a $C_{1-6}$ alkyl group or a $C_{1-6}$ alkoxy group.

Here, as the substituent of the "phenyl group having 1 or 2 substituents" represented by $R^{11a}$, those exemplified for the substituent of the aforementioned $R^{11}$ can be used. The substituent is preferably an optionally substituted $C_{1-6}$ alkyl group, an optionally substituted $C_{1-6}$ alkoxy group, a halogen atom and the like. Here, as the optionally substituted $C_{1-6}$ alkyl group, the optionally substituted $C_{1-6}$ alkoxy group and the halogen atom, those exemplified for the aforementioned substituent group A can be respectively used.

$R^{11a}$ is preferably a phenyl group having two substituents selected from an optionally substituted $C_{1-6}$ alkyl group, an optionally substituted $C_{1-6}$ alkoxy group and a halogen atom.

As the "optionally substituted methylene" represented by Ea, the aforementioned "optionally substituted alkylene group" exemplified for $E^2$, wherein the alkylene group is methylene, can be mentioned. Ea is more preferably a bond, an oxygen atom or methylene, and particularly preferably a bond.

The benzene ring represented by ring $S^{1a}$ may further have substituent(s) selected from an optionally substituted $C_{1-6}$ alkyl group, an optionally substituted $C_{1-6}$ alkoxy group and a halogen atom at substitutable position(s). Here, as the optionally substituted $C_{1-6}$ alkyl group, the optionally substituted $C_{1-6}$ alkoxy group and the halogen atom, those exemplified for the aforementioned substituent group A can be respectively used. Ring $S^{1a}$ is preferably a benzene ring without additional substituent.

$R^{16}$ and $R^{17}$ are the same or different and each is a hydrogen atom, a halogen atom (e.g., fluorine, chlorine, bromine, iodine), a $C_{1-6}$ alkyl group (e.g., methyl, ethyl, propyl), or a $C_{1-6}$ alkoxy group (e.g., methoxy, ethoxy, propoxy). Particularly, $R^{16}$ is preferably a hydrogen atom and $R^{17}$ is preferably a fluorine atom.

A compound (I-2A) wherein $R^{11a}$ is a phenyl group having two substituents selected from an optionally substituted $C_{1-6}$ alkyl group, an optionally substituted $C_{1-6}$ alkoxy group and a halogen atom; Ea is a bond, an oxygen atom or methylene; and $R^{16}$ and $R^{17}$ are the same or different and each is a hydrogen atom or a halogen atom is preferable. In this compound, Ea is preferably a bond; or $R^{16}$ is preferably a hydrogen atom and $R^{17}$ is preferably a fluorine atom.

A compound (I-2A) wherein the partial structural formula

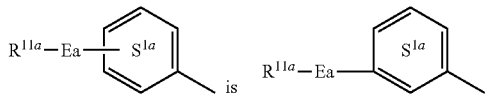

is wherein the symbols in the formula are as defined above, is preferable, and the compound wherein $R^{11a}$ is a phenyl group having two substituents selected from an optionally substituted $C_{1-6}$ alkyl group, an optionally substituted $C_{1-6}$ alkoxy group and a halogen atom; Ea is a bond; and ring $S^{1a}$ is a benzene ring without additional substituent is more preferable.

In compound (I-3), ring M is a benzene ring optionally having substituent(s). As the substituent that the benzene ring represented by ring M may have, a substituent selected from the aforementioned substituent group A can be used.

Ring N is a 5-membered heterocycle optionally having substituent(s).

As the 5-membered heterocycle represented by ring N, for example, a 5-membered heterocycle containing, besides carbon atom, 1 to 3 hetero atoms selected from a nitrogen atom, an oxygen atom and a sulfur atom, and the like can be used, and specifically, thiophene, furan, thiazole, oxazole, pyran, pyrrole, imidazole, pyrazole, isothiazole, isoxazole and the like can be used.

As the substituent that the 5-membered heterocycle represented by ring N may have, a substituent selected from the aforementioned substituent group A can be used. The number of the substituents is, for example, 1 to 3.

As the substituent for ring M or ring N, a halogen atom, an optionally substituted $C_{1-6}$ alkyl group (e.g., an optionally halogenated $C_{1-6}$ alkyl group), an optionally substituted $C_{1-6}$ alkoxy (e.g., a $C_{1-6}$ alkoxy optionally substituted by a $C_{1-6}$ alkoxy), a $C_{1-6}$ alkoxy-carbonyl, an optionally substituted $C_{7-16}$ aralkyloxy (e.g., a $C_{7-16}$ aralkyloxy optionally substituted by a $C_{1-6}$ alkyl) and the like are preferable, In compound (I-3), the partial structural formula

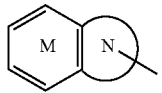

is preferably

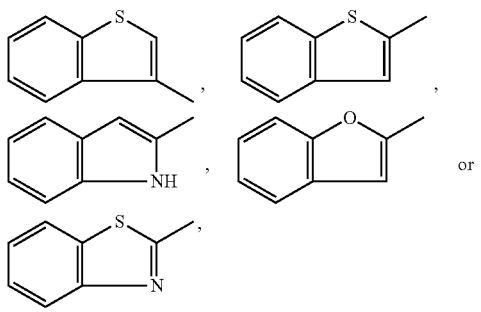

each optionally having substituent(s) selected from a halogen atom (e.g., chlorine atom), an optionally substituted $C_{1-6}$ alkyl group (e.g., an optionally halogenated $C_{1-6}$ alkyl group (e.g., methyl, trifluoromethyl)), an optionally substituted $C_{1-6}$ alkoxy (e.g., a $C_{1-6}$ alkoxy optionally substituted by a $C_{1-6}$ alkoxy (e.g., methoxymethoxy)), a $C_{1-6}$ alkoxy-carbonyl (e.g., tert-butoxycarbonyl) and an optionally substituted $C_{7-16}$ aralkyloxy (e.g., a $C_{7-16}$ aralkyloxy (e.g., benzyloxy) optionally substituted by a $C_{1-6}$ alkyl); and more preferably

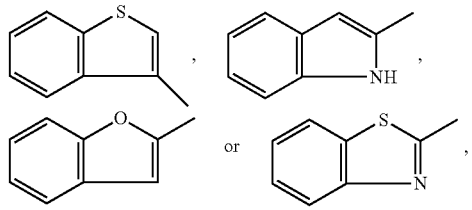

each optionally having substituent(s) selected from a halogen atom (e.g., chlorine atom) and an optionally substituted $C_{1-6}$ alkyl group (preferably an optionally halogenated $C_{1-6}$ alkyl group (e.g., methyl, trifluoromethyl)).

As ring E, an unsubstituted phenylene group is preferable.
As Ra, a hydrogen atom is preferable.

In compound (I-4), ring $S^2$ is a benzene ring further optionally having substituent(s), besides the substituent represented by the formula: $R^{13}$-$E^1$-(the symbols are as defined above).

As the substituent that ring $S^2$ may further have, a substituent selected from the aforementioned substituent group A can be used, but ring $S^2$ is preferably unsubstituted. That is, as ring $S^2$, a benzene ring is preferable.

$R^{13}$ is a thiazolyl group (preferably 2-thiazolyl group) optionally having substituent(s). As the substituent that the thiazolyl group may have, a substituent selected from the aforementioned substituent group A can be used, particularly, the aforementioned "optionally substituted $C_{6-14}$ aryl group" and the aforementioned "optionally substituted $C_{1-6}$ alkyl group" are preferable, and particularly (1) a $C_{6-14}$ aryl group (e.g., phenyl), (the $C_{6-14}$ aryl group may be partially saturated and as the partially saturated $C_{6-14}$ aryl group, for example, tetrahydronaphthyl and the like can be mentioned) optionally having 1 to 3 substituents selected from a halogen atom (e.g., fluorine, chlorine, bromine, iodine), an optionally halogenated $C_{1-6}$ alkyl group (e.g., methyl, trifluoromethyl), an optionally halogenated $C_{1-6}$ alkoxy group (e.g., methoxy, ethoxy), a $C_{3-8}$ cycloalkyl group (e.g., cyclohexyl) and the like; and (2) a $C_{1-6}$ alkyl group (e.g., a $C_{1-3}$ alkyl group such as methyl, ethyl, propyl, isopropyl and the like) optionally substituted by optionally esterified carboxyl (e.g., carboxyl) are preferable. The number of substituents is preferably 1 or 2.

The substituent of the thiazolyl group may form a ring together with a part of the thiazolyl group, and as such ring, for example, a $C_{3-10}$ cycloalkene (e.g., cyclopropene, cyclobutene, cyclopentene, cyclohexene) optionally condensed with a benzene ring and the like can be mentioned.

As $R^{13}$, a thiazolyl group (preferably, 2-thiazolyl group) optionally having 1 or 2 substituent(s) selected from (1) a $C_{6-14}$ aryl group (e.g., phenyl), (the $C_{6-14}$ aryl group is optionally partially saturated, and as the partially saturated $C_{6-14}$ aryl group, for example, tetrahydronaphthyl and the like can be mentioned) optionally having 1 to 3 substituent selected from a halogen atom (e.g., fluorine, chlorine, bromine, iodine), an optionally halogenated $C_{1-6}$ alkyl group (e.g., methyl, trifluoromethyl), an optionally halogenated $C_{1-6}$ alkoxy group (e.g., methoxy, ethoxy), a $C_{3-8}$ cycloalkyl group (e.g., cyclohexyl) and the like; and (2) a $C_{1-6}$ alkyl group (e.g., a $C_{1-3}$ alkyl group such as methyl, ethyl, propyl, isopropyl and the like) optionally substituted by optionally esterified carboxyl (e.g., carboxyl) is preferable; and a thiazolyl group (preferably, 2-thiazolyl group) optionally having 1 or 2 substituent(s) selected from a $C_{6-14}$ aryl (e.g., phenyl) and a $C_{1-6}$ alkyl (e.g., a $C_{1-3}$ alkyl such as methyl and the like) is more preferable. The substituent of the thiazolyl group may form a ring together with a part of the thiazolyl group, and as such ring, for example, a $C_{3-10}$ cycloalkene (e.g., cyclopropene, cyclobutene, cyclopentene, cyclohexene) optionally condensed with a benzene ring and the like can be mentioned.

As the spacer represented by $E^1$, those similar to the aforementioned spacer represented by E can be used.

As $E^1$, for example,
(i) a bond, or
(ii) a spacer represented by —$(CH_2)m^1$-$W^1$—$(CH_2)m^2$- ($m^1$, $m^2$ and $W^1$ are as defined above) is preferable, particularly,
(i) a bond,
(ii) a $C_{1-6}$ alkylene group,
(iii) —$N(R^{14})$—$(CH_2)m^2$- ($R^{14}$ is a hydrogen atom or a $C_{1-6}$ alkyl group and m is an integer of 0 to 3),
(iv) —S—$(CH_2)m^2$- ($m^2$ is an integer of 0 to 3) or the like is preferable, and particularly,
(i) —$N(R^{14})$—$(CH_2)m^2$- ($R^{14}$ is a hydrogen atom or a $C_{1-6}$ alkyl group and $m^2$ is an integer of 0 to 3),
(ii) —S—$(CH_2)m^2$- ($m^2$ is an integer of 0 to 3) or the like is preferable.

$R^{14}$ is a hydrogen atom or a $C_{1-6}$ alkyl group, and particularly, a $C_{1-6}$ alkyl group is preferable.

As the $C_{1-6}$ alkyl group represented by $R^{14}$, methyl, ethyl, propyl, isopropyl, butyl, isobutyl, sec-butyl, tert-butyl, pentyl, isopentyl, neopentyl and hexyl can be used, and particularly, a $C_{1-3}$ alkyl group such as methyl and the like are preferable.

As $m^2$, an integer of 1 to 3 is preferable, and 1 is particularly preferable.

As $E^1$, —$N(R^{14})$—$(CH_2)m^2$- or —S—$(CH_2)m^2$-($R^{14}$ is a hydrogen atom or a $C_{1-6}$ alkyl group and $m^2$ is an integer of 0 to 3) is preferable, particularly, $N(R^{14})$—$(CH_2)m^2$- is preferable.

As Ra, a hydrogen atom, a halogen atom (e.g., fluorine, chlorine, bromine, iodine), a $C_{1-6}$ alkyl group (e.g., methyl, ethyl, propyl) or a $C_{1-6}$ alkoxy group (e.g., methoxy, ethoxy, propoxy) is preferable; a hydrogen atom or a halogen atom (preferably fluorine) are more preferable.

The compound (I-4) is preferably a compound represented by the formula

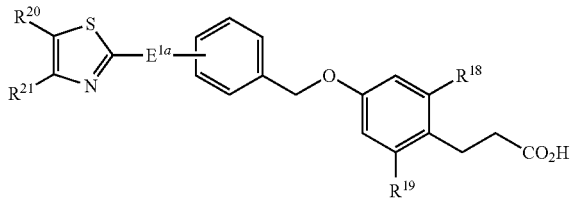

(I-4A)

wherein $E^{1a}$ is —$N(R^{14})$—$CH_2$—, —$CH(R^{22})$—O— or —$CH(R^{22})$—$CH_2$— ($R^{14}$ and $R^{22}$ are a hydrogen atom or a $C_{1-6}$ alkyl group), $R^{18}$ and $R^{19}$ are the same or different and each is a hydrogen atom, a halogen atom, a $C_{1-6}$ alkyl group or a $C_{1-6}$ alkoxy group, and $R^{20}$ and $R^{21}$ are the same or different and each is a hydrogen atom, an optionally substituted $C_{6-14}$ aryl group or an optionally substituted $C_{1-6}$ alkyl group, or $R^{20}$ and $R^{21}$ are bonded to form a ring).

As the $C_{1-6}$ alkyl group represented by $R^{22}$, those exemplified for the aforementioned $R^{14}$ can be mentioned.

$R^{18}$ and $R^{19}$ are the same or different and each is a hydrogen atom, a halogen atom (e.g., fluorine, chlorine, bromine, iodine), a $C_{1-6}$ alkyl group (e.g., methyl, ethyl, propyl) or a $C_{1-6}$ alkoxy group (e.g., methoxy, ethoxy, propoxy). Particularly, a compound wherein $R^{18}$ and $R^{19}$ are the same or different and each is a hydrogen atom or a halogen atom (preferably fluorine) is preferable.

As the "optionally substituted $C_{6-14}$ aryl group" and "optionally substituted $C_{1-6}$ alkyl group" represented by $R^{20}$ or $R^{21}$, those exemplified for the aforementioned substituent group A can be respectively used.

The "optionally substituted a $C_{6-14}$ aryl group" is preferably a $C_{6-14}$ aryl group (e.g., phenyl) optionally having 1 to 3 substituents selected from a halogen atom (e.g., fluorine, chlorine, bromine, iodine), an optionally halogenated $C_{1-6}$ alkyl group (e.g., methyl, trifluoromethyl), an optionally halogenated $C_{1-6}$ alkoxy group (e.g., methoxy, ethoxy), a $C_{3-8}$ cycloalkyl group (e.g., cyclohexyl) and the like. The $C_{6-14}$ aryl group is optionally partially saturated and as the partially saturated $C_{6-14}$ aryl group, for example, tetrahydronaphthyl and the like can be mentioned.

The "optionally substituted $C_{1-6}$ alkyl group" is preferably a $C_{1-6}$ alkyl group optionally substituted by an optionally esterified carboxyl (e.g., carboxyl), (e.g., methyl, carboxylmethyl, ethyl, propyl, isopropyl) and the like.

As the ring formed by $R^{20}$ and $R^{21}$ in junction is, for example, a $C_{3-10}$ cycloalkene (e.g., cyclopropene, cyclobutene, cyclopentene, cyclohexene) optionally condensed with a benzene ring and the like can be mentioned.

$E^{1a}$ is preferably —$N(R^{14})$—$CH_2$— ($R^{14}$ is as defined above). Further, $R^{18}$ and $R^{19}$ are preferably the same or different and each is a hydrogen atom or a halogen atom (preferably fluorine).

Specific examples of preferable compounds used in the present invention are shown in the following.

(R)-4-[(2,3-dihydro-1H-inden-1-yl)oxy]benzenepropanoic acid (Example 41);

4-[[3-[(2,3-dihydro-1H-inden-1-yl)oxy]phenyl]methoxy] benzenepropanoic acid (Example 136);

3-[4-[(2',6'-dimethylbiphenyl-3-yl)methoxy]-2-fluorophenyl]propionic acid (Example 205);

3-[4-[[4-[[4,5-dihydronaphtho[1,2-d][1,3]thiazol-2-yl(propyl)amino]methyl]benzyl]oxy]phenyl]propionic acid (Example 223);

3-[4-[[4-(2,6-dimethylbenzyl)benzyl]oxy]phenyl]propanoic acid (Example 253);

3-{4-[(4-{[isopropyl(4-phenyl-1,3-thiazol-2-yl)amino] methyl}benzyl)oxy]phenyl}propanoic acid (Example 259);

3-(4-((4-(((2-phenoxypropyl)amino)methyl)benzyl)oxy) phenyl)propanoic acid (Example 312);

3-(4-((4-((dibenzylamino)methyl)benzyl)oxy)phenyl)propanoic acid (Example 330);

3-(4-((4-(((2-imidazo[1,5-a]pyridin-3-ylethyl)(phenyl)amino)methyl)benzyl)oxy)phenyl)propanoic acid (Example 334);

3-(2-(4-((3-phenoxybenzyl)oxy)phenyl)ethyl)-1,2,4-oxadiazol-5(4H)-one (Reference Example 213).

Further, as the compound used in the present invention, the compounds described in JP-A-2002-265457, JP-A-2002-212171, JP-A-2001-226350, JP-A-2001-199971, JP-A-2000-198772, JP-A-2000-80086, JP-A-2000-34266, JP-A-09-323983, JP-A-08-311065 and the like can be also used.

As a salt of a compound used in the present invention, for example, metal salts, ammonium salts, salts with organic bases, salts with inorganic acids, salts with organic acids, salts with basic or acidic amino acids and the like. Preferable examples of the metal salt include alkali metal salts such as sodium salt, potassium salt and the like; alkaline earth metal salts such as calcium salt, magnesium salt, barium salt and the like; aluminum salt, and the like. Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include a salt with hydrochloric acid, hydrobromic acid, nitric acid, sulfuric acid, phosphoric acid and the like. Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include a salt with arginine, lysin, ornithine and the like. Preferable examples of the salt with acidic amino acid include a salt with aspartic acid, glutamic acid and the like.

Of these, a pharmacologically acceptable salt is preferable. For example, when the compound has an acidic functional group, inorganic salts such as alkali metal salts (e.g., sodium salt, potassium salt etc.), alkaline earth metal salts (e.g., calcium salt, magnesium salt, barium salt etc.) and the like, ammonium salt and the like are preferable, and when the compound has basic functional group, salts with inorganic acid such as hydrochloric acid, hydrobromic acid, nitric acid, sulfuric acid, phosphoric acid and the like; or salts with organic acid such as acetic acid, phthalic acid, fumaric acid, oxalic acid, tartaric acid, maleic acid, citric acid, succinic acid, methanesulfonic acid, p-toluenesulfonic acid and the like are preferable.

A prodrug of the compounds (I'), (I), compound (I-1), compound (I-2), compound (I-2A), compound (I-3), compound (I-4), compound (I-4A), compound (Ia), compound (Ib), compound (II), compound (IIa), compound (IIb), compound (III), compound (IV), compound (IVa), compound (IVb), compound (A), compound (B), compound (C), compound (D) and a salt thereof of the present invention (hereinafter sometimes to be abbreviated as compound (I) of the present invention) is a compound that converts to compound (I) of the present invention due to the reaction by enzyme, gastric acid and the like under the physiological conditions in the body; that is, a compound that converts to compound (I) of the present invention by enzymatic oxidation, reduction, hydrolysis and the like, and a compound that converts to compound (I) of the present invention by hydrolysis and the like by gastric acid and the like.

Examples of a prodrug of compound (I) of the present invention include a compound wherein an amino group of compound (I) of the present invention is acylated, alkylated or phosphorylated (e.g., compound where amino group of compound (I) of the present invention is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated and the like); a compound wherein a hydroxy group of compound (I) of the present invention is acylated, alkylated, phosphorylated or borated (e.g., a compound where a hydroxy group of compound (I) of the present invention is acetylated, palmitoylated, propanoylated, pivaloylated, succinylated, fumarylated, alanylated, dimethylaminomethylcarbonylated and the like); a compound wherein a carboxyl group of compound (I) of the present invention is esterified or amidated (e.g., a compound where a carboxyl group of compound (I) of the present invention is ethyl esterified, phenyl esterified, carboxymethyl esterified, dimethylaminomethyl esterified, pivaloyloxymethyl esterified, ethoxycarbonyloxyethyl esterified, phthalizyl esterified, (5-methyl-2-oxo-1,3-dioxolen-4-yl)methyl esterified, cyclohexyloxycarbonylethyl esterified, methylamidated and the like) and the like. Of these, a compound wherein a carboxyl group of compound (I) of the present invention is esterified by a $C_{1-6}$ alkyl group such as methyl, ethyl, tert-butyl and the like can be preferably used. These compounds can be produced from compound (I) of the present invention by a method known per se.

A prodrug of compound (I) of the present invention may be a compound that converts to compound (I) of the present invention under physiological conditions as described in IYAKUHIN NO KAIHATSU, vol. 7, BUNSHI SEKKEI, 163-198, Hirokawa Shoten (1990).

Hereinafter the production methods of the compound or a salt thereof of the present invention are explained.

The production methods of compound (I-1), compound (I-2), compound (I-3) and compound (I-4) of the present invention are described in the following.

The compound (I-2A) and compound (I-4A) of the present invention can be produced in the same manner as compound (I-2) and compound (I-4), respectively.

Each symbol of the compounds in the schematic drawings of the following reaction schemes is as defined above unless otherwise specified. The compound in the reaction schemes include salts, and as such salts, for example, those similar to the salts of the above-mentioned compounds to be used in the present invention and the like can be mentioned.

The resulting products can be used for the next reaction in the form of a reaction mixture or as a crude product. They can also be isolated from the reaction mixture by conventional methods, and can be easily purified by separation means such as recrystallization, distillation, chromatography and the like.

The compound (I-1) of the present invention can be produced by, for example, by the method shown in the following Reaction Scheme 1 or a method analogous thereto.

For compounds (V), (VI), (VII) and (VIII), commercially available ones can be easily obtained, or they can be also produced by a method known per se or a method analogous thereto.

Reaction Scheme 1

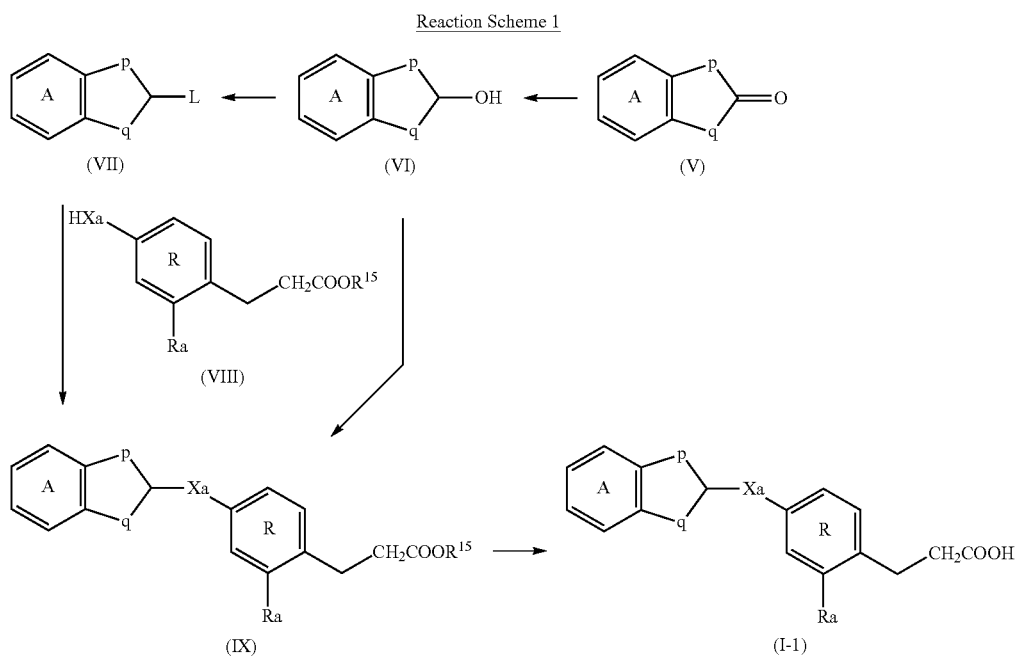

The compound (VI) can be produced by reducing the carbonyl group of compound (V).

As a reducing agent to be used for the reduction, for example, metal hydrides such as aluminum hydride, diisobutylaluminum hydride, tributyltin hydride and the like, metal hydride complex compounds such as lithium aluminum hydride, sodium borohydride and the like, borane complexes such as a borane tetrahydrofuran complex, a borane dimethyl sulfide complex and the like, alkylboranes such as thexylborane, disiamylborane and the like, metals such as diborane, zinc, aluminum, tin, iron and the like, alkali metal (e.g., sodium, lithium and the like)/liquid ammonia (Birch reduction) and the like can be mentioned. The amount of the reducing agent to be used is, for example, about 1 to about 10 mol, preferably about 1 to about 5 mol, per 1 mol of compound (V) in the case of metal hydrides or metal hydride complex compounds, about 1 to about 10 mol, preferably about 1 to about 5 mol, per 1 mol of compound (V) in the case of borane complexes, alkylboranes or diborane, and about 1 to about 20 equivalent, preferably about 1 to about 5 equivalent in the case of metals. In this reaction, a Lewis acid may be used when desired. As the "Lewis acid", for example, aluminum chloride, aluminum bromide, titanium (IV) chloride, tin (II) chloride, zinc chloride, boron trichloride, boron tribromide, boron trifluoride and the like can be used. The amount of the Lewis acid to be used is about 1 to about 10 mol, preferably about 1 to about 5 mol, per 1 mol of compound (V).

In addition, reduction can be performed by hydrogenation reaction, and in this case, for example, catalysts such as palladium carbon, platinum oxide (IV), Raney-nickel, Raney-cobalt and the like, and the like can be used. The amount of the catalyst to be used is about 5 to about 1000 wt %, preferably about 10 to about 300 wt %, per 1 mol of compound (V). Various hydrogen sources can be also used instead of the gaseous hydrogen. As the "hydrogen sources", formic acid, ammonium formate, triethylammonium formate, sodium phosphinate, hydrazine and the like can be used. The amount of the hydrogen sources to be used is about 1 to about 10 mol, preferably about 1 to about 5 mol, per 1 mol of compound (V).

This reaction is advantageously carried out in a solvent inert to the reaction. Such solvent is not particularly limited as long as the reaction proceeds, but a solvent, for example, alcohols such as methanol, ethanol, 1-propanol, 2-propanol, tert-butyl alcohol and the like, ethers such as diethyl ether, diisopropy ether, diphenyl ether, tetrahydrofuran, 1,4-dioxane, 1,2-dimethoxyethane and the like, hydrocarbons such as benzene, toluene, cyclohexane, hexane and the like, amides such as N,N-dimethylformamide, N,N-dimethylacetamide, hexamethylphosphoric triamide and the like, organic acids such as formic acid, acetic acid, propionic acid, trifluoroacetic acid, methanesulfonic acid and the like, and the like, a mixed solvent thereof and the like are preferable.

While the reaction time varies depending on the kind and amount of the reducing agent to be used or activity and amount of catalyst, it is generally about 1 hr to about 100 hr, preferably about 1 hr to about 50 hr. The reaction temperature is generally about −20 to about 120° C., preferably about 0 to about 80° C. When a hydrogenating catalyst is used, the pressure of hydrogen is generally about 1 to about 100 atm.

The compound (VII) wherein L is a leaving group can be produced by converting the hydroxy group of compound (VI) to a "leaving group".

As the "leaving group" represented by L, for example, a halogen atom such as fluorine, chlorine, bromine, iodine and the like, an optionally halogenated $C_{1-6}$ alkylsulfonyloxy group such as methanesulfonyloxy, ethanesulfonyloxy, trichloromethanesulfonyloxy and the like, a $C_{6-10}$ arylsulfonyloxy group optionally having substituent(s) and the like can be mentioned. As the "$C_{6-10}$ arylsulfonyloxy group optionally having substituent(s)", for example, a $C_{6-10}$ arylsulfonyloxy group (e.g., phenylsulfonyloxy, naphthylsulfonyloxy and the like) optionally having 1 to 3 substituent selected from a $C_{1-6}$ alkyl group (e.g., methyl, ethyl and the like), a $C_{1-6}$ alkoxy group (e.g., methoxy, ethoxy and the like) and nitro, and the like can be mentioned, and specific examples include phenylsulfonyloxy, m-nitrophenylsulfonyloxy, p-toluenesulfonyloxy and the like can be mentioned.

When the "leaving group" represented by L is a halogen atom, as a halogenating agent to be used for halogenation, for example, thionyl halides such as thionyl chloride, thionyl bromide and the like, phosphoryl halides such as phosphoryl chloride, phosphoryl bromide and the like, phosphorus halides such as phosphorus pentachloride, phosphorus trichloride, phosphorous pentabromide, phosphorus tribromide and the like, oxalyl halides such as oxalyl chloride and the like, phosgene and the like can be mentioned. A halogenating agent is used in a proportion of about 0.1 to about 30 mol, preferably about 0.2 to about 10 mol, more preferably about 1 to about 10 mol, per 1 mol of compound (VI).

When desired, this reaction is carried out in the presence of a base. As the "base", tertiary amines such as triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-methylmorpholine and the like, and the like can be mentioned, which is used in about 1 to about 20 mol, preferably about 1 to about 10 mol, per 1 mol of compound (VI).

This reaction is advantageously carried out without solvent or in a solvent inert to the reaction. Such solvent is not particularly limited as long as the reaction proceeds, but a solvent, for example, hydrocarbons such as benzene, toluene, cyclohexane, hexane and the like, ethers such as diethyl ether, diisopropy ether, diphenyl ether, tetrahydrofuran, 1,4-dioxane, 1,2-dimethoxyethane and the like, amides such as N,N-dimethylformamide, N,N-dimethylacetamide, hexamethylphosphoric triamide and the like, halogenated hydrocarbons such as dichloromethane, chloroform, carbon tetrachloride, 1,2-dichloroethane and the like, and the like, a mixed solvent thereof and the like are preferable.

The reaction time is generally about 10 min to about 12 hr, preferably about 10 min to about 5 hr. The reaction temperature is generally about −10 to about 200° C., preferably about −10 to about 120° C.

When the "leaving group" represented by L is an optionally halogenated $C_{1-6}$ alkylsulfonyloxy group or a $C_{6-10}$ arylsulfonyloxy group optionally having substituent(s), as the sulfonylating agent, for example, halogenated $C_{1-6}$ alkylsulfonyl (e.g., methanesulfonyl chloride and the like), halogenated $C_{6-10}$ arylsulfonyl (e.g., benzenesulfonyl chloride, p-toluenesulfonyl chloride and the like), and the like can be mentioned. The sulfonylating agent is used in about 1 to about 20 mol, preferably about 1 to about 10 mol, per 1 mol of compound (VI).

This reaction is advantageously carried out without solvent or in a solvent inert to the reaction. Such solvent is not particularly limited as long as the reaction proceeds, but a solvent, for example, hydrocarbons such as benzene, toluene, cyclohexane, hexane and the like, ethers such as diethyl ether, diisopropy ether, diphenyl ether, tetrahydrofuran, 1,4-dioxane, 1,2-dimethoxyethane and the like, halogenated hydrocarbons such as dichloromethane, chloroform, carbon tetrachloride, 1,2-dichloroethane and the like, esters such as methyl acetate, ethyl acetate, butyl acetate and the like, and the like, a mixed solvent thereof and the like are preferable.

This reaction is carried out in the presence of a base when desired. As the "base", tertiary amines such as triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-methylmorpholine and the like, inorganic bases such as sodium hydroxide, potassium hydroxide, lithium hydroxide, barium hydroxide and the like, basic salts such as sodium carbonate, potassium carbonate, cesium carbonate, sodium hydrogencarbonate, sodium acetate, ammonium acetate and the like, and the like can be mentioned. The base is used in about 1 to about 20 mol, preferably about 1 to about 10 mol, per 1 mol of compound (VI).

The reaction time is generally about 10 min to about 12 hr, preferably about 10 min to about 5 hr. The reaction temperature is generally about −30 to about 150° C., preferably about −20 to about 100° C.

The compound (IX) wherein $R^{15}$ is a hydrocarbon group optionally having substituent(s) and Xa is an oxygen atom or a sulfur atom, can be produced by condensing compound (VII) with compound (VIII) in the presence of a base.

As the "hydrocarbon group optionally having substituent(s)" represented by $R^{15}$, "optionally substituted lower($C_{1-6}$) alkyl", "optionally substituted lower($C_{2-6}$) alkenyl", "optionally substituted lower($C_{2-6}$) alkynyl", "optionally substituted lower($C_{2-6}$) alkynyl", "optionally substituted $C_{3-8}$ cycloalkyl", "optionally substituted $C_{6-14}$ aryl", "optionally substituted $C_{7-16}$ aralkyl" and the like of the above-mentioned substituent group A are preferable.

As the substituent that the "hydrocarbon group" of the "hydrocarbon group optionally having substituent(s)" represented by $R^{15}$ may have, the above-mentioned substituent group A and the like are preferable. The "hydrocarbon group" of the "hydrocarbon group optionally having substituent(s)" represented by $R^{13}$ may have 1 to 5, preferably 1 to 3 substituents mentioned above at substitutable position(s) of the hydrocarbon group. When the number of substituents is not less than 2, respective substituents may be the same or different.

As the base to be used for this reaction, inorganic bases such as sodium hydroxide, potassium hydroxide, lithium hydroxide, barium hydroxide and the like, basic salts such as sodium carbonate, potassium carbonate, cesium carbonate, sodium hydrogencarbonate, sodium acetate, ammonium acetate and the like, aromatic amines such as pyridine, lutidine and the like, tertiary amines such as triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, sodium tert-butoxide, potassium tert-butoxide and the like, and the like can be mentioned. These bases are used in about 1-10 mol, preferably about 1-3 mol, per 1 mol of compound (IX).

This reaction is advantageously carried out using a solvent inert to the reaction. Such solvent is not particularly limited as long as the reaction proceeds, but a solvent, for example, alcohols such as methanol, ethanol, 1-propanol, 2-propanol, tert-butyl alcohol and the like, ethers such as diethyl ether, diisopropy ether, diphenyl ether, tetrahydrofuran, 1,4-dioxane, 1,2-dimethoxyethane and the like, hydrocarbons such as benzene, toluene, cyclohexane, hexane and the like, amides such as N,N-dimethylformamide, N,N-dimethylacetamide, hexamethylphosphoric triamide and the like, halogenated hydrocarbons such as dichloromethane, chloroform, carbon tetrachloride, 1,2-dichloroethane and the like, nitriles such as acetonitrile, propionitrile and the like, esters such as methyl acetate, ethyl acetate, butyl acetate and the like, sulfoxides such as dimethyl sulfoxide and the like, water and the like, mixed solvent thereof and the like are preferable.

The reaction time is generally about 10 min to about 12 hr, preferably about 20 min to about 6 hr. The reaction temperature is generally about −50 to about 150° C., preferably about −20 to about 100° C.

The compound (IX) wherein Xa is an oxygen atom or a sulfur atom can be also produced by condensing compound (VI) with compound (VIII) in the presence of a dehydrating agent when desired.

As the dehydrating agent usable for this reaction, for example, acidic catalysts such as hydrochloric acid, sulfuric acid, phosphoric acid, potassium hydrosensulfate, oxalic acid, p-toluenesulfonic acid, 10-camphorsulfonic acid, borone trifluoride ether complex and the like, basic catalysts such as sodium hydroxide, potassium hydroxide and the like, and the like can be mentioned, further, for example, carbodiimides such as N,N'-dicyclohexylcarbodiimide and the like, alumina, sodium dioxide, phosphorus oxychloride, thionyl chloride, methanesulfonylchloride and the like may be used. These acid and base are used in about 0.1-10 mol, preferably about 0.1-5.0 mol, per 1 mol of compound (VIII).

This reaction is advantageously carried out without solvent or in a solvent inert to the reaction. While the solvent is not particularly limited as long as the reaction proceeds, a solvent, for example, alcohols such as methanol, ethanol, propanol and the like, ethers such as diethyl ether, tetrahydrofuran, dioxane, 1,2-dimethoxyethane and the like, organic acids such as formic acid, acetic acid and the like, hydrocarbons such as benzene, toluene, cyclohexane, hexane and the like, amides such as N,N-dimethylformamide, N,N-dimethylacetamide and the like, sulfoxides such as dimethyl sulfoxide and the like, and the like, a mixed solvent thereof and the like are preferable.

The reaction time is generally 30 min-24 hr, preferably 30 min-5 hr. The reaction temperature is generally 0-200° C., preferably 0-150° C.

The compound (IX) wherein Xa is an oxygen atom can be also produced by condensing compound (VI) with compound (VIII) by Mitsunobu reaction (*Synthesis*, 1981, 1-27).

For this reaction, compound (VIII) is reacted with compound (VI) in the presence of azodicarboxylates such as diethyl azodicarboxylate, diisopropyl azodicarboxylate, 1,1'-(azodicarbonyl)dipiperidine and the like, and the like and phosphines such as triphenylphosphine, tributylphosphine and the like.

The amount of compound (VI) to be used is about 1 to about 5 mol, preferably about 1 to about 2 mol, relative to 1 mol of compound (VIII).

The amount of the "azodicarboxylates" and "phosphines" to be used is about 1 to about 5 mol, preferably about 1 to about 2 mol, relative to 1 mol of compound (VIII), respectively.

This reaction is advantageously carried out using a solvent inert to the reaction. Such solvent is not particularly limited as long as the reaction proceeds, but a solvent, for example, ethers such as diethyl ether, diisopropy ether, diphenyl ether, tetrahydrofuran, 1,4-dioxane, 1,2-dimethoxyethane and the like, hydrocarbons such as benzene, toluene, cyclohexane, hexane and the like, amides such as N,N-dimethylformamide, N,N-dimethylacetamide, hexamethylphosphoric triamide and the like, halogenated hydrocarbons such as dichloromethane, chloroform, carbon tetrachloride, 1,2-dichloroethane and the like, nitriles such as acetonitrile, propionitrile and the like, ketones such as acetone, ethyl methyl ketone and the like, sulfoxides such as dimethyl sulfoxide and the like, and the like, a mixed solvent thereof and the like are preferable.

The reaction time is generally about 5 min to about 48 hr, preferably about 10 min to about 24 hr. The reaction temperature is generally about −20 to about 200° C., preferably about 0 to about 100° C.

The compound (I-1) is produced by hydrolyzing the ester group of compound (IX) using an acid or a base. For acid hydrolysis, mineral acids such as hydrochloric acid, sulfuric acid and the like, Lewis acids such as boron trichloride, boron tribromide and the like, Lewis acid and thiol or sulfide in combination, organic acids such as trifluoroacetic acid, p-toluenesulfonic acid and the like can be generally used. For alkaline hydrolysis, inorganic bases such as sodium hydroxide, potassium hydroxide, barium hydroxide and the like, basic salts such as sodium carbonate, potassium carbonate and the like, metal alkoxides such as sodium methoxide, sodium ethoxide, potassium tert-butoxide and the like, organic bases such as triethylamine, imidazole, formamidine and the like, and the like can be used. These acid and base are used in about 0.5-10 mol, preferably about 0.5-6 mol, per 1 mol of compound (IX).

This reaction is advantageously carried out without solvent or in a solvent inert to the reaction. Such solvent is not particularly limited as long as the reaction proceeds, but a solvent, for example, alcohols such as methanol, ethanol, propanol and the like, aromatic hydrocarbons such as benzene, toluene and the like, saturated hydrocarbons such as cyclohexane, hexane and the like, organic acids such as formic acid, acetic acid and the like, ethers such as tetrahydrofuran, dioxane, 1,2-dimethoxyethane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, ketones such as acetone, methyl ethyl ketone and the like, sulfoxides such as dimethyl sulfoxide and the like, water and the like, a mixed solvent thereof and the like are preferable.

The reaction time is generally 10 min-60 hr, preferably 10 min-12 hr. The reaction temperature is generally −10-200° C., preferably 0-120° C.

The compound (I-2) of the present invention can be produced by, for example, the method represented by the following Reaction Scheme 2 or a method analogous thereto.

Reaction Scheme 2

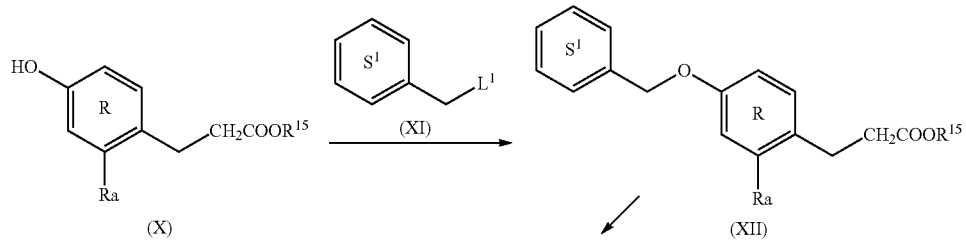

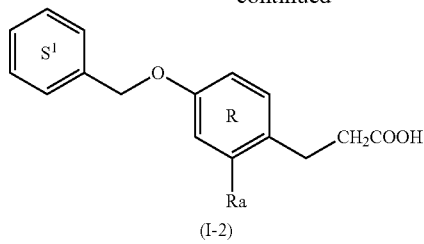

(I-2)

For compounds (X) and (XI), commercially available ones can be easily obtained, or they can be also produced by a method known per se or a method analogous thereto.

The compound (XII) can be produced by condensing compound (X) with compound (XI) wherein $L^1$ is a leaving group.

As the "leaving group" represented by $L^1$, those similar to the aforementioned "leaving group" represented by L, a hydroxy group and the like can be mentioned.

When the "leaving group" represented by $L^1$ is a hydroxy group, compound (XII) can be produced from compound (X) and compound (XI) by a method similar to the method of producing compound (IX) from compound (VI).

When the "leaving group" represented by $L^1$ is a halogen atom, an optionally halogenated $C_{1-6}$ alkylsulfonyloxy group or a $C_{6-10}$ arylsulfonyloxy group optionally having substituent(s), compound (XII) can be produced from compound (X) and compound (XI) by a method similar to the method of producing compound (IX) from compound (VII).

The compound (I-2) can be produced from compound (XII) by a method similar to the method of producing compound (I-1) from compound (IX).

The compound (I-2) of the present invention can be also produced by, for example, the method represented by the following Reaction Scheme 3 or a method analogous thereto.

(wherein M is a metal and $B^2$ is a benzene ring optionally further having substituent(s) besides M or an aromatic ring further having, besides M, substituent(s) having a benzene ring).

As the "benzene ring optionally having substituent(s)" represented by $B^1$ or $B^2$, those similar to ring A and the like can be mentioned. As the "metal" represented by M, potassium, sodium, lithium, magnesium, mercury, zinc, thallium, tin, boron and the like can be mentioned. They may be in the form of complex.

As the substituent that the "benzene ring optionally having substituent(s)" represented by $B^1$ and $B^2$ may have, a substituent selected from the above-mentioned substituent group A and the like can be mentioned.

This reaction is advantageously carried out in the presence of a catalyst when desired. As the "catalyst", nickel complex, palladium complex, copper and the like can be mentioned. The catalyst is used in about 0.005 to about 2 mol, preferably about 0.01 to about 1 mol, per 1 mol of compound (XIII).

This reaction is advantageously carried out using a solvent inert to the reaction. Such solvent is not particularly limited as long as the reaction proceeds, but a solvent, for example, hydrocarbons such as benzene, toluene, cyclohexane, hexane

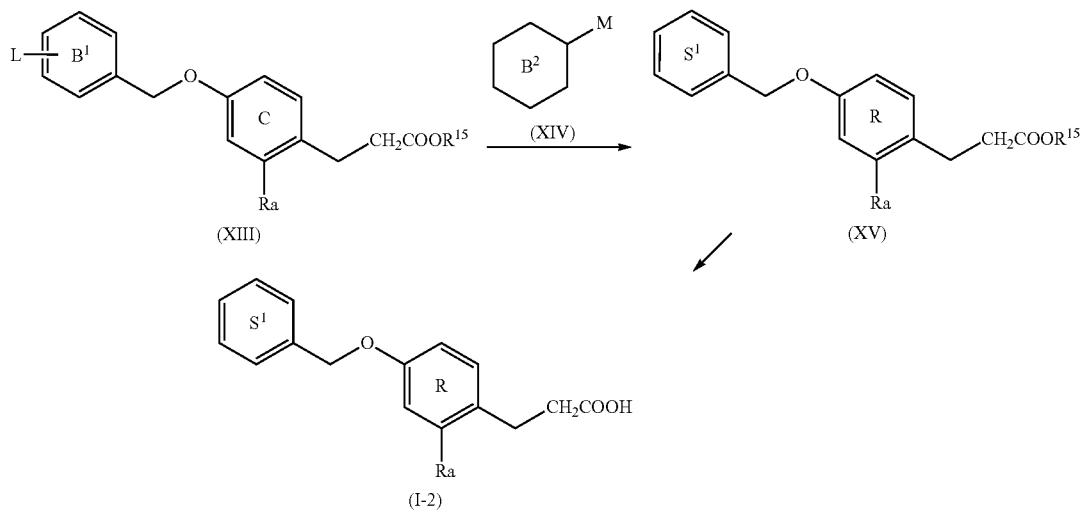

Reaction Scheme 3

For compounds (XIII) and (XIV), commercially available ones can be easily obtained, or they can be also produced by a method known per se or a method analogous thereto.

The compound (XV) can be produced by condensing compound (XIII) (wherein $B^1$ is a benzene ring optionally further having substituent(s) besides L) with compound (XIV)

and the like, ethers such as diethyl ether, diisopropy ether, diphenyl ether, tetrahydrofuran, 1,4-dioxane, 1,2-dimethoxyethane and the like, halogenated hydrocarbons such as dichloromethane, chloroform, carbon tetrachloride, 1,2-dichloroethane and the like, and the like, a mixed solvent thereof and the like are preferable.

The reaction time is generally about 10 min to about 48 hr, preferably about 10 min to about 24 hr. The reaction temperature is generally about −80 to about 250° C., preferably about −20 to about 150° C.

The compound (I-2) can be also produced from compound (XV) by a method similar to the method of producing compound (I-1) from compound (IX).

The compound (I-3) of the present invention can be produced by, for example, the method represented by the following Reaction Scheme 4 or a method analogous thereto.

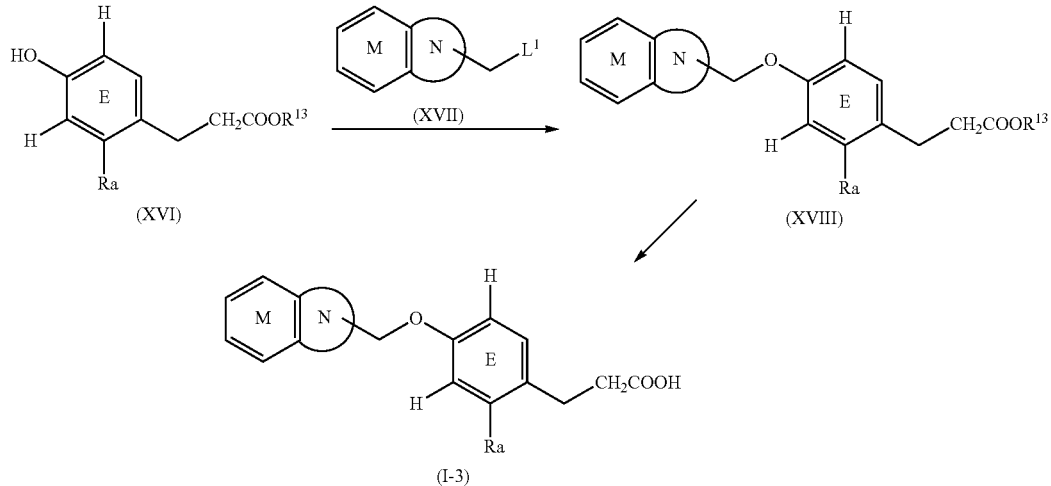

Reaction Scheme 4

For compounds (XVI) and (XVII), commercially available ones can be easily obtained, or they can be also produced by a method known per se or a method analogous thereto.

The compound (XVIII) can be produced by condensing compound (XVI) with compound (XVII) by a method similar to that of producing compound (XII) from compound (X) and compound (XI).

The compound (I-3) can be produced from compound (XVIII) by a method similar to the method of producing compound (I-1) from compound (IX).

The compound (I-4) of the present invention can be produced by, for example, the method represented by the following Reaction Scheme 5 or a method analogous thereto.

Reaction Scheme 5

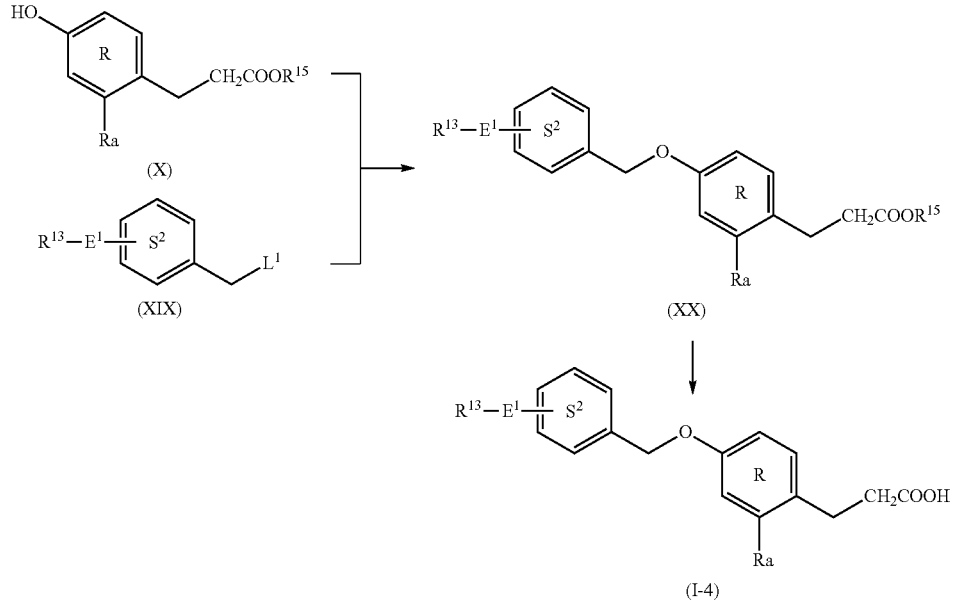

For compounds (X) and (XIX), commercially available ones can be easily obtained, or they can be also produced by a method known per se or a method analogous thereto.

The compound (XX) can be produced by condensing compound (X) with compound (XIX) by a method similar to that of producing compound (XII) from compound (X) and compound (XI).

The compound (I-4) can be produced from compound (XX) by a method similar to the method of producing compound (I-1) from compound (IX).

Of the compounds (I-4) of the present invention, a compound wherein $E^1$ is —N($R^{14}$)—($CH_2$)$m^2$- can be also produced by, for example, the method represented by the following Reaction Scheme 6 or a method analogous thereto.

Reaction Scheme 6

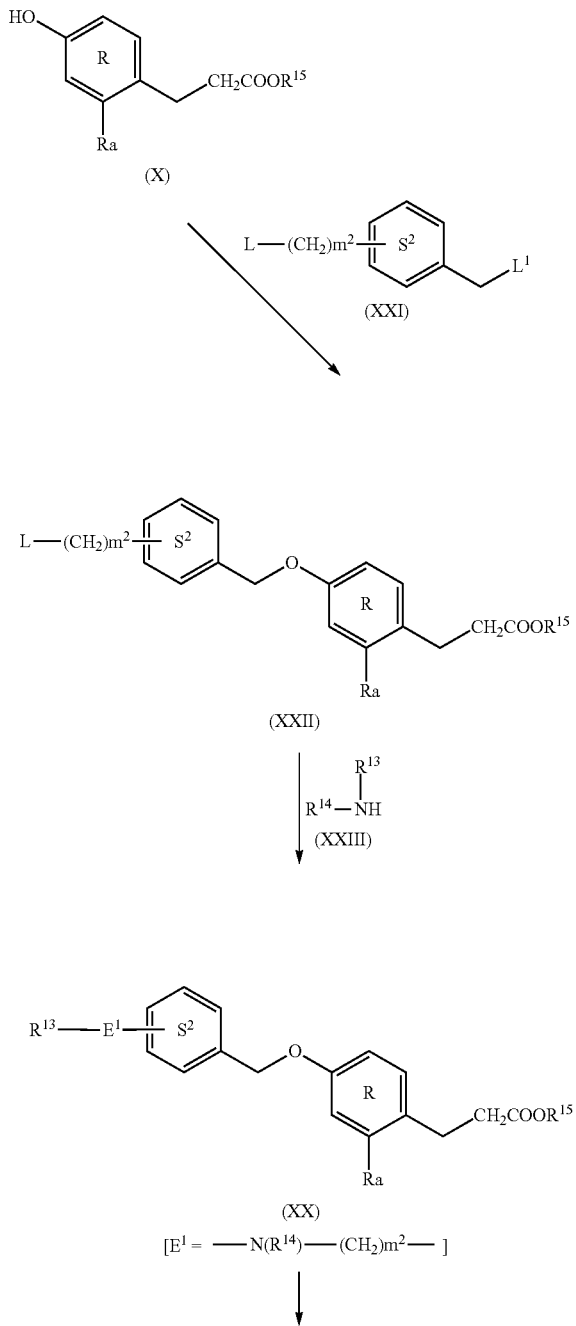

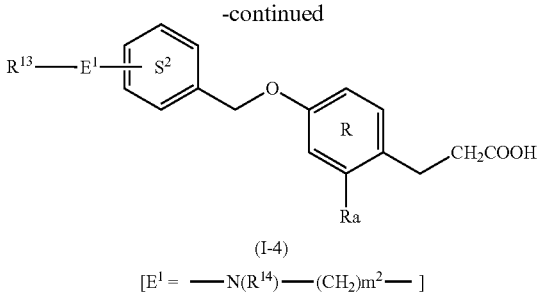

For compounds (X), (XXI) and (XXIII), commercially available ones can be easily obtained, or they can be also produced by a method known per se or a method analogous thereto.

The compound (XXII) can be produced by condensing compound (X) with compound (XXI) by a method similar to that of producing compound (XII) from compound (X) and compound (XI). In addition, the compound can be also produced from compound (X) by multi-step reactions including protection of functional group and deprotection thereof.

Of the compounds (XX), a compound wherein $E^1$ is —N($R^{14}$)—($CH_2$)$m^2$- can be also produced from compound (XXII) and compound (XXIII) by a method similar to that of producing compound (IX) from compound (VII) and compound (VIII).

Of the compounds (I-4), a compound wherein $E^1$ is —N($R^{14}$)—($CH_2$)$m^2$- can be also produced from compound (XX) wherein $E^1$ is —N($R^{14}$)—($CH_2$)$m^2$- by a method similar to the method of producing compound (I-1) from compound (IX).

In each of the aforementioned reactions, when the starting compound has amino group, a carboxyl group or hydroxy group as a substituent, a protecting group generally used in peptide chemistry and the like may be introduced into these groups. By removing the protecting group as necessary after the reaction, the objective compound can be obtained.

As the amino-protecting group, for example, formyl, or $C_{1-6}$ alkyl-carbonyl (e.g., acetyl, propionyl and the like), benzoyl, $C_{1-6}$ alkoxy-carbonyl (e.g., methoxycarbonyl, ethoxycarbonyl and the like), phenyloxycarbonyl, $C_{7-10}$ aralkyloxy-carbonyl (e.g., benzyloxycarbonyl and the like), trityl or phthaloyl, each of which optionally has substituent(s), can be mentioned. As the substituent, a halogen atom (e.g., fluorine, chlorine, bromine, iodine and the like), $C_{1-6}$ alkyl-carbonyl (e.g., acetyl, propionyl, valeryl and the like), nitro and the like can be used. The number of the substituent is about 1 to 3.

As the carboxy-protecting group, for example, $C_{1-6}$ alkyl (e.g., methyl, ethyl, propyl, isopropyl, butyl, tert-butyl and the like), phenyl, trityl or silyl and the like, each of which optionally has substituent(s), can be mentioned. As the substituent, a halogen atom (e.g., fluorine, chlorine, bromine, iodine and the like), formyl, $C_{1-6}$ alkyl-carbonyl (e.g., acetyl, propionyl, butylcarbonyl and the like), nitro, $C_{1-6}$ alkyl (e.g., methyl, ethyl, tert-butyl and the like), $C_{6-10}$ aryl (e.g., phenyl, naphthyl and the like) and the like can be used. The number of the substituent is about 1 to 3.

As the hydroxy-protecting group, for example, formyl, or $C_{1-6}$ alkyl (e.g., methyl, ethyl, propyl, isopropyl, butyl, tert-butyl and the like), phenyl, $C_{7-10}$ aralkyl (e.g., benzyl and the like), $C_{1-6}$ alkyl-carbonyl (e.g., acetyl, propionyl and the like), phenyloxycarbonyl, $C_{7-10}$ aralkyloxy-carbonyl (e.g., benzyloxycarbonyl and the like), tetrahydropyranyl, tetrahydrofuranyl or silyl and the like, each of which optionally has substituent(s), can be mentioned. As the substituent, a halogen atom (e.g., fluorine, chlorine, bromine, iodine and the like), $C_{1-6}$ alkyl (e.g., methyl, ethyl, tert-butyl and the like), $C_{7-10}$ aralkyl (e.g., benzyl and the like), $C_{6-10}$ aryl (e.g., phenyl, naphthyl and the like), nitro and the like can be used. The number of the substituent is about 1 to 4.

For elimination of the protecting group, a method known per se or a method analogous thereto is used. For example, treatment method with acid, base, ultraviolet rays, hydrazine, phenylhydrazine, sodium N-methyldithiocarbamate, tetrabutylammonium fluoride, palladium (II) acetate and the like or reductive reaction can be used.

In any case, further if necessary, compound (I-1), compound (I-2), compound (I-3) and compound (I-4) can be synthesized by using known deprotection reactions, acylation reactions, alkylation reactions, hydrogenation reactions, oxidation reactions, reduction reactions, carbon chain extension reactions, substituent exchange reactions, each alone or in combination of two or more of them. As these reactions, for example, methods described in *SHINJIKKEN KAGAKU KOUZA* 14, vol. 15, 1977 (Maruzen Press), etc. are adopted.

The compounds to be used in the present invention can be produced by the above-mentioned production methods and the methods described in JP-A-2002-265457, JP-A-2002-212171, JP-A-2001-226350, JP-A-2001-199971, JP-A-2000-198772, JP-A-2000-80086, JP-A-2000-34266, JP-A-09-323983, JP-A-08-311065 and the like.

When the intended substance is obtained in the free form by the above-mentioned reaction, it may be converted into a salt according to an ordinary method, while when obtained in the form of a salt, it can also be converted into a free form or other salt according to an ordinary method. Thus obtained compound or a salt thereof can be isolated and purified from a reaction solution by known means, for example, rolling, concentration, solvent extraction, fractionation, crystallization, recrystallization, chromatography and the like.

When compound of the present invention is present as a configurational isomer (stereoisomer), diastereomer, conformer or the like, each can be isolated by the above separation and purification methods on demand. In addition, when compound of the present invention is in the form of racemates, they can be separated into S- and R-forms by any conventional optical resolution.

When compound of the present invention includes stereoisomers, both the isomers alone and mixtures of each isomers are included in the scope of the present invention.

In addition, compound of the present invention may be a hydrate or non-hydrate.

The compound of the present invention may be labeled with an isotope (e.g., $^3H$, $^{14}C$, $^{35}S$ and the like) or the like.

The GPR40 receptor function regulating action of the compounds of the present invention can be determined by the method described in Experimental Example 4 to be mentioned later or a method analogous thereto.

The compound of the present invention, a salt thereof and a prodrug thereof (hereinafter sometimes to be abbreviated as the compound of the present invention) show GPR40 receptor function regulating action, particularly GPR40 receptor agonist activity, show low toxicity and a fewer side effects. Therefore, they are useful as a safe GPR40 receptor function regulator, preferably GPR40 agonist.

A pharmaceutical agent containing the compound of the present invention shows a superior GPR40 receptor function regulating action in mammal (e.g., mouse, rat, hamster, rabbit, cat, dog, bovine, sheep, monkey, human etc.), and is useful as a modulator of physiological function in which GPR40 receptor is involved or an agent for the prophylaxis or treatment of disease state or disease in which GPR40 receptor is involved.

To be specific, the pharmaceutical agent containing the compound of the present invention is useful as an insulin secretion modulator (preferably insulin secretagogue), hypoglycemic agent and pancreatic β cell protector.

Moreover, the pharmaceutical agent containing the compound of the present invention is useful as an agent for the prophylaxis or treatment of diseases such as diabetes, impaired glucose tolerance, ketosis, acidosis, diabetic neuropathy, diabetic nephropathy, diabetic retinopathy, hyperlipidemia, genital disorder, skin disease, arthropathy, osteopenia, arteriosclerosis, thrombotic disease, dyspepsia, memory and learning disorder, obesity, hypoglycemia, hypertension, edema, insulin resistance, unstable diabetes, fatty atrophy, insulin allergy, insulinoma, lipotoxicity, hyperinsulinemia, cancers and the like, particularly, diseases such as diabetes, impaired glucose tolerance, ketosis, acidosis, diabetic neuropathy, diabetic nephropathy, diabetic retinopathy, hyperlipidemia, genital disorder, skin disease, arthropathy, osteopenia, arteriosclerosis, thrombotic disease, dyspepsia, memory and learning disorder and the like. Here, diabetes includes insulin-dependent (type I) diabetes, non-insulin-dependent (type II) diabetes and gestational diabetes can be mentioned. In addition, hyperlipidemia includes hypertriglyceridemia, hypercholesterolemia, hypoHDL-emia, postprandial hyperlipidemia and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) reported new diagnostic criteria of diabetes in 1997 and WHO in 1998.

According to these reports, diabetes is a condition showing a fasting blood glucose level (glucose concentration of intravenous plasma) of not less than 126 mg/dl and a 75 g oral glucose tolerance test 2 h level (glucose concentration of intravenous plasma) of not less than 200 mg/dl.

According to the above-mentioned reports, impaired glucose tolerance is a condition showing a fasting blood glucose level (glucose concentration of intravenous plasma) of less than 126 mg/dl and a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 h level (glucose concentration of intravenous plasma) of less than 140 mg/dl is called IFG (Impaired Fasting Glycemia).

The compound of the present invention can be also used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

The pharmaceutical agent comprising the compound of the present invention shows low toxicity and can be safely administered orally or parenterally (e.g., topical, rectal, intravenous administration etc.) as a pharmaceutical preparation of the compound of the present invention as it is or after admixing with a pharmacologically acceptable carrier to give, for example, tablet (including sugar-coated tablet and film-coated tablet), powder, granule, capsules (including soft capsules), liquid, injection, suppository, sustained-release preparation and the like, according to a methods known per se used for the general production method for pharmaceutical preparations.

The content of the compound of the present invention in the pharmaceutical preparation of the present invention is about 0.01 to about 100% by weight relative to the whole preparation. The dose varies depending on administration subjects, administration route, diseases, condition and the like. When the compound is orally administered to a patient with diabetes (body weight about 60 kg), the dose is about 0.01 to about 30 mg/kg body weight per day, preferably about 0.1 to about 20 mg/kg body weight per day, more preferably about 1 to about 20 mg/kg body weight per day, as an active ingredient [the compound of the present invention], which may be given at once or in several portions a day.

As pharmacologically acceptable carriers that can be used for the production of the pharmaceutical agent of the present invention, various organic or inorganic carriers conventionally used as materials for pharmaceutical preparations can be mentioned. For example, excipient, lubricant, binder and disintegrant for solid preparations; and solvent, dissolution aids, suspending agent, isotonizing agent, buffer and soothing agent and the like for liquid preparations can be mentioned. Where necessary, conventional additives such as preservative, antioxidant, coloring agent, sweetening agent, adsorbing agent, wetting agent and the like can be used.

As the excipient, for example, lactose, sucrose, D-mannitol, starch, corn starch, crystalline cellulose, light silicic anhydride and the like can be mentioned.

As the lubricant, for example, magnesium stearate, calcium stearate, talc, colloidal silica and the like can be mentioned.

As the binder, for example, crystalline cellulose, sucrose, D-mannitol, dextrin, hydroxypropylcellulose, hydroxypropylmethylcellulose, polyvinylpyrrolidone, starch, sucrose, gelatin, methylcellulose, carboxymethylcellulose sodium and the like can be mentioned.

As the disintegrant, for example, starch, carboxymethylcellulose, carboxymethylcellulose calcium, carboxymethylstarch sodium, L-hydroxypropylcellulose and the like can be mentioned.

As the solvent, for example, water for injection, alcohol, propyleneglycol, macrogol, sesame oil, corn oil, olive oil and the like can be mentioned.

As the dissolution aids, for example, polyethylene glycol, propyleneglycol, D-mannitol, benzyl benzoate, ethanol, trisaminomethane, cholesterol, triethanolamine, sodium carbonate, sodium citrate and the like can be mentioned.

As the suspending agent, for example, surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like, and the like can be mentioned.

As an isotonizing agent, for example, glucose, D-sorbitol, sodium chloride, glycerin, D-mannitol and the like can be mentioned.

As the buffer, for example, buffers such as phosphate, acetate, carbonate, citrate and the like, and the like can be mentioned.

As the soothing agent, for example, benzyl alcohol and the like can be mentioned.

As the preservative, for example, p-hydroxybenzoates, chlorobutanol, benzyl alcohol, phenethyl alcohol, dehydroacetic acid, sorbic acid and the like can be mentioned.

As the antioxidant, for example, sulfite, ascorbic acid, α-tocopherol and the like can be mentioned.

Furthermore, the compound of the present invention can be used in combination with a drug other than the compound of the present invention.

As the drug that can be used in combination with the compound of the present invention (hereinafter sometimes to be abbreviated as concomitant drug), for example, other therapeutic agents for diabetes, therapeutic agents for diabetic complications, therapeutic agent for hyperlipidemia, antihypertensive agent, antiobesitic agent, diuretic, chemotherapeutic agent, immunotherapeutic agent, immunomodulator, antiinflammatory drug, antithrombotic agent, therapeutic agent for osteoporosis, antibacterial agent, antifungal agent, antiprotozoal agent, antibiotic, antitussive and expectorant drug, sedative, anesthetic, antiulcer drug, tranquilizer, antipsychotic, antitumor drug, muscle relaxant, anticonvulsant, antidepressant, antiallergic drug, cardiac, antiarrhythmic agent, vasodilator, vasoconstrictor, antinarcotic, vitamin, vitamin derivative, antiasthmatic, antidementia agent, therapeutic agent for incontinentia or pollakiuria, therapeutic agent for dysuria, therapeutic agent for atopic dermatitis, therapeutic agent for allergic rhinitis, hypertensor, endotoxin-antagonist or -antibody, signal transduction inhibitor, inhibitor of inflammatory mediator activity, antibody to inhibit inflammatory mediator activity, inhibitor of anti-inflammatory mediator activity, antibody to inhibit anti-inflammatory mediator activity and the like. Specific examples thereof include the following.

As the other therapeutic agent for diabetes, insulin preparations (e.g., animal insulin preparations extracted from the pancreas of bovine and pig; human insulin preparations genetically synthesized using *Escherichia coli*, yeast; zinc insulin; protamine zinc insulin; fragment or derivative of insulin (e.g., INS-1 etc.), oral insulin preparation and the like), insulin sensitizers (e.g., Pioglitazone or a salt thereof (preferably hydrochloride), troglitazone, Rosiglitazone or a salt thereof (preferably maleate), Reglixane (JTT-501), Netoglitazone (MCC-555), YM-440, GI-262570, KRP-297, FK-614, CS-011, (γE)-γ-[[[4-[(5-methyl-2-phenyl-4-oxazolyl)methoxy]phenyl]methoxy]imino]benzenebutanoic acid and the like, compounds described in WO99/58510 (e.g., (E)-4-[4-(5-methyl-2-phenyl-4-oxazolylmethoxy)benzyloxyimino]-4-phenylbutyric acid), compounds described in WO01/38325, Tesaglitazar (AZ-242), Ragaglitazar (N,N-622), BMS-298585, ONO-5816, BM-13-1258, LM-4156, MBX-102, LY-519818, MX-6054, LY-510929, Balaglitazone (N,N-2344), T-131 or a salt thereof, THR-0921 etc.), α-glucosidase inhibitors (e.g., voglibose, acarbose, miglitol, emiglitate etc.), biguanides (e.g., phenformin, metformin, buformin etc.), insulin secretagogues [sulfonylurea (e.g., tolbutamide, glibenclamide, gliclazide, chlorpropamide, tolazamide, acetohexamide, glyclopyramide, glimepiride etc.), repaglinide, senaglinide, mitiglinide or calcium salt hydrate thereof, nateglinide, etc.], GLP-1 receptor agonists [e.g., GLP-1, GLP-1MR agent, N,N-2211, AC-2993 (exendin-4), BIM-51077, Aib(8,35)hGLP-1(7,37)NH$_2$, CJC-1131 etc.], dipeptidyl peptidase IV inhibitor (e.g., NVP-DPP-278, PT-100, P32/98, P93/01, NVP-DPP-728, LAF237, TS-021 etc.), β3 agonist (e.g., CL-316243, SR-58611-A, UL-TG-307, AJ-9677, AZ40140 etc.), amylin agonists (e.g., pramlintide etc.), phosphotyrosine phosphatase inhibitors (e.g., vanadic acid etc.), gluconeogenesis inhibitors (e.g., glycogen phosphorylase inhibitor, glucose-6-phosphatase inhibitor, glucagon antagonist etc.), SGLT (sodium-glucose cotransporter) inhibitors (e.g., T-1095 etc.), 11β-hydroxysteroid dehydrogenase inhibitors (e.g., BVT-3498 etc.), adiponectin or agonist thereof, IKK inhibitors (e.g., AS-2868 etc.), leptin resistance improving drugs, somatostatin receptor agonists (compounds described in WO01/25228, WO03/42204, WO98/44921, WO98/45285, WO99/22735 etc.), glucokinase activators (e.g., Ro-28-1675) and the like can be mentioned.

Examples of the therapeutic agent for diabetic complications include aldose reductase inhibitors (e.g., Tolrestat, Epalrestat, Zenarestat, Zopolrestat, Fidarestat (SNK-860), Minalrestat (ARI-509), CT-112 etc.), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole etc.) and the like), protein kinase C (PKC) inhibitors (e.g., LY-333531 etc.), AGE inhibitors (e.g., ALT-945, pimagedine, pyratoxanthine, N-phenacylthiazolium bromide (ALT-766), EXO-226, ALT-711, Pyridorin, Pyridoxamine etc.), active oxygen scavengers (e.g., thioctic acid etc.), cerebral vasodilators (e.g., tiapride etc.), somatostatin receptor agonists (BIM23190) and apoptosis signal regulating kinase-1 (ASK-1) inhibitors.

Examples of the therapeutic agent of hyperlipidemia include statin compounds, which are cholesterol synthesis inhibitors (e.g., pravastatin, simvastatin, lovastatin, atorvastatin, fluvastatin, cerivastatin and salts thereof (e.g., sodium salt etc.) etc.), squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid etc.), fibrate compounds (e.g., bezafibrate, clofibrate, simfibrate, clinofibrate etc.), antioxidant (e.g., lipoic acid, probucol) and the like.

Examples of the antihypertensive agent include angiotensin converting enzyme inhibitors (e.g., captopril, enalapril, delapril etc.), angiotensin II receptor antagonists (e.g., losartan, candesartan cilexetil, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid etc.), calcium antagonist (e.g., manidipine, nifedipine, amlodipine, efonidipine, nicardipine etc.), Clonidine and the like.

Examples of the antiobestic agent include antiobestic agents acting on the central nervous system (e.g., Dexfenfluramine, fenfluramine, phentermine, Sibutramine, amfepramone, dexamphetamine, Mazindol, phenylpropanolamine, clobenzorex; MCH receptor antagonists (e.g., SB-568849; SNAP-7941; compounds encompassed in WO01/82925 and WO01/87834 etc.); neuropeptide Y antagonists (e.g., CP-422935 etc.); cannabinoid receptor antagonists (e.g., SR-141716, SR-147778 etc.); ghrelin antagonist; 11β-hydroxysteroid dehydrogenase inhibitors (e.g., BVT-3498 etc.) and the like), pancreatic lipase inhibitors (e.g., orlistat, ATL-962 etc.), β3 agonists (e.g., CL-316243, SR-58611-A, UL-TG-307, AJ-9677, AZ40140 etc.), peptidic anorexiants (e.g., leptin, CNTF (Ciliary Neurotropic Factor) etc.), cholecystokinin agonists (e.g., lintitript, FPL-15849 etc.), feeding deterrent (e.g., P-57 etc.) and the like.

Examples of the diuretic include xanthine derivatives (e.g., sodium salicylate and theobromine, calcium salicylate and theobromine etc.), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide etc.), antialdosterone preparations (e.g., spironolactone, triamterene etc.), carbonate dehydratase inhibitors (e.g., acetazolamide and the like), chlorobenzenesulfonamide preparations (e.g., chlortalidone, mefruside, indapamide etc.), azosemide, isosorbide, etacrynic acid, piretanide, bumetanide, furosemide and the like.

Examples of the chemotherapeutic agent include alkylation agents (e.g., cyclophosphamide, ifosfamide etc.), metabolic antagonists (e.g., methotrexate, 5-fluorouracil etc.), anti-cancer antibiotics (e.g., mitomycin, adriamycin etc.), plant-derived anti-cancer agents (e.g., vincristin, vindesine, taxol etc.), cisplatin, carboplatin, etoposide and the like. Of these, furtulon and neofurtulon, which are 5-fluorouracil derivatives, and the like are preferable.

Examples of the immunotherapeutic agent include microorganism or bacterial components (e.g., muramyl dipeptide derivative, picibanil etc.), polysaccharides having immunity potentiating activity (e.g., lentinan, sizofuran, krestin etc.), cytokines obtained by genetic engineering techniques (e.g., interferon, interleukin (IL) etc.), colony stimulating factors (e.g., granulocyte colony stimulating factor, erythropoietin etc.) and the like, with preference given to interleukins such as IL-1, IL-2, IL-12 and the like.

As the antiinflammatory drug, for example, non-steroidal antiinflammatory agents such as aspirin, acetoaminofen, indomethacin and the like can be mentioned.

Examples of the antithrombotic agent include heparin (e.g., heparin sodium, heparin calcium, dalteparin sodium etc.), warfarin (e.g., warfarin potassium etc.), anti-thrombin drugs (e.g., aragatroban etc.), thrombolytic agents (e.g., urokinase, tisokinase, alteplase, nateplase, monteplase, pamiteplase etc.), platelet aggregation inhibitors (e.g., ticlopidine hydrochloride, cilostazol, ethyl icosapentate, beraprost sodium, sarpogrelate hydrochloride etc.) and the like.

Examples of the therapeutic agent of osteoporosis include alfacalcidol, calcitriol, elcatonin, calcitonin salmon, estriol, ipriflavone, pamidronate disodium, alendronate sodium hydrate, incadronate disodium and the like.

As the vitamin, for example, vitamin $B_1$, vitamin $B_{12}$ and the like can be mentioned.

Examples of the antidementia agent include tacrine, donepezil, rivastigmine, galanthamine and the like.

Examples of the therapeutic agent for incontinentia or pollakiuria include flavoxate hydrochloride, oxybutynin hydrochloride, propiverine hydrochloride and the like.

Examples of the therapeutic agent for dysuria include acetylcholine esterase inhibitors (e.g., distigmine) and the like.

Furthermore, drugs having a cachexia-improving action established in animal models and clinical situations, such as cyclooxygenase inhibitors (e.g., Indometacin etc. [*Cancer Research*, vol. 49, 5935-5939, 1989], Progesterone derivatives (e.g., Megesterol acetate) [*Journal of Clinical Oncology*, vol. 12, 213-225, 1994], glucosteroid (e.g., dexamethasone etc.), metoclopramide agents, tetrahydrocannabinol agents (literatures are as mentioned above), fat metabolism improving agents (e.g., eicosapentaenoic acid etc.) [*British Journal of Cancer*, vol. 68, 314-318, 1993], growth hormones, IGF-1, or antibodies to a cachexia-inducing factor such as TNF-α, LIF, IL-6, Oncostatin M and the like, can be used in combination with the compound of the present invention.

Further, glycosylation inhibitors (e.g., ALT-711, etc.), nerve regeneration promoting drugs (e.g., Y-128, VX853, prosaptide, etc.), antidepressants (e.g., desipramine, amitriptyline, imipramine, etc.), anticonvulsants (e.g., lamotrigine, Trileptal, Keppra, Zonegran, Pregabalin, Harkoseride, carbamazepine), antiarrhythmic drugs (e.g., mexiletine), acetylcholine receptor ligands (e.g., ABT-594), endothelin receptor antagonists (e.g., ABT-627), monoamine uptake inhibitors (e.g., tramadol), narcotic analgesics (e.g., morphine), GABA receptor agonists (e.g., gabapentin, gabapentin MR agent), m receptor agonists (e.g., clonidine), local analgesics (e.g., capsaicin), antianxiety drugs (e.g., benzothiazepines), phosphodiesterase inhibitors (e.g., sildenafil), dopamine receptor agonists (e.g., apomorphine) and the like can be also used in combination with the compound of the present invention.

By combining the compound of the present invention and a concomitant drug, a superior effect such as
(1) the dose of the compound of the present invention or a concomitant drug can be reduced as compared to single administration of the compound of the present invention or a concomitant drug,
(2) the drug to be used in combination with the compound of the present invention can be selected depending on the condition of patients (mild, severe and the like),
(3) the period of treatment can be set longer by selecting a concomitant drug having different action and mechanism from those of the compound of the present invention,
(4) a sustained treatment effect can be designed by selecting a concomitant drug having different action and mechanism from those of the compound of the present invention,
(5) a synergistic effect can be afforded by a combined use of the compound of the present invention and a concomitant drug, and the like, can be achieved.

In the following, use of the compound of the present invention and a concomitant drug in combination is to be referred to as the "concomitant agent of the present invention".

For the use of the concomitant agent of the present invention, the administration time of the compound of the present invention and the concomitant drug is not restricted, and the compound of the present invention and the concomitant drug can be administered to an administration subject simultaneously, or may be administered at staggered times. The dosage of the concomitant drug may be determined according to the dose clinically used, and can be appropriately selected depending on an administration subject, administration route, disease, combination and the like.

The administration mode of the concomitant agent of the present invention is not particularly restricted, as long as the compound of the present invention and the concomitant drug are combined in administration. Examples of such administration mode include the following methods: (1) The compound of the present invention and the concomitant drug are simultaneously formulated to give a single preparation which is administered. (2) The compound of the present invention and the concomitant drug are separately formulated to give two kinds of preparations which are administered simultaneously by the same administration route. (3) The compound of the present invention and the concomitant drug are separately formulated to give two kinds of preparations which are administered by the same administration route at staggered times. (4) The compound of the present invention and the concomitant drug are separately formulated to give two kinds of preparations which are administered simultaneously by the different administration routes. (5) The compound of the present invention and the concomitant drug are separately formulated to give two kinds of preparations which are administered by the different administration routes at staggered times (for example, the compound of the present invention and the concomitant drug are administered in this order, or in the reverse order), and the like.

A concomitant agent of the present invention has low toxicity, and for example, the compound of the present invention and/or the above-mentioned concomitant drug can be mixed, according to a method known per se, with a pharmacologically acceptable carrier to give pharmaceutical compositions, for example, tablets (including a sugar-coated tablet, film-coated tablet), powders, granules, capsules (including soft capsules), liquids, injections, suppositories, sustained-release preparations and the like, which can be safely administered orally or parenterally (e.g., topical, rectal, intravenous administration, and the like). An injection can be administered by intravenous, intramuscular, subcutaneous or intraorgan route, or directly to the lesion.

As a pharmacologically acceptable carrier which may be used for preparing the concomitant agent of the present invention, those similar to the aforementioned pharmacologically acceptable carriers that can be used for the production of the pharmaceutical agent of the present invention can be mentioned. Further, if needed, the aforementioned additives that can be used for the production of the pharmaceutical agent of the present invention, such as preservative, antioxidant, coloring agent, sweetening agent, adsorbing agent, wetting agent and the like, can be appropriately used in an appropriate amount.

The compounding ratio of the compound of the present invention to the concomitant drug in the concomitant agent of the present invention can be appropriately selected depending on an administration subject, administration route, diseases and the like.

For example, the content of the compound of the present invention in the concomitant agent of the present invention differs depending on the form of a preparation, and usually from about 0.01 to 100% by weight, preferably from about 0.1 to 50% by weight, further preferably from about 0.5 to 20% by weight, based on the preparation.

The content of the concomitant drug in the concomitant agent of the present invention differs depending on the form of a preparation, and usually from about 0.01 to 100% by weight, preferably from about 0.1 to 50% by weight, further preferably from about 0.5 to 20% by weight, based on the preparation.

The content of additives such as a carrier and the like in the concomitant agent of the present invention differs depending on the form of a preparation, and usually from about 1 to 99.99% by weight, preferably from about 10 to 90% by weight, based on the preparation.

In the case when the compound of the present invention and the concomitant drug are separately prepared respectively, the same contents may be adopted.

These preparations can be produced by a method known per se usually used in a preparation process.

For example, the compound of the present invention and the concomitant drug can be made into an aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin and the like), a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, mannitol, sorbitol, glucose and the like), a pH regulator (e.g., hydrochloric acid, sodium hydroxide and the like), a preservative (e.g., ethyl p-hydroxybenzoate, benzoic acid, methyl p-hydroxybenzoate, propyl p-hydroxybenzoate, benzyl alcohol and the like), a dissolving agent (e.g., conc. glycerin, meglumine and the like), a dissolution aid (e.g., propylene glycol, sucrose and the like), a soothing agent (e.g., glucose, benzyl alcohol and the like), and the like, or can be dissolved, suspended or emulsified in a vegetable oil such as olive oil, sesame oil, cotton seed oil, corn oil and the like or a dissolution aid such as propylene glycol and molded into an oily injection.

In addition, an excipient (e.g., lactose, sucrose, starch and the like), a disintegrant (e.g., starch, calcium carbonate and the like), a binder (e.g., starch, acacia, carboxymethylcellulose, polyvinylpyrrolidone, hydroxypropylcellulose and the like), a lubricant (e.g., talc, magnesium stearate, polyethylene glycol 6000 and the like) and the like, for example, can be added to the compound of the present invention or the concomitant drug, according to a method known per se, and the mixture can be compression-molded, then if desirable, the molded product can be coated by a method known per se for the purpose of masking of taste, enteric property or durability, to obtain a preparation for oral administration. As this coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (methacrylic acid-acrylic acid copolymer, manufactured by Rohm, DE), pigment (e.g., iron oxide red, titanium dioxide, etc.) and the like can be used. The preparation for oral administration may be any of a quick release preparation and a sustained release preparation.

Furthermore, the compound of the present invention and the concomitant drug can be made into an oily or aqueous solid, a semisolid or liquid suppository by admixing with an oily base, aqueous base or aqueous gel base according to a method known per se. As the oily base used in the above-mentioned, for example, glycerides of higher fatty acids [e.g., cacao butter, Witepsols (manufactured by Dynamite Nobel, DE), etc.], intermediate grade fatty acids [e.g., Miglyols (manufactured by Dynamite Nobel, DE), etc.], or vegetable oils (e.g., sesame oil, soy bean oil, cotton seed oil and the like), and the like are mentioned. Further, as the aqueous base, for example, polyethylene glycols, propylene glycol and the like are mentioned, and as the aqueous gel base, for example, natural gums, cellulose derivatives, vinyl polymers, acrylic acid polymers and the like are mentioned.

As the above-mentioned sustained release preparation, sustained release microcapsules and the like are mentioned. The sustained-release microcapsule can be produced by a method known per se, such as the method shown in the following [2].

A compound of the present invention is preferably molded into a preparation for oral administration such as a solid preparation (e.g., powder, granule, tablet, capsule) and the like, or molded into a preparation for rectal administration such as a suppository. Particularly, a preparation for oral administration is preferable.

The concomitant drug can be made into the above-mentioned preparation form depending on the kind of the drug.

[1] An injection of the compound of the present invention or the concomitant drug, and preparation thereof, [2] a sustained release preparation or quick release preparation of the compound of the present invention or the concomitant drug, and preparation thereof, [3] a sublingual, buccal or intraoral quick integrating agent of the compound of the present invention or the concomitant drug, and preparation thereof, will be described below specifically.

[1] Injection and Preparation Thereof

An injection prepared by dissolving the compound of the present invention or the concomitant drug into water is preferable. This injection may be allowed to contain a benzoate and/or salicylate.

The injection is obtained by dissolving the compound of the present invention or the concomitant drug, and if desirable, a benzoate and/or salicylate, into water.

As the above-mentioned benzoate and salicylate, for example, salts of alkali metals such as sodium, potassium and the like, salts of alkaline earth metals such as calcium, magnesium and the like, ammonium salts, meglumine salts, organic acid salts such as tromethamol etc., and the like are mentioned.

The concentration of the compound of the present invention or the concomitant drug in an injection is from 0.5 to 50% (w/v), preferably from about 3 to 20% (w/v). The concentration of the benzoate or/and salicylate is from 0.5 to 50% (w/v), preferably from 3 to 20% (w/v).

Into a preparation of the present invention, additives usually used in an injection, for example, a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, and the like), a dispersing agent (e.g., hydroxypropylmethylcellulose, dextrin, and the like), a pH regulator (e.g., hydrochloric acid, sodium hydroxide and the like), a preservative (e.g., ethyl p-hydroxybenzoate, benzoic acid and the like), a dissolving agent (e.g., conc. glycerin, meglumine and the like), a dissolution aid (e.g., propylene glycol, sucrose and the like), a soothing agent (e.g., glucose, benzyl alcohol and the like), and the like, can be appropriately compounded. These additives are generally compounded in a proportion usually used in an injection.

It is advantageous that pH of an injection is controlled from 2 to 12, preferably from 2.5 to 8.0 by addition of a pH regulator.

An injection is obtained by dissolving the compound of the present invention or the concomitant drug and if desirable, a benzoate and/or a salicylate, and if necessary, the above-mentioned additives into water. These may be dissolved in any order, and can be appropriately dissolved in the same manner as in a conventional method of producing an injection.

An aqueous solution for injection may be advantageously be heated, alternatively, for example, filter sterilization, high pressure heat sterilization and the like can be conducted in the same manner as for a usual injection, to provide an injection.

It may be advantageous that an aqueous solution for injection is subjected to high pressure heat sterilization at 100 to 121° C. for 5 to 30 minutes.

Further, a preparation endowed with an antibacterial property of a solution may also be produced so that it can be used as a preparation which is divided and administered multiple times.

[2] Sustained Release Preparation or Quick Release Preparation, and Preparation Thereof A sustained release preparation is preferable which is obtained, if desirable, by coating a nucleus containing the compound of the present invention or the concomitant drug with a film agent such as a water-insoluble substance, swellable polymer and the like. For example, a sustained release preparation for oral-administration for a single administration per day type is preferable.

As the water-insoluble substance used in a film agent, there are mentioned, for example, cellulose ethers such as ethylcellulose, butylcellulose and the like, cellulose esters such as cellulose acetate, cellulose propionate and the like, polyvinyl esters such as polyvinyl acetate, polyvinyl butyrate and the like, acrylic acid/methacrylic acid copolymers, methyl methacrylate copolymers, ethoxyethyl methacrylate/cinnamoethyl methacrylate/aminoalkyl methacrylate copolymers, polyacrylic acid, polymethacrylic acid, methacrylic acid alkylamide copolymers, poly(methyl methacrylate), polymethacrylate, polymethacrylamide, aminoalkyl methacrylate copolymers, poly(methacrylic anhydride), glycidyl methacrylate copolymer, particularly, acrylic acid-based polymers such as Eudragits (Rohm Pharma) such as Eudragit RS-100, RL-100, RS-30D, RL-30D, RL-PO, RS-PO (ethyl acrylate-methyl methacrylate-trimethyl chloride methacrylate-ammoniumethyl copolymer), Eudragit NE-30D (methyl methacrylate-ethyl acrylate copolymer), and the like, hardened oils such as hardened castor oil (e.g., Lovery wax (Freunt) and the like), waxes such as carnauba wax, fatty acid glycerin ester, paraffin and the like, polyglycerin fatty acid esters, and the like.

As the swellable polymer, polymers having an acidic dissociating group and showing pH dependent swelling are preferable, and polymers manifesting slight swelling in acidic regions such as in the stomach and greater swelling in neutral regions such as in the small intestine and the large intestine are preferable.

As such a polymer having an acidic dissociating group and showing pH dependent swelling, cross-linkable polyacrylic acid copolymers such as, for example, Carbomer 934P, 940, 941, 974P, 980, 1342 and the like, polycarbophil, calcium polycarbophil (all are manufactured by BF Goodrich), Hibiswako 103, 104, 105, 304 (all are manufactured by Wako Pure Chemical Co., Ltd.), and the like, are mentioned.

The film agent used in a sustained release preparation may further contain a hydrophilic substance.

As the hydrophilic substance, for example, polysaccharides which may contain a sulfate group such as pullulan, dextrin, alkali metal alginate and the like, polysaccharides having a hydroxyalkyl group or carboxyalkyl group such as hydroxypropylcellulose, hydroxypropylmethylcellulose, carboxymethylcellulose sodium and the like, methylcellulose, polyvinylpyrrolidone, polyvinyl alcohol, polyethylene glycol and the like.

The content of a water-insoluble substance in the film agent of a sustained release preparation is from about 30 to about 90% (w/w), preferably from about 35 to about 80% (w/w), further preferably from about 40 to about 75% (w/w), the content of a swellable polymer is from about 3 to 30% (w/w), preferably from about 3 to about 15% (w/w). The film agent may further contain a hydrophilic substance, and in which case, the content of a hydrophilic substance in the film agent is about 50% (w/w) or less, preferably about 5 to about 40% (w/w), further preferably from about 5 to about 35% (w/w).

This % (w/w) indicates % by weight based on a film agent composition which is obtained by removing a solvent (e.g., water, lower alcohols such as methanol, ethanol and the like) from a film agent solution.

The sustained release preparation is produced by preparing a nucleus containing a drug as exemplified below, then, coating the resulting nucleus with a film agent solution prepared by heat-solving a water-insoluble substance, swellable polymer and the like or by dissolving or dispersing it in a solvent.

I. Preparation of Nucleus Containing Drug

The form of nucleus containing a drug to be coated with a film agent (hereinafter, sometimes simply referred to as nucleus) is not particularly restricted, and preferably, the nucleus is formed into particles such as a granule or fine particle.

When the nucleus is composed of granules or fine particles, the average particle size thereof is preferably from about 150 to 2000 μm, further preferably, from about 500 to about 1400 μm.

Preparation of the nucleus can be effected by a usual production method. For example, a suitable excipient, binder, disintegrant, lubricant, stabilizer and the like are mixed into a drug, and the mixture is subjected to a wet extrusion granulating method, fluidized bed granulating method or the like, to prepare a nucleus.

The content of drugs in a nucleus is from about 0.5 to about 95% (w/w), preferably from about 5.0 to about 80% (w/w), further preferably from about 30 to about 70% (w/w).

As the excipient contained in the nucleus, for example, saccharides such as sucrose, lactose, mannitol, glucose and the like, starch, crystalline cellulose, calcium phosphate, corn starch and the like are used. Among them, crystalline cellulose and cornstarch are preferable.

As the binder, for example, polyvinyl alcohol, hydroxypropyl cellulose, polyethylene glycol, polyvinyl pyrrolidone, Pluronic F68, gum Arabic, gelatin, starch and the like are used. As the disintegrant, for example, carboxymethylcellulose calcium (ECG505), crosscarmelose sodium (Ac-Di-Sol), crosslinked polyvinylpyrrolidone (Crospovidone), low-substituted hydroxypropylcellulose (L-HPC) and the like are used. Among them, hydroxypropylcellulose, polyvinylpyrrolidone, low-substituted hydroxypropylcellulose are preferable. As the lubricant and coagulation inhibitor, for example, talc, magnesium stearate and inorganic salts thereof are used, and as the lubricant, polyethylene glycol and the like are used. As the stabilizer, acids such as tartaric acid, citric acid, succinic acid, fumaric acid, maleic acid and the like, are used.

A nucleus can also be prepared by, in addition to the above-mentioned, for example, a rolling granulation method in which a drug or a mixture of a drug with an excipient, lubricant and the like is added portionwise onto an inert carrier particle which is the core of the nucleus while spraying a binder dissolved in a suitable solvent such as water, lower alcohol (e.g., methanol, ethanol and the like) and the like, a pan coating method, a fluidized bed coating method or a melt granulating method. As the inert carrier particle, for example, those made of sucrose, lactose, starch, crystalline cellulose, waxes can be used, and the average particle size thereof is preferably from about 100 μm to about 1500 μm.

For separating a drug and a film agent contained in a nucleus, the surface of the nucleus may be coated with a protective agent. As the protective agent, for example, the above-mentioned hydrophilic substances, water-insoluble substances and the like are used. As the protective agent, preferably polyethylene glycol, and polysaccharides having a hydroxyalkyl group or carboxyalkyl group are used, more preferably, hydroxypropylmethylcellulose and hydroxypropylcellulose are used. The protective agent may contain, as a stabilizer, acids such as tartaric acid, citric acid, succinic acid, fumaric acid, maleic acid and the like, and lubricants such as talc and the like. When the protective agent is used, the coating amount is from about 1 to about 15% (w/w), preferably from about 1 to about 10% (w/w), further preferably from about 2 to about 8% (w/w), based on the nucleus.

The protective agent can be coated by a usual coating method, and specifically, the protective agent can be spray coated on a nucleus by, for example, a fluidized bed coating method, pan coating method and the like.

II. Coating of Nucleus with Film Agent

A nucleus obtained in the above-mentioned step I is coated with a film agent solution obtained by heat-solving the above-mentioned water-insoluble substance and pH-dependent swellable polymer, and a hydrophilic substance, or by dissolving or dispersing them in a solvent, to give a sustained release preparation.

As the method for coating a nucleus with a film agent solution, for example, a spray coating method and the like are mentioned.

The composition ratio of a water-insoluble substance, swellable polymer and hydrophilic substance in a film agent solution is appropriately selected so that the contents of these components in a coated film are the above-mentioned contents, respectively.

The coating amount of a film agent is from about 1 to about 90% (w/w), preferably from about 5 to about 50% (w/w), further preferably from about 5 to about 35% (w/w), based on a nucleus (not including coating amount of protective agent).

As the solvent in a film agent solution, water or an organic solvent can be used alone or in admixture thereof. In the case of use in admixture, the mixing ratio of water to an organic solvent (water/organic solvent: by weight) can be varied in the range from 1 to 100%, and preferably from 1 to about 30%. The organic solvent is not particularly restricted providing it dissolves a water-insoluble substance, and for example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Among them, lower alcohols are preferable, and ethyl alcohol and isopropyl alcohol are particularly preferable. Water, and a mixture of water with an organic solvent are preferably used as a solvent for a film agent. In this case, if necessary, an acid such as tartaric acid, citric acid, succinic acid, fumaric acid, maleic acid and the like may also be added into a film agent solution for stabilizing the film agent solution.

An operation of coating by spray coating can be effected by a usual coating method, and specifically, it can be effected by spray-coating a film agent solution onto a nucleus by a fluidized bed coating method, pan coating method and the like. In this case, if necessary, talc, titanium oxide, magnesium stearate, calcium stearate, light anhydrous silicic acid and the like may also be added as a lubricant, and glycerin fatty acid ester, hardened castor oil, triethyl citrate, cetyl alcohol, stearyl alcohol and the like may also be added as a plasticizer.

After coating with a film agent, if necessary, an antistatic agent such as talc and the like may be mixed.

The quick release preparation may be liquid (e.g., solution, suspension, emulsion and the like) or solid (e.g., particle, pill, tablet and the like). As the quick release preparation, oral agents and parenteral agents such as an injection and the like are used, and oral agents are preferable.

The quick release preparation, usually, may contain, in addition to an active component drug, also carriers, additives and excipients conventionally used in the production field (hereinafter, sometimes abbreviated as excipient). The excipient used is not particularly restricted providing it is an excipient ordinarily used as a preparation excipient. For example, as the excipient for an oral solid preparation, lactose, starch, corn starch, crystalline cellulose (Avicel PH101, manufactured by Asahi Chemical Industry Co., Ltd., and the like), powder sugar, granulated sugar, mannitol, light anhydrous silicic acid, magnesium carbonate, calcium carbonate, L-cysteine and the like are mentioned, and preferably, corn starch and mannitol and the like are mentioned. These excipients can be used alone or in combination of two or more. The content of the excipient is, for example, from about 4.5 to about 99.4% (w/w), preferably from about 20 to about 98.5% (w/w), further preferably from about 30 to about 97% (w/w), based on the total amount of the quick release preparation.

The content of a drug in the quick release preparation can be appropriately selected in the range from about 0.5 to about 95% (w/w), preferably from about 1 to about 60% (w/w) based on the total amount of the quick release preparation.

When the quick release preparation is an oral solid preparation, it usually contains, in addition to the above-mentioned components, also a disintegrant. As this disintegrant, there are used, for example, carboxymethylcellulose calcium (ECG-505, manufactured by Gotoku Yakuhin), crosscarmelose sodium (e.g., Ac-Di-Sol, manufactured by Asahi Chemical Industry Co., Ltd.), Crospovidone (e.g., Kollidon CL, manufactured by BASF), low-substituted hydroxypropylcellulose (manufactured by Shin-Etsu Chemical Co., Ltd.), carboxymethylstarch (manufactured by Matsutani Kagaku K.K.), carboxymethylstarch sodium (Exprotab, manufactured by Kimura Sangyo), partially pregelatinized starch (PCS, manufactured by Asahi Chemical Industry Co., Ltd.), and the like are used, and for example, those which disintegrate a granule by adsorbing water in contact with water, causing swelling, or making a channel between an effective ingredient constituting the nucleus and an excipient, can be used. These disintegrants can be used alone or in combination of two or more. The amount of the disintegraent used is appropriately selected depending on the kind and compounding amount of a drug used, design of releasing property, and the like, and for example, from about 0.05 to about 30% (w/w), preferably from about 0.5 to about 15% (w/w), based on the total amount of the quick releasing agent.

When the quick release preparation is an oral solid preparation, it may further contain, in addition to the above-mentioned composition, if desired, additives conventional in solid preparations. As such an additive, there are used, for example, a binder (e.g., sucrose, gelatin, gum Arabic powder, methylcellulose, hydroxypropylcellulose, hydroxypropylmethylcellulose, carboxymethylcellulose, polyvinylpyrrolidone, pullulan, dextrin and the like), a lubricant (e.g., polyethylene glycol, magnesium stearate, talc, light anhydrous silicic acid (e.g., aerosil (Nippon Aerosil)), a surfactant (e.g., anionic surfactants such as sodium alkylsulfate and the like, nonionic surfactants such as polyoxyethylene fatty acid ester and polyoxyethylene sorbitan fatty acid ester, polyoxyethylene castor oil derivatives and the like), a coloring agent (e.g., tar pigment, caramel, iron oxide red, titanium oxide, riboflavins, and the like), if necessary, an appetizing agent (e.g., sweetening agent, aroma and the like), an adsorbing agent, preservative, wetting agent, antistatic agent, and the like. Further, as the stabilizer, an organic acid such as tartaric acid, citric acid, succinic acid, fumaric acid and the like may also be added.

As the above-mentioned binder, hydroxypropylcellulose, polyethylene glycol and polyvinylpyrrolidone and the like are preferably used.

The quick releasing preparation can be prepared by, based on a usual technology of producing preparations, mixing the above-mentioned components, and if necessary, further kneading the mixture, and molding it. The above-mentioned mixing is conducted by generally used methods, for example, mixing, kneading and the like. Specifically, when a quick release preparation is formed, for example, into a particle, it can be prepared, according to the same methods as in the above-mentioned method for preparing a nucleus of a sustained release preparation, by mixing the components using a vertical granulator, universal kneader (manufactured by Hata Tekkosho), fluidized bed granulator ED-5S (manufactured by Powrex), and the like, then, subjecting the mixture to a wet extrusion granulation method, fluidized bed granulation method and the like.

Thus obtained quick releasing preparation and sustained releasing preparation may be themselves made into products or made into products appropriately together with preparation excipients and the like, separately, by an ordinary method, then, may be administered simultaneously or may be administered in combination at any administration interval, or they may be themselves made into one oral preparation (e.g., granule, fine particle, tablet, capsule and the like) or made into one oral preparation together with preparation excipients and the like. It may also be permissible that they are made into granules or fine particles, and filled in the same capsule to be used as a preparation for oral administration.

[3] Sublingual, Buccal or Intraoral Quick Disintegrating Agent and Preparation Thereof Sublingual, buccal or intraoral quick disintegrating agents may be a solid preparation such as tablet and the like, or may be an oral mucosa membrane patch (film).

As the sublingual, buccal or intraoral quick disintegrating agent, a preparation containing the compound of the present invention or the concomitant drug and an excipient is preferable. It may contain also auxiliary agents such as a lubricant, isotonizing agent, hydrophilic carrier, water-dispersible polymer, stabilizer and the like. Further, for easy absorption and increase in in vivo use efficiency, β-cyclodextrin or β-cyclodextrin derivatives (e.g., hydroxypropyl-β-cyclodextrin and the like) and the like may also be contained.

As the above-mentioned excipient, lactose, sucrose, D-mannitol, starch, crystalline cellulose, light anhydrous silicic acid and the like are mentioned. As the lubricant, magnesium stearate, calcium stearate, talc, colloidal silica and the like are mentioned, and particularly, magnesium stearate and colloidal silica are preferable. As the isotonizing agent, sodium chloride, glucose, fructose, mannitol, sorbitol, lactose, saccharose, glycerin, urea and the like are mentioned, and particularly, mannitol is preferable. As the hydrophilic carrier, swellable hydrophilic carriers such as crystalline cellulose, ethylcellulose, crosslinkable polyvinylpyrrolidone, light anhydrous silicic acid, silicic acid, dicalcium phosphate, calcium carbonate and the like are mentioned, and particularly, crystalline cellulose (e.g., fine crystalline cellulose and the like) is preferable. As the water-dispersible polymer, gums (e.g., gum tragacanth, acacia gum, cyamoposis gum), alginates (e.g., sodium alginate), cellulose derivatives (e.g., methylcellulose, carboxymethylcellulose, hydroxymethylcellulose, hydroxypropylcellulose, hydroxypropylmethylcellulose), gelatin, water-soluble starch, polyacrylic acids (e.g., Carbomer), polymethacrylic acid, polyvinyl alcohol, polyethylene glycol, polyvinylpyrrolidone, polycarbofil, ascorbate palmitates and the like are mentioned, and hydroxypropylmethylcellulose, polyacrylic acid, alginate, gelatin, carboxymethylcellulose, polyvinylpyrrolidone, polyethylene glycol and the like are preferable. Particularly, hydroxypropylmethylcellulose is preferable. As the stabilizer, cysteine, thiosorbitol, tartaric acid, citric acid, sodium carbonate, ascorbic acid, glycine, sodium sulfite and the like are mentioned, and particularly, citric acid and ascorbic acid are preferable.

The sublingual, buccal or intraoral quick disintegrating agent can be produced by mixing the compound of the present invention or the concomitant drug and an excipient by a method known per se. Further, if desirable, auxiliary agents such as a lubricant, isotonizing agent, hydrophilic carrier, water-dispersible polymer, stabilizer, coloring agent, sweetening agent, preservative and the like may be mixed. The sublingual, buccal or intraoral quick disintegrating agent is obtained by mixing the above-mentioned components simultaneously or at a time interval, then subjecting the mixture to tablet-making molding under pressure. For obtaining suitable hardness, it may also be permissible that the materials are moistened by using a solvent such as water, alcohol and the like if desired before and after the tablet making process, and after the molding, the materials are dried, to obtain a product.

In the case of molding into a mucosa membrane patch (film), the compound of the present invention or the concomitant drug and the above-mentioned water-dispersible polymer (preferably, hydroxypropylcellulose, hydroxypropylmethylcellulose), excipient and the like are dissolved in a solvent such as water and the like, and the resulted solution is cast, to give a film. Further, additives such as a plasticizer, stabilizer, antioxidant, preservative, coloring agent, buffer, sweetening agent and the like may also be added. For imparting suitable elasticity to the film, glycols such as polyethylene glycol, propylene glycol and the like may be contained, or for enhancing adhesion of the film to an intraoral mucosa membrane lining, a bio-adhesive polymer (e.g., polycarbofil, carbopol) may also be contained. In the casting, a solution is poured on the non-adhesive surface, spread to uniform thickness (preferably 10 to 1000 micron) by an application tool such as a doctor blade and the like, then, the solution is dried to form a film. It may be advantageous that thus formed film is dried at room temperature or under heat, and cut into given area.

As the preferable intraoral quick disintegrating agent, there are mentioned solid quick scattering dose agents composed of a network body comprising the compound of the present invention or the concomitant drug, and a water-soluble or water-diffusible carrier which is inert to the compound of the present invention or concomitant drug, are mentioned. This network body is obtained by sublimating a solvent from the solid composition constituted of a solution prepared by dissolving the compound of the present invention or the concomitant drug in a suitable solvent.

It is preferable that the composition of an intraoral quick disintegrating agent contains a matrix forming agent and a secondary component, in addition to the compound of the present invention or the concomitant drug.

Examples of the matrix forming agent include animal proteins or vegetable proteins such as gelatins, dextrins and, soybean, wheat and psyllium seed protein and the like; rubber substances such as gum Arabic, cyamoposis gum, agar, xanthan gum and the like; polysaccharides; alginic acids; carboxymethylcelluloses; carageenans; dextrans; pectins; synthetic polymers such as polyvinylpyrrolidone and the like; substances derived from a gelatin-gum Arabic complex, and the like. Further, saccharides such as mannitol, dextrose, lactose, galactose, trehalose and the like; cyclic saccharides such as cyclodextrin and the like; inorganic salts such as sodium phosphate, sodium chloride and aluminum silicate and the like; amino acid s having 2 to 12 carbon atoms such as glycine, L-alanine, L-aspartic acid, L-glutamic acid, L-hydroxyproline, L-isoleucine, L-leucine, L-phenylalanine and the like, are contained.

One or more of the matrix forming agents can be introduced in a solution or suspension before solidification. Such matrix forming agent may be present in addition to a surfactant, or may be present while a surfactant being excluded. The matrix forming agent aids to maintain the compound of the present invention or the concomitant drug in the solution or suspension in diffused condition, in addition to formation of the matrix.

The composition may contain secondary components such as preservative, antioxidant, surfactant, thickening agent, coloring agent, pH regulator, flavoring agent, sweetening agent, food taste masking agent and the like. As the suitable coloring agent, red, black and yellow iron oxides, and FD & C dyes such as FD & C Blue 2, FD & C Red 40 and the like manufactured by Elis and Eberald can be mentioned. Examples of suitable flavoring agents include mint, raspberry, licorice, orange, lemon, grape fruit, caramel, vanilla, cherry, grape flavor and combinations thereof. Examples of suitable pH regulators include citric acid, tartaric acid, phosphoric acid, hydrochloric acid and maleic acid. Examples of suitable sweetening agents include aspartame, acesulfame K and thaumatin and the like. Examples of suitable food taste masking agents include sodium bicarbonate, ion exchange resin, cyclodextrin-containing compounds, adsorbent substances and microcapsulated apomorphine.

The preparation contains the compound of the present invention or a concomitant drug in an amount generally from about 0.1 to about 50% by weight, preferably from about 0.1 to about 30% by weight, and preferred are preparations (such as the above-mentioned sublingual agent, buccal and the like) which can dissolve 90% or more of the compound of the present invention or the concomitant drug (into water) within the time range of about 1 to about 60 minutes, preferably about 1 to about 15 minutes, more preferably about 2 to about 5 minutes, and intraoral quick disintegrating preparations which are disintegrated within the range of 1 to 60 seconds, preferably 1 to 30 seconds, further preferably 1 to 10 seconds, after placement in an oral cavity.

The content of the above-mentioned excipient in the whole preparation is from about 10 to about 99% by weight, preferably from about 30 to about 90% by weight. The content of cyclodextrin or β-cyclodextrin derivative in the whole preparation is from 0 to about 30% by weight. The content of the lubricant in the whole preparation is from about 0.01 to about 10% by weight, preferably from about 1 to about 5% by weight. The content of the isotonizing agent in the whole preparation is from about 0.1 to about 90% by weight, preferably, from about 10 to about 70% by weight. The content of the hydrophilic carrier agent in the whole preparation is from about 0.1 to about 50% by weight, preferably, from about 10 to about 30% by weight. The content of the water-dispersible polymer in the whole preparation is from about 0.1 to about 30% by weight, preferably, from about 10 to about 25% by weight. The content of the stabilizer in the whole preparation is from about 0.1 to about 10% by weight, preferably, from about 1 to about 5% by weight. The above-mentioned preparation may further contain additives such as a coloring agent, sweetening agent, preservative and the like, if necessary.

The dosage of a concomitant agent of the present invention differs depending on the kind of the compound of the present invention, age, body weight, condition, preparation form, administration method, administration period and the like, and for example, for one diabetic patient (adult, body weight: about 60 kg), the concomitant agent is administered intravenously, at a dose of about 0.01 to about 1000 mg/kg/day, preferably about 0.01 to about 100 mg/kg/day, more preferably about 0.1 to about 100 mg/kg/day, particularly about 0.1 to about 50 mg/kg/day, especially about 1.5 to about 30 mg/kg/day, in terms of the compound of the present invention or the concomitant drug, respectively, once or divided several times in a day. Of course, since the dosage as described above varies depending on various conditions, amounts smaller than the above-mentioned dosage may sometimes be sufficient, further, amounts over that range sometimes have to be administered.

The amount of the concomitant drug can be set at any value unless side effects are problematical. The daily dosage in terms of the concomitant drug differs depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, usually from about 0.001 to 2000 mg, preferably from about 0.01 to 500 mg, further preferably from about 0.1 to 100 mg, per 1 kg of a mammal and this is usually administered once to 4-times divided in a day.

For administration of a concomitant agent of the present invention, the compound of the present invention may be administered after administration of the concomitant drug or the concomitant drug may be administered after administration of the compound of the present invention, though they may be administered simultaneously. When administered at a time interval, the interval varies depending on the effective ingredient, preparation form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is exemplified. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is exemplified.

In a preferable administration method, for example, the concomitant drug which has been formed into an oral administration preparation is administered orally at a daily dose of about 0.001 to 200 mg/kg, and about 15 minutes after, the compound of the present invention which has been formed into an oral administration preparation is administered orally at a daily dose of about 0.005 to 100 mg/kg.

The G-protein-coupled receptor protein (GPR40) of this invention is a receptor protein containing an amino acid sequence identical or substantially identical to the amino acid sequence presented by SEQ ID NO:1, SEQ ID NO:3, SEQ ID NO:5, SEQ ID NO:7 or SEQ ID NO:9.

GPR40 may be derived from any type of cells of humans and mammals (e.g. guinea pigs, rats, mice, rabbits, pigs, sheep, cattle, monkeys, others), for example, splenocytes, neurons, glia cells, pancreatic β cells, pancreatic islet, bone marrow cells, mesangium cells, Langerhans cells, epidermal cells, epithelial cells, endothelial cells, fibroblasts, fibre cells, muscle cells, adipocytes, immune cells (e.g. macrophages, T cells, B cells, natural killer cells, mast cells, neutrophils, basophils, eosinophils, monocytes), megakaryocytes, synovial cells, chondrocytes, osteocytes, osteoblasts, osteoclasts, mammary cells, hepatocytes and interstitial cells, precursor cells, stem cells and cancer cells of said cells, and cells in the blood cell system. The receptor protein may also derived from any tissue in which said cells are present, for example, the brain, each region of the brain (e.g. olfactory bulbs, amyglada, basal ganglia, hippocampus, thalamus, hypothalamus, subthalamic nucleus, cerebral cortex, medulla oblongata, cerebelleum, occipital lobes, frontal lobe, lateral lobe, putamen, caudate nucleus, corpus callosum, substantia nigra), spinal cord, pituitary gland, stomach, pancreas, kidneys, liver, gonads, thyroid gland, gallbladder, bone marrow, adrenal glands, skin, muscle, lung, digestive tract (e.g. large intestine, small intestine), vascular vessels, heart, thymus, spleen, submandibular gland, peripheral blood, peripheral blood cells, prostate, orchis, testes, ovaries, placenta, uterus, bones, joints, skeletal muscles and the like. The receptor protein may also be synthetic. Particularly, GPR40 is highly expressed in pancreatic islet.

Amino acid sequences substantially identical to the amino acid sequence presented by SEQ ID NO:1, SEQ ID NO:3, SEQ ID NO:5, SEQ ID NO:7 or SEQ ID NO:9 are amino acid sequences having about 85% or more homology, preferably about 90% or more homology, more preferably about 95% or more homology to the amino acid sequences presented by SEQ ID NO:1, SEQ ID NO:3, SEQ ID NO:5, SEQ ID NO:7 or SEQ ID NO:9.

As proteins containing amino acid sequences substantially identical to the amino acid sequence of this invention presented by SEQ ID NO:1, SEQ ID NO:3, SEQ ID NO:5, SEQ ID NO:7 or SEQ ID NO:9, for example, proteins that contain amino acid sequences that are substantially identical to the amino acid sequence presented by SEQ ID NO:1, SEQ ID NO:3, SEQ ID NO:5, SEQ ID NO:7 or SEQ ID NO:9 and have substantially the same activity as that of the amino acid presented by SEQ ID NO:1, SEQ ID NO:3, SEQ ID NO:5, SEQ ID NO:7 or SEQ ID NO:9 are preferred.

As to the substantially same activity, ligand-binding activity, signal transduction activity and the like are included. 'Substantially same' means that the quality of the activity is same. Therefore, although it is preferable that the activities such as ligand-binding and signal transduction activities are equivalent (e.g. about 0.01- to 100-fold, preferably about 0.5- to 20-fold, more preferably about 0.5- to 2-fold), quantitative factors such as the level of activity and the molecular weight of the protein may differ.

The activities such as the ligand-binding activity, signal transduction activity and the like can be determined according to methods known per se and, for example, these activities can be measured according to the method for screening described below.

Proteins containing the following amino acid sequences are also used as GPR40: a) amino acid sequences presented by SEQ ID NO:1, SEQ ID NO:3, SEQ ID NO:5, SEQ ID NO:7 or SEQ ID NO:9 in which one, two, or more amino acids (preferably 1-30 amino acids, more preferably 1-10 amino acids, most preferably several (1-5) amino acids) are deleted, b) amino acid sequences presented by SEQ ID NO:1, SEQ ID NO:3, SEQ ID NO:5, SEQ ID NO:7 or SEQ ID NO:9 in which one, two, or more amino acids (preferably 1-30 amino acids, more preferably 1-10 amino acids, and most preferably several (1-5) amino acids) are added, c) amino acid sequences presented by SEQ ID NO:1, SEQ ID NO:3, SEQ ID NO:5, SEQ ID NO:7 or SEQ ID NO:9 in which one, two, or more amino acids (preferably 1-30 amino acids, more preferably 1-10 amino acids, and most preferably several (1-5) amino acids) are substituted by other amino acids; or d) a protein containing a combination of such amino acid sequences and the like.

GPR40 in the present specification is presented according to the conventional presentation manner of peptides: the left end presents the N terminal (amino terminal) and the right end presents the C terminal (carboxyl terminal) In GPR40s including GPR40 containing the amino acid sequence presented by SEQ ID NO:1, the C terminal may be any of a carboxyl group (—COOH), carboxylate (—COO⁻), amide (—CONH$_2$) and ester (—COORx).

For Rx in the esters, for example, a $C_{1-6}$ alkyl groups such as methyl, ethyl, n-propyl, isopropyl and n-butyl, for example, $C_{3-8}$ cycloalkyl groups such as cyclopentyl and cyclohexyl, for example, $C_{6-12}$ aryl groups such as phenyl and α-naphthyl, for example, $C_{7-14}$ aralkyl groups including phenyl-$C_{1-2}$ alkyl groups such as benzyl and phenethyl and α-naphthyl-$C_{1-2}$ alkyl groups such as α-naphthylmethyl are used, and pivaloyloxymethyl groups, which are commonly used for oral esters, is also used.

When the GPR40 has a carboxyl group (or carboxylate) at a site other than the C terminal, GPR40 having an amidated or esterified carboxyl group are also included in GPR40 of this invention. For the ester form in this case, for example, the C-terminal esters described above are used.

Further, the GPR40 also includes proteins described above in which the amino group of the N-terminal methionine residue is protected by a protecting group (e.g. $C_{1-6}$ acyl group such as formyl group, $C_{2-6}$ alkanoyl group such as acetyl and the like, and the like), those in which the N-terminal is cleaved in vivo and the glutamyl group produced is converted to pyroglutamate, those in which substituents on amino acid side chains in the molecule (e.g. —OH, —SH, amino group, imidazole group, indole group, guanidino group) are protected by appropriate protecting groups (e.g. $C_{1-6}$ acyl group such as formyl group, $C_{2-6}$ alkanoyl group such as acetyl and the like, and the like), or complex proteins to which sugar chains are bound, that is glycoproteins.

As a specific example of GPR40, for example, mouse GPR40 containing an amino acid sequence presented by SEQ ID NO:1, rat GPR40 containing an amino acid sequence presented by SEQ ID NO:3, human GPR40 containing an amino acid sequence presented by SEQ ID NO:5, cynomolgus GPR40 containing an amino acid sequence presented by SEQ ID NO:7, hamster GPR40 containing an amino acid sequence presented by SEQ ID NO:9 and the like are used. Of these, mouse GPR40, rat GPR40, cynomolgus GPR40 and hamster GPR40 are novel proteins. Human GPR40 is a known protein described in WO2000-22129, *Biochem Biophys Res Commun.* 1997, October 20; 239 (2): 543-547.

For the partial peptides of GPR40 (hereinafter sometimes to be abbreviated as partial peptides), any partial peptide of the GPR40 described above may be used. For example, among the protein molecules of GPR40, the region exposed to outside of the cell membrane having substantially identical receptor-binding activity is used.

Concretely, the partial peptides of GPR40 having amino acid sequence presented by SEQ ID NO:1, SEQ ID NO:3, SEQ ID NO:5, SEQ ID NO:7 or SEQ ID NO:9 are peptides containing the regions that were shown to be the extracellular domains (hydrophilic regions) by the hydrophobicity plot analysis. Part of peptides partially containing hydrophobic region may also be used. Peptides containing individual domains can be used, but peptides of a part containing multiple domains may also be used.

The number of amino acids in the partial peptides of this invention is preferably peptide having at least 20 or more, preferably 50 or more, and more preferably 100 or more of the constitutive amino acid sequence of the receptor protein of this invention described above and the like.

The substantially identical amino acid sequences are amino acid sequences that have about 85% or more, preferably about 90% or more, more preferably about 95% or more homology to these amino acid sequences.

Here, the 'substantially identical receptor activity' means the same definition as described above. The 'substantially identical receptor activity' can be measured as described above.

In the partial peptides of this invention, one, two, or more amino acids (preferably about 1-10 amino acids, more preferably several (1-5) amino acids) may be deleted, one, two, or more amino acids (preferably about 1-20 amino acids, preferably about 1-10 amino acids, and more preferably several (1-5) amino acids) may be added, or one, two, or more amino acids (preferably about 1-10 amino acids, more preferably several amino acids, and most preferably about 1-5 amino acids) may be substituted by other amino acids.

In the partial peptides of this invention, the C-terminal may be any of carboxyl group (—COOH), carboxylate (—COO⁻), amide (—CONH$_2$) and ester (—COOR). When the partial peptide of the present invention has a carboxyl group (or carboxylate) besides C-terminal, the partial peptide of the present invention also encompasses one wherein a carboxyl group is amidated or esterified. As the ester in this case, for example, an ester of the above-mentioned C-terminal and the like are used.

The partial peptides of this invention include peptides in which the amino group of the N-terminal methionine residue is protected by a protecting group, those in which the N-terminal residue is cleaved in vivo and the glutamine residue is converted to pyroglutaminate, those in which substituents in amino acid side chains in the molecule are protected by appropriate protecting groups, or those in which sugar chains are bound, that is glycopeptides, as in the GPR40 mentioned above.

The salts of the GPR40 or partial peptides include physiologically acceptable salts formed with acids or bases, especially physiologically acceptable salts formed with acids are preferred. For examples, the salts formed with inorganic acids (e.g. hydrochloric acid, phosphoric acid, hydrobromic acid, sulfuric acid) and the salts formed with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid) are used.

The GPR40 and its salts can be manufactured by the methods known per se for purifying receptor protein from the human and mammalian cells or tissues described above. They may also be manufactured by culturing transformants containing the DNA encoding the GPR40 described below, and by the protein synthesis method described below or the method analogous thereto.

When the receptor protein is produced from human or mammalian tissues or cells, human or mammalian tissues or cells are homogenized, followed by extracting with acid or the like, and the extract is subjected to a combination of chromatography such as reverse-phase chromatography and ion-exchange chromatography to isolate and purify the receptor protein.

For the synthesis of GPR40 or a partial peptide thereof or a salt thereof or an amide thereof, commercially available resins for protein synthesis can be used. Such resins include for example, chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethyl phenyl acetoamidomethyl resin, polyacrylamide resin, 4-(2',4'-dimethoxyphenyl-hydroxymethyl)phenoxy resin, and 4-(2',4'-dimethoxyphenyl-Fmoc aminoethyl)phenoxy resin. Using these resins, amino acids in which the α-amino groups and the side-chain functional groups are appropriately protected are condensed in the order of the sequence of the objective protein on the resin according to the various condensation methods known per se. At the end of the reaction, the protein is excised from the resin and the protecting groups are simultaneously removed. Then, intramolecular disulfide bond-forming reaction is performed in a highly diluted solution to obtain the objective protein or its amide form.

For condensation of the protected amino acids described above, various activation reagents for protein synthesis can be used, but carbodiimides are particularly good. For carbodiimides, DCC, N,N'-diisopropylcarbodiimide, and N-ethyl-N'-(3-dimethylaminoprolyl)carbodiimide are used. For activation by these reagents, the protected amino acids are added with a racemization inhibitor (e.g. HOBt, HOOBt) directly to the resin, or the protected amino acids are previously activated as symmetric acid anhydrides, HOBt esters, or HOOBt esters, then added to the resin.

The solvent used for activation of the protected amino acids and condensation with the resin can be appropriately selected from solvents known to be useful in protein condensation reaction. For example, acid amides such as N,N-dimethylformamide, N,N-dimethylacetoamide, and N-methylpyrrolidone, halogenated hydrocarbons such as methylene hydrochloride and chloroform, alcohols such as trifluoroethanol, sulfoxide such as dimethylsufoxide, pyridine, ethers such as dioxane and tetrahydrofuran, nitriles such as acetonitrile and propionitrile, esters such as methyl acetate and ethyl acetate, and appropriate mixtures of these solvents. The suitable reaction temperature is appropriately selected from the range known to be used in protein bonding reaction, and usually appropriately selected from the range from about −20° C. to 50° C. The activated amino acid derivatives are usually used in 1.5- to 4-fold excess. The condensation is tested using ninhydrin reaction, and when the condensation is not sufficient, sufficient condensation can be carried out by repeating the condensation reaction without elimination of the protecting groups. When sufficient condensation can not obtained even after repeating the reaction, non-reacted amino acids can be acetylated using acetic anhydride or acetylimidazole.

For the protecting groups for amino group of raw material, for examples, Z, Boc, tert-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulfenyl, diphenylphosphinothioyl and Fmoc are used.

Carboxyl group can be protected by, for example, alkyl esterification (straight-chain, branched and cyclic alkyl esterification such as methyl, ethyl, propyl, butyl, tert-butyl, cyclopentyl, cyclohexyl, cycloheptyl, cyclooctyl and 2-adamantyl), aralkyl esterification (e.g. benzyl ester, 4-nitrobenzyl ester, 4-methoxybenzyl ester, 4-chlorobenzyl ester, benzhydryl ester), phenacyl esterification, benzyloxycarbonyl hydrazidation, tert-butoxycarbonyl hydrazidation and trityl hydrazidation.

The hydroxyl group of serine can be protected, for example, by esterification or etherification. Groups appropriate for this esterification include, for example, lower alkanoyl groups such as acetyl group, aroyl groups such as benzoyl group, and groups derived from carbonic acid such as benzyloxycarbonyl group and ethoxycarbonyl group. In addition, groups appropriate for etherification include, for example, benzyl group, tetrahydropyranyl group, and t-butyl group.

As a protecting group of the phenolic hydroxyl group of tyrosine, for example, Bzl, Cl$_2$-Bzl, 2-nitrobenzyl, Br-Z, and tert-butyl are used.

As a protecting group of the imidazole of histidine, for example, Tos, 4-methoxy-2,3,6-trimethylbenzenesulfonyl, DNP, benzyloxymethyl, Bum, Boc, Trt, and Fmoc are used.

As activated carboxyl groups in the raw material, for example, corresponding acid anhydride, azide, active ester [ester formed with alcohol (e.g. pentachlorophenol, 2,4,5-trichlorophenol, 2,4-dinitrophenol, cyanomethyl alcohol, paranitrophenol, HONB, N-hydroxysuccinimide, N-hydroxyphthalimide, HOBt)] are used.

Activated amino groups in the raw material include, for example, corresponding phosphoric amide.

For the method for eliminating the protecting groups, for example, catalytic reduction in hydrogen gas flow in the presence of a catalyst such as Pd-black and Pd-carbon, acid treatment with hydrogen fluoride anhydride, methanesulfonic acid, trifluoromethanesulfonic acid or trifluoroacetic acid, or mixture of these acids, basic treatment with diisopropylethylamine, triethylamine, piperidine and piperazine, and reduction by sodium in liquid ammonia are used. The elimination reaction by the acid treatment described above is generally performed at a temperature ranging from about $-20°$ C. to $40°$ C. In acid treatment, addition of a cation scavenger such as anisole, phenol, thioanisole, m-cresol, p-cresol, dimethylsulfide, 1,4-butanedithiol and 1,2-ethanedithiol and the like is effective. 2,4-dinitrophenyl group used as the protecting group of the imidazole of histidine is removed by treatment with thiophenol. Formyl group used as the protecting group of the indole of tryptophan is removed by the acid treatment in the presence of the aforementioned 1,2-ethanedithiol, 1,4-butanedithiol and the like, as well as alkaline treatment with diluted sodium hydroxide solution and diluted ammonia.

Protection of functional groups that should not be involved in the reaction of the raw materials, protecting groups, elimination of the protecting groups, and activation of functional groups involved in the reaction may be appropriately selected from known per se groups and means.

In another method for obtaining an amide form of protein, for example, first, the α-carboxyl group of the carboxy terminal amino acid is protected by amidation, and the peptide (protein) chain is extended for a desired length from the amino group side. Then, a protein in which only the protecting group of the N-terminal α-amino group was removed from said peptide chain and a protein in which only the protecting group of the C-terminal carboxyl group is removed are produced. These two proteins are condensed in the mixed solvent as described above. The details of the condensation reaction are the same as described above. After the protected protein obtained by condensation is purified, all protecting groups are removed by the method described above, and the desired crude protein is obtained. The desired protein in amide form can be obtained by purifying this crude protein using various known means for purification and by lyophilizing the major fraction.

To obtain esterified protein, for example, the α-carboxyl group of the carboxy terminal amino acid is condensed with a desired alcohol to prepare amino acid ester, and the desired esterified protein can be obtained by the same procedure as in the preparation of the amide form of protein.

The partial peptides of GPR40 or their salts can be manufactured by a method for peptide synthesis known per se or by cleaving GPR40 with appropriate peptidase. For the method for peptide synthesis, for example, either solid phase synthesis or liquid phase synthesis may be used. The partial peptides or amino acids that may compose GPR40 are condensed with the residual portion. When the product has protecting groups, the objective peptide can be produced by eliminating the protecting groups. The condensation and elimination methods known per se include the methods described in a)-e) below.

a) M. Bodanszky and M. A. Ondetti: Peptide Synthesis. Interscience Publishers, New York (1966)
b) Schroeder and Luebke: The Peptide. Academic Press, New York (1965)
c) N. Izumiya, et al.: Basics and experiments of peptide synthesis, Maruzen Co. (1975)
d) H. Yajima and S. Sakakibara: Biochemical Experiment 1, Chemistry of Proteins IV, 205 (1977)
e) H. Yajima ed.: A sequel to Development of Pharmaceuticals Vol. 14, Peptide Synthesis, Hirokawa Shoten After the reaction, the partial peptides of this invention are purified by a combination of conventional purification methods for example, solvent extraction, distillation, column chromatography, liquid chromatography, recrystallization and the like. When the partial peptide obtained by the above methods is free form, it can be converted to an appropriate salt form by known methods. On the other hand, when a salt form is obtained, it can be converted to the free form by known methods.

For the polynucleotide encoding GPR40, any polynucleotide containing the nucleotide sequence (DNA or RNA, preferably DNA) encoding GPR40 described above can be used. Said polynucleotide may be DNA and RNA including mRNA encoding GPR40, which may be double-stranded or single-stranded. When the polynucleotide is double-stranded, it may be double-stranded DNA, double-stranded RNA, or DNA:RNA hybrid. When the polynucleotide is single-stranded, it may be sense strand (i.e. coding strand) or antisense strand (i.e. non-coding strand).

Using the polynucleotide encoding GPR40, mRNA of GPR40 can be quantified by, for example, the known method described in separate volume of Jikken Igaku 15 (7) 'New PCR and its application' (1997) or the method analogous thereto.

The DNA encoding GPR40 may be any DNA of genomic DNA, genomic DNA library, cDNA and cDNA library derived from the cells and tissues described above, and synthetic DNA. For the vector used for library, bacteriophage, plasmid, cosmid, and phagemid may be used. The DNA may be directly amplified by Reverse Transcriptase Polymerase Chain Reaction (hereinafter to be abbreviated as RT-PCR) using total RNA or mRNA fraction prepared from the cells and tissues described above.

Concretely, the DNA encoding GPR40 may be, for example, any DNA containing the nucleotide sequence presented by SEQ ID NO:2, SEQ ID NO:4, SEQ ID NO:6, SEQ ID NO:8 or SEQ ID NO:10 or DNA having the nucleotide sequence that hybridize to the nucleotide sequence presented by SEQ ID NO:2, SEQ ID NO:4, SEQ ID NO:6, SEQ ID NO:8 or SEQ ID NO:10 under a high stringent condition, and encoding the receptor protein having substantially identical activity (e.g. ligand-binding activity and signal transduction activity) with that of GPR40 comprising the amino acid sequence presented by SEQ ID NO:1, SEQ ID NO:3, SEQ ID NO:5, SEQ ID NO:7 or SEQ ID NO:9.

For the DNA that can hybridize to the nucleotide sequence presented by SEQ ID NO:2, SEQ ID NO:4, SEQ ID NO:6, SEQ ID NO:8 or SEQ ID NO:10, for example, DNAs containing a nucleotide sequence that have about 85% or more homology, preferably about 90% or more homology, more preferably about 95% or more homology to the nucleotide sequence presented by SEQ ID NO:2, SEQ ID NO:4, SEQ ID NO:6, SEQ ID NO:8 or SEQ ID NO:10 are used.

Hybridization can be performed using a method known per se or the method analogous thereto for example, the method described in Molecular Cloning, 2nd (J. Sambrook et al., Cold Spring Harbor Lab. Press, 1989) and the like. When a commercial library is used, hybridization may be performed according to a method described in the attached instruction. Preferably, hybridization may be performed according to a high stringent condition.

In said high stringent condition, for example, the sodium concentration is about 19-40 mM, preferably about 19-20 mM, and the temperature is about 50-70° C., preferably about 60-65° C. In the most preferred condition, the sodium concentration is about 19 mM and the temperature is about 65° C.

More concretely, for the DNA encoding mouse GPR40 containing an amino acid sequence presented by SEQ ID:1, the DNAs encoding the nucleotide sequence presented by SEQ ID:2 are used.

As the DNA encoding mouse GPR40 containing an amino acid sequence presented by SEQ ID NO:3, a DNA containing a nucleotide sequence presented by SEQ ID NO:4 and the like are used.

As the DNA encoding mouse GPR40 containing an amino acid sequence presented by SEQ ID NO:5, a DNA containing a nucleotide sequence presented by SEQ ID NO:6 and the like are used.

As the DNA encoding cynomolgus GPR40 containing an amino acid sequence presented by SEQ ID NO:7, a DNA containing a nucleotide sequence presented by SEQ ID NO:8 and the like are used.

As the DNA encoding hamster GPR40 containing an amino acid sequence presented by SEQ ID NO:9, a DNA containing a nucleotide sequence presented by SEQ ID NO:10 and the like are used.

The DNAs encoding the partial peptides of this invention may be any DNA that contains a nucleotide sequence encoding the aforementioned partial peptide of this invention, and may be genomic DNA, genomic DNA library, cDNA and cDNA library derived from the cells and tissues described above, and synthetic DNA. Vectors used for library may be bacteriophage, plasmid, cosmid, and phagemid. The DNA may be directly amplified using a mRNA fraction prepared from the cells and tissues described above by Reverse Transcriptase Polymerase Chain Reaction (hereinafter to be abbreviated as RT-PCR method).

Concretely, as the DNA encoding the partial peptides of this invention, for example: (1) DNA containing a partial nucleotide sequence of the DNA presented by SEQ ID NO:2, SEQ ID NO:4, SEQ ID NO:6, SEQ ID NO:8 or SEQ ID NO:10, and (2) DNA containing a partial nucleotide sequence of the DNA that contains a nucleotide sequence that hybridizes to the nucleotide sequence presented by SEQ ID NO:2, SEQ ID NO:4, SEQ ID NO:6, SEQ ID NO:8 or SEQ ID NO:10 under a high stringent condition and encoding a receptor protein having substantially identical activities (e.g., ligand binding activity, signal transduction activity and the like) with those of GPR40 having an amino acid sequence presented by SEQ ID NO:1, SEQ ID NO:3, SEQ ID NO:5, SEQ ID NO:7 or SEQ ID NO:9 and the like are used.

For the DNAs that hybridize to the nucleotide sequence presented by SEQ ID NO:2, SEQ ID NO:4, SEQ ID NO:6, SEQ ID NO:8 or SEQ ID NO:10, for example, DNAs containing about 85% or more, preferably about 90% or more, more preferably about 95% or more homology to the nucleotide sequence presented by SEQ ID NO:2, SEQ ID NO:4, SEQ ID NO:6, SEQ ID NO:8 or SEQ ID NO:10 are used.

For the means for cloning the DNA completely encoding GPR40 or its partial peptides (hereinafter sometimes to be abbreviated as GPR40), the DNA is amplified by PCR using synthetic DNA primers containing a partial nucleotide sequence of GPR40, or the DNA inserted in an appropriate vector can be selected by hybridization with the labeled DNA fragment encoding a part or entire region of GPR40 or synthetic DNA. Hybridization can be performed, for example, by the method described in Molecular Cloning, 2nd (J. Sambrook et al., Cold Spring Harbor Lab. Press, 1989) and the like. Hybridization can also be performed when a commercial library is used according to the method described in the attached instruction.

Conversion of the DNA nucleotide sequences can be performed by PCR or methods known per se such as ODA-LA PCR, Gapped duplex method and Kunkel method or methods analogous thereto using a known kit such as Mutan™-super Express Km (TAKARA SHUZO CO., LTD.), Mutan™-K (TAKARA SHUZO CO., LTD.) and the like.

The cloned DNAs encoding GPR40 can be used without treatment or used after digestion with restriction enzymes or addition of linkers when desired. Said DNA may contain the translational initiation codon ATG at the 5'-end and translational stop codon TAA, TGA, or TAG at the 3'-end. These translational initiation codon and stop codon can be added using an appropriate synthetic DNA adaptor.

Expression vectors for GPR40 can be manufactured, for example, as follows: (i) The objective DNA fragment is excised from the DNA encoding GPR40, and (ii) the DNA fragment is ligated to downstream of the promoter in an appropriate vector.

For the vector, *Escherichia coli*-derived plasmid (e.g. pBR322, pBR325, pUC12, pUC13), *Bacillus subtilis*-derived plasmid (e.g. pUB110, pTP5, pC194), yeast-derived plasmid (e.g. pSH19, pSH15), bacteriophages such as λ phage, animal viruses such as retrovirus, vaccinia virus, baculovirus, and pA1-11, pXT1, pRC/CMV, pRC/RSV, and pcDNAI/Neo are used.

Any promoter that is appropriate and corresponds to the host used for the gene expression may be used as the promoter used in this invention. For example, when animal cells are used as the host, SRα promoter, SV40 promoter, LTR promoter, CMV promoter, and HSV-TK promoter are used.

Among them, CMV promoter and SRα promoter are preferred. When the host is bacteria of *Escherichia* genus, trp promoter, lac promoter, recA promoter, λP$_L$ promoter, and lpp promoter and the like are preferred. When the host is bacteria of *Bacillus* genus, SPO1 promoter, SPO2 promoter, penP promoter and the like are preferred. When the host is yeast, PHO5 promoter, PGK promoter, GAP promoter, ADH promoter and the like are preferred. When the host is insect cells, polyhedrin promoter, P10 promoter and the like are preferred.

In addition to the vectors described above, expression vectors containing enhancer, splicing signal, polyA addition signal, selection marker, and SV40 replication origin (hereinafter sometimes to be abbreviated as SV40ori) may be used when desired. For the selection marker, for example, dihydrofolate reductase (hereinafter sometimes to be abbreviated as dhfr) gene [methotrexate (MTX)-resistant], ampicillin resistance gene (hereinafter to be abbreviated as Amp$^r$), and neomycin resistance gene (hereinafter sometimes to be abbreviated as Neo$^r$, G418 resistant) are used. Especially, when dhfr gene is used as a selection marker using CHO (dhfr$^-$) cells, the objective gene can be selected using a thymidine-free medium.

Where necessary, moreover, a signal sequence appropriate for the host is added to the N-terminal of the receptor protein of this invention. When the host is bacteria of *Escherichia* genus, PhoA signal sequence and OmpA signal sequence and the like are used. When the host is bacteria of *Bacillus* genus, α-amylase signal sequence and subtilisin signal sequence and the like are used. When the host is yeast, MFα signal sequence and SUC2 signal sequence are used. When the host is animal cells, insulin signal sequence, α-interferon signal sequence, and the signal sequence of antibody molecule and the like can be used.

Using the vectors containing the DNA encoding GPR40 constructed as described above, transformants can be manufactured.

For the host, for example, *Escherichia* genus, *Bacillus* genus, yeast, insect cells, insects, animal cells and the like are used.

Specific examples of the host of *Escherichia* genus are *Escherichia coli* K12 DH1 [Proceedings of the National Academy of Sciences of the USA (Proc. Natl. Acad. Sci. USA) Vol. 60, 160 (1968)], JM103 [Nucleic Acids Research Vol. 9, 309 (1981)], JA221 [Journal of Molecular Biology Vol. 120, 517 (1978)], HB101 [Journal of Molecular Biology Vol. 41, 459 (1969)], C600 [Genetics Vol. 39, 440 (1954)] and the like.

For the host of *Bacillus* genus, for example, *Bacillus subtilis* MI114 [Gene Vol. 24, 255 (1983)] 207-21 [Journal of Biochemistry Vol. 95, 87 (1984)] and the like are used.

For the host of yeast, for example, *Saccharomyces cerevisiae* AH22, AH22R⁻, NA87-11A, DKD-5D, 20B-12, *Schizosaccharomyces pombe* NCYC1913, NCYC2036, and *Pichia pastoris* are used.

For the host of insect cells, for example, when the virus is AcNPV, *Spodoptera frugiperda* cells (Sf cells), MG1 cells derived from the middle gut of *Trichoplusia ni*, High Five™ cells derived from *Trichoplusia ni* eggs, *Mamestra brassicae*-derived cells, or *Estigmena acrea*-derived cells are used. When the virus is BmNPV, silkworm-derived cells *Bombyx mori* N (BmN cells) are used. For said Sf cells, for example, SF9 cells (ATCC CRL1711), Sf21 cells (Vaughn, J. L. et al., In Vivo 13, 213-217 (1977)) are used.

For the host of insect, for example, silkworm larvae are used [Maeda et al., Nature, Vol. 315, 592 (1985)].

For the host of animal cells, for example, monkey COS-7 cells, Vero, Chinese hamster CHO cells (hereinafter to be abbreviated as CHO cells), dhfr gene-deficient Chinese hamster cells CHO (hereinafter to be abbreviated as CHO (dhfr⁻) cells), mouse L cells, mouse AtT-20, mouse myeloma cells, rat GH3, and human FL cells are used.

Bacteria of *Escherichia* genus can be transformed according to, for example, the methods described in Proc. Natl. Acad. Sci. USA Vol. 69, 2110 (1972) and Gene Vol. 17, 107 (1982) and the like.

Bacteria of *Bacillus* genus can be transformed according to, for example, the method described in Molecular & General Genetics Vol. 168, 111 (1979) and the like.

Yeast can be transformed according to, for example, the methods described in Methods in Enzymology Vol. 194, 182-187 (1991) and Proc. Natl. Acad. Sci. USA Vol. 75, 1929 (1978) and the like.

Insect cells and insects can be transformed according to, for example, the method described in Bio/Technology, 6, 47-55 (1988) and the like.

Animal cells can be transformed by, for example, the methods described in Cell Engineering (Saibo Kogaku) Separate Vol. 8, New Cell Engineering Experimental Protocol, 263-267 (1995) (Shujun-sha) and Virology Vol. 52, 456 (1973).

As described above, the transformants transformed by the expression vector containing the DNA encoding GPR40 can be obtained.

For the medium for culturing the transformants wherein the host is *Escherichia* or *Bacillus* host, liquid medium is suitable, in which carbon source, nitrogen source, inorganic compounds, and other substances necessary for the growth of the transformants are contained. The carbon source includes for example, glucose, dextrin, soluble starch, sucrose and the like. The nitrogen source includes for example, inorganic and organic compounds such as ammonium salts, nitrates, corn steep liquor, peptone, casein, meat extract, soybean cake, potato extract and the like. The inorganic compounds include for example, calcium chloride, sodium dihydrogen phosphate, magnesium chloride and the like. Yeast extract, vitamins, and growth factors may be added. The pH of about 5-8 is desirable for the culture.

For the culture medium for bacteria of *Escherichia* genus, for example, M9 medium containing glucose and casamino acids (Miller, Journal of Experiments in Molecular Genetics, 431-433, Cold Spring Harbor Laboratory, New York, 1972) is preferred. When more efficiency is required for the function of the promoter, reagent such as 3β-indolyl acrylate may be added.

When the host is bacteria of *Escherichia* genus, the bacteria are generally cultured at about 15-43° C. for about 3-24 hours, and aeration or agitation may be added to the culture, when necessary.

When the host is bacteria of *Bacillus* genus, the bacteria are generally cultured at about 30-40° C. for about 6-24 hours, and aeration or agitation may be added to the culture, when necessary.

For the medium for culturing the transformant of yeast host, for example, Burkholder minimum medium [Bostian, K. L. et al., Proc. Natl. Acad. Sci. USA Vol. 77, 4505 (1980)] and SD medium containing 0.5% casamino acid [Bitter, G. A. et al., Proc. Natl. Acad. Sci. USA Vol. 81, 5330 (1984)] are used. The pH of the medium is preferably adjusted to about 5-8. The culture are generally performed at about 20-35° C. for about 24-72 hours, and aeration or agitation may be added to the culture, when necessary.

When transformants of insect cell host or insect host are cultured, Grace's insect medium (Grace, T. C. C., Nature, 195, 788 (1962)) containing appropriate supplements such as inactivated 10% bovine serum is used as a medium. The pH of the medium is preferably adjusted to about 6.2-6.4. Usually, the culture is performed at 27° C. for about 3-5 days, and aeration or agitation may be added to the culture, when necessary.

When the transformants of animal cell host are cultured, for example, MEM medium containing about 5-20% fetal calf serum [(Science Vol. 122, 501 (1952)], DMEM medium [Virology Vol. 8, 396 (1959)], RPMI 1640 medium [The Journal of the American Medical Association vol. 199, 519 (1967)], 199 medium [Proceeding of the Society for the Biological Medicine Vol. 73, 1 (1950)] and the like are used as the medium. The pH is preferably adjusted to about 6-8. Usually, the culture is performed at about 30-40° C. for about 15-60 hours, and aeration or agitation may be added to the culture, when necessary.

As described above, GPR40 can be produced intracellularly, on cell membrane or extracellularly of the transformants.

GPR40 can be purified from the culture described above by, for example, the methods described below.

When GPR40 is extracted from the cultured bacteria or cells, the bacteria or cells are collected after culture by a known method, and suspended in appropriate buffer. The bacteria or cells are then disrupted using ultrasonication, lysozymes, and/or by freezing-thawing and the like, and the crude extract of GPR40 is obtained by centrifugation or filtration. The buffer may contain protein-denaturants such as urea and guanidine hydrochloride and a surfactant such as Triton X-100™. When GPR40 is secreted into the culture supernatant, the supernatant is separated from the bacteria or cells after the completion of culture and collected using a method known per se.

For purification of GPR40 from the culture supernatant or the extract obtained as described above, methods known per se for separation and purification can be appropriately combined. These methods known per se for separation and purification include methods using solubility such as salting out and solvent precipitation, methods mainly using differences in molecular weight such as dialysis, ultrafiltration, gel filtration, and SDS-polyacrylamide gel electophoresis, methods using differences in electric charge such as ion-exchange chromatography, methods using specific affinity such as affinity chromatography, methods using differences in hydrophobicity such as reverse-phase high performance liquid chromatography, methods using differences in isoelectric point such as isoelectric focusing and the like.

When GPR40 thus obtained is in a free form, the free form can be converted to salts by methods known per se or methods analogous thereto. Conversely, when GPR40 is obtained in a salt form, the salt form can be converted to the free form or other salts by methods known per se or methods analogous thereto.

GPR40 produced by transformants can be optionally modified or partially removed a polypeptide from GPR40 by treating GPR40 with an appropriate protein-modifying enzyme before or after purification. For the protein-modifying enzyme, for example, trypsin, chymotrypsin, arginylendopeptidase, protein kinase, glycosidase and the like are used.

The activity of GPR40 thus produced can be measured by binding assay using labeled ligands and by enzyme immunoassay using specific antibody and the like.

In the following, a screening method for a compound that changes the bindability between GPR40 and fatty acid, which is a physiological ligand thereof (i.e., other ligand to GPR40, GPR40 agonist, GPR40 antagonist and the like) is described in detail.

As mentioned above, since the compound of the present invention has a GPR40 activating activity, GPR40 ligand, agonist or antagonist can be efficiently screened for from the test compound by the use of a binding assay system using GPR40 (including cells expressing recombinant or endogenous GPR40, cell membrane fraction thereof and the like) and the compound of the present invention as a surrogate ligand.

The GPR40 ligand and agonist are physiological and non-physiological compounds that bind with GPR40 to show a cell stimulating activity (hereinafter to be generally referred to as "GPR40 agonist").

As the cell stimulating activity, for example, an activity promoting or suppressing arachidonic acid release, acetylcholine release, intracellular $Ca^{2+}$ release, intracellular CAMP production, intracellular cGHP production, inositol phosphate production, cell membrane potential variation, phosphorylation of intracellular protein, c-fos activation, pH reduction and the like, and the like, particularly intracellular $Ca^{2+}$ concentration increasing activity and intracellular cAMP production suppressing activity can be mentioned.

The GPR40 antagonist is a compound that binds with GPR40 but does not show a cell stimulating activity, or shows an activity reverse to the cell stimulating activity (reverse activating activity). In the present specification, therefore, the "GPR40 antagonist" is used as a concept encompassing not only what is called neutral antagonists but also inverse agonists.

In addition, by the screening method of the present invention, a compound that potentiates binding force of fatty acid and GPR40, or a compound that decreases the binding force of fatty acid and GPR40 and the like can be screened for.

That is, the present invention provides a screening method of a GPR40 agonist or a GPR40 antagonist, which comprises comparing (i) when GPR40 and the compound of the present invention are brought into contact and (ii) when GPR40, the compound of the present invention and a test compound are brought into contact.

The screening method of the present invention is characterized in that, for example, binding amount, cell stimulating activity and the like of the compound of the present invention relative to GPR40 in the cases of (i) and (ii) are determined and compared.

More specifically, the present invention provides a) a screening method of GPR40 agonist or GPR40 antagonist, which is characterized in that the amounts of the labeled compound of the present invention bound to GPR40 in the cases of when a labeled compound of the present invention is brought into contact with GPR40 and when a labeled compound of the present invention and a test compound are brought into contact with GPR40 are determined and compared, b) a screening method of GPR40 agonist or GPR40 antagonist, which is characterized in that the amounts of the labeled compound of the present invention bound to a cell or a membrane fraction in the cases of when a labeled compound of the present invention is brought into contact with the cell containing GPR40 or the membrane fraction of the cell and when a labeled compound of the present invention and a test compound are brought into contact with the cell containing GPR40 or the membrane fraction of the cell are determined and compared, c) a screening method of GPR40 agonist or GPR40 antagonist, which is characterized in that the amount of the labeled compound of the present invention bound to GPR40 in the cases of when a labeled compound of the present invention is brought into contact with GPR40 expressed on a cell membrane by culture of a transformant containing GPR40 DNA and when a labeled compound of the present invention and a test compound are brought into contact with GPR40 expressed on a cell membrane by culture of a transformant containing GPR40 DNA are determined and compared, d) a screening method of GPR40 agonist or GPR40 antagonist, which is characterized in that the cell stimulating activity via GPR40 in cells containing GPR40 are determined in the presence or absence of a test compound and compared, e) a screening method of GPR40 agonist or GPR40 antagonist, which is characterized in that the cell stimulating activity via GPR40 expressed on a cell membrane by culture of a transformant containing GPR40 DNA are determined in the presence or absence of a test compound and compared, f) a screening method of GPR40 agonist or GPR40 antagonist, which is characterized in that the cell stimulating activity via GPR40 in the cases of when a compound of the present invention is brought into contact with a cell containing GPR40 and when a compound of the present invention and a test compound are brought into contact with a cell containing GPR40 are determined and compared, and g) a screening method of GPR40 agonist or GPR40 antagonist, which is characterized in that the cell stimulating activity via GPR40 in the cases of when a compound of the present invention is brought into contact with GPR40 expressed on a cell membrane by culture of a transformant containing GPR40 DNA and when a compound of the present invention and a test compound are brought into contact with GPR40 expressed on a cell membrane by culture of a transformant containing GPR40 DNA are determined and compared.

Since the compound of the present invention can be easily labeled as compared to fatty acid which is a natural ligand, it is suitable for screening.

As the test compound, for example, peptide, protein, non-peptidic compound, synthetic compound, fermentation product, cell extract, plant extract, animal tissue extract and the like are used and these compounds may be novel compounds or known compounds.

The test compound may form a salt, and as the salt of the test compound, salts with physiologically acceptable acid (e.g., inorganic acid and the like), base (e.g., organic acid and the like) and the like are used, and physiologically acceptable acid addition salts are particularly preferable. As such salts, for example, salts with inorganic acid (e.g., hydrochloric acid, phosphoric acid, hydrobromic acid, sulfuric acid and the like), salts with organic acid (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid and the like) and the like are used.

As the test compound, a compound designed to bind with a ligand binding pocket, based on the atomic coordinate of the active site of GPR40 and the site of ligand binding pocket, is preferably used. The atomic coordinate of the active site of GPR40 and the site of ligand binding pocket can be determined by a known method or a method analogous thereto.

The screening method of the present invention is concretely described in the following.

First, GPR40 to be used for the screening method of the present invention may be any as long as it contains the above-mentioned GPR40, but a cell membrane fraction of an organ of a mammal containing GPR40 is preferable. Particularly, however, since a human-derived organ is extremely difficult to obtain, human-derived GPR40 expressed in large amounts using a recombinant and the like are suitable for screening.

To manufacture GPR40, the methods described above are used, and it is preferred to express GPR40 DNA in mammalian and insect cells. For the DNA fragment encoding the objective protein region, the complementary DNA, but not necessarily limited thereto, is employed. For example, the gene fragments and synthetic DNA may also be used. To introduce a GPR40 DNA fragment into host animal cells and efficiently express the DNA there, it is preferred to insert the DNA fragment downstream of a polyhedrin promoter of nuclear polyhedrosis virus (NPV) belonging to baculovirus hosted by insects, SV40-derived promoter, retrovirus promoter, metallothionein promoter, human heat shock promoter, cytomegalovirus promoter, SRα promoter and the like. The amount and quality of the expressed receptor protein are examined by methods known per se, for example, the method described in the literature [Nambi, P. et al., *The Journal of Biological Chemistry* (J. Biol. Chem.), 267, 19555-19559, 1992].

Therefore, in the screening method of the present invention, as a material that contains GPR40, GPR40 purified by methods known per se or cells containing said GPR40 may be used. In addition, a membrane fraction of cells containing GPR40 may be used.

In the screening method of the present invention, when cells containing GPR40 are used, the cells may be fixed with glutaraldehyde, formalin, etc. The cells can be fixed by a method known per se.

The cells containing GPR40 are host cells that express said GPR40. For the host cells, *Escherichia coli, Bacillus subtilis*, yeast, insect cells, animal cells and the like are preferred.

The cell membrane fraction is a fraction containing the abundant cell membrane obtained after disruption of the cells by a method known per se. The cell disruption methods include crushing the cells using a Potter-Elvehjem homogenizer, disruption using a Waring blender or polytron (Kinematica Co.), disruption by ultrasonication, and disruption by passing the cells through a narrow nozzle with compressing the cells using a French Press. For the cell membrane fractionation method, fractionation based on centrifugal force such as centrifugation for fractionation and density gradient centrifugation are mainly used. For example, disrupted cell suspension is centrifuged at a low speed (500-3,000 rpm) for a short time (usually about 1-10 minutes), the supernatant is then centrifuged at a high speed (15,000-30,000 rpm) for usually 30 minutes-2 hours, and the obtained precipitate is used as the membrane fraction. The membrane fraction contains many membrane components such as the expressed GPR40, and phospholipids and membrane proteins derived from the cells.

The amount of GPR40 in the cells and membrane fractions containing GPR40 is preferably $10^3$-$10^8$ molecules and suitably $10^5$-$10^7$ molecules per cell. A higher expression amount enhances ligand binding activity (specific activity) per membrane fraction, which makes not only construction of a highly sensitive screening system but also assay of a large amount of specimen in a single lot possible.

To perform the above-mentioned a)-c) for screening for a GPR40 agonist or antagonist, for example, a suitable GPR40 fraction and a labeled compound of the present invention are necessary.

As the GPR40 fraction, natural type GPR40 fraction, a recombinant type GPR40 fraction having an activity equivalent thereto and the like are desirable. Here, the equivalent activity means the same level of ligand binding activity, signal transduction activity and the like.

As the labeled compound of the present invention, for example, a compound of the present invention labeled with radioisotope such as [$^3$H], [$^{125}$I], [$^{14}$C], [$^{35}$S] or the like, fluorescence substance, enzyme or the like, or the like is used.

Concretely, to perform screening for a GPR40 agonist or antagonist, firstly, GPR40 specimen is prepared by suspending the cells or cell membrane fraction containing GPR40 into buffer appropriate for the screening. For the buffer, any buffer that does not inhibit the binding of ligands to GPR40 such as phosphate buffer and Tris-hydrochloride buffer and the like having pH 4-10 (preferably pH 6-8) can be used. To reduce non-specific binding, a surfactant such as CHAPS, Tween-80™ (Kao-Atras Co.), digitonin, deoxycholate and the like may be added to the buffer. Further, to inhibit degradation of GR40 and the test compound (peptidic compound) by proteases, protease inhibitors such as PMSF, leupeptin, E-64 (Peptide Research Laboratory, Co.), and pepstatin may be added. To 0.01-10 ml of the receptor protein solution, a specified amount (5,000-500,000 cpm) of labeled ligand is added so that $10^{-4}$ M to $10^{-10}$ M of the test compound can be exist simultaneously. To examine the amount of non-specific binding (NSB), reaction tubes containing a highly excessive amount of non-labeled compound of the present invention are also prepared. The reaction is performed at about 0° C.-50° C., preferably about 4° C.-37° C., for about 20 minutes-24 hours, preferably for about 30 minutes-3 hours. After the reaction, the reaction solution is filtered through a glass fiber filter and the like and the filter was washed with an appropriate amount of the buffer. The radioactivity remaining on the glass fiber filter is measured using a liquid scintillation counter or γ-counter. A test compound showing a specific binding amount (B-NSB) of, for example, not more than 50%, wherein a count ($B_0$-NSB) obtained by subtracting a non-specific binding amount (NSB) from a count ($B_0$) free of antagonistic substance is taken as 100%, can be selected as a candidate substance having an antagonistic inhibitory ability.

To perform the above-mentioned d)-g) of screening for a GPR40 agonist or antagonist, GPR40 mediated cell stimulating activity (e.g. activity promoting or suppressing arachidonic acid release, acetylcholine release, intracellular $Ca^{2+}$ release, intracellular cAMP production, intracellular cGMP production, inositol phosphate production, cell membrane potential variation, phosphorylation of intracellular protein, c-fos activation, pH reduction and the like, particularly intracellular $Ca^{2+}$ concentration increasing activity and intracellular cAMP production suppressing activity) can be measured using method known per se or commercial assay kits.

Concretely, first, cells containing GPR40 are cultured in multiwell plates and the like. Before screening, the medium is exchanged to fresh medium or an appropriate buffer that exhibits no toxicity for the cells. After the cells are incubated by adding a test compound and the like for a specified time, the cells are extracted or the supernatant is collected, and the product is quantified according to the corresponding method. When detection of the production of a substance (e.g., $Ca^{2+}$, cAMP and the like) to be used as an index of cell stimulating activity is difficult due to catabolic enzymes contained in the cell, an inhibitor of the catabolic enzymes may be added before assay. As regards the activity of CAMP production inhibition and the like, it can be detected as a production inhibitory action on the cell made to show increased basic production amount with forskolin and the like.

To perform screening by determining the cell stimulating activity, the cells expressing suitable GPR40 are necessary. As the cells expressing GPR40, cell lines having natural type GPR40, cell lines expressing the above-mentioned recombinant type GPR40 and the like are desirable.

A specific evaluation method to determine whether the compound obtained by screening is a GPR40 agonist or a GPR40 antagonist comprises the following (i) or (ii).

(i) Using the screening method of the aforementioned a)-c), a compound that changes the bindability of the compound of the present invention and GPR40 (particularly, binding is inhibited) or a salt thereof is obtained, and whether the compound or a salt thereof has the above-mentioned cell stimulating activity or not is determined. The compound having said cell stimulating activity or a salt thereof is an agonist and the compound free of said cell stimulating activity or a salt thereof is an antagonist.

(ii) (a) A test compound is brought into contact with a cell containing GPR40 and the above-mentioned cell stimulating activity is determined. A test compound having said cell stimulating activity is an agonist of GPR40.

(b) The cell stimulating activity when the compound of the present invention is brought into contact with a cell containing GPR40 and when the compound of the present invention and a test compound are brought into contact with a cell containing GPR40 are determined and compared. A test compound capable of decreasing the cell stimulating activity of the compound of the present invention is an antagonist of GPR40.

More specifically, the evaluation criterion described in Example 202 can be used.

The screening kit for GPR40 agonist or GPR40 antagonist comprises the compound of this invention, GPR40, a cell containing GPR40 or a membrane fraction of a cell containing GPR40 and the like.

Examples of the screening kit of this invention are as follow.

1. Reagents for Screening
a) Buffers For Measurement And Washing
   Hanks' Balanced Salt Solution (Gibco Co.) supplemented with 0.05% bovine serum albumin (Sigma Co.).
   The solution is sterilized by filtration through a 0.45 μm filter, and stored at 4° C. or may be prepared at use.
b) Standard GPR40
   CHO cells expressing GPR40 are passed in 12-well plates at a density of $5 \times 10^5$ cells/well and cultured at 37° C. under 5% $CO_2$ and 95% air for two days.
c) Labeled Compound of the Present Invention (Hereinafter to be Referred to as Labeled Compound)
   The compound of the present invention labeled with Commercial [$^3$H], [$^{125}$I], [$^{14}$C], [$^{35}$S] or the like. The compound in the form of aqueous solution is stored at 4° C. or −20° C., and the solution is diluted to 1 μM with measurement buffer at use.
d) Standard Solution of the Compound of the Present Invention (Hereinafter to be Referred to as Non-Labeled Compound Standard Solution)
   The compound of the present invention is dissolved in PBS containing 0.1% bovine serum albumin (manufactured by SIGMA) to 1 mM and preserved at −20° C.

2. Measurement Methods
a) CHO cells expressing GPR40 are cultured in a 12-well tissue culture plate and washed twice with 1 ml of measurement buffer, and 490 μl of the measurement buffer is added to each well.
b) A solution of a test compound (5 μl) at $10^{-3}$-$10^{-10}$ M is added, 5 μl of labeled test compound is added, and the cell are reacted at room temperature for one hour. To measure the non-specific binding, 5 μl of the non-labeled compound standard solution ($10^{-3}$ M) is added in place of the test compound.
c) The reaction solution is removed, and the wells are washed three times with 1 ml of washing buffer. The labeled ligand bound to the cells is dissolved with 0.2N NaOH-1% SDS, and mixed with 4 ml of liquid scintillator A (Wako Pure Chemical Industries, Ltd.)
d) The radioactivity is measured using a liquid scintillation counter (Beckman Co.), and Percent Maximum Binding (PMB) is determined by the following formula:

$$PMB=[(B-NSB)/(B_0-NSB)]\times 100$$

PMB: Percent Maximum Binding
B: value with addition of sample
NSB: Non-specific Binding (amount of non-specific binding)
$B_0$: maximum binding amount The screening method of the present invention is characterized by screening for a GPR40 agonist or GPR40 antagonist using, as a surrogate ligand, the compound of the present invention screened using GPR40 and its endogenous ligand, fatty acid. Use of such synthetic ligand is advantageous as compared to screening using an endogenous ligand, which is a naturally occurring substance, in that labeling of the ligand is easy and the screening can be performed efficiently.

The compound obtained by the screening method or screening kit of the present invention, and a salt thereof are GPR40 agonists or GPR40 antagonists.

The GPR40 agonist and GPR40 antagonist obtained using the screening method or screening kit of the present invention may form a salt, and as such salt, salts with physiologically acceptable acids (e.g., inorganic acid and the like), base (e.g., organic acid and the like) and the like are used, physiologically acceptable acid addition salts are particularly preferable. As such salts, for example, salts with inorganic acid (e.g., hydrochloric acid, phosphoric acid, hydrobromic acid, sulfuric acid and the like), salts with organic acid (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid and the like) and the like are used.

Since GPR40 agonist has a physiological activity similar to that of fatty acid, which is a ligand to GPR40, it is useful as a safe and low toxic pharmaceutical agent according to the physiological activity of the fatty acid.

Since GPR40 antagonist can inhibit the physiological activity of fatty acid, which is a ligand to GPR40, it is useful as a safe and low toxic pharmaceutical agent to suppress the physiological activity of fatty acid.

Since a compound that potentiates the binding force between fatty acid and GPR40 can potentiate the physiological activity of fatty acid, which is a ligand to GPR40, it is useful as a safe and low toxic pharmaceutical agent according to the physiological activity of the fatty acid.

Since a compound that decreases the binding force between fatty acid and GPR40 can decrease the physiological activity of fatty acid, which is a ligand to GPR40, it is useful as a safe and low toxic pharmaceutical agent to suppress the physiological activity of fatty acid.

Specifically, the (i) GPR40 agonist and (ii) compound potentiating the binding force between fatty acid and GPR40 or a salt thereof, which are obtained using the screening method or screening kit of the present invention, are useful as an agent for the prophylaxis or treatment of, for example, diseases such as diabetes, impaired glucose tolerance, ketosis, acidosis, diabetic neuropathy, diabetic nephropathy, diabetic retinopathy, hyperlipidemia, genital disorder, skin disease, arthropathy, osteopenia, arteriosclerosis, thrombotic disease, dyspepsia, memory and learning disorder and the like, pancreatic function regulator (e.g., pancreatic function improving agent), insulin secretagogue, a hypoglycemic agent or pancreatic β cell protector. Diabetes includes insulin-dependent (type I) diabetes, non-insulin-dependent (type II) diabetes, gestational diabetes and the like.

The (i) GPR40 antagonist and (ii) compound decreasing the binding force between fatty acid and GPR40 or a salt thereof, which are obtained using the screening method or screening kit of the present invention, are useful as an agent for the prophylaxis or treatment of, for example, diseases such as obesity, hyperlipidemia, type II diabetes, hypoglycemia, hypertension, diabetic neuropathy, diabetic nephropathy, diabetic retinopathy, edema, insulin resistance syndrome, unstable diabetes, fatty atrophy, insulin allergy, insulinoma, arteriosclerosis, thrombotic disease, lipotoxicity, hyperinsulinemia, cancer and the like, pancreatic function regulator (e.g., pancreatic function improving agent), insulin secretion suppressing agent, pancreatic β cell protector, hypoglycemic drug. Here, hyperlipidemia includes hypertriglyceridemia, hypercholesterolemia, hypo-HDL-cholesterolemia, postprandial hyperlipidemia and the like. Particularly, an antagonist to GPR40 is effective for hypoglycemia since it suppresses excess insulin secretion, and prevents fatigue of pancreatic β cell caused by excessive insulin secretion (protection of pancreatic β cells) and thus effective for type II diabetes.

The GPR40 agonist or GPR40 antagonist obtained using the screening method or screening kit of the present invention can be used in combination with the aforementioned concomitant drugs. In this case, the administration period of a GPR40 agonist or GPR40 antagonist obtained using the screening method or screening kit of the present invention, and a concomitant drug is not limited, and they may be simultaneously administered to the administration subject, or may be administered in a staggered manner. The dose of the concomitant drug can be appropriately selected based on the dose clinically employed. In addition, the mixing rate of the GPR40 agonist or GPR40 antagonist obtained using the screening method or screening kit of the present invention and a concomitant drug can be appropriately determined according to the administration subject, administration route, target disease, condition, combination and the like. For example, when the administration subject is a human, for example, 0.01 to 100 parts by weight of a concomitant drug is used per 1 part by weight of the GPR40 agonist.

When the GPR40 agonist or GPR40 antagonist obtained using the screening method or screening kit of the present invention is used as the above-mentioned pharmaceutical agent, it can be prepared in the same manner as the aforementioned pharmaceutical agent containing the compound of the present invention.

Since the preparation obtained in this way is safe and low toxic, it can be administered to, for example, human and mammals (e.g., rats, mice, rabbits, sheep, pigs, cattle, cats, dogs, monkeys and the like).

While the dose of GPR40 agonist or GPR40 antagonist varies depending on the administration subject, target organ, condition, administration method and the like, in the case of oral administration, it is generally, for example, about 0.1 to 100 mg, preferably about 1.0 to 50 mg, more preferably about 1.0 to 20 mg, of a GPR40 agonist for diabetic patients (body weight 60 kg) for one day. For parenteral administration, while the dose varies depending on the administration subject, target organ, condition, administration method and the like, it is generally conveniently, for example, about 0.01 to about 30 mg, preferably about 0.1 to about 20 mg, more preferably about 0.1 to about 10 mg of a GPR40 agonist for diabetic patients (body weight 60 kg) by intravenous injection. For other animals, a dose converted to the amount per on the body weight 60 kg can be administered.

The present invention is explained in detail in the following by referring to Reference Examples, Examples, Formulation Examples and Experimental Examples, which are mere embodiments and do not limit the present invention. They may be modified within the range that does not deviate from the scope of the present invention.

In the following Reference Examples and Examples, the "room temperature" generally means about 10° C. to about 35° C. As to %, yield means mol/mol %, the solvent used for chromatography means % by volume, and others mean wt %. Those that cannot be confirmed by proton NMR spectrum, such as OH and NH protons that are broad, are not described in the data.

Other abbreviations used in the specification mean the following.

s: singlet
d: doublet
t: triplet
q: quartet
m: multiplet br: broad
J: coupling constant
Hz: Hertz
CDCl$_3$: deuterated chloroform
DMSO-d$_6$: deuterated dimethyl sulfoxide
$^1$H NMR: proton nuclear magnetic resonance When bases or amino acids are expressed in abbreviations in the present specification and drawings, the following abbreviations in accordance with IUPAC-IUB Commission on Biochemical Nomenclature or based on customary abbreviations in this field are used. If amino acids can occur as optical isomers, L-isomers are referred to unless otherwise specified.

DNA: deoxyribonucleic acid
cDNA: complementary deoxyribonucleic acid
A: adenine
T: thymine
G: guanine
C: cytosine
U: uracil
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediamine tetraacetic acid
SDS: sodium dodecyl sulfate
Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysin
Arg: arginine
His: histidine
Phe: phenylalanine
Tyr: tyrosine
Trp: tryptophan
Pro: proline
Asn: asparagine
Gln: glutamine
pGlu: pyroglutamic acid
*: corresponds to termination codon
Me: methyl group
Et: ethyl group
Bu: butyl group
Ph: phenyl group
TC: thiazolidine-4(R)-carboxamide group The substituent groups, protecting groups and reagents appearing frequently in the present specification are expressed in the following symbols.

Tos: p-toluenesulfonyl
CHO: formyl
Bzl: benzyl
Cl$_2$Bzl: 2,6-dichlorobenzyl
Bom: benzyloxymethyl
Z: benzyloxycarbonyl
Cl-Z: 2-chlorobenzyloxycarbonyl
Br-Z: 2-bromobenzyloxycarbonyl
Boc: t-butoxycarbonyl
DNP: dinitrophenol
Trt: trityl
Bum: t-butoxymethyl
Fmoc: N-9-fluorenylmethoxycarbonyl
HOBt: 1-hydroxybenzotriazole
HOOBt: 3,4-dihydro-3-hydroxy-4-oxo-1,2,3-benzotriazine
HONB: 1-hydroxy-5-norbornene-2,3-dicarboxylmide
DCC: N,N'-dicyclohexylcarbodiimide In the following Examples, mass spectrum (MS) was measured under the following conditions.
MS measurement tools: ZMD (Waters Corporation), ZQ2000 (Waters Corporation) or Platform II (Micromass Ltd.).
Ionization method: Electron Spray Ionization (ESI) or Atmospheric Pressure Chemical Ionization (APCI). Unless specifically indicated, ESI was used.

In Examples, purification by preparative HPLC was performed under the following conditions.
preparative HPLC tools: high through-put purification system (Gilson, Inc.)
column: YMC Combiprep ODS-A S-5 μm, 20×50 mm solvent:
Solution A; 0.1% trifluoroacetic acid-containing water,
Solution B; 0.1% trifluoroacetic acid-containing acetonitrile
gradient cycle A: 0.00 min (Solution A/Solution B=90/10), 1.20 min (Solution A/Solution B=90/10), 4.75 min (Solution A/Solution B=0/100), 7.30 min (Solution A/Solution B=0/100), 7.40 min (Solution A/Solution B=90/10), 7.50 min (Solution A/Solution B=90/10).
gradient cycle B: 0.00 min (Solution A/Solution B=95/5), 1.00 min (Solution A/Solution B=95/5), 5.20 min (Solution A/Solution B=5/95), 6.40 min (Solution A/Solution B=5/95), 6.50 min (Solution A/Solution B=95/5), 6.60 min (Solution A/Solution B=95/5).
flow rate: 25 ml/min,
detection method: UV 220 nm The sequence numbers in the Sequence Listing in the present specification show the following sequences.
SEQ ID NO: 1
Shows the amino acid sequence of mouse GPR40.
SEQ ID NO: 2
Shows the nucleotide sequence of cDNA encoding mouse GPR40.
SEQ ID NO: 3
Shows the amino acid sequence of rat GPR40.
SEQ ID NO: 4
Shows the nucleotide sequence of cDNA encoding rat GPR40.
SEQ ID NO: 5
Shows the amino acid sequence of human GPR40.
SEQ ID NO: 6
Shows the nucleotide sequence of cDNA encoding human GPR40.
SEQ ID NO: 7
Shows the amino acid sequence of *Macaca fascicularis* GPR40.
SEQ ID NO: 8
Shows the nucleotide sequence of cDNA encoding Macaca fascicularis GPR40.
SEQ ID NO: 9
Shows the amino acid sequence of hamster GPR40.
SEQ ID NO: 10
Shows the nucleotide sequence of cDNA encoding hamster GPR40.
SEQ ID NO: 11

Shows the nucleotide sequence of a sense strand primer used for PCR reaction in Reference Example 129 below.

SEQ ID NO: 12

Shows the nucleotide sequence of an antisense strand primer used for PCR reaction in Reference Example 129 below.

SEQ ID NO: 13

Shows the nucleotide sequence of primer 1 used for PCR reaction in Reference Example 130 below.

SEQ ID NO: 14

Shows the nucleotide sequence of primer 2 used for PCR reaction in Reference Example 130 below.

SEQ ID NO: 15

Shows the nucleotide sequence of primer 3 used for PCR reaction in Reference Example 131 below.

SEQ ID NO: 16

Shows the nucleotide sequence of primer 4 used for PCR reaction in Reference Example 131 below.

SEQ ID NO: 17

Shows the nucleotide sequence of primer 1 used for PCR reaction in Reference Example 132 below.

SEQ ID NO: 18

Shows the nucleotide sequence of primer 2 used for PCR reaction in Reference Example 132 below.

SEQ ID NO: 19

Shows the nucleotide sequence of primer 3 used for PCR reaction in Reference Example 132 below. SEQ ID NO: 20

Shows the nucleotide sequence of primer 4 used for PCR reaction in Reference Example 132 below.

SEQ ID NO: 21

Shows the nucleotide sequence of primer 1 used for PCR reaction in Reference Example 133 below.

SEQ ID NO: 22

Shows the nucleotide sequence of primer 2 used for PCR reaction in Reference Example 133 below.

The transformant *Escherichia coli* TOP10/Zero Blunt-mGPR40 obtained in Reference Example 130 below has been deposited under FERM BP-7967 at National Institute of Advanced Industrial Science and Technology, International Patent Organism Depository, Central 6, 1-1-1 Higashi, Tsukuba-shi, Ibaraki 305-8566 Japan from Mar. 18, 2002, and under IFO 16762 with Institution Fermentation Organization (IFO), 17-85, Juso-honmachi 2-chome, Yodogawa-ku, Osaka 532-8686, Japan from Feb. 14, 2002.

The transformant *Escherichia coli* JM109/pCR2.1-rGPR40 obtained in Reference Example 131 below has been deposited under FERM BP-7968 at National Institute of Advanced Industrial Science and Technology International Patent Organism Depositary, from Mar. 18, 2002, and under IFO 16763 with Institution Fermentation Organization (IFO) from Feb. 14, 2002.

The transformant *Escherichia coli* JM109/pCR2.1-monkey GPR40 obtained in Reference Example 132 below has been deposited under FERM BP-8125 at National Institute of Advanced Industrial Science and Technology International Patent Organism Depositary from Jul. 23, 2002.

The transformant *Escherichia coli* JM109/pTA hamster GPR40 obtained in Reference Example 133 below has been deposited under FERM BP-8258 with National Institute of Advanced Industrial Science and Technology International Patent Organism Depositary from Dec. 11, 2002, as transformant *Escherichia coli* JM109/pTA hamster GPR40.

REFERENCE EXAMPLE 1 methyl 4-(phenylmethoxy)benzenepropanoate

To an ice-cooled solution of methyl 4-hydroxybenzenepropanoate (0.70 g, 3.9 mmol), benzyl alcohol (0.48 mL, 4.7 mmol) and triphenylphosphine (1.2 g, 4.7 mmol) in tetrahydrofuran (5 mL) was added dropwise diethyl azodicarboxylate (0.73 mL, 4.7 mmol), and the mixture was stirred under ice-cooling for 2 hr. Water was added to the reaction mixture, and the mixture was extracted with ethyl acetate. The extract was washed with water and concentrated under reduced pressure. The residue was purified by silica gel column chromatography (hexane/ethyl acetate=17:3) to give the title compound (0.62 g, yield 59%) as a powder.

$^1$H NMR (CDCl$_3$) δ 2.59 (2H, t, J=7.5 Hz), 2.89 (2H, t, J=7.5 Hz), 3.66 (3H, s), 5.04 (2H, s), 6.90 (2H, d, J=8.6 Hz), 7.11 (2H, d, J=8.6 Hz), 7.29-7.44 (5H, m).

REFERENCE EXAMPLE 2

4-(phenylmethoxy)benzenepropanoic acid

To a suspension of methyl 4-(phenylmethoxy)benzenepropanoate (0.60 g, 2.2 mmol) in methanol (20 mL) was added 2N aqueous sodium hydroxide solution (2 mL), and the mixture was stirred at 60° C. for 15 hrs. 2N Hydrochloric acid (3 mL) was added to the reaction mixture, and the mixture was extracted with ethyl acetate. The extract was washed with water and concentrated under reduced pressure. The residue was recrystallized from ethyl acetate-hexane to give the title compound (0.38 g, yield 67%).

melting point: 123-124° C.

$^1$H NMR (CDCl$_3$) δ 2.65 (2H, t, J=7.5 Hz), 2.90 (2H, t, J=7.5 Hz), 5.04 (2H, s), 6.91 (2H, d, J=8.6 Hz), 7.11 (2H, d, J=8.6 Hz), 7.28-7.44 (5H, m).

REFERENCE EXAMPLE 3 methyl 4-(2-phenylethoxy)benzenepropanoate

The title compound was obtained from methyl 4-hydroxybenzenepropanoate and phenethyl alcohol by a method similar to that of Reference Example 1. yield 89%, oil.

$^1$H NMR (CDCl$_3$) δ 2.58 (2H, t, J=7.5 Hz), 2.88 (2H, t, J=7.5 Hz), 3.08 (2H, t, J=7.1 Hz), 4.14 (2H, t, J=7.1 Hz), 6.81 (2H, d, J=8.6 Hz), 7.09 (2H, d, J=8.6 Hz), 7.20-7.34 (5H, m).

REFERENCE EXAMPLE 4

4-(2-phenylethoxy)benzenepropanoic acid

To a solution of methyl 4-(2-phenylethoxy)benzenepropanoate (0.65 g, 2.3 mmol) in methanol (3 mL) was added 2N aqueous sodium hydroxide solution (3 mL), and the mixture was stirred at 50° C. for 1 hr. 2N Hydrochloric acid (2.5 mL) was added to the reaction mixture, and the mixture was extracted with ethyl acetate. The extract was washed with water and concentrated under reduced pressure. The residue was recrystallized from ethyl acetate-hexane to give the title compound (0.50 g, yield 81%).

melting point: 91-92° C.

$^1$H NMR (CDCl$_3$) δ 2.63 (2H, t, J=7.5 Hz), 2.89 (2H, t, J=7.5 Hz), 3.08 (2H, t, J=7.2 Hz), 4.15 (2H, t, J=7.2 Hz), 6.82 (2H, d, J=8.6 Hz), 7.10 (2H, d, J=8.6 Hz), 7.20-7.34 (5H, m).

REFERENCE EXAMPLE 5 ethyl 4-(3-phenylpropoxy)benzenepropanoate

To an ice-cooled solution of ethyl 4-hydroxybenzenepropanoate (0.40 g, 2.1 mmol) in N,N-dimethylformamide (15 mL) was added 60% sodium hydride (0.11 g, 2.7 mmol), and the mixture was stirred for 30 min. 1-Bromo-3-phenylpropane (0.53 g, 2.7 mmol) was added, and the mixture was stirred at room temperature for 3 hrs. Water was added to the reaction mixture, and the mixture was extracted with ethyl acetate. The extract was washed with water, dried and concentrated. The residue was purified by silica gel column chromatography (hexane/ethyl acetate=18:1) to give the title compound (0.29 g, yield 46%). oil.

$^1$H NMR (CDCl$_3$) δ 1.23 (3H, t, J=7.1 Hz), 2.04-2.13 (2H, m), 2.58 (2H, t, J=8.1 Hz), 2.88 (2H, t, J=8.1 Hz), 3.94 (2H, t, J=6.3 Hz), 4.12 (2H, q, J=7.1 Hz), 6.81 (2H, d, J=8.6 Hz), 7.10 (2H, d, J=8.6 Hz), 7.19-7.31 (5H, m).

REFERENCE EXAMPLE 6

4-(3-phenylpropoxy)benzenepropanoic acid

The title compound was obtained from ethyl 4-(3-phenylpropoxy)benzenepropanoate by a method similar to that of Reference Example 4. yield 45%.

melting point: 109-110° C. (recrystallized from diethyl ether-hexane).

$^1$H NMR (CDCl$_3$) δ 2.05-2.13 (2H, m), 2.65 (2H, t, J=7.8 Hz), 2.80 (2H, t, J=7.8 Hz), 2.90 (2H, t, J=7.9 Hz), 3.94 (2H, t, J=6.3 Hz), 6.82 (2H, d, J=8.5 Hz), 7.11 (2H, d, J=8.5 Hz), 7.16-7.31 (5H, m).

REFERENCE EXAMPLE 7 ethyl 4-(4-phenylbutoxy)benzenepropanoate

The title compound was obtained from ethyl 4-hydroxybenzenepropanoate by a method similar to that of Reference Example 5. yield 55%, oil.

$^1$H NMR (CDCl$_3$) δ 1.23 (3H, t, J=7.1 Hz), 1.76-1.85 (4H, m), 2.57 (2H, t, J=7.4 Hz), 2.66-2.70 (2H, m), 2.88 (2H, t, J=8.1 Hz), 3.92-3.96 (2H, m), 4.12 (2H, q, J=7.1 Hz), 6.79-6.82 (m, 2H), 7.08-7.11 (m, 2H), 7.18-7.20 (m, 3H), 7.26-7.30 (m, 2H).

REFERENCE EXAMPLE 8

4-(4-phenylbutoxy)benzenepropanoic acid

The title compound was obtained from ethyl 4-(4-phenylbutoxy)benzenepropanoate by a method similar to that of Reference Example 4. yield 61%.

melting point: 79.5-80.0° C. (recrystallized from diethyl ether-hexane).

$^1$H NMR (CDCl$_3$) δ 1.70-1.90 (4H, m), 2.61-2.70 (4H, m), 2.89 (2H, t, J=7.9 Hz), 3.92-3.96 (2H, m), 6.81 (2H, d, J=8.6 Hz), 7.06 (2H, d, J=8.6 Hz), 7.12-7.31 (m, 5H).

REFERENCE EXAMPLE 9 ethyl 4-[(4-phenoxybenzoyl)amino]benzenepropanoate

To a solution of ethyl 4-aminobenzenepropanoate (0.70 g, 3.6 mmol) in N,N-dimethylformamide (25 mL) were added 4-phenoxybenzoic acid (0.85 g, 4.0 mmol), 1-ethyl-3-(3-dimethylaminopropyl)carbodiimide hydrochloride (0.76 g, 4.0 mmol) and 1-hydroxybenzotriazole monohydrate (0.61 g, 4.0 mmol), and the mixture was stirred at room temperature for 16 hrs. Water was added to the reaction mixture, and the mixture was extracted with ethyl acetate. The extract was washed with water, dried and concentrated. The residue was purified by silica gel column chromatography (hexane/ethyl acetate=2:1) to give the title compound (0.96 g, yield 68%) as a white powder.

$^1$H NMR (CDCl$_3$) δ 1.24 (3H, t, J=7.1 Hz), 2.61 (2H, t, J=8.0 Hz), 2.94 (2H, t, J=7.9 Hz), 4.13 (2H, q, J=7.1 Hz), 7.03-7.08 (4H, m), 7.16-7.21 (3H, m), 7.36-7.43 (2H, m), 7.54 (2H, t, J=8.5 Hz), 7.73 (1H, s), 7.84 (2H, d, J=8.7 Hz).

REFERENCE EXAMPLE 10

4-[(4-phenoxybenzoyl)amino]benzenepropanoic acid

The title compound was obtained from ethyl 4-[(4-phenoxybenzoyl)amino]benzenepropanoate by a method similar to that of Reference Example 4. yield 76%.

melting point: 214-215° C. (recrystallized from tetrahydrofuran-hexane).

$^1$H NMR (DMSO-d$_6$) δ 2.52 (2H, t, J=7.6 Hz), 2.79 (2H, t, J=7.6 Hz), 7.07-7.12 (4H, m), 7.18-7.25 (3H, m), 7.45 (2H, t, J=7.4 Hz), 7.65 (2H, d, J=8.4 Hz), 7.98 (2H, d, J=8.7 Hz), 10.11 (1H, s).

REFERENCE EXAMPLE 11 ethyl 4-[3-[methyl(4-phenyl-2-thiazolyl)amino]propoxy]benzenepropanoate

To an ice-cooled solution of N-methyl-4-phenyl-2-thiazolamine (0.30 g, 1.7 mmol) in N,N-dimethylformamide (5 mL) was added 60% sodium hydride (72 mg, 1.8 mmol), and the mixture was stirred for 30 min. Ethyl 4-[(3-bromopropyl)oxy]benzenepropanoate (0.57 g, 1.8 mmol), was added, and the mixture was stirred at room temperature for 3 hrs. Water was added to the reaction mixture, and the mixture was extracted with ethyl acetate. The extract was washed with water, dried and concentrated. The residue was purified by silica gel column chromatography (hexane/ethyl acetate=15:1) to give the title compound (0.58 g, yield 80%). oil.

$^1$H NMR (CDCl$_3$) δ 1.25 (3H, t, J=7.1 Hz), 2.10-2.30 (2H, m), 2.58 (2H, t, J=6.8 Hz), 2.88 (2H, t, J=6.8 Hz), 3.14 (3H, s), 3.73 (2H, t, J=6.8 Hz), 4.03 (2H, t, J=6.0 Hz), 4.12 (2H, q, J=7.1 Hz), 6.70 (1H, d, J=3.8 Hz), 6.83 (2H, d, J=8.6 Hz), 7.10 (2H, d, J=8.6 Hz), 7.20-7.30 (1H, m), 7.30-7.38 (2H, m), 7.82-7.85 (2H, m).

REFERENCE EXAMPLE 12

4-[3-[methyl(4-phenyl-2-thiazolyl)amino]propoxy]benzenepropanoic acid

The title compound was obtained from ethyl 4-[3-[methyl(4-phenyl-2-thiazolyl)amino]propoxy]benzenepropanoate by a method similar to that of Reference Example 4. yield 13%.

melting point: 89-90° C. (recrystallized from diethyl ether-hexane).

$^1$H NMR (CDCl$_3$) δ 2.14-2.23 (2H, m), 2.64 (2H, t, J=7.9 Hz), 2.90 (2H, t, J=7.9 Hz), 3.14 (3H, s), 3.73 (2H, d, J=6.8 Hz), 4.03 (2H, t, J=6.0 Hz), 6.69 (1H, s), 6.84 (2H, d, J=8.5 Hz), 7.11 (2H, d, J=8.5 Hz), 7.23-7.33 (1H, m), 7.35 (2H, t, J=7.7 Hz), 7.82 (2H, d, J=7.2 Hz).

REFERENCE EXAMPLE 13

1-[(4-bromo-2,6-difluorophenyl)oxy]-2,3-dihydro-1H-indene

The title compound was obtained from 1-indanol and 4-bromo-2,6-difluorophenol by a method similar to that of Reference Example 1. yield 74%.

melting point: 46-46° C. (recrystallized from ethyl acetate).

$^1$H NMR (CDCl$_3$) δ 2.34-2.40 (2H, m), 2.83-2.92 (1H, m), 3.20-3.31 (1H, m), 5.64 (1H, t, J=4.4 Hz), 7.04-7.13 (2H, m), 7.17-7.22 (1H, m), 7.28-7.32 (3H, m).

REFERENCE EXAMPLE 14 ethyl 4-[[4-[[methyl(4-phenyl-2-thiazolyl)amino] methyl]benzoyl]amino]benzenepropanoate The title compound was obtained as a white powder from ethyl 3-(4-aminophenyl)propionate and 4-[[methyl(4-phenyl-2-thiazolyl)amino]methyl]benzoic acid by a method similar to that of Reference Example 9. yield 89%.

$^1$H NMR (CDCl$_3$) δ 1.24 (3H, t, J=7.1 Hz), 2.61 (2H, t, J=7.9 Hz), 2.94 (2H, t, J=7.9 Hz), 3.10 (3H, s), 4.12 (2H, q, J=7.1 Hz), 4.86 (2H, s), 6.75 (1H, s), 7.20 (2H, d, J=8.4 Hz), 7.26-7.30 (2H, m), 7.38 (2H, t, J=7.8 Hz), 7.46 (2H, d, J=8.2 Hz), 7.54 (2H, d, J=8.4 Hz), 7.75 (1H, s), 7.82-7.87 (3H, m).

REFERENCE EXAMPLE 15

4-[[4-[[methyl(4-phenyl-2-thiazolyl)amino]methyl] benzoyl]amino]benzenepropanoic acid The title compound was obtained from ethyl 4-[[4-[[methyl(4-phenyl-2-thiazolyl)amino]methyl]benzoyl]amino] benzenepropanoate by a method similar to that of Reference Example 4. yield 79%.

melting point: 183-184° C. (recrystallized from ethyl acetate-hexane).

$^1$H NMR (CDCl$_3$) δ2.66 (2H, t, J=7.5 Hz), 2.94 (2H, t, J=7.5 Hz), 3.08 (3H, s), 4.84 (2H, s), 6.75 (1H, s), 7.20 (2H, d, J=8.5 Hz), 7.22-7.30 (1H, m), 7.30-7.44 (4H, m), 7.55 (2H, d, J=8.4 Hz), 7.80-7.87 (5H, m).

REFERENCE EXAMPLE 16 methyl (E)-3-[4-[(2,3-dihydro-1H-inden-1-yl)oxy]-3,5-difluorophenyl]-2-propenoate The title compound was obtained from 1-[(4-bromo-2,6-difluorophenyl)oxy]-2,3-dihydro-1H-indene by a method similar to that of Reference Example 34. yield 40%.

melting point: 74-75° C. (recrystallized from ethyl acetate-diisopropyl ether).

$^1$H NMR (CDCl$_3$) δ 2.37-2.43 (2H, m), 2.84-2.93 (1H, m), 2.32-3.32 (1H, m), 3.81 (3H, s), 5.74 (1H, t, J=4.5 Hz), 6.34 (1H, d, J=16 Hz), 7.03-7.12 (2H, m), 7.16-7.23 (1H, m), 7.28-7.35 (2H, m), 7.53 (1H, d, J=16 Hz).

REFERENCE EXAMPLE 17 methyl 4-[(2,3-dihydro-1H-inden-1-yl)oxy]benzeneacetate

The title compound was obtained from methyl 4-hydroxybenzeneacetate and 2,3-dihydro-1H-inden-1-ol by a method similar to that of Reference Example 1. yield 69%, oil.

$^1$H NMR (CDCl$_3$) δ 2.10-2.30 (1H, m), 2.45-2.65 (1H, m), 2.52-2.57 (1H, m), 3.09-3.19 (1H, m), 3.59 (2H, s), 3.70 (3H, s), 5.75 (1H, dd, J=6.6 Hz, 4.4 Hz), 6.95-6.98 (2H, m), 7.21-7.32 (5H, m), 7.43 (1H, d, J=7.2 Hz).

REFERENCE EXAMPLE 18 methyl 4-[(4-nitrophenyl)methoxy]benzenepropanoate

The title compound was obtained as a yellow powder from methyl 4-hydroxybenzenepropanoate and 4-nitrobenzylbromide by a method similar to that of Reference Example 5. yield 41%.

$^1$H NMR (CDCl$_3$) δ 2.60 (2H, t, J=8.0 Hz), 2.90 (2H, t, J=8.0 Hz), 3.66 (3H, s), 5.15 (2H, s), 6.88 (2H, d, J=8.6 Hz), 7.13 (2H, d, J=8.6 Hz), 7.60 (2H, d, J=8.7 Hz), 8.23-8.28 (2H, m).

REFERENCE EXAMPLE 19

4-[(4-nitrophenyl)methoxy]benzenepropanoic acid

The title compound was obtained from methyl 4-[(4-nitrophenyl)methoxy]benzenepropanoate by a method similar to that of Reference Example 4. yield 26%.

melting point: 179-181° C. (recrystallized from ethyl acetate-hexane).

$^1$H NMR (CDCl$_3$) δ 2.65 (2H, t, J=7.7 Hz), 2.91 (2H, t, J=7.7 Hz), 5.15 (2H, s), 6.89 (2H, d, J=8.5 Hz), 7.15 (2H, d, J=8.5 Hz), 7.60 (2H, d, J=8.5 Hz), 8.24 (2H, d, J=8.6 Hz).

REFERENCE EXAMPLE 20

4-[(2,3-dihydro-1H-inden-1-yl)oxy]benzeneacetic acid

The title compound was obtained from methyl 4-[(2,3-dihydro-1H-inden-1-yl)oxy]benzeneacetate by a method similar to that of Reference Example 4. yield 52%.

melting point: 121.0-121.5° C. (recrystallized from ethyl acetate-hexane).

$^1$H NMR (CDCl$_3$) δ 2.10-2.26 (1H, m), 2.45-2.60 (1H, m), 2.80-2.97 (1H, m), 3.09-3.14 (1H, m), 3.61 (2H, s), 5.74 (1H, dd, J=6.7 Hz, 4.4 Hz), 6.97 (2H, d, J=8.6 Hz), 6.99-7.34 (5H, m), 7.42 (1H, d, J=7.2 Hz).

REFERENCE EXAMPLE 21

4-(4-phenoxyphenoxy)benzaldehyde

To a solution of 4-phenoxyphenol (1.0 g, 5.4 mmol) in N,N-dimethylformamide (20 mL) were added 4-fluorobenzaldehyde (0.67 g, 5.4 mmol) and potassium carbonate (0.75 g, 5.4 mmol), and the mixture was stirred at 100° C. for 15 hrs. Water was added to the reaction mixture, and the mixture was extracted with ethyl acetate. The extract was washed with water, dried and concentrated. The residue was purified by silica gel column chromatography (hexane/ethyl acetate=9:1) to give the title compound (1.4 μg, yield 89%).

$^1$H NMR (CDCl$_3$) δ 7.02-7.12 (9H, m), 7.36 (2H, dd, J=7.5 Hz, 8.5 Hz), 7.85 (2H, d, J=8.7 Hz), 9.92 (1H, s).

REFERENCE EXAMPLE 22

4-([1,1'-biphenyl]-4-yloxy)benzaldehyde

The title compound was obtained from 4-hydroxybiphenyl and 4-fluorobenzaldehyde by a method similar to that of Reference Example 21. yield 37%.

¹H NMR (CDCl₃) δ 7.10-7.19 (4H, m), 7.35-7.49 (3H, m), 7.58-7.66 (4H, m), 7.87 (2H, d, J=8.7 Hz), 9.94 (1H, s).

REFERENCE EXAMPLE 23

4-[4-(phenylmethoxy)phenoxy]benzaldehyde

The title compound was obtained from 4-benzyloxyphenol and 4-fluorobenzaldehyde by a method similar to that of Reference Example 21. yield 57%.
¹H NMR (CDCl₃) δ 5.08 (2H, s), 7.00-7.03 (6H, m), 7.34-7.46 (5H, m), 7.83 (2H, d, J=8.7 Hz), 9.91 (1H, s).

REFERENCE EXAMPLE 24

4-(4-phenoxyphenoxy)benzyl alcohol

The title compound was obtained from 4-(4-phenoxyphenoxy)benzaldehyde by a method similar to that of Reference Example 32. yield 82%.
¹H NMR (CDCl₃) δ 1.64 (1H, s), 4.66 (2H, s), 6.98-7.01 (8H, m), 7.09 (1H, t, J=7.3 Hz), 7.31-7.36 (4H, m).

REFERENCE EXAMPLE 25

4-([1,1'-biphenyl]-4-yloxy)benzyl alcohol

The title compound was obtained from 4-([1,1'-biphenyl]-4-yloxy)benzaldehyde by a method similar to that of Reference Example 32. yield 66%.
¹H NMR (CDCl₃) δ 1.64 (1H, s), 4.69 (2H, s), 7.03-7.08 (4H, m), 7.35-7.48 (5H, m), 7.54-7.58 (4H, m).

REFERENCE EXAMPLE 26

4-[[methyl(4-phenyl-2-thiazolyl)amino]methyl]benzaldehyde

To a solution of 4-[[methyl(4-phenyl-2-thiazolyl)amino]methyl]benzenemethanol (1.0 g, 3.2 mmol) in ethyl acetate (40 mL) was added manganese dioxide (4.0 g), and the mixture was stirred at room temperature for 3 hrs. Insoluble material was filtered off, and the filtrate was concentrated. The residue was purified by silica gel column chromatography (hexane/ethyl acetate=5:1) to give the title compound (0.80 g, yield 81%). oil.
¹H NMR (CDCl₃) δ 3.10 (3H, s), 4.88 (2H, s), 6.75 (1H, s), 7.25-7.30 (1H, m), 7.35-7.40 (2H, m), 7.51 (2H, d, J=8.0 Hz), 7.83-7.88 (4H, m), 10.00 (1H, s).

REFERENCE EXAMPLE 27 ethyl (E)-3-[4-[[methyl(4-phenyl-2-thiazolyl)amino]methyl]phenyl]propenoate

To an ice-cooled solution of ethyl diethylphosphonoacetate (0.81 g, 3.6 mmol) in tetrahydrofuran (10 mL) was added 60% sodium hydride (0.14 g, 3.4 mmol), and the mixture was stirred for 30 min. A solution of 4-[[methyl(4-phenyl-2-thiazolyl)amino]methyl]benzaldehyde (0.80 g, 2.6 mmol) in tetrahydrofuran (10 mL) was added dropwise. The mixture was stirred at room temperature for 3 hrs, water was added, and the mixture was extracted with ethyl acetate. The extract was dried and concentrated. The residue was purified by silica gel column chromatography (hexane/ethyl acetate=18:1) to give the title compound (0.96 g, yield 98%) as a powder.

¹H NMR (CDCl₃) δ 1.33 (3H, t, J=7.1 Hz), 3.08 (3H, s), 4.26 (2H, q, J=7.1 Hz), 4.80 (2H, s), 6.42 (1H, d, J=16.0 Hz), 6.74 (1H, s), 7.25-7.39 (5H, m), 7.50 (2H, d, J=8.2 Hz), 7.67 (1H, d, J=16.0 Hz), 7.86 (2H, d, J=7.2 Hz).

REFERENCE EXAMPLE 28 ethyl 4-[[methyl(4-phenyl-2-thiazolyl)amino]methyl]benzenepropanoate

To a solution of ethyl (E)-3-[4-[[methyl(4-phenyl-2-thiazolyl)amino]methyl]phenyl]propenoate (0.60 g, 1.6 mmol) and nickel chloride hexahydrate (0.41 g, 3.2 mmol) in ethanol (25 mL) was added sodium borohydride (0.30 g, 8.0 mmol), and the mixture was stirred at room temperature for 2 hrs. Water was added to the reaction mixture, and the mixture was extracted with ethyl acetate. The extract was washed with water, dried and concentrated. The residue was purified by silica gel column chromatography (hexane/ethyl acetate=18:1) to give the title compound (0.39 g, yield 64%). oil.
¹H NMR (CDCl₃) δ 1.23 (3H, t, J=7.1 Hz), 2.60 (2H, t, J=8.0 Hz), 2.94 (2H, t, J=8.0 Hz), 3.06 (3H, s), 4.12 (2H, q, J=7.1 Hz), 4.73 (2H, s), 6.72 (1H, s), 7.17 (2H, d, J=8.0 Hz), 7.25-7.30 (3H, m), 7.35-7.40 (2H, m), 7.85-7.88 (2H, m).

REFERENCE EXAMPLE 29

4-[[methyl(4-phenyl-2-thiazolyl)amino]methyl]benzenepropanoic acid

The title compound was obtained from ethyl 4-[[methyl(4-phenyl-2-thiazolyl)amino]methyl]benzenepropanoate by a method similar to that of Reference Example 4. yield 64%.
melting point: 109-110° C. (recrystallized from ethyl acetate-hexane).
¹H NMR (CDCl₃) δ 2.66 (2H, t, J=7.9 Hz), 2.94 (2H, t, J=7.9 Hz), 3.06 (3H, s), 4.73 (2H, s), 6.71 (1H, s), 7.17 (2H, d, J=8.0 Hz), 7.25-7.34 (3H, m), 7.37 (2H, t, J=7.8 Hz), 7.86 (2H, d, J=7.2 Hz).

REFERENCE EXAMPLE 30

4-[4-(phenylmethoxy)phenoxy]benzyl alcohol

The title compound was obtained from 4-[4-(phenylmethoxy)phenoxy]benzaldehyde by a method similar to that of Reference Example 32. yield 88%.
¹H NMR (CDCl₃) δ 1.60 (1H, s), 4.65 (2H, s), 5.05 (2H, s), 6.92-6.96 (6H, m), 7.29-7.45 (7H, m).

REFERENCE EXAMPLE 31

2,3-dihydro-5-(phenylmethoxy)-1H-inden-1-one

To a solution of 5-hydroxyindanone (1.0 g, 6.2 mmol), benzyl alcohol (0.65 g, 5.6 mmol) and tributylphosphine (1.7 g, 8.4 mmol) in tetrahydrofuran (30 mL) was added 1,1'-(azodicarbonyl)dipiperidine (2.1 g, 8.4 mmol), and the mixture was stirred at room temperature for 16 hrs. Insoluble material was filtered off, and the filtrate was concentrated. The residue was purified by silica gel column chromatography (hexane/ethyl acetate=10:1) to give the title compound (1.3 g, yield 97%) as a powder.
¹H NMR (CDCl₃) δ 2.67 (2H, t, J=6.1 Hz), 3.08 (2H, t, J=6.1 Hz), 5.15 (2H, s), 6.97 (2H, s), 7.30-7.45 (5H, m), 7.70 (1H, d, J=9.1 Hz).

REFERENCE EXAMPLE 32

2,3-dihydro-5-(phenylmethoxy)-1H-inden-1-ol 2,3-Dihydro-5-(phenylmethoxy)-1H-inden-1-one (1.3 g, 5.46 mmol) was dissolved in a mixture of tetrahydrofuran (20 mL) and methanol (10 mL), sodium borohydride (0.41 g, 11 mmol) was added, and the mixture was stirred at room temperature for 2 hrs. Water was added to the reaction mixture, and the mixture was extracted with ethyl acetate. The extract was dried and concentrated under reduced pressure. The residue was purified by silica gel column chromatography (hexane/ethyl acetate=3:1) to give the title compound (1.16 g, yield 89%) as a white powder.

$^1$H NMR (CDCl$_3$) δ 1.70 (1H, d, J=5.0 Hz), 1.85-2.05 (1H, m), 2.40-2.55 (1H, m), 2.70-2.85 (1H, m), 2.95-3.10 (1H, m), 5.05 (2H, s), 5.10-5.20 (1H, m), 6.85-6.87 (1H, m), 7.25-7.45 (6H, m).

REFERENCE EXAMPLE 33

2-(4-bromophenoxy)-2,3-dihydro-1H-indene

The title compound was obtained from 2-indanol and 4-bromophenol by a method similar to that of Reference Example 1. yield 59%.

melting point: 83-84° C. (recrystallized from ethyl acetate-diisopropyl ether).

$^1$H NMR (CDCl$_3$) δ 3.13 (1H, d, J=3.0 Hz), 3.18 (1H, d, J=3.0 Hz), 3.33 (1H, d, J=6.2 Hz), 3.39 (1H, d, J=6.2 Hz), 5.09-5.15 (1H, m), 6.78 (2H, d, J=9.0 Hz), 7.16-7.26 (4H, m), 7.37 (2H, d, J=9.0 Hz).

REFERENCE EXAMPLE 34 methyl (E)-3-[4-[(2,3-dihydro-1H-inden-2-yl)oxy]phenyl]-2-propenoate

To a solution of 2-(4-bromophenoxy)-2,3-dihydro-1H-indene (1.4 g, 4.7 mmol) in N,N-dimethylformamide (4.7 mL) were added sodium hydrogencarbonate (1.0 g, 12 mmol), methyl acrylate (0.86 mL, 9.5 mmol), tetrabutylammonium chloride (2.0 g, 7.1 mmol) and palladium acetate (31 mg, 0.14 mmol), and the mixture was stirred at 100° C. for 24 hrs. The reaction mixture was allowed to return to room temperature and filtered. Water was added, and the mixture was extracted with ethyl acetate. The extract was washed with saturated brine, and dried over anhydrous magnesium sulfate and concentrated. The residue was recrystallized from ethyl acetate-hexane to give the title compound (0.96 g, yield 69%).

melting point: 115-116° C.

$^1$H NMR (CDCl$_3$) δ 3.16 (1H, d, J=2.9 Hz), 3.21 (1H, d, J=2.9 Hz), 3.37 (1H, d, J=6.4 Hz), 3.43 (1H, d, J=6.4 Hz), 3.80 (3H, s), 5.17-5.23 (1H, m), 6.31 (1H, d, J=16 Hz), 6.91 (2H, d, J=9.0 Hz), 7.17-7.27 (4H, m), 7.47 (2H, d, J=9.0 Hz), 7.65 (1H, d, J=16 Hz).

REFERENCE EXAMPLE 35 ethyl (4-methoxyphenoxy)acetate

To a solution of 4-methoxyphenol (5.0 g, 40 mmol) in N,N-dimethylformamide (50 mL) was added 60% sodium hydride (1.6 g, 40 mmol) under ice-cooling, and the mixture was stirred for 30 min. Ethyl bromoacetate (7.4 g, 44 mmol) was added thereto, and the mixture was stirred at room temperature for 1 hr. Water was added to the reaction mixture, and the mixture was extracted with ethyl acetate. The extract was washed with water and concentrated under reduced pressure. The residue was purified by silica gel column chromatography (hexane/ethyl acetate=7:1) to give the title compound (8.0 g, yield 94%). oil.

$^1$H NMR (CDCl$_3$) δ 1.30 (3H, t, J=7.1 Hz), 3.77 (3H, s), 4.26 (2H, q, J=7.1 Hz), 4.57 (2H, s), 6.81-6.89 (4H, m).

REFERENCE EXAMPLE 36 ethyl (4-hydroxyphenoxy)acetate

A solution of ethyl (4-methoxyphenoxy)acetate (2.0 g, 9.5 mmol), ethanethiol (2.8 mL, 38 mmol) and aluminum chloride (5.1 g, 38 mmol) in dichloromethane (20 mL) was stirred under ice-cooling for 40 min. The reaction mixture was poured into a mixture of chloroform and saturated aqueous sodium hydrogencarbonate, and filtered through celite. The organic layer was separated, washed with saturated brine, dried over anhydrous magnesium sulfate, and concentrated under reduced pressure. The residue was recrystallized from ethyl acetate-diisopropyl ether to give the title compound (1.4 g, yield 75%).

melting point: 123-124° C.

$^1$H NMR (CDCl$_3$) δ 1.30 (3H, t, J=7.1 Hz), 4.26 (2H, q, J=7.1 Hz), 4.56 (2H, s), 6.73-6.84 (4H, m).

REFERENCE EXAMPLE 37 ethyl [4-(4-phenylbutoxy)phenoxy]acetate

A solution of ethyl (4-hydroxyphenoxy)acetate (0.49 g, 2.5 mmol), 4-phenylbutyl bromide (0.59 g, 2.8 mmol), potassium carbonate (0.69 g, 5.0 mmol) and potassium iodide (30 mg, 0.50 mmol) in N,N-dimethylformamide (5 mL) was stirred at room temperature for 30 min., and further at 50° C. for 3 hrs. The solvent was evaporated under reduced pressure, and the residue was partitioned between ethyl acetate and saturated brine. The organic layer was concentrated under reduced pressure. The residue was purified by silica gel column chromatography (hexane/ethyl acetate=4:1) to give the title compound (0.62 g, yield 76%). oil.

$^1$H NMR (CDCl$_3$) δ 1.30 (3H, t, J=7.1 Hz), 1.78-1.83 (4H, m), 2.66-2.71 (2H, m), 3.90-3.94 (2H, m), 4.26 (2H, q, J=7.1 Hz), 4.56 (2H, s), 6.79-6.87 (4H, m), 7.18-7.21 (3H, m), 7.27-7.31 (2H, m).

REFERENCE EXAMPLE 38

[4-(4-phenylbutoxy)phenoxy]acetic acid

A mixture of ethyl [4-(4-phenylbutoxy)phenoxy]acetate (0.59 g, 1.8 mmol), lithium hydroxide monohydrate (0.15 g, 3.6 mmol), tetrahydrofuran (5 mL), methanol (1 mL) and water (3 mL) was stirred at room temperature for 48 hrs. The mixture was acidified with 1N hydrochloric acid, and extracted with ethyl acetate. The extract was washed with saturated brine, and dried over anhydrous magnesium sulfate. The solvent was evaporated under reduced pressure. The residue was recrystallized from ethyl acetate to give the title compound (0.48 g, yield 89%).

melting point: 116-117° C.

$^1$H NMR (CDCl$_3$) δ 1.78-1.82 (4H, m), 2.66-2.71 (2H, m), 3.90-3.94 (2H, m), 4.62 (2H, s), 6.81-6.88 (4H, m), 7.16-7.21 (3H, m), 7.27-7.31 (2H, m).

REFERENCE EXAMPLE 39 ethyl [(4-methoxyphenyl)thio]acetate

To an ice-cooled mixture of 4-methoxythiophenol (15 g, 0.11 mol), triethylamine (28 mL, 0.20 mol) and tetrahydrofuran (150 mL) was added ethyl bromoacetate (21 g, 0.13 mol), and the mixture was stirred overnight at room temperature. Ethanol (10 mL) was added, the solvent was evaporated under reduced pressure, and the residue was partitioned between ethyl acetate and water. The organic layer was concentrated under reduced pressure. The residue was purified by silica gel column chromatography (hexane/ethyl acetate=10:1) to give title compound (22 g, yield 92%). oil.
$^1$H NMR (CDCl$_3$) δ 1.22 (3H, t, J=7.1 Hz), 3.51 (2H, s), 3.79 (3H, s), 4.14 (2H, q, J=7.1 Hz), 6.83 (2H, d, J=8.8 Hz), 7.42 (2H, d, J=8.8 Hz).

REFERENCE EXAMPLE 40 ethyl [(4-hydroxyphenyl)thio]acetate

The title compound was obtained from ethyl [(4-methoxyphenyl)thio]acetate by a method similar to that of Reference Example 36. yield 91%, oil.
$^1$H NMR (CDCl$_3$) δ 1.22 (3H, t, J=7.1 Hz), 3.51 (2H, s), 4.14 (2H, q, J=7.1 Hz), 6.76 (2H, d, J=8.8 Hz), 7.37 (2H, d, J=8.8 Hz).

REFERENCE EXAMPLE 41 ethyl [[4-(4-phenylbutoxy)phenyl]thio]acetate

The title compound was obtained from ethyl [(4-hydroxyphenyl)thio]acetate by a method similar to that of Reference Example 37. yield 88%, oil.
$^1$H NMR (CDCl$_3$) δ 1.22 (3H, t, J=7.1 Hz), 1.76-1.84 (4H, m), 2.66-2.71 (2H, m), 3.50 (2H, s), 3.93-3.97 (2H, m), 4.13 (2H, q, J=7.1 Hz), 6.82 (2H, d, J=8.8 Hz), 7.18-7.21 (3H, m), 7.26-7.29 (2H, m), 7.39 (2H, d, J=8.8 Hz).

REFERENCE EXAMPLE 42

[[4-(4-phenylbutoxy)phenyl]thio]acetic acid

The title compound was obtained from ethyl [[4-(4-phenylbutoxy)phenyl]thio]acetate by a method similar to that of Reference Example 38. yield 75%.
melting point: 73.5-74.5° C. (recrystallized from ethyl acetate).
$^1$H NMR (CDCl$_3$) δ 1.76-1.82 (4H, m), 2.66-2.71 (2H, m), 3.55 (2H, s), 3.93-3.97 (2H, m), 6.83 (2H, d, J=8.8 Hz), 7.16-7.21 (3H, m), 7.26-7.31 (2H, m), 7.43 (2H, d, J=8.8 Hz).

REFERENCE EXAMPLE 43 methyl 4-[(2,3-dihydro-1H-inden-2-yl)oxy]benzenepropanoate

A mixture of methyl (E)-3-[4-[(2,3-dihydro-1H-inden-2-yl)oxy]phenyl]-2-propenoate (0.76 g, 2.6 mmol), tetrahydrofuran (10 mL), methanol (5 mL) and 10% palladium carbon (50% water-containing product, 0.10 g) was stirred overnight at room temperature under a hydrogen atmosphere. The reaction mixture was filtered and concentrated. Water was added, and the mixture was extracted with ethyl acetate. The extract was washed with water, dried over anhydrous magnesium sulfate and concentrated. The residue was recrystallized from ethyl acetate-methanol to give the title compound (0.85 g, yield 89%).
melting point: 73-74° C.
$^1$H NMR (CDCl$_3$) δ 2.60 (2H, t, J=7.9 Hz), 2.90 (2H, t, J=7.9 Hz), 3.13 (1H, d, J=3.2 Hz), 3.19 (1H, d, J=3.2 Hz), 3.33 (1H, d, J=6.3 Hz), 3.38 (1H, d, J=6.3 Hz), 5.11-5.17 (1H, m), 6.84 (2H, d, J=8.6 Hz), 7.12 (2H, d, J=6.6 Hz), 7.17-7.25 (4H, m).

REFERENCE EXAMPLE 44

4-[(2,3-dihydro-1H-inden-2-yl)oxy]benzenepropanoic acid

The title compound was obtained from methyl 4-[(2,3-dihydro-1H-inden-2-yl)oxy]benzenepropanoate by a method similar to that of Reference Example 38. yield 90%.
melting point: 138-139° C. (recrystallized from ethyl acetate-diisopropyl ether).
$^1$H NMR (CDCl$_3$) δ2.66 (2H, t, J=7.9 Hz), 2.91 (2H, t, J=7.9 Hz), 3.13 (1H, d, J=3.2 Hz), 3.19 (1H, d, J=3.2 Hz), 3.33 (1H, d, J=6.3 Hz), 3.38 (1H, d, J=6.3 Hz), 5.11-5.17 (1H, m), 6.84 (2H, d, J=8.6 Hz), 7.12 (2H, d, J=6.6 Hz), 7.16-7.25 (4H, m).

REFERENCE EXAMPLE 45 methyl 4-[(4-aminophenyl)methoxy]benzenepropanate

To a solution of methyl 4-[(4-nitrophenyl)methoxy]benzenepropanoate (0.55 g, 1.67 mmol) and bismuth (III) chloride (0.79 g, 2.5 mmol) in methanol (30 mL) was added sodium borohydride (0.51 g, 13 mmol), and the mixture was stirred at room temperature for 2 hrs. Insoluble material was filtered off, and the filtrate was concentrated. Water was added to the residue, and the mixture was extracted with ethyl acetate. The extract was washed with saturated aqueous sodium hydrogencarbonate, dried and concentrated. The residue was purified by silica gel column chromatography (hexane/ethyl acetate=5:1) to give the title compound (0.13 g, yield 25%) as a powder.
$^1$H NMR (CDCl$_3$) δ 2.59 (2H, t, J=8.0 Hz), 2.89 (2H, t, J=8.0 Hz), 3.66 (5H, br s), 4.90 (2H, s), 6.69 (2H, d, J=8.6 Hz), 6.89 (2H, d, J=8.6 Hz), 7.10 (2H, d, J=8.3 Hz), 7.21 (2H, d, J=8.3 Hz).

REFERENCE EXAMPLE 46 methyl 4-(naphthalen-2-ylmethoxy)benzenepropanoate

The title compound was obtained from methyl 4-hydroxybenzenepropanoate and naphthalene-2-methanol by a method similar to that of Reference Example 1. yield 83%.
melting point: 111-112° C. (recrystallized from ethyl acetate-diisopropyl ether).
$^1$H NMR (CDCl$_3$) δ 2.60 (2H, t, J=7.4 Hz), 2.90 (2H, t, J=7.4 Hz), 3.86 (3H, s), 5.21 (2H, s), 6.94 (2H, d, J=8.6 Hz), 7.12 (2H, d, J=8.6 Hz), 7.47-7.55 (3H, m), 7.82-7.88 (4H, m).

REFERENCE EXAMPLE 47

4-(naphthalen-2-ylmethoxy)benzenepropanoic acid

The title compound was obtained from methyl 4-(naphthalen-2-ylmethoxy)benzenepropanoate by a method similar to that of Reference Example 38. yield 96%.

melting point: 173-174° C. (recrystallized from ethyl acetate-diisopropyl ether).
$^1$H NMR (CDCl$_3$) δ 2.65 (2H, t, J=7.4 Hz), 2.91 (2H, t, J=7.4 Hz), 5.21 (2H, s), 6.94 (2H, d, J=8.6 Hz), 7.13 (2H, d, J=8.6 Hz), 7.47-7.55 (3H, m), 7.82-7.88 (4H, m).

REFERENCE EXAMPLE 48 methyl 4-(naphthalen-1-ylmethoxy)benzenepropanoate

The title compound was obtained from methyl 4-hydroxybenzenepropanoate and naphthalene-1-methanol by a method similar to that of Reference Example 1. yield 84%, oil.
$^1$H NMR (CDCl$_3$) δ 2.62 (2H, t, J=7.4 Hz), 2.92 (2H, t, J=7.4 Hz), 3.68 (3H, s), 5.47 (2H, s), 6.98 (2H, d, J=8.6 Hz), 6.99 (2H, d, J=8.6 Hz), 7.44-7.60 (4H, m), 7.84-7.91 (2H, m), 8.03-8.06 (1H, m).

REFERENCE EXAMPLE 49

4-(naphthalen-1-ylmethoxy)benzenepropanoic acid

The title compound was obtained from methyl 4-(naphthalen-1-ylmethoxy)benzenepropanoate by a method similar to that of Reference Example 38. yield 81%.
melting point: 105-106° C. (recrystallized from ethyl acetate-diisopropyl ether).
$^1$H NMR (CDCl$_3$) δ 2.65 (2H, t, J=7.4 Hz), 2.91 (2H, t, J=7.4 Hz), 5.44 (2H, s), 6.97 (2H, d, J=8.6 Hz), 7.13 (2H, d, J=8.6 Hz), 7.42-7.58 (4H, m), 7.82-7.90 (2H, m), 8.01-8.05 (1H, m).

REFERENCE EXAMPLE 50

1H-indole-2-methanol

To a mixture of indole-2-carboxylic acid (2.0 g, 12 mmol), N,N-dimethylformamide (10 mL), tetrahydrofuran (20 mL) and N-hydroxysuccinimide (1.5 g, 13 mmol) was added 1-ethyl-3-(3-dimethylaminopropyl)carbodiimide hydrochloride (2.9 g, 15 mmol), and the mixture was stirred overnight at room temperature. 0.5 M Aqueous citric acid solution was added, and the mixture was extracted with ethyl acetate. The extract was dried over anhydrous magnesium sulfate and concentrated. Tetrahydrofuran (20 mL) and sodium tetrahydroborate (1.9 g, 50 mmol) were added to the residue under ice-cooling, and the mixture was stirred at room temperature for 6 hrs. 0.5 M Aqueous citric acid solution was added, and the mixture was extracted with ethyl acetate. The extract was dried over anhydrous magnesium sulfate and concentrated. The residue was purified by silica gel column chromatography (hexane/ethyl acetate=5:1) to give the title compound. yield 56%.
melting point: 73.5-74.4° C. (recrystallized from ethyl acetate-diisopropyl ether).
$^1$H NMR (CDCl$_3$) δ 1.79 (1H, br s), 4.83 (2H, s), 6.41 (1H, s), 7.07-7.13 (1H, m), 7.16-7.21 (1H, m), 7.34 (1H, d, J=8.3 Hz), 7.58 (1H, d, J=7.9 Hz), 8.33 (1H, br s).

REFERENCE EXAMPLE 51 methyl 4-[(3-bromophenyl)methoxy]benzenepropanoate

The title compound was obtained as a white powder from methyl 4-hydroxybenzenepropanoate and 3-bromobenzyl alcohol by a method similar to that of Reference Example 1. yield 68%.

$^1$H NMR (CDCl$_3$) δ 2.60 (2H, t, J=8.0 Hz), 2.90 (2H, t, J=8.0 Hz), 3.66 (3H, s), 5.00 (2H, s), 6.88 (2H, d, J=8.6 Hz), 7.12 (2H, d, J=8.6 Hz), 7.21-7.27 (1H, m), 7.34 (1H, d, J=7.5 Hz), 7.45 (1H, d, J=7.8 Hz), 7.59 (1H, s).

REFERENCE EXAMPLE 52

4-[(3-bromophenyl)methoxy]benzenepropanoic acid

The title compound was obtained from methyl 4-[(3-bromophenyl)methoxy]benzenepropanoate by a method similar to that of Reference Example 4. yield 43%.
melting point: 97-98° C. (recrystallized from diisopropyl ether-hexane).
$^1$H NMR (CDCl$_3$) δ 2.65 (2H, t, J=7.8 Hz), 2.91 (2H, t, J=7.8 Hz), 5.01 (2H, s), 6.89 (2H, d, J=8.5 Hz), 7.13 (2H, d, J=8.5 Hz), 7.22-7.27 (1H, m), 7.34 (1H, d, J=7.6 Hz), 7.45 (1H, d, J=7.8 Hz), 7.59 (1H, s).

REFERENCE EXAMPLE 53 methyl 4-[(2,3-dihydrobenzofuran-3-yl)oxy]benzenepropanoate

To a solution of 3-coumaranone (0.50 g, 3.7 mmol) in ethanol (20 mL) was added sodium tetrahydroborate (0.28 g, 7.5 mmol), and the mixture was stirred at room temperature for 1 hr. 0.5N Hydrochloric acid (10 mL) was added and the mixture was stirred at room temperature for 10 min. Saturated brine was added, and the mixture was extracted with ethyl acetate. The extract was dried over anhydrous magnesium sulfate and concentrated. Tetrahydrofuran (10 mL), methyl 4-hydroxybenzenepropanoate (0.46 g, 2.6 mmol), triphenylphosphine (0.98 g, 3.8 mmol) and diethyl azodicarboxylate (0.91 mL, 4.7 mmol) were added to the residue, and the mixture was stirred at room temperature for 2 hrs. Water was added to the reaction mixture, and the mixture was extracted with ethyl acetate. The extract was washed with water and concentrated under reduced pressure. The residue was purified by silica gel column chromatography (hexane/ethyl acetate=20:1) to give the title compound. yield 17%, oil.
$^1$H NMR (CDCl$_3$) δ 2.61 (2H, t, J=8.0 Hz), 2.91 (2H, t, J=8.0 Hz), 3.67 (3H, s), 4.58-4.70 (2H, m), 5.85-5.88 (1H, m), 6.85 (2H, d, J=8.6 Hz), 6.91-6.96 (2H, m), 7.14 (2H, d, J=8.6 Hz), 7.25-7.33 (1H, m), 7.38-7.40 (1H, m).

REFERENCE EXAMPLE 54

4-[(2,3-dihydrobenzofuran-3-yl)oxy]benzenepropanoic acid

The title compound was obtained from methyl 4-[(2,3-dihydrobenzofuran-3-yl)oxy]benzenepropanoate by a method similar to that of Reference Example 38. yield 60%.
melting point: 106-107° C. (recrystallized from ethyl acetate-diisopropyl ether).
$^1$H NMR (CDCl$_3$) δ 2.67 (2H, t, J=8.0 Hz), 2.93 (2H, t, J=8.0 Hz), 4.59-4.71 (2H, m), 5.86-5.89 (1H, m), 6.85 (2H, d, J=8.6 Hz), 6.91-6.96 (2H, m), 7.15 (2H, d, J=8.6 Hz), 7.26-7.33 (1H, m), 7.38-7.40 (1H, m).

REFERENCE EXAMPLE 55 methyl 4-[[3-(3-thienyl)phenyl]methoxy]benzenepropanoate

Methyl 4-[(3-bromophenyl)methoxy]benzenepropanoate (0.96 g, 2.8 mmol), bis(pinacolato)diboron (0.77 g, 3.0 mmol) and potassium acetate (0.81 g, 8.3 mmol) were dissolved in N,N-dimethylformamide (30 mL) and, after argon substitution, 1,1'-bis(diphenyphosphino)ferrocenedichloropalladium (II) (0.067 g, 0.083 mmol) was added. The reaction mixture was heated overnight under an argon atmosphere at 80° C. The reaction mixture was cooled, and 3-bromothiophene (0.43 g, 2.6 mmol), 1,1'-bis(diphenyphosphino)ferrocenedichloropalladium (II) (0.067 g, 0.083 mmol) and 2N aqueous sodium carbonate solution (6.9 mL, 14 mmol) were added to the reaction mixture. The reaction mixture was heated overnight under an argon atmosphere at 80° C. The reaction mixture was cooled, and the mixture was extracted with ethyl acetate. The extract was washed with water, dried and concentrated. The residue was purified by silica gel column chromatography (hexane/ethyl acetate=15:1) to give the title compound (0.21 g, yield 22%) as an oil.

$^1$H NMR (CDCl$_3$) δ 2.60 (2H, t, J=8.0 Hz), 2.90 (2H, t, J=8.0 Hz), 3.66 (3H, s), 5.08 (2H, s), 6.89-6.94 (2H, m), 7.10-7.14 (2H, m), 7.33-7.44 (4H, m), 7.47 (1H, t, J=2.2 Hz), 7.55 (1H, dt, J=7.5 Hz, 1.6 Hz), 7.66 (1H, s).

REFERENCE EXAMPLE 56

4-[[3-(3-thienyl)phenyl]methoxy]benzenepropanoic acid

The title compound was obtained from methyl 4-[[3-(3-thienyl)phenyl]methoxy]benzenepropanoate by a method similar to that of Reference Example 4. yield 33%.

melting point: 153.0-153.5° C. (recrystallized from diisopropyl ether-hexane).

$^1$H NMR (CDCl$_3$) δ 2.65 (2H, t, J=8.0 Hz), 2.91 (2H, t, J=8.0 Hz), 5.08 (2H, s), 6.93 (2H, d, J=8.6 Hz), 7.14 (2H, d, J=8.6 Hz), 7.33-7.47 (5H, m), 7.55 (1H, dt, J=7.5 Hz, 1.5 Hz), 7.65 (1H, 5).

REFERENCE EXAMPLE 57 methyl 4-[[3-[[5-(trifluoromethyl)-2-pyridinyl]oxy]phenyl]methoxy]benzenepropanoate The title compound was obtained from methyl 4-hydroxybenzenepropanoate and 3-[[5-(trifluoromethyl)-2-pyridinyl]oxy]benzyl alcohol by a method similar to that of Reference Example 1. yield 89%, oil.

$^1$H NMR (CDCl$_3$) δ 2.60 (2H, t, J=8.0 Hz), 2.89 (2H, t, J=8.0 Hz), 3.66 (3H, s), 5.07 (2H, s), 6.89 (2H, d, J=8.6 Hz), 7.01 (1H, d, J=8.7 Hz), 7.09-7.13 (3H, m), 7.23 (1H, br s), 7.31 (1H, d, J=7.6 Hz), 7.44 (1H, t, J=7.9 Hz), 7.90 (1H, dd, J=8.7 Hz, 2.4 Hz), 8.44 (1H, br s).

REFERENCE EXAMPLE 58

4-[[3-[[5-(trifluoromethyl)-2-pyridinyl]oxy]phenyl]methoxy]benzenepropanoic acid The title compound was obtained from methyl 4-[[3-[[5-(trifluoromethyl)-2-pyridinyl]oxy]phenyl]methoxy]benzenepropanoate by a method similar to that of Reference Example 4. yield 28%.

melting point: 112-113° C. (recrystallized from diisopropyl ether-hexane).

$^1$H NMR (CDCl$_3$) δ 2.60 (2H, t, J=8.0 Hz), 2.90 (2H, t, J=8.0 Hz), 5.07 (2H, s), 6.93 (2H, d, J=8.6 Hz), 7.01 (1H, d, J=8.7 Hz), 7.09-7.17 (3H, m), 7.24 (1H, br s), 7.31 (1H, d, J=9.2 Hz), 7.44 (1H, t, J=7.9 Hz), 7.90 (1H, dd, J=8.7 Hz, 2.5 Hz), 8.44-8.45 (1H, m).

REFERENCE EXAMPLE 59 methyl 4-[[3-(2-thienyl)phenyl]methoxy]benzenepropanoate

The title compound was obtained as a white powder from 2-thiopheneboronic acid by a method similar to that of Reference Example 22. yield 33%.

$^1$H NMR (CDCl$_3$) δ 2.60 (2H, t, J=8.1 Hz), 2.90 (2H, t, J=8.1 Hz), 3.66 (3H, s), 5.06 (2H, s), 6.92 (2H, d, J=8.6 Hz), 7.06-7.14 (3H, m), 7.28 (1H, dd, J=5.1 Hz, 1.1 Hz), 7.30-7.41 (3H, m), 7.56 (1H, dt, J=7.4 Hz, 1.6 Hz), 7.66 (1H, s).

REFERENCE EXAMPLE 60

4-[[3-(2-thienyl)phenyl]methoxy]benzenepropanoic acid

The title compound was obtained from methyl 4-[[3-(2-thienyl)phenyl]methoxy]benzenepropanoate by a method similar to that of Reference Example 4. yield 52%.

melting point: 127-128° C. (recrystallized from ethyl acetate-hexane).

$^1$H NMR (CDCl$_3$) δ 2.65 (2H, t, J=8.0 Hz), 2.91 (2H, t, J=8.0 Hz), 5.07 (2H, s), 6.93 (2H, d, J=8.6 Hz), 7.08 (1H, dd, J=4.5 Hz, 3.5 Hz), 7.14 (2H, d, J=8.6 Hz), 7.27-7.41 (4H, m), 7.57 (1H, dt, J=7.4 Hz, 1.6 Hz), 7.66 (1H, s).

REFERENCE EXAMPLE 61 methyl 4-[[3-(2-pyrimidinyl)phenyl]methoxy]benzenepropanoate

Methyl 4-[(3-bromophenyl)methoxy]benzenepropanoate (0.70 g, 2.0 mmol), bis(pinacolato)diboron (0.56 g, 2.2 mmol) and potassium acetate (0.59 g, 6.0 mmol) were dissolved in N,N-dimethylformamide (20 mL) and, after argon substitution, 1,1'-bis(diphenyphosphino)ferrocenedichloropalladium (II) (0.049 g, 0.060 mmol) was added. The reaction mixture was heated under an argon atmosphere at 80° C. for 8 hrs. The reaction mixture was cooled, water was added to the reaction mixture and the mixture was extracted with ethyl acetate. The extract was washed with water, dried and concentrated. The residue was dissolved in toluene-methanol-water (5:1:1, 35 mL), sodium carbonate (0.64 g, 6.0 mmol) was added and, after argon substitution, tetrakistriphenylphosphinepalladium (0.12 g, 0.10 mmol) was added. The reaction mixture was heated under reflux overnight under an argon atmosphere. The reaction mixture was cooled, water was added to the reaction mixture and the mixture was extracted with ethyl acetate. The extract was washed with water, dried and concentrated. The residue was purified by silica gel column chromatography (hexane/ethyl acetate=5:1) to give the title compound (0.13 g, yield 16%) as a colorless oil.

$^1$H NMR (CDCl$_3$) δ 2.59 (2H, t, J=8.1 Hz), 2.89 (2H, t, J=8.1 Hz), 3.66 (3H, s), 5.13 (2H, s), 6.92-6.94 (2H, m), 7.09-7.13 (2H, m), 7.17-7.20 (1H, m), 7.41-7.86 (2H, m), 8.41 (1H, dt, J=7.6 Hz, 1.6 Hz), 8.42-8.52 (1H, m), 8.80 (2H, d, 4.8 Hz).

REFERENCE EXAMPLE 62

4-[[3-(2-pyrimidinyl)phenyl]methoxy]benzenepropanoic acid

The title compound was obtained from methyl 4-[[3-(2-pyrimidinyl)phenyl]methoxy]benzenepropanoate by a method similar to that of Reference Example 4. yield 26%.

melting point: 152-153° C. (recrystallized from ethyl acetate-hexane).
$^1$H NMR (CDCl$_3$) δ 2.65 (2H, t, J=7.9 Hz), 2.91 (2H, t, J=7.9 Hz), 5.14 (2H, s), 6.94 (2H, d, J=8.6 Hz), 7.13 (2H, d, J=8.6 Hz), 7.22 (1H, t, J=4.9 Hz), 7.49-7.60 (2H, m), 8.40 (1H, d, J=7.6 Hz), 8.50 (1H, s), 8.83 (2H, d, J=4.8 Hz).

REFERENCE EXAMPLE 63 methyl 4-[[3-(2-pyridinyl)phenyl]methoxy]benzenepropanoate

Methyl 4-[(3-bromophenyl)methoxy]benzenepropanoate (0.70 g, 2.0 mmol) and 2-pyridyltrimethyltin (0.60 g, 2.4 mmol) were dissolved in N,N-dimethylformamide (15 mL) and, after argon substitution, dichlorobistriphenylphosphinepalladium (II) (0.10 g, 0.070 mmol) was added. The reaction mixture was heated under reflux overnight under an argon atmosphere. The reaction mixture was cooled, water was added to the reaction mixture and the mixture was extracted with ethyl acetate. The extract was washed with water, dried and concentrated. The residue was purified by silica gel column chromatography (hexane/ethyl acetate=5:1) to give the title compound (0.24 g, yield 35%) as a colorless oil.
$^1$H NMR (CDCl$_3$) δ 2.60 (2H, t, J=8.1 Hz), 2.90 (2H, t, J=8.1 Hz), 3.66 (3H, s), 5.13 (2H, s), 6.93 (2H, d, J=8.6 Hz), 7.12 (2H, d, J=8.6 Hz), 7.22-7.27 (1H, m), 7.46-7.51 (2H, m), 7.73-7.79 (2H, m), 7.93 (1H, dt, J=1.8 Hz, 5.0 Hz), 8.07 (1H, s), 8.70 (1H, dt, J=4.7 Hz, 1.4 Hz).

REFERENCE EXAMPLE 64

4-[[3-(2-pyridinyl)phenyl]methoxy]benzenepropanoic acid

The title compound was obtained from methyl 4-[[3-(2-pyridinyl)phenyl]methoxy]benzenepropanoate by a method similar to that of Reference Example 4. yield 57%.
melting point: 160-161° C. (recrystallized from ethyl acetate-hexane).
$^1$H NMR (CDCl$_3$) δ 2.63 (2H, t, J=8.0 Hz), 2.90 (2H, t, J=8.0 Hz), 5.12 (2H, s), 6.93 (2H, d, J=8.6 Hz), 7.12 (2H, d, J=8.6 Hz), 7.24-7.29 (1H, m), 7.46-7.52 (2H, m), 7.71-7.81 (2H, m), 7.87-7.91 (1H, m), 8.05 (1H, s), 8.72-8.75 (1H, m).

REFERENCE EXAMPLE 65 methyl 4-[[3-(2-naphthyl)phenyl]methoxy]benzenepropanoate

The title compound was obtained as a white powder from 2-naphthylboronic acid by a method similar to that of Reference Example 22. yield 93%.
$^1$H NMR (CDCl$_3$) δ 2.60 (2H, t, J=8.0 Hz), 2.90 (2H, t, J=8.0 Hz), 3.66 (3H, s), 5.13 (2H, s), 6.94 (2H, d, J=8.6 Hz), 7.13 (2H, d, J=8.6 Hz), 7.42-7.53 (4H, m), 7.68 (1H, dt, J=7.4 Hz, 1.5 Hz), 7.73-7.80 (2H, m), 7.85-7.93 (3H, m), 8.05 (1H, br s).

REFERENCE EXAMPLE 66

4-[[3-(2-naphthyl)phenyl]methoxy]benzenepropanoic acid

The title compound was obtained from methyl 4-[[3-(2-naphthyl)phenyl]methoxy]benzenepropanoate by a method similar to that of Reference Example 4. yield 52%.

melting point: 134-135° C. (recrystallized from ethyl acetate-hexane).
$^1$H NMR (CDCl$_3$) δ 2.65 (2H, t, J=7.9 Hz), 2.91 (2H, t, J=7.9 Hz), 5.13 (2H, s), 6.95 (2H, d, J=8.6 Hz), 7.14 (2H, d, J=8.6 Hz), 7.43-7.53 (4H, m), 7.68 (1H, dt, J=7.5 Hz, 1.5 Hz), 7.75 (1H, dd, J=8.6 Hz, 1.8 Hz), 7.78 (1H, s), 7.85-7.93 (3H, m), 8.05 (1H, br s).

REFERENCE EXAMPLE 67

4-[[3-(5-pyrimidinyl)phenyl]methoxy]benzenepropanoic acid

Methyl 4-[(3-bromophenyl)methoxy]benzenepropanoate (0.70 g, 2.0 mmol), bis(pinacolato)diboron (0.56 g, 2.2 mmol) and potassium acetate (0.59 g, 6.0 mmol) were dissolved in N,N-dimethylformamide (20 mL) and, after argon substitution, 1,1'-bis(diphenyphosphino)ferrocenedichloropalladium (II) (0.049 g, 0.060 mmol) was added. The reaction mixture was heated overnight under an argon atmosphere at 80° C. The reaction mixture was cooled, water was added to the reaction mixture and the mixture was extracted with ethyl acetate. The extract was washed with water, dried and concentrated. The residue was dissolved in toluene-methanol-water (5:1:1, 35 mL), sodium carbonate (0.64 g, 6.0 mmol) was added and, after argon substitution, tetrakistriphenylphosphinepalladium (0.12 g, 0.10 mmol) was added. The reaction mixture was heated under reflux overnight under an argon atmosphere. The reaction mixture was cooled, water was added and the reaction mixture was washed with ethyl acetate. Then the aqueous layer was neutralized with 1N hydrochloric acid, and the mixture was extracted with ethyl acetate. The extract was washed with water, dried and concentrated. The residue was recrystallized from tetrahydrofuran-hexane to give the title compound (0.94 g, yield 14%).
melting point: 166-167° C.
$^1$H NMR (CDCl$_3$+DMSO-d$_6$) δ 2.60 (2H, t, J=8.1 Hz), 2.91 (2H, t, J=8.1 Hz), 5.13 (2H, s), 6.92 (2H, d, J=8.6 Hz), 7.16 (2H, d, J=8.6 Hz), 7.54 (3H, s), 7.65 (1H, s), 8.96 (2H, s), 9.21 (1H, s).

REFERENCE EXAMPLE 68

5,6-dihydro-4H-cyclopenta[b]thien-4-one

To a solution of N,N-dimethylacrylamide (6.6 g, 71 mmol) in dichloroethane (400 ml) was gradually added dropwise a solution of trifluoromethanesulfonic acid anhydride (20 g, 71 mmol) in dichloroethane (50 mL) under ice-cooling. A solution of thiophene (6.0 g, 71 mmol) in dichloroethane (50 mL) was added to the mixture, and the mixture was heated under reflux for 15 hrs. The reaction mixture was concentrated under reduced pressure, saturated sodium hydrogencarbonate solution was added, and the mixture was extracted with ethyl acetate. The extract was washed with water and concentrated under reduced pressure. The residue was purified by silica gel column chromatography (hexane/ethyl acetate=9:5 to 4:1) to give the title compound (3.8 g, yield 39%) as a white powder.
$^1$H NMR (CDCl$_3$) δ 3.00 (2H, t, J=4.7 Hz), 3.19 (2H, t, J=4.7 Hz), 7.15 (1H, d, J=5.1 Hz), 7.31 (1H, d, J=5.1 Hz).

REFERENCE EXAMPLE 69

4-hydroxybenzenepropanamide

25% Aqueous ammonia (30 mL) was added to methyl 4-hydroxybenzenepropanoate (1.5 g, 8.3 mmol), and the mixture was stirred at room temperature for 15 hrs. Dil. hydrochloric acid was added to the reaction mixture, and the mixture was extracted with ethyl acetate. The extract was washed with water and concentrated under reduced pressure. The residue was recrystallized from ethyl acetate-hexane to give the title compound (0.43 g, yield 31%).

$^1$H NMR (CDCl$_3$) δ 2.49 (2H, t, J=7.9 Hz), 2.90 (2H, t, J=7.9 Hz), 4.65 (1H, s), 5.25 (2H, br s), 6.76 (2H, d, J=8.5 Hz), 7.08 (2H, d, J=8.5 Hz).

REFERENCE EXAMPLE 70

4-[(5-chloro-2,3-dihydro-1H-inden-1-yl)oxy]benzenepropanamide

5-Chloro-2,3-dihydro-1H-inden-1-ol was obtained from 5-chloro-1-indanone by a method similar to that of Reference Example 32. This was condensed with 4-hydroxybenzenepropanamide by a method similar to that of Reference Example 1 to give the title compound. yield from 5-chloro-1-indanone 21%.

melting point: 158-159° C. (recrystallized from ethyl acetate-hexane).

$^1$H NMR (CDCl$_3$) δ2.21 (1H, m), 2.49-2.61 (3H, m), 2.83-2.96 (3H, m), 3.11 (1H, m), 5.36 (2H, br s), 5.67 (1H, dd, J=4.3 Hz, 6.6 Hz), 6.91 (2H, d, J=8.6 Hz), 7.14-7.33 (5H, m).

REFERENCE EXAMPLE 71

5-[[4-([1,1'-biphenyl]-3-ylmethoxy)phenyl]methyl]-2,4-thiazolidinedione

To a solution of 5-[(4-hydroxyphenyl)methyl]-2,4-thiazolidinedione (0.30 g, 1.3 mmol) in dimethyl sulfoxide (20 mL) were added 3-(chloromethyl)biphenyl (0.26 g, 1.3 mmol) and 60% sodium hydride (0.11 g, 2.6 mmol), and the mixture was stirred at room temperature for 1 hr and further at 50° C. for 1 hr. Water was added to the reaction mixture, and the mixture was extracted with ethyl acetate. The extract was washed with water and concentrated under reduced pressure. The residue was purified by silica gel column chromatography (hexane/ethyl acetate=8:2) to give the title compound (1.3 g, yield 96%).

melting point: 109-111° C. (recrystallized from diethyl ether-hexane).

$^1$H NMR (CDCl$_3$) δ 3.11 (1H, dd, J=9.4 Hz, 14.1 Hz), 3.46 (1H, dd, J=3.9 Hz, 14.1 Hz), 4.80 (1H, dd, J=3.9 Hz, 9.4 Hz), 5.11 (2H, s), 6.95 (2H, d, J=8.7 Hz), 7.16 (2H, d, J=8.7 Hz), 7.30-7.65 (9H, m), 7.99 (1H, s).

REFERENCE EXAMPLE 72

5-[[4-[(3-phenoxyphenyl)methoxy]phenyl]methyl]-2,4-thiazolidinedione

The title compound was obtained from 5-(4-hydroxybenzyl)-2,4-thiazolidinedione and 1-(chloromethyl)-3-phenoxybenzene by a method similar to that of Reference Example 71. yield 23%.

melting point: 101-102° C. (recrystallized from diethyl ether-hexane).

$^1$H NMR (CDCl$_3$) δ 3.10 (1H, dd, J=9.5 Hz, 14.2 Hz), 3.45 (1H, dd, J=3.8 Hz, 14.2 Hz), 4.50 (1H, dd, J=3.8 Hz, 9.5 Hz), 5.01 (2H, s), 6.89-7.19 (10H, m), 7.31-7.36 (3H, m), 8.25 (1H, s).

REFERENCE EXAMPLE 73

4-[(5-chloro-2,3-dihydro-1H-inden-1-yl)oxy]benzenepropanenitrile

5-Chloro-2,3-dihydro-1H-inden-1-ol was obtained from 5-chloro-1-indanone by a method similar to that of Reference Example 32. This was condensed with 4-hydroxybenzenepropanenitrile by a method similar to that of Reference Example 1 to give the title compound. yield from 5-chloro-1-indanone 59%.

melting point: 97-98° C. (recrystallized from diethyl ether-hexane).

$^1$H NMR (CDCl$_3$) δ 2.24 (1H, m), 2.49-2.63 (3H, m), 2.85-2.95 (3H, m), 3.12 (1H, m), 5.69 (1H, dd, J=4.3 Hz, 6.6 Hz), 6.95 (2H, d, J=8.6 Hz), 7.18 (2H, d, J=8.6 Hz), 7.22-7.34 (3H, m).

REFERENCE EXAMPLE 74

4-[(5-chloro-2,3-dihydro-1H-inden-1-yl)oxy]-N-(methylsulfonyl)benzenepropanamide To a solution of 4-[(5-chloro-2,3-dihydro-1H-inden-1-yl)oxy]benzenepropanoic acid (0.3 g, 0.95 mmol) in dichloromethane (10 mL) were added methanesulfonamide (90 mg, 0.95 mmol), N,N-dimethylaminopyridine (0.12 g, 0.95 mmol) and 1-ethyl-3-(3-dimethylaminopropyl)carbodiimide hydrochloride (0.17 mL, 0.95 mmol), and the mixture was stirred at room temperature for 15 hrs. Water was added to the reaction mixture, and the mixture was extracted with ethyl acetate. The extract was washed with water, concentrated under reduced pressure to give the title compound (0.10 g, yield 30%).

melting point: 140-141° C. (recrystallized from ethyl acetate-hexane).

$^1$H NMR (CDCl$_3$) δ 2.22 (1H, m), 2.54 (1H, m), 2.62 (2H, d, J=7.4 Hz), 2.85-2.98 (3H, m), 3.10 (1H, m), 3.25 (3H, s), 5.68 (1H, dd, J=4.3 Hz, 6.6 Hz), 6.93 (2H, d, J=8.6 Hz), 7.13 (2H, d, J=8.6 Hz), 7.19-7.34 (3H, m), 7.67 (1H, br s).

REFERENCE EXAMPLE 75

N-[3-[4-[(5-chloro-2,3-dihydro-1H-inden-1-yl)oxy]phenyl]propyl]acetamide

To a solution of 4-[(5-chloro-2,3-dihydro-1H-inden-1-yl)oxy]benzenepropanenitrile (0.50 g, 1.7 mmol) in tetrahydrofuran (25 mL) was added lithium aluminum hydride (77 mg, 2.0 mmol) under ice-cooling, and the mixture was stirred in an ice bath for 3 hrs. Water was added to the reaction mixture, and the mixture was extracted with ethyl acetate. The extract was washed with water and concentrated under reduced pressure. The obtained oil was dissolved in pyridine (20 mL), acetic anhydride (0.18 mL, 0.95 mmol) was added, and the mixture was stirred at room temperature for 3 hrs. Water was added to the reaction mixture, and the mixture was extracted with ethyl acetate. The extract was washed with water and concentrated under reduced pressure. The residue was purified by silica gel column chromatography (ethyl acetate) to give the title compound (0.11 g, yield 18%).

melting point: 111-112° C. (recrystallized from diethyl ether).

$^1$H NMR (CDCl$_3$) δ 1.85 (2H, m), 1.95 (3H, s), 2.24 (1H, m), 2.50-2.64 (3H, m), 2.90 (1H, m), 3.12 (1H, m), 3.28 (2H, dt, J=6.6 Hz, 6.7 Hz), 5.40 (1H, br s), 5.68 (1H, t, J=4.6 Hz), 6.90 (2H, d, J=8.4 Hz), 7.11 (2H, d, J=8.4 Hz), 7.19-7.34 (3H, m).

REFERENCE EXAMPLE 76

N-[3-[4-[(5-chloro-2,3-dihydro-1H-inden-1-yl)oxy] phenyl]propyl]methanesulfonamide To a solution of 4-[(5-chloro-2,3-dihydro-1H-inden-1-yl) oxy]benzenepropanenitrile (1.0 g, 3.4 mmol) in tetrahydrofuran (50 mL) was added lithium aluminum hydride (0.16 g, 4.1 mmol) under ice-cooling, and the mixture was stirred in an ice bath for 1 hr. Water was added to the reaction mixture, and the mixture was extracted with ethyl acetate. The extract was washed with water and concentrated under reduced pressure. The obtained oil was dissolved in chloroform (20 mL) and ice-cooled. Triethylamine (0.47 mL, 3.4 mmol) and methanesulfonyl chloride (0.36 mL, 3.4 mmol) were added thereto, and the mixture was stirred under ice-cooling for 3 hrs. Water was added to the reaction mixture, and the mixture was extracted with ethyl acetate. The extract was washed with water and concentrated under reduced pressure.

The residue was purified by silica gel column chromatography (hexane/ethyl acetate=7:3) to give the title compound (0.15 g, yield 11%).

melting point: 89-90° C. (recrystallized from diethyl ether).

$^1$H NMR (CDCl$_3$) δ 1.89 (2H, m), 2.24 (1H, m), 2.55 (1H, m), 2.66 (2H, t, J=7.4 Hz), 2.90 (1H, m), 2.94 (3H, s), 3.07-3.19 (3H, m), 4.29 (1H, br), 5.67 (1H, dd, J=4.4 Hz, 6.5 Hz), 6.90 (2H, d, J=8.6 Hz), 7.11 (2H, d, J=8.6 Hz), 7.19-7.34 (3H, m).

REFERENCE EXAMPLE 77

2,3-dihydro-2,2-dimethyl-1H-inden-1-one

To a solution of 60% sodium hydride (2.7 g, 68 mmol) in 1,2-dimethoxyethane (30 mL) was slowly added 1-indanone (3.0 g, 23 mmol). The mixture was stirred at room temperature for 10 min., methyl iodide (5.7 ml, 91 mmol) was added, and the mixture was stirred at room temperature for 1 hr. Water was added to the reaction mixture, and the mixture was extracted with ethyl acetate. The extract was washed with water and concentrated under reduced pressure. The residue was purified by silica gel column chromatography (hexane) to give the title compound (4.0 g, yield 99%).

$^1$H NMR (CDCl$_3$) δ 1.24 (6H, s), 3.01 (2H, s), 7.35-7.44 (2H, m), 7.59 (1H, dt, J=1.2 Hz, 7.6 Hz), 7.76 (1H, d, J=7.8 Hz).

REFERENCE EXAMPLE 78 methyl [4-([1,1'-biphenyl]-3-ylmethoxy)phenoxy] acetate

The title compound was obtained as a white powder from methyl (4-hydroxyphenoxy)acetate and [1,1'-biphenyl]-3-methanol by a method similar to that of Reference Example 1. yield 42%.

$^1$H NMR (CDCl$_3$) δ 3.80 (3H, s), 4.59 (2H, s), 5.08 (2H, s), 6.86 (2H, d, J=9.2 Hz), 6.94 (2H, d, J=9.2 Hz), 7.33-7.64 (9H, m).

REFERENCE EXAMPLE 79

[4-([1,1'-biphenyl]-3-ylmethoxy)phenoxy]acetic acid

The title compound was obtained from methyl [4-([1,1'-biphenyl]-3-ylmethoxy)phenoxy]acetate by a method similar to that of Reference Example 4. yield 88%.

melting point: 132-133° C. (recrystallized from diethyl ether-hexane).

$^1$H NMR (CDCl$_3$) δ 4.63 (2H, s), 5.08 (2H, s), 6.88 (2H, d, J=9.3 Hz), 6.95 (2H, d, J=9.3 Hz), 7.31-7.64 (9H, m).

REFERENCE EXAMPLE 80 ethyl 2-[4-([1,1'-biphenyl]-3-ylmethoxy)phenoxy]-2-methylpropanoate

The title compound was obtained from ethyl 2-(4-hydroxyphenoxy)-2-methylpropanoate and [1,1'-biphenyl]-3-methanol by a method similar to that of Reference Example 1. yield 65%, oil.

$^1$H NMR (CDCl$_3$) δ 1.27 (3H, t, J=7.1 Hz), 1.54 (6H, s), 4.24 (2H, q, J=7.1 Hz), 5.06 (2H, s), 6.86 (4H, m), 7.30-7.47 (5H, m), 7.53-7.64 (4H, m).

REFERENCE EXAMPLE 81

2-[4-([1,1'-biphenyl]-3-ylmethoxy)phenoxy]-2-methylpropanoic acid

The title compound was obtained from ethyl 2-[4-([1,1'-biphenyl]-3-ylmethoxy)phenoxy]-2-methylpropanoate by a method similar to that of Reference Example 4. yield 93%.

melting point: 114-115° C. (recrystallized from diethyl ether-hexane).

$^1$H NMR (CDCl$_3$) δ 1.55 (6H, s), 5.08 (2H, s), 6.92 (4H, m), 7.31-7.45 (5H, m), 7.54-7.64 (4H, m).

REFERENCE EXAMPLE 82 methyl [4-[(3-phenoxyphenyl)methoxy]phenoxy]acetate

The title compound was obtained as a white powder from methyl (4-hydroxyphenoxy)acetate and (3-phenoxyphenyl) methanol by a method similar to that of Reference Example 1. yield 47%.

$^1$H NMR (CDCl$_3$) δ 3.80 (3H, s), 4.58 (2H, s), 4.98 (2H, s), 6.86 (4H, m), 6.90-7.18 (6H, m), 7.30-7.36 (3H, m).

REFERENCE EXAMPLE 83

[4-[(3-phenoxyphenyl) methoxy]phenoxy]acetic acid

The title compound was obtained from methyl [4-[(3-phenoxyphenyl) methoxy]phenoxy]acetate by a method similar to that of Reference Example 4. yield 86%.

melting point: 115-116° C. (recrystallized from ethyl acetate-hexane).

¹H NMR (CDCl₃) δ 4.63 (2H, s), 4.98 (2H, s), 6.81-7.16 (10H, m), 7.31-7.36 (3H, m).

REFERENCE EXAMPLE 84 ethyl 2-[4-[(2,3-dihydro-1H-inden-1-yl) oxy]phenoxy]-2-methylpropanoate

The title compound was obtained from ethyl 2-(4-hydroxyphenoxy)-2-methylpropanoate and 2,3-dihydro-1H-inden-1-ol by a method similar to that of Reference Example 1. yield 63%, oil.
¹H NMR (CDCl₃) δ 1.29 (3H, t, J=7.1 Hz), 1.56 (6H, s), 2.20 (1H, m), 2.51 (1H, m), 2.91 (1H, m), 3.13 (1H, m), 4.25 (2H, q, J=7.1 Hz), 5.67 (1H, dd, J=4.3 Hz, 6.6 Hz), 6.88 (4H, s), 7.20-7.31 (3H, m), 7.40 (1H, d, J=7.2 Hz).

REFERENCE EXAMPLE 85

2-[4-[(2,3-dihydro-1H-inden-1-yl) oxy]phenoxy]-2-methylpropanoic acid

The title compound was obtained from ethyl 2-[4-[(2,3-dihydro-1H-inden-1-yl)oxy]phenoxy]-2-methylpropanoate by a method similar to that of Reference Example 4. yield 71%.
melting point: 107-108° C. (recrystallized from diethyl ether-hexane).
¹H NMR (CDCl₃) δ 1.56 (6H, s), 2.22 (1H, m), 2.53 (1H, m), 2.92 (1H, m), 3.14 (1H, m), 5.70 (1H, dd, J=4.3 Hz, 6.6 Hz), 6.94 (4H, s), 7.21-7.32 (3H, m), 7.41 (1H, d, J=7.3 Hz).

REFERENCE EXAMPLE 86 ethyl 2-methyl-2-[4-[(3-phenoxyphenyl)methoxy]phenoxy]propanoate

The title compound was obtained from ethyl 2-(4-hydroxyphenoxy)-2-methylpropanoate and (3-phenoxyphenyl)methanol by a method similar to that of Reference Example 1. yield 78%, oil.
¹H NMR (CDCl₃) δ 1.27 (3H, t, J=7.1 Hz), 1.54 (6H, s), 4.23, (2H, q, J=7.1 Hz), 4.97 (2H, s), 6.82 (4H, s), 6.89-7.14 (6H, m), 7.30-7.36 (3H, m).

REFERENCE EXAMPLE 87

2-methyl-2-[4-[(3-phenoxyphenyl)methoxy]phenoxy]propanoic acid

The title compound was obtained from ethyl 2-methyl-2-[4-[(3-phenoxyphenyl) methoxy]phenoxy]propanoate by a method similar to that of Reference Example 4. yield 99%, amorphous.
¹H NMR (CDCl₃) δ 1.54 (6H, s), 4.99 (2H, s), 6.85-7.15 (10H, m), 7.31-7.36 (3H, m).

REFERENCE EXAMPLE 88 methyl [4-[(2,3-dihydro-1H-inden-1-yl) oxy]phenoxy]acetate

The title compound was obtained from ethyl 2-(4-hydroxyphenoxy)-2-methylpropanoate and 2,3-dihydro-1H-inden-1-ol by a method similar to that of Reference Example 1. yield 52%, oil.
¹H NMR (CDCl₃) δ 2.22 (1H, m), 2.51 (1H, m), 2.90 (1H, m), 3.14 (1H, m), 3.82 (3H, s), 4.61 (2H, s), 5.67 (1H, dd, J=4.4 Hz, 6.6 Hz), 6.86-6.96 (4H, m), 7.21-7.30 (3H, m), 7.40 (1H, d, J=7.3 Hz).

REFERENCE EXAMPLE 89

[4-[(2,3-dihydro-1H-inden-1-yl) oxy]phenoxy]acetic acid

The title compound was obtained from methyl [4-[(2,3-dihydro-1H-inden-1-yl)oxy]phenoxy]acetate by a method similar to that of Reference Example 4. yield 48%.
melting point: 99-100° c. (recrystallized from diethyl ether-hexane).
¹H NMR (CDCl₃) δ 2.22 (1H, m), 2.50 (1H, m), 2.94 (1H, m), 3.12 (1H, m), 4.66 (2H, s), 5.68 (1H, dd, J=4.3 Hz, 6.6 Hz), 6.90 (2H, d, J=9.3 Hz), 6.95 (2H, d, J=7.2 Hz), 7.20-7.30 (3H, m), 7.40 (1H, d, J=7.3 Hz).

REFERENCE EXAMPLE 90

(2,3-dihydro-1H-inden-1-yl) 3-[(2,3-dihydro-1H-inden-1-yl)oxy]benzeneacetate

The title compound was obtained from (3-hydroxyphenyl) acetic acid and 2,3-dihydro-1H-inden-1-ol by a method similar to that of Example 105. yield 81%, oil.
¹H NMR (CDCl₃) δ 2.03-2.24 (2H, m), 2.44-2.59 (2H, m), 2.83-2.96 (2H, m), 3.05-3.18 (2H, m), 3.61 (2H, s), 5.71-5.75 (1H, m), 6.21-6.24 (1H, m), 6.88-6.94 (3H, m), 7.18-7.31 (7H, m), 7.36-7.43 (2H, m).

REFERENCE EXAMPLE 91

3-[(2,3-dihydro-1H-inden-1-yl) oxy]benzeneacetic acid

The title compound was obtained from (2,3-dihydro-1H-inden-1-yl) 3-[(2,3-dihydro-1H-inden-1-yl)oxy]benzeneacetate by a method similar to that of Example 106. yield 61%, oil.
¹H NMR (CDCl₃) δ 2.14-2.25 (1H, m), 2.49-2.61 (1H, m), 2.85-2.95 (1H, m), 3.08-3.18 (1H, m), 3.62 (2H, s), 5.73-5.77 (1H, m), 6.87-6.94 (3H, m), 7.20-7.30 (4H, m), 7.41 (1H, d, J=7.3 Hz), 9.65 (1H, br s).

REFERENCE EXAMPLE 92

2,3-dihydro-1-(3-iodophenoxy)-1H-indene

The title compound was obtained from 3-iodophenol and 2,3-dihydro-1H-inden-1-ol by a method similar to that of Example 105. yield 37%, oil.
¹H NMR (CDCl₃) δ 2.18-2.23 (1H, m), 2.52-2.57 (1H, m), 2.93-2.98 (1H, m), 3.10-3.14 (1H, m), 5.71-5.75 (1H, m), 6.97-7.02 (2H, m), 7.22-7.32 (4H, m), 7.37-7.40 (2H, m).

REFERENCE EXAMPLE 93 ethyl 3-(2,3-dihydro-1H-inden-1-yloxy)benzenebutanoate

A mixture of 2,3-dihydro-1-(3-iodophenoxy)-1H-indene (1.5 g, 4.5 mmol), tetrahydrofuran (8 mL), 0.5 M 4-ethoxy-4-oxobutylzinc bromide-tetrahydrofuran solution (13 mL, 6.5 mmol) and bis(triphenylphosphine)palladium chloride (28 mg, 0.04 mmol) was stirred at 60° C. for 1 hr. The solvent was evaporated, and the residue was diluted with ethyl acetate and washed with water, and dried over anhydrous magnesium sulfate. The solvent was evaporated, and the residue was purified by silica gel column chromatography (hexane/ethyl acetate=5:1) to give the title compound (0.70 g, yield 48%). oil.

$^1$H NMR (CDCl$_3$) δ 1.28 (3H, t, J=7.1 Hz), 1.94-2.04 (2H, m), 2.18-2.36 (3H, m), 2.53-2.67 (3H, m), 2.87-2.97 (1H, m), 3.09-3.19 (1H, m), 4.12 (2H, d, J=7.1 Hz), 5.74-5.78 (1H, m), 6.79-6.87 (2H, m), 7.21-7.30 (5H, m), 7.43 (1H, d, J=7.2 Hz).

REFERENCE EXAMPLE 94

3-(2,3-dihydro-1H-inden-1-yloxy) benzenebutanoic acid

The title compound was obtained from ethyl 3-(2,3-dihydro-1H-inden-1-yloxy)benzenebutanoate by a method similar to that of Example 106. yield 80%, oil.

$^1$H NMR (CDCl$_3$) δ 1.93 (2H, m), 2.16-2.27 (1H, m), 2.39 (2H, t, J=7.5 Hz), 2.57-2.62 (1H, m), 2.67 (2H, t, J=7.5 Hz), 2.87-2.97 (1H, m), 3.10-3.20 (1H, m), 5.74-5.78 (1H, m), 6.79-6.88 (3H, m), 7.21-7.31 (4H, m), 7.43 (1H, d, J=7.2 Hz), 9.76 (1H, br s).

REFERENCE EXAMPLE 95 methyl 4-[(4-chloro-2-trifluoromethyl-5-quinolinyl)methoxy]benzenepropanoate

The title compound was obtained from methyl 4-hydroxybenzenepropanoate and 4-chloro-2-trifluoromethyl-5-quinolinemethanol by a method similar to that of Example 105. yield 65%.

melting point: 111-112° C. (recrystallized from ethyl acetate-diisopropyl ether).

$^1$H NMR (CDCl$_3$) δ 2.61 (2H, t, J=7.5 Hz), 2.91 (2H, t, J=7.5 Hz), 3.67 (3H, s), 5.30 (2H, s), 6.95 (2H, d, J=8.6 Hz), 7.14 (2H, d, J=8.6 Hz), 7.84 (1H, s), 7.93-7.97 (1H, m), 8.26 (1H, d, J=8.7 Hz), 8.35 (1H, s).

REFERENCE EXAMPLE 96

4-(2-trifluoromethyl-4-chloroquinolin-5-ylmethoxy)benzenepropanoic acid

The title compound was obtained from methyl 4-[(4-chloro-2-trifluoromethyl-5-quinolinyl)methoxy]benzenepropanoate by a method similar to that of Example 106. yield 90%.

melting point: 175-176° C. (recrystallized from ethyl acetate-hexane).

$^1$H NMR (DMSO-d$_6$) δ 2.47 (2H, t, J=7.5 Hz), 2.76 (2H, t, J=7.5 Hz), 5.33 (2H, s), 6.96-7.02 (2H, m), 7.15-7.17 (2H, m), 7.42 (1H, s), 7.93 (1H, d, J=8.7 Hz), 8.07-8.13 (1H, m), 8.29 (1H, s), 12.08 (1H, br s).

REFERENCE EXAMPLE 97 methyl 4-[2-(1-naphthatenyl)ethoxy]benzenepropanoate

The title compound was obtained from methyl 4-hydroxybenzenepropanoate and 1-naphthalenethanol by a method similar to that of Example 105. yield 63%.

melting point: 112-114° C. (recrystallized from ethyl acetate-diisopropyl ether-hexane).

$^1$H NMR (CDCl$_3$) δ 2.58 (2H, t, J=7.5 Hz), 2.88 (2H, t, J=7.5 Hz), 3.57 (2H, t, J=7.4 Hz), 3.66 (3H, s), 4.28 (2H, t, J=7.4 Hz), 6.82 (2H, t, J=8.6 Hz), 7.09 (2H, d, J=8.6 Hz), 7.42-7.56 (4H, m), 7.75-7.78 (1H, m), 7.86-7.89 (1H, m), 8.10-8.11 (1H, m).

REFERENCE EXAMPLE 98

4-[2-(1-naphthalenyl) ethoxy]benzenepropanoic acid

The title compound was obtained from methyl 4-[2-(1-naphthalenyl) ethoxy]benzenepropanoate by a method similar to that of Example 106. yield 89%.

melting point: 111-112° C. (recrystallized from ethyl acetate-diisopropyl ether).

$^1$H NMR (CDCl$_3$) δ 2.64 (2H, t, J=7.5 Hz), 2.89 (2H, t, J=7.5 Hz), 3.57 (2H, t, J=7.4 Hz), 4.28 (2H, t, J=7.4 Hz), 6.83 (2H, t, J=8.6 Hz), 7.10 (2H, d, J=8.6 Hz), 7.42-7.55 (4H, m), 7.73-7.78 (1H, m), 7.86-7.89 (1H, m), 8.10-8.11 (1H, m), 9.85 (1H, br s).

REFERENCE EXAMPLE 99 methyl 4-hydroxy-3-iodobenzenepropanoate and methyl 4-hydroxy-3,5-diiodobenzenepropanoate 28% Aqueous ammonia solution (10 mL) of methyl 4-hydroxybenzenepropanoate (3.0 g, 17 mmol) was cooled with water, and a mixture of iodine (4.7 g, 18 mmol), potassium iodide (4.6 g, 28 mmol) and water (10 mL) was added dropwise. The reaction mixture was stirred for 1.5 hrs, neutralized with 1N hydrochloric acid, and extracted with ethyl acetate. The organic layer was washed with 1% aqueous sodium thiosulfate solution and saturated brine, and dried over anhydrous magnesium sulfate. The solvent was evaporated, and the residue was subjected to silica gel column chromatography to give methyl 4-hydroxy-3,5-diiodobenzenepropanoate (3.0 g, yield 59%) from the eluate of hexane/ethyl acetate=5:1.

melting point: 64-66° C. (recrystallized from ethyl acetate-petroleum ether).

$^1$H NMR (CDCl$_3$) δ 2.57 (2H, t, J=7.5 Hz), 2.81 (2H, t, J=7.5 Hz), 3.68 (3H, s), 5.63 (1H, s), 7.52 (2H, s).

Further, methyl 4-hydroxy-3-iodobenzenepropanoate (1.6 g, yield 22%) was obtained from the eluate of hexane/ethyl acetate=5:1. oil.

$^1$H NMR (CDCl$_3$) δ 2.58 (2H, t, J=7.5 Hz), 2.84 (2H, t, J=7.5 Hz), 3.67 (3H, s), 5.81 (1H, s), 6.86 (1H, d, J=8.3 Hz), 7.03-7.07 (1H, m), 7.50 (1H, s).

REFERENCE EXAMPLE 100 methyl 2-(4-methoxyphenyl)-7-iodo-5-benzofuranpropanoate

A solution of methyl 4-hydroxy-3,5-diiodobenzenepropanoate (0.89 g, 2.1 mmol) and 4-methoxyethynylbenzenecopper (0.63 g) in N,N-dimethylformamide (15 mL) was stirred overnight at 120° C. The solvent was evaporated, and the residue was diluted with ethyl acetate, and washed with water. The organic layer was dried over anhydrous magnesium sulfate and concentrated. The residue was purified by silica gel column chromatography (hexane/ethyl acetate=6:1) to give the title compound (0.67 g, yield 74%).

melting point: 103-104° C. (recrystallized from ethyl acetate-diisopropyl ether).

¹H NMR (CDCl₃) δ 2.66 (2H, t, J=7.5 Hz), 2.99 (2H, t, J=7.5 Hz), 3.68 (3H, s), 3.87 (3H, s), 6.91 (1H, s), 6.98 (2H, d, J=8.8 Hz), 7.32 (1H, s), 7.44 (1H, s), 7.81 (2H, d, J=8.8 Hz).

REFERENCE EXAMPLE 101 methyl 2-(4-methoxyphenyl)-5-benzofuranpropanoate

A mixture of methyl 2-(4-methoxyphenyl)-7-iodo-5-benzofuranpropanoate (0.61 g, 1.4 mmol), zinc (0.92 g, 14 mmol), tetrahydrofuran (10 mL), methanol (30 mL) and 2N hydrogen chloride-methanol solution (3.0 mL) was heated under reflux overnight. The reaction mixture was filtered, and the filtrate was concentrated. The residue was diluted with ethyl acetate, washed with water, and dried over anhydrous magnesium sulfate. After concentration under reduced pressure, and the residue was purified by silica gel column chromatography (hexane/ethyl acetate=6:1) to give the title compound (0.11 g, yield 26%).
melting point: 74-75° C. (recrystallized from ethyl acetate-diisopropyl ether).
¹H NMR (CDCl₃) δ 2.68 (2H, t, J=7.5 Hz), 3.04 (2H, t, J=7.5 Hz), 3.67 (3H, s), 3.88 (3H, s), 6.88-6.91 (1H, m), 6.92 (1H, s), 7.10-7.13 (1H, m), 7.32-7.44 (5H, m).

REFERENCE EXAMPLE 102

2-(4-methoxyphenyl)-5-benzofuranpropanoic acid

The title compound was obtained from methyl 2-(4-methoxyphenyl)-5-benzofuranpropanoate by a method similar to that of Example 106. yield 74%.
melting point: 211-212° C. (recrystallized from ethyl acetate-diisopropyl ether).
¹H NMR (DMSO-d₆) δ 2.58 (2H, t, J=7.5 Hz), 2.91 (2H, t, J=7.5 Hz), 3.82 (3H, s), 7.06 (2H, d, J=8.9 Hz), 7.12-7.16 (1H, m), 7.21 (1H, s), 7.44-7.50 (2H, m), 7.84 (2H, d, J=8.8 Hz), 12.08 (1H, br s).

REFERENCE EXAMPLE 103 methyl 2-(3-methoxyphenyl)-5-benzofuranpropanoate

The title compound was obtained from methyl 4-hydroxy-3-iodobenzenepropanoate and 3-methoxyethynylbenzenecopper by a method similar to that of Reference Example 100. yield 19%.
melting point: 74-75° C. (recrystallized from ethyl acetate-diisopropyl ether).
¹H NMR (CDCl₃) δ 2.68 (2H, t, J=7.5 Hz), 3.04 (2H, t, J=7.5 Hz), 3.67 (3H, s), 3.88 (3H, s), 6.88-6.91 (1H, m), 6.91 (1H, s), 7.10-7.13 (1H, m), 7.32-7.44 (5H, m).

REFERENCE EXAMPLE 104

2-(3-methoxyphenyl)-5-benzofuranpropanoic acid

The title compound was obtained from methyl 2-(3-methoxyphenyl)-5-benzofuranpropanoate by a method similar to that of Example 106. yield 83%.
melting point: 134-135° C. (recrystallized from ethyl acetate-diisopropyl ether).
¹H NMR (DMSO-d₆) δ 2.58 (2H, t, J=7.5 Hz), 2.92 (2H, t, J=7.5 Hz), 3.85 (3H, s), 6.96-7.00 (1H, m), 7.17-7.21 (1H, m), 7.38-7.54 (6H, m), 12.12 (1H, br s).

REFERENCE EXAMPLE 105

4-methoxyethynylbenzenecopper

To an ice-cooled mixture of copper sulfate pentahydrate (2.5 g, 10 mmol), 28% aqueous ammonia (10 mL), water (100 mL) and hydroxylamine hydrochloride (1.4 g, 20 mmol) was added a solution of 4-methoxyethynylbenzene (1.3 g, 10 mmol) in ethanol (60 mL), and the mixture was stirred for 5 min. The precipitate was filtered, washed with water, ethanol and diethyl ether and dried under reduced pressure to give the title compound (1.8 g, yield 92%) as a yellow powder.
¹H-NMR (DMSO-d₆) δ 3.77 (3H, s), 6.93 (2H, d, J=8.8 Hz), 7.40 (2H, d, J=8.8 Hz).

REFERENCE EXAMPLE 106

3-methoxyethynylbenzenecopper

The title compound was obtained as a yellow powder from 3-methoxyethynylbenzene by a method similar to that of Reference Example 105. yield 90%.
¹H-NMR (DMSO-d₆) δ 3.76 (3H, s), 6.97-7.07 (3H, m), 7.30 (1H, t, J=8.1 Hz).

REFERENCE EXAMPLE 107 methyl 4-[[3-(3-furyl)phenyl]methoxy]benzenepropanoate

The title compound was obtained from 3-furylboronic acid by a method similar to that of Example 22. yield 83%, oil.
¹H NMR (CDCl₃) δ 2.60 (2H, t, J=8.0 Hz), 2.90 (2H, t, J=8.0 Hz), 3.66 (3H, s), 5.06 (2H, s), 6.71 (1H, dd, J=1.8 Hz, 0.7 Hz), 6.92 (2H, d, J=8.7 Hz), 7.12 (2H, t, J=8.7 Hz), 7.31-7.48 (4H, m), 7.54 (1H, s), 7.74-7.75 (1H, m).

REFERENCE EXAMPLE 108

4-[[3-(3-furyl)phenyl]methoxy]benzenepropanoic acid

The title compound was obtained from methyl 4-[[3-(3-furyl)phenyl]methoxy]benzenepropanoate by a method similar to that of Reference Example 4. yield 26%.
melting point: 120-122° C. (recrystallized from ethyl acetate-hexane).
¹H NMR (CDCl₃) δ 2.65 (2H, t, J=8.0 Hz), 2.91 (2H, t, J=8.0 Hz), 5.06 (2H, s), 6.70-6.71 (1H, m), 6.92 (2H, t, J=8.6 Hz), 7.13 (2H, d, J=8.6 Hz), 7.30-7.48 (4H, m), 7.54 (1H, s), 7.74 (1H, s).

REFERENCE EXAMPLE 109 methyl 4-[[3-(1H-pyrrol-1-yl)phenyl]methoxy]benzenepropanoate

Methyl 4-[(3-bromophenyl)methoxy]benzenepropanoate (0.80 g, 2.3 mmol), pyrrole (0.17 g, 2.5 mmol), tri-tert-butylphosphine (19 mg, 0.092 mmol) and cesium carbonate (1.3 g, 3.9 mmol) were dissolved in toluene (25 mL) and, after argon substitution, tris(dibenzylideneacetone)dipalladium(0) (84 mg, 0.092 mmol) was added. The reaction mixture was heated under an argon atmosphere at 100° C. for 18 hrs. The reaction mixture was cooled, water was added to the reaction mixture and the mixture was extracted with ethyl acetate. The extract was washed with water, dried and concentrated. The residue was purified by silica gel column chromatography (ethyl acetate/hexane=15:1) to give the title compound (56 mg, yield 7%) as a yellow powder.

$^1$H NMR (CDCl$_3$) δ 2.60 (2H, t, J=8.1 Hz), 2.90 (2H, t, J=8.1 Hz), 3.66 (3H, s), 5.08 (2H, s), 6.35 (2H, t, J=2.2 Hz), 6.91 (2H, d, J=8.6 Hz), 7.09-7.15 (4H, m), 7.24-7.36 (4H, m).

REFERENCE EXAMPLE 110

4-[[3-(1H-pyrrol-1-yl) phenyl]methoxy]benzenepropanoic acid

The title compound was obtained from methyl 4-[[3-(1H-pyrrol-1-yl)phenyl]methoxy]benzenepropanoate by a method similar to that of Reference Example 4. yield 16%.

melting point: 120-122° C. (recrystallized from diisopropyl ether-hexane).

$^1$H NMR (CDCl$_3$) δ 2.65 (2H, t, J=7.9 Hz), 2.91 (2H, t, J=7.9 Hz), 5.08 (2H, s), 6.35 (2H, t, J=2.1 Hz), 6.91 (2H, d, J=8.6 Hz), 7.10 (2H, t, J=2.1 Hz), 7.14 (2H, d, J=8.6 Hz), 7.26-7.47 (4H, m).

REFERENCE EXAMPLE 111 methyl 4-[[3-(2-thiazolyl) phenyl]methoxy]benzenepropanoate

The title compound was obtained from 2-bromothiazole by a method similar to that of Reference Example 61. yield 38%, oil.

$^1$H NMR (CDCl$_3$) δ 2.60 (2H, t, J=8.1 Hz), 2.90 (2H, t, J=8.1 Hz), 3.66 (3H, s), 5.10 (2H, s), 6.92 (2H, d, J=8.6 Hz), 7.12 (2H, d, J=8.6 Hz), 7.35 (1H, d, J=3.3 Hz), 7.43-7.52 (2H, m), 7.88 (1H, d, J=3.3 Hz), 7.91 (1H, dt, J=7.2 Hz, 1.7 Hz), 8.05 (1H, s).

REFERENCE EXAMPLE 112

4-[[3-(2-thiazolyl) phenyl]methoxy]benzenepropanoic acid

The title compound was obtained from methyl 4-[[3-(2-thiazolyl) phenyl]methoxy]benzenepropanoate by a method similar to that of Reference Example 4. yield 81%.

melting point: 126-127° C. (recrystallized from ethyl acetate-hexane).

$^1$H NMR (CDCl$_3$) δ 2.65 (2H, t, J=8.0 Hz), 2.91 (2H, t, J=8.0 Hz), 5.10 (2H, s), 6.93 (2H, d, J=8.6 Hz), 7.14 (2H, d, J=8.6 Hz), 7.35 (1H, d, J=3.3 Hz), 7.43-7.52 (2H, m), 7.88-7.92 (2H, m), 8.04 (1H, s).

REFERENCE EXAMPLE 113 methyl 4-[[3-(2-pyrazinyl) phenyl]methoxy]benzenepropanoate

The title compound was obtained from iodopyrazine by a method similar to that of Reference Example 61. yield 54%, oil.

$^1$H NMR (CDCl$_3$) δ 2.60 (2H, t, J=8.0 Hz), 2.90 (2H, t, J=8.0 Hz), 3.66 (3H, s), 5.14 (2H, s), 6.93 (2H, d, J=8.6 Hz), 7.13 (2H, d, J=8.6 Hz), 7.51-7.55 (2H, m), 7.95-7.99 (1H, m), 8.10 (1H, s), 8.53 (1H, d, J=2.5 Hz), 8.64-8.67 (1H, m), 9.05 (1H, d, J=1.4 Hz).

REFERENCE EXAMPLE 114

4-[[3-(2-pyrazinyl) phenyl]methoxy]benzenepropanoic acid

The title compound was obtained from methyl 4-[[3-(2-pyrazinyl) phenyl]methoxy]benzenepropanoate by a method similar to that of Reference Example 4. yield 62%.

melting point: 167.0-167.5° C. (recrystallized from ethyl acetate-hexane).

$^1$H NMR (CDCl$_3$+DMSO-d$_6$) δ 2.26 (2H, t, J=8.2 Hz), 2.90 (2H, t, J=8.2 Hz), 5.14 (2H, s), 6.92 (2H, d, J=8.6 Hz), 7.15 (2H, d, J=8.6 Hz), 7.51-7.58 (2H, m), 7.94-7.99 (1H, m), 8.10 (1H, s), 8.53 (1H, d, J=2.5 Hz), 8.65 (1H, dd, J=2.4 Hz, 1.6 Hz), 9.05 (1H, d, J=1.5 Hz).

REFERENCE EXAMPLE 115 methyl 4-[(5-bromo-2-chlorophenyl) methoxy]benzenepropanoate

The title compound was obtained from 3-bromo-2-chlorobenzyl alcohol by a method similar to that of Reference Example 1. yield 54%, oil.

$^1$H NMR (CDCl$_3$) δ 2.61 (2H, t, J=8.1 Hz), 2.91 (2H, t, J=8.1 Hz), 3.69 (3H, s), 5.09 (2H, s), 6.91 (2H, d, J=8.6 Hz), 7.14 (2H, d, J=8.6 Hz), 7.24-7.27 (1H, m), 7.38 (1H, dd, J=8.5 Hz, 2.3 Hz), 7.73 (1H, d, J=2.3 Hz).

REFERENCE EXAMPLE 116

4-[(5-bromo-2-chlorophenyl) methoxy]benzenepropanoic acid

The title compound was obtained from methyl 4-[(5-bromo-2-chlorophenyl) methoxy]benzenepropanoate by a method similar to that of Reference Example 4. yield 66%.

melting point: 120.0-120.5° C. (recrystallized from ethyl acetate-hexane).

$^1$H NMR (CDCl$_3$) δ 2.66 (2H, t, J=7.8 Hz), 2.92 (2H, t, J=7.8 Hz), 5.09 (2H, s), 6.92 (2H, d, J=8.6 Hz), 7.16 (2H, d, J=8.6 Hz), 7.24-7.27 (1H, m), 7.38 (1H, dd, J=8.5 Hz, 2.3 Hz), 7.73 (1H, d, J=2.3 Hz).

REFERENCE EXAMPLE 117 methyl 4-[(3-bromo-4-chlorophenyl) methoxy]benzenepropanoate

The title compound was obtained from 3-bromo-4-chlorobenzyl alcohol by a method similar to that of Reference Example 1. yield 65%, oil.

$^1$H NMR (CDCl$_3$) δ 2.60 (2H, t, J=7.6 Hz), 2.89 (2H, t, J=7.6 Hz), 3.66 (3H, s), 5.04 (2H, s), 6.85-6.89 (2H, m), 7.10-7.13 (2H, m), 7.35 (3H, s).

REFERENCE EXAMPLE 118

4-[(3-bromo-4-chlorophenyl) methoxy]benzenepropanoic acid

The title compound was obtained from methyl 4-[(3-bromo-4-chlorophenyl) methoxy]benzenepropanoate by a method similar to that of Reference Example 4.

melting point: 156-158° C. (recrystallized from ethyl acetate-hexane).

$^1$H NMR (CDCl$_3$) δ 2.65 (2H, t, J=7.9 Hz), 2.90 (2H, t, J=7.9 Hz), 5.00 (2H, s), 6.88 (2H, d, J=8.6 Hz), 7.13 (2H, d, J=8.6 Hz), 7.35 (3H, s).

REFERENCE EXAMPLE 119 methyl 4-[[3-[5-(trifluoromethyl)-2-pyridinyl]phenyl]methoxy]benzenepropanoate

The title compound was obtained from 2-chloro-5-(trifluoromethyl) pyridine by a method similar to that of Reference Example 61. yield 41%, oil.

$^1$H NMR (CDCl$_3$) δ 2.61 (2H, t, J=8.0 Hz), 2.90 (2H, t, J=8.0 Hz), 3.66 (3H, s), 5.14 (2H, s), 6.93 (2H, d, J=8.6 Hz), 7.13 (2H, d, J=8.6 Hz), 7.50-7.60 (2H, m), 7.86 (1H, d, J=8.3 Hz), 7.97-8.01 (2H, m), 8.11 (1H, br s), 8.95 (1H, br s).

REFERENCE EXAMPLE 120

4-[[3-[5-(trifluoromethyl)-2-pyridinyl]phenyl]methoxy]benzenepropanoic acid

The title compound was obtained from methyl 4-[[3-[5-(trifluoromethyl)-2-pyridinyl]phenyl]methoxy]benzenepropanoate by a method similar to that of Reference Example 4. yield 32%.

melting point: 155-156° C. (recrystallized from ethyl acetate-hexane).

$^1$H NMR (CDCl$_3$) δ 2.64 (2H, t, J=7.7 Hz), 2.90 (2H, t, J=7.7 Hz), 5.12 (2H, s), 6.92 (2H, d, J=8.4 Hz), 7.13 (2H, d, J=8.4 Hz), 7.49-7.54 (2H, m), 7.85 (1H, d, J=8.3 Hz), 7.90-8.00 (2H, m), 8.10 (1H, s), 8.95 (1H, s).

REFERENCE EXAMPLE 121 methyl 4-[[2-methyl-5-[4-(trifluoromethyl)phenyl]-3-furyl]methoxy]benzenepropanoate The title compound was obtained from 2-methyl-5-[4-(trifluoromethyl) phenyl]-3-furanmethanol by a method similar to that of Reference Example 1. yield 74%, oil.

$^1$H NMR (CDCl$_3$) δ 2.40 (3H, s), 2.61 (2H, t, J=8.0 Hz), 2.91 (2H, t, J=8.0 Hz), 3.67 (3H, s), 4.85 (2H, s), 6.78 (1H, s), 6.90 (2H, d, J=8.6 Hz), 7.14 (2H, d, J=8.6 Hz), 7.60 (2H, d, J=8.4 Hz), 7.71 (2H, d, J=8.4 Hz).

REFERENCE EXAMPLE 122

4-[[2-methyl-5-[4-(trifluoromethyl)phenyl]-3-furyl]methoxy]benzenepropanoic acid The title compound was obtained from methyl 4-[[2-methyl-5-[4-(trifluoromethyl)phenyl]-3-furyl]methoxy]benzenepropanoate by a method similar to that of Reference Example 4. yield 53%.

melting point: 182-183° C. (recrystallized from ethyl acetate-hexane).

$^1$H NMR (CDCl$_3$) δ 2.40 (3H, s), 2.66 (2H, t, J=7.8 Hz), 2.92 (2H, t, J=7.8 Hz), 4.85 (2H, s), 6.78 (1H, s), 6.91 (2H, d, J=8.6 Hz), 7.15 (2H, d, J=8.6 Hz), 7.60 (2H, d, J=8.4 Hz), 7.71 (2H, d, J=8.4 Hz).

REFERENCE EXAMPLE 123

4-[[5-(2,6-dimethylphenyl)-2-thienyl]methoxy]benzenepropanoic acid

Methyl 4-[[5-(2,6-dimethylphenyl)-2-thienyl]methoxy]benzenepropanoate was obtained from methyl 4-[(5-bromo-2-thienyl)methoxy]benzenepropanoate and 2,6-dimethylphenylboronic acid by a method similar to that of Example 22. yield 83%. Then, the title compound was obtained from methyl 4-[[5-(2,6-dimethylphenyl)-2-thienyl]methoxy]benzenepropanoate by a method similar to that of Reference Example 4. yield 26%.

melting point: 120-121° C. (recrystallized from ethyl acetate-hexane).

$^1$H NMR (CDCl$_3$) δ 2.17 (6H, s), 2.65 (2H, t, J=7.7 Hz), 2.91 (2H, t, J=7.7 Hz), 5.20 (2H, s), 6.70 (1H, d, J=3.4 Hz), 6.94 (2H, d, J=8.5 Hz), 7.08-7.20 (6H, m).

REFERENCE EXAMPLE 124

4-[[3-(2-pyridinyloxy) phenyl]methoxy]benzenepropanoic acid

Methyl 4-[[3-(2-pyridinyloxy) phenyl]methoxy]benzenepropanoate was obtained from methyl 4-hydroxybenzenepropanoate and 3-(2-pyridinyloxy) benzenemethanol by a method similar to that of Reference Example 1. yield 77%. Further, the title compound was obtained from methyl 4-[[3-(2-pyridinyloxy) phenyl]methoxy]benzenepropanoate by a method similar to that of Reference Example 4. yield 55%.

melting point: 146-147° C. (recrystallized from ethyl acetate-hexane).

$^1$H NMR (CDCl$_3$+DMSO-d$_6$) δ 2.57 (2H, t, J=7.5 Hz), 2.89 (2H, t, J=7.5 Hz), 5.05 (2H, s), 6.86-6.92 (3H, m), 6.99-7.14 (4H, m), 7.21-7.26 (2H, m), 7.40 (1H, t, J=7.8 Hz), 7.67-7.72 (1H, m), 8.19 (1H, d, J=4.3 Hz).

REFERENCE EXAMPLE 125 methyl 4-[[4-(bromomethyl) phenyl]methoxy]benzenepropanoate

α, α'-Dibromo-p-xylene (11 g, 40 mmol), methyl 4-hydroxybenzenepropanoate (1.7 g, 10 mmol) and potassium carbonate (1.6 g, 12 mmol) were dissolved in acetone (200 mL), and the mixture was heated under reflux for 8 hrs. The reaction mixture was cooled, water was added to the reaction mixture and extracted with ethyl acetate and tetrahydrofuran. The extract was washed with water, dried and concentrated.

The residue was purified by silica gel column chromatography (ethyl acetate/hexane=18:1) to give the title compound (0.78 g, yield 21%) as a white powder.

$^1$H NMR (CDCl$_3$) δ 2.60 (2H, t, J=8.0 Hz), 2.89 (2H, t, J=8.0 Hz), 3.66 (3H, s), 4.50 (2H, s), 5.03 (2H, s), 6.86-6.91 (2H, m), 7.11 (2H, d, J=8.6 Hz), 7.40 (4H, m).

REFERENCE EXAMPLE 126 methyl 3-bromo-4-hydroxybenzenepropanoate

To a solution of methyl 4-hydroxybenzenepropanoate (1.0 g, 5.6 mmol) in acetic acid (10 mL) was added sodium acetate (0.46 g, 6.1 mmol), and bromine (0.89 g, 5.6 mmol) was added dropwise while cooling to prevent heat of the reaction mixture.

The mixture was stirred at room temperature for 30 min., water was added, and the mixture was extracted with ethyl acetate. The extract was washed with water and concentrated under reduced pressure. The residue was purified by silica gel column chromatography (hexane/ethyl acetate=9:1) to give the title compound (0.68 g, yield 47%). oil.

$^1$H NMR (CDCl$_3$) δ 2.59 (2H, t, J=7.5 Hz), 2.86 (2H, t, J=7.5 Hz), 3.67 (3H, s), 5.45 (1H, s), 6.93 (1H, d, J=8.3 Hz), 7.04 (1H, dd, J=1.9 Hz, 8.3 Hz), 7.30 (1H, d, J=1.9 Hz).

REFERENCE EXAMPLE 127 methyl 4-(6-benzothiazolylmethoxy) benzenepropanoate

The title compound was obtained from methyl 4-hydroxybenzenepropanoate and 6-benzothiazolemethanol by a method similar to that of Example 105. yield 66%.

melting point: 103-106° C. (recrystallized from ethyl acetate-diisopropyl ether-hexane).

$^1$H NMR (CDCl$_3$) δ 2.60 (2H, t, J=7.5 Hz), 2.90 (2H, t, J=7.5 Hz), 3.66 (3H, s), 5.20 (2H, s), 6.92 (2H, d, J=8.7 Hz), 7.12 (2H, d, J=8.7 Hz), 7.55-7.58 (1H, m), 8.05 (1H, s), 8.13 (1H, d, J=8.4 Hz), 9.00 (1H, s).

REFERENCE EXAMPLE 128

4-(6-benzothiazolylmethoxy) benzenepropanoic acid

The title compound was obtained from methyl 4-(6-benzothiazolylmethoxy) benzenepropanoate by a method similar to that of Example 105. yield 88%.

melting point: 176-177° C. (recrystallized from ethyl acetate-diisopropyl ether).

$^1$H NMR (DMSO-d$_6$) δ 2.48 (2H, t, J=7.5 Hz), 2.75 (2H, t, J=7.5 Hz), 5.22 (2H, s), 6.95 (2H, d, J=8.7 Hz), 7.14 (2H, d, J=8.6 Hz), 7.59-7.63 (1H, m), 8.10 (1H, d, J=8.4 Hz), 8.24 (1H, s), 9.40 (1H, s), 12.08 (1H, br s).

EXAMPLE 1

4-[(2,3-dihydro-1H-inden-1-yl)oxy]benzenepropanoic acid

The title compound was obtained from methyl 4-[(2,3-dihydro-1H-inden-1-yl)oxy]benzenepropanoate by a method similar to that of Reference Example 4. yield 33%.

melting point: 103-104° C. (recrystallized from ethyl acetate-hexane).

$^1$H NMR (CDCl$_3$) δ 2.14-2.38 (1H, m), 2.50-2.63 (1H, m), 2.67 (2H, t, J=7.4 Hz), 2.87-2.96 (3H, m), 3.08-3.19 (1H, m), 5.73 (1H, dd, J=4.9 Hz, 6.5 Hz), 6.94 (2H, d, J=8.5 Hz), 7.15 (2H, d, J=8.5 Hz), 7.21-7.33 (3H, m), 7.42 (1H, d, J=7.2 Hz).

EXAMPLE 2

4-[(1,2,3,4-tetrahydronaphthalen-1-yl) oxy]benzenepropanoic acid

The title compound was obtained from methyl 4-[(1,2,3,4-tetrahydronaphthalen-1-yl)oxy]benzenepropanoate by a method similar to that of Reference Example 4. yield 51%.

melting point: 69-70° C. (recrystallized from diisopropyl ether-hexane).

$^1$H NMR (CDCl$_3$) δ 1.70-1.85 (1H, m), 1.98-2.16 (3H, m), 2.74-2.89 (2H, m), 2.67 (2H, t, J=7.4 Hz), 2.93 (2H, t, J=7.4 Hz), 5.33 (1H, t, J=4.1 Hz), 6.96 (2H, d, J=8.6 Hz), 7.14-7.24 (5H, m), 7.36-7.39 (1H, m).

EXAMPLE 3

4-[[2,3-dihydro-5-(phenylmethoxy)-1H-inden-1-yl] oxy]benzenepropanoic acid

The title compound was obtained from methyl 4-[[2,3-dihydro-5-(phenylmethoxy)-1H-inden-1-yl]oxy]benzenepropanoate by a method similar to that of Reference Example 4. yield 33%.

melting point: 99-100° C. (recrystallized from ethyl acetate-hexane).

$^1$H NMR (CDCl$_3$) δ 2.15-2.30 (1H, m), 2.45-2.60 (1H, m), 2.67 (2H, t, J=7.8 Hz), 2.82-2.90 (1H, m), 2.92 (2H, t, J=7.8 Hz), 3.06-3.14 (1H, m), 5.07 (2H, s), 5.67 (1H, dd, J=6.5, 3.6 Hz), 6.85-6.93 (4H, m), 7.14 (2H, d, J=8.5 Hz), 7.30-7.44 (6H, m).

EXAMPLE 4

4-[[4-[[methyl(4-phenyl-2-thiazolyl) amino]methyl]phenyl]methoxy]benzenepropanoic acid The title compound was obtained from ethyl 4-[[4-[[methyl (4-phenyl-2-thiazolyl) amino]methyl]phenyl]methoxy] benzenepropanoate by a method similar to that of Reference Example 4. yield 60%.

melting point: 130-131° C. (recrystallized from ethyl acetate-hexane).

$^1$H NMR (CDCl$_3$) δ 2.64 (2H, t, J=7.9 Hz), 2.90 (2H, t, J=7.9 Hz), 3.07 (3H, s), 4.78 (2H, s), 5.02 (2H, s), 6.72 (1H, s), 6.89 (2H, d, J=8.6 Hz), 7.12 (2H, d, J=8.6 Hz), 7.26-7.30 (1H, m), 7.34-7.41 (6H, m), 7.85-7.88 (2H, m).

EXAMPLE 5

4-[(4-phenoxyphenyl)methoxy]benzenepropanoic acid

The title compound was obtained from methyl 4-[(4-phenoxyphenyl) methoxy]benzenepropanoate by a method similar to that of Reference Example 4. yield 51%.

melting point: 144-145° C. (recrystallized from ethyl acetate-hexane).

$^1$H NMR (CDCl$_3$) δ 2.65 (2H, t, J=7.9 Hz), 2.91 (2H, t, J=7.9 Hz), 5.00 (2H, s), 6.91 (2H, d, J=8.6 Hz), 7.00-7.03 (4H, m), 7.08-7.15 (3H, m), 7.34 (2H, t, J=8.3 Hz), 7.39 (2H, d, J=8.6 Hz).

EXAMPLE 6

4-[[4-(phenylmethoxy)phenyl]methoxy]benzenepropanoic-acid

The title compound was obtained as a powder from methyl 4-[[4-(phenylmethoxy)phenyl]methoxy]benzenepropanoate by a method similar to that of Reference Example 4. yield 11%.

$^1$H NMR (CDCl$_3$) δ 2.65 (2H, t, J=7.9 Hz), 2.90 (2H, t, J=7.9 Hz), 4.96 (2H, s), 5.07 (2H, s), 6.90 (2H, d, J=8.6 Hz), 6.98 (2H, d, J=8.6 Hz) 7.12 (2H, d, J=8.6 Hz), 7.30-7.50 (7H, m).

EXAMPLE 7

4-([1,1'-biphenyl]-4-ylmethoxy)benzenepropanoic acid

Methyl 4-([1,1'-biphenyl]-4-ylmethoxy)benzenepropanoate was obtained from methyl 4-hydroxybenzenepropanoate and 4-phenylbenzyl bromide by a method similar to that of Reference Example 5. This was led to the title compound by a method similar to that of Reference Example 4. yield from methyl 4-hydroxybenzenepropanoate 11%.

melting point: 187-189° C. (recrystallized from tetrahydrofuran-hexane).

$^1$H NMR (CDCl$_3$) δ 2.66 (2H, t, J=7.7 Hz), 2.91 (2H, t, J=7.7 Hz), 5.08 (2H, s), 6.93 (2H, d, J=8.4 Hz), 7.14 (2H, d, J=8.4 Hz), 7.30-7.50 (5H, m), 7.50-7.60 (4H, m).

EXAMPLE 8

4-([1,1'-biphenyl]-3-ylmethoxy)benzenepropanoic acid

The title compound was obtained from methyl 4-([1,1'-biphenyl]-3-ylmethoxy)benzenepropanoate by a method similar to that of Reference Example 4. yield 48%.

melting point: 125-126° C. (recrystallized from ethyl acetate-hexane).

$^1$H NMR (CDCl$_3$) δ 2.65 (2H, t, J=7.9 Hz), 2.91 (2H, t, J=7.9 Hz), 5.10 (2H, s), 6.93 (2H, d, J=8.6 Hz), 7.13 (2H, d, J=8.6 Hz), 7.30-7.47 (5H, m), 7.50-7.61 (3H, m), 7.65 (1H, s).

EXAMPLE 9

4-[(3-phenoxyphenyl)methoxy]benzenepropanoic acid

The title compound was obtained from methyl 4-[(3-phenoxyphenyl) methoxy]benzenepropanoate by a method similar to that of Reference Example 4. yield 50%.

melting point: 94-95° C. (recrystallized from ethyl acetate-hexane).

$^1$H NMR (CDCl$_3$) δ 2.64 (2H, t, J=7.9 Hz), 2.90 (2H, t, J=7.9 Hz), 5.01 (2H, s), 6.86-6.90 (2H, m), 6.88-6.98 (1H, m), 7.00-7.03 (2H, m), 7.08-7.17 (5H, m), 7.30-7.36 (3H, m).

EXAMPLE 10

4-([1,1'-biphenyl]-2-ylmethoxy)benzenepropanoic acid

The title compound was obtained from methyl 4-([1,1'-biphenyl]-2-ylmethoxy)benzenepropanoate by a method similar to that of Reference Example 4. yield 45%.

melting point: 103-104° C. (recrystallized from ethyl acetate-hexane).

$^1$H NMR (CDCl$_3$) δ 2.63 (2H, t, J=7.9 Hz), 2.88 (2H, t, J=7.9 Hz), 4.91 (2H, s), 6.79 (2H, d, J=8.6 Hz), 7.08 (2H, d, J=8.6 Hz), 7.33-7.50 (8H, m), 7.60-7.70 (1H, m).

EXAMPLE 11

4-[(2-phenoxyphenyl)methoxy]benzenepropanoic acid

The title compound was obtained from methyl 4-[(2-phenoxyphenyl) methoxy]benzenepropanoate by a method similar to that of Reference Example 4. yield 45%.

melting point: 114-115° C. (recrystallized from ethyl acetate-hexane).

$^1$H NMR (CDCl$_3$) δ 2.63 (2H, t, J=7.9 Hz), 2.89 (2H, t, J=7.9 Hz), 5.13 (2H, s), 6.86-6.92 (3H, m), 6.95-7.00 (2H, m), 7.06-7.12 (3H, m), 7.16 (1H, dd, J=7.5 Hz, 1.0 Hz), 7.24-7.36 (3H, m), 7.58 (1H, dd, J=7.5 Hz, 1.4 Hz).

EXAMPLE 12

4-[(4-benzoylphenyl)methoxy]benzenepropanoic acid

The title compound was obtained from methyl 4-[(4-benzoylphenyl) methoxy]benzenepropanoate by a method similar to that of Reference Example 4. yield 84%.

melting point: 141-142° C. (recrystallized from ethyl acetate-hexane).

$^1$H NMR (CDCl$_3$) δ 2.66 (2H, t, J=8.0 Hz), 2.92 (2H, t, J=8.0 Hz), 5.14 (2H, s), 6.92 (2H, d, J=8.6 Hz), 7.15 (2H, d, J=8.6 Hz), 7.42-7.65 (5H, m), 7.79-7.84 (4H, m).

EXAMPLE 13

4-[[4-(4-chlorobenzoyl)phenyl]methoxy]benzenepropanoic acid

The title compound was obtained from methyl 4-[[4-(4-chlorobenzoyl) phenyl]methoxy]benzenepropanoate by a method similar to that of Reference Example 4. yield 90%.

melting point: 177-178° C. (recrystallized from ethyl acetate-hexane).

$^1$H NMR (CDCl$_3$) δ 2.66 (2H, t, J=7.9 Hz), 2.92 (2H, t, J=7.9 Hz), 5.14 (2H, s), 6.91 (2H, d, J=8.6 Hz), 7.15 (2H, d, J=8.6 Hz), 7.46 (2H, d, J=8.5 Hz), 7.55 (2H, d, J=8.2 Hz), 7.74-7.81 (4H, m).

EXAMPLE 14

4-[(3-benzoylphenyl)methoxy]benzenepropanoic acid

Methyl 4-[(3-benzoylphenyl)methoxy]benzenepropanoate was obtained from methyl 4-hydroxybenzenepropanoate and 3-(bromomethyl) benzophenone by a method similar to that of Reference Example 43. Then, the title compound was obtained from methyl 4-[(3-benzoylphenyl)methoxy]benzenepropanoate by a method similar to that of Reference Example 4. yield from methyl 4-hydroxybenzenepropanoate 73%.

melting point: 84-85° C. (recrystallized from ethyl acetate-hexane).

$^1$H NMR (CDCl$_3$) δ 2.65 (2H, t, J=8.0 Hz), 2.91 (2H, t, J=8.0 Hz), 5.11 (2H, s), 6.90 (2H, d, J=8.6 Hz), 7.13 (2H, d, J=8.6 Hz), 7.45-7.86 (9H, m).

EXAMPLE 15

4-[[4-(benzoylamino)phenyl]methoxy]benzenepropanoic acid

The title compound was obtained from methyl 4-[[4-(benzoylamino) phenyl]methoxy]benzenepropanoate by a method similar to that of Reference Example 38. yield 42%.

melting point: 204-205° C. (recrystallized from tetrahydrofuran-hexane).

$^1$H NMR (CDCl$_3$+DMSO-d$_6$) δ 2.57 (2H, t, J=8.1 Hz), 2.89 (2H, t, J=8.1 Hz), 5.02 (2H, s), 6.89 (2H, d, J=8.6 Hz), 7.13 (2H, d, J=8.6 Hz), 7.40-7.60 (5H, m), 7.76 (2H, d, J=8.5 Hz), 7.96-7.93 (2H, m), 9.04 (1H, s).

EXAMPLE 16 methyl 4-[(4-phenoxyphenyl)methoxy]benzenepropanoate

The title compound was obtained as a white powder from methyl 4-hydroxybenzenepropanoate and 4-phenoxybenzyl alcohol by a method similar to that of Reference Example 1. yield 92%.
$^1$H NMR (CDCl$_3$) δ 2.60 (2H, t, J=8.0 Hz), 2.90 (2H, t, J=8.0 Hz), 3.67 (3H, s), 5.00 (2H, s), 6.90 (2H, d, J=8.5 Hz), 6.97-7.03 (4H, m), 7.08-7.13 (3H, m), 7.34 (1H, t, J=7.8 Hz), 7.39 (2H, d, J=8.5 Hz).

EXAMPLE 17 methyl 4-[[4-(phenylmethoxy)phenyl]methoxy]benzenepropanoate

The title compound was obtained from methyl 4-hydroxybenzenepropanoate and 4-(benzyloxy)benzyl alcohol by a method similar to that of Reference Example 1. yield 27%, oil.
$^1$H NMR (CDCl$_3$) δ 2.59 (2H, t, J=8.0 Hz), 2.89 (2H, t, J=8.0 Hz), 3.66 (3H, s), 4.96 (2H, s), 5.07 (2H, s), 6.89 (2H, d, J=8.5 Hz), 6.98 (2H, d, J=8.5 Hz) 7.11 (2H, d, J=8.5 Hz), 7.26-7.44 (7H, m).

EXAMPLE 18 methyl 4-[(2,3-dihydro-1H-inden-1-yl)oxy]benzenepropanoate

The title compound was obtained from methyl 4-hydroxybenzenepropanoate and 2,3-dihydro-1H-inden-1-ol by a method similar to that of Reference Example 1. yield 62%, oil.
$^1$H NMR (CDCl$_3$) δ 2.15-2.28 (1H, m), 2.51-2.68 (3H, m), 2.79-2.95 (3H, m), 3.07-3.23 (1H, m), 3.69 (3H, s), 5.73 (1H, dd, J=4.4 Hz, 4.8 Hz), 6.94 (2H, d, J=8.6 Hz), 7.14 (2H, d, J=8.6 Hz), 7.22-7.31 (3H, m), 7.42 (1H, d, J=7.2 Hz).

EXAMPLE 19 methyl 4-[(1,2,3,4-tetrahydronaphthalen-1-yl)oxy]benzenepropanoate

The title compound was obtained as a white powder from methyl 4-hydroxybenzenepropanoate and 1,2,3,4-tetrahydro-1-naphthol by a method similar to that of Reference Example 1. yield 63%.
$^1$H NMR (CDCl$_3$) δ 1.70-1.75 (1H, m), 1.98-2.16 (3H, m), 2.62 (2H, t, J=8.2 Hz), 2.77-2.87 (2H, m), 2.92 (2H, t, J=8.2 Hz), 3.68 (3H, s), 5.23 (1H, t, J=4.2 Hz), 6.95 (2H, d, J=8.6 Hz), 7.11-7.16 (3H, m), 7.21 (2H, dt, J=2.2 Hz, 6.8 Hz) 7.38-7.36 (1H, m).

EXAMPLE 20 methyl 4-[(3'-formyl-[1,1'-biphenyl]-3-yl)methoxy]benzenepropanoate

The title compound was obtained from methyl 4-[(3-bromophenyl) methoxy]benzenepropanoate by a method similar to that of Example 22. yield 92%, oil.
$^1$H NMR (CDCl$_3$) δ 2.60 (2H, t, J=7.1 Hz), 2.90 (2H, t, J=7.1 Hz), 3.66 (3H, s), 5.11 (2H, s), 6.93 (2H, d, J=8.6 Hz), 7.13 (2H, d, J=8.6 Hz), 7.43-7.53 (2H, m), 7.55-7.67 (2H, m), 7.69 (1H, s), 7.85-7.88 (2H, m), 8.11-8.12 (1H, m), 10.10 (1H, s).

EXAMPLE 21

4-[(3'-formyl-[1,1'-biphenyl]-3-yl)methoxy]benzenepropanoic acid

The title compound was obtained from methyl 4-[(3'-formyl-[1,1'-biphenyl]-3-yl)methoxy]benzenepropanoate by a method similar to that of Reference Example 4. yield 83%.
melting point: 81-82° C. (recrystallized from ethyl acetate-hexane).
$^1$H NMR (CDCl$_3$) δ 2.66 (2H, t, J=7.5 Hz), 2.91 (2H, t, J=7.5 Hz), 5.12 (2H, s), 6.93 (2H, d, J=8.4 Hz), 7.14 (2H, d, 8.4 Hz), 7.45-7.53 (2H, m), 7.57-7.64 (2H, m), 7.69 (1H, s), 7.87 (2H, d, J=7.6 Hz), 8.11 (1H, s), 10.09 (1H, s).

EXAMPLE 22 methyl 4-([1,1'-biphenyl]-3-ylmethoxy)benzenepropanoate

Methyl 4-[(3-bromophenyl)methoxy]benzenepropanoate (0.60 g, 1.7 mmol), phenylboronic acid (0.25 g, 2.1 mmol) and sodium carbonate (0.55 g, 5.2 mmol) was dissolved in toluene-methanol-water (5:1:1, 35 mL) and, after argon substitution, tetrakistriphenylphosphinepalladium (99 mg, 0.086 mmol) was added. The reaction mixture was heated under reflux overnight under an argon atmosphere. The reaction mixture was cooled, water was added to the reaction mixture and the mixture was extracted with ethyl acetate. The extract was washed with water, dried and concentrated. The residue was purified by silica gel column chromatography (hexane/ethyl acetate=18:1) to give the title compound (0.55 g, yield 92%) as a white powder.
$^1$H NMR (CDCl$_3$) δ 2.60 (2H, t, J=8.0 Hz), 2.90 (2H, t, J=8.0 Hz), 3.66 (3H, s), 5.10 (2H, s), 6.92 (2H, d, J=8.5 Hz), 7.12 (2H, d, J=8.5 Hz), 7.35-7.47 (5H, m), 7.54-7.65 (4H, m).

EXAMPLE 23 methyl 4-[(3-phenoxyphenyl)methoxy]benzenepropanoate

The title compound was obtained from methyl 4-hydroxybenzenepropanoate and 3-phenoxybenzyl alcohol by a method similar to that of Reference Example 1. yield 66%, oil.
$^1$H NMR (CDCl$_3$) δ 2.59 (2H, t, J=8.1 Hz), 2.89 (2H, t, J=8.1 Hz), 3.66 (3H, s), 5.01 (2H, s), 6.90-7.20 (9H, m), 7.20-7.36 (4H, m).

EXAMPLE 24 methyl 4-([1,1'-biphenyl]-2-ylmethoxy)benzenepropanoate

The title compound was obtained from methyl 4-hydroxybenzenepropanoate and 2-phenylbenzyl bromide by a method similar to that of Reference Example 5. yield 52%, oil.

$^1$H NMR (CDCl$_3$) δ 2.58 (2H, t, J=8.1 Hz), 2.87 (2H, t, J=8.1 Hz), 3.66 (3H, s), 4.91 (2H, s), 6.78 (2H, d, J=8.6 Hz), 7.06 (2H, d, J=8.6 Hz), 7.33-7.40 (8H, m), 7.50-7.70 (1H, m).

EXAMPLE 25 methyl 4-[[2,3-dihydro-5-(phenylmethoxy)-1H-inden-1-yl]oxy]benzenepropanoate

The title compound was obtained as a white powder from methyl 4-hydroxybenzenepropanoate and 2,3-dihydro-5-(phenylmethoxy)-1H-inden-1-ol by a method similar to that of Reference Example 1. yield 65%.

$^1$H NMR (CDCl$_3$) δ 2.18-2.23 (1H, m), 2.45-2.60 (1H, m), 2.61 (2H, t, J=8.0 Hz), 2.82-2.90 (1H, m), 2.91 (2H, t, J=8.0 Hz), 3.06-3.20 (1H, m), 3.68 (3H, s), 5.07 (2H, s), 5.67 (1H, dd, J=6.5 Hz, 3.7 Hz), 6.84-6.93 (4H, m), 7.13 (2H, d, J=8.5 Hz), 7.26-7.44 (6H, m).

EXAMPLE 26 methyl 4-[(2-phenoxyphenyl)methoxy]benzenepropanoate

The title compound was obtained as a white powder from methyl 4-hydroxybenzenepropanoate and 2-phenoxybenzyl alcohol by a method similar to that of Reference Example 1. yield 93%.

$^1$H NMR (CDCl$_3$) δ 2.59 (2H, t, J=8.1 Hz), 2.88 (2H, t, J=8.1 Hz), 3.66 (3H, s), 5.13 (2H, s), 6.89 (3H, t, J=8.6 Hz), 6.98 (2H, d, J=8.1 Hz), 7.07-7.20 (4H, m), 7.25-7.40 (3H, m), 7.50-7.60 (1H, m).

EXAMPLE 27 methyl 4-[(4-benzoylphenyl)methoxy]benzenepropanoate

To a solution of methyl 4-hydroxybenzenepropanoate (0.65 -(bromomethyl) g, 3.6 mmol) in N,N-dimethylformamide (20 mL) were added 4benzophenone (1.0 g, 3.6 mmol) and potassium carbonate (0.50 g, 3.6 mmol), and the mixture was stirred at room temperature for 15 hrs. Water was added to the reaction mixture, and the mixture was extracted with ethyl acetate. The extract was washed with water and concentrated under reduced pressure. The residue was purified by silica gel column chromatography (hexane/ethyl acetate=9:1) to give the title compound (1.3 g, yield 96%) as a powder.

$^1$H NMR (CDCl$_3$) δ 2.60 (2H, t, J=8.0 Hz), 2.90 (2H, t, J=8.0 Hz), 3.67 (3H, s), 5.17 (2H, s), 6.91 (2H, d, J=8.7 Hz), 7.13 (2H, d, J=8.7 Hz), 7.46-7.60 (5H, m), 7.79-7.84 (4H, m).

EXAMPLE 28 methyl 4-[[4-(4-chlorobenzoyl)phenyl]methoxy]benzenepropanoate

The title compound was obtained as a powder from methyl 4-hydroxybenzenepropanoate and [4-(bromomethyl)phenyl](4-chlorophenyl) ketone by a method similar to that of Example 27. yield 57%.

$^1$H NMR (CDCl$_3$) δ 2.60 (2H, t, J=8.0 Hz), 2.90 (2H, t, J=8.0 Hz), 3.67 (3H, s), 5.13 (2H, s), 6.91 (2H, d, J=8.6 Hz), 7.13 (2H, d, J=8.6 Hz), 7.46 (2H, d, J=8.5 Hz), 7.55 (2H, d, J=7.0 Hz), 7.74-7.80 (4H, m).

EXAMPLE 29 methyl 4-[[4-(benzoylamino)phenyl]methoxy]benzenepropanoate

To a solution of methyl 4-[(4-aminophenyl) methoxy]benzenepropanoate (0.13 g, 0.44 mmol) and triethylamine (0.50 mL) in tetrahydrofuran (9 mL) was added benzoyl chloride (74 mg, 0.53 mmol), and the mixture was stirred at room temperature for 2 hrs. Water was added to the reaction mixture, and the mixture was extracted with ethyl acetate. The extract was washed with water, dried and concentrated. The residue was purified by silica gel column chromatography (hexane/ethyl acetate=18:1) to give the title compound (0.23 g, quantitative). oil.

$^1$H NMR (CDCl$_3$) δ 2.60 (2H, t, J=8.0 Hz), 2.90 (2H, t, J=8.0 Hz), 3.67 (3H, s), 5.10 (2H, s), 6.90 (2H, d, J=8.6 Hz), 7.11 (2H, d, J=8.6 Hz), 7.26-7.56 (5H, m), 7.66 (2H, d, J=8.5 Hz), 7.84-7.89 (3H, m).

EXAMPLE 30 methyl 4-[[4-[[methyl(4-phenyl-2-thiazolyl)amino]methyl]phenyl]methoxy]benzenepropanoate The title compound was obtained as a white powder from methyl 4-hydroxybenzenepropanoate and 4-[[methyl(4-phenyl-1,3-thiazol-2-yl)amino]methyl]benzenemethanol by a method similar to that of Reference Example 1. yield 77%.

$^1$H NMR (CDCl$_3$) δ 2.59 (2H, t, J=8.1 Hz), 2.89 (2H, t, J=8.1 Hz), 3.08 (3H, s), 3.66 (3H, s), 4.79 (2H, s), 5.02 (2H, s), 6.72 (1H, s), 6.89 (2H, d, J=8.6 Hz), 7.11 (2H, d, J=8.6 Hz), 7.25-7.30 (1H, m), 7.34-7.41 (6H, m), 7.86 (2H, d, J=7.1 Hz).

EXAMPLE 31

4-[(5,6-dihydro-4H-cyclopenta[b]thien-4-yl)oxy]benzenepropanoic acid 5,6-Dihydro-4H-cyclopenta[b]thien-4-ol was obtained from 5,6-dihydro-4H-cyclopenta[b]thien-4-one by a method similar to that of Reference Example 32. This was condensed with methyl 4-hydroxybenzenepropanoate by a method similar to that of Reference Example 1 to give methyl 4-[(5,6-dihydro-4H-cyclopenta[b]thien-4-yl)oxy]benzenepropanoate. The title compound was obtained from methyl 4-[(5,6-dihydro-4H-cyclopenta[b]thien-4-yl)oxy]benzenepropanoate by a method similar to that of Reference Example 4. yield from 5,6-dihydro-4H-cyclopenta[b]thien-4-one 19%.

melting point: 87-88° C. (recrystallized from diethyl ether-hexane).

$^1$H NMR (CDCl$_3$) δ 2.53-2.69 (3H, m), 2.85-3.01 (4H, m), 3.15 (1H, m), 5.64 (1H, dd, J=2.0 Hz, 5.8 Hz), 6.88-6.93 (3H, m), 7.13 (2H, d, J=8.6 Hz), 7.20 (1H, d, J=5.0 Hz).

EXAMPLE 32 methyl 4-[(4,5,6,7-tetrahydrobenzo[b]thien-4-yl)oxy]benzenepropanoate 4,5,6,7-Tetrahydrobenzo[b]thien-4-ol was obtained from 6,7-dihydrobenzo[b]thien-4(5H)-one by a method similar to that of Reference Example 32. This was condensed with methyl 4-hydroxybenzenepropanoate by a method similar to that of Reference Example 1 to give the title compound. yield from 6,7-dihydrobenzo[b]thien-4(5H)-one 72%. oil.

$^1$H NMR (CDCl$_3$) δ 1.80-2.15 (4H, m), 2.61 (2H, t, J=7.4 Hz), 2.76 (1H, m), 2.78-2.94 (3H, m), 3.68 (3H, s), 5.33 (1H, t, J=4.4 Hz), 6.91-6.95 (3H, m), 7.08-7.15 (3H, m).

EXAMPLE 33 methyl 4-[(2,3-dihydro-1H-inden-1-yl)oxy]-3,5-difluorobenzenepropanoate

To a mixture of methyl (E)-3-[4-[(2,3-dihydro-1H-inden-1-yl) oxy]-3,5-difluorophenyl]-2-propenoate (0.52 g, 1.6 mmol), samarium (1.2 g, 7.9 mmol), tetrahydrofuran (3 mL) and methanol (7 mL) was added iodine (0.80 g, 3.2 mmol), and the mixture was stirred overnight at room temperature. 1N Hydrochloric acid (20 mL) was added and the mixture was stirred for 20 min. The mixture was diluted with water, and extracted with ethyl acetate. The extract was washed with water, dried over anhydrous sodium sulfate, and concentrated. The residue was purified by silica gel column chromatography (hexane/ethyl acetate=10:1) to give the title compound. yield 60%, oil.

$^1$H NMR (CDCl$_3$) δ 2.34-2.40 (2H, m), 2.61 (2H, t, J=7.5 Hz), 2.81-2.91 (3H, m), 3.20-3.30 (1H, m), 5.61 (1H, t, J=4.4 Hz), 6.72-6.78 (2H, m), 7.16-7.22 (1H, m), 7.29-7.31 (2H, m), 7.34 (1H, d, J=7.4 Hz).

EXAMPLE 34

3,5-difluoro-4-[(2,3-dihydro-1H-inden-1-yl)oxy]benzenepropanoic acid

The title compound was obtained from methyl 3,5-difluoro-4-[(2,3-dihydro-1H-inden-1-yl)oxy]benzenepropanoate by a method similar to that of Reference Example 38. yield 75%.

melting point: 88-89° C. (recrystallized from ethyl acetate-hexane).

$^1$H NMR (CDCl$_3$) δ 2.34-2.40 (2H, m), 2.67 (2H, t, J=7.5 Hz), 2.81-2.92 (3H, m), 3.20-3.30 (1H, m), 5.62 (1H, t, J=4.4 Hz), 6.72-6.80 (2H, m), 7.17-7.23 (1H, m), 7.29-7.36 (3H, m).

EXAMPLE 35

4-[[2,3-dihydro-4-(phenylmethoxy)-1H-inden-1-yl]oxy]benzenepropanoic acid

Methyl 4-[[2,3-dihydro-4-(phenylmethoxy)-1H-inden-1-yl]oxy]benzenepropanoate was obtained from methyl 4-hydroxybenzenepropanoate and 2,3-dihydro-4-(phenylmethoxy)-1H-inden-1-ol by a method similar to that of Reference Example 1. oil. The title compound was obtained from methyl 4-[[2,3-dihydro-4-(phenylmethoxy)-1H-inden-1-yl]oxy]benzenepropanoate by a method similar to that of Reference Example 4. yield from methyl 4-hydroxybenzenepropanoate 27%.

melting point: 111-111.5° C. (recrystallized from diethyl ether-hexane).

$^1$H NMR (CDCl$_3$) δ.2.10-2.30 (1H, m), 2.50-2.60 (1H, m), 2.67 (2H, t, J=7.9 Hz), 2.40-3.00 (3H, m), 3.09-3.14 (1H, m), 5.12 (2H, s), 5.74 (1H, dd, J=6.7 Hz, 4.4 Hz), 6.85 (1H, d, J=8.0 Hz), 6.94 (2H, d, J=8.6 Hz), 7.05 (1H, d, J=7.5 Hz), 7.13-7.23 (3H, m), 7.29-7.45 (5H, m).

EXAMPLE 36 methyl 4-[[2,3-dihydro-6-(phenylmethoxy)-1H-inden-1-yl]oxy]benzenepropanoate

The title compound was obtained from methyl 4-hydroxybenzenepropanoate and 2,3-dihydro-6-(phenylmethoxy)-1H-inden-1-ol by a method similar to that of Reference Example 1. yield 40%, oil.

$^1$H NMR (CDCl$_3$) δ 2.10-2.30 (1H, m), 2.53-2.55 (3H, m), 2.75-2.94 (3H, m), 3.01-3.10 (1H, m), 3.68 (3H, s), 5.01 (1H, d, J=11.7 Hz), 5.06 (1H, d, J=11.7 Hz), 5.68 (1H, dd, J=6.5 Hz, 4.9 Hz), 6.91-6.96 (3H, m), 7.03 (1H, d, J=1.7 Hz), 7.08-7.20 (3H, m), 7.31-7.43 (5H, m).

EXAMPLE 37

4-[[2,3-dihydro-6-(phenylmethoxy)-1H-inden-1-yl]oxy]benzenepropanoic acid

The title compound was obtained from methyl 4-[[2,3-dihydro-6-(phenylmethoxy)-1H-inden-1-yl]oxy]benzenepropanoate by a method similar to that of Reference Example 4. yield 51%.

melting point: 106-107° C. (recrystallized from diisopropyl ether-hexane).

$^1$H NMR (CDCl$_3$) δ 2.14-2.25 (1H, m), 2.51-2.63 (1H, m), 2.67 (2H, t, 8.0 Hz), 2.79-2.95 (3H, m), 3.01-3.10 (1H, m), 5.01 (1H, d, J=11.8 Hz), 5.06 (1H, d, J=11.8 Hz), 5.69 (1H, t, J=4.8 Hz), 6.92-6.96 (3H, m), 7.05 (1H, d, J=7.9 Hz), 7.14-7.20 (3H, m), 7.20-7.43 (5H, m).

EXAMPLE 38 methyl (S)-4-[(2,3-dihydro-1H-inden-1-yl) oxy]benzenepropanoate

Methyl 4-hydroxybenzenepropanoate (4.1 g, 22 mmol) was dissolved in tetrahydrofuran (50 mL) and the mixture was stirred at −30° C. (R)-1-Indanol (98% ee) (3.0 g, 22 mmol), 1,1'-(azodicarbonyl)dipiperidine (5.66 g, 22 mmol) and tributylphosphine (5.6 mL, 22 mmol) were added and the mixture was stirred at −30° C. for 23 hrs. Water was added and the mixture was extracted with ethyl acetate. The organic layer was washed with saturated brine and dried over sodium sulfate. The mixture was concentrated under reduced pressure and the obtained oil was purified by silica gel chromatography (hexane to hexane/ethyl acetate=10:1) to give the title compound (4.4 g, yield 66%) as a yellow oil.

EXAMPLE 39 methyl (R)-4-[(2,3-dihydro-1H-inden-1-yl) oxy]benzenepropanoate

The title compound was obtained as an oil from (S)-1-indanol and methyl 4-hydroxybenzenepropanoate by a method similar to that of Example 38. yield 70%.

EXAMPLE 40

(S)-4-[(2,3-dihydro-1H-inden-1-yl) oxy]benzenepropanoic acid (Synthetic Method 1)

4-[(2,3-Dihydro-1H-inden-1-yl)oxy]benzenepropanoic acid (100 mg) was separated by high performance liquid chromatography (column:CHIRALCEL OJ (50 mmID×500 mm, manufactured by DAICEL CHEMICAL INDUSTRIES, LTD.), mobile phase: hexane/ethanol/trifluoroacetic acid=90:10:0.1, flow rate: 80 mL/min, column temperature: 50° C.) to give the title compound (36 mg). Optical rotation of this compound showed (+).
(Synthetic Method 2)

Methyl (S)-4-[(2,3-dihydro-1H-inden-1-yl) oxy]benzenepropanoate (4.4 g, 15 mmol) was dissolved in methanol (50 mL), 1N aqueous sodium hydroxide solution (25 mL) was added and the mixture was stirred at room temperature for 18.5 hrs. 1N Hydrochloric acid (25 mL) was added thereto, and the mixture was extracted with ethyl acetate. The organic layer was washed with saturated brine, and dried over sodium sulfate. The mixture was concentrated under reduced pressure and the obtained crystals were washed with hexane to give colorless crystals (4.2 g, 96% ee). The crystals were recrystallized from a mixed solvent of diisopropyl ether (70 mL) and hexane (70 mL) to give the title compound (2.3 g, 99.4% ee, yield 56%) as colorless crystals. As the secondary crystals, 0.67 g (yield 16%, 97% ee) of the title compound was obtained and as the tertiary crystals, 0.16 g (yield 4%, 92% ee) of the title compound was obtained.

melting point: 112-113° C. (primary crystals).
$[\alpha]_D^{23}$ +28.9° (c 0.997, $CHCl_3$).
IR (KBr) ν $cm^{-1}$: 2938, 1694, 1510, 1232, 957, 829, 761.
$^1$H NMR ($CDCl_3$) δ 2.20 (1H, m), 2.55 (1H, m), 2.67 (2H, t, J=7.6 Hz), 2.92 (2H, t, J=7.6 Hz), 2.92 (1H, m), 3.13 (1H, m), 5.73 (1H, dd, J=4.4 Hz, 6.8 Hz), 6.94 (2H, dt J=2.6 Hz, 8.4 Hz), 7.16 (2H, dt, J=2.6 Hz, 8.4 Hz), 7.23 (1H, m), 7.30 (2H, m), 7.42 (1H, d, J=7.2 Hz), 11.0 (1H, br s).

EXAMPLE 41

(R)-4-[(2,3-dihydro-1H-inden-1-yl) oxy]benzenepropanoic acid (Synthetic Method 1)
4-[(2,3-Dihydro-1H-inden-1-yl)oxy]benzenepropanoic acid (100 mg) was separated by high performance liquid chromatography (column:CHIRALCEL OJ (50 mmID×500 mm, manufactured by DAICEL CHEMICAL INDUSTRIES, LTD.), mobile phase: hexane/ethanol/trifluoroacetic acid=90:10:0.1, flow rate: 80 mL/min, column temperature: 50° C.) to give the title compound (38 mg). Optical rotation of this compound showed (−).
(Synthetic Method 2)

The title compound was obtained from methyl (R)-4-[(2,3-dihydro-1H-inden-1-yl)oxy]benzenepropanoate by a method similar to that of Example 40. yield: primary crystals (99.0% ee) 39%, secondary crystals (97% ee)-20%, tertiary crystals (92% ee) 7%.

melting point: 110-111° C. (primary crystals).
$[\alpha]_D^{23}$ −28.8° (c 0.997, $CHCl_3$).
IR (KBr) ν $cm^{-1}$: 2938, 1694, 1510, 1232, 957, 829, 761.
$^1$H NMR ($CDCl_3$) δ 2.20 (1H, m), 2.55 (1H, m), 2.67 (2H, t, J=7.6 Hz), 2.92 (2H, t, J=7.6 Hz), 2.92 (1H, m), 3.13 (1H, m), 5.73 (1H, dd, J=4.4 Hz, 6.8 Hz), 6.94 (2H, dt J=2.6 Hz, 8.4 Hz), 7.16 (2H, dt, J=2.6 Hz, 8.4 Hz), 7.23 (1H, m), 7.30 (2H, m), 7.42 (1H, d, J=7.6 Hz), 11.0 (1H, br s).

EXAMPLE 42

4-[(4,5,6,7-tetrahydrobenzo[b]thien-4-yl) oxy]benzenepropanoic acid

The title compound was obtained from methyl 4-[(4,5,6,7-tetrahydrobenzo[b]thien-4-yl)oxy]benzenepropanoate by a method similar to that of Reference Example 4. yield 54%.

melting point: 87-89° C. (recrystallized from diethyl ether-hexane).
$^1$H NMR ($CDCl_3$) δ 1.79-2.17 (4H, m), 2.66 (2H, t, J=7.4 Hz), 2.76 (1H, m), 2.87-2.95 (3H, m), 5.33 (1H, t, J=4.4 Hz), 6.91-6.96 (3H, m), 7.09 (1H, d, J=5.2 Hz), 7.14 (2H, d, J=8.6 Hz).

EXAMPLE 43 methyl 4-[(6-bromo-2,3-dihydro-1H-inden-1-yl) oxy]benzenepropanoate

6-Bromo-1-indanol was obtained from 6-bromo-1-indanone by a method similar to that of Reference Example 32. This compound was condensed with methyl 4-hydroxybenzenepropanoate by a method similar to that of Reference Example 1 to give the title compound. yield from 6-bromo-1-indanone 84%. oil.
$^1$H NMR ($CDCl_3$) δ 2.20 (1H, m), 2.51-2.64 (3H, m), 2.79-2.94 (3H, m), 3.06 (1H, m), 3.68 (3H, s), 5.68 (1H, t, J=5.0 Hz), 6.91 (2H, d, J=8.6 Hz), 7.10-7.15 (3H, m), 7.40 (1H, dd, J=1.8 Hz, 8.0 Hz), 7.53 (1H, d, J=1.3 Hz).

EXAMPLE 44

4-[(6-bromo-2,3-dihydro-1H-inden-1-yl) oxy]benzenepropanoic acid

The title compound was obtained from methyl 4-[(6-bromo-2,3-dihydro-1H-inden-1-yl)oxy]benzenepropanoate by a method similar to that of Reference Example 4. yield 59%.

melting point: 108-109° C. (recrystallized from diethyl ether-hexane).
$^1$H NMR ($CDCl_3$) δ 2.20 (1H, m), 2.57 (1H, m), 2.69 (2H, t, J=8.0 Hz), 2.85 (1H, m), 2.96 (2H, t, J=8.0 Hz), 3.06 (1H, m), 5.68 (1H, dd, J=4.9 Hz, 6.5 Hz), 6.92 (2H, d, J=8.6 Hz), 7.10-7.19 (3H, m), 7.41 (1H, dd, J=1.9 Hz, 8.1 Hz), 7.54 (1H, d, J=1.4 Hz).

EXAMPLE 45

4-[(2,3-dihydro-6-phenyl-1H-inden-1-yl) oxy]benzenepropanoic acid

The title compound was obtained from methyl 4-[(6-bromo-2,3-dihydro-1H-inden-1-yl)oxy]benzenepropanoate and phenylboronic acid by a method similar to that of Example 22. yield 11%.

melting point: 121-122° C. (recrystallized from diethyl ether-hexane).
$^1$H NMR ($CDCl_3$) δ 2.25 (1H, m), 2.60 (1H, m), 2.68 (2H, t, J=8.0 Hz), 2.90-3.00 (3H, m), 3.17 (1H, m), 5.78 (1H, dd, J=4.5 Hz, 6.5 Hz), 6.97 (2H, d, J=8.6 Hz), 7.16 (2H, d, J=8.6 Hz), 7.27-7.63 (8H, m).

EXAMPLE 46 methyl 4-[(2-methyl[1,1'-biphenyl]-3-yl) methoxy]benzenepropanoate

The title compound was obtained from methyl 4-hydroxybenzenepropanoate and 2-methyl-3-biphenylmethanol by a method similar to that of Reference Example 1. yield 51%, white powder.

¹H NMR (CDCl₃) δ 2.24 (3H, s), 2.61 (2H, t, J=8.1 Hz), 2.91 (2H, t, J=8.1 Hz), 3.67 (3H, s), 5.06 (2H, s), 6.95 (2H, d, J=8.6 Hz), 7.14 (2H, d, J=8.6 Hz), 7.22-7.44 (8H, m).

EXAMPLE 47

4-[(2-methyl[1,1'-biphenyl]-3-yl)methoxy]benzenepropanoic acid

The title compound was obtained from methyl 4-[(2-methyl [1,1'-biphenyl]-3-yl)methoxy]benzenepropanoate by a method similar to that of Reference Example 4. yield 53%.
melting point: 154-155° C. (recrystallized from ethyl acetate-hexane).
¹H NMR (CDCl₃) δ 2.24 (3H, s), 2.66 (2H, t, J=7.9 Hz), 2.92 (2H, t, J=7.9 Hz), 5.06 (2H, s), 6.95 (2H, d, J=8.6 Hz), 7.15 (2H, d, J=8.6 Hz), 7.24-7.44 (8H, m).

EXAMPLE 48 methyl 4-[(4-bromo-2,3-dihydro-1H-inden-1-yl)oxy]benzenepropanoate

4-Bromo-1-indanol was obtained from 4-bromo-1-indanone by a method similar to that of Reference Example 32. This was condensed with methyl 4-hydroxybenzenepropanoate by a method similar to that of Reference Example 1 to give the title compound. yield from 4-bromo-1-indanone 31%.
¹H NMR (CDCl₃) δ 2.22 (1H, m), 2.51-2.64 (3H, m), 2.88-2.97 (3H, m), 3.12 (1H, m), 3.68 (3H, s), 5.78 (1H, dd, J=4.6 Hz, 6.8 Hz), 6.91 (2H, d, J=8.6 Hz), 7.09-7.16 (3H, m), 7.34 (1H, d, J=7.5 Hz), 7.46 (1H, d, J=7.8 Hz).

EXAMPLE 49

4-[(4-bromo-2,3-dihydro-1H-inden-1-yl)oxy]benzenepropanoic acid

The title compound was obtained from methyl 4-[(4-bromo-2,3-dihydro-1H-inden-1-yl)oxy]benzenepropanoate by a method similar to that of Reference Example 4. yield 77%.
melting point: 112-113° C. (recrystallized from diethyl ether-hexane).
¹H NMR (CDCl₃) δ 2.20 (1H, m), 2.57 (1H, m), 2.67 (2H, t, J=8.0 Hz), 2.87-2.98 (3H, m), 3.14 (1H, m), 5.78 (1H, dd, J=3.5 Hz, 6.6 Hz), 6.92 (2H, d, J=8.6 Hz), 7.09-7.17 (3H, m), 7.35 (1H, d, J=7.5 Hz), 7.47 (1H, d, J=7.9 Hz).

EXAMPLE 50 methyl 4-([4'-chloro-1,1'-biphenyl]-3-ylmethoxy)benzenepropanoate

The title compound was obtained as a oil from 4-chlorophenylboronic acid by a method similar to that of Example 22. yield 59%.
¹H NMR (CDCl₃) δ 2.60 (2H, t, J=8.1 Hz), 2.90 (2H, t, J=8.1 Hz), 3.66 (3H, s), 5.09 (2H, s), 6.92 (2H, d, J=8.6 Hz), 7.12 (2H, d, J=8.6 Hz), 7.38-7.54 (7H, m), 7.61 (1H, br s).

EXAMPLE 51

4-([4'-chloro-1,1'-biphenyl]-3-ylmethoxy) benzenepropanoic acid

The title compound was obtained from methyl 4-([4'-chloro-1,1'-biphenyl]-3-ylmethoxy)benzenepropanoate by a method similar to that of Reference Example 4. yield 52%.

melting point: 147-148° C. (recrystallized from ethyl acetate-hexane).
¹H NMR (CDCl₃) δ 2.65 (2H, t, J=7.9 Hz), 2.91 (2H, t, J=7.9 Hz), 5.09 (2H, s), 6.93 (2H, d, J=8.6 Hz), 7.14 (2H, d, J=8.6 Hz), 7.39-7.53 (7H, m), 7.61 (1H, s).

EXAMPLE 52 methyl 4-[(2,3-dihydro-4-phenyl-1H-inden-1-yl)oxy]benzenepropanoate

The title compound was obtained from methyl 4-[(4-bromo-2,3-dihydro-1H-inden-1-yl)oxy]benzenepropanoate and phenylboronic acid by a method similar to that of Example 22. yield 95%, oil.
¹H NMR (CDCl₃) δ 2.20 (1H, m), 2.51 (1H, m), 2.62 (2H, t, J=7.1 Hz), 2.90-3.01 (3H, m), 3.19 (1H, m), 3.68 (3H, s), 5.77 (1H, dd, J=4.6 Hz, 6.5 Hz), 6.96 (2H, d, J=8.6 Hz), 7.15 (2H, d, J=8.6 Hz), 7.33-7.45 (8H, m).

EXAMPLE 53

4-[(4-phenyl-2,3-dihydro-1H-inden-1-yl)oxy]benzenepropanoic acid

The title compound was obtained from methyl 4-[(2,3-dihydro-4-phenyl-1H-inden-1-yl)oxy]benzenepropanoate by a method similar to that of Reference Example 4. yield 65%.
melting point: 137-138° C. (recrystallized from diethyl ether-hexane).
¹H NMR (CDCl₃) δ 2.20 (1H, m), 2.52 (1H, m), 2.68 (2H, t, J=8.0 Hz), 2.91-3.01 (3H, m), 3.20 (1H, m), 5.78 (1H, dd, J=4.6 Hz, 6.5 Hz), 6.98 (2H, d, J=8.6 Hz), 7.17 (2H, d, J=8.6 Hz), 7.33-7.47 (8H, m).

EXAMPLE 54 methyl 4-([4'-trifluoromethyl-1,1'-biphenyl]-3-ylmethoxy) benzenepropanoate

The title compound was obtained as a white powder from 4-trifluoromethylphenylboronic acid by a method similar to that of Example 22. yield 82%.
¹H NMR (CDCl₃) δ 2.60 (2H, t, J=8.0 Hz), 2.91 (2H, t, J=8.0 Hz), 3.66 (3H, s), 5.11 (2H, s), 6.93 (2H, d, J=8.7 Hz), 7.13 (2H, d, J=8.7 Hz), 7.47-7.57 (3H, m), 7.66-7.70 (5H, m).

EXAMPLE 55

4-([4'-trifluoromethyl-1,1'-biphenyl]-3-ylmethoxy) benzenepropanoic acid

The title compound was obtained from methyl 4-([4'-trifluoromethyl-1,1'-biphenyl]-3-ylmethoxy)benzenepropanoate by a method similar to that of Reference Example 4. yield 53%.
melting point: 144° C. (recrystallized from ethyl acetate-hexane).
¹H NMR (CDCl₃) δ 2.65 (2H, t, J=7.9 Hz), 2.91 (2H, t, J=7.9 Hz), 5.11 (2H, s), 6.93 (2H, d, J=8.6 Hz), 7.14 (2H, d, J=8.8 Hz), 7.47-7.56 (3H, m), 7.66-7.09 (5H, m).

EXAMPLE 56 methyl 4-([2',6'-dimethyl-1,1'-biphenyl]-3-yl-methoxy) benzenepropanoate

The title compound was obtained as a oil from 2,6-dimethylphenylboronic acid by a method similar to that of Example 22. yield 88%.
$^1$H NMR (CDCl$_3$) δ 2.01 (6H, s), 2.59 (2H, t, J=8.1 Hz), 2.89 (2H, t, J=8.1 Hz), 3.66 (3H, s), 5.09 (2H, s), 6.89 (2H, d, J=8.6 Hz), 7.09-7.20 (7H, m), 7.38-7.44 (2H, m).

EXAMPLE 57

4-([2',6'-dimethyl-1,1'-biphenyl]-3-ylmethoxy) benzenepropanoic acid

The title compound was obtained from methyl 4-([2',6'-dimethyl-1,1'-biphenyl]-3-ylmethoxy)benzenepropanoate by a method similar to that of Reference Example 4. yield 51%.
melting point: 136-137° C. (recrystallized from ethyl acetate-hexane).
$^1$H NMR (CDCl$_3$) δ 2.00 (6H, s), 2.64 (2H, t, J=8.0 Hz), 2.90 (2H, t, J=8.0 Hz), 5.09 (2H, s), 6.90 (2H, d, J=8.6 Hz), 7.08-7.25 (7H, m), 7.35-7.50 (2H, m).

EXAMPLE 58 methyl 4-[[3-(phenylmethoxy) phenyl]methoxy]benzenepropanoate

The title compound was obtained from methyl 4-hydroxybenzenepropanoate and 3-benzyloxybenzyl alcohol by a method similar to that of Reference Example 1. yield 92%.
$^1$H NMR (CDCl$_3$) δ 2.59 (2H, t, J=8.1 Hz), 2.89 (2H, t, J=8.1 Hz), 3.66 (3H, s), 5.01 (2H, s), 5.07 (2H, s), 6.86-6.94 (3H, m), 7.01 (1H, d, J=7.5 Hz), 7.07-7.12 (3H, m), 7.25-7.45 (6H, m).

EXAMPLE 59

4-[[3-(phenylmethoxy) phenyl]methoxy]benzenepropanoic acid

The title compound was obtained from methyl 4-[[3-(phenylmethoxy) phenyl]methoxy]benzenepropanoate by a method similar to that of Reference Example 4. yield 73%.
melting point: 107-108° C. (recrystallized from ethyl acetate-hexane).
$^1$H NMR (CDCl$_3$) δ 2.65 (2H, t, J=7.9 Hz), 2.90 (2H, t, J=7.9 Hz), 5.01 (2H, s), 5.07 (2H, s), 6.87-6.94 (3H, m), 7.01 (1H, d, J=7.6 Hz), 7.06-7.13 (3H, m), 7.26-7.45 (6H, m).

EXAMPLE 60 methyl 4-[(2,3-dihydro-2,2-dimethyl-1H-inden-1-yl) oxy]benzenepropanoate 2,3-Dihydro-2,2-dimethyl-1H-inden-1-ol was obtained from 2,3-dihydro-2,2-dimethyl-1H-inden-1-one by a method similar to that of Reference Example 32. This was condensed with methyl 4-hydroxybenzenepropanoate by a method similar to that of Reference Example 1 to give the title compound. yield from 2,3-dihydro-2,2-dimethyl-1H-inden-1-one 60%. oil.
$^1$H NMR (CDCl$_3$) δ 1.13 (3H, s), 1.23, (3H, s), 2.62 (2H, t, J=7.5 Hz), 2.73 (1H, d, J=15.4 Hz), 2.86 (1H, d, J=15.4 Hz), 2.93 (2H, t, J=7.5 Hz), 3.86 (3H, s), 5.28 (1H, s), 6.98 (2H, d, J=8.6 Hz), 7.11-7.27 (6H, m).

EXAMPLE 61

4-[(2,3-dihydro-2,2-dimethyl-1H-inden-1-yl) oxy]benzenepropanoic acid

The title compound was obtained from methyl 4-[(2,3-dihydro-2,2-dimethyl-1H-inden-1-yl)oxy]benzenepropanoate by a method similar to that of Reference Example 4. yield 46%, oil.
$^1$H NMR (CDCl$_3$) δ 1.13 (3H, s), 1.23, (3H, s), 2.68 (2H, t, J=7.3 Hz), 2.73 (1H, d, J=18.9 Hz), 2.87 (1H, d, J=18.9 Hz), 2.93 (2H, t, J=7.3 Hz), 5.28 (1H, s), 6.98 (2H, d, J=8.6 Hz), 7.00-7.27 (6H, m).

EXAMPLE 62 methyl 4-[(2,3-dihydro-5-methyl-1H-inden-1oxy] benzenepropanoate-yl)

2,3-Dihydro-5-methyl-1H-inden-1-ol was obtained from 2,3-dihydro-5-methyl-1H-inden-1-one by a method similar to that of Reference Example 32. This was condensed with methyl 4-hydroxybenzenepropanoate by a method similar to that of Reference Example 1 to give the title compound. yield from 2,3-dihydro-5-methyl-1H-inden-1-one 99%, oil.
$^1$H NMR (CDCl$_3$) δ 2.21 (1H, m), 2.36 (3H, s), 2.50 (1H, m), 2.61 (2H, t, J=8.2 Hz), 2.82-2.91 (3H, m), 3.10 (1H, m), 3.68 (3H, s), 5.69 (1H, dd, J=4.0 Hz, 6.5 Hz), 6.92 (2H, d, J=8.6 Hz), 7.05 (2H, d, J=8.6 Hz), 7.14-7.16 (3H, m), 7.30 (1H, d, J=7.7 Hz).

EXAMPLE 63

4-[(2,3-dihydro-5-methyl-1H-inden-1-yl) oxy]benzenepropanoic acid

The title compound was obtained from methyl 4-[(2,3-dihydro-5-methyl-1H-inden-1-yl)oxy]benzenepropanoate by a method similar to that of Reference Example 4. yield 31%.
melting point: 108-109° C. (recrystallized from diethyl ether-hexane).
$^1$H NMR (CDCl$_3$) δ 2.20 (1H, m), 2.36 (3H, s), 2.51 (1H, m), 2.67 (2H, t, J=8.2 Hz), 2.80-2.94 (3H, m), 3.14 (1H, m), 5.69 (1H, dd, J=4.1 Hz, 6.4 Hz), 6.93 (2H, d, J=8.6 Hz), 7.04 (2H, d, J=7.7 Hz), 7.11-7.16 (3H, m), 7.30 (1H, d, J=7.7 Hz).

EXAMPLE 64 methyl 4-[(2,3-dihydro-7-methyl-1H-inden-1-yl) oxy]benzenepropanoate 2,3-Dihydro-7-methyl-1H-inden-1-ol was obtained from 2,3-dihydro-7-methyl-1H-inden-1-one by a method similar to that of Reference Example 32. This was condensed with methyl 4-hydroxybenzenepropanoate by a method similar to that of Reference Example 1 to give the title compound. yield from 2,3-dihydro-7-methyl-1H-inden-1-one 57%, oil.
$^1$H NMR (CDCl$_3$) δ 2.21-2.49 (2H, m), 2.30 (3H, s), 2.62 (2H, t, J=7.4 Hz), 2.85-2.97 (3H, m), 3.18 (1H, m), 3.68 (3H, s), 5.74 (1H, dd, J=2.0 Hz, 6.5 Hz), 6.91 (2H, d, J=8.6 Hz), 7.06 (1H, d, J=7.3 Hz), 7.13-7.23 (4H, m).

EXAMPLE 65 methyl 4-[[4-(4-phenoxyphenoxy) phenyl]methoxy]benzenepropanoate

The title compound was obtained as a white powder from methyl 4-hydroxybenzenepropanoate and 4-(4-phenoxyphenoxy)benzyl alcohol by a method similar to that of Reference Example 33. yield 26%.
$^1$H NMR (CDCl$_3$) δ 2.60 (2H, t, J=8.1 Hz), 2.90 (2H, t, J=8.1 Hz), 3.66 (3H, s), 4.99 (2H, s), 6.89 (2H, d, J=8.6 Hz), 6.99-7.13 (11H, m), 7.31-7.40 (4H, m).

EXAMPLE 66

4-[[4-(4-phenoxyphenoxy) phenyl]methoxy]benzenepropanoic acid

The title compound was obtained from methyl 4-[[4-(4-phenoxyphenoxy) phenyl]methoxy]benzenepropanoate by a method similar to that of Reference Example 4. yield 81%.
melting point: 167-168° C. (recrystallized from ethyl acetate-hexane).
$^1$H NMR (CDCl$_3$) δ 2.65 (2H, t, J=8.0 Hz), 2.91 (2H, t, J=8.0 Hz), 4.99 (2H, s), 6.91 (2H, d, J=8.6 Hz), 6.99-7.15 (11H, m), 7.31-7.40 (4H, m).

EXAMPLE 67 methyl 4-[[4-[4-(trifluoromethoxy) phenoxy]phenyl]methoxy]benzenepropanoate

4-[4-(Trifluoromethoxy)phenoxy]benzyl alcohol was obtained as an oil from 4-[4-(trifluoromethoxy) phenoxy] benzaldehyde by a method similar to that of Reference Example 32. The title compound was obtained as a white powder from methyl 4-hydroxybenzenepropanoate and 4-[4-(trifluoromethoxy)phenoxy]benzyl alcohol by a method similar to that of Reference Example 33. yield from 4-[4-(trifluoromethoxy) phenoxy]benzaldehyde 27%.
$^1$H NMR (CDCl$_3$) δ 2.60 (2H, t, J=8.1 Hz), 2.90 (2H, t, J=8.1 Hz), 3.67 (3H, s), 5.01 (2H, s), 6.90 (2H, d, J=6.7 Hz), 6.92-7.03 (4H, m), 7.11-7.20 (4H, m), 7.41 (2H, d, J=8.6 Hz).

EXAMPLE 68

4-[[4-[4-(trifluoromethoxy) phenoxy]phenyl]methoxy]benzenepropanoic acid

The title compound was obtained from methyl 4-[[4-[4-(trifluoromethoxy) phenoxy]phenyl]methoxy]benzenepropanoate by a method similar to that of Reference Example 4. yield 87%.
melting point: 137-138° C. (recrystallized from ethyl acetate-hexane).
$^1$H NMR (CDCl$_3$) δ 2.66 (2H, t, J=8.0 Hz), 2.91 (2H, t, J=8.0 Hz), 5.01 (2H, s), 6.90 (2H, d, J=8.6 Hz), 6.99-7.03 (4H, m), 7.12-7.20 (4H, m), 7.41 (2H, d, J=8.6 Hz).

EXAMPLE 69 methyl 4-[[4-([1,1'-biphenyl]-4-yloxy) phenyl]methoxy]benzenepropanoate

The title compound was obtained as a white powder from methyl 4-hydroxybenzenepropanoate and 4-([1,1'-biphenyl]-4-yloxy) benzyl alcohol by a method similar to that of Reference Example 33. yield 13%.
$^1$H NMR (CDCl$_3$) δ 2.60 (2H, t, J=8.0 Hz), 2.90 (2H, t, J=8.0 Hz), 3.67 (3H, s), 5.01 (2H, s), 6.91 (2H, d, J=8.6 Hz), 7.05-7.14 (6H, m), 7.30-7.48 (5H, m), 7.55-7.58 (4H, m).

EXAMPLE 70

4-[[4-([1,1'-biphenyl]-4-yloxy) phenyl]methoxy]benzenepropanoic acid

The title compound was obtained from methyl 4-[[4-([1,1'-biphenyl]-4-yloxy)phenyl]methoxy]benzenepropanoate by a method similar to that of Reference Example 4. yield 84%.
melting point: 196-197° C. (recrystallized from ethyl acetate-hexane).
$^1$H NMR (CDCl$_3$) δ 2.66 (2H, t, J=7.9 Hz), 2.92 (2H, t, J=7.9 Hz), 5.01 (2H, s), 6.92 (2H, d, J=8.6 Hz), 7.05-7.13 (6H, m), 7.31-7.48 (5H, m), 7.55-7.58 (4H, m).

EXAMPLE 71 methyl 4-[[4-4-(phenylmethoxy) phenoxy]phenyl]methoxy]benzenepropanoate

The title compound was obtained as a white powder from methyl 4-hydroxybenzenepropanoate and 4-[4-(phenylmethoxy) phenoxy]benzyl alcohol by a method similar to that of Reference Example 33. yield 24%.
$^1$H NMR (CDCl$_3$) δ 2.60 (2H, t, J=8.0 Hz), 2.89 (2H, t, J=8.0 Hz), 3.66 (3H, s), 4.97 (2H, s), 5.05 (2H, s), 6.88-6.97 (8H, m), 7.11 (2H, d, J=8.6 Hz), 7.34-7.47 (7H, m).

EXAMPLE 72

4-[[4-4-(phenylmethoxy) phenoxy]phenyl]methoxy]benzenepropanoic acid

The title compound was obtained from methyl 4-[[4-4-(phenylmethoxy) phenoxy]phenyl]methoxy]benzenepropanoate by a method similar to that of Reference Example 4. yield 55%.
melting point: 180-181° C. (recrystallized from ethyl acetate-hexane).
$^1$H NMR (CDCl$_3$) δ 2.65 (2H, t, J=8.0 Hz), 2.91 (2H, t, J=8.0 Hz), 4.98 (2H, s), 5.05 (2H, s), 6.89-6.97 (8H, m), 7.13 (2H, d, J=8.6 Hz), 7.26-7.45 (7H, m).

EXAMPLE 73 methyl 4-[(2,3-dihydro-5-methoxy-1H-inden-1-yl) oxy]benzenepropanoate

5-Methoxy-1-indanol was obtained from 5-methoxy-1-indanone by a method similar to that of Reference Example 32. oil. The title compound was obtained as a white powder from methyl 4-hydroxybenzenepropanoate and 5-methoxy-1-indanol by a method similar to that of Reference Example 33. yield from 5-methoxy-1-indanone 14%.
$^1$H NMR (CDCl$_3$) δ 2.19-2.29 (1H, m), 2.47-2.58 (1H, m), 2.61 (2H, t, J=8.1 Hz), 2.82-2.88 (1H, m), 2.91 (2H, t, J=8.1 Hz), 3.08-3.19 (1H, m), 3.68 (3H, s), 5.66 (1H, dd, J=3.6 Hz, 6.5 Hz), 6.78-6.82 (2H, m), 6.91 (2H, d, J=8.6 Hz), 7.12 (2H, d, J=8.6 Hz), 7.31 (1H, d, J=8.2 Hz).

EXAMPLE 74

4-[(2,3-dihydro-5-methoxy-1H-inden-1-yl) oxy]benzenepropanoic acid

The title compound was obtained from methyl 4-[(2,3-dihydro-5-methoxy-1H-inden-1-yl)oxy]benzenepropanoate by a method similar to that of Reference Example 4. yield 67%.

melting point: 87-88° C. (recrystallized from ethyl acetate-hexane).

$^1$H NMR (CDCl$_3$) δ 2.18-2.28 (1H, m), 2.46-2.59 (1H, m), 2.67 (2H, t, J=8.0 Hz), 2.81-2.90 (1H, m), 2.92 (2H, t, J=8.0 Hz), 3.06-3.17 (1H, m), 5.68 (1H, dd, J=3.6 Hz, 6.5 Hz), 6.74-6.82 (2H, m), 6.92 (2H, d, J=8.6 Hz), 7.14 (2H, d, J=8.6 Hz), 7.31 (1H, d, J=8.2 Hz).

EXAMPLE 75 methyl 4-[(5-chloro-2,3-dihydro-1H-inden-1-yl) oxy]benzenepropanoate

5-Chloro-1-indanol was obtained from 5-chloro-1-indanone by a method similar to that of Reference Example 32. oil. The title compound was obtained as a white powder from methyl 4-hydroxybenzenepropanoate and 5-chloro-1-indanol by a method similar to that of Reference Example 33. yield from 5-chloro-1-indanone 33%.

$^1$H NMR (CDCl$_3$) δ 2.16-2.27 (1H, m), 2.49-2.59 (1H, m), 2.62 (2H, t, J=8.2 Hz), 2.83-2.90 (1H, m), 2.91 (2H, t, J=8.2 Hz), 3.05-3.17 (1H, m), 3.68 (3H, s), 5.67 (1H, dd, J=4.3 Hz, 6.6 Hz), 6.91 (2H, d, J=8.6 Hz), 7.14 (2H, d, J=8.6 Hz), 7.19-7.33 (3H, m).

EXAMPLE 76

4-[(5-chloro-2,3-dihydro-1H-inden-1-yl) oxy]benzenepropanoic acid

The title compound was obtained from methyl 4-[(5-chloro-2,3-dihydro-1H-inden-1-yl)oxy]benzenepropanoate by a method similar to that of Reference Example 4. yield 80%.

melting point: 136-137° C. (recrystallized from ethyl acetate-hexane).

$^1$H NMR (CDCl$_3$) δ 2.17-2.28 (1H, m), 2.51-2.62 (1H, m), 2.67 (2H, t, J=7.9 Hz), 2.85-2.90 (1H, m), 2.93 (2H, t, J=7.9 Hz), 3.06-3.17 (1H, m), 5.67 (1H, dd, J=4.4 Hz, 6.6 Hz), 6.91 (2H, d, J=8.6 Hz), 7.14-7.33 (5H, m).

EXAMPLE 77

4-[(5-fluoro-2,3-dihydro-1H-inden-1-yl) oxy]benzenepropanoic acid

5-Fluoro-1-indanol was obtained from 5-fluoro-1-indanone by a method similar to that of Reference Example 32. oil. Methyl 4-[(5-fluoro-2,3-dihydro-1H-inden-1-yl) oxy]benzenepropanoate was obtained from methyl 4-hydroxybenzenepropanoate and 5-fluoro-1-indanol by a method similar to that of Reference Example 33. oil. Then the title compound was obtained from methyl 4-[(5-fluoro-2,3-dihydro-1H-inden-1-yl)oxy]benzenepropanoate by a method similar to that of Reference Example 4. yield from 5-fluoro-1-indanone 40%.

melting point: 124-125° C. (recrystallized from diethyl ether-hexane).

$^1$H NMR (CDCl$_3$) δ 2.18-2.29 (1H, m), 2.50-2.62 (1H, m), 2.67 (2H, t, J=8.0 Hz), 2.85-2.89 (1H, m), 2.93 (2H, t, J=8.0 Hz), 3.07-3.18 (1H, m), 5.68 (1H, dd, J=4.1 Hz, 6.5 Hz), 6.90-6.98 (4H, m), 7.15 (2H, d, J=8.6 Hz), 7.33-7.37 (1H, m).

EXAMPLE 78

4-[(2,3-dihydro-5-methyl-1H-inden-1-yl) oxy]benzenepropanoic acid

5-Methyl-1-indanol was obtained from 5-methyl-1-indanone by a method similar to that of Reference Example 32. oil. Methyl 4-[(2,3-dihydro-5-methyl-1H-inden-1-yl) oxy] benzenepropanoate was obtained from methyl 4-hydroxybenzenepropanoate and 5-methyl-1-indanol by a method similar to that of Reference Example 33. oil. Then the title compound was obtained from methyl 4-[(2,3-dihydro-5-methyl-1H-inden-1-yl)oxy]benzenepropanoate by a method similar to that of Reference Example 4. yield from 5-methyl-1-indanone 29%.

melting point: 74-75° C. (recrystallized from diethyl ether-hexane).

$^1$H NMR (CDCl$_3$) δ 2.13-2.25 (1H, m), 2.34 (3H, s), 2.49-2.60 (1H, m), 2.68 (2H, t, J=8.0 Hz), 2.80-2.91 (1H, m), 2.92 (2H, t, J=8.0 Hz), 3.04-3.13 (1H, m), 5.69 (1H, dd, J=4.5 Hz, 6.5 Hz), 6.94 (2H, d, J=8.6 Hz), 7.10-7.19 (4H, m), 7.24 (1H, s).

EXAMPLE 79

4-[(2,3-dihydro-6-methoxy-1H-inden-1-yl) oxy]benzenepropanoic acid

6-Methoxy-1-indanol was obtained from 6-methoxy-1-indanone by a method similar to that of Reference Example 32. oil. Methyl 4-[(2,3-dihydro-6-methoxy-1H-inden-1-yl) oxy] benzenepropanoate was obtained from methyl 4-hydroxybenzenepropanoate and 6-methoxy-1-indanol by a method similar to that of Reference Example 33. oil. Then the title compound was obtained from methyl 4-[(2,3-dihydro-6-methoxy-1H-inden-1-yl)oxy]benzenepropanoate by a method similar to that of Reference Example 4. yield from 6-methoxy-1-indanone 41%, oil.

$^1$H NMR (CDCl$_3$) δ 2.14-2.25 (1H, m), 2.51-2.63 (1H, m), 2.67 (2H, t, J=8.0 Hz), 2.79-2.88 (1H, m), 2.93 (2H, t, J=8.0 Hz), 3.01-3.09 (1H, m), 3.79 (3H, s), 5.69 (1H, dd, J=4.8 Hz, 6.5 Hz), 6.86-6.97 (4H, m), 7.13-7.20 (3H, m).

EXAMPLE 80

4-[(5-bromo-2,3-dihydro-1H-inden-1-yl) oxy]benzenepropanoic acid

5-Bromo-1-indanol was obtained from 5-bromo-1-indanone by a method similar to that of Reference Example 32. oil. Methyl 4-[(5-bromo-2,3-dihydro-1H-inden-1-yl)oxy] benzenepropanoate was obtained from methyl 4-hydroxybenzenepropanoate and 5-bromo-1-indanol by a method similar to that of Reference Example 33. oil. Then the title compound was obtained from methyl 4-[(5-bromo-2,3-dihydro-1H-inden-1-yl) oxy]benzenepropanoate by a method similar to that of Reference Example 4. yield from 5-bromo-1-indanone 29%.

melting point: 133-134° C. (recrystallized from diethyl ether-hexane).

$^1$H NMR (CDCl$_3$) δ 2.15-2.27 (1H, m), 2.47-2.59 (1H, m), 2.67 (2H, t, J=8.0 Hz), 2.83-2.89 (1H, m), 2.92 (2H, t, J=8.0 Hz), 3.06-3.18 (1H, m), 5.66 (1H, dd, J=4.5 Hz, 6.5 Hz), 6.91 (2H, d, J=8.6 Hz), 7.15 (2H, d, J=8.6 Hz), 7.26 (1H, d, J=8.0 Hz), 7.36 (1H, d, J=8.6 Hz), 7.44 (1H, s).

EXAMPLE 81

4-[(2,3-dihydro-5-phenoxy-1H-inden-1-yl) oxy]benzenepropanoic acid

5-Phenoxy-1-indanol was obtained from 5-phenoxy-1-indanone by a method similar to that of Reference Example 32. oil. Methyl 4-[(2,3-dihydro-5-phenoxy-1H-inden-1-yl) oxy]benzenepropanoate was obtained from methyl 4-hydroxybenzenepropanoate and 5-phenoxy-1-indanol by a method similar to that of Reference Example 33. oil. Then the title compound was obtained from methyl 4-[(2,3-dihydro-5-phenoxy-1H-inden-1-yl)oxy]benzenepropanoate by a method similar to that of Reference Example 4. yield from 5-phenoxy-1-indanone 19%.

melting point: 92-93° C. (recrystallized from diethyl ether-hexane).

$^1$H NMR (CDCl$_3$) δ 2.18-2.29 (1H, m), 2.50-2.61 (1H, m), 2.67 (2H, t, J=8.0 Hz), 2.81-2.90 (1H, m), 2.90 (2H, t, J=8.0 Hz), 3.05-3.18 (1H, m), 5.70 (1H, dd, J=3.9 Hz, 6.5 Hz), 6.87-6.90 (4H, m), 7.00-7.17 (5H, m), 7.29-7.38 (3H, m).

EXAMPLE 82 methyl 4-[(2,3-dihydro-4-methyl-1H-inden-1-yl) oxy]benzenepropanoate

4-Methyl-1-indanol was obtained from 4-methyl-1-indanone by a method similar to that of Reference Example 32. oil. The title compound was obtained as a white powder from methyl 4and 4-methyl-1-indanol by a method-hydroxybenzenepropanoate similar to that of Reference Example 33. yield from 4-methyl-1-indanone 4%.

$^1$H NMR (CDCl$_3$) δ 2.15-2.28 (1H, m), 2.30 (3H, s), 2.48-2.57 (1H, m), 2.62 (2H, t, J=8.1 Hz), 2.78-2.89 (1H, m), 2.91 (2H, t, J=8.1 Hz), 2.99-3.09 (1H, m), 3.68 (3H, s), 5.73 (1H, dd, J=4.1 Hz, 6.7 Hz), 6.93 (2H, d, J=8.6 Hz), 7.12-7.19 (4H, m), 7.25-7.27 (1H, m).

EXAMPLE 83

4-[(2,3-dihydro-4-methyl-1H-inden-1-yl) oxy]benzenepropanoic acid

The title compound was obtained from methyl 4-[(2,3-dihydro-4-methyl-1H-inden-1-yl)oxy]benzenepropanoate by a method similar to that of Reference Example 4. yield 65%.

melting point: 121-122° C. (recrystallized from diethyl ether-hexane).

$^1$H NMR (CDCl$_3$) δ 2.16-2.27 (1H, m), 2.29 (3H, s), 2.49-2.61 (1H, m), 2.68 (2H, t, J=8.1 Hz), 2.79-2.92 (1H, m), 2.92 (2H, t, J=8.1 Hz), 3.00-3.09 (1H, m), 5.73 (1H, dd, J=4.1 Hz, 6.7 Hz), 6.94 (2H, d, J=8.6 Hz), 7.11-7.19 (4H, m), 7.25-7.27 (1H, m).

EXAMPLE 84 methyl 4-[(2,3-dihydro-5,6-dimethoxy-1H-inden-1-yl) oxy]benzenepropanoate 5,6-Dimethoxy-1-indanol was obtained from 5,6-dimethoxy-1-indanone by a method similar to that of Reference Example 32. oil. Then the title compound was obtained as a white powder from methyl 4-hydroxybenzenepropanoate and 5,6-dimethoxy-1-indanol by a method similar to that of Reference Example 33. yield from 5,6-dimethoxy-1-indanone 42%.

$^1$H NMR (CDCl$_3$) δ 2.14-2.26 (1H, m), 2.49-2.60 (1H, m), 2.62 (2H, t, J=8.2 Hz), 2.79-2.89 (1H, m), 2.91 (2H, t, J=8.2 Hz), 3.04-3.14 (1H, m), 3.68 (3H, s), 3.86 (3H, s), 3.89 (3H, s), 5.68 (1H, dd, J=3.6 Hz, 6.6 Hz), 6.81 (1H, s), 6.91-6.94 (3H, m), 7.14 (2H, d, J=8.5 Hz).

EXAMPLE 85

4-[(2,3-dihydro-5,6-dimethoxy-1H-inden-1-yl) oxy]benzenepropanoic acid

The title compound was obtained from methyl 4-[(2,3-dihydro-5,6-dimethoxy-1H-inden-1-yl)oxy]benzenepropanoate by a method similar to that of Reference Example 4. yield 43%.

melting point: 90-92° C. (recrystallized from diethyl ether-hexane).

$^1$H NMR (CDCl$_3$) δ 2.16-2.25 (1H, m), 2.49-2.61 (1H, m), 2.67 (2H, t, J=8.0 Hz), 2.80-2.91 (1H, m), 2.93 (2H, t, J=8.0 Hz), 3.04-3.15 (1H, m), 3.89 (3H, s), 3.91 (3H, s), 5.69 (1H, dd, J=3.7 Hz, 6.6 Hz), 6.80 (1H, s), 6.89-6.96 (3H, m), 7.15 (2H, d, J=8.6 Hz).

EXAMPLE 86 methyl 4-[[2,3-dihydro-5-(4-methylphenyl)-1H-inden-1-yl]oxy]benzenepropanoate 5-(4-Methylphenyl)-1-indanol was obtained from 5-(4-methylphenyl)-1-indanone by a method similar to that of Reference Example 32. oil. Then the title compound was obtained as a white powder from methyl 4-hydroxybenzenepropanoate and 5-(4-methylphenyl)-1-indanol by a method similar to that of Reference Example 33. yield from 5-(4-methylphenyl)-1-indanone 31%.

$^1$H NMR (CDCl$_3$) δ 2.21-2.32 (1H, m), 2.40 (3H, s), 2.52-2.62 (1H, m), 2.63 (2H, t, J=8.0 Hz), 2.92 (2H, t, J=8.0 Hz), 2.96-3.03 (1H, m), 3.15-3.26 (1H, m), 3.68 (3H, s), 5.76 (1H, dd, J=4.1 Hz, 6.6 Hz), 6.95 (2H, d, J=8.6 Hz), 7.15 (2H, d, J=8.6 Hz), 7.23-7.26 (2H, m), 7.43-7.49 (5H, m).

EXAMPLE 87

4-[[2,3-dihydro-5-(4-methylphenyl)-1H-inden-1-yl]oxy]benzenepropanoic acid

The title compound was obtained from methyl 4-[[2,3-dihydro-5-(4-methylphenyl)-1H-inden-1-yl]oxy]benzenepropanoate by a method similar to that of Reference Example 4. yield 68%.

melting point: 159-160° C. (recrystallized from ethyl acetate-hexane).

$^1$H NMR (CDCl$_3$) δ 2.20-2.31 (1H, m), 2.40 (3H, s), 2.51-2.62 (1H, m), 2.68 (2H, t, J=8.0 Hz), 2.94 (2H, t, J=8.0 Hz), 2.95-3.00 (1H, m), 3.14-3.22 (1H, m), 5.76 (1H, dd, J=4.2 Hz, 6.6 Hz), 6.96 (2H, d, J=8.6 Hz), 7.16 (2H, d, J=8.6 Hz), 7.23-7.26 (2H, m), 7.43-7.50 (5H, m).

EXAMPLE 88 methyl 4-[[5-(4-fluorophenyl)-2,3-dihydro-1H-inden-1-yl]oxy]benzenepropanoate 5-(4-Fluorophenyl)-1-indanol was obtained from 5-(4-fluorophenyl)-1-indanone by a method similar to that of Reference Example 32. oil. The title compound was obtained as a white powder from methyl 4-hydroxybenzenepropanoate and 5-(4-fluorophenyl)-1-indanol by a method similar to that of Reference Example 33. yield from 5-(4-fluorophenyl)-1-indanone 31%.
$^1$H NMR (CDCl$_3$) δ 2.19-2.31 (1H, m), 2.52-2.62 (1H, m), 2.63 (2H, t, J=8.0 Hz), 2.92 (2H, t, J=8.0 Hz), 2.94-3.01 (1H, m), 3.14-3.25 (1H, m), 3.68 (3H, s), 5.76 (1H, dd, J=4.2 Hz, 6.6 Hz), 6.95 (2H, d, J=8.6 Hz), 7.09-7.16 (4H, m), 7.38-7.55 (5H, m).

EXAMPLE 89

4-[[5-(4-fluorophenyl)-2,3-dihydro-1H-inden-1-yl]oxy]benzenepropanoic acid

The title compound was obtained from methyl 4-[[5-(4-fluorophenyl)-2,3-dihydro-1H-inden-1-yl]oxy]benzenepropanoate by a method similar to that of Reference Example 4. yield 86%.
melting point: 169-170° C. (recrystallized from ethyl acetate-hexane).
$^1$H NMR (CDCl$_3$) δ 2.20-2.31 (1H, m), 2.53-2.64 (1H, m), 2.68 (2H, t, J=8.0 Hz), 2.93 (2H, t, J=8.0 Hz), 2.95-3.01 (1H, m), 3.14-3.25 (1H, m), 5.77 (1H, dd, J=4.2 Hz, 6.6 Hz), 6.96 (2H, d, J=8.6 Hz), 7.09-7.18 (4H, m), 7.39-7.54 (5H, m).

EXAMPLE 90 methyl 4-(dibenzo[b,d]furan-2-ylmethoxy)benzenepropanoate

The title compound was obtained as a white powder from methyl 4-hydroxybenzenepropanoate and 2-(chloromethyl)dibenzo[b,d]furan by a method similar to that of Reference Example 5. yield 35%.
$^1$H NMR (CDCl$_3$) δ 2.60 (2H, t, J=8.1 Hz), 2.90 (2H, t, J=8.1 Hz), 3.66 (3H, s), 5.17 (2H, s), 6.94 (2H, d, J=8.6 Hz), 7.13 (2H, d, J=8.6 Hz), 7.32-7.58 (5H, m), 7.95 (1H, d, J=7.8 Hz), 8.02 (1H, s).

EXAMPLE 91

4-(dibenzo[b,d]furan-2-ylmethoxy)benzenepropanoic acid

The title compound was obtained from methyl 4-(dibenzo[b,d]furan-2-ylmethoxy)benzenepropanoate by a method similar to that of Reference Example 4. yield 80%.
melting point: 175-176° C. (recrystallized from ethyl acetate-hexane).
$^1$H NMR (CDCl$_3$) δ 2.66 (2H, t, J=8.0 Hz), 2.92 (2H, t, J=8.0 Hz), 5.18 (2H, s), 6.94 (2H, d, J=8.6 Hz), 7.13 (2H, d, J=8.6 Hz), 7.32-7.58 (5H, m), 7.96 (1H, d, J=7.4 Hz), 8.03 (1H, s).

EXAMPLE 92 methyl 4-[(2,3-dihydro-5-phenyl-1H-inden-1-yl)oxy]benzenepropanoate

5-Phenyl-1-indanol was obtained from 5-phenyl-1-indanone by a method similar to that of Reference Example 32. oil. Then the title compound was obtained as a white powder from methyl 4-hydroxybenzenepropanoate and 5-phenyl-1-indanol by a method similar to that of Reference Example 33. yield from 5-phenyl-1-indanone 50%.
$^1$H NMR (CDCl$_3$) δ 2.20-2.31 (1H, m), 2.54-2.70 (1H, m), 2.62 (2H, t, J=8.1 Hz), 2.92 (2H, t, J=8.1 Hz), 2.98-3.04 (1H, m), 3.14-3.28 (1H, m), 3.68 (3H, s), 5.77 (1H, dd, J=4.2 Hz, 6.6 Hz), 6.95 (2H, d, J=8.6 Hz), 7.15 (2H, d, J=8.6 Hz), 7.32-7.60 (8H, m).

EXAMPLE 93

4-[(2,3-dihydro-5-phenyl-1H-inden-1-yl)oxy]benzenepropanoic acid

The title compound was obtained from methyl 4-[(2,3-dihydro-5-phenyl-1H-inden-1-yl)oxy]benzenepropanoate by a method similar to that of Reference Example 4. yield 72%.
melting point: 148-149° C. (recrystallized from ethyl acetate-hexane).
$^1$H NMR (CDCl$_3$) δ 2.21-2.32 (1H, m), 2.55-2.75 (1H, m), 2.69 (2H, t, J=8.0 Hz), 2.94 (2H, t, J=8.0 Hz), 2.95-3.01 (1H, m), 3.16-3.25 (1H, m), 5.78 (1H, dd, J=4.2 Hz, 6.6 Hz), 6.97 (2H, d, J=8.6 Hz), 7.17 (2H, d, J=8.6 Hz), 7.32-7.60 (8H, m).

EXAMPLE 94 methyl 4-[[2,3-dihydro-5-(4-methoxyphenyl)-1H-inden-1-yl]oxy]benzenepropanoate 5-(4-Methoxyphenyl)-1-indanol was obtained from 5-(4-methoxyphenyl)-1-indanone by a method similar to that of Reference Example 32. oil. The title compound was obtained as a white powder from methyl 4-hydroxybenzenepropanoate and 5-(4-methoxyphenyl)-1-indanol by a method similar to that of Reference Example 33. yield from 5-(4-methoxyphenyl)-1-indanone 38%.
$^1$H NMR (CDCl$_3$) δ 2.20-2.29 (1H, m), 2.49-2.60 (1H, m), 2.62 (2H, t, J=7.8 Hz), 2.92 (2H, t, J=7.8 Hz), 2.93-3.00 (1H, m), 3.15-3.23 (1H, m), 3.68 (3H, s), 3.85 (3H, s), 5.75 (1H, dd, J=4.1 Hz, 6.6 Hz), 6.94-6.99 (4H, m), 7.14 (2H, d, J=8.6 Hz), 7.41-7.53 (5H, m).

EXAMPLE 95

4-[[2,3-dihydro-5-(4-methoxyphenyl)-1H-inden-1-yl]oxy]benzenepropanoic acid

The title compound was obtained from methyl 4-[[2,3-dihydro-5-(4-methoxyphenyl)-1H-inden-1-yl]oxy]benzenepropanoate by a method similar to that of Reference Example 4. yield 94%.
melting point: 151-152° C. (recrystallized from ethyl acetate-hexane).
$^1$H NMR (CDCl$_3$) δ 2.19-2.30 (1H, m), 2.51-2.65 (1H, m), 2.68 (2H, t, J=8.0 Hz), 2.94 (2H, t, J=8.0 Hz), 2.96-3.00 (1H, m), 3.14-3.22 (1H, m), 3.85 (3H, s), 5.70 (1H, dd, J=4.1 Hz, 6.6 Hz), 6.94-7.00 (4H, m), 7.17 (2H, d, J=8.6 Hz), 7.41-7.53 (5H, m).

EXAMPLE 96 methyl 4-[[5-(4-chlorophenyl)-2,3-dihydro-1H-inden-1-yl]oxy]benzenepropanoate 5-(4-Chlorophenyl)-1-indanol was obtained from 5-(4-chlorophenyl)-1-indanone by a method similar to that of Reference Example 32. oil. The title compound was obtained as a white powder from methyl 4-hydroxybenzenepropanoate and 5-(4-chlorophenyl)-1-indanol by a method similar to that of Reference Example 33. yield from 5-(4-chlorophenyl)-1-indanone 43%.

$^1$H NMR (CDCl$_3$) δ 2.16-2.30 (1H, m), 2.50-2.56 (1H, m), 2.62 (2H, t, J=8.0 Hz), 2.92 (2H, t, J=8.0 Hz), 2.94-3.02 (1H, m), 3.14-3.23 (1H, m), 3.68 (3H, s), 5.76 (1H, dd, J=4.3 Hz, 6.5 Hz), 6.94 (2H, d, J=8.6 Hz), 7.15 (2H, d, J=8.6 Hz), 7.38-7.52 (7H, m).

EXAMPLE 97

4-[[5-(4-chlorophenyl)-2,3-dihydro-1H-inden-1-yl]oxy]benzenepropanoic acid

The title compound was obtained from methyl 4-[[5-(4-chlorophenyl)-2,3-dihydro-1H-inden-1-yl]oxy]benzenepropanoate by a method similar to that of Reference Example 4. yield 93%.

melting point: 165-166° C. (recrystallized from ethyl acetate-hexane).

$^1$H NMR (CDCl$_3$) δ 2.18-2.31 (1H, m), 2.51-2.63 (1H, m), 2.68 (2H, t, J=7.8 Hz), 2.93 (2H, t, J=7.8 Hz), 2.97-3.02 (1H, m), 3.15-3.19 (1H, m), 5.77 (1H, dd, J=4.3 Hz, 6.4 Hz), 6.96 (2H, d, J=8.4 Hz), 7.17 (2H, d, J=8.4 Hz), 7.38-7.55 (7H, m).

EXAMPLE 98

(+)-4-[(5-chloro-2,3-dihydro-1H-inden-1-yl) oxy]benzenepropanoic acid

4-[(5-Chloro-2,3-dihydro-1H-inden-1-yl) oxy]benzenepropanoic acid (50 mg) was separated by high performance liquid chromatography (column:CHIRALCEL OJ (50 mmID×500 mm, manufactured by DAICEL CHEMICAL INDUSTRIES, LTD.), mobile phase: hexane/ethanol=4:1, flow rate: 70 mL/min, column temperature: 35° C.) to give the title compound (24 mg).

[α]$_D^{23}$ +8.2° (c 0.45, CHCl$_3$)

EXAMPLE 99

(−)-4-[(5-chloro-2,3-dihydro-1H-inden-1-yl) oxy]benzenepropanoic acid

4-[(5-Chloro-2,3-dihydro-1H-inden-1-yl) oxy]benzenepropanoic acid (50 mg) was separated by high performance liquid chromatography (column:CHIRALCEL OJ (50 mmID×500 mm, manufactured by DAICEL CHEMICAL INDUSTRIES, LTD.), mobile phase: hexane/ethanol=4:1, flow rate: 70 mL/min, column temperature: 35° C.) to give the title compound (23 mg).

[α]$_D^{23}$ −6.2° (c 0.53, CHCl$_3$).

EXAMPLE 100 methyl 4-(benzo[b]thiophen-3-ylmethoxy)benzenepropanoate

The title compound was obtained from 3-benzo[b]thiophenecarboxaldehyde and methyl 4-hydroxybenzenepropanoate by a method similar to that of Reference Example 53. yield 79%, oil.

$^1$H NMR (CDCl$_3$) δ 2.67 (2H, t, J=7.4 Hz), 2.90 (2H, t, J=7.4 Hz), 3.69 (3H, s), 5.27 (2H, s), 6.96 (2H, d, J=8.6 Hz), 7.15 (2H, d, J=8.6 Hz), 7.33-7.40 (2H, m), 7.48 (1H, s), 7.80-7.90 (2H, m).

EXAMPLE 101

4-(benzo[b]thiophen-3-ylmethoxy)benzenepropanoic acid

The title compound was obtained from methyl 4-(benzo[b]thiophen-3-ylmethoxy)benzenepropanoate by a method similar to that of Reference Example 38. yield 86%.

melting point: 125-126° C. (recrystallized from ethyl acetate-diisopropyl ether).

$^1$H NMR (CDCl$_3$) δ 2.65 (2H, t, J=7.4 Hz), 2.90 (2H, t, J=7.4 Hz), 5.25 (2H, s), 6.95 (2H, d, J=8.6 Hz), 7.15 (2H, d, J=8.6 Hz), 7.30-7.40 (2H, m), 7.45 (1H, s), 7.81-7.89 (2H, m).

EXAMPLE 102 methyl 4-(1H-indol-2-ylmethoxy)benzenepropanoate

The title compound was obtained from 1H-indole-2-methanol and methyl 4-hydroxybenzenepropanoate by a method similar to that of Reference Example 1. yield 12%.

melting point: 156-157° C. (recrystallized from ethyl acetate-diisopropyl ether).

$^1$H NMR (CDCl$_3$) δ 2.59 (2H, t, J=7.4 Hz), 2.89 (2H, t, J=7.4 Hz), 3.66 (3H, s), 5.21 (2H, s), 6.52 (1H, s), 6.92 (2H, d, J=8.6 Hz), 7.08-7.21 (4H, m), 7.35 (1H, d, J=7.4 Hz), 7.59 (1H, d, J=7.5 Hz), 8.33 (1H, br s).

EXAMPLE 103

4-(1H-indol-2-ylmethoxy)benzenepropanoic acid

The title compound was obtained from methyl 4-(1H-indol-2-ylmethoxy)benzenepropanoate by a method similar to that of Reference Example 38. yield 53%.

melting point: 131-133° C. (recrystallized from ethyl acetate-diisopropyl ether).

$^1$H NMR (CDCl$_3$) δ 2.65 (2H, t, J=7.4 Hz), 2.91 (2H, t, J=7.4 Hz), 5.21 (2H, s), 6.52 (1H, s), 6.91 (2H, d, J=8.6 Hz), 7.09-7.22 (4H, m), 7.31 (1H, d, J=7.4 Hz), 7.57 (1H, d, J=7.5 Hz), 8.33 (1H, br s).

EXAMPLE 104

4-[(2,3-dihydro-7-methyl-1H-inden-1-yl)oxy]benzenepropanoic acid

The title compound was obtained from methyl 4-[(2,3-dihydro-7-methyl-1H-inden-1-yl)oxy]benzenepropanoate by a method similar to that of Reference Example 4. yield 38%.

melting point: 128-129° C. (recrystallized from diethyl ether-hexane).

$^1$H NMR (CDCl$_3$) δ 2.27-2.50 (2H, m), 2.33 (3H, s), 2.67 (2H, t, J=8.0 Hz), 2.90 (1H, m), 2.92 (2H, t, J=8.0 Hz), 3.15 (1H, m), 5.74 (1H, dd, J=1.7 Hz, 3.5 Hz), 6.92 (2H, d, J=8.6 Hz), 7.06 (1H, d, J=7.3 Hz), 7.12-7.23 (4H, m).

EXAMPLE 105 methyl 4-[(3-chlorobenzo[b]thien-2-yl)methoxy]benzenepropanoate

A mixture of methyl 4-hydroxybenzenepropanoate (0.91 g, 5.0 mmol), 3-chloro-2-benzothiophenemethanol (1.0 g, 5.0 mmol), tetrahydrofuran (50 mL), tributylphosphine (1.3 g, 6.5 mmol) and azodicarbonyldipiperazine (1.7 g, 6.5 mmol) was stirred overnight at room temperature. The reaction mixture was concentrated, and filtered. The filtrate was diluted with ethyl acetate, and washed with water. The organic layer was dried over anhydrous magnesium sulfate, and the solvent was evaporated under reduced pressure. The residue was purified by silica gel column chromatography (hexane/ethyl acetate=5:1) to give the title compound (1.6 g, yield 87%).

melting point: 97-98° C. (recrystallized from ethyl acetate-diisopropyl ether-hexane).

$^1$H NMR (CDCl$_3$) δ 2.59 (2H, t, J=7.5 Hz), 2.89 (2H, t, J=7.5 Hz), 3.66 (3H, s), 5.36 (2H, s), 6.93 (2H, d, J=8.6 Hz), 7.12 (2H, d, J=8.6 Hz), 7.37-7.48 (2H, m), 7.77-7.84 (2H, m).

EXAMPLE 106

4-[(3-chlorobenzo[b]thien-2-yl)methoxy]benzenepropanoic acid

A mixture of methyl 4-[(3-chlorobenzo[b]thien-2-yl)methoxy]benzenepropanoate (1.5 g, 4.0 mmol), tetrahydrofuran (20 mL), methanol (5 mL), water (2 mL) and lithium hydroxide monohydrate (0.34 g, 8.0 mmol) was stirred overnight at room temperature. The reaction mixture was neutralized with 0.5N hydrochloric acid, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=3:1) to give the title compound (1.3 g, yield 94%).

melting point: 136-137° C. (recrystallized from ethyl acetate-diisopropyl ether).

$^1$H NMR (CDCl$_3$) δ 2.65 (2H, t, J=7.5 Hz), 2.91 (2H, t, J=7.5 Hz), 5.37 (2H, s), 6.94 (2H, d, J=8.7 Hz), 7.13 (2H, d, J=8.7 Hz), 7.38-7.45 (2H, m), 7.77-7.83 (2H, m), 9.68 (1H, br s).

EXAMPLE 107 methyl 4-[(3-methylbenzo[b]thien-2-yl)methoxy]benzenepropanoate

The title compound was obtained from methyl 4-hydroxybenzenepropanoate and 3-methyl-2-benzo[b]thiophenemethanol by a method similar to that of Example 105. yield 52%.

melting point: 149-150° C. (recrystallized from ethyl acetate-diisopropyl ether-hexane).

$^1$H NMR (CDCl$_3$) δ 2.43 (3H, s), 2.60 (2H, t, J=7.5 Hz), 2.90 (2H, t, J=7.5 Hz), 3.66 (3H, s), 5.26 (2H, s), 6.93 (2H, d, J=8.7 Hz), 7.13 (2H, d, J=8.6 Hz), 7.31-7.41 (2H, m), 7.68-7.71 (1H, m), 7.79-7.82 (1H, m).

EXAMPLE 108

4-[(3-methylbenzo[b]thien-2-yl)methoxy]benzenepropanoic acid

The title compound was obtained from methyl 4-[(3-methylbenzo [b]thien-2-yl)methoxy]benzenepropanoate by a method similar to that of Example 106. yield 79%.

melting point: 155-156° C. (recrystallized from ethyl acetate-diisopropyl ether).

$^1$H NMR (CDCl$_3$) δ 2.42 (3H, s), 2.65 (2H, t, J=7.4 Hz), 2.91 (2H, t, J=7.4 Hz), 5.26 (2H, s), 6.94 (2H, d, J=8.7 Hz), 7.14 (2H, d, J=8.6 Hz), 7.30-7.41 (2H, m), 7.68-7.71 (1H, m), 7.78-7.82 (1H, m), 9.82 (1H, br s).

EXAMPLE 109 methyl 4-(2-benzofuranylmethoxy)benzenepropanoate

The title compound was obtained from methyl 4-hydroxybenzenepropanoate and 2-benzofuranmethanol by a method similar to that of Example 105. yield 81%.

melting point: 93-94° C. (recrystallized from ethyl acetate-hexane).

$^1$H NMR (CDCl$_3$) δ 2.60 (2H, t, J=7.5 Hz), 2.90 (2H, t, J=7.5 Hz), 3.66 (3H, s), 5.14 (2H, s), 6.77 (1H, s), 6.94 (2H, d, J=8.7 Hz), 7.13 (2H, d, J=8.7 Hz), 7.20-7.32 (2H, m), 7.48-7.57 (2H, m).

EXAMPLE 110

4-(2-benzofuranylmethoxy)benzenepropanoic acid

The title compound was obtained from methyl 4-(2-benzofuranylmethoxy) benzenepropanoate by a method similar to that of Example 106. yield 79%.

melting point: 155-156° C. (recrystallized from ethyl acetate-diisopropyl ether).

$^1$H NMR (CDCl$_3$) δ 2.65 (2H, t, J=7.5 Hz), 2.91 (2H, t, J=7.5 Hz), 5.15 (2H, s), 6.77 (1H, s), 6.95 (2H, d, J=8.6 Hz), 7.14 (2H, d, J=8.6 Hz), 7.20-7.32 (2H, m), 7.49-7.57 (2H, m), 9.67 (1H, br s).

EXAMPLE 111 methyl 4-(benzo[b]thien-2-ylmethoxy)benzenepropanoate

The title compound was obtained from methyl 4-hydroxybenzenepropanoate and 2-benzo[b]thiophenemethanol by a method similar to that of Example 105. yield 35%.

melting point: 154-156° C. (recrystallized from petroleum ether)

$^1$H NMR (CDCl$_3$) δ 2.59 (2H, t, J=7.5 Hz), 2.90 (2H, t, J=7.5 Hz), 3.66 (3H, s), 5.30 (2H, s), 6.93 (2H, d, J=8.7 Hz), 7.15 (2H, d, J=8.7 Hz), 7.27-7.37 (3H, m), 7.72-7.80 (2H, m).

EXAMPLE 112

4-(benzo[b]thien-2-ylmethoxy)benzenepropanoic acid

The title compound was obtained from methyl 4-(benzo[b]thien-2-ylmethoxy)benzenepropanoate by a method similar to that of Example 106. yield 81%.

melting point: 190-191° C. (recrystallized from ethyl acetate-diisopropyl ether).

$^1$H NMR (CDCl$_3$) δ 2.65 (2H, t, J=7.5 Hz), 2.91 (2H, t, J=7.5 Hz), 5.30 (2H, s), 6.93 (2H, d, J=8.7 Hz), 7.15 (2H, d, J=8.7 Hz), 7.28-7.37 (3H, m), 7.73-7.83 (2H, m), 9.82 (1H, br s).

EXAMPLE 113 methyl 4-([1,1'-biphenyl]-3-ylmethoxy)-3-bromobenzenepropanoate

The title compound was obtained from methyl 3-bromo-4-hydroxybenzenepropanoate and [1,1'-biphenyl]-3-methanol by a method similar to that of Reference Example 1. yield 96%, oil.

$^1$H NMR (CDCl$_3$) δ 2.59 (2H, t, J=7.3 Hz), 2.87 (2H, t, J=7.3 Hz), 3.66 (3H, s), 5.19 (2H, s), 6.88 (1H, d, J=8.4 Hz), 7.06 (1H, dd, J=1.8 Hz, 8.4 Hz), 7.33-7.37 (1H, m), 7.41-7.47 (5H, m), 7.52-7.62 (3H, m), 7.71 (1H, s).

EXAMPLE 114

4-([1,1'-biphenyl]-3-ylmethoxy)-3-bromobenzenepropanoic acid

The title compound was obtained from methyl 4-([1,1'-biphenyl]-3-ylmethoxy)-3-bromobenzenepropanoate by a method similar to that of Reference Example 4. yield 87%.

melting point: 83-84° C. (recrystallized from ethyl acetate-hexane).

$^1$H NMR (CDCl$_3$) δ 2.64 (2H, t, J=7.4 Hz), 2.88 (2H, t, J=7.4 Hz), 5.19 (2H, s), 6.89 (1H, d, J=8.4 Hz), 7.07 (1H, dd, J=2.0 Hz, 8.4 Hz), 7.33-7.38 (1H, m), 7.42-7.48 (5H, m), 7.53-7.62 (3H, m), 7.70 (1H, s).

EXAMPLE 115 methyl 4-(2-benzothiazolylmethoxy)benzenepropanoate

The title compound was obtained from methyl 4-hydroxybenzenepropanoate and 2-benzothiazolemethanol by a method similar to that of Example 105. yield 91%.

$^1$H NMR (CDCl$_3$) δ 2.59 (2H, t, J=7.5 Hz), 2.90 (2H, t, J=7.5 Hz), 3.66 (3H, s), 5.56 (2H, s), 6.96 (2H, d, J=8.7 Hz), 7.13 (2H, d, J=8.7 Hz), 7.37-7.53 (2H, m), 7.89 (1H, d, J=8.0 Hz), 8.03 (1H, d, J=8.0 Hz).

EXAMPLE 116

4-(2-benzothiazolylmethoxy)benzenepropanoic acid

The title compound was obtained from methyl 4-(2-benzothiazolylmethoxy) benzenepropanoate by a method similar to that of Example 106. yield 93%.

melting point: 158-159° C. (recrystallized from ethyl acetate-diisopropyl ether).

$^1$H NMR (DMSO-d$_6$) δ 2.48 (2H, t, J=7.5 Hz), 2.75 (2H, t, J=7.5 Hz), 5.56 (2H, s), 7.01 (2H, d, J=6.8 Hz), 7.16 (2H, d, J=6.8 Hz), 7.43-7.57 (2H, m), 8.01 (1H, d, J=7.7 Hz), 8.11 (1H, d, J=7.7 Hz), 12.01 (1H, br s).

EXAMPLE 117 methyl 4-[(1-methyl-1H-indol-2-yl)methoxy]benzenepropanoate

The title compound was obtained from methyl 4-hydroxybenzenepropanoate and 1-methyl-2-indolemethanol by a method similar to that of Example 105. yield 28%.

melting point: 157-158° C. (recrystallized from ethyl acetate-diisopropyl ether).

$^1$H NMR (CDCl$_3$) δ 2.60 (2H, t, J=7.5 Hz), 2.90 (2H, t, J=7.5 Hz), 3.67 (3H, s), 3.80 (3H, s), 5.16 (2H, s), 6.58 (1H, s), 6.93 (2H, d, J=8.6 Hz), 7.07-7.15 (2H, m), 7.21-7.25 (2H, m), 7.31-7.34 (1H, m), 7.59 (1H, d, J=7.9 Hz).

EXAMPLE 118

4-[(1-methyl-1H-indol-2-yl)methoxy]benzenepropanoic acid

The title compound was obtained from methyl 4-[(1-methyl-1H-indol-2-yl)methoxy]benzenepropanoate by a method similar to that of Example 106. yield 21%.

melting point: 151-152° C. (recrystallized from ethyl acetate-diisopropyl ether).

$^1$H NMR (DMSO-d$_6$) δ 2.51 (2H, t, J=7.5 Hz), 2.75 (2H, t, J=7.5 Hz), 3.32 (3H, s), 5.26 (2H, s), 6.59 (1H, s), 7.00-7.05 (3H, m), 7.14-7.19 (3H, m), 7.45 (1H, d, J=8.3 Hz), 7.53 (1H, d, J=8.3 Hz), 12.08 (1H, br s).

EXAMPLE 119 methyl 4-[(6,7,8,9-tetrahydro-5H-benzocyclohepten-5-yl)oxy]benzenepropanoate

The title compound was obtained from methyl 4-hydroxybenzenepropanoate and 6,7,8,9-tetrahydro-5H-benzocyclohepten-5-one by a method similar to that of Example 105. yield 36%, oil.

$^1$H NMR (CDCl$_3$) δ 1.43-1.55 (1H, m), 1.79-1.21 (3H, m), 2.04-2.15 (2H, m), 2.57 (2H, t, J=7.5 Hz), 2.76-3.00 (4H, m), 3.65 (3H, s), 5.28 (1H, d, J=9.1 Hz), 6.79 (2H, d, J=8.6 Hz), 7.05 (2H, d, J=8.6 Hz), 7.12-7.16 (3H, m), 7.33-7.35 (1H, m).

EXAMPLE 120

4-[(6,7,8,9-tetrahydro-5H-benzocyclohepten-5-yl)oxy]benzenepropanoic acid

The title compound was obtained from methyl 4-[(6,7,8,9-tetrahydro-5H-benzocyclohepten-5-yl)oxy]benzenepropanoate by a method similar to that of Example 106. yield 65%.

melting point: 129-130° C. (recrystallized from ethyl acetate-diisopropyl ether).

$^1$H NMR (DMSO-d$_6$) δ 1.39-1.48 (1H, m), 1.67-2.05 (5H, m), 2.46 (2H, t, J=7.5 Hz), 2.72 (2H, t, J=7.5 Hz), 2.81-2.97

(2H, m), 5.46 (1H, d, J=8.4 Hz), 6.84 (2H, d, J=8.6 Hz), 7.07-7.16 (5H, m), 7.24-7.30 (1H, m), 12.08 (1H, br s).

EXAMPLE 121 methyl 4-[[4-(trifluoromethyl)benzo[b]thien-2-yl]methoxy]benzenepropanoate

The title compound was obtained from methyl 4-hydroxybenzenepropanoate and 4-(trifluoromethyl)-2-benzo[b]thiophenemethanol by a method similar to that of Example 105. yield 69%.

melting point: 76-77° C. (recrystallized from petroleum ether).

$^1$H NMR (CDCl$_3$) δ 2.60 (2H, t, J=7.5 Hz), 2.90 (2H, t, J=7.5 Hz), 3.66 (3H, s), 5.34 (2H, s), 6.93 (2H, d, J=8.7 Hz), 7.14 (2H, d, J=8.7 Hz), 7.36-7.41 (1H, m), 7.53-7.55 (1H, m), 7.65 (1H, d, J=8.3 Hz), 7.98 (1H, d, J=8.3 Hz).

EXAMPLE 122

4-[[4-(trifluoromethyl)benzo[b]thien-2-yl]methoxy]benzenepropanoic acid

The title compound was obtained from methyl 4-[[4-(trifluoromethyl) benzo[b]thien-2-yl]methoxy]benzenepropanoate by a method similar to that of Example 106. yield 82%.

melting point: 151-152° C. (recrystallized from ethyl acetate-diisopropyl ether).

$^1$H NMR (DMSO-d$_6$) δ 2.46 (2H, t, J=7.5 Hz), 2.75 (2H, t, J=7.5 Hz), 5.50 (2H, s), 6.97 (2H, d, J=8.8 Hz), 7.15 (2H, d, J=8.8 Hz), 7.53 (1H, t, J=7.7 Hz), 7.65 (1H, s), 7.77 (1H, d, J=7.5 Hz), 8.31 (1H, d, J=7.5 Hz), 12.08 (1H, br s).

EXAMPLE 123 methyl 4-[(3'-chloro-[1,1'-biphenyl]-3-yl)methoxy]benzenepropanoate

The title compound was obtained from methyl 4-[(3-bromophenyl) methoxy]benzenepropanoate and 3-chlorophenylboronic acid by a method similar to that of Example 22. yield 86%, oil.

$^1$H NMR (CDCl$_3$) δ 2.60 (2H, t, J=8.0 Hz), 2.90 (2H, t, J=8.0 Hz), 3.66 (3H, s), 5.10 (2H, s), 6.92 (2H, d, J=8.6 Hz), 7.13 (2H, d, J=8.6 Hz), 7.30-7.39 (2H, m), 7.42-7.54 (4H, m), 7.58-7.62 (2H, m).

EXAMPLE 124

4-[(3'-chloro-[1,1'-biphenyl]-3-yl)methoxy]benzenepropanoic acid

The title compound was obtained from methyl 4-[(3'-chloro-[1,1'-biphenyl]-3-yl)methoxy]benzenepropanoate by a method similar to that of Reference Example 4. yield 34%.

melting point: 109-110° C. (recrystallized from ethyl acetate-hexane).

$^1$H NMR (CDCl$_3$) δ 2.65 (2H, t, J=7.8 Hz), 2.91 (2H, t, J=7.8 Hz), 5.10 (2H, s), 6.93 (2H, d, J=8.4 Hz), 7.14 (2H, d, J=8.4 Hz), 7.31-7.53 (6H, m), 7.62 (1H, s), 7.58 (1H, s).

EXAMPLE 125 methyl 4-[(2'-chloro-[1,1'-biphenyl]-3-yl)methoxy]benzenepropanoate

The title compound was obtained from methyl 4-[(3-bromophenyl) methoxy]benzenepropanoate and 2-chlorophenylboronic acid by a method similar to that of Example 22. yield 83%, oil.

$^1$H NMR (CDCl$_3$) δ 2.60 (2H, t, J=8.1 Hz), 2.90 (2H, t, J=8.1 Hz), 3.66 (3H, s), 5.09 (2H, s), 6.92 (2H, d, J=8.7 Hz), 7.12 (2H, d, J=8.6 Hz), 7.27-7.50 (8H, m).

EXAMPLE 126

4-[(2'-chloro-[1,1'-biphenyl]-3-yl)methoxy]benzenepropanoic acid

The title compound was obtained from methyl 4-[(2'-chloro-[1,1'-biphenyl]-3-yl)methoxy]benzenepropanoate by a method similar to that of Reference Example 4. yield 29%.

melting point: 127-128° C. (recrystallized from ethyl acetate-hexane).

$^1$H NMR (CDCl$_3$) δ 2.65 (2H, t, J=7.8 Hz), 2.91 (2H, t, J=7.8 Hz), 5.10 (2H, s), 6.93 (2H, d, J=8.5 Hz), 7.13 (2H, d, J=8.5 Hz), 7.28-7.50 (8H, m).

EXAMPLE 127 methyl 4-[(3'-methyl-[1,1'-biphenyl]-3-yl)methoxy]benzenepropanoate

The title compound was obtained from methyl 4-[(3-bromophenyl) methoxy]benzenepropanoate and 3-methylphenylboronic acid by a method similar to that of Example 22. yield 92%, oil.

$^1$H NMR (CDCl$_3$) δ 2.42 (3H, s), 2.60 (2H, t, J=8.0 Hz), 2.90 (2H, t, J=8.0 Hz), 3.66 (3H, s), 5.60 (2H, s), 6.93 (2H, d, J=8.6 Hz), 7.10-7.18 (3H, m), 7.30-7.47 (5H, m), 7.54 (1H, dt, J=7.3 Hz, 1.7 Hz), 7.64 (1H, s).

EXAMPLE 128

4-[(3'-methyl-[1,1'-biphenyl]-3-yl)methoxy]benzenepropanoic acid

The title compound was obtained from methyl 4-[(3'-methyl-[1,1'-biphenyl]-3-yl)methoxy]benzenepropanoate by a method similar to that of Reference Example 4. yield 62%.

melting point: 102-103° C. (recrystallized from ethyl acetate-hexane).

$^1$H NMR (CDCl$_3$) δ 2.42 (3H, s), 2.65 (2H, t, J=8.0 Hz), 2.91 (2H, t, J=8.0 Hz), 5.10 (2H, s), 6.93 (2H, d, J=8.6 Hz), 7.12-7.18 (3H, m), 7.30-7.47 (5H, m), 7.54 (1H, dt, J=7.3 Hz, 1.6 Hz), 7.64 (1H, s).

EXAMPLE 129 methyl 4-[(3'-fluoro-[1,1'-biphenyl]-3-yl)methoxy]benzenepropanoate

The title compound was obtained from methyl 4-[(3-bromophenyl)methoxy]benzenepropanate and 3-fluorophenylboronic acid by a method similar to that of Example 22. yield 89%, oil.

$^1$H NMR (CDCl$_3$) δ 2.60 (2H, t, J=8.1 Hz), 2.90 (2H, t, J=8.1 Hz), 3.66 (3H, s), 5.10 (2H, s), 6.92 (2H, d, J=8.6 Hz), 7.01-7.08 (1H, m), 7.13 (2H, d, J=8.6 Hz), 7.27-7.31 (1H, m), 7.36-7.55 (5H, m), 7.63 (1H, s).

EXAMPLE 130

4-[(3'-fluoro-[1,1'-biphenyl]-3-yl) methoxy]benzenepropanoic acid

The title compound was obtained from methyl 4-[(3'-fluoro-[1,1'-biphenyl]-3-yl)methoxy]benzenepropanoate by a method similar to that of Reference Example 4. yield 62%.

melting point: 113-114° C. (recrystallized from ethyl acetate-hexane).

$^1$H NMR (CDCl$_3$) δ 2.65 (2H, t, J=8.0 Hz), 2.91 (2H, t, J=8.0 Hz), 5.10 (2H, s), 6.93 (2H, d, J=8.6 Hz), 7.01-7.07 (1H, m), 7.14 (2H, d, J=8.6 Hz), 7.27-7.31 (1H, m), 7.35-7.55 (5H, m), 7.63 (1H, m).

EXAMPLE 131 methyl 4-[(3'-methoxy-[1,1'-biphenyl]-3-yl) methoxy]benzenepropanoate

The title compound was obtained from methyl 4-[(3-bromophenyl) methoxy]benzenepropanoate and 3-methoxyphenylboronic acid by a method similar to that of Example 22. yield 89%.

$^1$H NMR (CDCl$_3$) δ 2.60 (2H, t, J=8.1 Hz), 2.90 (2H, t, J=8.1 Hz), 3.66 (3H, s), 3.87 (3H, s), 5.10 (2H, s), 6.89-6.94 (3H, m), 7.11-7.14 (3H, m), 7.17-7.19 (1H, m), 7.33-7.47 (3H, m), 7.54 (1H, dt, J=7.1 Hz, 1.7 Hz), 7.64 (1H, s).

EXAMPLE 132

4-[(3'-methoxy-[1,1'-biphenyl]-3-yl) methoxy]benzenepropanoic acid

The title compound was obtained from methyl 4-[(3'-methoxy-[1,1'-biphenyl]-3-yl)methoxy]benzenepropanoate by a method similar to that of Reference Example 4. yield 62%.

$^1$H NMR (CDCl$_3$) δ 2.65 (2H, t, J=7.9 Hz), 2.91 (2H, t, J=7.9 Hz), 3.86 (3H, s), 5.10 (2H, s), 6.88-6.95 (3H, m), 7.11-7.19 (4H, m), 7.33-7.47 (3H, m), 7.54 (1H, dt, 7.1 Hz, 1.7 Hz), 7.64 (1H, s).

EXAMPLE 133 methyl 4-[(3'-nitro-[1,1'-biphenyl]-3-yl) methoxy]benzenepropanoate

The title compound was obtained from methyl 4-[(3-bromophenyl) methoxy]benzenepropanoate and 3-nitrophenylboronic acid by a method similar to that of Example 22. yield 74%, oil.

$^1$H NMR (CDCl$_3$) δ 2.60 (2H, t, J=8.1 Hz), 2.90 (2H, t, J=8.1 Hz), 3.66 (3H, s), 5.12 (2H, s), 6.93 (2H, d, J=8.6 Hz), 7.13 (2H, d, J=8.6 Hz), 7.48-7.65 (4H, m), 7.69 (1H, s), 7.91-7.94 (1H, m), 8.19-8.23 (1H, m), 8.46 (1H, t, J=2.0 Hz).

EXAMPLE 134

4-[(3'-nitro-[1,1'-biphenyl]-3-yl) methoxy]benzenepropanoic acid

The title compound was obtained from methyl 4-[(3'-nitro-[1,1'-biphenyl]-3-yl)methoxy]benzenepropanoate by a method similar to that of Reference Example 4. yield 51%.

melting point: 114-115° C. (recrystallized from ethyl acetate-hexane).

$^1$H NMR (CDCl$_3$) δ 2.66 (2H, t, J=7.8 Hz), 2.91 (2H, t, J=7.8 Hz), 5.12 (2H, s), 6.94 (2H, d, J=8.6 Hz), 7.15 (2H, d, J=8.6 Hz), 7.48-7.64 (4H, m), 7.69 (1H, s), 7.90-7.94 (1H, m), 8.19-8.23 (1H, m), 8.46 (1H, t, J=1.9 Hz).

EXAMPLE 135 methyl 4-[[3-[(2,3-dihydro-1H-inden-1-yl) oxy]phenyl]methoxy]benzenepropanoate The title compound was obtained from methyl 4-hydroxybenzenepropanoate and 3-[(2,3-dihydro-1H-inden-1-yl)oxy]benzenemethanol by a method similar to that of Reference Example 1. yield 82%, oil.

$^1$H NMR (CDCl$_3$) δ 2.10-2.30 (1H, m), 2.50-2.65 (3H, m), 2.87-3.00 (3H, m), 3.09-3.20 (1H, m), 3.66 (3H, s), 5.03 (2H, s), 5.78 (1H, dd, J=6.6 Hz, 4.4 Hz), 6.88-6.98 (3H, m), 7.02 (1H, d, J=7.6 Hz), 7.09-7.13 (3H, m), 7.19-7.35 (4H, m), 7.42 (1H, d, J=7.3 Hz).

EXAMPLE 136

4-[[3-[(2,3-dihydro-1H-inden-1-yl) oxy]phenyl]methoxy]benzenepropanoic acid

The title compound was obtained from methyl 4-[[3-[(2,3-dihydro-1H-inden-1-yl)oxy]phenyl]methoxy]benzenepropanoate by a method similar to that of Reference Example 4. yield 55%.

melting point: 119-121° C. (recrystallized from ethyl acetate-hexane).

$^1$H NMR (CDCl$_3$) δ 2.15-2.26 (1H, m), 2.50-2.59 (1H, m), 2.65 (2H, t, J=8.1 Hz), 2.90 (2H, t, J=8.1 Hz), 2.88-2.97 (1H, m), 3.09-3.19 (1H, m), 5.03 (2H, s), 5.78 (1H, dd, J=6.6 Hz, 4.3 Hz), 6.88-6.98 (3H, m), 7.02 (1H, d, J=7.5 Hz), 7.09-7.17 (3H, m), 7.20-7.34 (4H, m), 7.42 (1H, d, J=7.3 Hz).

EXAMPLE 137 methyl 4-[[3-((E)-2-phenylethenyl) phenyl]methoxy]benzenepropanoate

Methyl 4-[(3-bromophenyl)methoxy]benzenepropanoate (1.0 g, 2.9 mmol), styrene (0.45 g, 4.3 mmol), sodium hydrogencarbonate (0.60 g, 7.2 mmol), tetrabutylammonium chloride (1.6 g, 5.7 mmol) were dissolved in N,N-dimethylformamide (25 mL) and, after argon substitution, palladium acetate (19 mg, 0.086 mmol) was added. The reaction mixture was heated under an argon atmosphere at 100° C. for 18 hrs. The reaction mixture was cooled, water was added to the reaction mixture and the mixture was extracted with ethyl acetate. The extract was washed with water, dried and concentrated. The residue was purified by silica gel column chromatography (ethyl acetate/hexane=15:1) to give the title compound (0.63 g, yield 59%) as a white powder.

melting point: 100-101° C. (recrystallized from ethyl acetate-hexane).

$^1$H NMR (CDCl$_3$) δ 2.60 (2H, t, J=8.1 Hz), 2.90 (2H, t, J=8.1 Hz), 3.66 (3H, s), 5.06 (2H, s), 6.92 (2H, d, J=8.6 Hz), 7.11-7.14 (4H, m), 7.24-7.40 (5H, m), 7.46-7.58 (4H, m).

EXAMPLE 138

4-[[3-((E)-2-phenylethenyl)phenyl]methoxy]benzenepropanoic acid

The title compound was obtained from methyl 4-[[3-((E)-2-phenylethenyl) phenyl]methoxy]benzenepropanoate by a method similar to that of Reference Example 4. yield 64%.

melting point: 155-156° C. (recrystallized from ethyl acetate-hexane).

$^1$H NMR (CDCl$_3$) δ 2.59 (2H, t, J=7.4 Hz), 2.90 (2H, t, J=7.4 Hz), 5.06 (2H, s), 6.92 (2H, d, J=8.6 Hz), 7.13-7.16 (4H, m), 7.24-7.40 (5H, m), 7.46-7.58 (4H, m).

EXAMPLE 139 methyl 4-[(4-chloro-[1,1'-biphenyl]-3-yl)methoxy]benzenepropanoate

The title compound was obtained from methyl 4-[(5-bromo-2-chlorophenyl)methoxy]benzenepropanoate and phenylboronic acid by a method similar to that of Example 22. yield 89%, oil.

$^1$H NMR (CDCl$_3$) δ 2.60 (2H, t, J=8.0 Hz), 2.90 (2H, t, J=8.0 Hz), 3.66 (3H, s), 5.19 (2H, s), 6.95 (2H, d, J=8.7 Hz), 7.14 (2H, d, J=8.7 Hz), 7.30-7.57 (7H, m), 7.79 (1H, br s).

EXAMPLE 140

4-[(4-chloro-[1,1'-biphenyl]-3methoxy]benzenepropanoic acid-yl)

The title compound was obtained from methyl 4-[(4-chloro-[1,1'-biphenyl]-3-yl)methoxy]benzenepropanoate by a method similar to that of Reference Example 4. yield 62%.

melting point: 115-116° C. (recrystallized from ethyl acetate-hexane).

$^1$H NMR (CDCl$_3$) δ 2.65 (2H, t, J=8.0 Hz), 2.91 (2H, t, J=8.0 Hz), 5.19 (2H, s), 6.95 (2H, d, J=8.6 Hz), 7.15 (2H, d, J=8.6 Hz), 7.32-7.50 (5H, m), 7.54-7.57 (2H, m), 7.78 (1H, br s).

EXAMPLE 141 methyl 4-[[3-(2-phenylethyl)phenyl]methoxy]benzenepropanoate

To a solution of methyl 4-[[3-((E)-2-phenylethenyl) phenyl]methoxy]benzenepropanoate (0.35 g, 0.95 mmol) in methanol (15 mL) and tetrahydrofuran (25 mL) was added platinum oxide (0.018 g, 0.078 mmol), and the mixture was stirred under a hydrogen atmosphere at room temperature for 18 hrs. The catalyst was filtered off, and the filtrate was concentrated. The residue was purified by silica gel column chromatography (ethyl acetate/hexane=15:1) to give the title compound (0.21 g, yield 58%). oil.

$^1$H NMR (CDCl$_3$) δ 2.60 (2H, t, J=8.1 Hz), 2.90 (2H, t, J=8.1 Hz), 2.93 (4H, s), 3.67 (3H, s), 5.00 (2H, s), 6.90-6.95 (2H, m), 7.10-7.30 (11H, m).

EXAMPLE 142

4-[[3-(2-phenylethyl)phenyl]methoxy]benzenepropanoic acid

The title compound was obtained from methyl 4-[[3-(2-phenylethyl) phenyl]methoxy]benzenepropanoate by a method similar to that of Reference Example 4. yield 63%.

melting point: 105-106° C. (recrystallized from ethyl acetate-hexane).

$^1$H NMR (CDCl$_3$) δ 2.65 (2H, t, J=8.1 Hz), 2.91 (2H, t, J=8.1 Hz), 2.93 (4H, s), 5.00 (2H, s), 6.91 (2H, d, J=8.6 Hz), 7.16-7.32 (11H, m).

EXAMPLE 143 methyl 4-([1,1'-biphenyl]-3-ylmethoxy)-3-chlorobenzenepropanoate

The title compound was obtained from methyl 4-[(3-bromophenyl) methoxy]-3-chlorobenzenepropanoate and phenylboronic acid by a method similar to that of Example 22. yield 44%, oil.

$^1$H NMR (CDCl$_3$) δ 2.59 (2H, t, J=7.8 Hz), 2.87 (2H, t, J=7.8 Hz), 3.66 (3H, s), 5.19 (2H, s), 6.91 (1H, d, J=8.4 Hz), 7.02 (1H, dd, J=8.4 Hz, 2.1 Hz), 7.24 (1H, d, J=2.1 Hz), 7.33-7.38 (1H, m), 7.42-7.49 (4H, m), 7.54-7.62 (3H, m), 7.68 (1H, m).

EXAMPLE 144

4-([1,1'-biphenyl]-3-ylmethoxy)-3-chlorobenzenepropanoic acid

The title compound was obtained from methyl 4-([1,1'-biphenyl]-3-ylmethoxy)-3-chlorobenzenepropanoate by a method similar to that of Reference Example 4. yield 54%.

melting point: 77.0-77.5° C. (recrystallized from diisopropyl ether-hexane).

$^1$H NMR (CDCl$_3$) δ 2.64 (2H, t, J=7.8 Hz), 2.88 (2H, t, J=7.8 Hz), 5.19 (2H, s), 6.92 (1H, d, J=8.4 Hz), 7.03 (1H, dd, J=8.4 Hz, 2.1 Hz), 7.25-7.26 (1H, m), 7.32-7.38 (1H, m), 7.42-7.48 (4H, m), 7.53-7.62 (3H, m), 7.68 (1H, m).

EXAMPLE 145 methyl 4-[(2'-fluoro-[1,1'-biphenyl]-3-yl)methoxy]benzenepropanoate

The title compound was obtained from methyl 4-[(3-bromophenyl) methoxy]benzenepropanoate and 2-fluorophenylboronic acid by a method similar to that of Example 22. yield 83%, oil.

$^1$H NMR (CDCl$_3$) δ 2.60 (2H, t, J=8.0 Hz), 2.90 (2H, t, J=8.0 Hz), 3.66 (3H, s), 5.09 (2H, s), 6.92 (2H, d, J=8.6 Hz), 7.10-7.24 (4H, m), 7.29-7.36 (1H, m), 7.42-7.54 (4H, m), 7.61 (1H, s).

EXAMPLE 146

4-[(2'-fluoro-[1,1'-biphenyl]-3-yl)methoxy]benzenepropanoic acid

The title compound was obtained from methyl 4-[(2'-fluoro-[1,1'-biphenyl]-3-yl)methoxy]benzenepropanoate by a method similar to that of Reference Example 4. yield 70%.

melting point: 112-113° C. (recrystallized from ethyl acetate-hexane).

¹H NMR (CDCl₃) δ 2.66 (2H, t, J=7.9 Hz), 2.91 (2H, t, J=7.9 Hz), 5.10 (2H, s), 6.93 (2H, d, J=8.6 Hz), 7.12-7.24 (4H, m), 7.29-7.36 (1H, m), 7.42-7.54 (4H, m), 7.61 (1H, s).

EXAMPLE 147 methyl 4-([1,1'-biphenyl]-3-ylmethoxy)-2-methyl-benzenepropanoate

The title compound was obtained from methyl 4-hydroxy-2-methylbenzenepropanoate and [1,1'-biphenyl]-3-methanol by a method similar to that of Reference Example 1. yield 80%, oil.

¹H NMR (CDCl₃) δ 2.30 (3H, s), 2.56 (2H, t, J=7.5 Hz), 2.89 (2H, t, J=7.5 Hz), 3.68 (3H, s), 5.09 (2H, s), 6.75-6.83 (2H, m), 7.05 (1H, d, J=8.3 Hz), 7.32-7.48 (5H, m), 7.53-7.65 (4H, m).

EXAMPLE 148

4-([1,1'-biphenyl]-3-ylmethoxy)-2-methylbenzenepropanoic acid

The title compound was obtained from methyl 4-([1,1'-biphenyl]-3-ylmethoxy)-2-methylbenzenepropanoate by a method similar to that of Reference Example 4. yield 70%.

melting point: 103.0-103.5° C. (recrystallized from ethyl acetate-hexane).

¹H NMR (CDCl₃) δ 2.30 (3H, s), 2.61 (2H, t, J=8.4 Hz), 2.90 (2H, t, J=8.4 Hz), 5.09 (2H, s), 6.76-6.83 (2H, m), 7.07 (1H, d, J=8.3 Hz), 7.32-7.48 (5H, m), 7.54-7.65 (4H, m).

EXAMPLE 149 methyl 4-[[2,3-dihydro-5-(4-phenylbutoxy)-1H-inden-1-yl]oxy]benzenepropanoate

The title compound was obtained from methyl 4-hydroxybenzenepropanoate and 2,3-dihydro-5-(4-phenylbutoxy)-1H-inden-1-ol by a method similar to that of Reference Example 1. yield 49%, oil.

¹H NMR (CDCl₃) δ 1.75-1.83 (4H, m), 2.16-2.27 (1H, m), 2.46-2.71 (5H, m), 2.81-2.93 (3H, m), 3.06-3.16 (1H, m), 3.68 (3H, s), 3.95-3.99 (2H, m), 5.66 (1H, dd, J=6.5 Hz, 3.5 Hz), 6.75-6.80 (2H, m), 6.89-6.93 (1H, m), 7.10-7.21 (5H, m), 7.26-7.31 (4H, m).

EXAMPLE 150

4-[[2,3-dihydro-5-(4-phenylbutoxy)-1H-inden-1-yl]oxy]benzenepropanoic acid

The title compound was obtained from methyl 4-[[2,3-dihydro-5-(4-phenylbutoxy)-1H-inden-1-yl]oxy]benzenepropanoate by a method similar to that of Reference Example 4. yield 70%.

melting point: 89-90° C. (recrystallized from diisopropyl ether-hexane).

¹H NMR (CDCl₃) δ 1.78-1.83 (4H, m), 2.17-2.27 (1H, m), 2.46-2.58 (1H, m), 2.64-2.71 (4H, m), 2.81-2.95 (3H, m), 3.06-3.16 (1H, m), 3.95-3.99 (2H, m), 5.66 (1H, dd, J=6.5 Hz, 3.5 Hz), 6.75-6.79 (2H, m), 6.92 (2H, d, J=8.6 Hz), 7.17-7.21 (5H, m), 7.26-7.31 (3H, m).

EXAMPLE 151 methyl 2-methyl-4-[(3-phenoxyphenyl)methoxy]benzenepropanoate

The title compound was obtained from methyl 4-hydroxy-2-methyl-benzenepropanoate and 3-phenoxybenzyl alcohol by a method similar to that of Reference Example 1. yield 76%, oil.

¹H NMR (CDCl₃) δ 2.29 (3H, s), 2.55 (2H, t, J=8.4 Hz), 2.88 (2H, t, J=8.4 Hz), 3.68 (3H, s), 4.99 (2H, s), 6.70-6.77 (2H, m), 6.93-7.17 (7H, m), 7.30-7.36 (3H, m).

EXAMPLE 152

2-methyl-4-[(3-phenoxyphenyl)methoxy]benzenepropanoic acid

The title compound was obtained from methyl 2-methyl-4-[(3-phenoxyphenyl)methoxy]benzenepropanoate by a method similar to that of Reference Example 4. yield 72%.

melting point: 82-83° C. (recrystallized from diisopropyl ether-hexane).

¹H NMR (CDCl₃) δ 2.29 (3H, s), 2.60 (2H, t, J=8.4 Hz), 2.89 (2H, t, J=8.4 Hz), 4.99 (2H, s), 6.71-6.78 (2H, m), 6.93-7.17 (7H, m), 7.31-7.36 (3H, m).

EXAMPLE 153 methyl 3-chloro-4-[(2,3-dihydro-1H-inden-1-yl)oxy]benzenepropanoate

The title compound was obtained from methyl 3-chloro-4-hydroxybenzenepropanoate and 2,3-dihydro-1H-indan-1-ol by a method similar to that of Reference Example 1. yield 91%, oil.

¹H NMR (CDCl₃) δ 2.20-2.31 (1H, m), 2.50-2.60 (1H, m), 2.61 (2H, t, J=7.9 Hz), 2.87-2.97 (3H, m), 3.13-3.23 (1H, m), 3.68 (3H, s), 5.71 (1H, dd, J=4.9 Hz, 6.6 Hz), 7.01-7.08 (2H, m), 7.22-7.31 (4H, m), 7.43 (1H, d, J=7.3 Hz).

EXAMPLE 154

3-chloro-4-[(2,3-dihydro-1H-inden-1-yl)oxy]benzenepropanoic acid

The title compound was obtained from methyl 3-chloro-4-[(2,3-dihydro-1H-inden-1-yl)oxy]benzenepropanoate by a method similar to that of Reference Example 4. yield 56%.

¹H NMR (CDCl₃) δ 2.20-2.31 (1H, m), 2.50-2.61 (1H, m), 2.67 (2H, t, J=7.7 Hz), 2.86-2.99 (3H, m), 3.12-3.22 (1H, m), 5.71 (1H, dd, J=5.0 Hz, 6.5 Hz), 7.01-7.09 (2H, m), 7.20-7.31 (4H, m), 7.43 (1H, d, J=7.3 Hz).

EXAMPLE 155 methyl 4-[(2,3-dihydro-1H-inden-1-yl)oxy]-2-methylbenzenepropanoate

The title compound was obtained from methyl 4-hydroxy-2-methylbenzenepropanoate and 2,3-dihydro-1H-indan-1-ol by a method similar to that of Reference Example 1. yield 65%, oil.

¹H NMR (CDCl₃) δ 2.10-2.30 (1H, m), 2.31 (3H, s), 2.50-2.65 (3H, m), 2.75-3.00 (3H, m), 3.05-3.20 (1H, m), 3.69 (3H, s), 5.72 (1H, dd, J=4.4 Hz, 6.6 Hz), 6.78-6.81 (2H, m), 7.07 (1H, d, J=8.0 Hz), 7.21-7.33 (3H, m), 7.42 (1H, d, J=7.2 Hz).

EXAMPLE 156

4-[(2,3-dihydro-1H-inden-1-yl)oxy]-2-methylbenzenepropanoic acid

The title compound was obtained from methyl 4-[(2,3-dihydro-1H-inden-1-yl)oxy]-2-methylbenzenepropanoate by a method similar to that of Reference Example 4. yield 24%.

melting point: 79-80° C. (recrystallized from diisopropyl ether-hexane).

¹H NMR (CDCl₃) δ 2.14-2.25 (1H, m), 2.32 (3H, m), 2.50-2.66 (3H, m), 2.86-2.97 (3H, m), 3.09-3.19 (1H, m), 5.73 (1H, dd, J=4.5 Hz, 6.6 Hz), 6.79-6.82 (2H, m), 7.09 (1H, d, J=7.9 Hz), 7.21-7.31 (3H, m), 7.42 (1H, d, J=7.2 Hz).

EXAMPLE 157 methyl 4-[[3-(2-phenylethoxy)phenyl]methoxy]benzenepropanoate

The title compound was obtained from methyl 4-hydroxybenzenepropanoate and 2-phenylethanol by a method similar to that of Reference Example 1. yield 58%, oil.

¹H NMR (CDCl₃) δ 2.59 (2H, t, J=7.1 Hz), 2.89 (2H, t, J=7.5 Hz), 3.09 (2H, t, J=7.1 Hz), 3.66 (3H, s), 4.18 (2H, t, J=7.1 Hz), 4.99 (2H, s), 6.83-6.91 (3H, m), 6.97-6.99 (2H, m), 7.10 (2H, d, J=8.6 Hz), 7.21-7.35 (6H, m).

EXAMPLE 158

4-[[3-(2-phenylethoxy)phenyl]methoxy]benzenepropanoic acid

The title compound was obtained from methyl 4-[[3-(2-phenylethoxy) phenyl]methoxy]benzenepropanoate by a method similar to that of Reference Example 4. yield 63%.

melting point: 79-80° C. (recrystallized from ethyl acetate-hexane).

¹H NMR (CDCl₃) δ 2.64 (2H, t, J=8.0 Hz), 2.90 (2H, t, J=8.0 Hz), 3.09 (2H, t, J=7.1 Hz), 4.18 (2H, t, J=7.1 Hz), 5.00 (2H, s), 6.83-6.92 (3H, m), 6.97-7.00 (2H, m), 7.12 (2H, d, J=8.6 Hz), 7.21-7.35 (6H, m).

EXAMPLE 159 methyl 4-[[2,3-dihydro-5-(2-phenylethoxy)-1H-inden-1-yl]oxy]benzenepropanoate

The title compound was obtained from methyl 4-hydroxybenzenepropanoate and 2,3-dihydro-5-(2-phenylethoxy)-1H-indan-1-ol by a method similar to that of Reference Example 1. yield 65%, oil.

¹H NMR (CDCl₃) δ 2.16-2.26 (1H, m), 2.46-2.64 (3H, m), 2.78-2.93 (3H, m), 3.05-3.15 (3H, m), 3.67 (3H, s), 4.18 (2H, t, J=6.9 Hz), 5.66 (1H, dd, J=6.5 Hz, 3.6 Hz), 6.72-6.84 (2H, m), 6.95 (2H, d, J=8.6 Hz), 7.12 (2H, d, J=8.6 Hz), 7.20-7.35 (6H, m).

EXAMPLE 160

4-[[2,3-dihydro-5-(2-phenylethoxy)-1H-inden-1-yl]oxy]benzenepropanoic acid

The title compound was obtained from methyl 4-[[2,3-dihydro-5-(2-phenylethoxy)-1H-inden-1-yl]oxy]benzenepropanoate by a method similar to that of Reference Example 4. yield 52%.

melting point: 96-97° C. (recrystallized from ethyl acetate-hexane).

¹H NMR (CDCl₃) δ 2.17-2.27 (1H, m), 2.46-2.57 (1H, m), 2.67 (2H, t, J=8.0 Hz), 2.81-2.95 (3H, m), 3.05-3.15 (3H, m), 4.18 (2H, t, J=7.1 Hz), 5.66 (1H, dd, J=6.5 Hz, 3.6 Hz), 6.77-6.81 (2H, m), 6.92 (2H, d, J=8.3 Hz), 7.14 (2H, d, J=8.6 Hz), 7.21-7.35 (6H, m).

EXAMPLE 161 methyl 4-[[3-(3-phenylpropoxy)phenyl]methoxy]benzenepropanoate

The title compound was obtained from methyl 4-hydroxybenzenepropanoate and 3-phenylpropanol by a method similar to that of Reference Example 1. yield 58%, oil.

¹H NMR (CDCl₃) δ 2.05-2.15 (2H, m), 2.60 (2H, t, J=8.1 Hz), 2.81 (2H, t, J=7.9 Hz), 2.89 (2H, t, J=8.1 Hz), 3.67 (3H, s), 3.97 (2H, t, J=6.2 Hz), 5.00 (2H, s), 6.82-6.92 (3H, m), 6.97-7.00 (2H, m), 7.11 (2H, d, J=8.6 Hz), 7.17-7.32 (6H, m).

EXAMPLE 162

4-[[3-(3-phenylpropoxy)phenyl]methoxy]benzenepropanoic acid

The title compound was obtained from methyl 4-[[3-(2-phenylpropoxy) benzyl]oxy]benzenepropanoate by a method similar to that of Reference Example 4. yield 53%.

melting point: 97-98° C. (recrystallized from ethyl acetate-hexane).

¹H NMR (CDCl₃) δ 2.06-2.15 (2H, m), 2.65 (2H, t, J=8.0 Hz), 2.81 (2H, t, J=8.0 Hz), 2.90 (2H, t, J=7.0 Hz), 3.97 (2H, t, J=6.3 Hz), 5.00 (2H, s), 6.83-6.92 (3H, m), 6.99 (2H, d, J=7.4 Hz), 7.11-7.31 (8H, m).

EXAMPLE 163 methyl 4-[(2'-methoxy-[1,1'-biphenyl]-3-yl)methoxy]benzenepropanoate

The title compound was obtained from methyl 4-hydroxybenzenepropanoate and 2-methoxyphenylboronic acid by a method similar to that of Example 22. yield 65%, oil.

¹H NMR (CDCl₃) δ 2.60 (2H, t, J=8.0 Hz), 2.89 (2H, t, J=8.0 Hz), 3.66 (3H, s), 3.79 (3H, s), 6.92 (2H, d, J=8.5 Hz), 6.97-7.05 (2H, m), 7.11 (2H, d, J=8.5 Hz), 7.30-7.50 (5H, m), 7.58 (1H, s).

EXAMPLE 164

4-[(2'-methoxy-[1,1'-biphenyl]-3-yl)methoxy]benzenepropanoic acid

The title compound was obtained from methyl 4-[(2'-methoxy-[1,1'-biphenyl]-3-yl)methoxy]benzenepropanoate by a method similar to that of Reference Example 4. yield 69%.

melting point: 128-129° C. (recrystallized from ethyl acetate-hexane).
$^1$H NMR (CDCl$_3$) δ 2.65 (2H, t, J=7.9 Hz), 2.91 (2H, t, J=7.9 Hz), 3.79 (3H, s), 5.08 (2H, s), 6.90-7.05 (4H, m), 7.13 (2H, d, J=8.6 Hz), 7.29-7.50 (5H, m), 7.58 (1H, s).

EXAMPLE 165 methyl 4-[(2'-methyl-[1,1'-biphenyl]-3-yl) methoxy]benzenepropanoate

The title compound was obtained from methyl 4-hydroxybenzenepropanoate and 2-methylphenylboronic acid by a method similar to that of Example 22. yield 79%, oil.
$^1$H NMR (CDCl$_3$) δ 2.25 (3H, s), 2.60 (2H, t, J=8.2 Hz), 2.90 (2H, t, J=8.2 Hz), 3.66 (3H, s), 5.08 (2H, s), 6.91 (2H, d, J=8.6 Hz), 7.12 (2H, d, J=8.6 Hz), 7.22-7.30 (5H, m), 7.39-7.46 (3H, m).

EXAMPLE 166

4-[(2'-methyl-[1,1'-biphenyl]-3-yl) methoxy]benzenepropanoic acid

The title compound was obtained from methyl 4-[(2'-methyl-[1,1'-biphenyl]-3-yl)methoxy]benzenepropanoate by a method similar to that of Reference Example 4. yield 52%.
melting point: 135-136° C. (recrystallized from ethyl acetate-hexane).
$^1$H NMR (CDCl$_3$) δ 2.25 (3H, s), 2.65 (2H, t, J=7.9 Hz), 2.91 (2H, t, J=7.9 Hz), 5.09 (2H, s), 6.92 (2H, d, J=8.5 Hz), 7.13 (2H, d, J=8.5 Hz), 7.23-7.31 (5H, m), 7.39-7.45 (3H, m).

EXAMPLE 167 methyl 4-[(2-chloro-[1,1'-biphenyl]-5-yl) methoxy]benzenepropanoate

The title compound was obtained from methyl 4-[(3-bromo-4-chlorophenyl)methoxy]benzenepropanoate and phenylboronic acid by a method similar to that of Example 22. yield 40%, oil.
$^1$H NMR (CDCl$_3$) δ 2.60 (2H, t, J=8.1 Hz), 2.90 (2H, t, J=8.1 Hz), 3.66 (3H, s), 5.03 (2H, s), 6.89 (2H, d, J=8.5 Hz), 7.11 (2H, d, J=8.5 Hz), 7.32-7.49 (8H, m).

EXAMPLE 168

4-[(2-chloro-[1,1'-biphenyl]-5-yl) methoxy]benzenepropanoic acid

The title compound Was obtained from methyl 4-[(2-chloro-[1,1'-biphenyl]-5-yl)methoxy]benzenepropanoate by a method similar to that of Reference Example 4. yield 20%.
melting point: 116-117° C. (recrystallized from ethyl acetate-hexane).
$^1$H NMR (CDCl$_3$) δ 2.65 (2H, t, J=7.9 Hz), 2.91 (2H, t, J=7.9 Hz), 5.04 (2H, s), 6.90 (2H, d, J=8.6 Hz), 7.13 (2H, d, J=8.6 Hz), 7.32-7.49 (8H, m).

EXAMPLE 169 ethyl 4-([1,1'-biphenyl]-3-ylmethoxy)-2-methoxybenzenepropanoate

The title compound was obtained from ethyl 4-hydroxy-2-methoxybenzenepropanoate and [1,1'-biphenyl]-3-methanol by a method similar to that of Reference Example 1. yield 86%, oil.
$^1$H NMR (CDCl$_3$) δ 1.23 (3H, t, J=7.2 Hz), 2.56 (2H, t, J=8.1 Hz), 2.87 (2H, t, J=8.1 Hz), 3.79 (3H, s), 4.12 (2H, q, J=7.2 Hz), 5.09 (2H, s), 6.48-6.54 (2H, m), 7.05 (1H, d, J=8.2 Hz), 7.30-7.49 (5H, m), 7.54-7.66 (4H, m).

EXAMPLE 170

4-([1,1'-biphenyl]-3-ylmethoxy)-2-methoxybenzenepropanoic acid

The title compound was obtained from ethyl 4-([1,1'-biphenyl]-3-ylmethoxy)-2-methoxybenzenepropanoate by a method similar to that of Reference Example 4. yield 71%.
melting point: 71-73° C. (recrystallized from diisopropyl ether-hexane).
$^1$H NMR (CDCl$_3$) δ 2.63 (2H, t, J=7.9 Hz), 2.88 (2H, t, J=7.9 Hz), 3.79 (3H, s), 5.09 (2H, s), 6.49-6.55 (2H, m), 7.06 (1H, d, J=8.2 Hz), 7.33-7.49 (5H, m), 7.55-7.66 (4H, m).

EXAMPLE 171 methyl 4-[[3-[[methyl(4-phenyl-2-thiazolyl) amino]methyl]phenyl]methoxy]benzenepropanoate The title compound was obtained from methyl 4-hydroxybenzenepropanoate and 3-[[methyl(4-phenyl-1,3-thiazol-2-yl)amino]methyl]benzenemethanol by a method similar to that of Reference Example 1. yield 85%, oil.
$^1$H NMR (CDCl$_3$) δ 2.59 (2H, t, J=8.1 Hz), 2.89 (2H, t, J=8.1 Hz), 3.07 (3H, s), 3.66 (3H, s), 4.79 (2H, s), 5.02 (2H, s), 6.73 (1H, s), 6.88 (2H, d, J=8.7 Hz), 7.10 (2H, d, J=8.7 Hz), 7.24-7.40 (7H, m), 7.85-7.88 (2H, m).

EXAMPLE 172

4-[[3-[[methyl(4-phenyl-2-thiazolyl) amino]methyl]phenyl]methoxy]benzenepropanoic acid The title compound was obtained from methyl 4-[[3-[[methyl (4-phenyl-2-thiazolyl) amino]methyl]phenyl]methoxy] benzenepropanoate by a method similar to that of Reference Example 4. yield 65%.
melting point: 107.0-107.5° C. (recrystallized from ethyl acetate-hexane).
$^1$H NMR (CDCl$_3$) δ 2.63 (2H, t, J=7.8 Hz), 2.89 (2H, t, J=7.8 Hz), 3.06 (3H, s), 4.78 (2H, s), 5.03 (2H, s), 6.72 (1H, s), 6.88 (2H, d, J=8.6 Hz), 7.10 (2H, d, J=8.6 Hz), 7.24-7.39, (7H, m), 7.88-7.84 (2H, m).

EXAMPLE 173 ethyl 2-methoxy-4-[(3-phenoxyphenyl) methoxy]benzenepropanoate

The title compound was obtained from ethyl 2-methoxy-4-hydroxybenzenepropanoate and 3-phenoxybenzenemethanol by a method similar to that of Reference Example 1. yield 75%, oil.
$^1$H NMR (CDCl$_3$) δ 1.23 (3H, t, J=7.1 Hz), 2.55 (2H, t, J=8.1 Hz), 2.86 (2H, t, J=8.1 Hz), 3.78 (3H, s), 4.12 (2H, q, J=7.1 Hz), 5.00 (2H, s), 6.44 (1H, dd, J=8.2 Hz, 2.4 Hz), 6.49

(1H, d, J=2.4 Hz), 6.95 (1H, dd, J=7.8 Hz, 1.8 Hz), 6.99-7.04 (3H, m), 7.09-7.17 (3H, m), 7.30-7.34 (3H, m).

EXAMPLE 174

2-methoxy-4-[(3-phenoxyphenyl)methoxy]benzenepropanoic acid

The title compound was obtained from ethyl 2-methoxy-4-[(3-phenoxyphenyl)methoxy]benzenepropanoate by a method similar to that of Reference Example 4. yield 65%.

melting point: 77.0-77.5° C. (recrystallized from diisopropyl ether-hexane).

$^1$H NMR (CDCl$_3$) δ 2.62 (2H, t, J=8.0 Hz), 2.87 (2H, t, J=8.0 Hz), 3.77 (3H, s), 5.00 (2H, s), 6.44 (1H, dd, J=5.9 Hz, 2.4 Hz), 6.50 (1H, d, J=2.4 Hz), 6.93-7.17 (7H, m), 7.31-7.36 (3H, m).

EXAMPLE 175 methyl 4-([1,1'-biphenyl]-3-ylmethoxy)-2-chlorobenzenepropanoate

The title compound was obtained from methyl 2-chloro-4-hydroxybenzenepropanoate and [1,1'-biphenyl]-3-methanol by a method similar to that of Reference Example 1. yield 85%, oil.

$^1$H NMR (CDCl$_3$) δ 2.62 (2H, t, J=8.0 Hz), 3.00 (2H, t, J=8.0 Hz), 3.68 (3H, s), 5.09 (2H, s), 6.84 (1H, dd, J=8.5 Hz, 2.6 Hz), 7.02 (1H, d, J=2.6 Hz), 7.16 (1H, d, J=8.5 Hz), 7.33-7.49 (5H, m), 7.55-7.64 (4H, m).

EXAMPLE 176

4-([1,1'-biphenyl]-3-ylmethoxy)-2-chlorobenzenepropanoic acid

The title compound was obtained from methyl 4-([1,1'-biphenyl]-3-ylmethoxy)-2-chlorobenzenepropanoate by a method similar to that of Reference Example 4. yield 46%.

melting point: 84.0-84.5° C. (recrystallized from diisopropyl ether-hexane).

$^1$H NMR (CDCl$_3$) δ 2.67 (2H, t, J=7.8 Hz), 3.01 (2H, t, J=7.8 Hz), 5.09 (2H, s), 6.80-6.86 (1H, m), 7.03 (1H, d, J=2.1 Hz), 7.17 (1H, d, J=8.5 Hz), 7.36-7.46 (5H, m), 7.55-7.64 (4H, m).

EXAMPLE 177 methyl 4-[[2'-(1-methylethoxy)-[1,1'-biphenyl]-3-yl]methoxy]benzenepropanoate

The title compound was obtained from 2-(1-methylethoxy)phenylboronic acid by a method similar to that of Example 22. yield 85%, oil.

$^1$H NMR (CDCl$_3$) δ 1.22-1.28 (6H, m), 2.60 (2H, t, J=8.1 Hz), 2.89 (2H, t, J=8.1 Hz), 3.60 (3H, s), 4.40-4.48 (1H, m), 5.07 (2H, s), 6.92 (2H, d, J=8.6 Hz), 6.97-7.03 (2H, m), 7.11 (2H, d, J=8.6 Hz), 7.26-7.43 (4H, m), 7.51 (1H, d, J=7.2 Hz), 7.64 (1H, s).

EXAMPLE 178

4-[[2'-(1-methylethoxy)-[1,1'-biphenyl]-3-yl]methoxy]benzenepropanoic acid

The title compound was obtained from methyl 4-[[2'-(1-methylethoxy)-[1,1'-biphenyl]-3-yl]methoxy]benzenepropanoate by a method similar to that of Reference Example 4. yield 49%.

melting point: 111.0-111.5° C. (recrystallized from ethyl acetate-hexane).

$^1$H NMR (CDCl$_3$) δ 1.23 (6H, d, J=6.0 Hz), 2.65 (2H, t, J=8.1 Hz), 2.91 (2H, t, J=8.1 Hz), 4.40-4.48 (1H, m), 5.08 (2H, s), 6.91-7.04 (4H, m), 7.13 (2H, d, J=8.6 Hz), 7.25-7.43 (4H, m), 7.51 (1H, dt, J=7.1 Hz, 1.7 Hz), 7.64 (1H, s).

EXAMPLE 179 methyl 4-[[2'-(trifluoromethyl)-[1,1'-biphenyl]-3-yl]methoxy]benzenepropanoate

The title compound was obtained from 2-(trifluoromethyl)phenylboronic acid by a method similar to that of Example 22. yield 75%, oil.

$^1$H NMR (CDCl$_3$) δ 2.60 (2H, t, J=8.1 Hz), 2.89 (2H, t, J=8.1 Hz), 3.66 (3H, s), 5.08 (2H, s), 6.90 (2H, d, J=8.6 Hz), 7.11 (2H, d, J=8.6 Hz), 7.27-7.59 (7H, m), 7.75 (1H, d, J=7.6 Hz).

EXAMPLE 180

4-[[2'-(trifluoromethyl)-[1,1'-biphenyl]-3-yl]methoxy]benzenepropanoic acid

The title compound was obtained from methyl 4-[[2'-(trifluoromethyl)-[1,1'-biphenyl]-3-yl]methoxy]benzenepropanoate by a method similar to that of Reference Example 4. yield 48%.

melting point: 143-144° C. (recrystallized from ethyl acetate-hexane).

$^1$H NMR (CDCl$_3$) δ 2.65 (2H, t, J=8.0 Hz), 2.90 (2H, t, J=8.0 Hz), 5.08 (2H, s), 6.91 (2H, d, J=8.6 Hz), 7.13 (2H, d, J=8.6 Hz), 7.26-7.58 (7H, m), 7.75 (1H, d, J=7.6 Hz).

EXAMPLE 181 methyl 4-[(2'-ethyl-[1,1'-biphenyl]-3-yl)methoxy]benzenepropanoate

The title compound was obtained from 2-ethylphenylboronic acid by a method similar to that of Example 22. yield 80%, oil.

$^1$H NMR (CDCl$_3$) δ 1.08 (3H, t, J=7.5 Hz), 2.53-2.62 (4H, m), 2.89 (2H, t, J=8.0 Hz), 3.66 (3H, s), 5.08 (2H, s), 6.91 (2H, d, J=8.5 Hz), 7.11 (2H, d, J=8.5 Hz), 7.21-7.31 (5H, m), 7.37-7.42 (3H, m).

EXAMPLE 182

4-[(2'-ethyl-[1,1'-biphenyl]-3-yl)methoxy]benzenepropanoic acid

The title compound was obtained from methyl 4-[(2'-ethyl-[1,1'-biphenyl]-3-yl)methoxy]benzenepropanoate by a method similar to that of Reference Example 4. yield 51%.

melting point: 132.0-132.5° C. (recrystallized from ethyl acetate-hexane).

$^1$H NMR (CDCl$_3$) δ 1.07 (3H, t, J=7.5 Hz), 2.57 (2H, q, J=7.5 Hz), 2.65 (2H, t, J=7.9 Hz), 2.90 (2H, t, J=7.9 Hz), 5.09

(2H, s), 6.91 (2H, d, J=8.6 Hz), 7.12 (2H, d, J=8.6 Hz), 7.18-7.32 (5H, m), 7.37-7.45 (3H, m).

EXAMPLE 183 methyl 4-[(2',3'-dimethyl-[1,1'-biphenyl]-3-yl) methoxy]benzenepropanoate

The title compound was obtained from 2,3-dimethylphenylboronic acid by a method similar to that of Example 22. yield 93%, oil.
$^1$H NMR (CDCl$_3$) δ 2.13 (3H, s), 2.34 (3H, s), 2.60 (2H, t, J=8.0 Hz), 2.89 (2H, t, J=8.0 Hz), 3.66 (3H, s), 5.08 (2H, s), 6.90-6.92 (2H, m), 7.09-7.16 (5H, m), 7.25-7.26 (1H, m), 7.36-7.42 (3H, m).

EXAMPLE 184

4-[(2',3'-dimethyl-[1,1'-biphenyl]-3-yl) methoxy]benzenepropanoic acid

The title compound was obtained from methyl 4-[(2',3'-dimethyl-[1,1'-biphenyl]-3-yl)methoxy]benzenepropanoate by a method similar to that of Reference Example 4. yield 47%.
melting point: 146-147° C. (recrystallized from ethyl acetate-hexane).
$^1$H NMR (CDCl$_3$) δ 2.13 (3H, s), 2.33 (3H, s), 2.65 (2H, t, J=8.0 Hz), 2.90 (2H, t, J=8.0 Hz), 5.08 (2H, s), 6.90-6.93 (2H, m), 7.09-7.16 (5H, m), 7.24-7.27 (1H, m), 7.36-7.42 (3H, m).

EXAMPLE 185 methyl 4-[[4-[[(4-phenyl-2-thiazolyl) propylamino]methyl]phenyl]methoxy]benzenepropanoate The title compound was obtained from methyl 4-hydroxybenzenepropanoate and 4-[[(4-phenyl-2-thiazolyl) propylamino]methyl]benzenemethanol by a method similar to that of Reference Example 1. yield 90%, oil.
$^1$H NMR (CDCl$_3$) δ 0.93 (3H, t, J=7.4 Hz), 1.65-1.75 (2H, m), 2.59 (2H, t, J=8.0 Hz), 2.89 (2H, t, J=8.0 Hz), 3.40 (2H, t, J=7.7 Hz), 3.66 (3H, s), 4.79 (2H, s), 5.01 (2H, s), 6.70 (1H, s), 6.89 (2H, d, J=8.6 Hz), 7.11 (2H, d, J=8.6 Hz), 7.24-7.28 (1H, m), 7.34-7.40 (6H, m), 7.84-7.87 (2H, m).

EXAMPLE 186

4-[[4-[[(4-phenyl-2-thiazolyl) propylamino]methyl]phenyl]methoxy]benzenepropanoic acid The title compound was obtained from methyl 4-[[4-[[(4-phenyl-2-thiazolyl)propylamino]methyl]phenyl]methoxy] benzenepropanoate by a method similar to that of Reference Example 4. yield 50%.
melting point: 110-111° C. (recrystallized from ethyl acetate-hexane).
$^1$H NMR (CDCl$_3$) δ 0.93 (3H, t, J=7.4 Hz), 1.65-1.77 (2H, m), 2.64 (2H, t, J=7.3 Hz), 2.90 (2H, t, J=7.3 Hz), 3.40 (2H, t, J=9.2 Hz), 4.79 (2H, s), 5.01 (2H, s), 6.70 (1H, s), 6.89 (2H, d, J=8.4 Hz), 7.12 (2H, d, J=8.4 Hz), 7.24-7.37 (7H, m), 7.84-7.87 (2H, m).

EXAMPLE 187 methyl 4-[[4-[[(4-phenyl-2-thiazolyl) thio]methyl]phenyl]methoxy]benzenepropanoate The title compound was obtained from methyl 4-hydroxybenzenepropanoate and 4-[[(4-phenyl-2-thiazolyl) thio]methyl]benzenemethanol by a method similar to that of Reference Example 1. yield 30%, oil.
$^1$H NMR (CDCl$_3$) δ 2.59 (2H, t, J=8.1 Hz), 2.89 (2H, t, J=8.1 Hz), 3.66 (3H, s), 4.52 (2H, s), 5.01 (2H, s), 6.88 (2H, d, J=8.6 Hz), 7.11 (2H, d, J=8.6 Hz), 7.31-7.46 (8H, m), 7.89-7.92 (2H, m).

EXAMPLE 188

4-[[4-[[(4-phenyl-2-thiazolyl) thio]methyl]phenyl]methoxy]benzenepropanoic acid

The title compound was obtained from methyl 4-[[4-[[(4-phenyl-2-thiazolyl) thio]methyl]phenyl]methoxy]benzenepropanoate by a method similar to that of Reference Example 4. yield 38%.
melting point: 156.0-156.5° C. (recrystallized from tetrahydrofuran-hexane).
$^1$H NMR (DMSO-d$_6$) δ 2.38 (2H, t, J=7.7 Hz), 2.72 (2H, t, J=7.7 Hz), 4.56 (2H, s), 5.02 (2H, s), 6.87 (2H, d, J=8.5 Hz), 7.11 (2H, d, J=8.5 Hz), 7.33-7.49 (7H, m), 7.94 (2H, d, J=7.3 Hz), 8.02 (1H, s).

EXAMPLE 189 methyl 4-[[3-(1-naphthyl) phenyl]methoxy]benzenepropanoate

The title compound was obtained from 1-naphthaleneboronic acid by a method similar to that of Example 22. yield 93%, oil.
$^1$H NMR (CDCl$_3$) δ 2.60 (2H, t, J=8.0 Hz), 2.90 (2H, t, J=8.0 Hz), 3.66 (3H, s), 5.14 (2H, s), 6.95 (2H, t, J=8.6 Hz), 7.13 (2H, t, J=8.6 Hz), 7.43-7.54 (4H, m), 7.68 (1H, dt, J=7.5 Hz, 1.5 Hz), 7.75 (1H, dd, J=8.5 Hz, 1.8 Hz), 7.78 (1H, m), 7.85-7.93 (3H, m), 8.05 (1H, m).

EXAMPLE 190

4-[[3-(1-naphthyl)phenyl]methoxy]benzenepropanoic acid

The title compound was obtained from methyl 4-[[3-(1-naphthyl) phenyl]methoxy]benzenepropanoate by a method similar to that of Reference Example 4. yield 93%.
melting point: 134-135° C. (recrystallized from ethyl acetate-hexane).
$^1$H NMR (CDCl$_3$) δ 2.65 (2H, t, J=8.0 Hz), 2.91 (2H, t, J=8.0 Hz), 5.13 (2H, s), 6.95 (2H, t, J=8.6 Hz), 7.14 (2H, t, J=8.6 Hz), 7.42-7.54 (4H, m), 7.66-7.78 (3H, m), 7.84-7.93 (3H, m), 8.05 (1H, m).

EXAMPLE 191 methyl 4-[[2'-(1-methylethyl)-[1,1'-biphenyl]-3-yl] methoxy]benzenepropanoate

The title compound was obtained from 2-iodocumene by a method similar to that of Reference Example 61. yield 12%, oil.

¹H NMR (CDCl₃) δ 1.13 (6H, d, J=6.9 Hz), 2.59 (2H, t, J=7.4 Hz), 2.89 (2H, t, J=7.4 Hz), 2.97-3.06 (1H, m), 3.66 (3H, s), 5.09 (2H, s), 6.89-6.92 (2H, m), 7.10-7.26 (5H, m), 7.35-7.42 (5H, m).

EXAMPLE 192

4-[[2'-(1-methylethyl)-[1,1'-biphenyl]-3-yl]methoxy]benzenepropanoic acid

The title compound was obtained from methyl 4-[[2'-(1-methylethyl)-[1,1'-biphenyl]-3-yl]methoxy]benzenepropanoate by a method similar to that of Reference Example 4. yield 27%.
melting point: 120-121° C. (recrystallized from diethyl ether-hexane).
¹H NMR (CDCl₃) δ 1.13 (6H, d, J=6.9 Hz), 2.65 (2H, t, J=8.0 Hz), 2.91 (2H, t, J=8.0 Hz), 2.97-3.06 (1H, m), 5.09 (2H, s), 6.91 (2H, d, J=8.6 Hz), 7.11-7.26 (5H, m), 7.31-7.45 (5H, m).

EXAMPLE 193 methyl 4-[[4-[[methyl(5-methyl-4-phenyl-2-thiazolyl)amino]methyl]phenyl]methoxy]benzenepropanoate The title compound was obtained from methyl 4-hydroxybenzenepropanoate and 4-[[methyl(5-methyl-4-phenyl-2-thiazolyl) amino]methyl]benzenemethanol by a method similar to that of Reference Example 1. yield 86%, oil.
¹H NMR (CDCl₃) δ 2.42 (3H, s), 2.59 (2H, t, J=8.0 Hz), 2.89 (2H, t, J=8.0 Hz), 3.02 (3H, s), 3.66 (3H, s), 4.69 (2H, s), 5.02 (2H, s), 6.89 (2H, d, J=8.6 Hz), 7.11 (2H, d, J=8.6 Hz), 7.25-7.41 (7H, m), 7.63-7.66 (2H, m).

EXAMPLE 194

4-[[4-[[methyl(5-methyl-4-phenyl-2-thiazolyl)amino]methyl]phenyl]methoxy]benzenepropanoic acid The title compound was obtained from methyl 4-[[4-[[methyl (5-methyl-4-phenyl-2-thiazolyl) amino]methyl]phenyl]methoxy]benzenepropanoate by a method similar to that of Reference Example 4. yield 52%.
melting point: 113-114° C. (recrystallized from ethyl acetate-hexane).
¹H NMR (CDCl₃) δ 2.41 (3H, s), 2.63 (2H, t, J=7.9 Hz), 2.89 (2H, t, J=7.9 Hz), 3.02 (3H, s), 4.68 (2H, s), 5.01 (2H, s), 6.89 (2H, d, J=8.6 Hz), 7.12 (2H, d, J=8.6 Hz), 7.25-7.41 (7H, m), 7.63-7.66 (2H, m).

EXAMPLE 195 methyl 4-[[4-[(methylphenylamino)methyl]phenyl]methoxy]benzenepropanoate

N-Methylaniline (57 mg, 0.53 mmol) was dissolved in N,N-dimethylformamide (5 mL), and 60% sodium hydride (21 mg, 0.53 mmol) was added under ice-cooling. The reaction mixture was stirred for 30 min., and methyl 4-[[4-(bromomethyl) phenyl]methoxy]benzenepropanoate (0.15 g, 0.41 mmol) was added. The mixture was stirred at room temperature for 3 hrs, water was added to the reaction mixture and the mixture was extracted with ethyl acetate. The extract was washed with water, dried and concentrated. The residue was purified by silica gel column chromatography (ethyl acetate/hexane=18:1) to give the title compound (74 mg, yield 45%) as a yellow powder.
¹H NMR (CDCl₃) δ 2.59 (2H, t, J=8.1 Hz), 2.89 (2H, t, J=8.1 Hz), 3.02 (3H, s), 3.66 (3H, s), 4.54 (2H, s), 5.00 (2H, s), 6.69-6.76 (2H, m), 6.89 (2H, d, J=8.6 Hz), 7.11 (2H, d, J=8.6 Hz), 7.20-7.26 (5H, m), 7.37 (2H, d, J=8.1 Hz).

EXAMPLE 196

4-[[4-[(methylphenylamino)methyl]phenyl]methoxy]benzenepropanoic acid

The title compound was obtained from methyl 4-[[4-[(methylphenylamino) methyl]phenyl]methoxy]benzenepropanoate by a method similar to that of Reference Example 4. yield 45%.
melting point: 122-124° C. (recrystallized from ethyl acetate-hexane).
¹H NMR (CDCl₃) δ 2.65 (2H, t, J=8.0 Hz), 2.90 (2H, t, J=8.0 Hz), 3.01 (3H, s), 4.53 (2H, s), 5.00 (2H, s), 6.69-6.76 (3H, m), 6.90 (2H, d, J=8.6 Hz), 7.12 (2H, d, J=8.6 Hz), 7.18-7.26 (4H, m), 7.37 (2H, d, J=8.1 Hz).

EXAMPLE 197 methyl 4-[[3'-(hydroxymethyl)-[1,1'-biphenyl]-3-yl]methoxy]benzenepropanoate

A solution of methyl 4-[(3'-formyl-[1,1'-biphenyl]-3-yl)methoxy]benzenepropanoate (0.80 g, 2.1 mmol) in methanol (5 mL) and tetrahydrofuran (2 mL) was ice-cooled, and sodium borohydride (81 mg, 2.1 mmol) was added. The mixture was stirred under ice-cooling for 30 min. The reaction mixture was added to 0.2N hydrochloric acid (11 mL), and the mixture was extracted with ethyl acetate. The extract was washed with water and concentrated under reduced pressure to give the title compound 0.80 g (quantitative). oil.
¹H NMR (CDCl₃) δ 1.81 (1H, br s), 2.60 (2H, t, J=7.5 Hz), 2.90 (2H, t, J=7.5 Hz), 3.66 (3H, s), 4.77 (2H, d, J=4.6 Hz), 5.10 (2H, s), 6.92 (2H, d, J=8.5 Hz), 7.12 (2H, d, J=8.5 Hz), 7.34-7.48 (4H, m), 7.52-7.66 (4H, m).

EXAMPLE 198

4-[[3'-(hydroxymethyl)-[1,1'-biphenyl]-3-yl]methoxy]benzenepropanoic acid

The title compound was obtained from methyl 4-[[3'-(hydroxymethyl)-[1,1'-biphenyl]-3-yl]methoxy]benzenepropanoate by a method similar to that of Reference Example 4. yield 88%.
melting point: 99-100° C. (recrystallized from ethyl acetate-hexane).
¹H NMR (CDCl₃) δ 2.64 (2H, t, J=7.6 Hz), 2.90 (2H, t, J=7.6 Hz), 4.76 (2H, s), 5.10 (2H, s), 6.92 (2H, d, J=8.5 Hz), 7.13 (2H, d, J=8.5 Hz), 7.33-7.47 (4H, m), 7.51-7.58 (3H, m), 7.64 (1H, s).

EXAMPLE 199

4-[[3'-[[(3-carboxy-1-oxopropyl)amino]methyl]-[1,1'-biphenyl]-3-yl]methoxy]benzenepropanoic acid Methyl 4-[[3'-[(2,5-dioxo-1-pyrrolidinyl)methyl]-[1,1'-biphenyl]-3-yl]methoxy]benzenepropanoate was obtained from methyl 4-[[3'-(hydroxymethyl)-[1,1'-biphenyl]-3-yl]

methoxy]benzenepropanoate and 2,5-pyrrolidinedione by a method similar to that of Reference Example 1. The title compound was obtained from methyl 4-[[3'-[(2,5-dioxo-1-pyrrolidinyl) methyl]-[1,1'-biphenyl]-3-yl]methoxy]benzenepropanoate by a method similar to that of Reference Example 4. yield from methyl 4-[[3'-(hydroxymethyl)-[1,1'-biphenyl]-3-yl]methoxy]benzenepropanoate 62%.

melting point: 185-188° C. (recrystallized from ethyl acetate).

$^1$H NMR (DMSO-d$_6$) δ 2.41-2.51 (6H, m), 2.75 (2H, t, J=7.5 Hz), 4.34 (2H, d, J=5.8 Hz), 5.14 (2H, s), 6.94 (2H, d, J=8.5 Hz), 7.14 (2H, d, J=8.5 Hz), 7.26 (1H, d, J=7.5 Hz), 7.38-7.62 (6H, m), 7.72 (1H, s), 8.41 (1H, t, J=5.8 Hz), 12.06 (2H, br s).

EXAMPLE 200

3'-[[4-[2-(methoxycarbonyl)ethyl]phenoxy]methyl]-[1,1'-biphenyl]-3-carboxylic acid To a solution of methyl 4-[(3'-formyl-[1,1'-biphenyl]-3-yl)methoxy]benzenepropanoate (0.48 g, 1.3 mmol) in tetrahydrofuran (5 mL) and water (2 mL) was added sulfamic acid (0.15 g, 1.3 mmol), and a solution of sodium chlorite (0.17 g, 1.5 mmol) in water (1.5 mL) was added. The mixture was stirred at room temperature for 15 hrs., and water was added. The mixture was extracted with ethyl acetate. The extract was washed with water and concentrated under reduced pressure to give the title compound 0.50 g (quantitative).

melting point: 180-185° C. (recrystallized from ethyl acetate-hexane).

$^1$H NMR (CDCl$_3$) δ 2.60 (2H, t, J=7.5 Hz), 2.90 (2H, t, J=7.5 Hz), 3.66 (3H, s), 5.10 (2H, s), 6.93 (2H, d, J=8.5 Hz), 7.12 (2H, d, J=8.5 Hz), 7.42-7.54 (3H, m), 7.59 (1H, d, J=7.0 Hz), 7.69 (1H, s), 7.79 (1H, d, J=7.8 Hz), 8.04 (1H, d, J=7.8 Hz), 8.32 (1H, s).

EXAMPLE 201

3'-[[4-(2-carboxyethyl)phenoxy]methyl]-[1,1'-biphenyl]-3-carboxylic acid

The title compound was obtained from 3'-[[4-[2-(methoxycarbonyl) ethyl]phenoxy]methyl]-[1,1'-biphenyl]-3-carboxylic acid by a method similar to that of Reference Example 4. yield 75%.

melting point: 178-181° C. (recrystallized from ethyl acetate-hexane).

$^1$H NMR (DMSO-d$_6$) δ 2.50 (2H, t, J=7.7 Hz), 2.75 (2H, t, J=7.7 Hz), 5.17 (2H, s), 6.95 (2H, d, J=8.5 Hz), 7.14 (2H, d, J=8.5 Hz), 7.46-7.54 (2H, m), 7.58-7.68 (2H, m), 7.77 (1H, s), 7.92-8.00 (2H, m), 8.20 (1H, s), 12.63 (2H, br s).

EXAMPLE 202

Setting of Screening Method for GPR40 Agonist and GPR40 Antagonist and Criterion to Select Agonist Candidates (1) Setting of Screening Method for GPR40 Agonist and GPR40 Antagonist with Changes in Intracellular Calcium Concentration as an Indicator To set the system for searching a GPR40 agonist and a GPR40 antagonist, an assay system was set using the compound of the present invention.

The CHO cell line (CHO-hGPR40 No. 104), which was made to express human GPR40 prepared by a method known per se, using human GPR40 expression vector prepared in Reference Example 1 was diluted to contain 3×10$^4$ cells/100 μl, dispensed to a black walled 96-well plate (Costar) at 100 μl per well, incubated overnight in a CO$_2$ incubator. Changes in the intracellular calcium concentration was measured using FLIPR (Molecular Device). The method is described in the following.

Fluo-3AM (DOJIN) (50 μg) was dissolved in 21 μl DMSO (DOJIN), and an equal amount of 20% pluronic acid (Molecular Probes) was added and mixed, and the mixture was added to 10.6 ml of an assay buffer [prepared by adding 20 ml of 1M HEPES (pH 7.4) (DOJIN) to HBSS (Invitrogen), and adding a mixed solution (10 ml) obtained by dissolving probenecid (Sigma) (710 mg) in 1N NaOH (5 ml) and adding and mixing with the above-mentioned HBSS/HEPES solution (5 ml)] supplemented with 105 μl of fetal calf serum to give a fluorescence dye solution. The medium in the cell plate was removed, a fluorescence dye solution was immediately dispensed at 100 μl per well, and incubated in a CO$_2$ incubator at 37° C. for 1 hr to incorporate fluorescence dye into the cell. The incubated cells were washed with the above-mentioned assay buffer. The compound of the present invention to be added to the cell was diluted with an assay buffer to each concentration and dispensed to a plate. For antagonist measurement, 12 μM γ-linolenic acid solution (final concentration during reaction 3 μM) was dispensed to the plate, and simultaneously set on FLIPR. After the above-mentioned pretreatment, variation in the intracellular calcium concentration after addition of the compound of the present invention was measured by FLIPR, and the agonistic effect, subsequently an antagonistic effect upon addition of linolenic acid were examined. Since the compound of the present invention is an agonist, evaluation of the antagonist is not established by an experiment using the compound of the present invention, but when a compound having solely an antagonistic effect is added, the activity to suppress reaction of γ-linolenic acid to be added later can be observed. EC$_{50}$ value was calculated from a dose response curve based on the changes in the fluorescence intensity value at 30 or 40 sec after the start of the reaction.

(2) Criterion to Select Agonist Candidates from the Results of FLIPR Assay

A test compound used for selecting an agonist candidate was diluted in advance with DMSO (Wako) to a concentration of 10 mM, and diluted with the above-mentioned assay buffer when used for the measurement. Using the test compound and by a method similar to the above-mentioned method, the fluorescence intensity values in CHO cell line (CHO-hGPR40 No. 104), which was made to express human GPR40 prepared by a method known per se, using human GPR40 expression vector prepared in Reference Example 1, CHO cell line (CHO-H1), which was made to express human histamine H1 receptor prepared by a method known per se, using human histamine H1 receptor expression vector, and CHO cell line of Mock were measured at 30 or 40 sec after the start of the reaction. Moreover, the relative value when fluorescence strength of 30 μM γ-linolenic acid to CHO-hGPR40 was 100% was calculated, and a test compound showing a value of not less than 50 or 100% relative to CHO-hGPR40 and not more than 25% relative to both the human histamine H1 receptor and CHO cell line of Mock were selected as human GPR40 specific agonist candidates.

FORMULATION EXAMPLE 1

| | |
|---|---|
| (1) Compound obtained in Example 1 | 10.0 g |
| (2) Lactose | 60.0 g |
| (3) Cornstarch | 35.0 g |
| (4) gelatin | 3.0 g |
| (5) Magnesium stearate | 2.0 g |

A mixture of compound (10.0 g) obtained in Example 1, lactose (60.0 g) and cornstarch (35.0 g) was granulated with an aqueous solution (30 mL) of 10 wt % gelatin (3.0 g as gelatin) by passing through a 1 mm mesh sieve, dried at 40° C. and passing through the sieve again. The obtained granule was mixed with magnesium stearate (2.0 g) and the mixture was compressed. The obtained core tablets were coated with glycocalyx of an aqueous suspension of saccharose, titanium dioxide, talc and gum arabic. The tablets after coating were polished with bee wax to give 1000 coated tablets.

FORMULATION EXAMPLE 2

| | |
|---|---|
| (1) Compound obtained in Example 1 | 10.0 g |
| (2) lactose | 70.0 g |
| (3) cornstarch | 50.0 g |
| (4) soluble starch | 7.0 g |
| (5) magnesium stearate | 3.0 g |

The compound (10.0 g) obtained in Example 1 and magnesium stearate (3.0 g) were granulated with an aqueous solution (70 mL) of soluble starch (7.0 g as soluble starch), dried, and mixed with lactose (70.0 g) and cornstarch (50.0 g). The mixture was compressed to give 1000 tablets.

EXPERIMENTAL EXAMPLE 1

Confirmation of Reactivity of Fatty Acid to Human-Derived GPR40

Unless specifically indicated, CHO-K1 cell line was cultured using Ham's F-12 medium (Invitrogen) containing 10% fetal calf serum (Invitrogen). The day before transfection, $4.5 \times 10^5$ per 10 cm$^2$ of cells were seeded, and incubated at 37° C. for not less than 15 hrs in a CO$_2$ incubator adjusted to 5% CO$_2$ concentration. The transfection was performed using a lipofectamine reagent (Invitrogen) and according to the reagent attached method. When a 6-well plate was used for a culture plate, transfection was performed in the following manner. First two 1.5 ml volume tubes were prepared, and 100 µl of Opti-MEM-I medium (Invitrogen) was dispensed. Then, 1 g of an expression vector was added to one tube and 6 µl of a lipofectamine reagent was added to the other tube. They were mixed and stood still at room temperature for 20 min. A mixed solution for transfection containing this solution and Opti-MEM-I medium (800 µl) was added to CHO-K1 cell previously washed with Opti-MEM-I medium, and incubated in a CO$_2$ incubator for 6 hrs. The incubated cells were rinsed with PBS (Invitrogen), detached with 0.05% trypsin-EDTA solution (Invitrogen), recovered by centrifugation. The obtained cells were counted, diluted such that $5 \times 10^4$ cells were contained per 200 µl of the medium, dispensed to black walled 96-well plate (Costar) at 200 µl per well, incubated overnight in a CO$_2$ incubator. Various test samples were added to CHO-K1 cells transiently expressing the receptor by the above-mentioned transfection step, and changes in the intracellular calcium concentration then was measured using FLIPR (Molecular Device). For measurement of changes in intracellular calcium concentration by FLIPR, the following pretreatment was applied. First, an assay buffer for adding fluorescence dye Fluo-3AM (DOJIN) to the cell, or washing the cell immediately before FLIPR assay was prepared. To a solution (hereinafter HBSS/HEPES solution) obtained by adding 20 ml of 1M HEPES (pH 7.4) (DOJIN) to 1000 ml of HBSS (Invitrogen) was added a solution (10 ml) obtained by dissolving probenecid (710 mg, Sigma) in 1N NaOH (5 ml) and adding and mixing with HBSS/HEPES solution (5 ml) and the obtained solution was used as an assay buffer. Then, Fluo-3AM (50 µg) was dissolved in 21 µl of DMSO (DOJIN), and an equal amount of 20% pluronic acid (Molecular Probes) was added. The mixture was added to an assay buffer (10.6 ml) supplemented with 105 µl of fetal calf serum to give a fluorescence dye solution. The medium of the CHO-KL cell after transfection treatment was removed, a fluorescence dye solution was immediately dispensed at 100 µl per well and incubated in a CO$_2$ incubator for 1 hr to incorporate the fluorescence dye into the cell. The incubated cells were washed with the above-mentioned assay buffer and set on FLIPR. The test sample to be added to receptor expressing CHO-KL cell was prepared using the assay buffer and simultaneously set on FLIPR. After the above-mentioned pretreatment, changes in the intracellular calcium concentration after addition of various test samples were measured by FLIPR. As a result, it was found that CHO-KL cell that expresses the GPR40 receptor specifically responds (increase in intracellular calcium concentration) when farnesoic acid, 5.8.11-eicosatriynoic acid, 5.8.11.14-eicosatetraynoic acid, oleic acid, linoleic acid, linolenic acid, arachidonic acid, eicosapentaenoic acid (EPA), eicosadienoic acid, eicosatrienoic acid, docosahexaenoic acid (DHA), docosatrienoic acid, adrenic acid, lauric acid and the like are added at $10^{-5}$ M-$10^{-6}$ M. CHO-K1 cell into which only the control expression vector alone was introduced did not show such response. In other words, it was clarified that an endogenous ligand of GPR40 was fatty acid.

EXPERIMENTAL EXAMPLE 2

Expression Distribution (1) Cell and Medium

NIH-3T3 and B104 cells were purchased from the ATCC. As mouse pancreatic β cell line, MIN6 described in a literature (Jun-ichi Miyazaki et al. *Endocrinology*, Vol. 127, No. 1, p 126-132) was used. Respective cells were incubated in DMEM medium (Invitrogen) containing 10% FCS to preconfluent.

(2) Extraction of RNA and cDNA Synthesis

The cDNA used for the expression distribution in human and mouse tissues was obtained by reverse transcription reaction from polyA+RNA (1 µg, Clontech) derived from various tissues of human and mouse using random primer. Using reverse transcriptase SuperScriptII (GIBCO BRL), the reaction was carried out according to the attached protocol and ethanol precipitation was performed and the precipitate was dissolved in TE (100 µl).

As to cDNA from the mouse cell, the cells were detached with Trypsin-EDTA, the number of the cells was counted, and the total RNA was extracted and purified according to the manual of RNeasy mini KIT (QIAGEN). The extracted RNA (1 μg) was processed according to the manual of SuperScript II (Invitrogen) using random to synthesize a first strand cDNA, which was subjected to ethanol precipitation, and the precipitate was dissolved in TE (10 μl).

(3) Quantitation Using TaqMan

The tissue-derived cDNA (corresponding to 5 ng of RNA) and cell line-derived cDNA (corresponding to 25 ng of RNA) were adjusted to the total reaction mixture of 15 μl with amplification reaction reagent TaqMan (trademark) Universal PCR Master Mix (Applied Biosystems Japan Ltd.) and TaqMan (trademark) Probe Kit for GPR40 detection (sequence: 11-16, Applied Biosystems Japan Ltd.), and the reaction was carried out. The final concentration of each primer and probe followed the manual.

TaqMan (trademark) PCR was performed in ABI PRISM (trademark) 7900HT sequence detection system (Applied Biosystems Japan Ltd.), and the temperature cycle used followed the manual of TaqMan (trademark) Universal PCR Master Mix (Applied Biosystems Japan Ltd.).

The quantitative TaqMan analysis of the amplified product was performed using 7900HT SDS software (Applied Biosystems Japan Ltd.). The analytical curve used for the calculation of copy number was formed from $C_T$ values at 6 points in the logarithm from $10^7$ copies/well to $10^2$ copies/well using a concentration-known cDNA fragment (human GPR40) or Plasmid DNA (mouse GPR40) containing full length amplified region.

In human tissues, relatively high expression was observed in pancreas, lung, hippocampus, hypothalamus and spinal cord. In mouse, extremely high expression was observed in pancreatic cancer-derived cell.

EXPERIMENTAL EXAMPLE 3

Insulin Secretagogue Effect of Free Fatty Acid in Mouse Insulinoma MIN6 Cell

Unless otherwise specified, MIN6 cell was incubated in DMEM (high glucose, Invitrogen) containing 15% FCS (Trace Scientific Ltd.), 55 μM 2-mercaptoethanol, 100 U/ml penicillin, and 100 μg/ml streptomycin. Min6 cells were seeded in a 96 well plate at $10^5$ cells per well, and incubated at 37° C. for 3 days in a $CO_2$ incubator adjusted to 5% $CO_2$ concentration. The medium was exchanged to RPMI1640 (glucose-free, Invitrogen) containing 10% FCS (Trace Scientific Ltd.), 5.5 mM glucose, 100 U/ml penicillin and 100 μg/ml streptomycin and the cells were further incubated for 24 hrs. The medium was aspirated, free fatty acid-bovine serum albumin (BSA) mixed solution (4:1, molar ratio) diluted with RPMI1640 (glucose-free, Invitrogen) containing 10% FCS (Trace Scientific Ltd.), 11 mM glucose, 100 U/ml penicillin, and 100 μg/ml streptomycin was added to the cells and reacted at 37° C. for 90 min. (or 60 min.) in a $CO_2$ incubator adjusted to 5% $CO_2$ concentration. The 96 well plate after reaction was centrifuged at 1500 rpm for 5 min. and the culture supernatant was recovered. The insulin amount secreted in this culture supernatant liquid was determined by radioimmunoassay (RIA) using a rat insulin RIA system (Amersham Pharmacia Biotech). As a result, it was found that the insulin secretion by Min6 cell was promoted when 300 μM-1000 μM of free fatty acid such as palmitic acid, γ-linolenic acid, oleic acid and the like was added. That is, it was clarified that the free fatty acid promotes insulin secretion in mouse insulinoma MIN6 cell. Since MIN6 cell specifically and extremely highly expresses GPR40, it is considered that the added fatty acid insulin promotes secretion via GPR40.

EXPERIMENTAL EXAMPLE 4

Effect of Regulation of GPR40 Receptor Function (Agonistic Effect)

CHO cell line (No. 104) made to express human GPR40 was diluted such that $3\times10^4$ cells/100 μL were contained, dispensed to a black walled 96-well plate (Costar) at 100 μL per well, and incubated overnight in a $CO_2$ incubator. The changes in the intracellular calcium concentration were measured using FLIPR (Molecular Device). The method is described in the following.

Fluo-3AM (DOJIN) (50 μg) was dissolved in 21 μl DMSO (DOJIN), and an equal amount of 20% pluronic acid (Molecular Probes) was added and mixed, and the mixture was added to 10.6 ml of an assay buffer [prepared by adding 20 ml of 1M HEPES (pH 7.4) (DOJIN) to 1 L of HBSS (Invitrogen), and adding a mixed solution (10 ml) obtained by dissolving probenecid (Sigma) (710 mg) in 1N NaOH (5 ml) and adding and mixing with the above-mentioned HBSS/HEPES solution (5 ml)] supplemented with 105 μl of fetal calf serum to give a fluorescence dye solution. The medium in the cell plate was removed, a fluorescence dye solution was immediately dispensed at 100 μl per well, and incubated in a $CO_2$ incubator for 1 hr to incorporate fluorescence dye into the cell. The incubated cells were washed with the above-mentioned assay buffer. The compound to be added to the cell was diluted with the assay buffer to each concentration and dispensed to a test sample plate. After the above-mentioned pretreatment, changes in the intracellular calcium concentration after addition of the compound was measured by FLIPR, and the agonistic effect was examined. $EC_{50}$ value was calculated from a dose response curve based on the changes in the fluorescence intensity value at 30 sec after the start of the reaction. The results are shown in Table 1.

TABLE 1

| Effect of regulation of GPR40 receptor function | |
|---|---|
| compound No. | $EC_{50}$ (μM) |
| Reference Example 2 | 0.32 |
| Reference Example 6 | 0.46 |
| Reference Example 15 | 1.2 |
| Example 2 | 0.17 |
| Example 6 | 0.16 |
| Example 7 | 0.13 |
| Example 10 | 0.88 |
| Example 41 | 0.055 |
| γ.linolenic acid | 2.0 |

From the results of Table 1, it was found that the compound of the present invention has the superior effect of regulation of GPR40 receptor function.

REFERENCE EXAMPLE 129

Construction of Human GPR40 Expression Vector

A DNA fragment (SEQ ID NO: 6) encoding human GPR40 was obtained by the following PCR. That is, using oligo DNA (SEQ ID NO: 11) presented by

```
5'>CGTCGACCCGGCGGCCCCATGGACCTGCCCCCG<3'
``` as a sense strand primer, and oligo DNA (SEQ ID NO: 12) presented by

```
5'>CATCGATTAGCAGTGGCGTTACTTCTGGGACTT<3'
``` as an antisense strand primer, a mixed solution (50 µl) containing 20 pmol of each primer, 10× Advantage (trademark) 2 PCR Buffer (CLONTECH) 5 µl, 50×dNTP mix (CLONTECH) 1 µl, 50× Advantage 2 Polymerase Mix (CLONTECH) 1 µl, and human pancreas cDNA SOLUTION (CLONTECH) 1 µl as template DNA was prepared, and PCR was performed following a program comprising 35 cycles of 96° C., 1 min, then 96° C., 30 sec.→>61° C., 30 sec.→72° C., 120 sec. and elongation reaction at 72° C., 10 min was performed using a thermal cycler (GeneAmp (trademark) PCR system model 9700 (Applied Biosystems)). After the completion of the reaction, agarose gel electrophoresis was conducted to give a single product, which was cloned using a TA cloning kit (Invitrogen) to confirm the genetic sequence. The clone free of PCR error was double digested with restriction enzymes SalI (TAKARA SHUZO) and ClaI (TAKARA SHUZO), subjected to agarose gel electrophoresis to cut out a single product. The obtained fragment (about 1 kb) was introduced into a pAKKO-111 vector and used for the transfection of CHO cell.

REFERENCE EXAMPLE 130

Cloning of cDNA Encoding Mouse Spleen-derived GPR40 and Determination of Nucleotide Sequence Thereof PCR was performed using mouse spleen cDNA (Marathon-Ready™ cDNA; Clontech) as a template and two primers: primer 1 (SEQ ID NO: 13) and primer 2 (SEQ ID NO: 14). For PCR, Pyrobest DNA polymerase (TAKARA SHUZO) was used, and elongation reaction of (i) 98° C. 1 min, thereafter (ii) 40 cycles of 98° C. 10 sec, 55° C. 30 sec, 72° C. 60 sec, and then (iii) 72° C. 2 min was performed. After the reaction, the amplified product was cloned to plasmid vector pCR-Blunt (Invitrogen) according to the protocol of Zero Blunt PCR cloning kit (Invitrogen). This was introduced into Escherichia coli TOP10 (Invitrogen), and clones having plasmid were selected in an LB agar medium containing kanamycine. The nucleotide sequences of respective clones were analyzed and cDNA sequence (SEQ ID NO: 2) encoding novel G-protein-coupled receptor protein was obtained. A novel receptor protein containing amino acid sequence (SEQ ID NO: 1) derived from this cDNA was designated as mGPR40. In addition, the transformant was designated as Escherichia coli TOP10/Zero Blunt-mGPR40.

REFERENCE EXAMPLE 131

Cloning of cDNA Encoding Rat Spleen-derived GPR40 and Determination of Nucleotide Sequence Thereof PCR was performed using rat spleen cDNA (Marathon-Ready™ cDNA; Clontech) as a template and two primers: primer 3 (SEQ ID NO: 15) and primer 4 (SEQ ID NO: 16). For PCR, Advantage 2 Polymerase mix (Clontech) was used, and elongation reaction of (i) 96° C. 1 min, (ii) 5 cycles of 96° C. 10 sec, 72° C. 2 min, (iii) 25 cycles of 96° C. 10 sec, 70° C. 2 min, then 72° C. 5 min was performed. After the reaction, the amplified product was cloned to plasmid vector pCR2.1TOPO (Invitrogen) according to the protocol of TOPO TA Cloning Kit (Invitrogen). This was introduced into Escherichia coli JM109 (TAKARA SHUZO), and clones having plasmid were selected in an LB agar medium containing ampicilin. The nucleotide sequences of respective clones were analyzed and cDNA sequence (SEQ ID NO: 4) encoding novel G-protein-coupled receptor protein was obtained. A novel receptor protein containing amino acid sequence (SEQ ID NO: 3) derived from this cDNA was designated as rGPR40. In addition, the transformant was designated as Escherichia coli JM109/pCR2.1-rGPR40.

REFERENCE EXAMPLE 132

Cloning of cDNA Encoding Macaca fascicularis-derived GPR40 and Determination of Nucleotide Sequence Thereof PCR was performed using Macaca fascicularis DNA as a template, primer 1 (SEQ ID NO: 17) and primer 2 (SEQ ID NO: 18). For PCR, Pyrobest DNA Polymerase (TAKARA) was used, and elongation reaction of (i) 95° C. 1 min, (ii) 40 cycles of 95° C. 10 sec, 58° C. 20 sec, 72° C. 1 min and 30 sec, then 72° C. 7 min was performed. After the reaction, nested PCR was performed using the ⅟₅₀ diluted amplified product as a template, primer 3 (SEQ ID NO: 19) and primer 4 (SEQ ID NO: 20). After the reaction, the amplified product was cloned to plasmid vector pCR2.1TOPO (Invitrogen) according to the protocol of TOPO TA Cloning Kit (Invitrogen). This was introduced into Escherichia coli JM109 (TAKARA SHUZO), and clones having plasmid were selected in an LB agar medium containing ampicilin. The nucleotide sequences of respective clones were analyzed and cDNA sequence (SEQ ID NO: 8) encoding novel G-protein-coupled receptor protein was obtained. A novel receptor protein containing amino acid sequence (SEQ ID NO: 7) derived from this cDNA was designated as monkey GPR40. In addition, the transformant was designated as Escherichia coli JM109/pCR2.1-monkey GPR40.

REFERENCE EXAMPLE 133

Cloning of cDNA Encoding Hamster-derived GPR40 and Determination of Nucleotide Sequence Thereof PCR was performed using hamster cell line HIT-T15 cDNA as a template, primer 1 (SEQ ID NO: 21) and primer 2 (SEQ ID NO: 22). For PCR, Klentaq DNA Polymerase (CLONTECH) was used, and elongation reaction of (i) 95° C. 2 min, (ii) 35 cycles of 98° C. 10 sec, 63° C. 20 sec, 72° C. 1 min, then 72° C. 7 min was performed. After the reaction, the amplified product was cloned to plasmid vector pCR2.1TOPO (Invitrogen) according to the protocol of TOPO TA Cloning Kit (Invitrogen). This was introduced into Escherichia coli JM109 (TAKARA SHUZO), and clones having plasmid were selected in an LB agar medium containing ampicilin. The nucleotide sequences of respective clones were analyzed and cDNA sequence (SEQ ID NO: 10) encoding novel G-protein-coupled receptor protein was obtained. A novel receptor protein containing amino acid sequence (SEQ ID NO: 9) derived from this cDNA was designated as hamstar GPR40. In addition, the transformant was designated as Escherichia coli JM109/pTA hamsterGPR40.

EXPERIMENTAL EXAMPLE 5

Suppression of Expression of Mouse GPR40-GFP Fused Protein by Introduction of siRNA Specific to Mouse GPR40

CHO cell expressing fused protein of mouse GPR40 and GFP prepared by a method known per se was seeded in a 96 well plate at $3\times10^4$/well and incubated for one day. siRNA of various sequences (Dharmacon) (concentration of 2.86 Pmol/ 0.5 µl or 8.57 Pmol/1.5 µl) prepared using HVJ Envelope VECTOR KIT GenomONE™ (ISHIHARA SANGYO) and according to the report of Elbasir et al. (*Nature* 411 (6836), 494-498 (2001)) was introduced into the cells and the cells were further incubated for one day. The expression amount of mouse GPR40-GFP was detected by the following enzyme immunoassay. The culture supernatant was discarded, washed with HBSS (Invitrogen), fixed with 0.01% glutaraldehyde (Wako Pure Chemical Industries, Ltd.) for 5 min., and blocked with PBS (TAKARA SHUZO) containing 2% BSA. 500-fold diluted anti-GFP monoclonal antibody 3E6 (NIPPON GENE CO., LTD.) was added and the cells were incubated at room temperature for 2 hrs., washed and 500-fold diluted HRP-labeled anti-mouse IgG antibody (ICN) was added, and the cells were incubated at room temperature for 2 hrs. After washing, TMB microwell peroxydase substrate (Funakoshi) was added and, after incubation for 30 min., sulfuric acid was added to stop the color developing reaction, and the absorbance at 450 nm was measured. As a result, addition of m40i103, which is a mouse GPR40 specific siRNA (sense strand is SEQ ID NO: 23, antisense strand is SEQ ID NO: 24), m40i256 (sense strand is SEQ ID NO: 25, antisense strand is SEQ ID NO: 26) to mouse GPR40-GFP expressing CHO cell caused lower GPR40-GFP expression amount. Therefrom it was found that m40i103 and m40i256 specifically suppress mouse GPR40 expression.

EXPERIMENTAL EXAMPLE 6

Promotion by Various Fatty Acids of Insulin Secretion from MIN6

Mouse pancreatic β cell line MIN6 cultured in a flask was detached with PBS containing 2.5 mM EDTA, and seeded and incubated in a 96 well plate for 2 days. The medium used was obtained by adding 15% fetal bovine serum (ThermoTrace), 5.5 µM 2-mercaptoethanol (Invitrogen), 20 mM HEPES pH 7.3, 100 U/ml penicillin and 100 µg/ml streptomycin to Dulbecco's Modified Eagle Medium (DMEM, Invitrogen) containing 4.5 g/l of glucose. The cells were washed twice with modified Krebs-Ringer bicarbonate buffer (KRBH, 116 mM NaCl, 4.7 mM KCl, 1.2 mM $KH_2PO_4$, 1.2 mM $MgSO_4$, 2.5 mM $CaCl_2$, 25 mM $NaHCO_3$, 24 mM HEPES pH 7.3) and preincubated at 37° C. under 5% $CO_2$ conditions for 30 min. Fatty acid diluted and prepared with a buffer obtained by adding 22 mM glucose to the above-mentioned KRBH was added to the cell after preincubation and the cells were incubated at 37° C. under 5% $CO_2$ conditions for 90 min. After incubation, the cell supernatant was recovered and cryopreserved. The insulin content of the supernatant was measured using a commercially available insulin immunoassay kit (Amersham Pharmacia Biotech). As a result, a significant insulin secretion enhancing activity was found by oleic acid, linoleic acid, α-linolenic acid, γ-linolenic acid, arachidonic acid and DHA, which are fatty acid that showed a remarkable activity in an intracellular calcium ion mobilization assay using CHO cell expressing GPR40. In contrast, methyl linolate (linoleic methyl) and butyric acid that show no GPR40 agonistic activity did not show a significant insulin secretion enhancing activity. Since the GPR40 agonistic activity and the insulin secretion enhancing activity are almost correlated, it was demonstrated that GPR40 plays at least some role in insulin secretion enhancing action by fatty acid.

EXPERIMENTAL EXAMPLE 7

Glucose Dependency of Insulin Secretion Enhancing Activity Via GPR40

The effect of glucose concentration on the addition of fatty acid was examined based on the method of Experimental Example 6. The concentration of glucose added to KRBH during fatty acid addition was changed to 0, 5.5, 11, 22 mM and examined. As a result, insulin secretion enhancing activity of oleic acid and linoleic acid was found to be remarkable under high glucose concentration conditions of not less than 11 mM. Therefrom the insulin secretion enhancing activity by fatty acid showing GPR40 agonistic activity is expected to show insulin secretion enhancing activity and effect on blood glucose under hyperglycemia conditions.

EXPERIMENTAL EXAMPLE 8

Inhibitory Effect of Fatty Acid on Insulin Secretion Enhancing Activity in siRNA-introduced MIN6

In Experimental Example 5, m40i103, which is GPR40 specific siRNA, was confirmed to remarkably suppress expression of mouse GPR40. Insulin secretion enhancing activity in MIN6 cell, into which m40i103 was introduced using HVJ Envelope VECTOR KIT GenomONE based on the method of Experimental Example 5, was examined. The insulin secretion enhancing activity by fatty acid was examined by the method of Experimental Example 6. As a result, m40i103 introduced MIN6 no longer showed insulin secretion enhancing activity by linoleic acid and γ-linolenic acid. In contrast, MIN6 into which Scramble II duplex siRNA, which is a random sequence siRNA, was introduced showed retention of the insulin secretion enhancing activity by the above-mentioned fatty acid. From these results, it was confirmed that GPR40 plays at least some role in the insulin secretion enhancing mechanism by fatty acid.

EXPERIMENTAL EXAMPLE 9

Promoting Effect of Insulin Secretion from MIN6

Mouse pancreatic β cell line MIN6 cultured in a flask was detached with PBS containing 2.5 mM EDTA, and seeded and incubated in a 96 well plate for 2 days. The medium used was obtained by adding 15% fetal bovine serum (ThermoTrace), 5.5 µM 2-mercaptoethanol (Invitrogen), 20 mM HEPES pH 7.3, 100 U/ml penicillin and 100 µg/ml streptomycin to Dulbecco's Modified Eagle Medium (DMEM, Invitrogen) containing 4.5 g/l of glucose. The cells were washed twice with modified Krebs-Ringer bicarbonate buffer (KBH, 116 mM NaCl, 4.7 mM KCl, 1.2 mM $KH_2PO_4$, 1.2 mM $MgSO_4$, 2.5 mM $CaCl_2$, 25 mM $NaHCO_3$, 24 mM HEPES pH 7.3) and preincubated at 37° C. under 5% $CO_2$ conditions for 30 min. The compound diluted and prepared with a buffer obtained by adding 22 mM glucose to the above-mentioned KRBH was added to the cell after preincubation and the cells were incubated at 37° C. under 5% $CO_2$ conditions for 90 min. After incubation, the cell supernatant was recovered and cryopreserved. The insulin content of the supernatant was measured using a commercially available insulin immunoassay kit (Amersham Pharmacia Biotech). As a result, as shown in FIG. 1, a significant insulin secretion enhancing activity was observed by the addition of the compound of Example 41.

EXPERIMENTAL EXAMPLE 10

In Vivo Insulin Secretion Promoting Effect and Hypoglycemic Action

Figure 2:
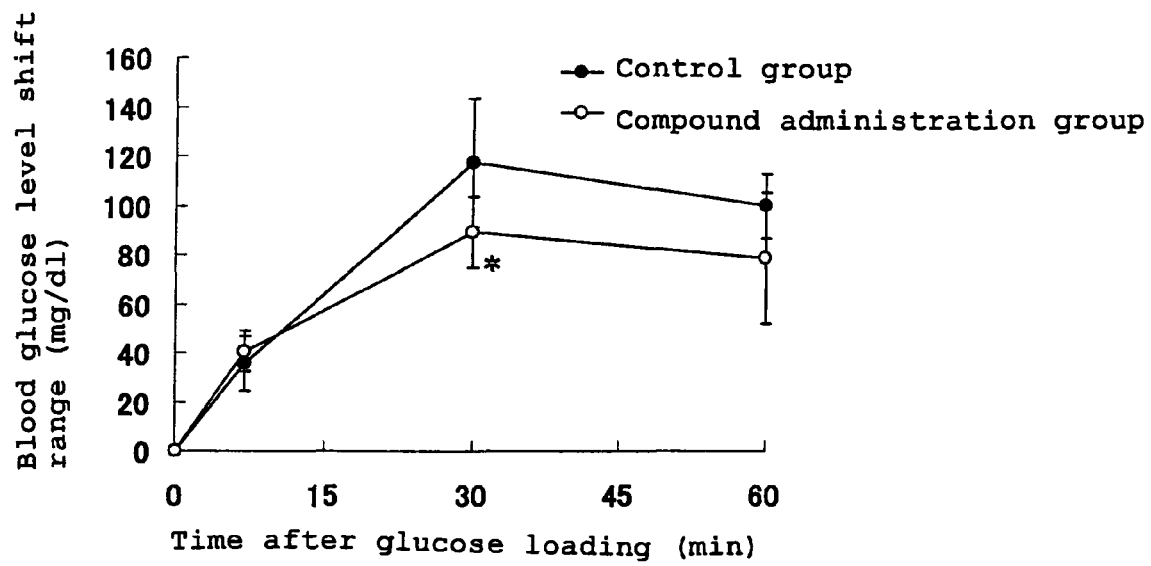
FIG. 2 shows the results of the hypoglycemic action of the compound of the present invention on rat, wherein ● means a control group (0.5% methyl cellulose administration group), ○ means a compound administration group (Example 41 compound administration group), the axis of abscissas shows time (min) after glucose loading, the axis of ordinate shows blood glucose level shift range (ng/dl), one group contained 6 rats, and the value is mean±standard deviation.
Figure 3:
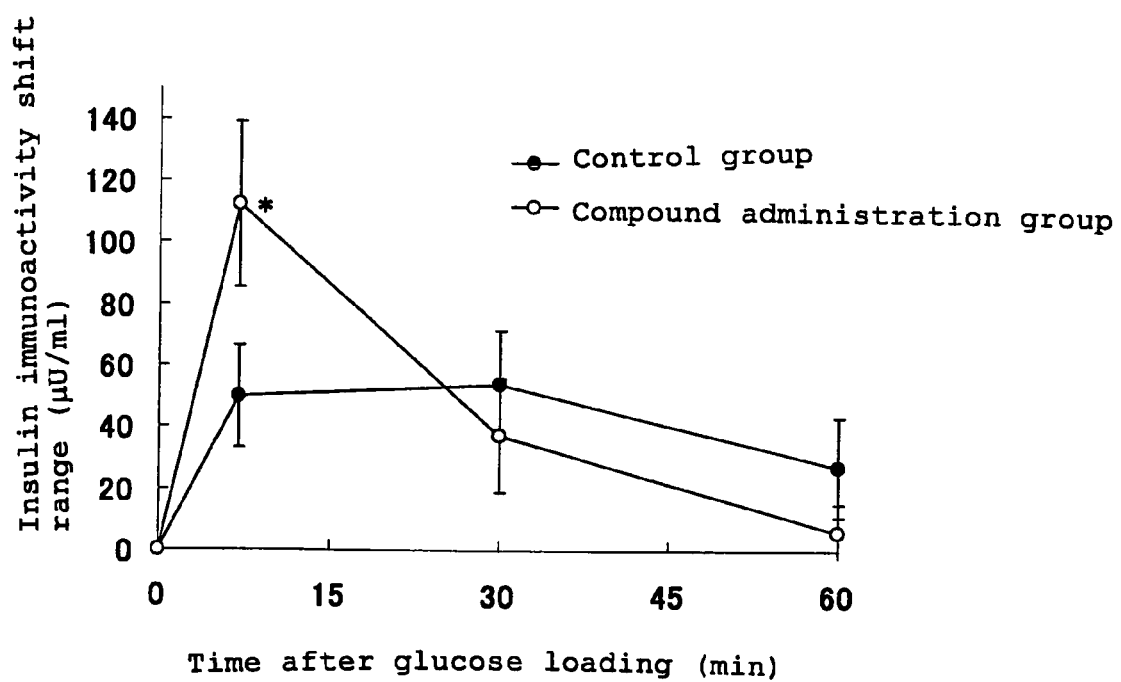
FIG. 3 shows the results of insulin secretion action of the compound of the present invention in rat, wherein ● means a control group (0.5% methyl cellulose administration group), ○ means a compound administration group (Example 41 compound administration group), the axis of abscissas shows time (min) after glucose loading, the axis of ordinate shows insulin immunoactivity shift range (μU/ml), one group contained 6 rats, and the value is mean±standard deviation.

Male SD rats (CLEA Japan, Inc, 7-week-old) were fasted for one day, and divided into groups (6 per group) based on blood glucose level and body weight. A suspension of the compound of Example 41 in 0.5% methyl cellulose was orally administered at the dose of 30 mg/kg and glucose (2 g/kg) was orally loaded at 30 min after administration. Only 0.5% methyl cellulose was administered to the control group, and similarly loaded with glucose. Plasma was taken before glucose tolerance test, and 7, 30 and 60 minutes after glucose tolerance test, and the blood glucose level and insulin concentration were measured. The blood glucose level was measured by HITACHI autoanalyzer 7070, and insulin was measured by radioimmunoassay ([$^{125}$L] Sionoria insulin, Shionogi & Co., Ltd.). As a result, as compared to the control group, the Example 41 compound administration group showed significantly suppressed increase in the blood glucose level at 30 minutes after glucose tolerance test (FIG. 2, Williams test, p<=0.025), and significantly greater increase in insulin at 7 minutes after glucose tolerance test (FIG. 3, Williams test, p<=0.025). From these results, it was clarified that the compound of Example 41 shows both the insulin secretion promoting effect and hypoglycemic action in rat.

REFERENCE EXAMPLE 134 ethyl (2E)-3-(2-fluoro-4-methoxyphenyl)acrylate

The title compound was obtained as a colorless oil in the same manner as in Reference Example 27 from 2-fluoro-4-methoxybenzaldehyde. yield 97%.
$^1$H NMR (CDCl$_3$) δ 1.33 (3 H, t, J=7.1 Hz), 3.83 (3 H, s), 4.26 (2 H, q, J=7.1 Hz), 6.41 (1 H, d, J=16.2 Hz), 6.61-6.73 (2 H, m), 7.45 (1 H, t, J=8.6 Hz), 7.75 (1 H, d, J=16.2 Hz).

REFERENCE EXAMPLE 135 ethyl 3-(2-fluoro-4-methoxyphenyl)propionate

The title compound was obtained as a colorless oil in the same manner as in Reference Example 43 from ethyl (2E)-3-(2-fluoro-4-methoxyphenyl)acrylate and platinum oxide. yield 84%.
$^1$H NMR (CDCl$_3$) δ 1.23 (3 H, t, J=7.2 Hz), 2.58 (2 H, t, J=7.6 Hz), 2.90 (2 H, t, J=7.6 Hz), 3.77 (3 H, s), 4.12 (2 H, q, J=7.2 Hz), 6.57-6.63 (2 H, m), 7.07-7.13 (1 H, m).

REFERENCE EXAMPLE 136 ethyl 3-(2-fluoro-4-hydroxyphenyl)propionate

The title compound was obtained as a colorless oil in the same manner as in Reference Example 36 from ethyl 3-(2-fluoro-4-methoxyphenyl)propionate and 1-octanethiol. yield 83%.
$^1$H NMR (CDCl$_3$) δ 1.23 (3 H, t, J=7.2 Hz), 2.58 (2 H, t, J=8.1 Hz), 2.89 (2 H, t, J=8.1 Hz), 4.12 (2 H, q, J=7.2 Hz), 6.51-6.56 (2 H, m), 7.01-7.06 (1 H, m).

REFERENCE EXAMPLE 137 methyl (2E)-3-(2-chloro-4-hydroxyphenyl)acrylate

The title compound was obtained as a colorless oil in the same manner as in Reference Example 34 from 4-bromo-3-chlorophenol. yield 17%.
$^1$H NMR (CDCl$_3$) δ 3.83 (3 H, s), 5.99 (1 H, br s), 6.33 (1 H, d, J=16.1 Hz), 6.79 (1 H, dd, J=8.6, 2.4 Hz), 6.94 (1 H, d, J=2.4 Hz), 7.53 (1 H, d, J=8.6 Hz), 8.05 (1 H, d, J=16.1 Hz).

REFERENCE EXAMPLE 138 methyl 3-(2-chloro-4-hydroxyphenyl)propionate

The title compound was obtained as a colorless oil in the same manner as in Reference Example 43 from methyl (2E)-3-(2-chloro-4-hydroxyphenyl)acrylate and platinum oxide. yield 44%.
$^1$H NMR (CDCl$_3$) δ 2.62 (2 H, t, J=7.9 Hz), 2.99 (2 H, t, J=7.9 Hz), 3.68 (3 H, s), 4.95 (1H, s), 6.67 (1 H, dd, J=8.3, 2.6 Hz), 6.87 (1 H, d, J=2.6 Hz), 7.10 (1 H, d, J=8.3 Hz).

REFERENCE EXAMPLE 139

4-phenyl-N-propyl-1,3-thiazol-2-amine

To a solution of 2-chloroacetophenone (4.45 g, 28.8 mmol) and N-propylthiourea (3.40 g, 28.8 mmol) in ethanol (50 mL) was added sodium acetate (3.07 g, 37.4 mmol), and the mixture was heated under reflux for 1.5 hrs. Water was added to the reaction mixture, and crystals were collected by filtration. The obtained crude crystals were recrystallized from diethyl ether-hexane to give the title compound (5.64 g, 92%) as colorless crystals.
$^1$H NMR (CDCl$_3$) δ 1.00 (3H, t, J=7.2 Hz), 1.60-1.78 (2H, m), 3.19-3.29 (2H, m), 5.38 (1H, br s), 6.70 (1H, s), 7.25-7.41 (3H, m), 7.77-7.81 (2H, m).

REFERENCE EXAMPLE 140

N,5-dimethyl-4-phenyl-1,3-thiazol-2-amine

The title compound was obtained as colorless crystals in the same manner as in Reference Example 139 from 2-bromo-1-phenylpropan-1-one and N-methylthiourea. yield 57%.
$^1$H NMR (CDCl$_3$) δ 2.40 (s, 3H), 2.85 (d, J=3.3 Hz, 3H), 5.79 (br s, 1H), 7.26-7.31 (m, 1H), 7.36-7.41 (m, 2H), 7.56-7.58 (m, 2H).

REFERENCE EXAMPLE 141

4,5-dimethyl-N-propyl-1,3-thiazol-2-amine

The title compound was obtained as yellow crystals in the same manner as in Reference Example 139 from 3-bromobutan-2-one and N-propylthiourea. yield 19%.
$^1$H NMR (CDCl$_3$) δ 0.97 (3H, t, J=7.0 Hz), 1.58-1.70 (2H, m), 2.10 (3H, s), 2.18 (3H, s), 3.15 (2H, t, J=7.0 Hz), 4.89-5.07 (1H, m).

REFERENCE EXAMPLE 142

5-methyl-4-phenyl-N-propyl-1,3-thiazol-2-amine

The title compound was obtained as yellow crystals in the same manner as in Reference Example 139 from 2-bromo-1-phenylpropan-1-one and N-propylthiourea. yield 23%.

$^1$H NMR (CDCl$_3$) δ 0.97 (3H, t, J=7.4 Hz), 1.57-1.70 (2H, m), 2.40 (3H, s), 3.17 (2H, q, J=7.4 Hz), 5.23 (1H, br s), 7.25-7.31 (1H, m), 7.36-7.41 (2H, m), 7.55-7.59 (2H, m).

REFERENCE EXAMPLE 143 methyl 4-[[methyl(4-phenyl-1,3-thiazol-2-yl)amino]methyl]benzoate

To a solution of N-methyl-4-phenyl-1,3-thiazol-2-amine (1.67 g, 8.8 mmol) in N,N-dimethylformamide (25 mL) was added 60% sodium hydride (350 mg, 8.8 mmol), and the mixture was stirred for 30 min. Methyl 4-(bromomethyl)benzoate (2.1 g, 9.2 mmol) was added and the mixture was stirred at room temperature for 1.5 hrs. Water was added to the reaction mixture, and the mixture was extracted with ethyl acetate. The extract was washed with water and concentrated under reduced pressure. The residue was purified by silica gel column chromatography (hexane/ethyl acetate=3:1) to give the title compound (2.6 g, yield 86%) as a yellow oil.

$^1$H NMR (CDCl$_3$) δ 3.08 (s, 3H), 3.90 (s. 3H), 4.85 (s. 2H), 6.75 (s, 1H), 7.27-7.43 (m, 5H), 7.86 (dd, J=8.4, 1.4 Hz, 2H), 8.02 (d, J=8.4 Hz, 2H).

REFERENCE EXAMPLE 144

[4-[[methyl(4-phenyl-1,3-thiazol-2-yl)amino]methyl]phenyl]methanol

Under ice-cooling, to a solution of methyl 4-[[methyl(4-phenyl-1,3-thiazol-2-yl)amino]methyl]benzoate (2.06 g, 6.1 mmol) in tetrahydrofuran (30 mL) was added 0.9 M diisobutylaluminum hydride-hexane solution (30 mL, 27 mmol). The reaction mixture was stirred at room temperature for 2 hrs, sodium sulfate 10 hydrate (8.7 g, 27 mmol) was added and the mixture was stirred at room temperature for 1 hr. Insoluble material was filtered off, and the filtrate was concentrated. The residue was purified by silica gel column chromatography (hexane/ethyl acetate=1:1) to give the title compound (1.9 g, yield 98%) as a white powder.

$^1$H NMR (CDCl$_3$) δ 3.07 (s, 3H), 4.67 (d, J=5.8 Hz, 2H), 4.77 (s, 2H), 6.72 (s, 1H), 7.23-7.42 (m, 7H), 7.83-7.89 (m, 2H).

REFERENCE EXAMPLE 145 methyl 4-[[ethyl(4-phenyl-1,3-thiazol-2-yl)amino]methyl]benzoate

The title compound was obtained as a yellow oil in the same manner as in Reference Example 143 from N-ethyl-4-phenyl-1,3-thiazol-2-amine. yield 60%.

$^1$H NMR (CDCl$_3$) δ 1.24 (t, J=7.2 Hz, 3H), 3.52 (q, J=7.2 Hz, 2H), 3.91 (s, 3H), 4.83 (s, 2H), 6.72 (s, 1H), 7.24-7.44 (m, 5H), 7.82-7.86 (m, 2H), 7.98-8.02 (m, 2H).

REFERENCE EXAMPLE 146

[4-[[ethyl(4-phenyl-1,3-thiazol-2-yl)amino]methyl]phenyl]methanol

The title compound was obtained as a colorless oil in the same manner as in Reference Example 144 from methyl 4-[[ethyl(4-phenyl-1,3-thiazol-2-yl)amino]methyl]benzoate. yield 69%.

$^1$H NMR (CDCl$_3$) δ 1.23 (t, J=7.1 Hz, 3H), 3.51 (q, J=7.1 Hz, 2H), 4.69 (d, J=4.8 Hz, 2H), 4.76 (s, 2H), 6.71 (s, 1H), 7.24-7.39 (m, 7H), 7.83-7.87 (m, 2H).

REFERENCE EXAMPLE 147 methyl 4-[[(4-phenyl-1,3-thiazol-2-yl)(propyl)amino]methyl]benzoate

The title compound was obtained as a colorless oil in the same manner as in Reference Example 143 from 4-phenyl-N-propyl-1,3-thiazol-2-amine. yield 75%.

$^1$H NMR (CDCl$_3$) δ 0.93 (t, J=7.7 Hz, 3H), 1.64-1.74 (m, 2H), 3.40 (t, J=7.7 Hz, 2H), 3.91: (s, 3H), 4.85 (s, 2H), 6.72 (s, 1H), 7.23-7.42 (m, 5H), 7.82-7.85 (m, 2H), 7.99-8.01 (m, 2H).

REFERENCE EXAMPLE 148

[4-[[(4-phenyl-1,3-thiazol-2-yl)(propyl)amino]methyl]phenyl]methanol

The title compound was obtained as a colorless oil in the same manner as in Reference Example 144 from methyl 4-[[(4-phenyl-1,3-thiazol-2-yl)(propyl)amino]methyl]benzoate. yield 67%.

$^1$H NMR (CDCl$_3$) δ 0.93 (t, J=7.4 Hz, 3H), 1.62 (t, J=5.8 Hz, 1H), 1.64-1.74 (m, 2H), 3.40 (t, J=7.7 Hz, 2H), 4.69 (d, J=5.8 Hz, 2H), 4.79 (s, 2H), 6.70 (s, 1H), 7.24-7.39 (m, 7H), 7.84-7.87 (m, 2H).

REFERENCE EXAMPLE 149 methyl 4-[[methyl(5-methyl-4-phenyl-1,3-thiazol-2-yl)amino]methyl]benzoate

The title compound was obtained as a yellow powder in the same manner as in Reference Example 143 from N,5-dimethyl-4-phenyl-1,3-thiazol-2-amine. yield 96%.

$^1$H NMR (CDCl$_3$) δ 2.42 (s, 3H), 3.03 (s, 3H), 3.91 (s, 3H), 4.75 (s, 2H), 7.26-7.31 (m, 1H), 7.36-7.41 (m, 4H), 7.62-7.65 (m, 2H), 8.01 (d, J=8.3 Hz, 2H).

REFERENCE EXAMPLE 150

[4-[[methyl(5-methyl-4-phenyl-1,3-thiazol-2-yl)amino]methyl]phenyl]methanol

The title compound was obtained as a white powder in the same manner as in Reference Example 144 from methyl 4-[[methyl(5-methyl-4-phenyl-1,3-thiazol-2-yl)amino]methyl]benzoate. yield 92%.

¹H NMR (CDCl₃) δ 2.42 (s, 3H), 3.02 (s, 3H), 4.68 (s, 4H), 7.26-7.41 (m, 7H), 7.64 (d, J=7.5 Hz, 2H).

REFERENCE EXAMPLE 151 methyl 4-[[(5-methyl-4-phenyl-1,3-thiazol-2-yl)(propyl)amino]methyl]benzoate

The title compound was obtained as a yellow oil in the same manner as in Reference Example 143 from 5-methyl-4-phenyl-N-propyl-1,3-thiazol-2-amine. yield 79%.
¹H NMR (CDCl₃) δ 0.92 (t, J=7.4 Hz, 3H), 1.66-1.72 (m, 2H), 2.41 (s, 3H), 3.32-3.37 (m, 2H), 3.91 (s, 3H), 4.77 (s, 2H), 7.26-7.41 (m, 5H), 7.61-7.63 (m, 2H), 7.98-8.01 (m, 2H).

REFERENCE EXAMPLE 152

[4-[[(5-methyl-4-phenyl-1,3-thiazol-2-yl)(propyl)amino]methyl]phenyl]methanol

The title compound was obtained as a colorless oil in the same manner as in Reference Example 144 from methyl 4-[[(5-methyl-4-phenyl-1,3-thiazol-2-yl)(propyl)amino]methyl]benzoate. yield 78%.
¹H NMR (CDCl₃) δ 0.91 (t, J=7.4 Hz, 3H), 1.57-1.72 (m, 2H), 2.41 (s, 3H), 3.32-3.37 (m, 2H), 4.68 (d, J=5.8 Hz, 2H), 4.70 (s, 2H), 7.24-7.41 (m, 7H), 7.63-7.65 (m, 2H).

REFERENCE EXAMPLE 153 methyl 3-[[methyl(4-phenyl-1,3-thiazol-2-yl)amino]methyl]benzoate

The title compound was obtained as a colorless oil in the same manner as in Reference Example 143 from N-methyl-4-phenyl-1,3-thiazol-2-amine and methyl 3-(bromomethyl)benzoate. yield 72%.
¹H NMR (CDCl₃) δ 3.08 (s, 3H), 3.91 (s, 3H), 4.83 (s, 2H), 6.74 (s, 1H), 7.25-7.44 (m, 4H), 7.58 (d, J=7.7 Hz, 1H), 7.85-7.88 (m, 2H), 7.96-7.98 (m, 1H), 8.03 (s, 1H).

REFERENCE EXAMPLE 154

[3-[[methyl(4-phenyl-1,3-thiazol-2-yl)amino]methyl]phenyl]methanol

The title compound was obtained as a colorless oil in the same manner as in Reference Example 144 from methyl 3-[[methyl(4-phenyl-1,3-thiazol-2-yl)amino]methyl]benzoate. yield 95%.
¹H NMR (CDCl₃) δ 3.09 (s, 3H), 4.69 (d, J=5.8 Hz, 2H), 4.78 (s, 2H), 6.73 (s, 1H), 7.24-7.40 (m, 7H), 7.85-7.88 (m, 2H).

REFERENCE EXAMPLE 155 methyl 4-[[(4-phenyl-1,3-thiazol-2-yl)thio]methyl]benzoate

The title compound was obtained as a white powder in the same manner as in Reference Example 143 from 4-phenyl-1,3-thiazole-2-thiol and methyl 4-(bromomethyl)benzoate. yield 79%.
¹H NMR (CDCl₃) δ 3.90 (s, 3H), 4.54 (s, 2H), 7.31-7.45 (m, 4H), 7.49 (d, J=8.3 Hz, 2H), 7.86-7.90 (m, 2H), 7.96-8.00 (m, 2H).

REFERENCE EXAMPLE 156

[4-[[(4-phenyl-1,3-thiazol-2-yl)thio]methyl]phenyl]methanol

The title compound was obtained as a white powder in the same manner as in Reference Example 144 from methyl 4-[[(4-phenyl-1,3-thiazol-2-yl)thio]methyl]benzoate. yield 85%.
¹H NMR (CDCl₃) δ 1.67 (t, J=5.4 Hz, 1H), 4.51 (s, 2H), 4.67 (d, J=5.3 Hz, 2H), 7.26-7.44 (m, 8H), 7.89 (d, J=8.1 Hz, 2H).

REFERENCE EXAMPLE 157

N-(4,5-dihydronaphtho[1,2-d][1,3]thiazol-2-yl)propanamide

Under ice-cooling, to a solution of 4,5-dihydronaphtho[1,2-d][1,3]thiazol-2-amine (1.50 g, 7.4 mmol) in pyridine (20 mL) was added propionyl chloride (1.03 g, 11 mmol), and the mixture was stirred at room temperature for 2 hrs. Water was added to the reaction mixture, and the mixture was extracted with ethyl acetate. The extract was washed with water and concentrated under reduced pressure. The residue was purified by silica gel column chromatography (hexane/ethyl acetate=3:1) to give the title compound (1.75 g, yield 91%) as a powder.
¹H NMR (CDCl₃) δ 1.14 (t, J=7.5 Hz, 3H), 2.33 (q, J=7.5 Hz, 2H), 2.96-3.09 (m, 4H), 7.18-7.28 (m, 3H), 7.71 (d, J=7.5 Hz, 1H).

REFERENCE EXAMPLE 158

N-propyl-4,5-dihydronaphtho[1,2-d][1,3]thiazol-2-amine

Under ice-cooling, to a solution of N-(4,5-dihydronaphtho[1,2-d][1,3]thiazol-2-yl)propanamide (1.70 g, 6.6 mmol) in tetrahydrofuran (30 mL) was added lithium aluminum hydride (749 mg, 20 mmol), and the mixture was stirred at room temperature for 3 hrs. Sodium sulfate 10 hydrate (9.6 g, 30 mmol) was added, and the mixture was stirred at room temperature for 1 hr. Insoluble material was filtered off, and the filtrate was concentrated. The residue was purified by silica gel column chromatography (hexane/ethyl acetate=4:1) to give the title compound (1.32 g, yield 82%) as a yellow powder.
¹H NMR (CDCl₃) δ 0.99 (t, J=7.5 Hz, 3H), 1.62-1.76 (m, 2H), 2.83-2.88 (m, 2H), 2.99-3.04 (m, 2H), 3.20-3.26 (m, 2H), 5.26 (s, 1H), 7.10-7.26 (m, 3H), 7.70 (d, J=7.9 Hz, 1H).

REFERENCE EXAMPLE 159 methyl 4-[[4,5-dihydronaphtho[1,2-d][1,3]thiazol-2-yl(propyl)amino]methyl]benzoate The title compound was obtained as a oil in the same manner as in Reference Example 143 from N-propyl-4,5-dihydronaphtho[1,2-d][1,3]thiazol-2-amine. yield 78%.
¹H NMR (CDCl₃) δ 0.93 (t, J=7.5 Hz, 3H), 1.63-1.73 (m, 2H), 2.82-2.88 (m, 2H), 3.02 (t, J=7.8 Hz, 2H), 3.38 (t, J=7.8

Hz, 2H), 3.90 (s, 3H), 4.81 (s, 2H), 7.09-7.26 (m, 4H), 7.41 (d, J=8.1 Hz, 2H), 7.99 (d, J=8.1 Hz, 2H).

REFERENCE EXAMPLE 160

[4-[[4,5-dihydronaphtho[1,2-d][1,3]thiazol-2-yl(propyl)amino]methyl]phenyl]methanol The title compound was obtained as a colorless oil in the same manner as in Reference Example 144 from methyl 4-[[4,5-dihydronaphtho[1,2-d][1,3]thiazol-2-yl(propyl)amino]methyl]benzoate. yield 63%.

$^1$H NMR (CDCl$_3$) δ 0.93 (t, J=7.4 Hz, 3H), 1.63-1.73 (m, 2H), 2.82-2.87 (m, 2H), 2.99-3.04 (m, 2H), 3.35-3.40 (m, 2H), 4.68 (d, J=5.1 Hz, 2H), 4.75 (s, 2H), 7.09-7.40 (m, 7H), 7.78 (d, J=7.5 Hz, 1H).

REFERENCE EXAMPLE 161 methyl 4-[[(4,5-dimethyl-1,3-thiazol-2-yl)(propyl)amino]methyl]benzoate

The title compound was obtained as a yellow oil in the same manner as in Reference Example 143 from 4,5-dimethyl-N-propyl-1,3-thiazol-2-amine. yield 68%.

$^1$H NMR (CDCl$_3$) δ 0.88 (t, J=7.4 Hz, 3H), 1.56-1.66 (m, 2H), 2.12 (d, J=0.8 Hz, 3H), 2.18 (d, J=0.8 Hz, 3H), 3.25-3.30 (m, 2H), 3.90 (s, 3H), 4.71 (s, 2H), 7.33 (d, J=8.5 Hz, 2H), 7.96-8.00 (m, 2H).

REFERENCE EXAMPLE 162

[4-[[(4,5-dimethyl-1,3-thiazol-2-yl)(propyl)amino]methyl]phenyl]methanol

The title compound was obtained as a colorless oil in the same manner as in Reference Example 144 from methyl 4-[[(4,5-dimethyl-1,3-thiazol-2-yl)(propyl)amino]methyl]benzoate. yield 63%.

$^1$H NMR (CDCl$_3$) δ 0.87 (t, J=7.4 Hz, 3H), 1.56-1.66 (m, 2H), 2.13 (s, 3H), 2.18 (s, 3H), 3.25-3.30 (m, 2H), 4.64 (s, 2H), 4.67 (s, 2H), 7.24-7.33 (m, 4H).

REFERENCE EXAMPLE 163

(2',6'-dimethylbiphenyl-4-yl)methanol (4-Bromophenyl)methanol (5.00 g, 32 mmol), (2,6-dimethylphenyl)boronic acid (5.77 g, 39 mmol) and sodium carbonate (10.2 g, 96 mmol) were dissolved in toluene-methanol-water (5:1:1, 210 mL) and, after argon substitution, tetrakistriphenylphosphinepalladium (1.85 g, 1.6 mmol) was added. The reaction mixture was heated under reflux overnight under an argon atmosphere. The reaction mixture was cooled, water was added to the reaction mixture and the mixture was extracted with ethyl acetate. The extract was washed with water, dried and concentrated. The residue was purified by silica gel column chromatography (hexane/ethyl acetate=7:3) to give the title compound (4.44 g, yield 65%) as a white powder.

$^1$H NMR (CDCl$_3$) δ 1.69 (1H, t, J=6.0 Hz), 2.03 (6H, s), 4.76 (2H, d, J=6.0 Hz), 7.09-7.19 (5H, m), 7.43 (2H, d, J=8.1 Hz).

REFERENCE EXAMPLE 164

3-(4-((3-phenoxybenzyl)oxy)phenyl)propanenitrile

The title compound was obtained as a pale-yellow oil in the same manner as in Reference Example 31 from 3-phenoxybenzyl alcohol and 3-(4-hydroxyphenyl)propanenitrile. yield 95%. MS 330.1 (MH$^+$).

REFERENCE EXAMPLE 165

(1Z)-N-hydroxy-3-(4-((3-phenoxybenzyl)oxy)phenyl)propanimideamide

A suspension of hydroxyamine hydrochloride (1.05 g, 15.1 mmol) and triethylamine (3.0 ml, 21.5 mmol) in dimethyl sulfoxide (30 ml) was stirred at room temperature for 30 min., and 3-(4-((3-phenoxybenzyl)oxy)phenyl)propanenitrile (0.5 g, 1.52 mmol) was added. The mixture was stirred at 70° C. for 18 hrs, reaction solution was diluted with ethyl acetate, washed successively with water and aqueous sodium chloride solution, dried over magnesium sulfate, and concentrated under reduced pressure. The obtained crystals were recrystallized from ethyl acetate-tetrahydrofuran to give the title compound (0.49 g, 89%) as colorless needles.

MS 363.1 (MH$^+$).

REFERENCE EXAMPLE 166

1-(tert-butoxycarbonyl)-3-hydroxymethyl-1H-indole

To a solution of methyl 1-(tert-butoxycarbonyl)-1H-indole-3-carboxylate (2.5 g, 9.08 mmol) in anhydrous tetrahydrofuran (40 ml) was added 1.5 M diisobutylaluminum hydride-toluene solution (14 ml, 21 mmol) under ice-cooling, and the mixture was stirred for 2 hrs. An aqueous citric acid solution was added, and the mixture was extracted with ethyl acetate. The extract was washed successively with aqueous sodium chloride solution, dried over magnesium sulfate and concentrated under reduced pressure to give the title compound (2.3 g, 100%) as a pale-yellow oil.

$^1$H-NMR (CDCl$_3$) δ 1.67 (9H, s), 4.84 (2H, d, J=6.0 Hz), 7.14-7.38 (3H, m), 7.58 (1H, s), 7.64 (1H, d, J=7.5 Hz), 8.13 (1H, br d, J=8.1 Hz).

REFERENCE EXAMPLE 167

2-hydroxymethyl-3-methoxymethoxy-1-benzothiophene

The title compound was obtained as a pale-yellow oil in the same manner as in Reference Example 166 from methyl 3-methoxymethoxy-1-benzothiophene-2-carboxylate (91%).

$^1$H-NMR (CDCl$_3$) δ 2.72 (1H, t, J=6.6 Hz), 3.68 (3H, s), 4.80 (2H, d, J=6.6 Hz), 5.11 (2H, s), 7.30-7.43 (2H, m), 7.66-7.82 (2H, m).

REFERENCE EXAMPLE 168

2-hydroxymethyl-3-(2-methylbenzyloxy)-1-benzothiophene

The title compound was obtained as a pale-yellow oil in the same manner as in Reference Example 166 from methyl 3-(2-methylbenzyloxy)-1-benzothiophene-2-carboxylate (58%).

¹H-NMR (CDCl₃) δ 2.42 (3H, s), 4.50 (2H, d, J=5.2 Hz), 5.17 (2H, s), 7.10-7.82 (8H, m).

REFERENCE EXAMPLE 169

(2',6'-dimethyl-6-methoxybiphenyl-3-yl)methanol

The title compound was obtained as a colorless oil in the same manner as in Reference Example 199 and Reference Example 200 to be mentioned later. yield 76%.
¹H-NMR (CDCl₃) δ 2.01 (6H, s), 3.74 (3H, s), 4.65 (2H, d, J=5.2 Hz), 6.97 (1H, d, J=8.4 Hz), 7.03 (1H, d, J=2.2 Hz), 7.06-7.24 (3H, m), 7.35 (1H, dd, J=2.6 & 8.4 Hz).

REFERENCE EXAMPLE 170

(2',6'-dimethyl-4-methoxybiphenyl-3-yl)methanol

The title compound was obtained as a colorless oil in the same manner as in Reference Example 199 and Reference Example 200 to be mentioned later. yield 82%.
¹H-NMR (CDCl₃) δ 2.03 (6H, s), 2.37 (1H, t, J=6.6 Hz), 3.92 (3H, s), 4.71 (2H, d, J=6.6 Hz), 6.94 (1H, d, J=8.8 Hz), 7.02-7.22 (5H, m).

REFERENCE EXAMPLE 171 ethyl (2E)-3-(4-benzyloxy-2,6-dimethoxyphenyl)propenoate

To a solution of 4-hydroxy-2,6-dimethoxybenzaldehyde (1.0 g, 5.49 mmol), benzyl alcohol (0.65 g, 6.01 mmol) and tributylphosphine (1.5 g, 7.41 mmol) in tetrahydrofuran (120 ml) was added 1,1'-(azodicarbonyl)dipiperidine (1.8 g, 7.13 mmol) by small portions, and the mixture was stirred at room temperature for 18 hrs. Diethyl ether (120 ml) was added to the reaction mixture, the precipitated insoluble material was filtered off and the filtrate was concentrated under reduced pressure. The residue was subjected to silica gel chromatography (ethyl acetate:hexane=2:3-1:1) to give 4-benzyloxy-2,6-dimethoxybenzaldehyde (1.2 g) as pale-yellow crystals. Separately, a solution of ethyl diethylphosphono acetate (1.1 g, 4.91 mmol) and 60% sodium hydride (0.17 g, 4.25 mmol) in tetrahydrofuran (40 ml) was stirred under ice-cooling for 10 min. A solution of 4-benzyloxy-2,6-dimethoxybenzaldehyde (1.2 g) was added, and the mixture was stirred while elevating the temperature to room temperature for 5 hrs. The reaction solution was diluted with ethyl acetate, washed successively with aqueous citric acid solution, water and aqueous sodium chloride solution, dried over magnesium sulfate, and concentrated under reduced pressure. The obtained residue was washed with diethyl ether-hexane to give the title compound (1.2 g) as colorless crystals. yield 64%. MS 343.1 (MH⁺).

REFERENCE EXAMPLE 172 ethyl (2E)-3-(4-hydroxy-2,6-dimethoxyphenyl)propanoate

A mixed solution of ethyl 3-(4-benzyloxy-2,6-dimethoxyphenyl)propenoate (1.2 g, 3.50 mmol) and 10% palladium-carbon (0.40 g) in a mixed solvent of ethanol (30 ml) and tetrahydrofuran (30 ml) was stirred under a hydrogen atmosphere at room temperature for 18 hrs. The catalyst was filtered off and the filtrate was concentrated under reduced pressure to give the title compound (800 mg) as colorless crystals. yield 90%. MS 255.1 (MH⁺).

REFERENCE EXAMPLE 173 ethyl 3-(2,6-difluoro-4-methoxyphenyl)propanoate

A solution of ethyl diethylphosphonoacetate (2.34 g, 10.4 mmol) and 60% sodium hydride (0.38 g, 9.50 mmol) in tetrahydrofuran (40 ml) was stirred under ice-cooling for 10 min. 2,6-Difluoro-4-methoxybenzaldehyde (1.5 g, 8.71 mmol) was added, and the mixture was stirred while elevating the temperature to room temperature for 4 hrs. The reaction solution was diluted with ethyl acetate, washed successively with aqueous citric acid solution, water and aqueous sodium chloride solution, dried over magnesium sulfate, and concentrated under reduced pressure. The obtained residue was subjected to silica gel chromatography (ethyl acetate:hexane=1:10-1:5), and then subjected to catalytic reduction in the same manner as in Reference Example 172 to give the title compound (1.17 g) as a colorless oil. yield 52%. MS 245.0 (MH⁺).

REFERENCE EXAMPLE 174 ethyl 3-(2,6-difluoro-4-hydroxyphenyl)propanoate

A solution (20 ml) of ethyl 3-(2,6-difluoro-4-methoxyphenyl)propanoate (1.17 g, 4.79 mmol), aluminum chloride (1.9 g, 14.2 mmol) and 1-octanethiol (1.7 ml, 9.80 mmol) in dichloromethane was stirred from ice-cooling to room temperature for 4 hrs. The reaction solution was poured into ice water, and the mixture was stirred for 1 hr. The mixed solution was extracted with dichloromethane, and the extract was washed with aqueous sodium chloride solution, dried over magnesium sulfate, and concentrated under reduced pressure. The obtained residue was subjected to silica gel chromatography (ethyl acetate:hexane=1:10-1:5) to give the title compound (1.0 g) as a colorless oil. yield 91%. MS 230.9 (MH⁺).

REFERENCE EXAMPLE 175

(6-benzyloxy-2',6'-dimethyl-biphenyl-3-yl)methanol

The title compound was obtained as a colorless oil in the same manner as in Reference Example 199 and Reference Example 200 to be mentioned later. yield 37%.
¹H-NMR (CDCl₃) δ 1.56 (1H, t, J=5.6 Hz), 2.04 (6H, s), 4.65 (2H, d, J=5.6 Hz), 5.03 (2H, s), 6.96-7.44 (11H, m).

REFERENCE EXAMPLE 176

(2,6-dimethylphenyl)[4-(1,3-dioxolan-2-yl)phenyl]methanol

Iodine (10 mg) was added to a mixture of magnesium (1.20 g) and tetrahydrofuran (50 mL) with vigorous stirring and 2-(4-bromophenyl)-1,3-dioxolane (10.0 g) was added dropwise at room temperature. After the completion of the dropwise addition, the reaction mixture was stirred at room temperature for 1 hr and a solution of 2,6-dimethylbenzaldehyde (5.0 g) in tetrahydrofuran (20 mL) was added dropwise at 0° C. After the completion of the dropwise addition, the temperature of the reaction mixture was allowed to return to room temperature and the mixture was further stirred for 1 hr. The reaction mixture was poured into saturated aqueous ammonium chloride, and the mixture was extracted with ethyl acetate. The ethyl acetate layer was concentrated and the residue was purified by silica gel column chromatography. The residue was developed with ethyl acetate-hexane (gradient of 1:9 to 7:3 by volume ratio) to give the title compound (9.10 g, yield 73%) as a yellow oil.

$^1$H NMR (300 MHz, Chloroform-D) δ: 2.14-2.23 (1H, m), 2.26 (6H, s), 3.97-4.19 (4H, m), 5.79 (1H, s), 6.35 (1H, d, J=4.1 Hz), 7.03 (2H, d, J=7.5 Hz), 7.05-7.2 (1H, m), 7.29 (2H, d, J=7.7 Hz), 7.35-7.45 (2H, m).

REFERENCE EXAMPLE 177

(2,6-dimethylphenyl)[3-(1,3-dioxolan-2-yl)phenyl]methanol

The title compound was obtained in the same manner as in Reference Example 176. yield: 74% (a yellow oil).

$^1$H NMR (300 MHz, Chloroform-D) δ: 2.17 (1H, d, J=4.3 Hz), 2.27 (6H, s), 3.87-4.23 (4H, m), 5.77 (1H, s), 6.25-6.4 (1H, m), 7.0-7.55 (7H, m).

REFERENCE EXAMPLE 178

[4-(2,6-dimethylbenzyl)phenyl]methanol

A mixture of (2,6-dimethylphenyl)[4-(1,3-dioxolan-2-yl)phenyl]methanol (7.10 g), chlorotrimethylsilane (10.8 g), sodium iodide (15.0 g) and acetonitrile (50 mL) was stirred at 50° C. for 1 hr. The reaction mixture was poured into water, and the mixture was extracted with ethyl acetate. The ethyl acetate layer was washed successively with 10% aqueous sodium hydrogencarbonate solution and saturated brine, dried over anhydrous magnesium sulfate, and concentrated. The residue was purified by silica gel column chromatography with ethyl acetate-hexane (gradient of 1:9 to 7:3 by volume ratio) to give 4-(2,6-dimethylbenzyl)benzaldehyde as pale-yellow crystals.

$^1$H NMR (300 MHz, Chloroform-D) δ: 2.23 (6H, s), 4.13 (2H, s), 7.05-7.2 (5H, m), 7.76 (2H, d, J=8.3 Hz), 9.95 (1H, s).

This compound (3.70 g) was dissolved in tetrahydrofuran (50 mL) and cooled to 0° C., and lithium aluminum hydride (1.0 g) was added with stirring. After stirring at 0° C. for 1 hr, sodium sulfate 10 hydrate (5.0 g) was added. The temperature of the reaction mixture was allowed to return to room temperature and the mixture was further stirred for 30 min. The insoluble material was removed by filtration, and the obtained organic layer was concentrated to give the title compound (3.43 g, yield 61%) as pale-yellow crystals.

$^1$H NMR (300 MHz, Chloroform-D) δ: 1.54 (1H, t, J=6 Hz), 2.23 (6H, s), 4.05 (2H, s), 4.64 (2H, d, J=6 Hz), 7.00 (2H, d, J=7.9 Hz), 7.05-7.15 (3H, m), 7.24 (2H, d, J=8.1 Hz)

REFERENCE EXAMPLE 179

[3-(2,6-dimethylbenzyl)phenyl]methanol

The title compound was obtained in the same manner as in Reference Example 178 from (2,6-dimethylphenyl)[3-(1,3-dioxolan-2-yl)phenyl]methanol. yield: 52% (a yellow oil).

$^1$H NMR (300 MHz, Chloroform-D) δ: 2.24 (6H, s), 4.06 (2H, s), 4.62 (2H, s), 6.8-7.4 (7H, m).

REFERENCE EXAMPLE 180 methyl 3-(4-{[4-(chloromethyl)benzyl]oxy}phenyl)propanoate 4-(Chloromethyl)benzyl alcohol (4.68 g), methyl 3-(4-hydroxyphenyl)propanoate (5.40 g) and triphenylphosphine (9.20 g) were dissolved in a mixed solvent of toluene-tetrahydrofuran (60-30 mL) and cooled to 0° C., and diethyl azodicarboxylate (40% toluene solution, 15.2 g) was added dropwise with vigorously stirring. After the completion of the dropwise addition, the temperature of the reaction mixture was allowed to return to room temperature and the mixture was further stirred for 1 hr. The reaction mixture was concentrated and the residue was purified by silica gel column chromatography with ethyl acetate-hexane (gradient of 1:19 to 1:1 by volume ratio) to give the title compound (5.19 g, yield 54%) as colorless crystals.

$^1$H NMR (300 MHz, Chloroform-D) δ: 2.59 (2H, t, J=7.7 Hz), 2.89 (2H, t, J=7.7 Hz), 3.66 (3H, s), 4.59 (2H, s), 5.04 (2H, s), 6.89 (2H, d, J=8.7 Hz), 7.11 (2H, d, J=8.7 Hz), 7.35-7.45 (4H, m).

REFERENCE EXAMPLE 181

N-isobutyl-4-phenyl-1,3-thiazol-2-amine

A mixture of 2-bromo-1-phenylethanone (4.0 g), N-isobutylthiourea (2.60 g) and N,N-dimethylformamide (15 mL) was stirred at room temperature for 1 hr. The reaction mixture was poured into saturated aqueous sodium hydrogencarbonate, and the mixture was extracted with ethyl acetate. The ethyl acetate layer was concentrated, and the residue was purified by silica gel column chromatography with ethyl acetate-hexane (gradient of 1:9 to 2:1 by volume ratio) to give the title compound (3.30 g, 71%) as a yellow oil.

$^1$H NMR (300 MHz, Chloroform-D) δ: 1.01 (6H, d, J=6.6 Hz), 1.89-2.04 (1H, m), 3.05-3.15 (2H, m), 5.26 (1H, broad s), 6.69 (1H, s), 7.25-7.3 (1H, m), 7.3-7.4 (2H, m), 7.75-7.85 (2H, m).

The following compounds of Reference Examples 182-184 were synthesized in the same manner as in Reference Example 181.

REFERENCE EXAMPLE 182

N-isopropyl-4-phenyl-1,3-thiazol-2-amine

Yield 80%. a yellow oil. $^1$H NMR (300 MHz, Chloroform-D) δ: 1.31 (6H, d, J=6.3 Hz), 3.65-3.80 (1H, m), 4.95-5.05 (1H, m), 6.69 (1H, s), 7.2-7.4 (3H, m), 7.7-7.8 (2H, m)

REFERENCE EXAMPLE 183

N-hexyl-4-phenyl-1,3-thiazol-2-amine

Yield 94%. a yellow oil. $^1$H NMR (300 MHz, Chloroform-D) δ: 0.8-1.0 (3H, m), 1.1-1.5 (6H, m), 1.5-1.8 (2H, m), 3.2-3.4 (2H, m), 5.20 (1H, broad s), 6.70 (1H, s), 7.15-7.5 (3H, m), 7.7-7.8 (2H, m)

REFERENCE EXAMPLE 184

N-(3-methylbutyl)-4-phenyl-1,3-thiazol-2-amine

Yield 91%. a yellow oil. $^1$H NMR (300 MHz, Chloroform-D) δ: 0.96 (6H, d, J=6.6 Hz), 1.40-1.65 (2H, m), 1.65-1.8 (1H, m), 3.2-3.4 (2H, m), 5.13 (1H, broad s), 6.70 (1H, s), 7.2-8.05 (5H, m)

REFERENCE EXAMPLE 185

N-propyl-4-[4-(trifluoromethyl)phenyl]-1,3-thiazol-2-amine hydrobromide

A mixture of 2-bromo-1-[4-(trifluoromethyl)phenyl]ethanone (5.34 g), N-propylthiourea (2.60 g) and ethanol (50 mL)

was stirred for 1 hr while heating under reflux. The reaction mixture was cooled and diluted with isopropyl ether. The precipitated solid was collected by filtration, washed with isopropyl ether and dried to give the title compound (5.11 g, yield 70%) as colorless crystals.

$^1$H NMR (300 MHz, DMSO-D6) δ: 0.96 (3H, t, J=7.4 Hz), 1.45-1.8 (2H, m), 3.31 (2H, t, J=7.0 Hz), 7.30 (1H, s), 7.75 (2H, d, J=8.5 Hz), 8.00 (2H, d, J=8.5 Hz)

The following compounds of Reference Examples 186 and 187 were synthesized in the same manner as in Reference Example 185.

REFERENCE EXAMPLE 186

4-(4-chlorophenyl)-N-propyl-1,3-thiazol-2-amine hydrobromide

Yield 71%. colorless crystals. $^1$H NMR (300 MHz, DMSO-D6) δ: 0.95 (3H, t, J=7.4 Hz), 1.4-1.8 (2H, m), 3.30 (2H, t, J=7.1 Hz), 7.15 (1H, s), 7.48 (2H, d, J=8.5 Hz), 7.66-7.96 (2H, m).

REFERENCE EXAMPLE 187

4-(3-methoxyphenyl)-N-propyl-1,3-thiazol-2-amine hydrobromide yields 71%. pale-yellow crystals. $^1$H NMR (300 MHz, DMSO-D6) δ: 0.95 (3H, t, J=7.4 Hz), 1.45-1.7 (2H, m), 3.32 (2H, t, J=7.1 Hz), 3.81 (3H, s), 6.85-7.0 (1H, m), 7.1-7.2 (1H, m), 7.25-7.4 (3H, m).

REFERENCE EXAMPLE 188

N-propyl-5-phenyl-1,3-thiazol-2-amine

To a solution of phenylacetaldehyde (1.20 g) in dichloromethane (10 mL) was added dropwise bromine (1.60 g) at 0° C. The temperature was allowed to return to room temperature and the mixture was stirred for 1 hr. The reaction mixture was poured into aqueous sodium sulfite, and the mixture was extracted with ethyl acetate. The ethyl acetate layer was concentrated, N-propylthiourea (1.18 g) and ethanol (30 mL) were added to the residue, and the mixture was stirred with heating under reflux for 1 hr. The reaction mixture was concentrated and poured into aqueous sodium hydrogencarbonate, and the mixture was extracted with ethyl acetate. The ethyl acetate layer was concentrated, and the residue was purified by silica gel column chromatography with ethyl acetate-hexane (gradient of 1:9 to 2:1 by volume ratio) to give the title compound (120 mg, yield 5%) as colorless crystals.

$^1$H NMR (300 MHz, Chloroform-D) δ: 1.02 (3H, t, J=7.4 Hz), 1.6-1.85 (2H, m), 3.28 (2H, t, J=6.7 Hz), 5.30 (1H, broad s), 7.20 (1H, t, J=7.3 Hz), 7.25-7.4 (3H, m), 7.4-7.45 (2H, m)

REFERENCE EXAMPLE 189

3-(3-methylphenoxy)benzaldehyde

A mixture of 3-bromobenzaldehyde (7.01 g, 37.9 mmol), m-cresol (4.51 g, 41.7 mmol), copper oxide (II) (4.53 g, 56.9 mmol), potassium carbonate (7.86 g, 56.9 mmol), pyridine (50 mL) and quinoline (25 mL) was stirred under a nitrogen atmosphere at 170° C. for 24 hrs. The reaction mixture was cooled and pyridine was evaporated under reduced pressure. Ethyl acetate was added to the residue, the insoluble material was filtered off, and the filtrate was washed with 1 M hydrochloric acid and saturated brine and dried over anhydrous sodium sulfate. The solvent was evaporated under reduced pressure and the residue was purified by silica gel column chromatography (hexane-10% ethyl acetate/hexane) to give the title compound (5.80 g, 72%) as a pale-brown oil.

MS: m/z 213 (MH$^+$).

REFERENCE EXAMPLE 190

[3-(3-methylphenoxy)phenyl]methanol 3-(3-Methylphenoxy)benzaldehyde (5.80 g, 27.3 mmol) was dissolved in a mixture of 1,2-dimethoxyethane (30 mL) and tetrahydrofuran (30 mL), sodium borohydride (0.567 g, 15.0 mmol) was added under ice-cooling and the mixture was stirred at the same temperature for 4 hrs. Dil. hydrochloric acid was added to the reaction mixture, and the mixture was extracted with ethyl acetate. The extract was washed with saturated brine, dried over anhydrous magnesium sulfate, and concentrated under reduced pressure. The residue was purified by silica gel column chromatography (20%-60% ethyl acetate/hexane) to give the title compound (4.83 g, yield 83%) as a pale-yellow oil.

$^1$H NMR (CDCl$_3$) δ 1.66 (t, J=6.0 Hz, 1H), 2.33 (s, 3H), 4.67 (d, J=6.0 Hz, 2H), 6.79-6.83 (m, 2H), 6.90-6.94 (m, 2H), 7.01 (s, 1H), 7.09 (d, J=7.5 Hz, 1H), 7.19-7.34 (m, 2H).

REFERENCE EXAMPLE 191

3-(4-methylphenoxy)benzaldehyde

The title compound was obtained as a yellow oil in the same manner as in Reference Example 189 from 3-bromobenzaldehyde and p-cresol. yield 83%.

MS: m/z 213 (MH$^+$).

REFERENCE EXAMPLE 192

[3-(4-methylphenoxy)phenyl]methanol

The title compound was obtained as a colorless oil in the same manner as in Reference Example 190 from 3-(4-methylphenoxy)benzaldehyde. yield 86%.

$^1$H NMR (CDCl$_3$) δ 1.62 (t, J=6.1 Hz, 1H), 2.34 (s, 3H), 4.66 (d, J=6.1 Hz, 2H), 6.88-6.94 (m, 3H), 6.98 (s, 1H), 7.06 (d, J=7.7 Hz, 1H), 7.14 (d, J=8.7 Hz, 2H), 7.30 (t, J=7.7 Hz, 1H).

REFERENCE EXAMPLE 193

(3-bromophenyl)(phenyl)methanone

Under ice-cooling, to a solution of 3-bromobenzoyl chloride (9.50 g, 43.3 mmol) in benzene (30 mL) was added aluminum chloride (III) (6.93 g, 52.0 mmol) by small portions, and the mixture was heated to 50° C. and stirred for 2 hrs. The reaction mixture was poured into ice water, and the mixture was extracted with ethyl acetate. The extract was washed with saturated brine, dried over magnesium sulfate, and the solvent was evaporated under reduced pressure. The residue was purified by silica gel column chromatography (hexane-5% ethyl acetate/hexane) to give the title compound (10.7 g, yield 95%) as pale-red crystals.

MS: m/z 261 (MH$^+$).

REFERENCE EXAMPLE 194

1-bromo-3-(1-phenylvinyl)benzene

To a suspension of methyltriphenylphosphonium iodide (13.3 g, 33.3 mmol) in tetrahydrofuran (80 mL) was added potassium t-butoxide (3.37 g, 30.0 mmol) by small portions under ice-cooling, and the mixture was stirred under a nitrogen atmosphere at the same temperature for 4 hrs. To the reaction mixture was added dropwise a solution of (3-bromophenyl)(phenyl)methanone (5.22 g, 20.0 mmol) in tetrahydrofuran (20 mL), and the mixture was further stirred under ice-cooling for 2 hrs. Water was added to the reaction mixture, and the mixture was extracted with ethyl acetate, washed with saturated brine, dried over magnesium sulfate, and the solvent was evaporated under reduced pressure. The residue was purified by silica gel column chromatography (hexane-10% ethyl acetate/hexane) to give the title compound (5.18 g, yield 92%) as a colorless oil.

MS: m/z 259 (MH$^+$).

REFERENCE EXAMPLE 195

3-(1-phenylvinyl)benzaldehyde

A solution of 1-bromo-3-(1-phenylvinyl)benzene (1.00 g, 3.86 mmol) in tetrahydrofuran (5 mL) was stirred under a nitrogen atmosphere at −78° C., and 1.6 M n-butyllithium/hexane solution (3 mL, 4.8 mmol) was added dropwise. After 1 hr, N,N-dimethylformamide (0.372 mL, 4.80 mmol) was added, and the mixture was further stirred at the same temperature for 2 hrs. Aqueous ammonium chloride solution was added to the reaction mixture, and the mixture was extracted with ethyl acetate. The extract was washed with saturated brine, dried over anhydrous magnesium sulfate, and concentrated under reduced pressure. The residue was purified by silica gel column chromatography (hexane-20% ethyl acetate/hexane) to give the title compound (0.626 g, yield 78%) as a colorless oil.

MS: m/z 209 (MH$^+$).

REFERENCE EXAMPLE 196

[3-(1-phenylvinyl)phenyl]methanol

The title compound was obtained as a colorless oil in the same manner as in Reference Example 190 from 3-(1-phenylvinyl)benzaldehyde. yield 84%.

$^1$H NMR (CDCl$_3$) δ 1.68 (t, J=5.3 Hz, 1H), 4.69 (d, J=5.3 Hz, 2H), 5.47 (s, 2H), 7.24-7.34 (m, 9H).

REFERENCE EXAMPLE 197

3-(2-methyl-1-naphthyl)benzaldehyde

1-Bromo-2-methylnaphthalene (3.32 g, 15.0 mmol) and (3-formylphenyl)boronic acid (2.13 g, 15.0 mmol) was dissolved in a mixture of 1 M sodium carbonate aqueous solution (30 mL), ethanol (15 mL) and toluene (30 mL) and, after argon substitution, tetrakis(triphenylphosphine)palladium (0) (0.867 g, 0.750 mmol) was added. The reaction mixture was stirred under an argon atmosphere at 80° C. for 24 hrs. The reaction mixture was cooled, diluted with water and ethyl acetate, and the insoluble material was filtered through celite. The organic layer of the filtrate was washed with saturated brine, dried over anhydrous magnesium sulfate, and concentrated under reduced pressure. The residue was purified by silica gel column chromatography (hexane-20% ethyl acetate/hexane) to give the title compound (2.39 g, yield 65%) as a pale-yellow oil.

MS: m/z 247 (MH$^+$).

REFERENCE EXAMPLE 198

[3-(2-methyl-1-naphthyl)phenyl]methanol

The title compound was obtained as a colorless viscous oil in the same manner as in Reference Example 190 from 3-(2-methyl-1-naphthyl)benzaldehyde. yield 81%.

$^1$H NMR (CDCl$_3$) δ 1.74 (t, J=5.3 Hz, 1H), 2.24 (s, 3H), 4.78 (d, J=5.3 Hz, 2H), 7.20-7.53 (m, 8H), 7.77-7.85 (m, 2H).

REFERENCE EXAMPLE 199

2',6'-dimethylbiphenyl-3-carbaldehyde

3-Bromobenzaldehyde (18.5 g, 100 mmol) and 2,6-dimethylphenylboronic acid (21.0 g, 140 mmol) were dissolved in a mixture of 1 M sodium carbonate aqueous solution (200 mL), ethanol (100 mL) and toluene (200 mL) and, after argon substitution, tetrakis(triphenylphosphine)palladium (0) (5.78 g, 5.00 mmol) was added. The reaction mixture was stirred under an argon atmosphere at 80° C. for 20 hrs. The reaction mixture was cooled, diluted with water and ethyl acetate, and the insoluble material was filtered through celite. The organic layer of the filtrate was washed with saturated brine, dried over anhydrous magnesium sulfate, and concentrated under reduced pressure. The residue was purified by silica gel column chromatography (hexane-10% ethyl acetate/hexane) to give the title compound (20.4 g, yield 97%) as a colorless oil.

MS: m/z 211 (MH$^+$).

REFERENCE EXAMPLE 200

(2',6'-dimethylbiphenyl-3-yl)methanol

2',6'-Dimethylbiphenyl-3-carbaldehyde (18.5 g, 88.0 mmol) was dissolved in a mixture of 1,2-dimethoxyethane (100 mL) and tetrahydrofuran (100 mL), and sodium borohydride (1.66 g, 44.0 mmol) was added under ice-cooling and the mixture was stirred at the same temperature for 3 hrs and then at room temperature for 3 hrs. Dil. hydrochloric acid was added to the reaction mixture, and the mixture was extracted with ethyl acetate. The extract was washed with saturated brine, dried over anhydrous magnesium sulfate, and concentrated under reduced pressure. The residue was purified by silica gel column chromatography (10%-50% ethyl acetate/hexane) to give the title compound (15.6 g, yield 83%) as a colorless oil.

$^1$H NMR (CDCl$_3$) δ 1.66 (t, J=5.9 Hz, 1H), 2.03 (s, 6H), 4.74 (d, J=5.9 Hz, 2H), 7.07-7.19 (m, 5H), 7.35 (d, J=7.5 Hz, 1H), 7.43 (t, J=7.5 Hz, 1H).

REFERENCE EXAMPLE 201

[3-(2,6-dimethylphenoxy)phenyl]methanol

A mixture of 3-bromobenzaldehyde (6.1 g, 32.7 mmol), 2,6-dimethylphenol (4.0 g, 32.7 mmol), copper oxide (II) (4.4 g, 55.6 mmol), potassium carbonate (9.0 g, 65.4 mmol), pyridine (40 mL) and m-xylene (20 mL) was stirred under a nitrogen atmosphere at 140° C. for 16 hrs. The reaction mixture was cooled, the insoluble material was filtered off, and the filtrate was concentrated under reduced pressure. The residue was partitioned between ethyl acetate and water. The organic layer was washed with saturated brine, dried (anhydrous sodium sulfate), and concentrated under reduced pressure to give crude 3-(2,6-dimethylphenoxy)benzaldehyde (including side product).

This compound was dissolved in methanol (74 mL), sodium borohydride (0.62 g, 16.4 mmol) was added under ice-cooling, and the mixture was stirred at the same temperature for 2 hrs. The reaction mixture was concentrated, and the residue was diluted with ethyl acetate, washed with 1N hydrochloric acid and saturated brine, dried, and concentrated under reduced pressure. The residue was purified by silica gel column chromatography (hexane/ethyl acetate=4/1-2/1) to give the title compound (1.7 g, yield 23%) as yellow crystals.

$^1$H NMR (CDCl$_3$) δ: 1.60 (1H, t, J=6.0 Hz), 2.12 (6H, s), 4.64 (2H, d, J=6.0 Hz), 6.65 (1H, dd, J=2.7, 8.1 Hz), 6.80 (1H, s), 6.97 (1H, d, J=7.5 Hz), 7.02-7.13 (3H, m), 7.22 (1H, d, J=7.5 Hz).

REFERENCE EXAMPLE 202

4-(benzyloxy)benzaldehyde

To a mixture of 4-hydroxybenzaldehyde (28.2 g, 231 mmol), potassium carbonate (47.9 g, 347 mmol), potassium iodide (3.84 g, 23.1 mmol) and N,N-dimethylformamide (280 mL) was added benzyl bromide (27.5 mL, 231 mmol) with stirring at room temperature, and the mixture was stirred at the same temperature for 24 hrs. The reaction mixture was diluted with ethyl acetate, washed successively with water, 1N hydrochloric acid and saturated brine, dried, and concentrated under reduced pressure to give the title compound (48 g, yield 98%) as beige crystals.

$^1$H NMR (CDCl$_3$) δ: 5.16 (2H, s), 7.08 (2H, d, J=8.7 Hz), 7.31-7.48 (5H, m), 7.84 (2H, d, J=8.7 Hz), 9.89 (1H, s).

REFERENCE EXAMPLE 203 tert-butyl (2E)-3-[4-(benzyloxy)phenyl]acrylate

To a solution (100 mL) of tert-butyl diethylphosphonoacetate (13.8 g, 51.8 mmol) in tetrahydrofuran was added 60% sodium hydride (2.45 g, 61.2 mmol) with stirring at 0° C., and the mixture was stirred at the same temperature for 15 min. Then, to this mixture was added dropwise a solution (138 mL) of 4-(benzyloxy)benzaldehyde (10 g, 47.1 mmol) in tetrahydrofuran with stirring at 0° C., and the mixture was stirred at room temperature for 3 hrs. The reaction mixture was concentrated, and the residue was diluted with ethyl acetate, and washed with 5% aqueous potassium hydrogensulfate solution and saturated brine. The ethyl acetate layer was dried over magnesium sulfate, and concentrated under reduced pressure to give the title compound (13.7 g, yield 94%) as colorless crystals.

$^1$H NMR (CDCl$_3$) δ: 1.53 (9H, s), 5.09 (2H, s), 6.24 (1H, d, J=15.9 Hz), 6.96 (2H, d, J=9.0 Hz), 7.32-7.49 (7H, m), 7.54 (1H, d, J=15.9 Hz).

REFERENCE EXAMPLE 204 tert-butyl 3-(4-hydroxyphenyl)propanoate

A mixture of tert-butyl (2E)-3-[4-(benzyloxy)phenyl]acrylate (13.3 g, 42.8 mmol), 10% Pd carbon (1.3 g), ethanol (100 mL) and tetrahydrofuran (30 mL) was stirred under a hydrogen atmosphere for 2 hrs. The catalyst was filtered off, and the filtrate was concentrated under reduced pressure to give the title compound (7.5 g, yield 79%) as colorless crystals.

$^1$H NMR (CDCl$_3$) δ: 1.41 (9H, s), 2.50 (2H, t, J=7.8 Hz), 2.83 (2H, t, J=7.8 Hz), 6.74 (2H, d, J=8.7 Hz), 7.06 (2H, d, J=8.7 Hz).

REFERENCE EXAMPLE 205 tert-butyl 3-[4-[(3-bromobenzyl)oxy]phenyl]propanoate

To a solution (100 mL) of tert-butyl 3-(4-hydroxyphenyl)propanoate (5.5 g, 24.7 mmol) in N,N-dimethylformamide was added 60% sodium hydride (1.09 g, 27.2 mmol) with stirring at 0° C., and the mixture was stirred at the same temperature for 15 min. Then, 3-bromobenzylbromide (6.55 g, 25.91 mmol) was added to this mixture with stirring at 0° C., and the mixture was stirred at room temperature for 12 hrs. The reaction mixture was diluted with ethyl acetate, and washed with water and saturated brine. The ethyl acetate layer was dried over magnesium sulfate, and concentrated under reduced pressure to give the title compound (7.5 g, yield 78%) as a colorless powder.

$^1$H NMR (CDCl$_3$) δ: 1.41 (9H, s), 2.50 (2H, t, J=7.8 Hz), 2.85 (2H, t, J=7.8 Hz), 5.01 (2H, s), 6.87 (2H, d, J=8.7 Hz), 7.12 (2H, d, J=8.7 Hz), 7.24 (1H, m), 7.34 (1H, d, J=7.5 Hz), 7.44 (1H, m), 7.59 (1H, s).

REFERENCE EXAMPLE 206

2',6'-diethylbiphenyl-3-carbaldehyde

A mixture of 1,3-diethyl-2-bromobenzene (3.87 g, 18.2 mmol), 3-formylphenylboronic acid (3.0 g, 20.0 mmol), tetrakistriphenylphosphinepalladium (0.84 g, 0.73 mmol), sodium carbonate (5.79 g, 54.6 mmol), water (20 mL), ethanol (20 mL) and toluene (200 mL) was heated under reflux overnight under an argon atmosphere. The reaction mixture was cooled, diluted with ethyl acetate, washed with water, dried, and concentrated under reduced pressure. The residue was purified by silica gel column chromatography (hexane-hexane/ethyl acetate=5/1) to give the title compound (3.48 g, yield 81%) as a yellow oil.

$^1$H NMR (CDCl$_3$) δ: 1.01 (6H, t, J=7.5 Hz), 2.30 (4H, q, J=7.5 Hz), 7.16 (2H, d, J=7.5 Hz), 7.31 (1H, m), 7.47 (1H, dt, J=1.5, 7.5 Hz), 7.60 (1H, d, J=7.5 Hz), 7.71 (1H, t, J=1.5 Hz), 7.89 (1H, dt, J=1.5, 7.5 Hz), 10.06 (1H, s).

REFERENCE EXAMPLE 207

(2',6'-diethylbiphenyl-3-yl)methanol

To a solution of 2',6'-diethylbiphenyl-3-carbaldehyde (3.48 g, 14.6 mmol) in a mixture of methanol (35 mL) and tetrahydrofuran (35 mL) was added sodium borohydride (0.28 g, 7.3 mmol) under ice-cooling, and the mixture was stirred at the same temperature for 1 hr. The reaction mixture was adjusted to pH 3 with 1N hydrochloric acid, diluted with ethyl acetate, washed successively with water and saturated brine, dried (magnesium sulfate), and concentrated under reduced pressure. The residue was purified by silica gel column chromatography (hexane/ethyl acetate=10/1-2/1) to give the title compound (2.82 g, yield 80%) as a colorless oil.

¹H NMR (CDCl₃) δ: 1.02 (6H, t, J=7.5 Hz), 1.68 (1H, t, J=5.7 Hz), 2.31 (4H, q, J=7.5 Hz), 4.74 (2H, d, J=5.7 Hz), 7.08-7.21 (4H, m), 7.27 (1H, m), 7.33-7.46 (2H, m).

REFERENCE EXAMPLE 208

2',6'-difluorobiphenyl-3-carbaldehyde

The title compound was synthesized in the same manner as in Reference Example 206 from 1,3-difluoro-2-bromobenzene and 3-formylphenylboronic acid. colorless oil (3.0 g, yield 93%).

¹H NMR (CDCl₃) δ: 6.97-7.09 (2H, m), 7.34 (1H, m), 7.64 (1H, t, J=7.5 Hz), 7.75 (1H, m), 7.93 (1H, dt, J=1.5, 7.5 Hz), 7.99 (1H, m), 10.08 (1H, s).

REFERENCE EXAMPLE 209

(2',6'-difluorobiphenyl-3-yl)methanol

The title compound was synthesized as a colorless oil in the same manner as in Reference Example 207 from 2',6'-difluorobiphenyl-3-carbaldehyde. colorless crystals (yield 90%).

¹H NMR (CDCl₃) δ: 1.72 (1H, br), 4.76 (2H, s), 6.92-7.04 (2H, m), 7.29 (1H, m), 7.35-7.51 (4H, m).

REFERENCE EXAMPLE 210 methyl 3-anilinobenzoate

A mixture of methyl 3-bromobenzoate (5.87 g, 27.3 mmol), aniline (3.73 mL, 41.0 mmol), cesium carbonate (12.5 g, 38.2 mmol), tris(dibenzylideneacetone)dipalladium (0) (1.0 g, 1.09 mmol), rac-2,2'-bis(diphenylphosphino)-1,1'-binaphthyl (1.02 g, 1.64 mmol) and toluene (60 mL) was stirred under a nitrogen atmosphere at 80° C. for 16 hrs. The reaction mixture was cooled, washed with water and saturated brine, dried over magnesium sulfate, and concentrated under reduced pressure. The residue was purified by silica gel column chromatography (hexane/ethyl acetate=10/1-4/1) to give the title compound (2.13 g, yield 34%) as pale-yellow crystalsitle compound.

¹H NMR (CDCl₃) δ: 3.90 (3H, s), 5.79 (1H, s), 6.98 (1H, t, J=7.5 Hz), 7.09 (2H, d, J=7.5 Hz), 7.21-7.36 (4H, m), 7.57 (1H, dt, J=1.5, 7.5 Hz), 7.72 (1H, t, J=1.8 Hz).

REFERENCE EXAMPLE 211

(3-anilinophenyl)methanol

To a solution (22 mL) of methyl 3-anilinobenzoate (2.13 g, 9.37 mmol) in tetrahydrofuran was added lithium aluminum hydride (0.36 g, 9.37 mmol) with stirring at 0° C., and the mixture was stirred at the same temperature for 2 hrs. Sodium sulfate 10 hydrate (9.1 g, 28.1 mmol) was gradually added to the reaction mixture and the mixture was stirred at room temperature for 5 hrs. The insoluble material was filtered off, and the filtrate was concentrated under reduced pressure. The residue was purified by silica gel column chromatography (hexane/ethyl acetate=10/1-4/1) to give the title compound (1.12 g, yield 60%) as a colorless oil.

¹H NMR (CDCl₃) δ: 1.61 (1H, t, J=5.4 Hz), 4.65 (2H, d, J=3.6 Hz), 5.73 (1H, s), 6.88-7.04 (3H, m), 7.05-7.13 (3H, m), 7.22-7.33 (3H, m).

REFERENCE EXAMPLE 212

5-(2-(4-((3-phenoxybenzyl)oxy)phenyl)ethyl)-1H-tetrazole

A solution of 3-(4-((3-phenoxybenzyl)oxy)phenyl)propanenitrile (0.5 g, 1.52 mmol), sodium azide (0.49 g, 7.54 mmol) and ammonium chloride (0.41 g, 7.66 mmol) in N,N-dimethylformamide (20 ml) was stirred at 110° C. for 28 hrs. The reaction solution was diluted with ethyl acetate, washed successively with aqueous citric acid solution, water and aqueous sodium chloride solution, dried over magnesium sulfate, and concentrated under reduced pressure. The obtained residue was subjected to silica gel chromatography (ethyl acetate:hexane=2:3-2:1) to give an oil, which was crystallized from ethyl acetate-tetrahydrofuran to give the title compound (0.24 g, 43%).

MS 373.1 (MH⁺).

REFERENCE EXAMPLE 213

3-(2-(4-((3-phenoxybenzyl)oxy)phenyl)ethyl)-1,2,4-oxadiazol-5(4H)-one

A solution of (1Z)-N-hydroxy-3-(4-((3-phenoxybenzyl)oxy)phenyl)propanimideamide (0.50 g, 1.38 mmol) and carbonyldiimidazole (0.56 g, 3.45 mmol) in tetrahydrofuran (20 ml) was stirred at room temperature for 5 hrs. The reaction solution was diluted with ethyl acetate, washed successively with aqueous citric acid solution, water and aqueous sodium chloride solution, dried over magnesium sulfate, and concentrated under reduced pressure. The obtained residue was subjected to silica gel chromatography (ethyl acetate:hexane=1:1-ethyl acetate-ethyl acetate:methanol=10:1) to give pale-yellow crystals (0.165 g). Then, the crystals were dissolved in dioxane (6 ml) and stirred at 110° C. for 1 hr. The reaction solution was diluted with ethyl acetate, washed successively with aqueous citric acid solution, water and aqueous sodium chloride solution, dried over magnesium sulfate, and concentrated under reduced pressure. The obtained residue was subjected to silica gel chromatography (ethyl acetate:hexane=1:1) and recrystallized from ethyl acetate-hexane to give the title compound (94 mg, 74%) as colorless prism crystals.

MS 389.2 (MH⁺)

REFERENCE EXAMPLE 214

4-(2-{4-[(3-phenoxybenzyl)oxy]phenyl}ethyl)-3H-1,2,3,5-oxathiadiazole 2-oxide A solution of (1Z)-N-hydroxy-3-(4-((3-phenoxybenzyl)oxy)phenyl)propanimideamide (0.50 g, 1.38 mmol) and thionyl chloride (0.105 ml, 1.44 mmol) in dimethylacetamide (20 ml) was stirred at room temperature for 5 hrs. The reaction solution was diluted with ethyl acetate, washed successively with water and aqueous sodium chloride solution, dried over magnesium sulfate, and concentrated under reduced pressure. The obtained residue was subjected to silica gel chromatography (ethyl acetate:hexane=1:2-2:3) to give the title compound (75 mg, 13%) as a pale-yellow oil.

MS 409.1 (MH⁺)

REFERENCE EXAMPLE 215

4-isopropyl-N-(3-methylbutyl)-1,3-thiazol-2-amine

A solution of 3-methyl-2-butanone (2.64 g) in methanol (30 ml) was cooled to −30° C. bromine (4.8 g) was added, and heated to room temperature with stirring. To the obtained colorless solution were added N-(3-methylbutyl)thiourea (2.92 g) and sodium acetate (2.40 g) and the mixture was stirred with heating under reflux for 2 hrs. The reaction mixture was concentrated, diluted with ethyl acetate and washed with water. The ethyl acetate layer was concentrated, and the residue was purified by silica gel column chromatography with ethyl acetate-hexane (gradient of 1:9 to 2:1 by volume ratio) to give the title compound (0.90 g, yield 21%) as a yellow oil.
$^1$H NMR (300 MHz, Chloroform-D) δ: 0.94 (6H, d, J=6.6 Hz), 1.23 (6H, d, J=6.8 Hz), 1.45-1.8 (3H, m), 2.75-2.9 (1H, m), 3.1-3.25 (2H, m), 5.0-5.25 (1H, m), 6.05 (1H, d, J=0.9 Hz).

REFERENCE EXAMPLE 216 methyl 2'-formyl-6'-methylbiphenyl-3-carboxylate

A mixture of 2-bromo-3-methylbenzaldehyde (0.30 g, 1.51 mmol), tris(dibenzylidenacetone)dipalladium (0) (0.055 g, 0.060 mmol), 2-(dicyclohexylphosphino)biphenyl (0.032 g, 0.091 mmol), tripotassium phosphate (0.64 g, 3.0 mmol), 3-(methoxycarbonylphenyl)boronic acid (0.35 g, 1.96 mmol) and toluene (6 mL) was stirred under an argon atmosphere at 90° C. for 17 hrs. The reaction mixture was cooled, diluted with ethyl acetate, washed with water and saturated brine, dried (anhydrous sodium sulfate), and concentrated under reduced pressure. The residue was purified by silica gel column chromatography (hexane-hexane/ethyl acetate=4/1) to give the title compound (0.25 g, yield 65%) as a yellow oil.
$^1$H NMR (CDCl$_3$) δ: 2.12 (3H, s), 3.93 (3H, s), 7.39-7.48 (2H, m), 7.50-7.60 (2H, m), 7.87 (1H, dd, J=0.9, 7.8 Hz), 7.95 (1H, t, J=1.5 Hz), 8.12 (1H, dt, J=1.5, 7.8 Hz), 9.68 (1H, s).

REFERENCE EXAMPLE 217 methyl 2'-methyl-6'-propylbiphenyl-3-carboxylate

To a suspension (21 mL) of ethyltriphenylphosphonium bromide (1.55 g, 4.13 mmol) in tetrahydrofuran was added sodium hydride (0.14 g, 3.58 mmol) at room temperature with stirring, and the mixture was stirred at the same temperature for 20 min. A solution (20 mL) of methyl 2'-formyl-6'-methylbiphenyl-3-carboxylate (0.70 g, 2.75 mmol) in tetrahydrofuran was added and the mixture was stirred at 70° C. for 3 hrs. The reaction mixture was cooled, diluted with ethyl acetate, washed with water and saturated brine, dried, and concentrated under reduced pressure. Then a mixture of the obtained residue, 10% Pd carbon (0.1 g) and methanol (14 mL) was stirred under a hydrogen atmosphere for 2 hrs. The catalyst was filtered off, and the filtrate was concentrated under reduced pressure. The residue was purified by silica gel column chromatography (hexane-hexane/ethyl acetate=4/1) to give the title compound (0.63 g, yield 85%) as a colorless oil.
$^1$H NMR (CDCl$_3$) δ: 0.75 (3H, t, J=7.2 Hz), 1.33-1.50 (2H, m), 1.98 (3H, s), 2.23-2.32 (2H, m), 3.92 (3H, s), 7.08-7.16 (2H, m), 7.22 (1H, t, J=7.5 Hz), 7.36 (1H, m), 7.50 (1H, t, J=7.5 Hz), 7.86 (1H, t, J=1.5 Hz), 8.03 (1H, m).

REFERENCE EXAMPLE 218

(2'-methyl-6'-propylbiphenyl-3-yl)methanol

To a solution (6.3 mL) of methyl 2'-methyl-6'-propylbiphenyl-3-carboxylate (0.63 g, 2.35 mmol) in tetrahydrofuran was added lithium aluminum hydride (0.089 g, 2.35 mmol) with stirring at 0° C., and the mixture was stirred at the same temperature for 2 hrs. Sodium sulfate 10 hydrate (1.5 g, 4.7 mmol) was gradually added to the reaction mixture, and the mixture was stirred at room temperature for 5 hrs. The insoluble material was filtered off, and the filtrate was concentrated under reduced pressure. The residue was purified by silica gel column chromatography (hexane/ethyl acetate=10/1-2/1) to give the title compound (0.50 g, yield 88%) as a colorless oil.
$^1$H NMR (CDCl$_3$) δ: 0.77 (3H, t, J=7.5 Hz), 1.36-1.51 (2H, m), 1.65 (1H, t, J=5.4 Hz), 2.00 (3H, s), 2.25-2.34 (2H, m), 4.74 (2H, d, J=5.4 Hz), 7.06-7.16 (4H, m), 7.20 (1H, t, J=7.5 Hz), 7.35 (1H, m), 7.42 (1H, t, J=7.5 Hz).

REFERENCE EXAMPLE 219 methyl 2'-isobutyl-6'-methylbiphenyl-3-carboxylate

The title compound was synthesized in the same manner as in Reference Example 217 from methyl 2'-formyl-6'-methylbiphenyl-3-carboxylate and isopropyltriphenylphosphonium iodide. colorless oil (yield 45%).
$^1$H NMR (CDCl$_3$) δ: 0.68-0.74 (6H, m), 1.61 (1H, m), 1.98 (3H, s), 2.20 (2H, d, J=7.5 Hz), 3.91 (3H, s), 7.05-7.12 (2H, m), 7.19 (1H, t, J=7.5 Hz), 7.33 (1H, m), 7.48 (1H, t, J=7.5 Hz), 7.83 (1H, t, J=1.8 Hz), 8.01 (1H, m).

REFERENCE EXAMPLE 220

(2'-isobutyl-6'-methylbiphenyl-3-yl)methanol

The title compound was synthesized in the same manner as in Reference Example 218 from methyl 2'-isobutyl-6'-methylbiphenyl-3-carboxylate. colorless oil (yield 90%).
$^1$H NMR (CDCl$_3$) δ: 0.69-0.76 (6H, m), 1.58-1.72 (2H, m), 2.00 (3H, s), 2.22 (2H, d, J=7.2 Hz), 4.74 (2H, d, J=4.2 Hz), 7.04-7.15 (4H, m), 7.19 (1H, t, J=7.2 Hz), 7.34 (1H, m), 7.41 (1H, t, J=7.2 Hz).

REFERENCE EXAMPLE 221 methyl 2'-ethyl-6'-methylbiphenyl-3-carboxylate

The title compound was synthesized in the same manner as in Reference Example 217 from methyl 2'-formyl-6'-methylbiphenyl-3-carboxylate and methyltriphenylphosphonium bromide. colorless oil (yield 82%).
$^1$H NMR (CDCl$_3$) δ: 1.01 (3H, t, J=7.5 Hz), 1.99 (3H, s), 2.32 (2H, q, J=7.5 Hz), 3.92 (3H, s), 7.08-7.18 (2H, m), 7.24 (1H, t, J=7.5 Hz), 7.37 (1H, m), 7.50 (1H, t, J=7.5 Hz), 7.87 (1H, m), 8.03 (1H, m).

REFERENCE EXAMPLE 222

(2'-ethyl-6'-methylbiphenyl-3-yl)methanol

The title compound was synthesized in the same manner as in Reference Example 218 from methyl 2'-ethyl-6'-methylbiphenyl-3-carboxylate. colorless oil (yield 91%).

$^1$H NMR (CDCl$_3$) δ: 1.02 (3H, t, J=7.5 Hz), 1.67 (1H, t, J=6.0 Hz), 2.00 (3H, s), 2.34 (2H, q, J=7.5 Hz), 4.74 (2H, d, J=6.0 Hz), 7.07-7.17 (4H, m), 7.22 (1H, t, J=7.5 Hz), 7.36 (1H, m), 7.42 (1H, t, J=7.5 Hz).

REFERENCE EXAMPLE 223

(2,2',6'-trimethylbiphenyl-3-yl)methanol

The title compound was obtained as a colorless oil in the same manner as in Reference Example 199 and Reference Example 200. yield 19%.
$^1$H-NMR (CDCl$_3$) δ 1.94 (6H, s), 1.97 (3H, s), 4.69 (2H, d, J=6.0 Hz), 7.01 (1H, s), 7.06-7.32 (5H, m).

EXAMPLE 202A methyl 3-[4-[(2',6'-dimethylbiphenyl-3-yl)methoxy]-2-methylphenyl]propionate The title compound was obtained in the same manner as in Reference Example 31 from methyl 3-(4-hydroxy-2-methylphenyl)propionate and (2',6'-dimethylbiphenyl-3-yl)methanol. yield 67%. oil.
$^1$H NMR (CDCl$_3$) δ 2.01 (s, 6H), 2.28 (s, 3H), 2.52-2.57 (m, 2H), 2.85-2.90 (m, 2H), 3.67 (s, 3H), 5.08 (s, 2H), 6.70-6.79 (m, 2H), 7.02-7.20 (m, 6H), 7.37-7.46 (m, 2H).

EXAMPLE 203

3-[4-[(2',6'-dimethylbiphenyl-3-yl)methoxy]-2-methylphenyl]propionic acid

The title compound was obtained as colorless crystals in the same manner as in Reference Example 38 from methyl 3-[4-[(2',6'-dimethylbiphenyl-3-yl)methoxy]-2-methylphenyl]propionate. yield 56%.
$^1$H NMR (CDCl$_3$) δ 2.01 (s, 6H), 2.28 (s, 3H), 2.60 (t, J=7.8 Hz, 2H), 2.89 (t, J=7.8 Hz, 2H), 5.08 (s, 2H), 6.73-6.80 (m, 2H), 7.04-7.20 (m, 6H), 7.38-7.46 (m, 2H).

EXAMPLE 204 ethyl 3-[4-[(2',6'-dimethylbiphenyl-3-yl)methoxy]-2-fluorophenyl]propionate

The title compound was obtained in the same manner as in Reference Example 31 from ethyl 3-(2-fluoro-4-hydroxyphenyl)propionate and (2',6'-dimethylbiphenyl-3-yl)methanol. yield 56%. oil.
$^1$H NMR (CDCl$_3$) δ 1.23 (t, J=7.2 Hz, 3H), 2.00 (s, 6H), 2.57 (t, J=7.7 Hz, 2H), 2.90 (t, J=7.7 Hz, 2H), 4.12 (q, J=7.2 Hz, 2H), 5.07 (s, 2H), 6.63-6.70 (m, 2H), 7.06-7.19 (m, 6H), 7.37-7.47 (m, 2H).

EXAMPLE 205

3-[4-[(2',6'-dimethylbiphenyl-3-yl)methoxy]-2-fluorophenyl]propionic acid

The title compound was obtained as colorless crystals in the same manner as in Reference Example 38 from ethyl 3-[4-[(2',6'-dimethylbiphenyl-3-yl)methoxy]-2-fluorophenyl]propionate. yield 52%.
$^1$H NMR (CDCl$_3$) δ 2.00 (s, 6H), 2.63 (t, J=7.6 Hz, 2H), 2.90 (t, J=7.6 Hz, 2H), 5.06 (s, 2H), 6.63-6.70 (m, 2H), 7.06-7.18 (m, 6H), 7.36-7.46 (m, 2H).

EXAMPLE 206 ethyl 3-[4-[(2',6'-dimethylbiphenyl-3-yl)methoxy]-2-methoxyphenyl]propionate

The title compound was obtained as a colorless oil in the same manner as in Reference Example 31 from ethyl 3-(4-hydroxy-2-methoxyphenyl)propionate and (2',6'-dimethylbiphenyl-3-yl)methanol. yield 24%. oil.
$^1$H NMR (CDCl$_3$) δ 1.23 (t, J=7.2 Hz, 3H), 2.01 (s, 6H), 2.55 (t, J=7.7 Hz, 2H), 2.86 (t, J=7.7 Hz, 2H), 3.77 (s, 3H), 4.12 (q, J=7.2 Hz, 2H), 5.08 (s, 2H), 6.45-6.51 (m, 2H), 7.02 (d, J=8.1 Hz, 1H), 7.09-7.14 (m, 5H), 7.39-7.47 (m, 2H).

EXAMPLE 207

3-[4-[(2',6'-dimethylbiphenyl-3-yl)methoxy]-2-methoxyphenyl]propionic acid

The title compound was obtained as a colorless oil in the same manner as in Reference Example 38 from ethyl 3-[4-[(2',6'-dimethylbiphenyl-3-yl)methoxy]-2-methoxyphenyl]propionate. yield 69%.
$^1$H NMR (CDCl$_3$) δ 2.01 (s, 6H), 2.62 (t, J=7.6 Hz, 2H), 2.87 (t, J=7.6 Hz, 2H), 3.77 (s, 3H), 5.08 (s, 2H), 6.45-6.52 (m, 2H), 7.02-7.21 (m, 6H), 7.38-7.47 (m, 2H).

EXAMPLE 208 methyl 3-[2-chloro-4-[(2',6'-dimethylbiphenyl-3-yl)methoxy]phenyl]propionate

The title compound was obtained as a colorless oil in the same manner as in Reference Example 31 from methyl 3-(2-chloro-4-hydroxyphenyl)propionate and (2',6'-dimethylbiphenyl-3-yl)methanol. yield 69%.
$^1$H NMR (CDCl$_3$) δ 2.01 (6H, s), 2.61 (2H, t, J=7.7 Hz), 2.98 (2H, t, J=7.7 Hz), 3.67 (3H, s), 5.08 (2H, s), 6.81 (1H, dd, J=8.5, 2.6 Hz), 6.98 (1H, d, J=2.6 Hz), 7.07-7.20 (6H, m), 7.35-7.47 (2H, m).

EXAMPLE 209

3-[2-chloro-4-[(2',6'-dimethylbiphenyl-3-yl)methoxy]phenyl]propionic acid

The title compound was obtained as a colorless oil in the same manner as in Reference Example 38 from methyl 3-[2-chloro-4-[(2',6'-dimethylbiphenyl-3-yl)methoxy]phenyl]propionate. yield 85%.
$^1$H NMR (CDCl$_3$) δ 2.01 (6H, s), 2.66 (2H, t, J=7.7 Hz), 2.99 (2H, t, J=7.7 Hz), 5.08 (2H, s), 6.80-6.83 (1H, m), 6.96-7.01 (1H, m), 7.09-7.18 (6H, m), 7.37-7.47 (2H, m).

EXAMPLE 210 methyl 3-[4-[(2',6'-dimethylbiphenyl-4-yl)methoxy]phenyl]propionate

The title compound was obtained as a colorless oil in the same manner as in Reference Example 31 from methyl 3-(4-hydroxyphenyl)propionate and (2',6'-dimethylbiphenyl-4-yl)methanol. yield 56%.
$^1$H NMR (CDCl$_3$) δ 2.04 (6H, s), 2.62 (2H, t, J=7.7 Hz), 2.91 (2H, t, J=7.7 Hz), 3.67 (3H, s), 5.08 (2H, s), 6.95 (2H, d, J=8.7 Hz), 7.07-7.20 (7H, m), 7.49 (2H, d, J=8.1 Hz).

EXAMPLE 211

3-[4-[(2',6'-dimethylbiphenyl-4-yl)methoxy]phenyl]
propionic acid

The title compound was obtained as colorless crystals in the same manner as in Reference Example 38 from methyl 3-[4-[(2',6'-dimethylbiphenyl-4-yl)methoxy]phenyl]propionate. yield 52%.
$^1$H NMR (CDCl$_3$) δ 2.04 (6H, s), 2.67 (2H, t, J=7.6 Hz), 2.93 (2H, t, J=7.6 Hz), 5.08 (2H, s), 6.96 (2H, d, J=8.7 Hz), 7.07-7.20 (7H, m), 7.49 (2H, d, J=8.1 Hz).

EXAMPLE 212 ethyl 3-[4-[(2',6'-dimethylbiphenyl-4-yl)methoxy]-2-fluorophenyl]propionate

The title compound was obtained as a colorless oil in the same manner as in Reference Example 31 from ethyl 3-(2-fluoro-4-hydroxyphenyl)propionate and (2',6'-dimethylbiphenyl-4-yl)methanol. yield 37%
$^1$H NMR (CDCl$_3$) δ 1.24 (3H, t, J=7.1 Hz), 2.03 (6H, s), 2.60 (2H, t, J=7.6 Hz), 2.92 (2H, t, J=7.6 Hz), 4.13 (2H, q, J=7.1 Hz), 5.07 (2H, s), 6.64-6.80 (2H, m), 7.07-7.22 (6H, m), 7.47 (2H, d, J=7.9 Hz).

EXAMPLE 213

3-[4-[(2',6'-dimethylbiphenyl-4-yl)methoxy]-2-fluorophenyl]propionic acid

The title compound was obtained as colorless crystals in the same manner as in Reference Example 38 from ethyl 3-[4-[(2',6'-dimethylbiphenyl-4-yl)methoxy]-2-fluorophenyl]propionate. yield 33%.
$^1$H NMR (CDCl$_3$) δ 2.03 (6H, s), 2.67 (2H, t, J=7.6 Hz), 2.94 (2H, t, J=7.6 Hz), 5.07 (2H, s), 6.68-6.79 (2H, m), 7.07-7.21 (6H, m), 7.48 (2H, d, J=8.1 Hz).

EXAMPLE 214 methyl 3-[4-[(2-benzylbenzyl)oxy]phenyl]propionate

The title compound was obtained as an oil in the same manner as in Reference Example 5 from 1-benzyl-2-(bromomethyl)benzene and methyl 3-(4-hydroxyphenyl)propionate. yield 16%.
$^1$H NMR (CDCl$_3$) δ 2.59 (t, J=7.8 Hz, 2H), 2.89 (t, J=7.8 Hz, 2H), 3.66 (s, 3H), 4.09 (s, 2H), 4.95 (s, 2H), 6.81 (d, J=8.1 Hz, 2H), 7.07-7.29 (m, 10H), 7.46-7.43 (m, 1H).

EXAMPLE 215

3-[4-[(2-benzylbenzyl)oxy]phenyl]propionic acid

The title compound was obtained as colorless crystals in the same manner as in Reference Example 38 from methyl 3-[4-[(2-benzylbenzyl)oxy]phenyl]propionate. yield 52%.
$^1$H NMR (CDCl$_3$) 2.64 (t, J=7.7 Hz, 2H), 2.90 (t, J=7.7 Hz, 2H), 4.09 (s, 2H), 4.95 (s, 2H), 6.78-6.83 (m, 2H), 7.08-7.32 (m, 10H), 7.40-7.46 (m, 1H).

EXAMPLE 216 methyl 3-[4-[[4-[[ethyl(4-phenyl-1,3-thiazol-2-yl)amino]methyl]benzyl]oxy]phenyl]propionate The title compound was obtained in the same manner as in Reference Example 31 from methyl 3-(4-hydroxyphenyl) propionate and [4-[[ethyl(4-phenyl-1,3-thiazol-2-yl)amino]methyl]phenyl]methanol. yield 60%. oil.
$^1$H NMR (CDCl$_3$) δ 1.21-1.28 (m, 3H), 2.59 (t, J=7.7 Hz, 2H), 2.89 (t, J=7.7 Hz, 2H), 3.51 (q, J=7.2 Hz, 2H), 3.66 (s, 3H), 4.77 (s, 2H), 5.02 (s, 2H), 6.71 (s, 1H), 6.88-6.91 (m, 2H), 7.08-7.12 (m, 2H), 7.24-7.41 (m, 7H), 7.83-7.77 (m, 2H).

EXAMPLE 217

3-[4-[[4-[[ethyl(4-phenyl-1,3-thiazol-2-yl)amino]methyl]benzyl]oxy]phenyl]propionic acid The title compound was obtained as colorless crystals in the same manner as in Reference Example 38 from methyl 3-[4-[[4-[[ethyl(4-phenyl-1,3-thiazol-2-yl)amino]methyl]benzyl]oxy]phenyl]propionate. yield 63%.
MS: m/z 473.1 (M+1)$^+$.

EXAMPLE 218 methyl 3-[2-methyl-4-[[4-[[(4-phenyl-1,3-thiazol-2-yl)(propyl)amino]methyl]benzyl]oxy]phenyl]propionate The title compound was obtained in the same manner as in Reference Example 31 from methyl 3-(4-hydroxy-2-methylphenyl)propionate and [4-[[(4-phenyl-1,3-thiazol-2-yl)(propyl)amino]methyl]phenyl]methanol. yield 58%. oil.
$^1$H NMR (CDCl$_3$) δ 0.95 (t, J=7.5 Hz, 3H) 1.60-1.75 (m, 2H), 2.29 (s, 3H), 2.55 (t, J=8.4 Hz, 2H), 2.88 (t, J=8.4 Hz, 2H), 3.39-3.44 (m, 2H) 3.68 (s, 3H), 4.80 (s, 2H), 5.00 (s, 2H), 6.69-6.78 (m, 3H), 7.04 (d, J=8.4 Hz, 1H), 7.26-7.39 (m, 7H), 7.84-7.87 (m, 2H).

EXAMPLE 219

3-[2-methyl-4-[[4-[[(4-phenyl-1,3-thiazol-2-yl)(propyl)amino]methyl]benzyl]oxy]phenyl]propionic acid The title compound was obtained as a colorless crystals in the same manner as in Reference Example 38 from methyl 3-[2-methyl-4-[[4-[[(4-phenyl-1,3-thiazol-2-yl)(propyl)amino]methyl]benzyl]oxy]phenyl]propionate. yield 57%.
MS: m/z 501.1 (M+1)$^+$.

EXAMPLE 220 methyl 3-[4-[[4-[[(5-methyl-4-phenyl-1,3-thiazol-2-yl)(propyl)amino]methyl]benzyl]oxy]phenyl]propionate The title compound was obtained in the same manner as in Reference Example 31 from methyl 3-(4-hydroxyphenyl) propionate and [4-[[(5-methyl-4-phenyl-1,3-thiazol-2-yl)(propyl)amino]methyl]phenyl]methanol. yield 32%. oil.
$^1$H NMR (CDCl$_3$) δ 0.91 (t, J=7.4 Hz, 3H), 1.60-1.72 (m, 2H), 2.41 (s, 3H), 2.59 (t, J=7.7 Hz, 2H), 2.89 (t, J=7.7 Hz, 2H), 3.32-3.37 (m, 2H), 3.66 (s, 3H), 4.71 (s, 2H), 5.02 (s, 2H), 6.88-6.92 (m, 2H), 7.10-7.13 (m, 2H) 7.25-7.40 (m, 7H), 7.62-7.65 (m, 2H).

EXAMPLE 221

3-[4-[[4-[[(5-methyl-4-phenyl-1,3-thiazol-2-yl)(propyl)amino]methyl]benzyl]oxy]phenyl]propionic acid The title compound was obtained as a colorless crystals in the same manner as in Reference Example 38 from methyl 3-[4-[[4-[[(5-methyl-4-phenyl-1,3-thiazol-2-yl)(propyl) amino]methyl]benzyl]oxy]phenyl]propionate. yield 59%. MS: m/z 501.1 (M+1)⁺.

EXAMPLE 222 methyl 3-[4-[[4-[[4,5-dihydronaphtho[1,2-d][1,3] thiazol-2-yl(propyl)amino]methyl]benzyl]oxy]phenyl]propionate The title compound was obtained in the same manner as in Reference Example 31 from methyl 3-(4-hydroxyphenyl) propionate and [4-[[(4,5-dihydronaphtho[1,2-d][1,3]thiazol-2-yl(propyl)amino]methyl]phenyl]methanol. yield 34%. oil.
¹H NMR (CDCl₃) δ 0.93 (t, J=7.4 Hz, 3H) 1.66-1.74 (m, 2H), 2.59 (t, J=7.7 Hz, 2H), 2.82-2.91 (m, 4H), 3.02 (t, J=7.7 Hz, 2H), 3.35-3.40 (m, 2H), 3.66 (s, 3H), 4.76 (s, 2H), 5.02 (s, 2H), 6.88-6.92 (m, 2H), 7.09-7.40 (m, 9H), 7.78 (d, J=7.5 Hz, 1H).

EXAMPLE 223

3-[4-[[4-[[4,5-dihydronaphtho[1,2-d][1,3]thiazol-2-yl(propyl)amino]methyl]benzyl]oxy]phenyl]propionic acid The title compound was obtained as colorless crystals in the same manner as in Reference Example 38 from methyl 3-[4-[[4-[[4,5-dihydronaphtho[1,2-d][1,3]thiazol-2-yl(propyl)amino]methyl]benzyl]oxy]phenyl]propionate. yield 34%.
MS: m/z 513.1 (M+1)⁺.

EXAMPLE 224 ethyl 3-[2-fluoro-4-[[4-[[(4-phenyl-1,3-thiazol-2-yl) (propyl)amino]methyl]benzyl]oxy]phenyl]propionate The title compound was obtained in the same manner as in Reference Example 31 from ethyl 3-(2-fluoro-4-hydroxyphenyl)propionate and [4-[[(4-phenyl-1,3-thiazol-2-yl) (propyl)amino]methyl]phenyl]methanol. yield 32%. oil.
¹H NMR (CDCl₃) δ 0.93 (t, J=7.2 Hz, 3H), 1.26 (t, J=7.2 Hz, 3H), 1.65-1.75 (m, 2H), 2.58 (t, J=7.6 Hz, 2H), 2.90 (t, J=7.6 Hz, 2H), 3.40 (t, J=7.8 Hz, 2H), 4.12 (q, J=7.2 Hz, 2H), 4.80 (m, 2H), 5.00 (s, 2H), 6.63-6.70 (m, 3H), 7.06-7.12 (m, 1H), 7.24-7.29 (m, 1H), 7.34-7.41 (m, 6H), 7.84-7.87 (m, 2H).

EXAMPLE 225

3-[2-fluoro-4-[[4-[[(4-phenyl-1,3-thiazol-2-yl)(propyl)amino]methyl]benzyl]oxy]phenyl]propionic acid The title compound was obtained as a colorless crystals in the same manner as in Reference Example 38 from ethyl 3-[2-fluoro-4-[[4-[[(4-phenyl-1,3-thiazol-2-yl)(propyl) amino]methyl]benzyl]oxy]phenyl]propionate. yield 29%.
MS: m/z 505.0 (M+1)⁺.

EXAMPLE 226 methyl 3-[4-[[4-[[(4,5-dimethyl-1,3-thiazol-2-yl) (propyl)amino]methyl]benzyl]oxy]phenyl]propionate The title compound was obtained in the same manner as in Reference Example 31 from [4-[[(4,5-dimethyl-1,3-thiazol-2-yl)(propyl)amino]methyl]phenyl]methanol. yield 56%. oil.

¹H NMR (CDCl₃) 0.88 (t, J=7.4 Hz, 3H), 1.58-1.67 (m, 2H), 2.13 (s, 3H), 2.18 (s, 3H), 2.59 (t, J=8.4 Hz, 2H), 2.89 (t, J=8.4 Hz, 2H), 3.25-3.30 (m, 2H), 3.66 (s, 3H), 4.65 (s, 2H), 5.01 (s, 2H), 6.87-6.90 (m, 2H), 7.09-7.12 (m, 2H), 7.26-7.27 (m, 2H), 7.35-7.38 (m, 2H).

EXAMPLE 227

3-[4-[[4-[[(4,5-dimethyl-1,3-thiazol-2-yl)(propyl) amino]methyl]benzyl]oxy]phenyl]propionic acid The title compound was obtained as colorless crystals in the same manner as in Reference Example 38 from methyl 3-[4-[[4-[[(4,5-dimethyl-1,3-thiazol-2-yl)(propyl)amino] methyl]benzyl]oxy]phenyl]propionate. yield 51%.
MS: m/z 513.1 (M+1)⁺.

EXAMPLE 228 methyl 3-[4-[[4-[[(4-phenyl-1,3-thiazol-2-yl)amino] methyl]benzyl]oxy]phenyl]propionate To a solution of 4-phenyl-1,3-thiazol-2-amine (0.25 g, 1.4 mmol), methyl 3-[4-[(4-formylbenzyl)oxy]phenyl]propionate (0.58 g, 2.0 mmol) and acetic acid (0.25 g, 4.2 mmol) in 1,2-dichloroethane (15 mL) was added triacetoxysodium borohydride (0.83 g, 3.9 mmol), and the mixture was stirred at room temperature for 2 days. The reaction mixture was poured into aqueous sodium hydrogen carbonate, and the mixture was extracted with ethyl acetate. The extract was washed with water and concentrated under reduced pressure. The residue was purified by silica gel column chromatography (hexane/ethyl acetate=4:1) to give the title compound (0.31 g, yield 49%) as an oil.
¹H NMR (CDCl₃) δ 2.60 (t, J=7.7 Hz, 2H), 2.89 (t, J=7.7 Hz, 2H), 3.66 (s, 3H), 4.54 (d, J=5.5 Hz, 2H), 5.04 (s, 2H), 5.50 (br s, 1H), 6.71 (s, 1H), 6.87-6.92 (m, 2H), 7.09-7.14 (m, 2H) 7.26-7.43 (m, 7H), 7.78-7.82 (m, 2H).

EXAMPLE 229

3-[4-[[4-[[(4-phenyl-1,3-thiazol-2-yl)amino]methyl] benzyl]oxy]phenyl]propionic acid The title compound was obtained as colorless crystals in the same manner as in Reference Example 38 from methyl 3-[4-[[4-[[(4-phenyl-1,3-thiazol-2-yl)amino]methyl]benzyl] oxy]phenyl]propionate. yield 69%.
MS: m/z 445.1 (M+1)⁺.

EXAMPLE 230

3-[4-[(2'-methyl-6'-propylbiphenyl-3-yl)methoxy] phenyl]propanoic acid

To a solution of methyl 3-(4-hydroxyphenyl)propanoate (0.21 g, 1.14 mmol), (2'-methyl-6'-propylbiphenyl-3-yl) methanol (0.25 g, 1.04 mmol) and tributylphosphine (0.39 mL, 1.56 mmol) in tetrahydrofuran (6 mL) was added 1,1'-(azodicarbonyl)dipiperidine (0.39 g, 1.56 mmol) with stirring at 0° C., and the mixture was stirred at room temperature for 16 hrs. Diethyl ether was added to the reaction mixture, the insoluble material was filtered off, and the filtrate was concentrated under reduced pressure. The residue was purified by silica gel column chromatography (hexane-hexane/ethyl acetate=4/1) to give as a colorless oil. This product was then dissolved in a mixed solution of methanol (4.0 mL) and tetrahydrofuran (6.0 mL), 1N aqueous sodium hydroxide solution (2.28 mL) was added at room temperature with stirring, and the mixture was stirred at room temperature for 1 hr. The reaction mixture was adjusted to pH 3 with 1N hydrochloric acid and the mixture was extracted with ethyl acetate. The organic layer was washed with water and saturated brine, dried (anhydrous magnesium sulfate), and concentrated under reduced pressure. The residue was purified by silica gel column chromatography (hexane/ethyl acetate=4/1-1/2) to give the title compound (0.24 g, yield 59%) as colorless crystals. MS (APCI−): 387 (M−H).

EXAMPLE 231

3-[4-[(2'-isobutyl-6'-methylbiphenyl-3-yl)methoxy]phenyl]propanoic acid

The title compound was synthesized in the same manner as in Reference Example 230 from methyl 3-(4-hydroxyphenyl)propanoate and (2'-isobutyl-6'-methylbiphenyl-3-yl)methanol. colorless oil (yield 58%). MS (APCI−): 401 (M−H).

EXAMPLE 232

3-[4-[(2'-ethyl-6'-methylbiphenyl-3-yl)methoxy]phenyl]propanoic acid

The title compound was synthesized in the same manner as in Reference Example 230 from methyl 3-(4-hydroxyphenyl)propanoate and (2'-ethyl-6'-methylbiphenyl-3-yl)methanol. colorless crystals (yield 57%). MS (APCI−): 373 (M−H).

EXAMPLE 233 methyl 3-(4-((1-(tert-butoxycarbonyl)-1H-indol-3-yl)methoxy)phenyl)propanoate

The title compound was obtained as a pale-yellow oil in the same manner as in Reference Example 31 from 1-(tert-butoxycarbonyl)-3-hydroxymethyl-1H-indole and methyl 3-(4-hydroxyphenyl)propanoate. yield 74%.
$^1$H-NMR (CDCl$_3$) δ 1.67 (9H, s), 2.61 (2H, t, J=8.0 Hz), 2.91 (2H, t, J=8.0 Hz), 3.67 (3H, s), 5.17 (2H, s), 6.94 (2H, d, J=8.8 Hz), 7.13 (2H, d, J=8.8 Hz), 7.20-7.70 (4H, m), 8.14 (1H, d, J=8.0 Hz).

EXAMPLE 234

3-(4-((1-(tert-butoxycarbonyl)-1H-indol-3-yl)methoxy)phenyl)propanoic acid

The title compound was obtained as pale-brown crystals in the same manner as in Reference Example 4 from methyl 3-(4-((1-(tert-butoxycarbonyl)-1H-indol-3-yl)methoxy)phenyl)propanoate. yield 11%.
$^1$H-NMR (CDCl$_3$) δ 1.67 (9H, s), 2.66 (2H, t, J=7.8 Hz), 2.92 (2H, t, J=7.8 Hz), 5.18 (2H, s), 6.95 (2H, d, J=8.8 Hz), 7.15 (2H, d, J=8.8 Hz), 7.20-7.40 (2H, m), 7.60-7.68 (2H, m), 8.14 (1H, d, J=8.4 Hz).

EXAMPLE 235 methyl 3-(4-((3-(methoxymethoxy)-1-benzothiophen-2-yl)methoxy)phenyl)propanoate

The title compound was obtained as a pale-brown in the same manner as in Reference Example 31 from 2-hydroxymethyl-3-methoxymethoxy-1-benzothiophene and methyl 3-(4-hydroxyphenyl)propanoate. yield 50%.
$^1$H-NMR (CDCl$_3$) δ 2.59 (2H, t, J=7.8 Hz), 2.89 (2H, t, J=7.8 Hz), 3.63 (3H, s), 3.66 (3H, s), 5.19 (2H, s), 5.30 (2H, s), 6.95 (2H, d, J=8.4 Hz), 7.12 (2H, d, J=8.4 Hz), 7.34-7.42 (2H, m), 7.72-7.80 (2H, m).

EXAMPLE 236

3-(4-((3-(methoxymethoxy)-1-benzothiophen-2-yl)methoxy)phenyl)propanoic acid

The title compound was obtained as a pale-yellow needles in the same manner as in Reference Example 4 from methyl 3-(4-((3-(methoxymethoxy)-1-benzothiophen-2-yl)methoxy)phenyl)propanoate. yield 74%.
$^1$H-NMR (CDCl$_3$) δ 2.64 (2H, t, J=7.6 Hz), 2.90 (2H, t, J=7.6 Hz), 3.63 (3H, s), 5.19 (2H, s), 5.30 (2H, s), 6.95 (2H, d, J=8.8 Hz), 7.13 (2H, d, J=8.8 Hz), 7.32-7.42 (2H, m), 7.72-7.80 (2H, m).

EXAMPLE 237 methyl 3-(4-((3-(2-methylbenzyloxy)-1-benzothiophen-2-yl)methoxy)phenyl)propanoate The title compound was obtained as a pale-yellow oil in the same manner as in Reference Example 31 from 2-hydroxymethyl-3-(2-methylbenzyloxy)-1-benzothiophene and methyl 3-(4-hydroxyphenyl)propanoate. yield 32%.
$^1$H-NMR (CDCl$_3$) δ 2.39 (3H, s), 2.57 (2H, t, J=7.4 Hz), 2.88 (2H, t, J=7.4 Hz), 3.65 (3H, s), 4.92 (2H, s), 5.17 (2H, s), 6.83 (2H, d, J=8.6 Hz), 7.08 (2H, d, J=8.6 Hz), 7.14-7.80 (8H, m).

EXAMPLE 238

3-(4-((3-(2-methylbenzyloxy)-1-benzothiophen-2-yl)methoxy)phenyl)propanoic acid

The title compound was obtained as colorless prism crystals in the same manner as in Reference Example 4 from methyl 3-(4-((3-(2-methylbenzyloxy)-1-benzothiophen-2-yl)methoxy)phenyl)propanoate. yield 75%.
$^1$H-NMR (CDCl$_3$) δ 2.40 (3H, s), 2.63 (2H, t, J=7.4 Hz), 2.89 (2H, t, J=7.4 Hz), 4.92 (2H, s), 5.17 (2H, s), 6.84 (2H, d, J=8.6 Hz), 7.10 (2H, d, J=8.6 Hz), 7.16-7.80 (8H, m).

EXAMPLE 239 methyl 3-(4-((2,2',6'-trimethylbiphenyl-3-yl)methoxy)phenyl)propanoate

The title compound was obtained as a colorless oil in the same manner as in Reference Example 31 from (2,2',6'-trimethylbiphenyl-3-yl)methanol and methyl 3-(4-hydroxyphenyl)propanoate. yield 78%.
$^1$H-NMR (CDCl$_3$) δ 1.93 (6H, s), 1.97 (3H, s), 2.58 (2H, t, J=7.8 Hz), 2.88 (2H, t, J=7.8 Hz), 3.66 (3H, s), 5.04 (2H, s), 6.88 (2H, d, J=8.4 Hz), 7.06-7.34 (8H, m).

EXAMPLE 240

3-(4-((2,2',6'-trimethylbiphenyl-3-yl)methoxy)phenyl)propanoic acid

The title compound was obtained as colorless needles in the same manner as in Reference Example 4 from methyl 3-(4-((2,2',6'-trimethylbiphenyl-3-yl)methoxy)phenyl)propanoate. yield 98%.

¹H-NMR (CDCl₃) δ 1.92 (6H, s), 1.96 (3H, s), 2.63 (2H, t, J=7.4 Hz), 2.89 (2H, t, J=7.4 Hz), 5.04 (2H, s), 6.88 (2H, d, J=8.4 Hz), 7.05-7.34 (8H, m).

EXAMPLE 241 methyl 3-(4-((6-methoxy-2',6'-dimethyl-biphenyl-3-yl)methoxy)phenyl)propanoate

The title compound was obtained as a pale-yellow oil in the same manner as in Reference Example 31 from (6-methoxy-2',6'-dimethyl-biphenyl-3-yl)methanol and methyl 3-(4-hydroxyphenyl)propanoate. yield 32%.
¹H-NMR (CDCl₃) δ 1.99 (6H, s), 2.58 (2H, t, J=7.8 Hz), 2.89 (2H, t, J=7.8 Hz), 3.66 (3H, s), 3.74 (3H, s), 5.00 (2H, s), 6.88 (2H, d, J=8.8 Hz), 6.98 (1H, d, J=8.4 Hz), 7.06-7.22 (6H, m), 7.40 (1H, dd, J=2.2 & 8.0 Hz).

EXAMPLE 242

3-(4-((6-methoxy-2',6'-dimethyl-biphenyl-3-yl)methoxy)phenyl)propanoic acid

The title compound was obtained as colorless prism crystals in the same manner as in Reference Example 4 from methyl 3-(4-((6-methoxy-2',6'-dimethyl-biphenyl-3-yl)methoxy)phenyl)propanoate. yield 94%.
¹H-NMR (CDCl₃) δ 2.00 (6H, s), 2.64 (2H, t, J=7.8 Hz), 2.90 (2H, t, J=7.8 Hz), 3.74 (3H, s), 5.00 (2H, s), 6.85-7.44 (10H, m).

EXAMPLE 243 methyl 3-(4-((2',6'-dimethyl-4-methoxybiphenyl-3-yl)methoxy)phenyl)propanoate

The title compound was obtained as a colorless oil in the same manner as in Reference Example 31 from (2',6'-dimethyl-4-methoxybiphenyl-3-yl)methanol and methyl 3-(4-hydroxyphenyl)propanoate. yield 87%.
¹H-NMR (CDCl₃) δ 1.99 (6H, s), 2.58 (2H, t, J=8.0 Hz), 2.88 (2H, t, J=8.0 Hz), 3.66 (3H, s), 3.91 (3H, s), 5.14 (2H, s), 6.04-7.25 (10H, m).

EXAMPLE 244

3-(4-((2',6'-dimethyl-4-methoxybiphenyl-3-yl)methoxy)phenyl)propanoic acid

The title compound was obtained as colorless prism crystals in the same manner as in Reference Example 4 from methyl 3-(4-((2',6'-dimethyl-4-methoxybiphenyl-3-yl)methoxy)phenyl)propanoate. yield 91%.
¹H-NMR (CDCl₃) δ 1.99 (6H, s), 2.63 (2H, t, 7.8 Hz), 2.89 (2H, t, J=J=7.8 Hz), 3.91 (2H, s), 5.14 (2H, s), 6.85-7.24 (10H, m).

EXAMPLE 245 ethyl (2,6-dimethoxy-4-((3-phenoxybenzyl)oxy)phenyl)propanoate

The title compound was obtained as a colorless oil in the same manner as in Reference Example 31 from 3-phenoxybenzyl alcohol and ethyl 3-(4-hydroxy-2,6-dimethoxyphenyl)propanoate. yield 87%.
¹H-NMR (CDCl₃) δ 1.25 (3H, t, J=7.2 Hz), 2.40-2.48 (2H, m), 2.84-2.94 (2H, m), 3.75 (6H, s), 4.12 (2H, q, J=7.2 Hz), 5.01 (2H, s), 6.16 (2H, s), 6.94-7.38 (9H, m).

EXAMPLE 246

(2,6-dimethoxy-4-((3-phenoxybenzyl)oxy)phenyl) propanoic acid

The title compound was obtained as colorless needles in the same manner as in Reference Example 4 from ethyl (2,6-dimethoxy-4-((3-phenoxybenzyl)oxy)phenyl)propanoate. yield 78%.
¹H-NMR (CDCl₃) δ 2.43-2.58 (2H, m), 2.86-2.98 (2H, m), 3.76 (6H, s), 5.01 (2H, s), 6.17 (2H, s), 6.94-7.40 (9H, m).

EXAMPLE 247 ethyl 3-(2,6-difluoro-4-((2',6'-dimethylbiphenyl-3-yl)methoxy)phenyl)propanoate

The title compound was obtained as a colorless oil in the same manner as in Reference Example 31 from (2',6'-dimethylbiphenyl-3-yl)methanol and ethyl 3-(2,6-difluoro-4-hydroxyphenyl)propanoate. yield 89%.
¹H-NMR (CDCl₃) δ 1.24 (3H, t, J=7.0 Hz), 2.01 (6H, s), 2.54 (2H, t, J=7.6 Hz), 2.91 (2H, t, J=7.6 Hz), 4.12 (2H, q, J=7.0 Hz), 5.05 (2H, s), 6.49 (2H, d, J=9.4 Hz), 7.06-7.50 (7H, m).

EXAMPLE 248

3-(2,6-difluoro-4-((2',6'-dimethylbiphenyl-3-yl)methoxy)phenyl)propanoic acid

The title compound was obtained as colorless needles in the same manner as in Reference Example 4 from ethyl 3-(2,6-difluoro-4-((2',6'-dimethylbiphenyl-3-yl)methoxy)phenyl)propanoate. yield 95%.
¹H-NMR (CDCl₃) δ 2.01 (6H, s), 2.61 (2H, t, J=7.8 Hz), 2.93 (2H, t, J=7.8 Hz), 5.06 (2H, s), 6.50 (2H, d, J=9.6 Hz), 7.08-7.48 (7H, m).

EXAMPLE 249 methyl 3-[4-[[3-(2,6-dimethylbenzyl)benzyl]oxy]phenyl]propanoate

To a solution of methyl 3-(4-hydroxyphenyl)propanoate (180 mg), 3-(2,6-dimethylbenzyl)benzyl alcohol (226 mg) and triphenylphosphine (286 mg) in toluene (2 mL) was added dropwise diethyl azodicarboxylate (40% toluene solution 500 mg) at room temperature, and the mixture was stirred at room temperature for 1 hr. The reaction mixture was purified by silica gel column chromatography with ethyl acetate-hexane (gradient of 1:9 to 3:2 by volume ratio) to give the title compound (125 mg, yield 32%) as a pale-yellow oil.
¹H NMR (300 MHz, Chloroform-D) δ: 2.23 (6H, s) 2.60 (2H, t, J=7.8 Hz) 2.89 (2H, t, J=7.8 Hz) 3.67 (3H, s) 4.06 (2H, s) 4.96 (2H, s) 6.8-6.95 (3H, m) 7.0-7.1 (6H, m) 7.2-7.3 (2H, m).

The following compounds of Examples 250 and 251 were synthesized in the same manner as in Example 249.

EXAMPLE 250 methyl 3-[4-[[4-(2,6-dimethylbenzyl)benzyl]oxy]phenyl]propanoate: 95%. a pale-yellow oil $^1$H NMR (300 MHz, Chloroform-D) δ: 2.24 (6H, s), 2.59 (2H, t, J=7.8 Hz), 2.89 (2H, t, J=7.8 Hz), 3.66 (3H, s), 4.06 (2H, s), 4.97 (2H, s), 6.8-6.95 (2H, m), 7.02 (2H, d, J=7.9 Hz), 7.05-7.15 (5H, m), 7.29 (2H, d, J=7.9 Hz).

EXAMPLE 251 methyl 3-[4-[(3-benzylbenzyl)oxy]phenyl]propanoate yield: 62%. a pale-yellow oil.
$^1$H NMR (300 MHz, Chloroform-D) δ: 2.60 (2H, t, J=7.8 Hz) 2.89 (2H, t, J=7.8 Hz) 3.66 (3H, s) 4.00 (2H, s) 4.99 (2H, s) 6.85-6.9 (2H, m) 7.1-7.3 (11H, m).

EXAMPLE 252

3-[4-[[3-(2,6-dimethylbenzyl)benzyl]oxy]phenyl]propanoic acid

A mixture of methyl 3-[4-[[3-(2,6-dimethylbenzyl)benzyl]oxy]phenyl]propanoate (125 mg), 2N aqueous sodium hydroxide solution (3 mL) and ethanol (10 mL) was stirred at room temperature for 1 hr. The reaction mixture was concentrated and added to a mixture of 1N hydrochloric acid aqueous solution (10 mL) and water (30 mL). The precipitated solid was collected by filtration, washed with water and hexane and dried to give the title compound (99 mg, yield 82%) as colorless crystals.
MS (APCI−) 373 (M−H).
The following compounds of Examples 253 and 254 were synthesized in the same manner as in Example 252.

EXAMPLE 253

3-[4-[[4-(2,6-dimethylbenzyl)benzyl]oxy]phenyl]propanoic acid yield: 96%. colorless crystals.
MS (APCI−) 373 (M−H).

EXAMPLE 254

3-[4-[(3-benzylbenzyl)oxy]phenyl]propanoic acid yield: 96%. colorless crystals.
MS (APCI−) 345 (M−H).

EXAMPLE 255 methyl 3-{4-[(4-{[hexyl(4-phenyl-1,3-thiazol-2-yl)amino]methyl}benzyl)oxy]phenyl}propanoate To a solution of N-hexyl-4-phenyl-1,3-thiazol-2-amine (390 mg) in N,N-dimethylformamide (1.0 mL) was added sodium hydride (60%, oil, 50 mg) at room temperature and the mixture was stirred at room temperature for 30 min. Methyl 3-(4-{[4-(chloromethyl)benzyl]oxy}phenyl)propanoate (318 mg) was added to the reaction mixture and the mixture was stirred at room temperature for 1 hr. The reaction mixture was poured into 1N aqueous hydrochloric acid, and the mixture was extracted with ethyl acetate. The ethyl acetate layer was concentrated, and the residue was purified by silica gel column chromatography with ethyl acetate-hexane (gradient of 1:19 to 1:1 by volume ratio) to give the title compound (260 mg, yield 48%) as a pale-yellow oil.
$^1$H NMR (300 MHz, Chloroform-D) 6:0.8-0.9 (3H, m), 1.2-1.4 (6H, m), 1.6-1.7 (2H, m), 2.59 (2H, t, J=7.7 Hz), 2.89 (2H, t, J=7.7 Hz), 3.35-3.5 (2H, m), 3.66 (3H, s), 4.78 (2H, s), 5.01 (2H, s), 6.70 (1H, s), 6.89 (2H, d, J=8.7 Hz), 7.11 (2H, d, J=8.5 Hz), 7.2-7.3 (1H, m), 7.3-7.45 (6H, m), 7.85 (2H, d, J=7.9 Hz).

EXAMPLE 256 methyl 3-{4-[(4-{[isopropyl(4-phenyl-1,3-thiazol-2-yl)amino]methyl}benzyl)oxy]phenyl}propanoate The title compound was synthesized in the same manner as in Example 255. yield: 72%. a pale-yellow oil.
MS (ESI+) 501 (M+H).

EXAMPLE 257

3-{4-[(4-{[isobutyl(4-phenyl-1,3-thiazol-2-yl)amino]methyl}benzyl)oxy]phenyl}propanoic acid To a solution of N-isobutyl-4-phenyl-1,3-thiazol-2-amine (232 mg) in N,N-dimethylformamide (2 mL) was added sodium hydride (60%, oil, 50 mg) at room temperature and the mixture was stirred at room temperature for 30 min. Methyl 3-(4-{[4-(chloromethyl)benzyl]oxy}phenyl)propanoate (318 mg) was added to the reaction mixture, and the mixture was stirred at room temperature for 1 hr. The reaction mixture was poured into 1N aqueous hydrochloric acid, and the mixture was extracted with ethyl acetate. The ethyl acetate layer was concentrated, and the residue was purified by silica gel column chromatography with ethyl acetate-hexane (gradient of 1:19 to 1:1 by volume ratio) to give a yellow oil (322 mg). This yellow oil was dissolved in a mixed solvent of methanol (2 mL) and tetrahydrofuran (2 mL) and 2N aqueous sodium hydroxide solution (2 mL) was added. The mixture was stirred at room temperature for 1 hr. The reaction mixture was poured into water, acidified with 1N aqueous hydrochloric acid solution, and the mixture was extracted with ethyl acetate. The ethyl acetate layer was concentrated, and the residue was purified by preparative HPLC (gradient cycle A) to give the title compound (159 mg, yield 31%) as a colorless oil.
MS (ESI+) 501 (M+H).

EXAMPLE 258

3-{4-[(4-{[hexyl(4-phenyl-1,3-thiazol-2-yl)amino]methyl}benzyl)oxy]phenyl}propanoic acid Methyl 3-{4-[(4-{[hexyl(4-phenyl-1,3-thiazol-2-yl)amino]methyl}benzyl)oxy]phenyl}propanoate (250 mg) was dissolved in a mixed solvent of methanol (2 mL) and tetrahydrofuran (2 mL), and 2N aqueous sodium hydroxide solution (2 mL) was added. The mixture was stirred at room temperature for 1 hr. The reaction mixture was poured into water, acidified with 1N aqueous hydrochloric acid solution, and the mixture was extracted with ethyl acetate. The ethyl acetate layer was dried using Presep Dehydration tube (manufactured by Wako Pure Chemical Industries, Ltd.) and concentrated to give the title compound (220 mg, yield 90%) as pale-yellow crystals.

MS (ESI+) 529 (M+H).

EXAMPLE 259

3-{4-[(4-{[isopropyl(4-phenyl-1,3-thiazol-2-yl)amino]methyl}benzyl)oxy]phenyl}propanoic acid The title compound was synthesized in the same manner as in Example 258 from methyl 3-{4-[(4-{[isopropyl(4-phenyl-1,3-thiazol-2-yl)amino]methyl}benzyl)oxy]phenyl}propanoate. yield 63%. pale-yellow crystal.

MS (ESI+) 487 (M+H).

EXAMPLE 260

3-[4-({4-[(propyl{4-[4-(trifluoromethyl)phenyl]-1,3-thiazol-2-yl}amino)methyl]benzyl}oxy)phenyl]propanoic acid To a solution of N-propyl-4-[4-(trifluoromethyl)phenyl]-1,3-thiazol-2-amine hydrobromide (477 mg) in N,N-dimethylformamide (10 mL) was added sodium hydride (60%, oil, 104 mg) at 0° C., the temperature was raised to room temperature and the mixture was stirred for 30 min. Methyl 3-(4-{[4-(chloromethyl)benzyl]oxy}phenyl)propanoate (318 mg) was added to the reaction mixture at 0° C., the temperature was raised to room temperature and the mixture was stirred for 1 hr. The reaction mixture was poured into water, and the mixture was extracted with ethyl acetate. The ethyl acetate layer was concentrated, and the residue was purified by silica gel column chromatography with ethyl acetate-hexane (gradient of 1:19 to 1:1 by volume ratio) to give a pale-yellow oil. This oil was dissolved in methanol (5 mL), 2N aqueous sodium hydroxide solution (5 mL) was added, and the mixture was stirred at room temperature for 3 hr. The reaction mixture was poured into 1N aqueous hydrochloric acid solution, and the precipitated solid was collected by filtration, washed successively with water and isopropyl ether and dried to give the title compound (230 mg, yield 42%) as colorless crystals.

MS (ESI+) 555 (M+H).

The following compounds of Examples 261-263 were synthesized in the same manner as in Example 260.

EXAMPLE 261

3-{4-[(4-{[[4-(4-chlorophenyl)-1,3-thiazol-2-yl](propyl)amino]methyl}benzyl)oxy]phenyl}propanoic acid yield: 28%. pale-yellow crystal.
MS (ESI+) 521 (M+H).

EXAMPLE 262

3-{4-[(4-{[[4-(3-methoxyphenyl)-1,3-thiazol-2-yl](propyl)amino]methyl}benzyl)oxy]phenyl}propanoic acid yield: 41%. pale-yellow crystal.
MS (ESI+) 517 (M+H).

EXAMPLE 263

3-{4-[(4-{[(5-phenyl-1,3-thiazol-2-yl)(propyl)amino]methyl}benzyl)oxy]phenyl}propanoic acid yield: 68%. pale-yellow crystal.
MS (ESI+) 487 (M+H).

EXAMPLE 264 methyl 3-(4-{[3-(3-methylphenoxy)benzyl]oxy}phenyl)propanoate

A solution of methyl 3-(4-hydroxyphenyl)propanoate (0.396 g, 2.20 mmol), [3-(3-methylphenoxy)phenyl]methanol (0.429 g, 2.00 mmol) and tributylphosphine (0.747 mL, 3.00 mmol) in toluene (30 mL) was stirred under ice-cooling, 1,1'-(azodicarbonyl)dipiperidine (0.757 g, 3.00 mmol) was added by small portions, the temperature was raised to room temperature and the mixture was stirred for 18 hrs. Hexane (15 mL) was added to the reaction mixture, the precipitated insoluble material was filtered off, and the filtrate was concentrated under reduced pressure. The residue was purified by silica gel chromatography (hexane-20% ethyl acetate/hexane) and preparative HPLC (10-95% acetonitrile/water, containing 0.1% trifluoroacetic acid) to give the title compound (0.414 g, yield 55%) as a pale-yellow oil.

MS: m/z 377 (MH$^+$).

EXAMPLE 265

3-(4-{[3-(3-methylphenoxy)benzyl]oxy}phenyl)propanoic acid

To a solution of methyl 3-(4-{[3-(3-methylphenoxy)benzyl]oxy}phenyl)propanoate (0.380 g, 1.01 mmol) in a mixture of methanol (4 mL) and tetrahydrofuran (4 mL) was added 2 M aqueous sodium hydroxide solution (1.5 mL), and the mixture was stirred at room temperature for 24 hrs. Water was added to the reaction mixture, acidified with 1 M hydrochloric acid, and the mixture was extracted with ethyl acetate. The extract was washed with saturated brine, dried over anhydrous magnesium sulfate, and concentrated under reduced pressure. The residue was recrystallized from ethyl acetate-hexane to give the title compound (0.214 g, yield 58%) as colorless prism crystals.

$^1$H NMR (CDCl$_3$) δ 2.32 (s, 3H), 2.65 (t, J=7.7 Hz, 2H), 2.90 (t, J=7.7 Hz, 2H), 5.01 (s, 2H), 6.79-6.96 (m, 6H), 7.06-7.24 (m, 5H), 7.33 (t, J=7.8 Hz, 1H).

MS: m/z 363 (MH$^+$).

EXAMPLE 266 methyl 3-(4-{[3-(4-methylphenoxy)benzyl]oxy}phenyl)propanoate

The title compound was obtained as a pale-yellow oil in the same manner as in Example 264 from methyl 3-(4-hydroxyphenyl)propanoate and [3-(4-methylphenoxy)phenyl]methanol. yield 59%.

MS: m/z 377 (MH$^+$).

EXAMPLE 267

3-(4-{[3-(4-methylphenoxy)benzyl]oxy}phenyl)propanoic acid

The title compound was obtained as colorless prism crystals in the same manner as in Example 265 from methyl 3-(4-{[3-(4-methylphenoxy)benzyl]oxy}phenyl)propanoate. yield 58% (recrystallized from hexane-ethyl acetate).

$^1$H NMR (CDCl$_3$) δ 2.32 (s, 3H), 2.65 (t, J=7.7 Hz, 2H), 2.90 (t, J=7.7 Hz, 2H), 5.01 (s, 2H), 6.79-6.96 (m, 6H), 7.06-7.24 (m, 5H), 7.33 (t, J=7.8 Hz, 1H).

MS: m/z 363 (MH$^+$)

EXAMPLE 268 methyl 3-(4-{[3-(1-phenylvinyl)benzyl]oxy}phenyl)propanoate

A solution of methyl 3-(4-hydroxyphenyl)propanoate (0.360 g, 2.00 mmol), [3-(1-phenylvinyl)phenyl]methanol (0.421 g, 2.00 mmol) and tributylphosphine (0.747 mL, 3.00 mmol) in toluene (30 mL) was stirred under ice-cooling, 1,1'-(azodicarbonyl)dipiperidine (0.757 g, 3.00 mmol) was added by small portions under a nitrogen atmosphere, and the mixture was stirred at room temperature for 18 hrs. Hexane (15 mL) was added to the reaction mixture, the precipitated insoluble material was filtered off, and the filtrate was concentrated under reduced pressure. The residue was purified by silica gel chromatography (hexane-20% ethyl acetate/hexane) to give the title compound as a colorless oil (0.641 g, yield 86%).

MS: m/z 373 (MH$^+$).

EXAMPLE 269

3-(4-{[3-(1-phenylvinyl)benzyl]oxy}phenyl)propanoic acid

The title compound was obtained as colorless plate crystals in the same manner as in Example 265 from methyl 3-(4-{[3-(1-phenylvinyl)benzyl]oxy}phenyl)propanoate. yield 77% (recrystallized from hexane-ethyl acetate).

MS: m/z 359 (MH$^+$).

EXAMPLE 270 methyl 3-(4-{[3-(2-methyl-1-naphthyl)benzyl]oxy}phenyl)propanoate

The title compound was obtained as a colorless oil in the same manner as in Example 268 from methyl 3-(4-hydroxyphenyl)propanoate and [3-(2-methyl-1-naphthyl)phenyl]methanol. yield 87%.

$^1$H NMR (CDCl$_3$) δ 2.22 (s, 3H), 2.59 (t, J=7.8 Hz, 2H), 2.89 (t, J=7.8 Hz, 2H), 3.65 (s, 3H), 5.11 (s, 2H), 6.90 (d, J=8.5 Hz, 2H), 7.10 (d, J=8.5 Hz, 2H), 7.21-7.26 (m, 1H), 7.28-7.44 (m, 5H), 7.48-7.54 (m, 2H), 7.78 (d, J=8.3 Hz, 1H), 7.83 (d, J=8.1 Hz, 1H).

MS: m/z 411 (MH$^+$).

EXAMPLE 271

3-(4-{[3-(2-methyl-1-naphthyl)benzyl]oxy}phenyl)propanoic acid

To a solution of methyl 3-(4-{[3-(2-methyl-1-naphthyl)benzyl]oxy}phenyl)propanoate (0.648 g, 1.58 mmol) in a mixture of methanol (6 mL) and tetrahydrofuran (6 mL) was added 2 M aqueous sodium hydroxide solution (2 mL), and the mixture was stirred at room temperature for 75 hrs. Water was added to the reaction mixture, acidified with 10% aqueous citric acid solution, and the mixture was extracted with ethyl acetate. The extract was washed with saturated brine, dried over anhydrous sodium sulfate, and concentrated under reduced pressure. The residue was recrystallized from ethyl acetate-hexane to give the title compound (0.534 g, yield 85%) as colorless needle crystals.

$^1$H NMR (CDCl$_3$) δ2.22 (s, 3H), 2.64 (t, J=7.8 Hz, 2H), 2.90 (t, J=7.8 Hz, 2H), 5.12 (s, 2H), 6.91 (d, J=8.7 Hz, 2H), 7.12 (d, J=8.5 Hz, 2H), 7.21-7.33 (m, 3H), 7.37-7.42 (m, 3H), 7.48-7.55 (m, 2H), 7.78 (d, J=8.5 Hz, 1H), 7.83 (d, J=7.9 Hz, 1H).

MS: m/z 397 (MH$^+$).

EXAMPLE 272

3-(4-((2'-ethoxybiphenyl-3-yl)methoxy)phenyl)propanoic acid

A mixture of methyl 3-[4-[(3-bromobenzyl)oxy]phenyl]propanoate (0.30 g, 0.86 mmol), 2-ethoxyphenylboronic acid (0.16 g, 0.95 mmol), tetrakistriphenylphosphine palladium (40 mg, 0.034 mmol), 2N potassium carbonate aqueous solution (0.3 mL), ethanol (0.3 mL) and toluene (3 mL) was heated under reflux overnight under an argon atmosphere. The reaction mixture was cooled, diluted with ethyl acetate, washed with water, dried, and concentrated under reduced pressure. The residue was purified by silica gel column chromatography (hexane/ethyl acetate=10/1-2/1) to give methyl 3-(4-((2'-ethoxybiphenyl-3-yl)methoxy)phenyl)propanoate (0.21 g, 63%) as a colorless oil.

To a solution of this compound in methanol (4.2 mL) was added 1N aqueous sodium hydroxide solution (1.3 mL), and the mixture was stirred at room temperature for 2 hrs. The reaction mixture was adjusted to pH 7 with 1N hydrochloric acid and extracted with ethyl acetate. The organic layer was washed with water and saturated brine, dried, and concentrated under reduced pressure. The residue was purified by silica gel column chromatography (hexane/ethyl acetate=3/2-1/4) to give the title compound (0.17 g, yield 84%) as colorless crystals. MS (APCI−): 375 (M−H).

EXAMPLE 273

3-(4-((2'-cyanobiphenyl-3-yl)methoxy)phenyl)propanoic acid

The title compound was synthesized in the same manner as in Example 272 from methyl 3-[4-[(3-bromobenzyl)oxy]phenyl]propanoate and 2-cyanophenylboronic acid. colorless crystals (yield 6%). MS (APCI−): 356 (M−H).

EXAMPLE 274

3-(4-((2'-hydroxybiphenyl-3-yl)methoxy)phenyl)propanoic acid

The title compound was synthesized in the same manner as in Example 272 from methyl 3-[4-[(3-bromobenzyl)oxy]phenyl]propanoate and 2-(4,4,5,5-tetramethyl-1,3,2-dioxaborolan-2-yl)phenol. colorless crystals (yield 33%). MS (APCI−): 347 (M−H).

EXAMPLE 275

3-(4-((2'-(methylthio)biphenyl-3-yl)methoxy)phenyl)propanoic acid

The title compound was synthesized in the same manner as in Example 272 from methyl 3-[4-[(3-bromobenzyl)oxy]

phenyl]propanoate and 2-(methylthio)phenylboronic acid. colorless crystals (yield 39%). MS (APCI−): 377 (M−H).

EXAMPLE 276

3-(4-((2'-(ethoxycarbonyl)biphenyl-3-yl)methoxy)phenyl)propanoic acid

The title compound was synthesized in the same manner as in Example 272 from methyl 3-[4-[(3-bromobenzyl)oxy]phenyl]propanoate and 2-ethoxycarbonylphenylboronic acid. colorless oil (yield 12%).

MS (APCI−): 403 (M−H).

EXAMPLE 277 methyl 3-(4-((3-(2,6-dimethylphenoxy)benzyl)oxy)phenyl)propanoate

To a solution of methyl 3-(4-hydroxyphenyl)propanoate (0.25 g, 1.39 mmol), [3-(2,6-dimethylphenoxy)phenyl]methanol (0.41 g, 1.81 mmol) and triphenylphosphine (0.47 g, 1.81 mmol) in tetrahydrofuran (5 mL) was added dropwise diethyl azodicarboxylate toluene solution (40%, 0.82 mL) with stirring at 0° C., and the mixture was stirred at room temperature for 16 hrs. The reaction mixture was concentrated under reduced pressure. The residue was purified by silica gel column chromatography (hexane-hexane/ethyl acetate=4/1) to give the title compound (0.27 g, yield 50%) as a yellow oil.

$^1$H NMR (CDCl$_3$) δ: 2.11 (6H, m), 2.59 (2H, t, J=7.8 Hz), 2.89 (2H, t, J=7.8 Hz), 3.66 (3H, s), 4.97 (2H, s), 6.66 (1H, dd, J=2.4, 8.1 Hz), 6.81-6.91 (3H, m), 7.00-7.14 (6H, m), 7.24 (1H, t, J=7.8 Hz).

EXAMPLE 278

3-(4-((3-(2,6-dimethylphenoxy)benzyl)oxy)phenyl)propanoic acid

To a solution (5.0 mL) of methyl 3-(4-((3-(2,6-dimethylphenoxy)benzyl)oxy)phenyl)propanoate (0.24 g, 0.62 mmol) in methanol was added 1N aqueous sodium hydroxide solution (1.2 mL), and the mixture was stirred at room temperature for 2 hrs. The reaction mixture was concentrated, and the residue was diluted with ethyl acetate, washed with 1N hydrochloric acid and water, dried, and concentrated under reduced pressure. The residue was purified by silica gel column chromatography (hexane/ethyl acetate=3/2-1/4) to give the title compound (0.15 g, yield 64%) as colorless crystals.

MS (APCI−): 375 (M−H)

EXAMPLE 279 methyl 3-(4-((4-(2-methylphenoxy)benzyl)oxy)phenyl)propanoate

The title compound was synthesized in the same manner as in Example 277 from methyl 3-(4-hydroxyphenyl)propanoate and [4-(2-methylphenoxy)phenyl]methanol (synthesized in the same manner as in Reference Example 201 from o-cresol and 4-bromobenzaldehyde (mixture with side product)) (preparative HPLC (gradient cycle A) was used for purification). colorless crystals (yield 56%).

$^1$H NMR (CDCl$_3$) δ: 2.23 (3H, s), 2.60 (2H, t, J=7.8 Hz), 2.90 (2H, t, J=7.8 Hz), 3.67 (3H, s), 4.97 (2H, s), 6.86-6.95 (5H, m), 7.04-7.21 (4H, m), 7.23-7.29 (1H, m), 7.35 (2H, d, J=8.7 Hz).

EXAMPLE 280

3-(4-((4-(2-methylphenoxy)benzyl)oxy)phenyl)propanoic acid

The title compound was synthesized in the same manner as in Example 278 from methyl 3-(4-((4-(2-methylphenoxy)benzyl)oxy)phenyl)propanoate. colorless crystals (yield 63%). MS (APCI−): 361 (M−H).

EXAMPLE 281 methyl 3-(4-((3-(2-methylphenoxy)benzyl)oxy)phenyl)propanoate

The title compound was synthesized in the same manner as in Example 277 from methyl 3-(4-hydroxyphenyl)propanoate and [3-(2-methylphenoxy)phenyl]methanol (synthesized in the same manner as in Reference Example 201 from o-cresol and 3-bromobenzaldehyde (mixture with side product)) (preparative HPLC (gradient cycle A) was used for purification). colorless oil (yield 28%).

$^1$H NMR (CDCl$_3$) δ: 2.22 (3H, s), 2.60 (2H, t, J=7.8 Hz), 2.89 (2H, t, J=7.8 Hz), 3.67 (3H, s), 4.99 (2H, s), 6.79-6.94 (4H, m), 6.98 (1H, s), 7.03-7.21 (5H, m), 7.22-7.34 (2H, m).

EXAMPLE 282

3-(4-((3-(2-methylphenoxy)benzyl)oxy)phenyl)propanoic acid

The title compound was synthesized in the same manner as in Example 278 from methyl 3-(4-((3-(2-methylphenoxy)benzyl)oxy)phenyl)propanoate. colorless crystals (yield 58%). MS (APCI−): 361 (M−H).

EXAMPLE 283 tert-butyl 3-[4-[(2'-formylbiphenyl-3-yl)methoxy]phenyl]propanoate

A mixture of tert-butyl 3-[4-[(3-bromobenzyl)oxy]phenyl]propanoate (3.5 g, 8.94 mmol), 2-formylphenylboronic acid (1.47 g, 9.83 mmol), tetrakistriphenylphosphine palladium (413 mg, 0.36 mmol), 2N potassium carbonate aqueous solution (7 mL), ethanol (7 mL) and toluene (70 mL) was stirred under an argon atmosphere at 80° C. for 14 hrs. The reaction mixture was cooled, diluted with ethyl acetate, washed with water, dried, and concentrated under reduced pressure. The residue was purified by silica gel column chromatography (hexane/ethyl acetate=10/1-4/1) to give the title compound (3.62 g, 97%) as a colorless oil.

$^1$H NMR (CDCl$_3$) δ: 1.41 (9H, s), 2.50 (2H, t, J=7.8 Hz), 2.85 (2H, t, J=7.8 Hz), 5.11 (2H, s), 6.90 (2H, d, J=8.7 Hz), 7.13 (2H, d, J=8.7 Hz), 7.33 (1H, m), 7.42-7.55 (5H, m), 7.65 (1H, m), 8.03 (1H, dd, J=1.5, 7.8 Hz), 9.98 (1H, s).

EXAMPLE 284

3'-[4-(2-tert-butoxycarbonylethyl)phenoxymethyl]biphenyl-2-carboxylic acid

To a mixture of tert-butyl 3-[4-(2'-formylbiphenyl-3-yl-methoxy)phenyl]propanoate (1.5 g, 3.60 mmol), sodium dihydrogenphosphate (0.43 g, 3.60 mmol), 2-methyl-2-butene (1.72 mL, 16.2 mmol), tert-butanol (7 mL), water (15 mL) and tetrahydrofuran (15 mL) was added sodium chlorite (1.22 g, 10.8 mmol) with stirring at 0° C., and the mixture was stirred at the same temperature for 2 hrs. The reaction mixture was diluted with ethyl acetate, washed with water, dried (anhydrous magnesium sulfate), and concentrated under reduced pressure. The residue was purified by silica gel column chromatography (hexane/ethyl acetate=2/1-1/2) to give the title compound (1.12 g, 72%) as a yellow oil.

$^1$H NMR (CDCl$_3$) δ: 1.40 (9H, s), 2.50 (2H, t, J=7.2 Hz), 2.84 (2H, t, J=7.2 Hz), 5.09 (2H, s), 6.88 (2H, d, J=8.7 Hz), 7.10 (2H, d, J=8.7 Hz), 7.20-7.47 (6H, m), 7.56 (1H, m), 7.93 (1H, m).

EXAMPLE 285

3-(4-((2'-((dimethylamino)carbonyl)biphenyl-3-yl)methoxy)phenyl)propanoic acid

To a mixture of 3'-[4-(2-tert-butoxycarbonylethyl)phenoxymethyl]biphenyl-2-carboxylic acid (0.24 g, 0.56 mmol), dimethylaniline (2M tetrahydrofuran solution, 0.42 mL, 0.84 mmol), 1-hydroxybenzotriazole monohydrate (0.13 g, 0.84 mmol) and N,N-dimethylformamide (6.0 mL) was added 1-ethyl-3-(3-dimethylaminopropyl)carbodiimide hydrochloride (0.16 g, 0.84 mmol) at room temperature with stirring, and the mixture was stirred at the same temperature for 12 hrs. The reaction mixture was diluted with ethyl acetate, saturated aqueous sodium hydrogen carbonate, washed successively with 5% aqueous potassium hydrogensulfate solution and saturated brine, dried (anhydrous magnesium sulfate), and concentrated under reduced pressure. The residue was purified by silica gel column chromatography (hexane/ethyl acetate=2/1-1/2) to give tert-butyl 3-(4-((2'-((dimethylamino)carbonyl)biphenyl-3-yl)methoxy)phenyl)propanoate as a colorless oil. This compound was dissolved in trifluoroacetic acid (2 mL), and the mixture was stirred at room temperature for 1 hr, and concentrated under reduced pressure. The residue was purified by preparative HPLC (gradient cycle A) to give the title compound (58 mg, yield 26%) as colorless crystals. MS (APCI−): 402 (M−H).

EXAMPLE 286

3-(4-((2'-(aminocarbonyl)biphenyl-3-yl)methoxy)phenyl)propanoic acid

The title compound was synthesized in the same manner as in Example 285 from 3'-[4-(2-tert-butoxycarbonylethyl)phenoxymethyl]biphenyl-2-carboxylic acid and 1-hydroxybenzotriazole ammonium salt. colorless crystals (yield 66%). MS (APCI−): 374 (M−H).

EXAMPLE 287

3'-((4-(2-carboxyethyl)phenoxy)methyl)biphenyl-2-carboxylic acid

3'-[4-(2-tert-Butoxycarbonylethyl)phenoxymethyl]biphenyl-2-carboxylic acid (0.15 g, 0.35 mmol) was dissolved in trifluoroacetic acid (3 mL), and the mixture was stirred at room temperature for 1 hr. The reaction mixture was concentrated, and the residue was purified by silica gel column chromatography (hexane/ethyl acetate=1/2-ethyl acetate) to give the title compound (21 mg, yield 16%) as a colorless powder. MS (APCI−): 375 (M−H).

EXAMPLE 288 methyl 3-(4-((2',6'-dimethoxybiphenyl-3-yl)methoxy)phenyl)propanoate

The title compound was synthesized in the same manner as in Example 22 from methyl 3-[4-[(3-bromobenzyl)oxy]phenyl]propanoate and 2,6-dimethoxyphenylboronic acid. colorless oil (yield 93%).

$^1$H NMR (CDCl$_3$) δ: 2.59 (2H, t, J=7.8 Hz), 2.89 (2H, t, J=7.8 Hz), 3.66 (3H, s), 3.71 (6H, s), 5.08 (2H, s), 6.65 (2H, d, J=8.4 Hz), 6.92 (2H, d, J=8.7 Hz), 7.11 (2H, d, J=8.7 Hz), 7.23-7.33 (2H, m), 7.34-7.45 (3H, m).

EXAMPLE 289

3-(4-((2',6'-dimethoxybiphenyl-3-yl)methoxy)phenyl)propanoic acid

The title compound was synthesized in the same manner as in Example 278 from methyl 3-(4-((2',6'-dimethoxybiphenyl-3-yl)methoxy)phenyl)propanoate. colorless crystals (yield 86%).

MS (APCI−): 391 (M−H).

EXAMPLE 290 methyl 3-(4-((2',6'-diethylbiphenyl-3-yl)methoxy)phenyl)propanoate

The title compound was synthesized in the same manner as in Example 277 from methyl 3-(4-hydroxyphenyl)propanoate and (2',6'-diethylbiphenyl-3-yl)methanol. a yellow oil (yield 80%).

$^1$H NMR (CDCl$_3$) δ: 0.99 (6H, t, J=7.5 Hz), 2.30 (4H, q, J=7.5 Hz), 2.59 (2H, t, J=7.8 Hz), 2.88 (2H, t, J=7.8 Hz), 3.66 (3H, s), 5.10 (2H, s), 6.88 (2H, d, J=8.4 Hz), 7.05-7.20 (5H, m), 7.21-7.33 (2H, m), 7.38-7.48 (2H, m).

EXAMPLE 291

3-(4-((2',6'-diethylbiphenyl-3-yl)methoxy)phenyl)propanoic acid

The title compound was synthesized in the same manner as in Example 278 from methyl 3-(4-((2',6'-diethylbiphenyl-3-yl)methoxy)phenyl)propanoate. colorless crystals (yield 52%).

$^1$H NMR (CDCl$_3$) δ: 0.99 (6H, t, J=7.5 Hz), 2.30 (4H, q, J=7.5 Hz), 2.64 (2H, t, J=7.8 Hz), 2.90 (2H, t, J=7.8 Hz), 5.10 (2H, s), 6.86-6.93 (2H, m), 7.07-7.17 (5H, m), 7.21-7.31 (2H, m), 7.39-7.46 (1H, m).

MS (APCI−): 387 (M−H).

EXAMPLE 292 methyl 3-(4-((2',6'-difluorobiphenyl-3-yl)methoxy)phenyl)propanoate

The title compound was synthesized in the same manner as in Example 277 from methyl 3-(4-hydroxyphenyl)propanoate and (2',6'-difluorobiphenyl-3-yl)methanol. colorless oil (yield 60%).

¹H NMR (CDCl₃) δ: 2.60 (2H, t, J=7.8 Hz), 2.90 (2H, t, J=7.8 Hz), 3.66 (3H, s), 5.09 (2H, s), 6.88-7.04 (4H, m), 7.12 (2H, d, J=8.7 Hz), 7.29 (1H, m), 7.39-7.56 (4H, m).

EXAMPLE 293

3-(4-((2',6'-difluorobiphenyl-3-yl)methoxy)phenyl) propanoic acid

The title compound was synthesized in the same manner as in Example 278 from methyl 3-(4-((2',6'-difluorobiphenyl-3-yl)methoxy)phenyl)propanoate. colorless crystals (yield 86%).

¹H NMR (CDCl₃) δ: 2.65 (2H, t, J=7.8 Hz), 2.91 (2H, t, J=7.8 Hz), 5.09 (2H, s), 6.89-7.04 (4H, m), 7.13 (2H, d, J=8.7 Hz), 7.29 (1H, m), 7.39-7.55 (4H, m).

EXAMPLE 294 ethyl 3-(4-((2',6'-diethylbiphenyl-3-yl)methoxy)-2-fluorophenyl)propanoate

The title compound was synthesized in the same manner as in Example 277 from ethyl 3-(2-fluoro-4-hydroxyphenyl) propanoate and (2',6'-diethylbiphenyl-3-yl)methanol. a yellow oily substance (yield 80%).

¹H NMR (CDCl₃) δ: 0.99 (6H, t, J=7.5 Hz), 1.23 (3H, t, J=7.2 Hz), 2.30 (4H, q, J=7.5 Hz), 2.57 (2H, t, J=7.8 Hz), 2.89 (2H, t, J=7.8 Hz), 4.12 (2H, q, J=7.2 Hz), 5.08 (2H, s), 6.60-6.71 (2H, m), 7.03-7.17 (4H, m), 7.19-7.31 (2H, m), 7.35-7.48 (2H, m).

EXAMPLE 295

3-(4-((2',6'-diethylbiphenyl-3-yl)methoxy)-2-fluorophenyl)propanoic acid

The title compound was synthesized in the same manner as in Example 278 from ethyl 3-(4-((2',6'-diethylbiphenyl-3-yl) methoxy)-2-fluorophenyl)propanoate. colorless crystals (yield 71%). MS (APCI–): 405 (M–H).

EXAMPLE 296 tert-butyl 3-(4-((2'-(hydroxymethyl)biphenyl-3-yl) methoxy)phenyl)propanoate tert-Butyl 3-(4-(2'-formylbiphenyl-3-ylmethoxy)phenyl) propanoate (0.30 g, 0.72 mmol) was dissolved in a mixed solution of methanol (6 mL) and tetrahydrofuran (6 mL), and sodium borohydride (14 mg, 0.36 mmol) was added under ice-cooling, and the mixture was stirred at the same temperature for 2 hrs. The reaction mixture was concentrated, and the residue was diluted with ethyl acetate, washed with 1N hydrochloric acid and saturated brine, dried, and concentrated under reduced pressure. The residue was purified by silica gel column chromatography (hexane/ethyl acetate=10/1-1/1) to give the title compound (0.25 g, yield 83%) as a colorless oil.

¹H NMR (CDCl₃) δ: 1.41 (9H, s), 2.50 (2H, t, J=7.8 Hz), 2.85 (2H, t, J=7.8 Hz), 4.56 (2H, s), 5.10 (2H, s), 6.90 (2H, d, J=8.7 Hz), 7.12 (2H, d, J=8.7 Hz), 7.23-7.45 (7H, m), 7.56 (1H, m).

EXAMPLE 297

3-(4-((2'-(hydroxymethyl)biphenyl-3-yl)methoxy) phenyl)propanoic acid tert-Butyl 3-(4-((2'-(hydroxymethyl)biphenyl-3-yl)methoxy)phenyl)propanoate (0.25 g, 0.60 mmol) was dissolved in trifluoroacetic acid (2 mL), and the mixture was stirred at room temperature for 1 hr. The reaction mixture was concentrated, and the residue was purified by preparative HPLC (gradient cycle A) to give the title compound (10 mg, 5%) as colorless crystals. MS (APCI–): 361 (M–H).

EXAMPLE 298

3-[4-[[3-[benzyl(ethyl)amino]benzyl]oxy]phenyl] propanoic acid

A mixture of methyl 3-[4-[(3-bromobenzyl)oxy]phenyl] propanoate (0.30 g, 0.86 mmol), benzyl(ethyl)amine (0.20 mL, 1.29 mmol), cesium carbonate (0.39 g, 1.20 mmol), tris(dibenzylidenacetone)dipalladium (0) (0.031 g, 0.034 mmol), rac-2,2'-bis(diphenylphosphino)-1,1'-binaphthyl (0.032 g, 0.052 mmol) and toluene (6 mL) was stirred under a nitrogen atmosphere at 80° C. for 16 hrs. The reaction mixture was cooled, washed with water and saturated brine, dried over magnesium sulfate, and concentrated under reduced pressure. Then the residue was dissolved in a mixed solution of methanol (4 mL) and tetrahydrofuran (6 mL), 1N aqueous sodium hydroxide solution (1.8 mL) was added, and the mixture was stirred at room temperature for 2 hrs. The reaction mixture was adjusted to pH 7 with 1N hydrochloric acid, and separated and extracted with ethyl acetate. The organic layer was washed with water and saturated brine, dried over magnesium sulfate, and concentrated under reduced pressure. The residue was purified by silica gel column chromatography (hexane/ethyl acetate=2/1-1/2) to give the title compound (42 mg, yield 13%) as yellow crystals. MS (APCI–): 388 (M–H).

EXAMPLE 299

3-[4-[[3-[ethyl(phenyl)amino]benzyl]oxy]phenyl] propanoic acid

The title compound was synthesized in the same manner as in Example 298 from methyl 3-[4-[(3-bromobenzyl)oxy] phenyl]propanoate and ethyl (phenyl). Beige crystals (yield 11%). MS (APCI–): 374 (M–H).

EXAMPLE 300

3-[4-[[3-(biphenyl-3-ylamino)benzyl]oxy]phenyl] propanoic acid

The title compound was synthesized in the same manner as in Example 298 from methyl 3-[4-[(3-bromobenzyl)oxy] phenyl]propanoate and biphenyl-3-ylamine. colorless crystals (yield 6%).

¹H NMR (CDCl₃) δ: 2.65 (2H, t, J=7.8 Hz), 2.90 (2H, t, J=7.8 Hz), 5.00 (2H, s), 6.90 (2H, d, J=8.7 Hz), 6.98 (1H, d, J=7.5 Hz), 7.02-7.20 (6H, m), 7.27-7.46 (6H, m), 7.53-7.59 (2H, m).

EXAMPLE 301 methyl 3-[4-[(3-anilinobenzyl)oxy]phenyl]propanoate

To a mixture of (3-anilinophenyl)methanol (1.12 g, 5.62 mmol), methyl 3-(4-hydroxyphenyl)propanoate (1.22 g, 6.75 mmol), triphenylphosphine (1.92 g, 7.31 mmol) and tetrahydrofuran (20 mL) was added diethyl azodicarboxylate toluene solution (40%, 3.32 mL) with stirring at 0° C. and the mixture was stirred at room temperature for 14 hrs. The reaction mixture was concentrated, and the residue was purified by silica gel column chromatography (hexane/ethyl acetate=10/1-2/1) to give the title compound (1.01 g, yield 50%) as beige crystals.
$^1$H NMR (CDCl$_3$) δ: 2.60 (2H, t, J=7.8 Hz), 2.89 (2H, t, J=7.8 Hz), 3.66 (3H, s), 4.99 (2H, s), 5.74 (1H, s), 6.89 (2H, d, J=8.7 Hz), 6.92-7.15 (7H, m), 7.22-7.30 (4H, m).

EXAMPLE 302

3-[4-[[3-[phenyl(propyl)amino]benzyl]oxy]phenyl] propanoic acid

To a solution of methyl 3-[4-[(3-anilinobenzyl)oxy]phenyl]propanoate (0.20 g, 0.58 mmol) in N,N-dimethylformamide (4 mL) was added 60% sodium hydride (0.035 g, 0.86 mmol) with stirring at 0° C., and the mixture was stirred at the same temperature for 10 min. n-Propylbromide (0.063 mL, 0.69 mmol) and sodium iodide (0.10 g, 0.69 mmol) were added to this mixture with stirring at 0° C., and the mixture was stirred at room temperature for 16 hrs. The reaction mixture was diluted with ethyl acetate, washed with water and saturated brine, dried, and concentrated under reduced pressure. Then the residue was dissolved in a mixed solution of methanol (3 mL) and tetrahydrofuran (6 mL), 1N aqueous sodium hydroxide solution (1.5 mL) was added, and the mixture was stirred at room temperature for 1 hr. The reaction mixture was adjusted to pH 3 with 1N hydrochloric acid, separated and extracted with ethyl acetate. The organic layer was dried over anhydrous magnesium sulfate, and concentrated under reduced pressure. The residue was purified by silica gel column chromatography (hexane/ethyl acetate=4/1-1/2) to give the title compound (0.11 g, yield 47%) as colorless crystals. MS (APCI-): 388 (M-H).

EXAMPLE 303

3-[4-[[3-[butyl(phenyl)amino]benzyl]oxy]phenyl] propanoic acid

The title compound was synthesized in the same manner as in Example 302 from methyl 3-[4-[(3-anilinobenzyl)oxy] phenyl]propanoate and n-butylbromide. colorless crystals (yield 57%). MS (APCI-): 402 (M-H).

EXAMPLE 304

3-[4-[[3-[benzyl(phenyl)amino]benzyl]oxy]phenyl] propanoic acid

The title compound was synthesized in the same manner as in Example 302 from methyl 3-[4-[(3-anilinobenzyl)oxy] phenyl]propanoate and benzylbromide. colorless crystals (yield 74%). MS (APCI-): 436 (M-H).

EXAMPLE 305

3-[4-[(3-anilinobenzyl)oxy]phenyl]propanoic acid

The title compound was synthesized in the same manner as in Example 278 from methyl 3-[4-[(3-anilinobenzyl)oxy] phenyl]propanoate. colorless crystals (yield 70%). MS (APCI-): 346 (M-H).

EXAMPLE 306

3-[4-[[3-[isobutyl(phenyl)amino]benzyl]oxy]phenyl] propanoic acid

The title compound was synthesized in the same manner as in Example 302 from methyl 3-[4-[(3-anilinobenzyl)oxy] phenyl]propanoate and isobutyl bromide. beige powder (yield 12%). MS (APCI-): 402 (M-H).

EXAMPLE 307

3-(4-((4-((ethyl(3-methylphenyl)amino)methyl)benzyl)oxy)phenyl)propanoic acid

To a solution of methyl 3-(4-((4-(chloromethyl)benzyl) oxy)phenyl)propanoate (50 mg, 0.16 mmol) in N,N-dimethylformamide (1 mL) was added a solution of N-ethyl-m-toluidine (51 mg, 0.19 mmol) in N,N-dimethylformamide (0.5 mL). Potassium carbonate (33 mg, 0.24 mmol) was added and the mixture was stirred at 70° C. for 66 hrs. Water (2 mL) was added to the reaction mixture and the mixture was extracted with dichloromethane (2 mL). The organic layer was concentrated with a GeneVac centrifugation concentration apparatus under reduced pressure.

The obtained product was dissolved in methanol (2 mL), 1N aqueous sodium hydroxide solution (0.32 mL, 0.32 mmol) was added, and the mixture was stirred at room temperature for 18 hrs. The reaction mixture was acidified with 1N hydrochloric acid and the mixture was extracted with dichloromethane (2 mL). The organic layer was concentrated with a GeneVac centrifugation concentration apparatus under reduced pressure. The residue was purified by preparative HPLC (gradient cycle B) to give the title compound (21 mg, 26%). MS (ESI+, m/e) 404 (M+1).

The compounds of the following Example 308-Example 338 were synthesized in the same manner as in Example 307 from methyl 3-(4-((4-(chloromethyl)benzyl)oxy)phenyl) propanoate (50 mg, 0.16 mmol) and the corresponding amine.

EXAMPLE 308

3-(4-((4-((methyl(2-(phenylsulfonyl)ethyl)amino) methyl)benzyl)oxy)phenyl)propanoic acid yield 43 mg. MS (ESI+, m/e) 468 (M+1).

EXAMPLE 309

3-(4-((4-(((3-phenoxybenzyl)amino)methyl)benzyl) oxy)phenyl)propanoic acid yield 40 mg. MS (ESI+, m/e) 468 (M+1).

EXAMPLE 310

3-(4-((4-(((4-phenoxybenzyl)amino)methyl)benzyl)oxy)phenyl)propanoic acid yield 37 mg. MS (ESI+, m/e) 468 (M+1).

EXAMPLE 311

3-(4-((4-(((4-(2-pyrazinyloxy)benzyl)amino)methyl)benzyl)oxy)phenyl)propanoic acid yield 13 mg. MS (ESI+, m/e) 470 (M+1).

EXAMPLE 312

3-(4-((4-(((2-phenoxypropyl)amino)methyl)benzyl)oxy)phenyl)propanoic acid yield 33 mg. MS (ESI+, m/e) 420 (M+1).

EXAMPLE 313

3-(4-((4-(((2,2-diphenylethyl)amino)methyl)benzyl)oxy)phenyl)propanoic acid yield 45 mg. MS (ESI+, m/e) 466 (M+1).

EXAMPLE 314

3-(4-((4-(((biphenyl-2-ylmethyl)amino)methyl)benzyl)oxy)phenyl)propanoic acid yield 47 mg. MS (ESI+, m/e) 452 (M+1).

EXAMPLE 315

3-(4-((4-(((biphenyl-3-ylmethyl)amino)methyl)benzyl)oxy)phenyl)propanoic acid yield 32 mg. MS (ESI+, m/e) 452 (M+1).

EXAMPLE 316

3-(4-((4-(((biphenyl-4-ylmethyl)amino)methyl)benzyl)oxy)phenyl)propanoic acid yield 12 mg. MS (ESI+, m/e) 452 (M+1).

EXAMPLE 317

3-(4-((4-(((2-phenyl-2-(1-pyrrolidinyl)ethyl)amino)methyl)benzyl)oxy)phenyl)propanoic acid yield 40 mg. MS (ESI+, m/e) 459 (M+1).

EXAMPLE 318

3-(4-((4-((methyl(1-phenyl-2-(1-pyrrolidinyl)ethyl)amino)methyl)benzyl)oxy)phenyl)propanoic acid yield 18 mg. MS (ESI+, m/e) 473 (M+1).

EXAMPLE 319

3-(4-((4-(((2-cyanoethyl)(phenyl)amino)methyl)benzyl)oxy)phenyl)propanoic acid yield 15 mg. MS (ESI+, m/e) 415 (M+1).

EXAMPLE 320

3-(4-((4-((benzyl(phenyl)amino)methyl)benzyl)oxy)phenyl)propanoic acid yield 21 mg. MS (ESI+, m/e) 452 (M+1).

EXAMPLE 321

3-(4-((4-((ethyl(2-methylphenyl)amino)methyl)benzyl)oxy)phenyl)propanoic acid yield 22 mg. MS (ESI+, m/e) 404 (M+1).

EXAMPLE 322

3-(4-((4-((butyl(phenyl)amino)methyl)benzyl)oxy)phenyl)propanoic acid yield 39 mg. MS (ESI+, m/e) 418 (M+1).

EXAMPLE 323

3-(4-((4-((phenyl(propyl)amino)methyl)benzyl)oxy)phenyl)propanoic acid yield 23 mg. MS (ESI+, m/e) 404 (M+1).

EXAMPLE 324

3-(4-((4-((pentyl(phenyl)amino)methyl)benzyl)oxy)phenyl)propanoic acid yield 21 mg. MS (ESI+, m/e) 432 (M+1).

EXAMPLE 325

3-(4-((4-((ethyl(2-naphthyl)amino)methyl)benzyl)oxy)phenyl)propanoic acid yield 7 mg. MS (ESI+, m/e) 440 (M+1).

EXAMPLE 326

3-(4-((4-((isopropyl(phenyl)amino)methyl)benzyl)oxy)phenyl)propanoic acid yield 6 mg. MS (ESI+, m/e) 404 (M+1).

EXAMPLE 327

3-(4-((4-((benzyl(methyl)amino)methyl)benzyl)oxy)phenyl)propanoic acid yield 51 mg. MS (ESI+, m/e) 390 (M+1).

EXAMPLE 328

3-(4-((4-(((4-chlorophenyl)(methyl)amino)methyl) benzyl)oxy)phenyl)propanoic acid yield 20 mg. MS (ESI+, m/e) 410 (M+1).

EXAMPLE 329

3-(4-((4-(((3-methylphenyl)(propyl)amino)methyl) benzyl)oxy)phenyl)propanoic acid yield 29 mg. MS (ESI+, m/e) 418 (M+1).

EXAMPLE 330

3-(4-((4-((dibenzylamino)methyl)benzyl)oxy)phenyl)propanoic acid yield 58 mg. MS (ESI+, m/e) 466 (M+1).

EXAMPLE 331

3-(4-((4-((benzyl(ethyl)amino)methyl)benzyl)oxy)phenyl)propanoic acid yield 46 mg. MS (ESI+, m/e) 404 (M+1).

EXAMPLE 332

3-(4-((4-((benzyl(butyl)amino)methyl)benzyl)oxy)phenyl)propanoic acid yield 63 mg. MS (ESI+, m/e) 432 (M+1).

EXAMPLE 333

3-(4-((4-(((4-cyclohexylphenyl)amino)methyl)benzyl)oxy)phenyl)propanoic acid yield 7 mg. MS (ESI+, m/e) 444 (M+1).

EXAMPLE 334

3-(4-((4-(((2-imidazo[1,5-a]pyridin-3-ylethyl)(phenyl)amino)methyl)benzyl)oxy)phenyl)propanoic acid yield 9 mg. MS (ESI+, m/e) 506 (M+1).

EXAMPLE 335

3-(4-((4-(((4-(4-chlorophenyl)-1,3-thiazol-2-yl)(methyl)amino)methyl)benzyl)oxy)phenyl)propanoic acid yield 18 mg. MS (ESI+, m/e) 493 (M+1).

EXAMPLE 336

3-(4-((4-(((4-(4-cyclohexylphenyl)-1,3-thiazol-2-yl)(methyl)amino)methyl)benzyl)oxy)phenyl)propanoic acid yield 2 mg. MS (ESI+, m/e) 541 (M+1).

EXAMPLE 337

3-{2-[(4-{[4-(2-carboxyethyl)phenoxy]methyl}benzyl)(methyl)amino]-4-phenyl-1,3-thiazol-5-yl}propanoic acid yield 10 mg. MS (ESI+, m/e) 531 (M+1).

EXAMPLE 338

3-(4-((4-((methyl(4-(5,6,7,8-tetrahydro-2-naphthyl)-1,3-thiazol-2-yl)amino)methyl)benzyl)oxy)phenyl)propanoic acid yield 6 mg. MS (ESI+, m/e) 513 (M+1).

EXAMPLE 339 methyl 3-(4-((6-benzyloxy-2',6'-dimethyl-biphenyl-3-yl)methoxy)phenyl)propanoate The title compound was obtained as colorless prism crystals in the same manner as in Reference Example 31 from (6-benzyloxy-2',6'-dimethyl-biphenyl-3-yl)methanol and methyl 4-hydroxyphenylpropanoate. yield 55%.
$^1$H-NMR (CDCl$_3$) δ 2.03 (6H, s), 2.59 (2H, t, J=7.6 Hz), 2.89 (2H, t, J=7.6 Hz), 3.66 (3H, s), 4.95-5.08 (4H, m), 6.88 (2H, d, J=8.8 Hz), 6.94-7.42 (13H, m).

EXAMPLE 340

3-(4-((6-benzyloxy-2',6'-dimethyl-biphenyl-3-yl)methoxy)phenyl)propanoic acid

The title compound was obtained as colorless prisms in the same manner as in Reference Example 4 from ethyl 3-(4-((6-benzyloxy-2',6'-dimethyl-biphenyl-3-yl)methoxy)phenyl)propanoate. yield 69%.
$^1$H-NMR (CDCl$_3$) δ 2.03 (6H, s), 2.64 (2H, t, J=7.8 Hz), 2.90 (2H, t, J=7.8 Hz), 4.97-5.10 (4H, m), 6.88 (2H, d, J=8.4 Hz), 6.95-7.46 (13H, m).

EXAMPLE 341 methyl 3-{4-[(4-{[(3-methylbutyl)(4-phenyl-1,3-thiazol-2-yl)amino]methyl}benzyl)oxy]phenyl}propanoate A mixture of N-(3-methylbutyl)-4-phenyl-1,3-thiazol-2-amine (370 mg), sodium hydride (60% oil, 50 mg) and N,N-dimethylformamide (5 mL) was stirred at room temperature for 1 hr. Methyl 3-(4-{[4-(chloromethyl)benzyl]oxy}phenyl) propanoate (318 mg) was added to the reaction mixture, and the mixture was stirred at room temperature for 1 hr. The reaction mixture was poured into water, acidified with 1N aqueous hydrochloric acid solution and extracted with ethyl acetate. The ethyl acetate layer was dried using Presep Dehydration tube (manufactured by Wako Pure Chemical Industries, Ltd.), and concentrated. The residue was purified by preparative HPLC (gradient cycle A) to give the title compound (250 mg, yield 47%) as a yellow oil.
MS (ESI+) 529 (M+H).

EXAMPLE 342

3-{4-[(4-{[(3-methylbutyl)(4-phenyl-1,3-thiazol-2-yl)amino]methyl}benzyl)oxy]phenyl}propanoic acid Methyl 3-{4-[(4-{[(3-methylbutyl)(4-phenyl-1,3-thiazol-2-yl)amino]methyl}benzyl)oxy]phenyl}propanoate (240 mg) was dissolved in a mixed solvent of methanol (2 mL) and tetrahydrofuran (2 mL), and 2N aqueous sodium hydroxide solution (2 mL) was added. The mixture was stirred at room temperature for 1 hr. The reaction mixture was poured into water, acidified with 1N aqueous hydrochloric acid solution, and extracted with ethyl acetate. The ethyl acetate layer was dried using Presep Dehydration tube (manufactured by Wako Pure Chemical Industries, Ltd.), and concentrated to give the title compound (220 mg, yield 90%) as a pale-yellow oil.

MS (ESI+) 515 (M+H).

EXAMPLE 343 methyl 3-{4-[(4-{[(4-isopropyl-1,3-thiazol-2-yl)(3-methylbutyl)amino]methyl}benzyl)oxy]phenyl}propanoate A mixture of 4-isopropyl-N-(3-methylbutyl)-1,3-thiazol-2-amine (313 mg), sodium hydride (60% oil, 50 mg) and N,N-dimethylformamide (5 mL) was stirred at room temperature for 1 hr. Methyl 3-(4-{[4-(chloromethyl)benzyl]oxy}phenyl)propanoate (318 mg) was added to the reaction mixture, and the mixture was stirred at room temperature for 1 hr. The reaction mixture was poured into water, acidified with 1N aqueous hydrochloric acid solution, and extracted with ethyl acetate. The ethyl acetate layer was dried using Presep Dehydration tube (manufactured by Wako Pure Chemical Industries, Ltd.), and concentrated. The residue was purified by preparative HPLC (gradient cycle A) to give the title compound (150 mg, yield 28%) as a yellow oil.

MS (ESI+) 495 (M+H).

EXAMPLE 344

3-{4-[(4-{[(4-isopropyl-1,3-thiazol-2-yl)(3-methylbutyl)amino]methyl}benzyl)oxy]phenyl}propanoic acid Methyl 3-{4-[(4-{[(4-isopropyl-1,3-thiazol-2-yl)(3-methylbutyl)amino]methyl}benzyl)oxy]phenyl}propanoate (140 mg) was dissolved in a mixed solvent of methanol (2 mL) and tetrahydrofuran (2 mL), and 2N aqueous sodium hydroxide solution (2 mL) was added. The mixture was stirred at room temperature for 1 hr. The reaction mixture was poured into water, acidified with 1N aqueous hydrochloric acid solution, and extracted with ethyl acetate. The ethyl acetate layer was dried using Presep Dehydration tube (manufactured by Wako Pure Chemical Industries, Ltd.), and concentrated to give the title compound (120 mg, yield 88%) as a pale-yellow oil.

MS (ESI+) 481 (M+H).

EXAMPLE 345

3-[4-({4-[1-(4-phenyl-1,3-thiazol-2-yl)butoxy]benzyl}oxy)phenyl]propanoic acid

A mixture of (4-phenyl-1,3-thiazol-2-yl)methanol (3.82 g), activated manganese dioxide (15 g) and tetrahydrofuran (30 mL) was stirred at room temperature for 3 hrs. The reaction mixture was filtered, and the filtrate was concentrated. The obtained oil was dissolved in tetrahydrofuran (30 mL). Propylmagnesium bromide (2N tetrahydrofuran solution, 10 mL) was added at 0° C. and the mixture was stirred for 1 hr. The reaction mixture was poured into 1N aqueous hydrochloric acid solution, and the mixture was extracted with ethyl acetate. The ethyl acetate layer was concentrated, and the residue was purified by silica gel column chromatography with ethyl acetate-hexane (gradient of 1:19 to 1:1 by volume ratio) to give a yellow oil (1.1 g). To a solution of this yellow oil (233 mg), methyl 4-hydroxybenzoate (152 mg) and triphenylphosphine (399 mg) in toluene (2 mL) was added dropwise diethyl azodicarboxylate (40% toluene solution 650 mg) at room temperature, and the mixture was stirred at room temperature for 1 hr. The reaction mixture was concentrated and the residue was purified by silica gel column chromatography with ethyl acetate-hexane (gradient of 1:19 to 1:1 by volume ratio) to give a yellow oil. This oil was dissolved in tetrahydrofuran (10 mL). A lithium aluminum hydride (40 mg) solution was added at 0° C., and the temperature was allowed to return to room temperature. The mixture was stirred for 1 hr., sodium sulfate 10 hydrate (1.0 g) was added, and the insoluble material was filtered off. The filtrate was concentrated and methyl 3-(4-hydroxyphenyl)propanoate (180 mg), triphenylphosphine (399 mg) and toluene (2 mL) were added to the residue, and diethyl azodicarboxylate (40% toluene solution 650 mg) was added dropwise at room temperature, and the mixture was stirred at room temperature for 1 hr. The reaction mixture was concentrated and the residue was purified by silica gel column chromatography with ethyl acetate-hexane (gradient of 1:19 to 1:1 by volume ratio) to give as a yellow oil. This yellow oil was dissolved in a mixed solvent of methanol (2 mL) and tetrahydrofuran (2 mL) and 2N aqueous sodium hydroxide solution (2 mL) was added. The mixture was stirred at room temperature for 1 hr. The reaction mixture was poured into water, acidified with 1N aqueous hydrochloric acid solution, and extracted with ethyl acetate. The ethyl acetate layer was dried using Presep Dehydration tube (manufactured by Wako Pure Chemical Industries, Ltd.) and concentrated to give the title compound (93 mg) as colorless crystals.

MS (ESI+) 488 (M+H).

The structural formulas of the compounds obtained in Examples 1-201, 202A and 203-345 are shown in the following.

| Ex.No. | structural formula |
|---|---|
| 1 | (structure: indane-O-phenyl-CH$_2$CH$_2$-COOH) |

| Ex.No. | structural formula |
|---|---|
| 2 | 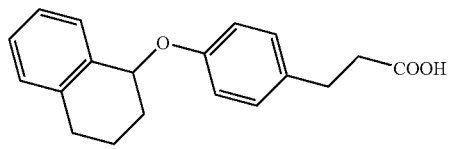 |
| 3 | 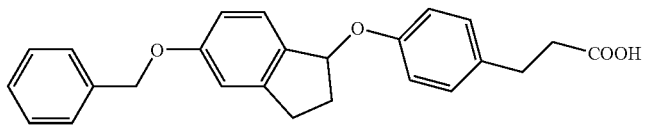 |
| 4 | 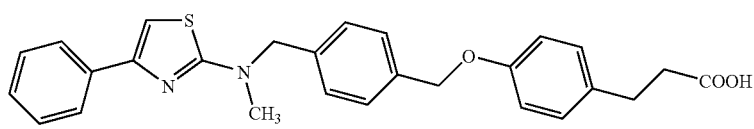 |
| 5 | 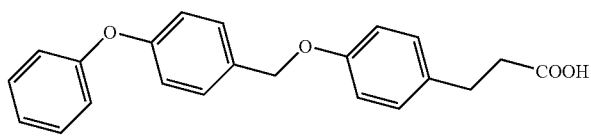 |
| 6 | 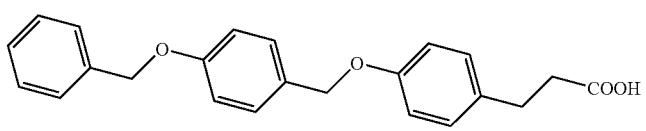 |
| 7 | 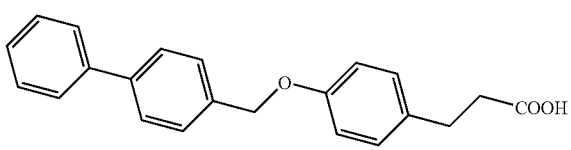 |
| 8 | 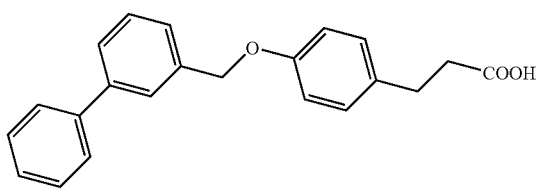 |
| 9 | 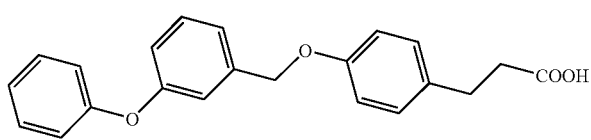 |
| 10 | 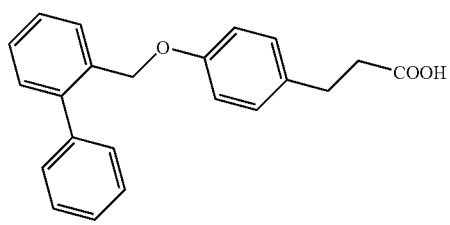 |

| Ex.No. | structural formula |
|---|---|
| 11 | 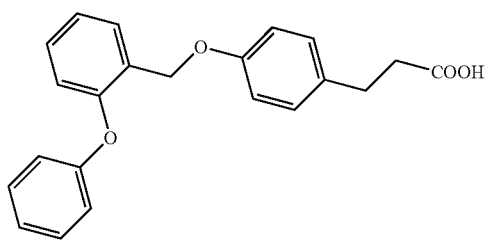 |
| 12 | 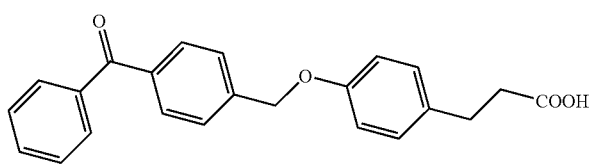 |
| 13 | 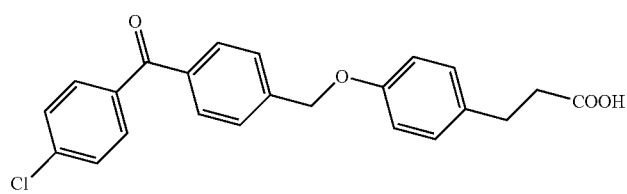 |
| 14 | 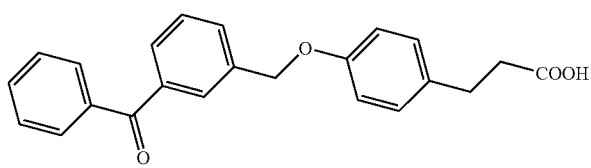 |
| 15 | 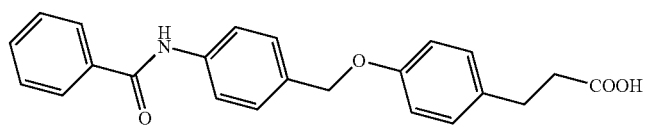 |
| 16 | 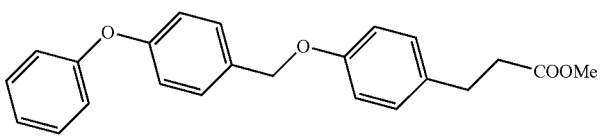 |
| 17 | 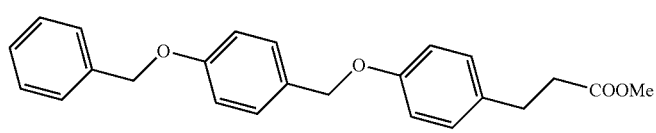 |
| 18 | 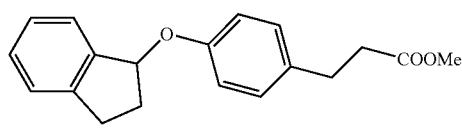 |
| 19 | 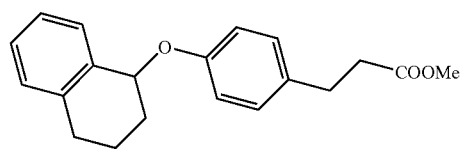 |

-continued

| Ex.No. | structural formula |
|---|---|
| 20 | 3'-formyl-biphenyl-3-yl-methyl 4-(2-methoxycarbonylethyl)phenyl ether (OHC-C₆H₄-C₆H₄-CH₂-O-C₆H₄-CH₂CH₂-COOMe) |
| 21 | 3'-formyl-biphenyl-3-yl-methyl 4-(2-carboxyethyl)phenyl ether (OHC-C₆H₄-C₆H₄-CH₂-O-C₆H₄-CH₂CH₂-COOH) |
| 22 | biphenyl-3-yl-methyl 4-(2-methoxycarbonylethyl)phenyl ether |
| 23 | 3-phenoxybenzyl 4-(2-methoxycarbonylethyl)phenyl ether |
| 24 | biphenyl-2-yl-methyl 4-(2-methoxycarbonylethyl)phenyl ether |
| 25 | 5-benzyloxy-1-[4-(2-methoxycarbonylethyl)phenoxy]indane |
| 26 | 2-phenoxybenzyl 4-(2-methoxycarbonylethyl)phenyl ether |
| 27 | 4-benzoylbenzyl 4-(2-methoxycarbonylethyl)phenyl ether |

-continued

| Ex.No. | structural formula |
|---|---|
| 28 | (4-chlorophenyl)(4-((4-(3-methoxy-3-oxopropyl)phenoxy)methyl)phenyl)methanone |
| 29 | N-(4-((4-(3-methoxy-3-oxopropyl)phenoxy)methyl)phenyl)benzamide |
| 30 | methyl 3-(4-((4-((methyl(4-phenylthiazol-2-yl)amino)methyl)benzyl)oxy)phenyl)propanoate |
| 31 | 3-(4-((5,6-dihydro-4H-cyclopenta[b]thiophen-4-yl)oxy)phenyl)propanoic acid |
| 32 | methyl 3-(4-((4,5,6,7-tetrahydrobenzo[b]thiophen-4-yl)oxy)phenyl)propanoate |
| 33 | methyl 3-(4-((2,3-dihydro-1H-inden-1-yl)oxy)-3,5-difluorophenyl)propanoate |
| 34 | 3-(4-((2,3-dihydro-1H-inden-1-yl)oxy)-3,5-difluorophenyl)propanoic acid |
| 35 | 3-(4-((4-(benzyloxy)-2,3-dihydro-1H-inden-1-yl)oxy)phenyl)propanoic acid |
| 36 | methyl 3-(4-((6-(benzyloxy)-2,3-dihydro-1H-inden-1-yl)oxy)phenyl)propanoate |
| 37 | 3-(4-((6-(benzyloxy)-2,3-dihydro-1H-inden-1-yl)oxy)phenyl)propanoic acid |

-continued
| Ex.No. | structural formula |
|---|---|
| 38 | 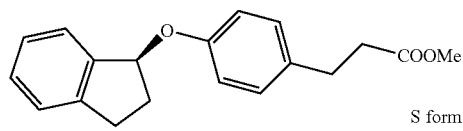 S form |
| 39 | 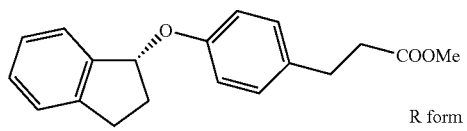 R form |
| 40 | 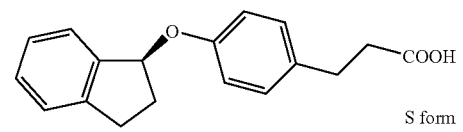 S form |
| 41 | 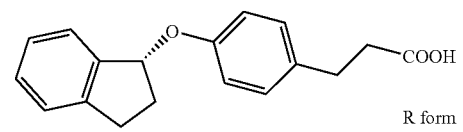 R form |
| 42 | 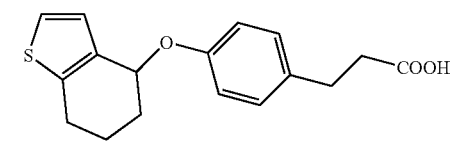 |
| 43 | 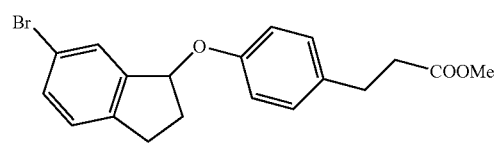 |
| 44 | 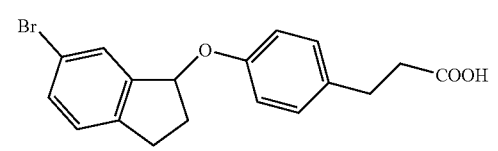 |
| 45 | 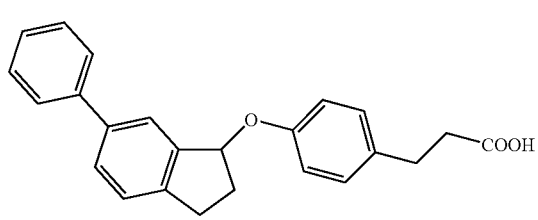 |
| 46 | 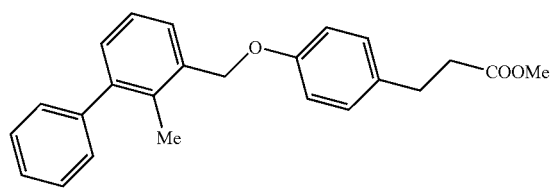 |

-continued
| Ex.No. | structural formula |
|---|---|
| 47 | 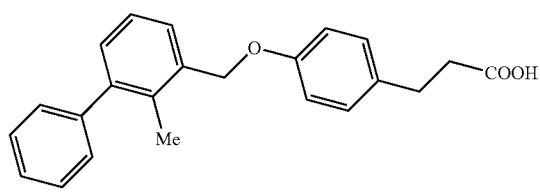 |
| 48 | 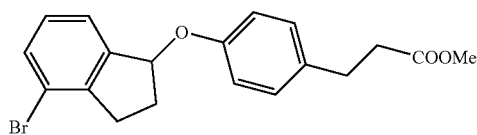 |
| 49 | 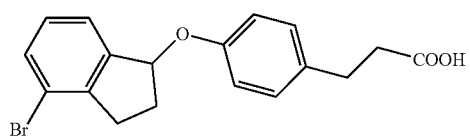 |
| 50 | 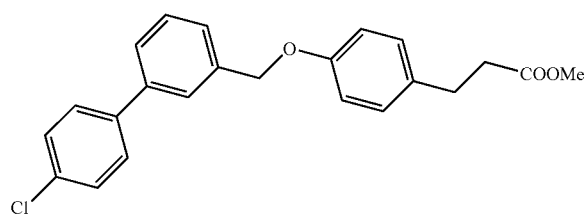 |
| 51 | 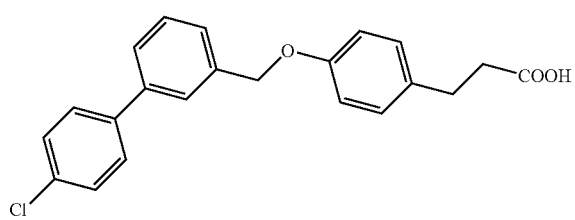 |
| 52 | 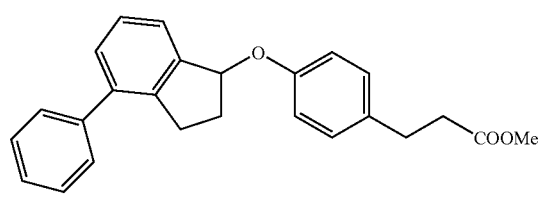 |
| 53 | 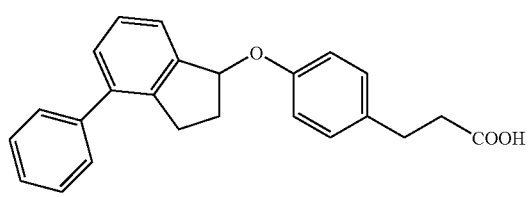 |
| 54 | 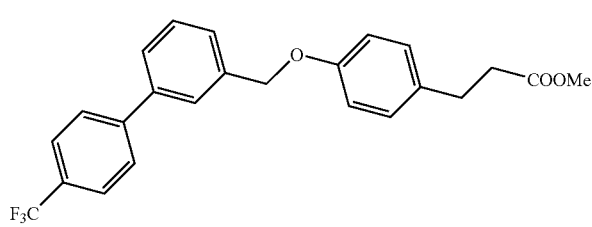 |

| Ex.No. | structural formula |
|---|---|
| 55 | 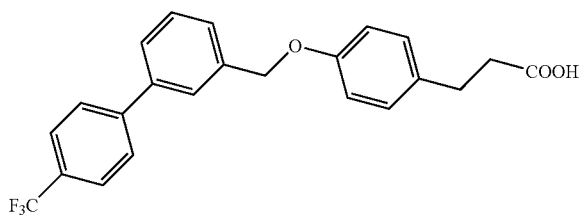 |
| 56 | 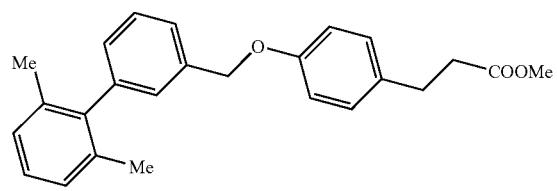 |
| 57 | 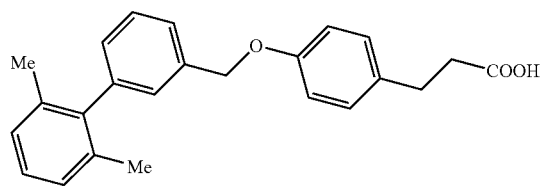 |
| 58 | 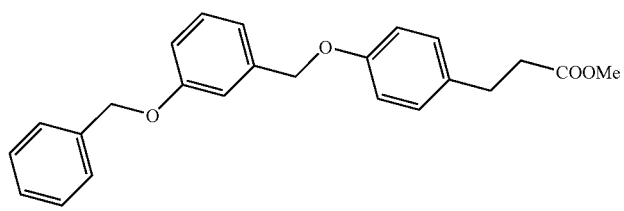 |
| 59 | 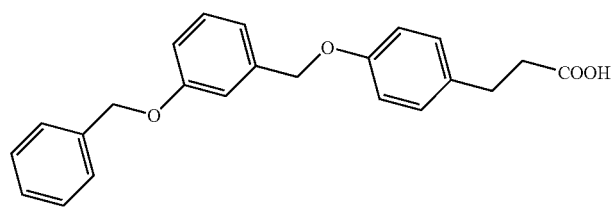 |
| 60 | 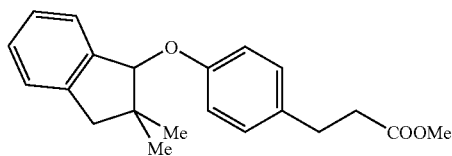 |
| 61 | 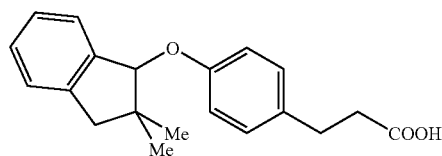 |
| 62 | 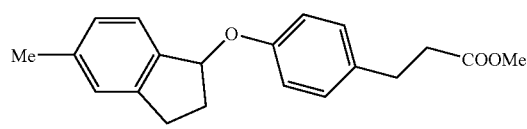 |

| Ex.No. | structural formula |
|---|---|
| 63 | 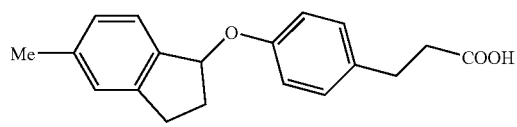 |
| 64 | 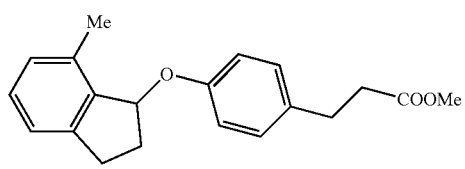 |
| 65 | 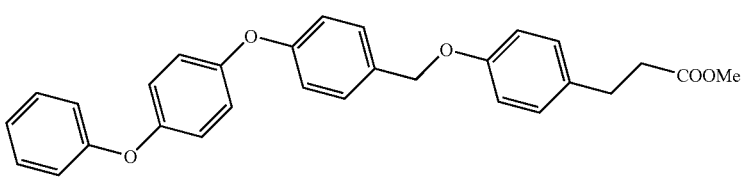 |
| 66 | 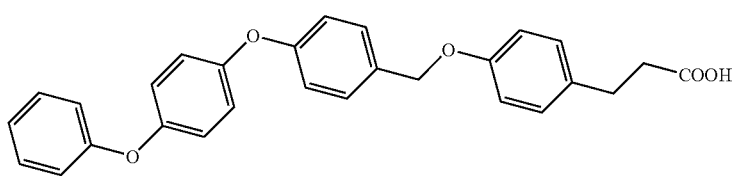 |
| 67 | 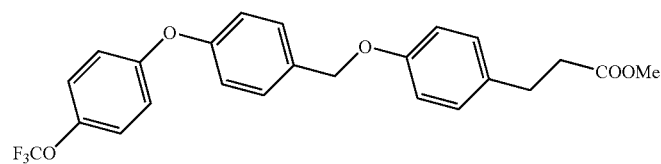 |
| 68 | 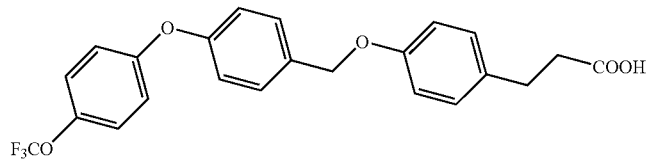 |
| 69 | 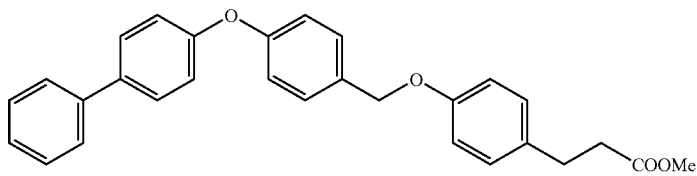 |
| 70 | 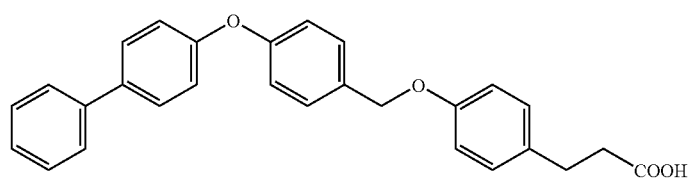 |
| 71 | 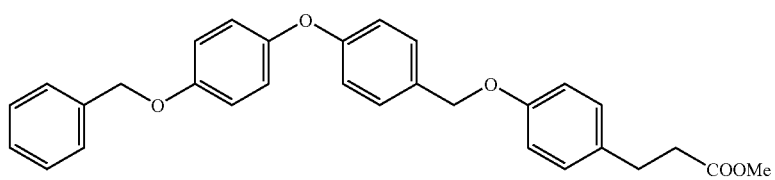 |

-continued
| Ex.No. | structural formula |
|---|---|
| 72 | 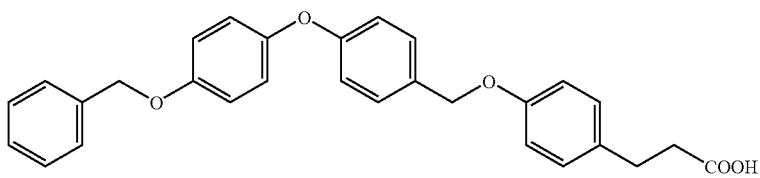 |
| 73 | 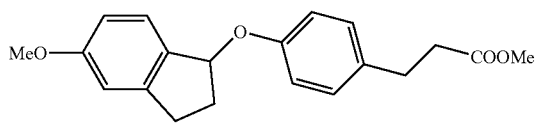 |
| 74 | 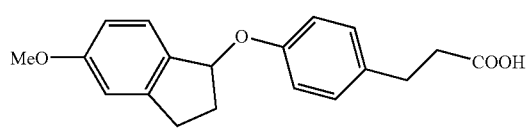 |
| 75 | 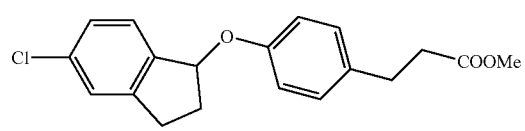 |
| 76 | 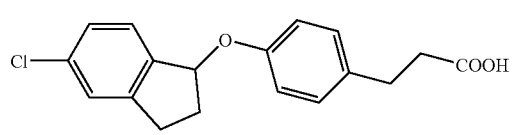 |
| 77 | 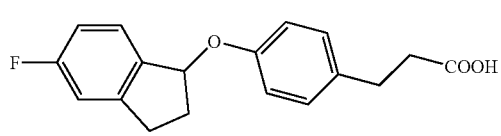 |
| 78 | 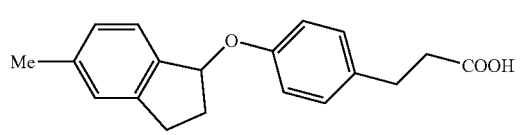 |
| 79 | 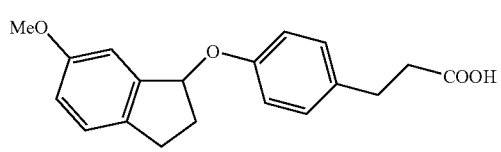 |
| 80 | 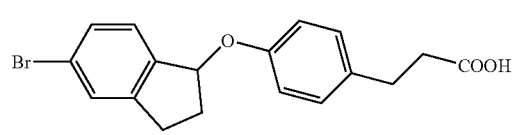 |
| 81 | 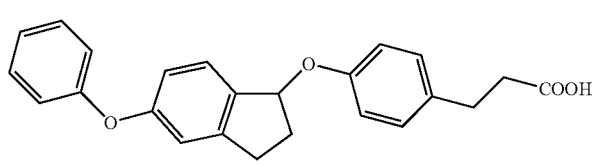 |
| 82 | 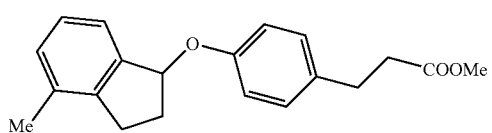 |

| Ex.No. | structural formula |
|---|---|
| 83 | 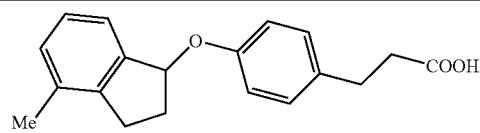 |
| 84 | 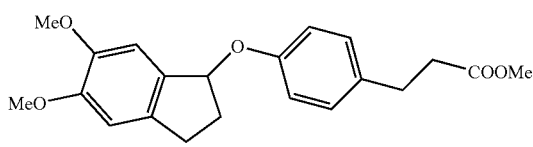 |
| 85 | 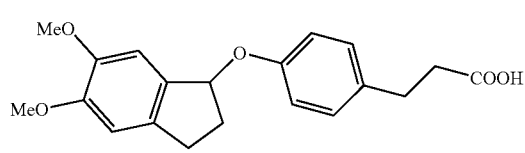 |
| 86 | 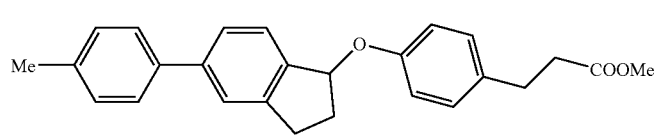 |
| 87 | 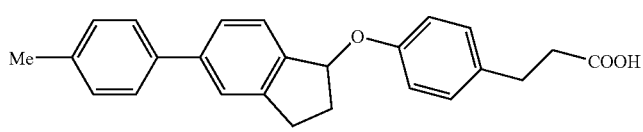 |
| 88 | 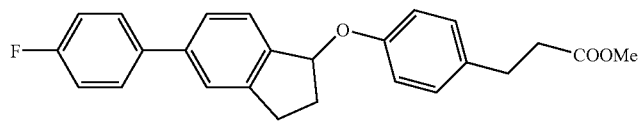 |
| 89 | 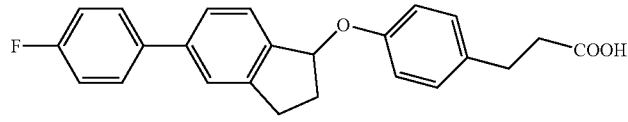 |
| 90 | 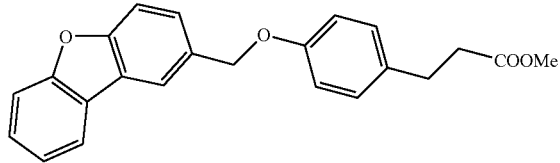 |
| 91 | 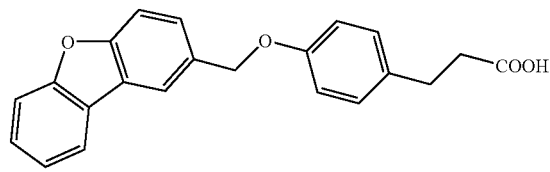 |
| 92 | 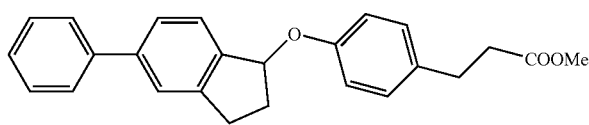 |
| 93 | 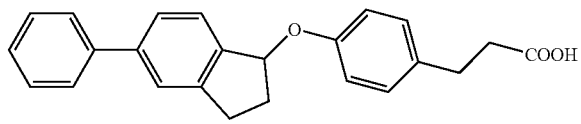 |

-continued
| Ex.No. | structural formula |
|---|---|
| 94 | 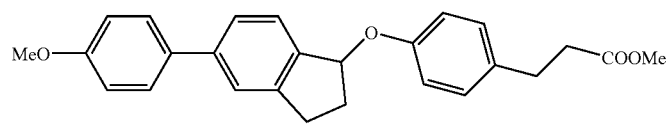 |
| 95 | 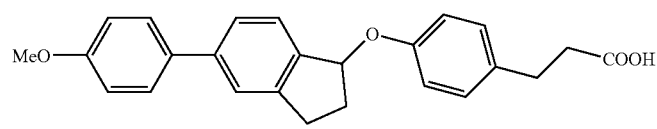 |
| 96 | 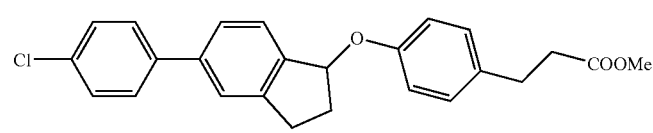 |
| 97 | 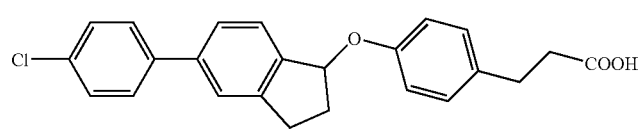 |
| 98 | 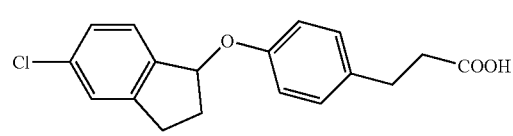<br>(+)-form |
| 99 | 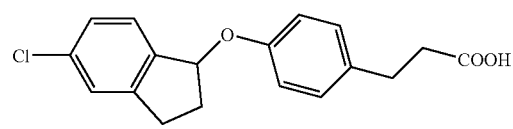<br>(−)-form |
| 100 | 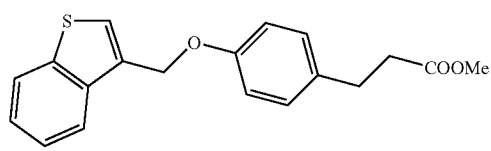 |
| 101 | 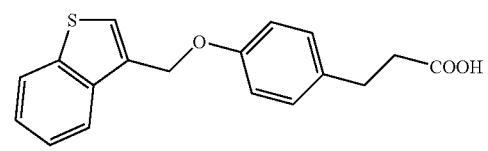 |
| 102 | 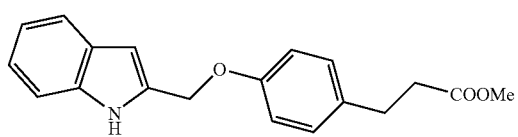 |
| 103 | 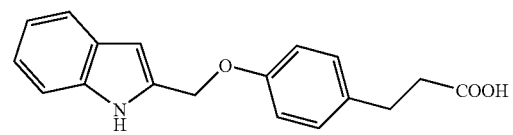 |

-continued
| Ex.No. | structural formula |
|---|---|
| 104 | 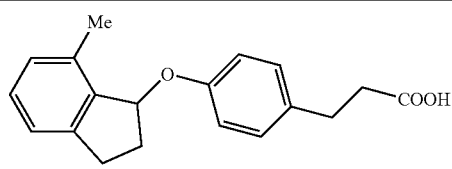 |
| 105 | 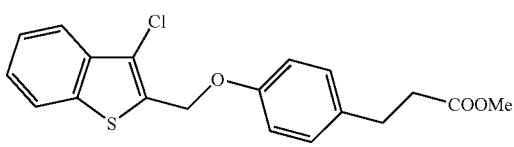 |
| 106 | 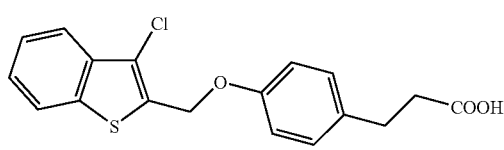 |
| 107 | 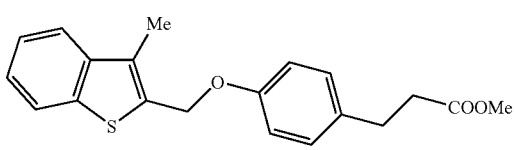 |
| 108 | 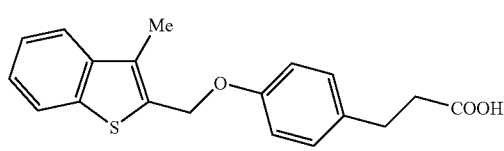 |
| 109 | 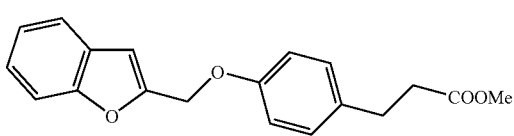 |
| 110 | 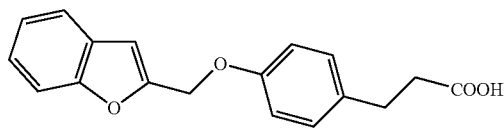 |
| 111 | 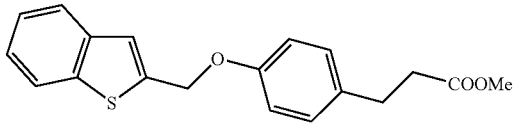 |
| 112 | 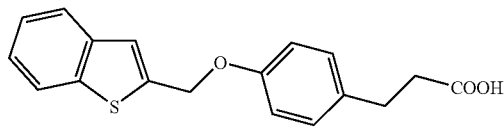 |
| 113 | 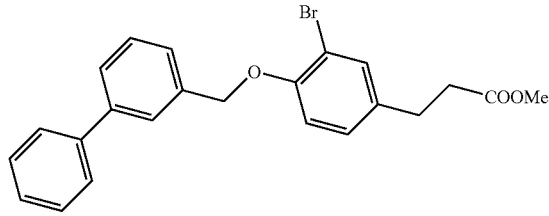 |

| Ex.No. | structural formula |
|---|---|
| 114 | 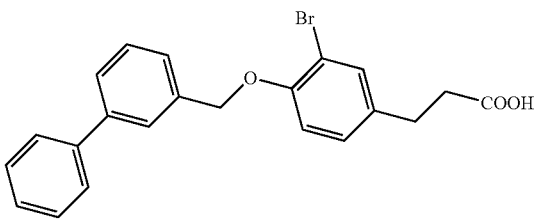 |
| 115 | 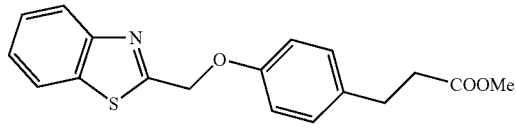 |
| 116 | 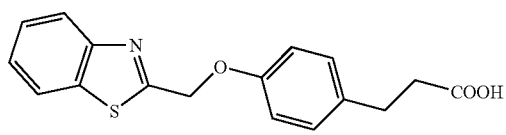 |
| 117 | 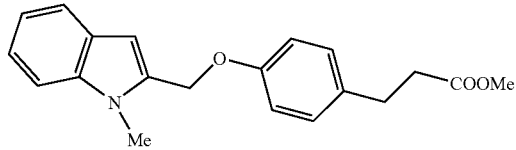 |
| 118 | 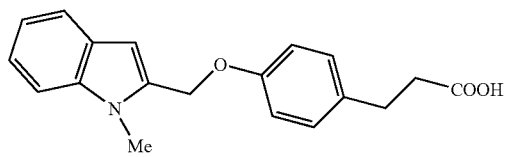 |
| 119 | 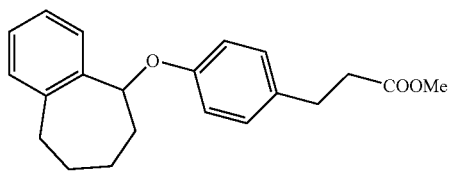 |
| 120 | 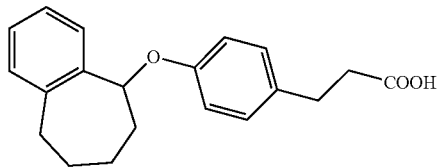 |
| 121 | 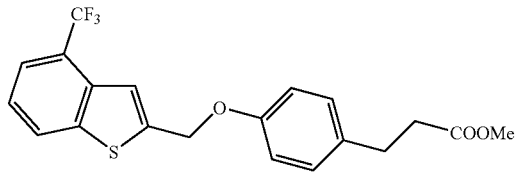 |
| 122 | 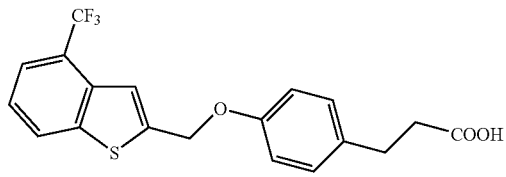 |

| Ex.No. | structural formula |
|---|---|
| 123 | 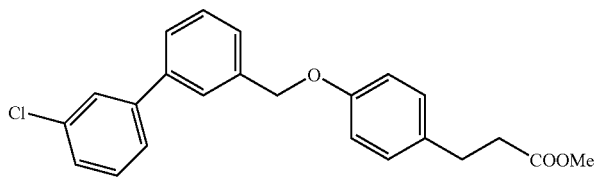 |
| 124 | 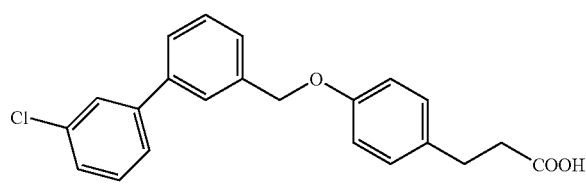 |
| 125 | 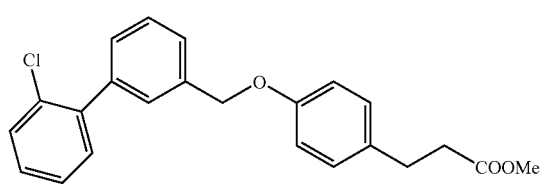 |
| 126 | 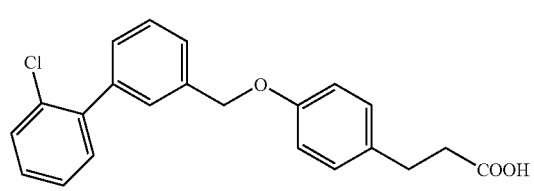 |
| 127 | 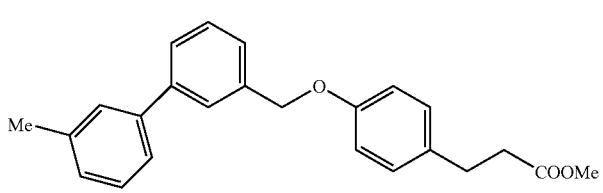 |
| 128 | 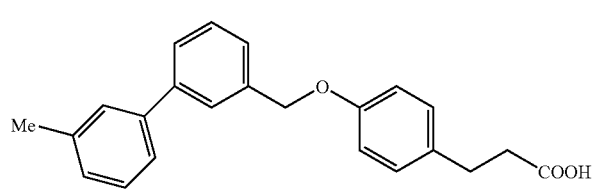 |
| 129 | 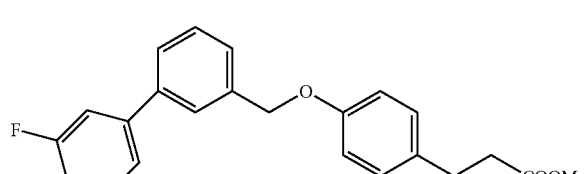 |
| 130 | 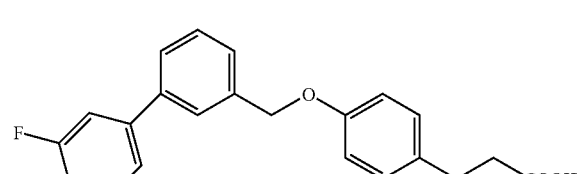 |

| Ex.No. | structural formula |
|---|---|
| 131 | 3-MeO-biphenyl-3'-CH2-O-C6H4-CH2CH2-COOMe |
| 132 | 3-MeO-biphenyl-3'-CH2-O-C6H4-CH2CH2-COOH |
| 133 | 3-O2N-biphenyl-3'-CH2-O-C6H4-CH2CH2-COOMe |
| 134 | 3-O2N-biphenyl-3'-CH2-O-C6H4-CH2CH2-COOH |
| 135 | indan-1-yl-O-C6H4-3-CH2-O-C6H4-CH2CH2-COOMe |
| 136 | indan-1-yl-O-C6H4-3-CH2-O-C6H4-CH2CH2-COOH |
| 137 | (E)-PhCH=CH-C6H4-3-CH2-O-C6H4-CH2CH2-COOMe |
| 138 | (E)-PhCH=CH-C6H4-3-CH2-O-C6H4-CH2CH2-COOH |

| Ex.No. | structural formula |
|---|---|
| 139 | 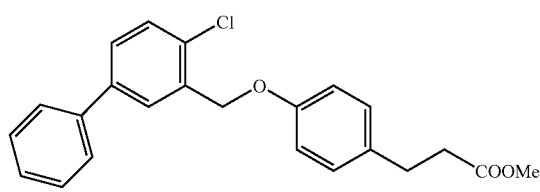 |
| 140 | 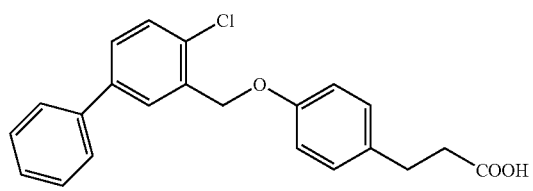 |
| 141 | 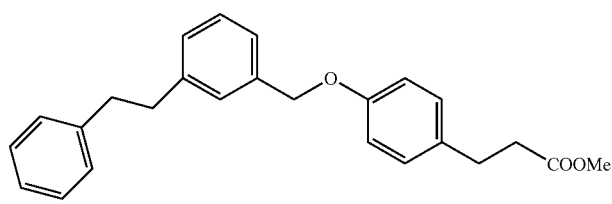 |
| 142 | 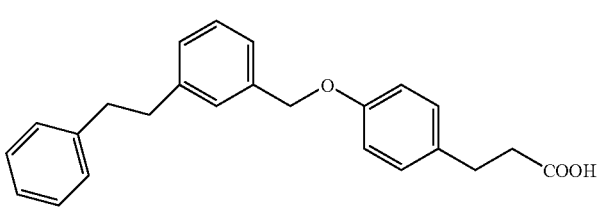 |
| 143 | 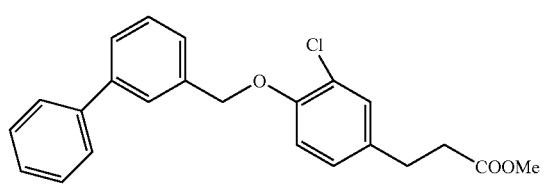 |
| 144 | 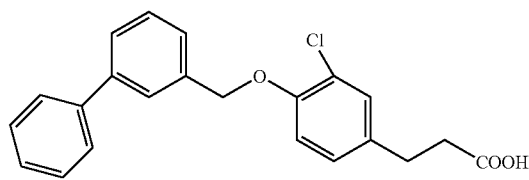 |
| 145 | 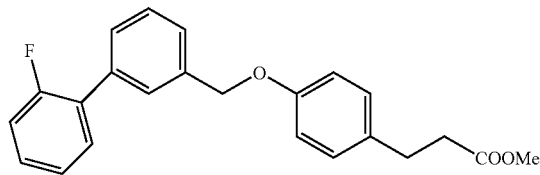 |
| 146 | 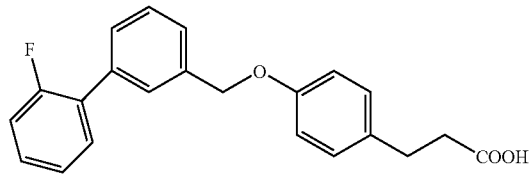 |

| Ex.No. | structural formula |
|---|---|
| 147 | 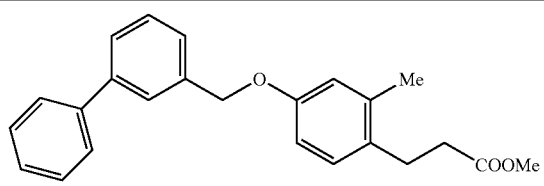 |
| 148 | 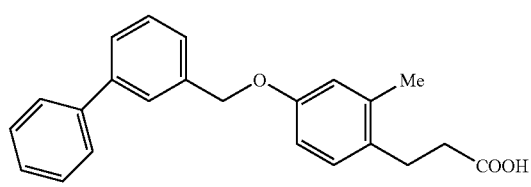 |
| 149 | 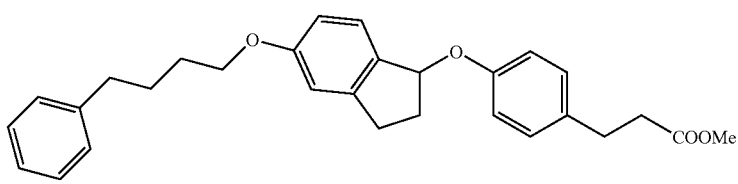 |
| 150 | 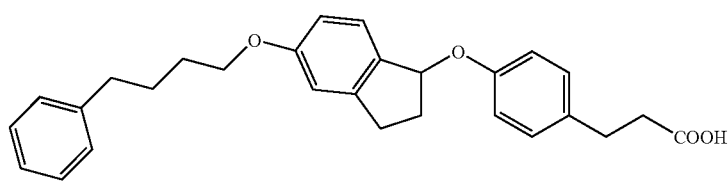 |
| 151 | 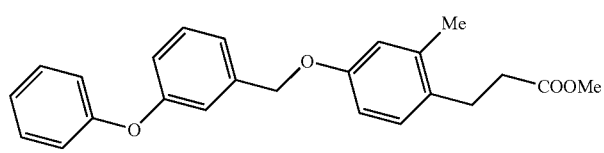 |
| 152 | 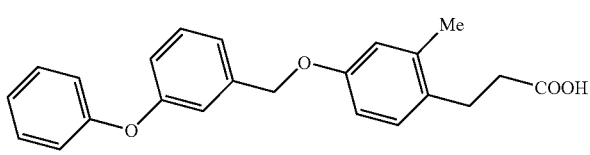 |
| 153 | 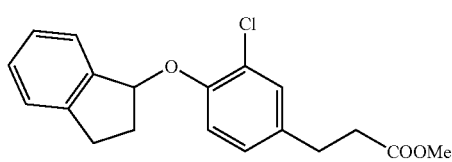 |
| 154 | 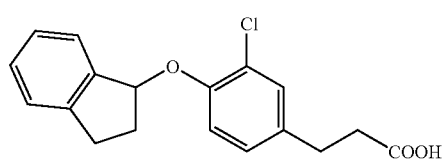 |
| 155 | 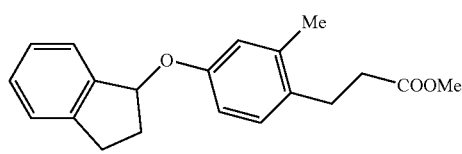 |

| Ex.No. | structural formula |
|---|---|
| 156 | 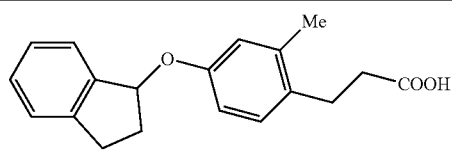 |
| 157 | 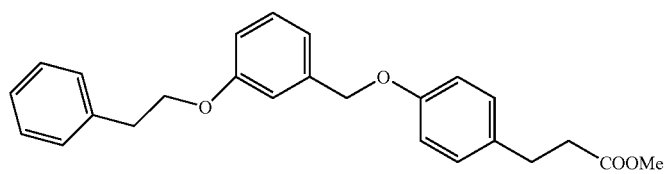 |
| 158 | 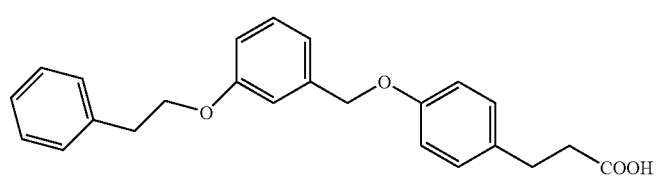 |
| 159 | 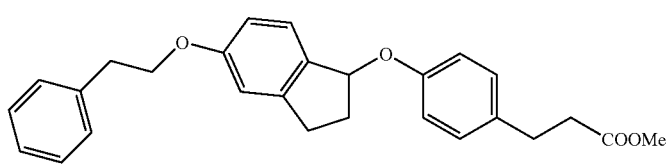 |
| 160 | 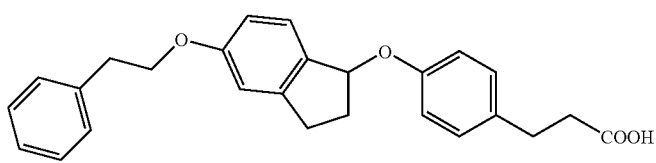 |
| 161 | 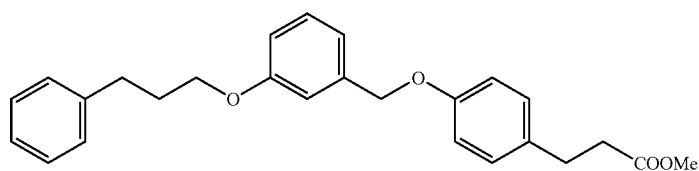 |
| 162 | 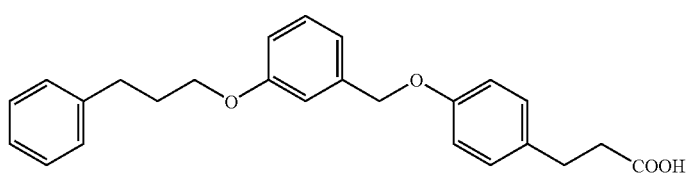 |
| 163 | 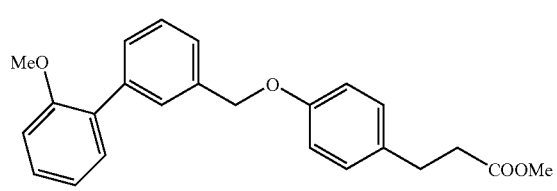 |
| 164 | 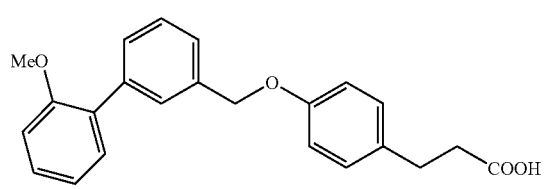 |

| Ex.No. | structural formula |
|---|---|
| 165 | 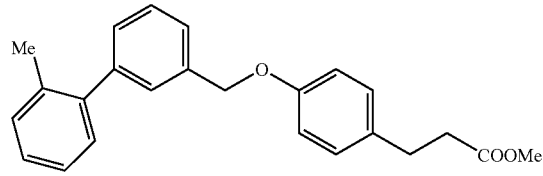 |
| 166 | 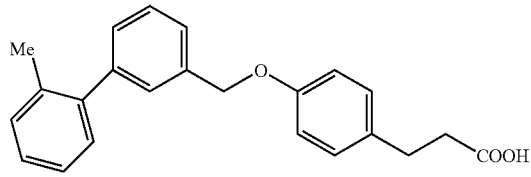 |
| 167 | 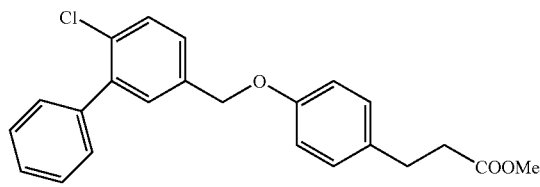 |
| 168 | 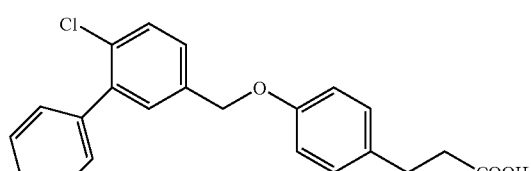 |
| 169 | 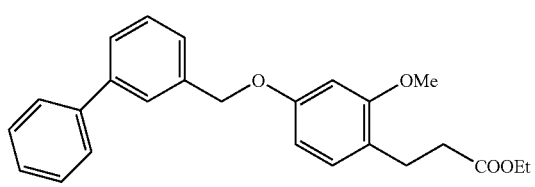 |
| 170 | 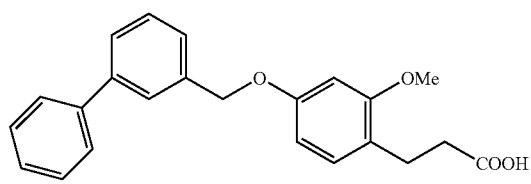 |
| 171 | 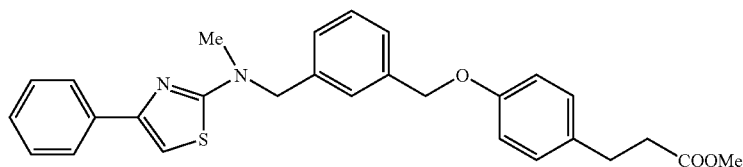 |
| 172 | 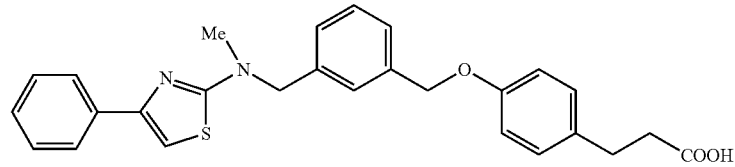 |

-continued
| Ex.No. | structural formula |
|---|---|
| 173 | 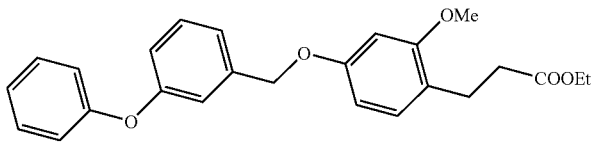 |
| 174 | 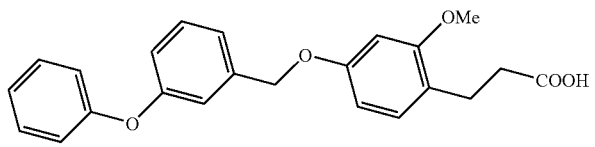 |
| 175 | 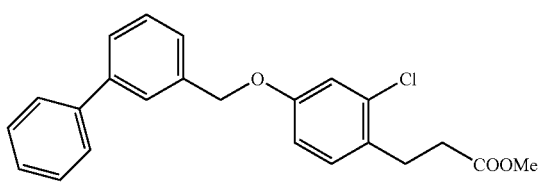 |
| 176 | 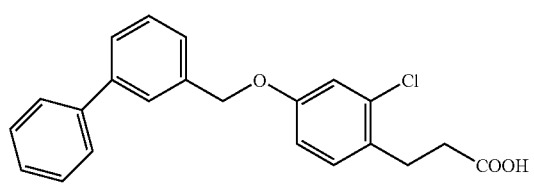 |
| 177 | 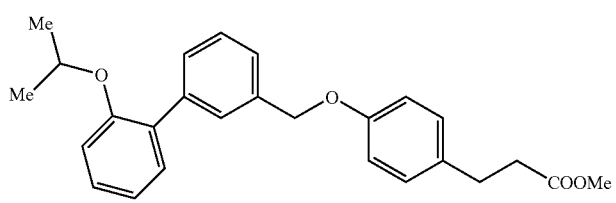 |
| 178 | 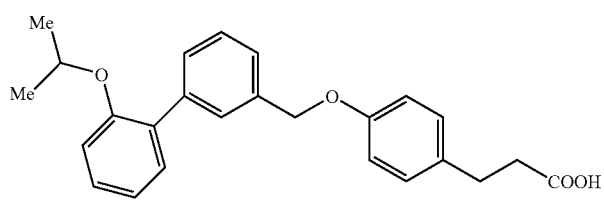 |
| 179 | 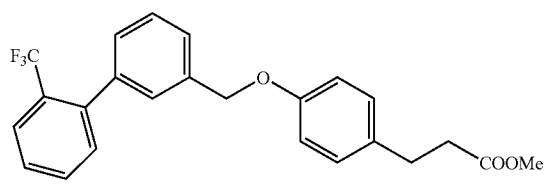 |
| 180 | 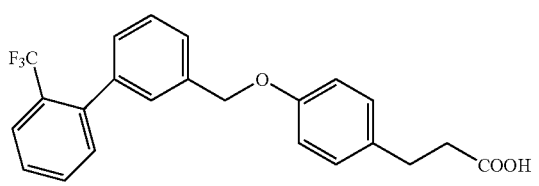 |

|Ex.No.|structural formula|
|---|---|
|181|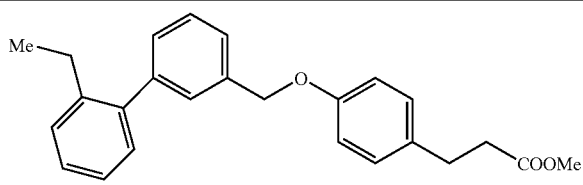|
|182|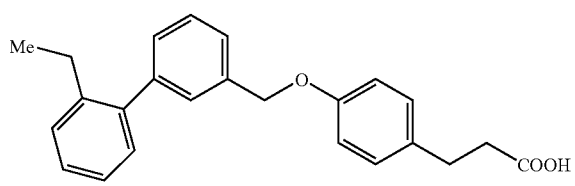|
|183|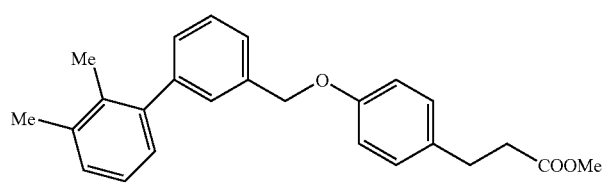|
|184|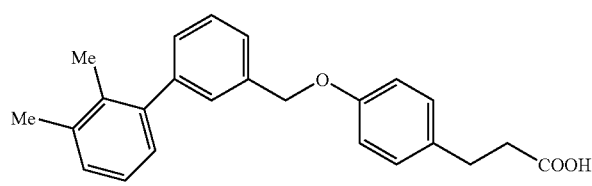|
|185|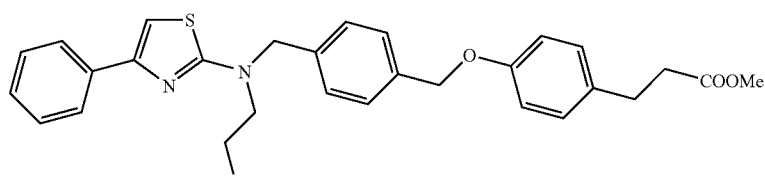|
|186|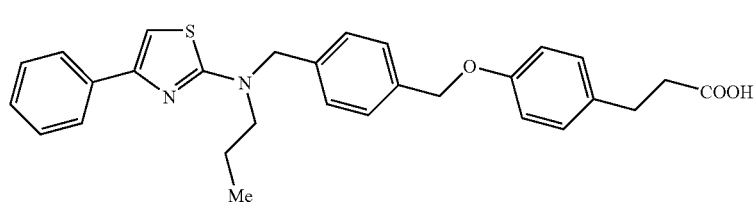|
|187|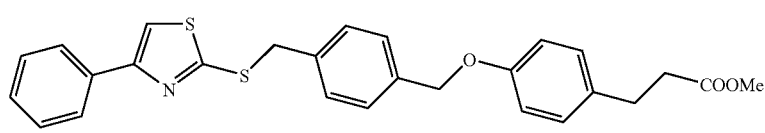|
|188|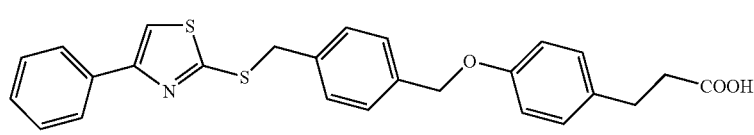|
|189|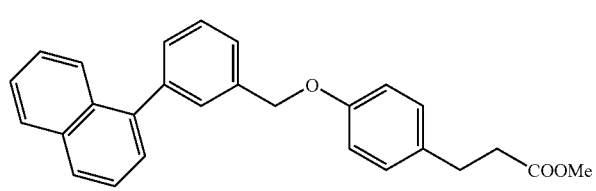|

| Ex.No. | structural formula |
|---|---|
| 190 | 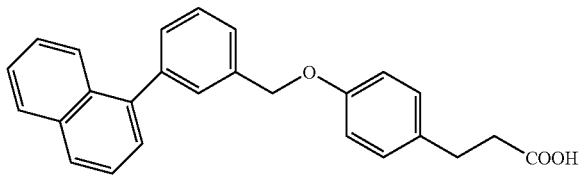 |
| 191 | 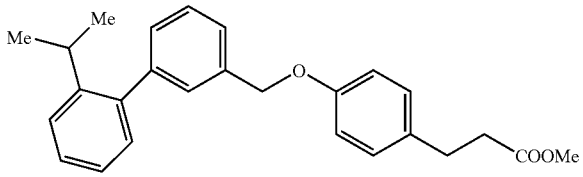 |
| 192 | 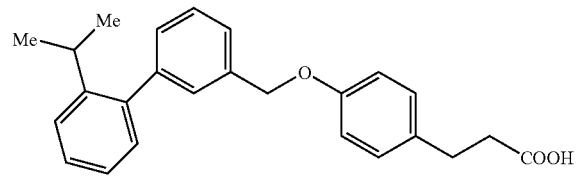 |
| 193 | 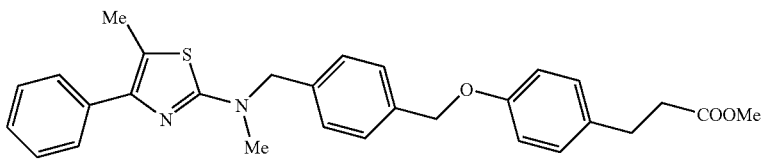 |
| 194 | 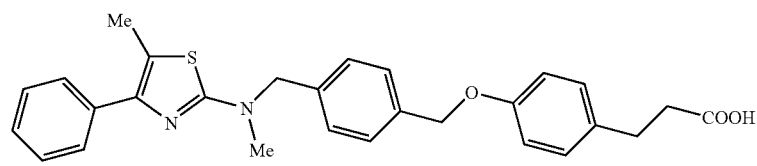 |
| 195 | 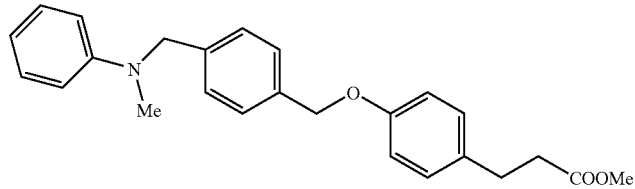 |
| 196 | 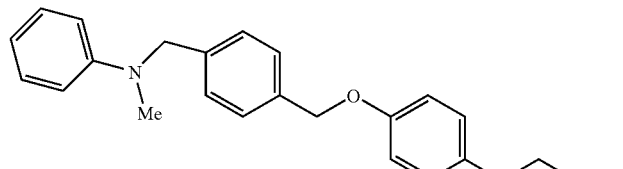 |
| 197 | 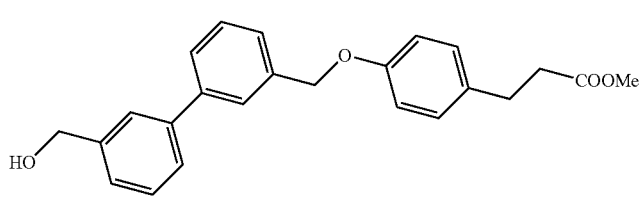 |

| Ex.No. | structural formula |
|---|---|
| 198 | 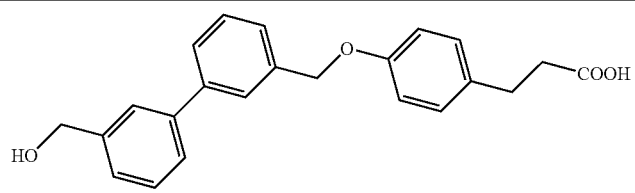 |
| 199 | 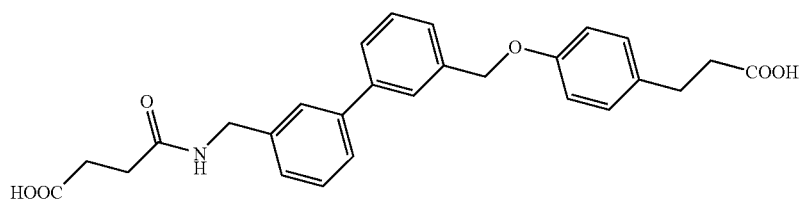 |
| 200 | 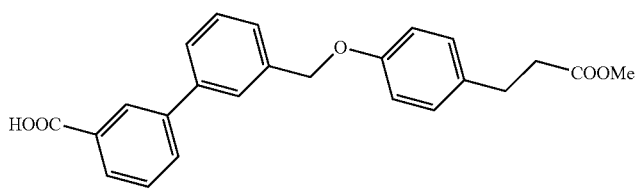 |
| 201 | 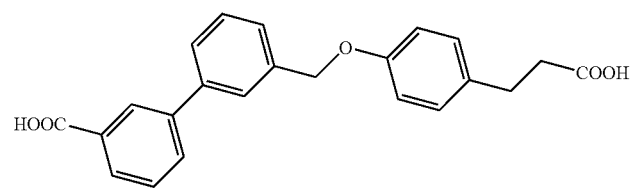 |
| 202A | 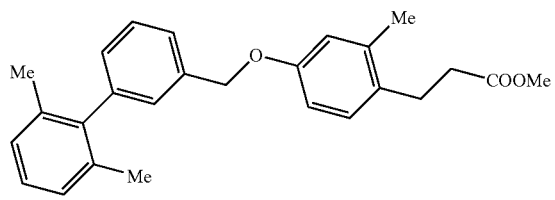 |
| 203 | 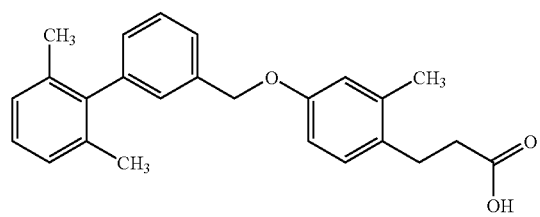 |
| 204 | 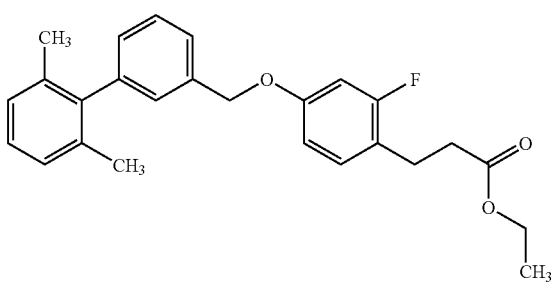 |

| Ex.No. | structural formula |
|---|---|
| 205 | 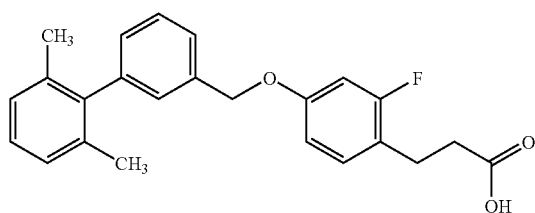 |
| 206 | 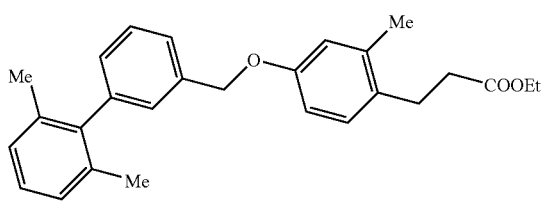 |
| 207 | 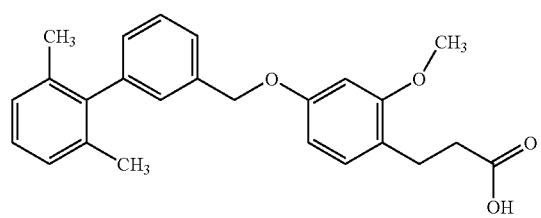 |
| 208 | 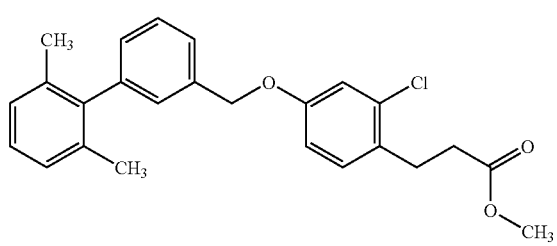 |
| 209 | 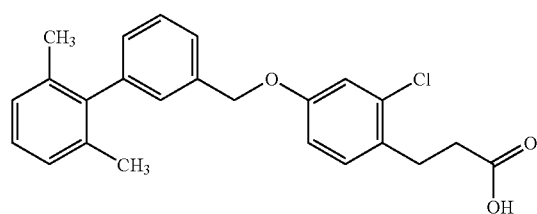 |
| 210 | 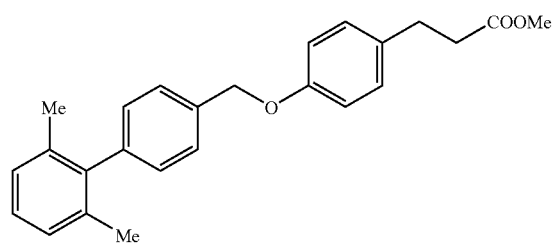 |

| Ex.No. | structural formula |
|---|---|
| 211 | 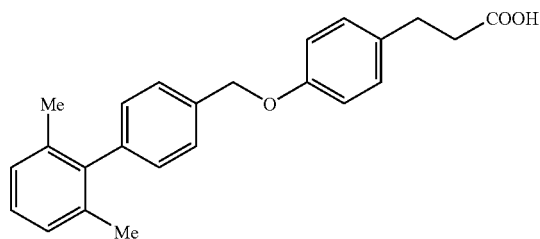 |
| 212 | 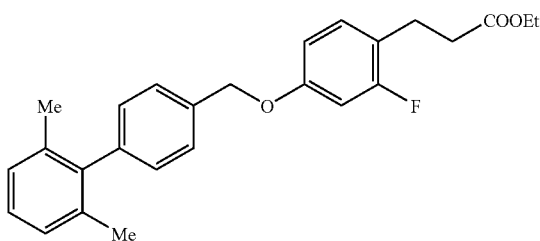 |
| 213 | 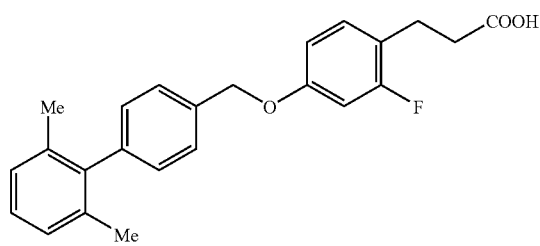 |
| 214 | 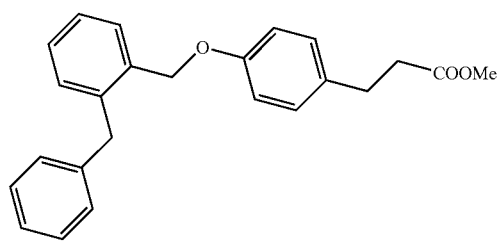 |
| 215 | 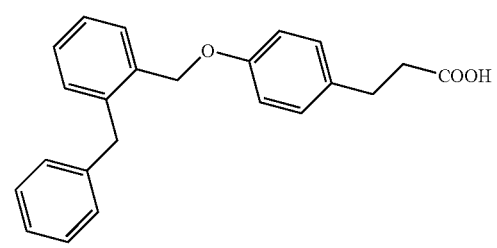 |
| 216 | 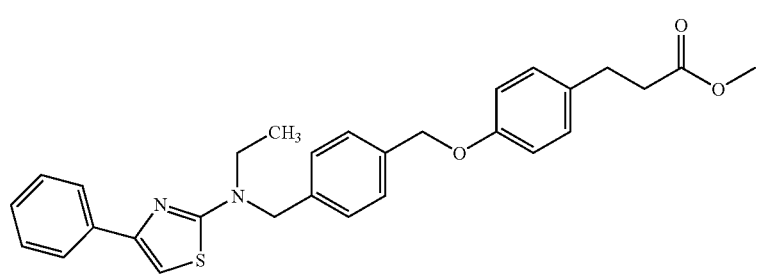 |

| Ex.No. | structural formula |
|---|---|
| 217 | |
| 218 | |
| 219 | |
| 220 | |
| 221 | |

| Ex.No. | structural formula |
|---|---|
| 222 | 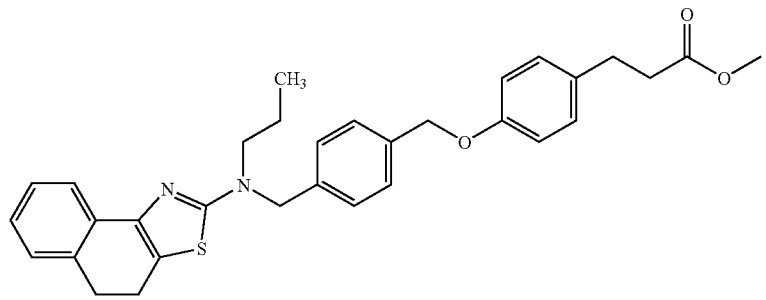 |
| 223 | 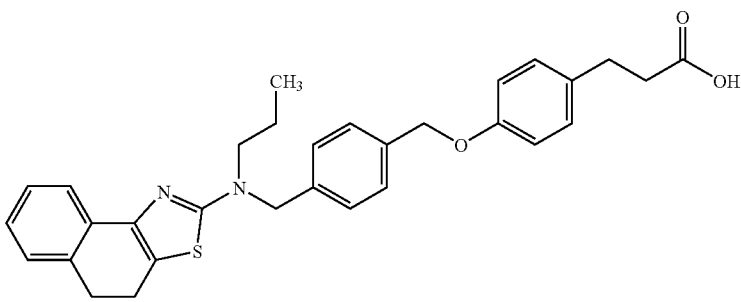 |
| 224 | 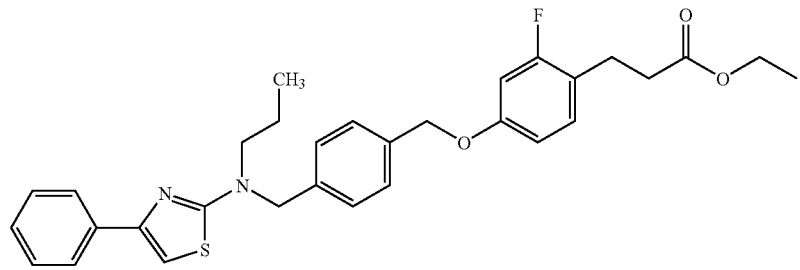 |
| 225 | 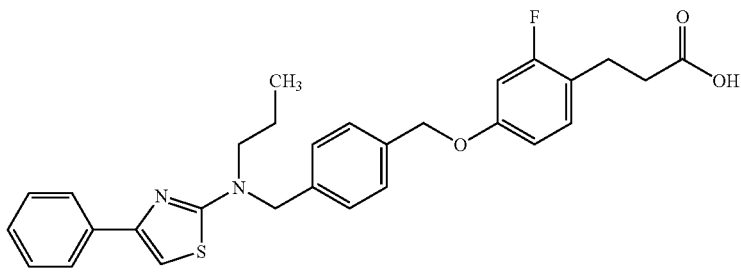 |
| 226 | 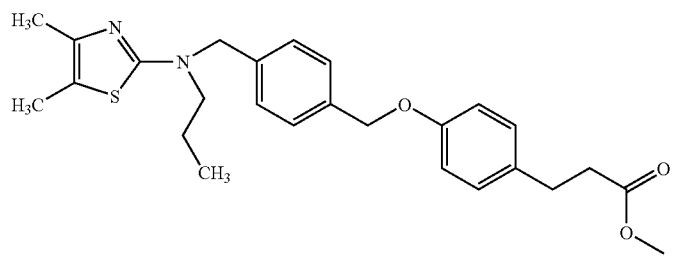 |

-continued
| Ex.No. | structural formula |
|---|---|
| 227 | 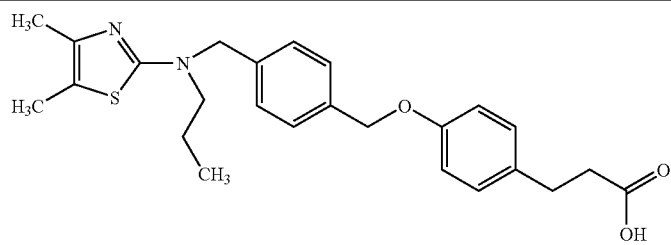 |
| 228 | 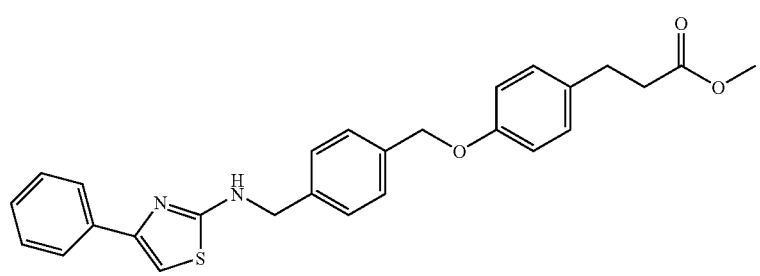 |
| 229 | 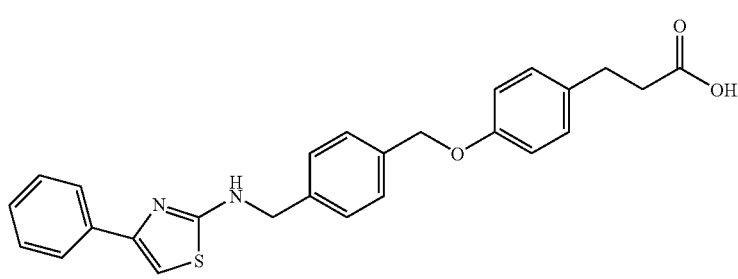 |
| 230 | 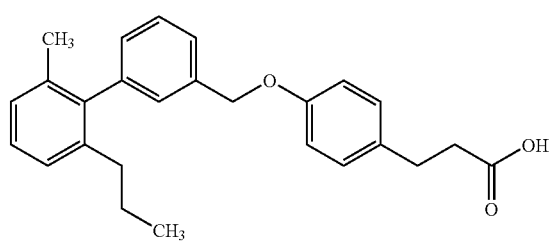 |
| 231 | 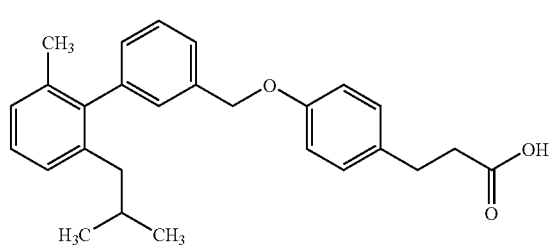 |
| 232 | 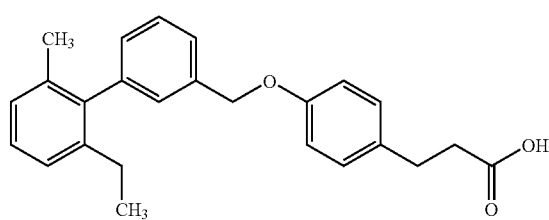 |

| Ex.No. | structural formula |
|---|---|
| 233 | 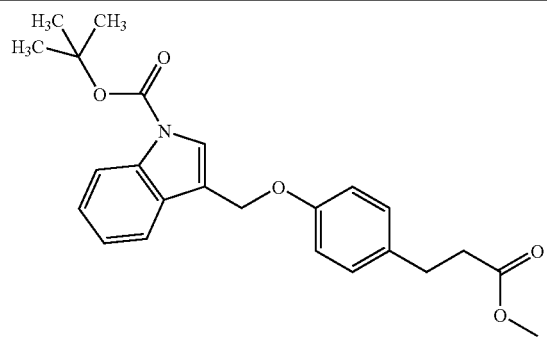 |
| 234 | 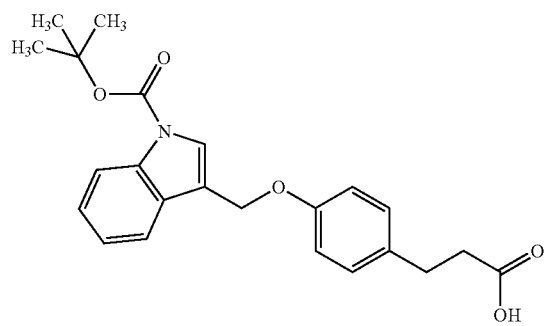 |
| 235 | 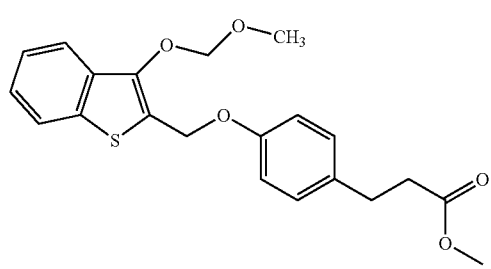 |
| 236 | 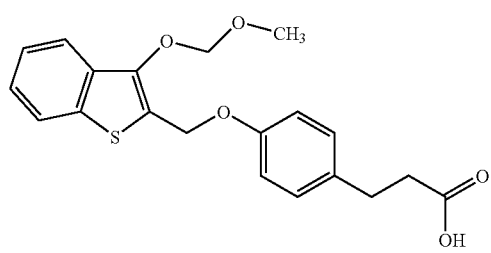 |
| 237 | 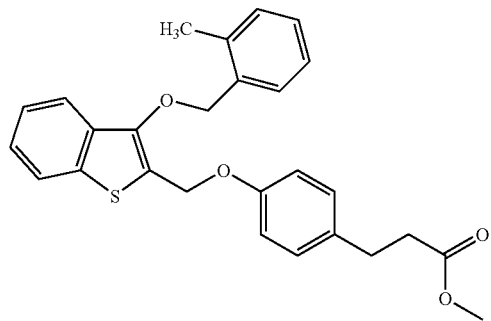 |

| Ex.No. | structural formula |
|---|---|
| 238 | 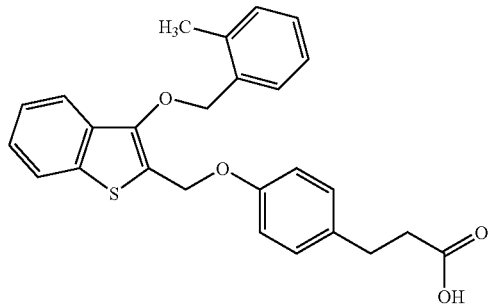 |
| 239 | 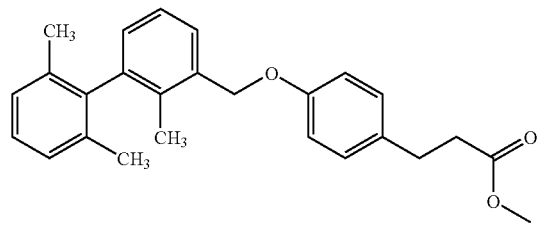 |
| 240 | 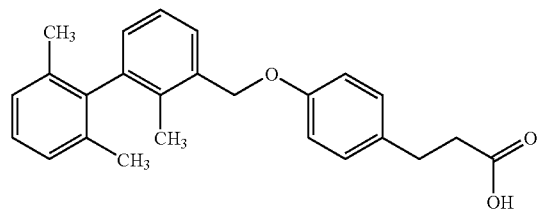 |
| 241 | 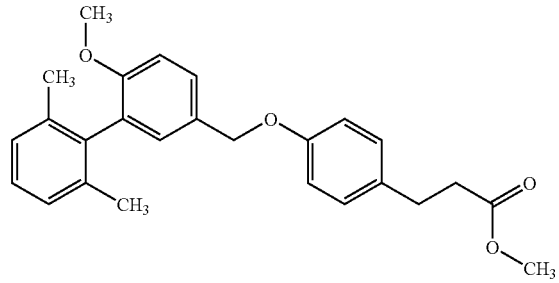 |
| 242 | 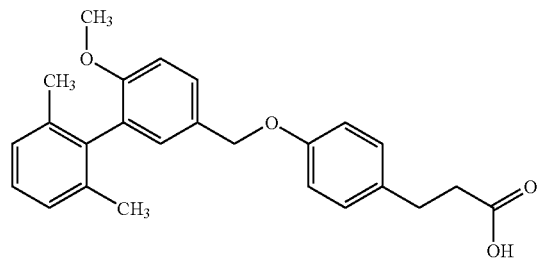 |

| Ex.No. | structural formula |
|---|---|
| 243 | 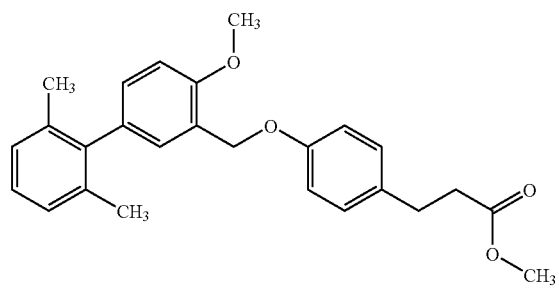 |
| 244 | 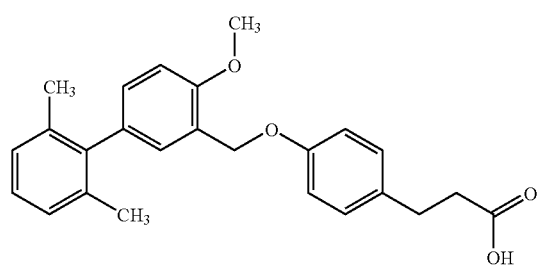 |
| 245 | 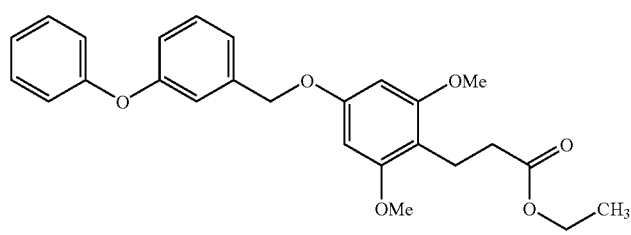 |
| 246 | 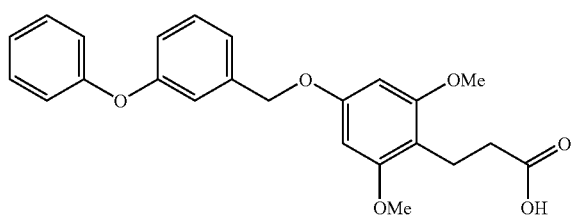 |
| 247 | 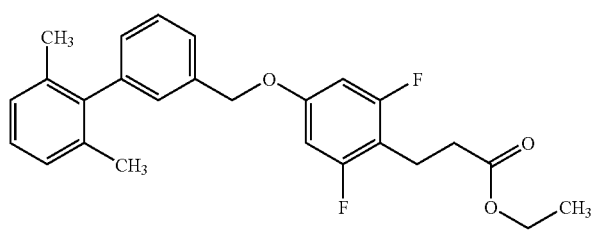 |
| 248 | 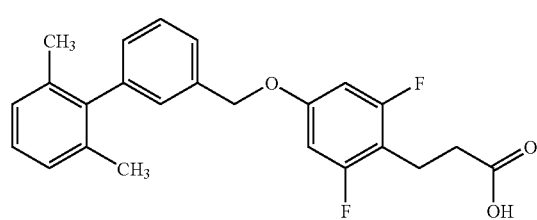 |

| Ex.No. | structural formula |
|---|---|
| 249 | 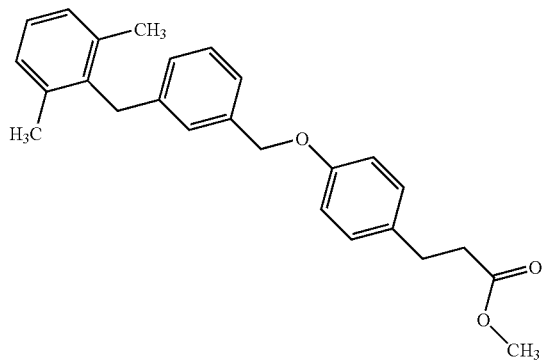 |
| 250 | 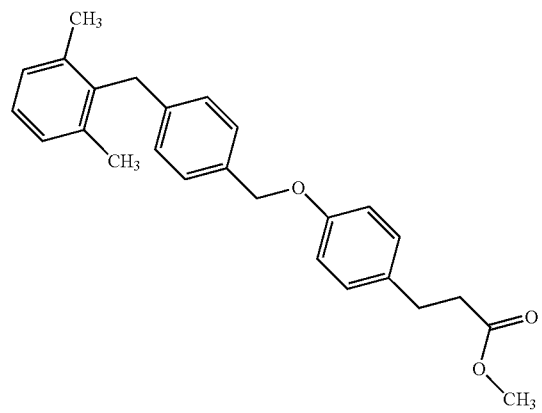 |
| 251 | 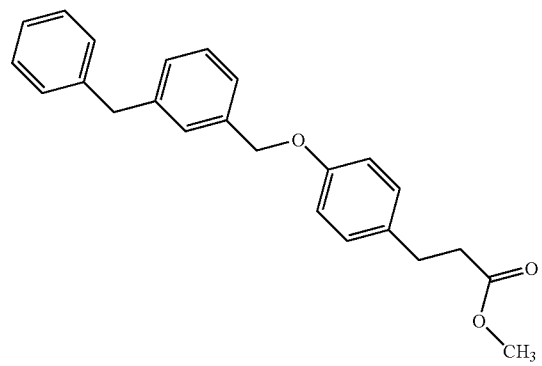 |
| 252 | 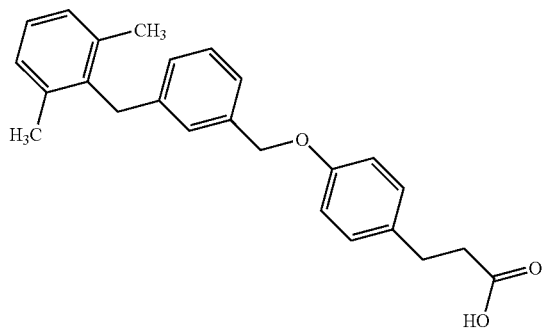 |

| Ex.No. | structural formula |
|---|---|
| 253 | (structure: 2,6-dimethylbenzyl-phenyl-CH2-O-phenyl-CH2CH2-COOH) |
| 254 | (structure: benzyl-phenyl-CH2-O-phenyl-CH2CH2-COOH) |
| 255 | (structure: 4-phenylthiazol-2-yl-N(hexyl)-CH2-phenyl-CH2-O-phenyl-CH2CH2-COOCH3) |
| 256 | (structure: 4-phenylthiazol-2-yl-N(isopropyl)-CH2-phenyl-CH2-O-phenyl-CH2CH2-COOCH3) |
| 257 | (structure: 4-phenylthiazol-2-yl-N(isobutyl)-CH2-phenyl-CH2-O-phenyl-CH2CH2-COOH) |

| Ex.No. | structural formula |
|---|---|
| 258 | 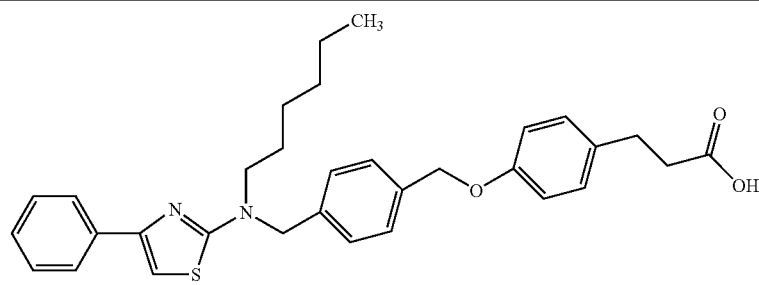 |
| 259 | 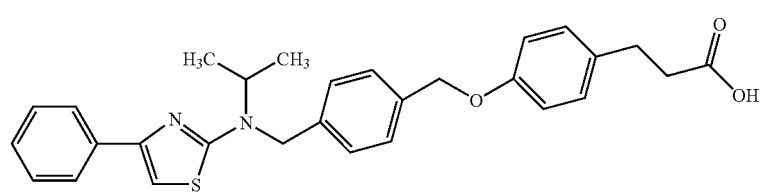 |
| 260 | 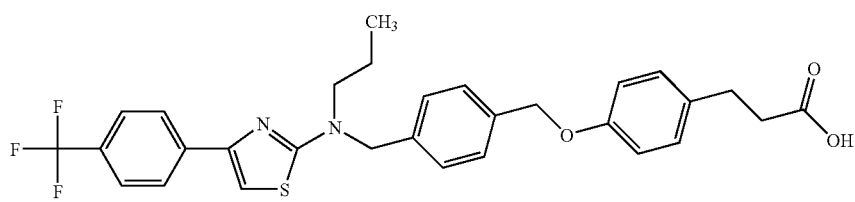 |
| 261 | 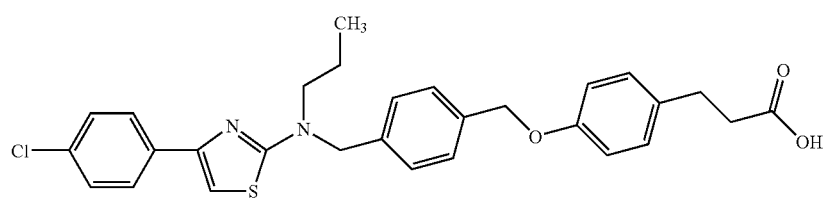 |
| 262 | 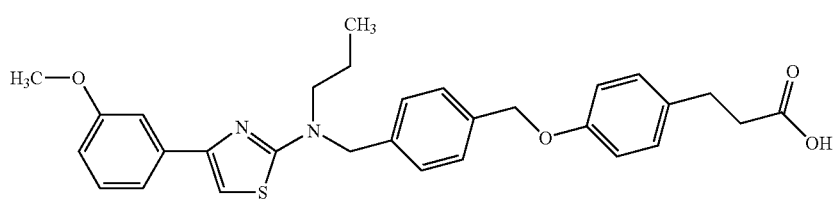 |
| 263 | 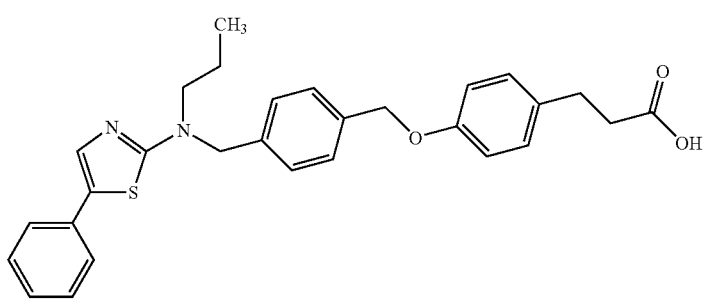 |
| 264 | 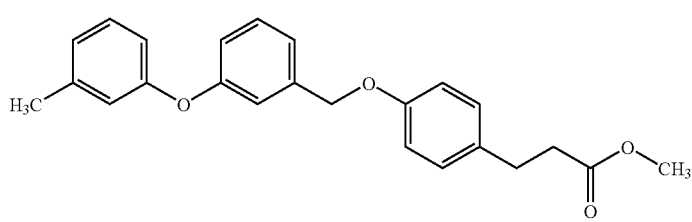 |

| Ex.No. | structural formula |
|---|---|
| 265 | 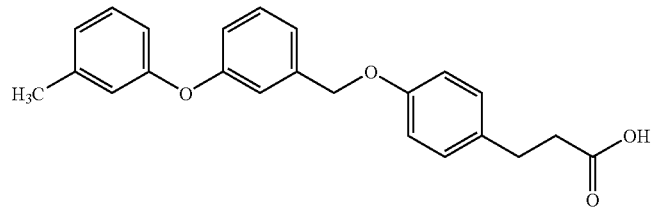 |
| 266 | 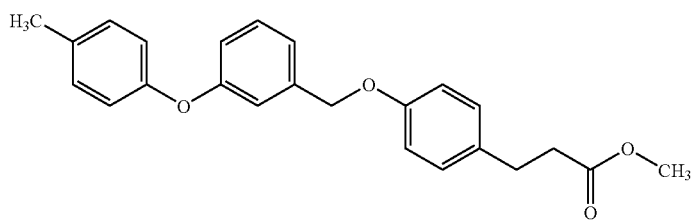 |
| 267 | 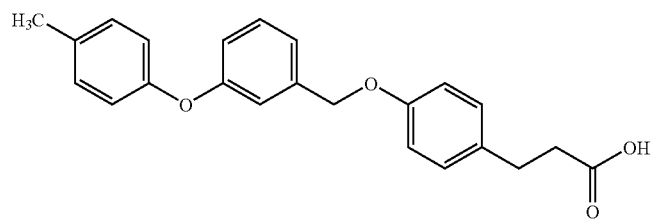 |
| 268 | 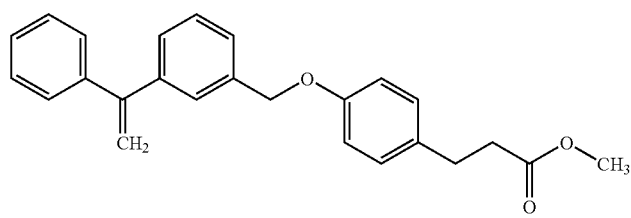 |
| 269 | 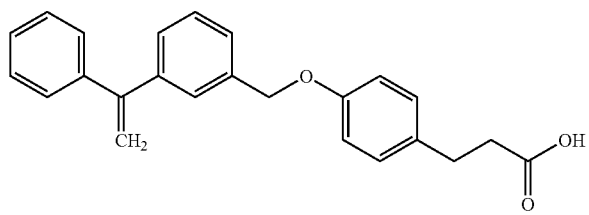 |
| 270 | 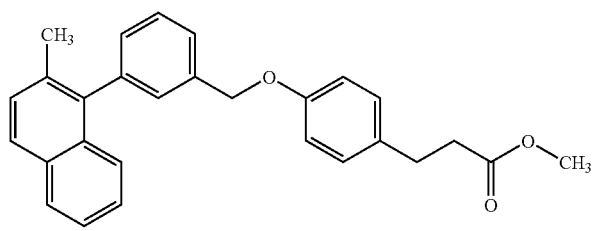 |
| 271 | 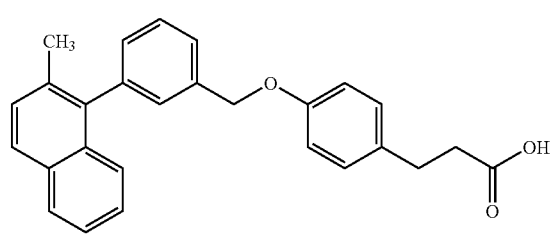 |

| Ex.No. | structural formula |
|---|---|
| 272 | 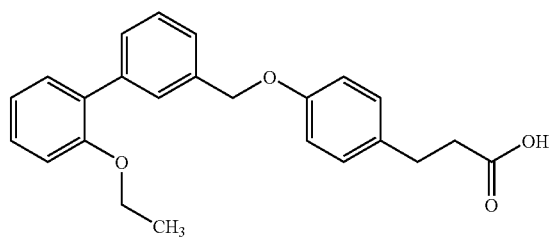 |
| 273 | 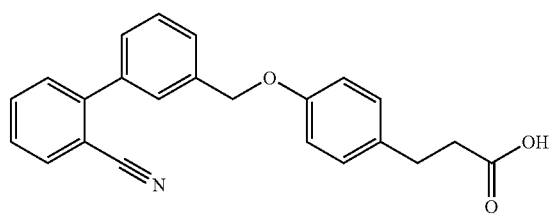 |
| 274 | 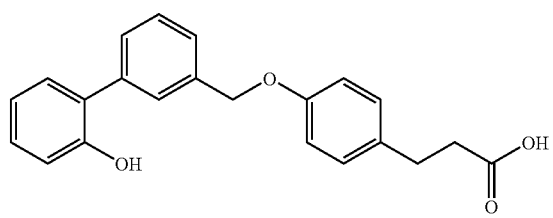 |
| 275 | 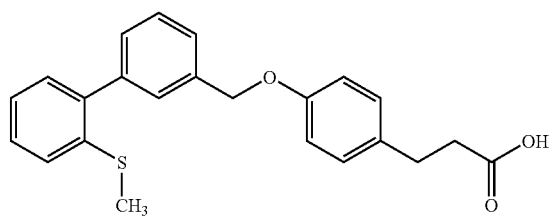 |
| 276 | 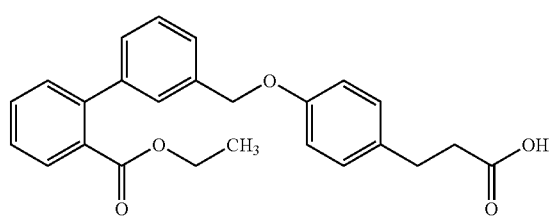 |
| 277 | 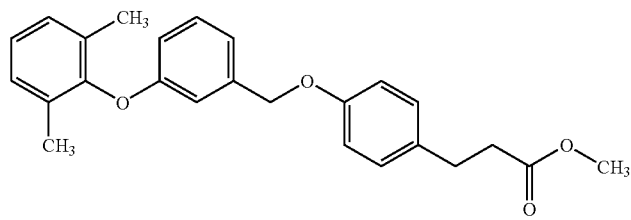 |
| 278 | 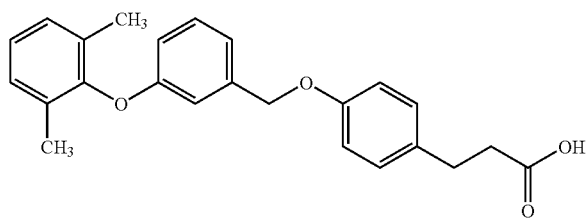 |

| Ex.No. | structural formula |
|---|---|
| 279 | 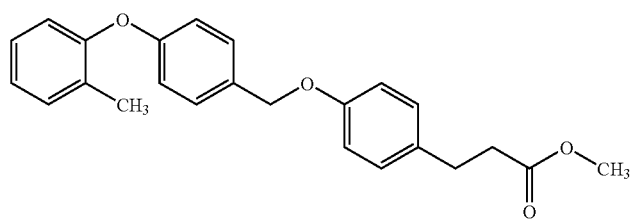 |
| 280 | 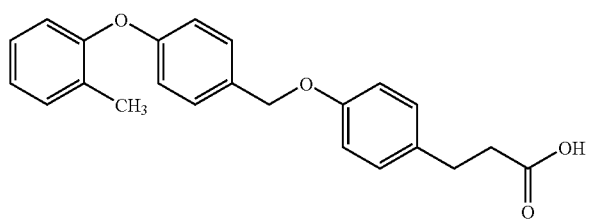 |
| 281 | 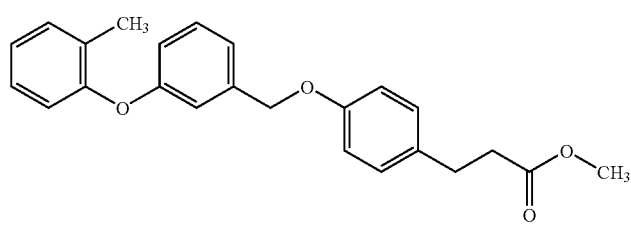 |
| 282 | 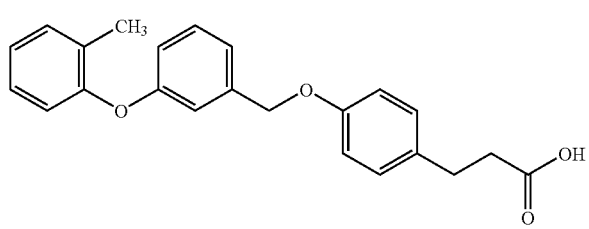 |
| 283 | 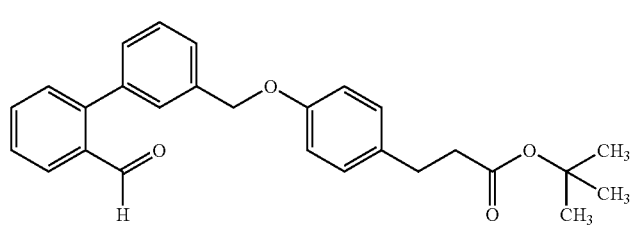 |
| 284 | 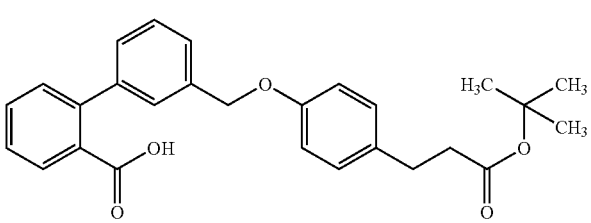 |
| 285 | 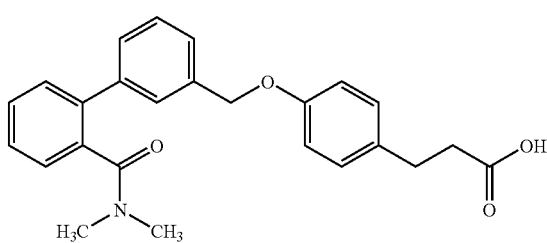 |

| Ex.No. | structural formula |
|---|---|
| 286 | 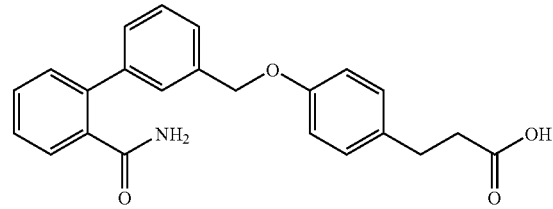 |
| 287 | 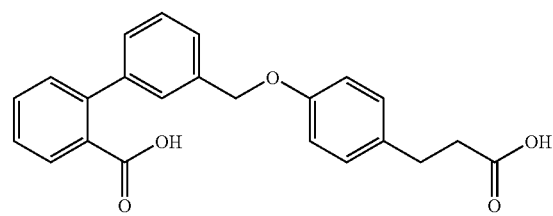 |
| 288 | 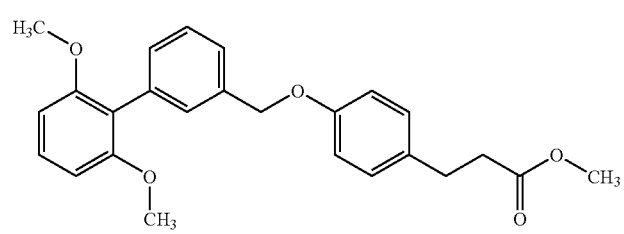 |
| 289 | 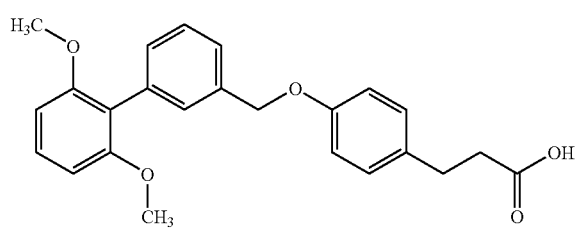 |
| 290 | 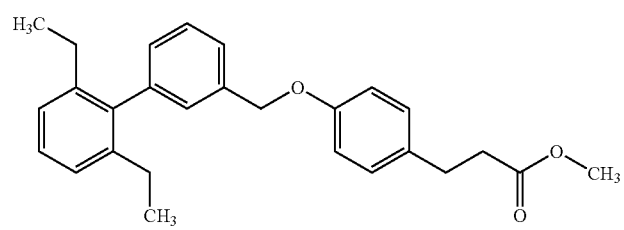 |
| 291 | 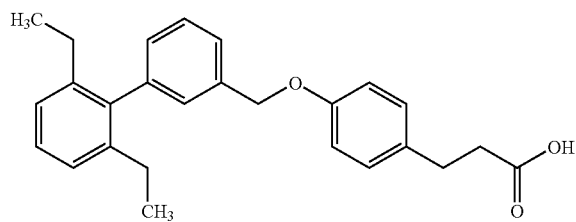 |
| 292 | 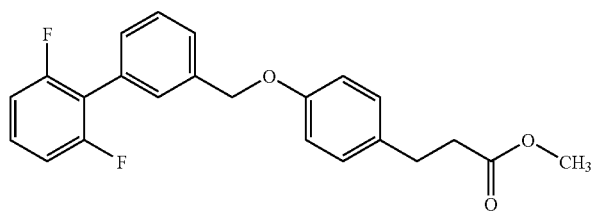 |

-continued
| Ex.No. | structural formula |
|---|---|
| 293 | 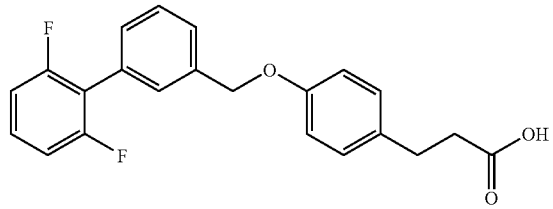 |
| 294 | 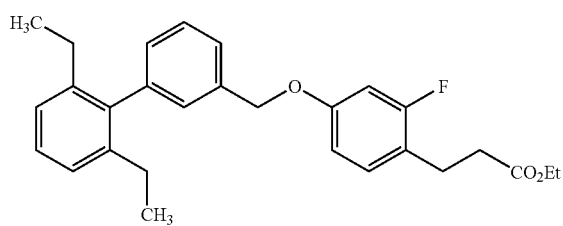 |
| 295 | 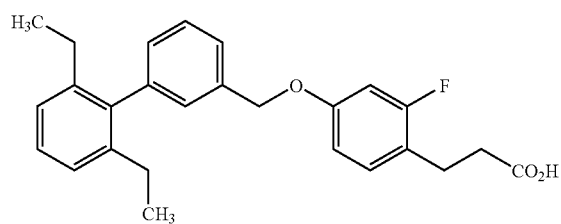 |
| 296 | 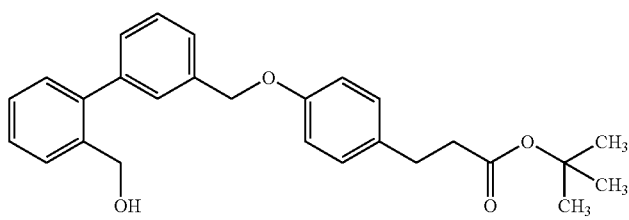 |
| 297 | 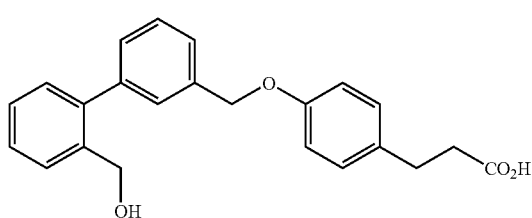 |
| 298 | 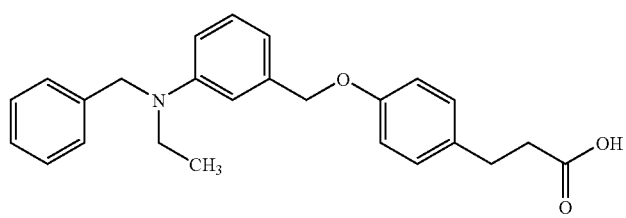 |
| 299 | 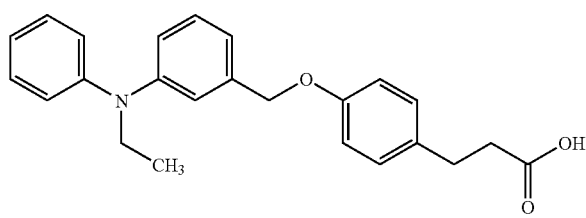 |

| Ex.No. | structural formula |
|---|---|
| 300 | 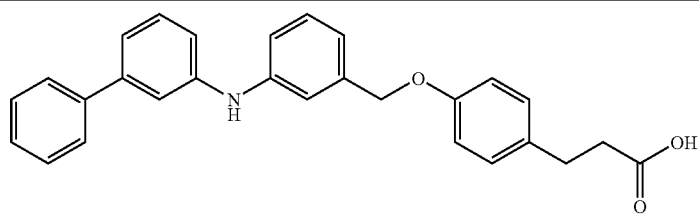 |
| 301 | 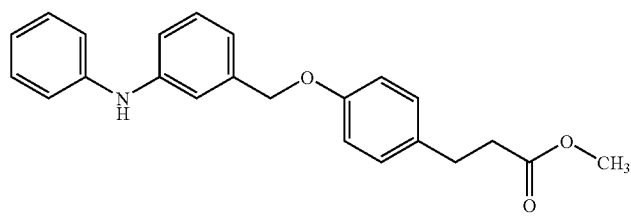 |
| 302 | 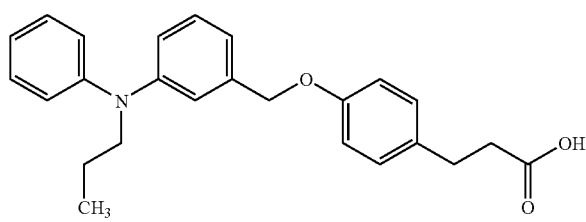 |
| 303 | 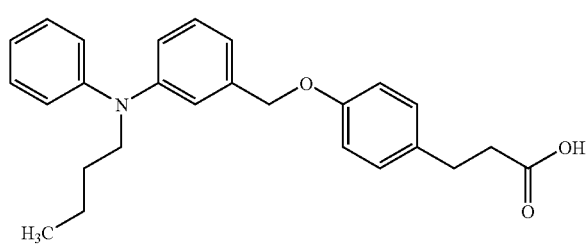 |
| 304 | 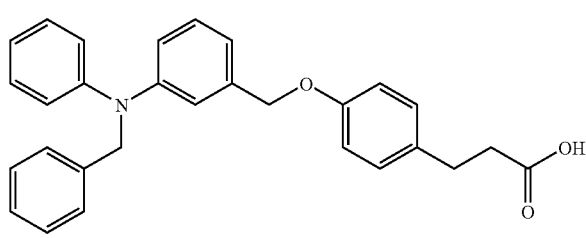 |
| 305 | 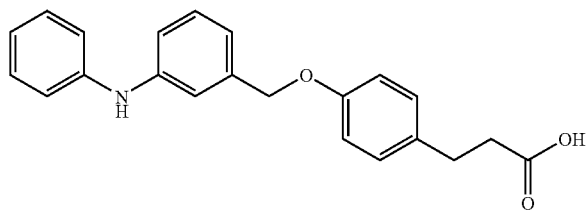 |
| 306 | 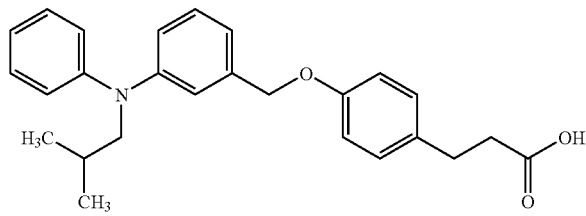 |

| Ex.No. | structural formula |
|---|---|
| 307 | 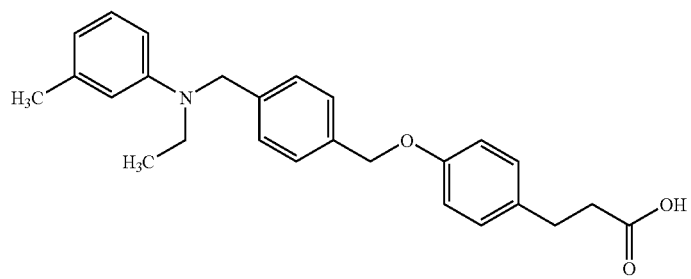 |
| 308 | 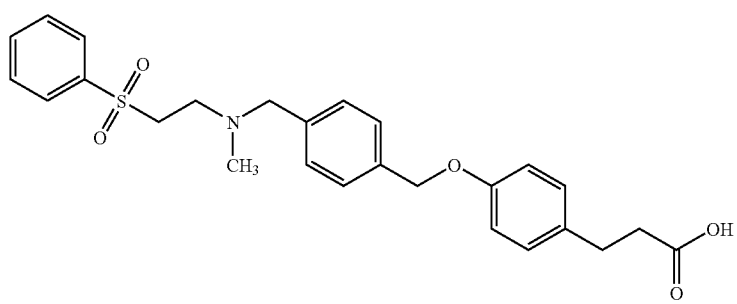 |
| 309 | 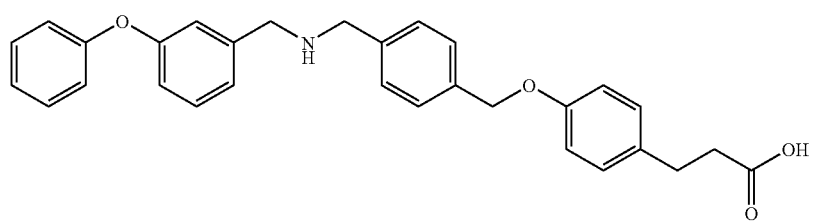 |
| 310 | 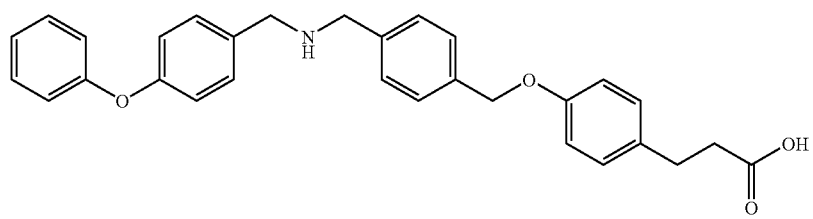 |
| 311 | 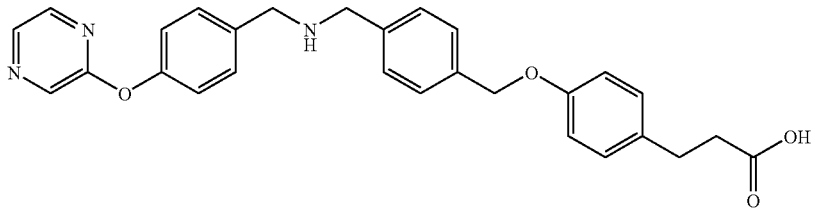 |
| 312 | 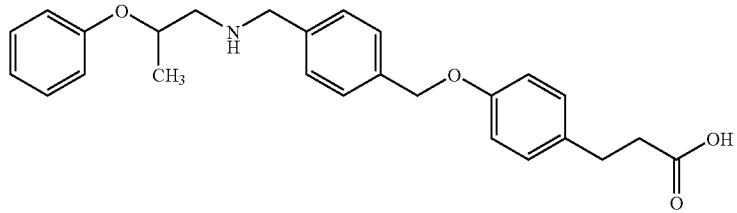 |

| Ex.No. | structural formula |
|---|---|
| 313 | 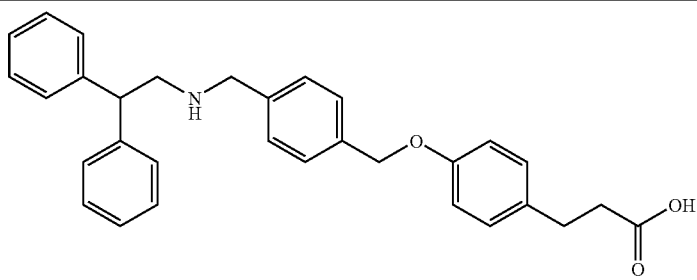 |
| 314 | 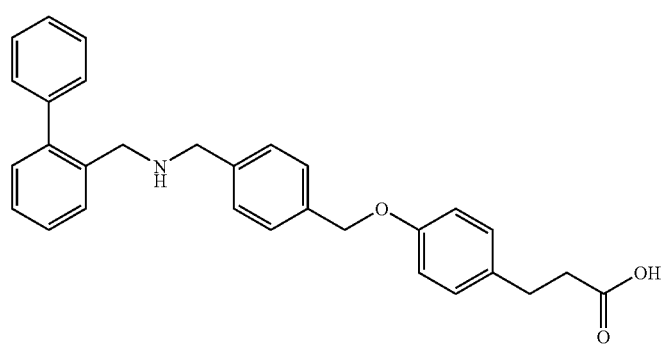 |
| 315 | 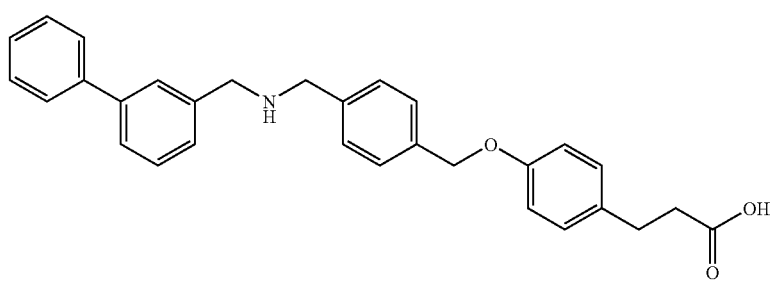 |
| 316 | 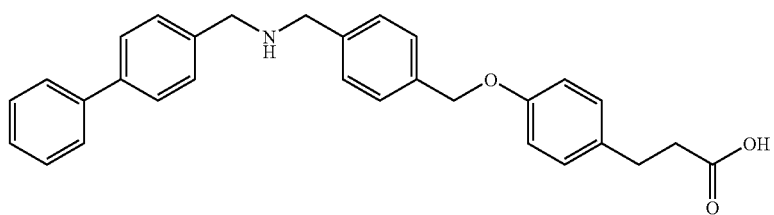 |
| 317 | 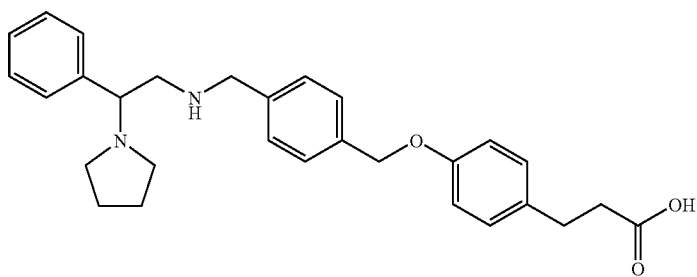 |

-continued
| Ex.No. | structural formula |
|---|---|
| 318 | 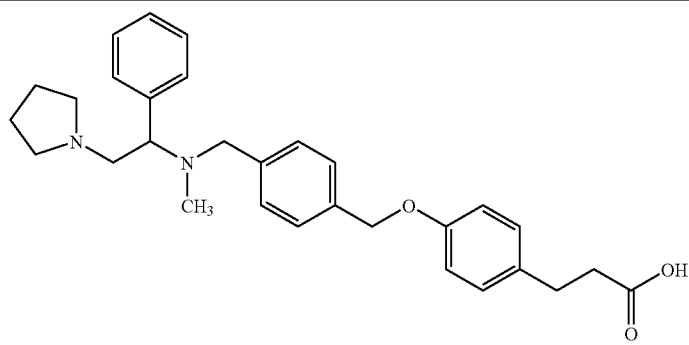 |
| 319 | 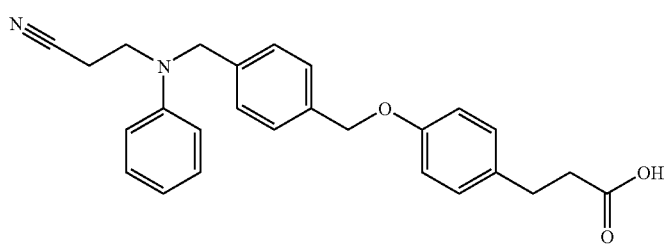 |
| 320 | 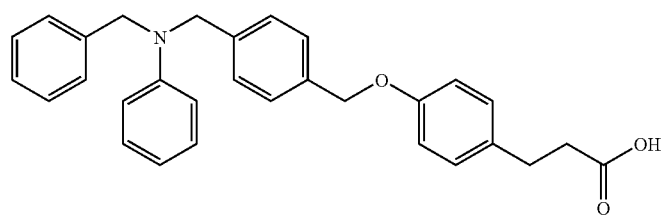 |
| 321 | 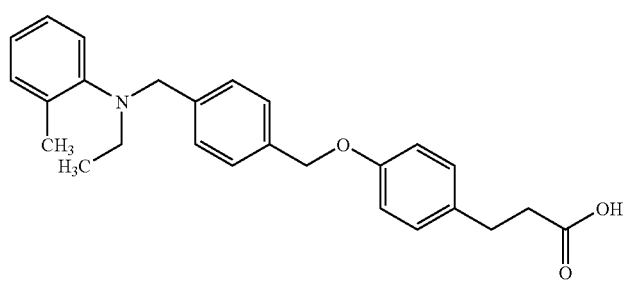 |
| 322 | 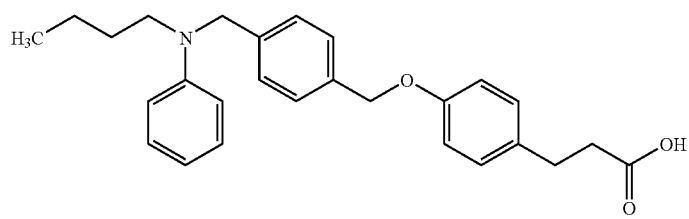 |
| 323 | 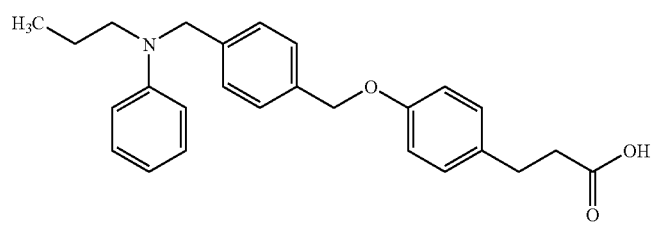 |

| Ex.No. | structural formula |
|---|---|
| 324 | 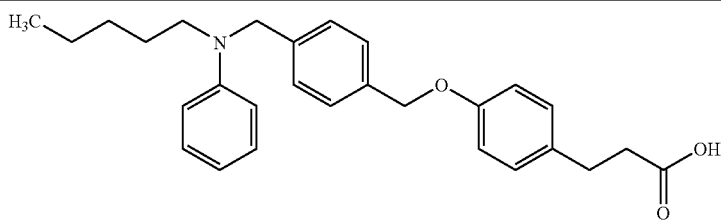 |
| 325 | 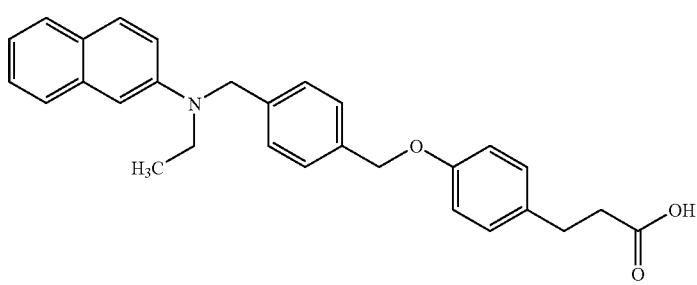 |
| 326 | 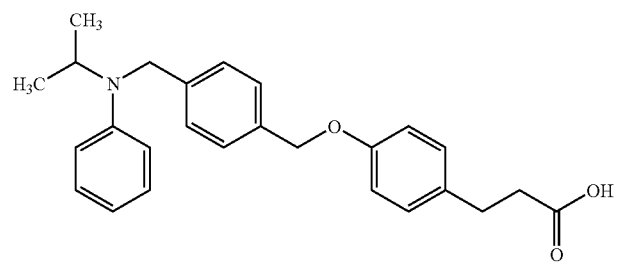 |
| 327 | 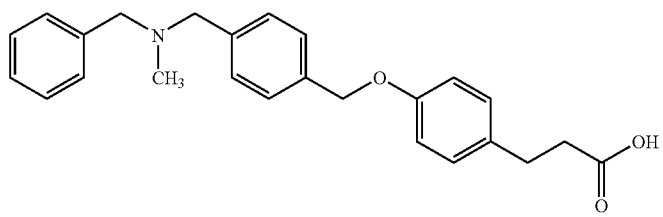 |
| 328 | 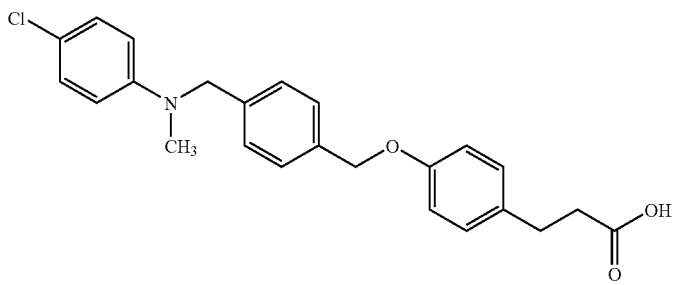 |
| 329 | 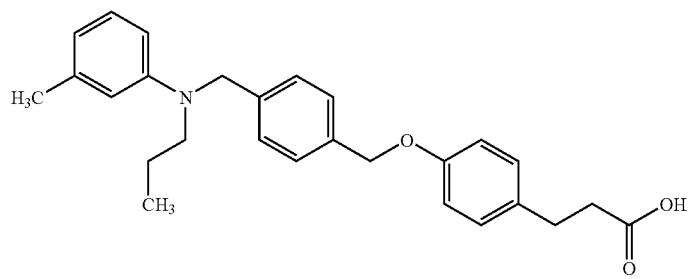 |

| Ex.No. | structural formula |
|---|---|
| 330 | 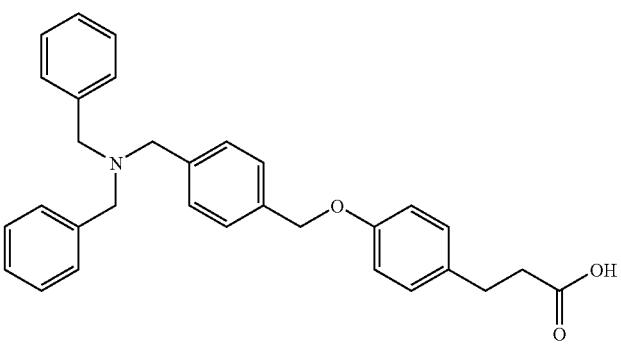 |
| 331 | 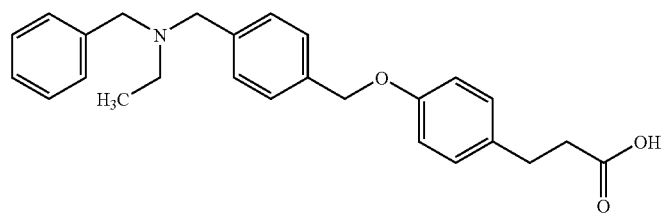 |
| 332 | 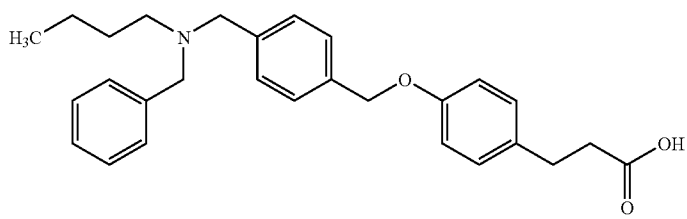 |
| 333 | 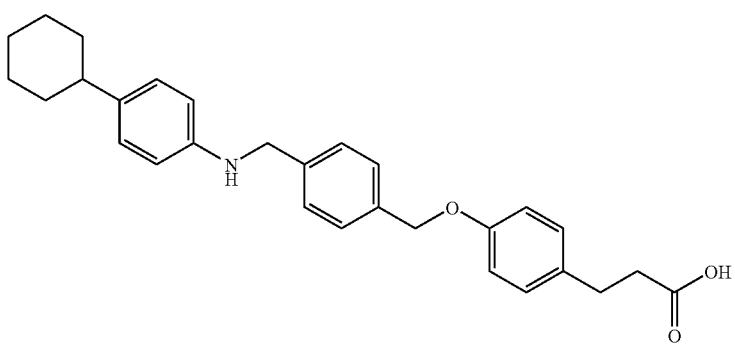 |
| 334 | 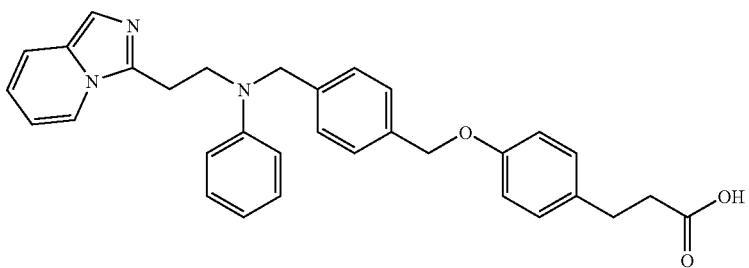 |

| Ex.No. | structural formula |
|---|---|
| 335 | 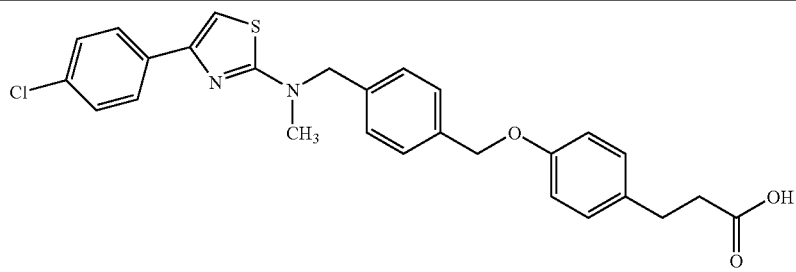 |
| 336 | 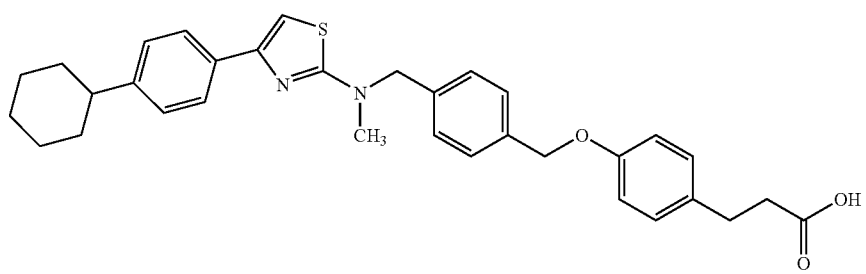 |
| 337 | 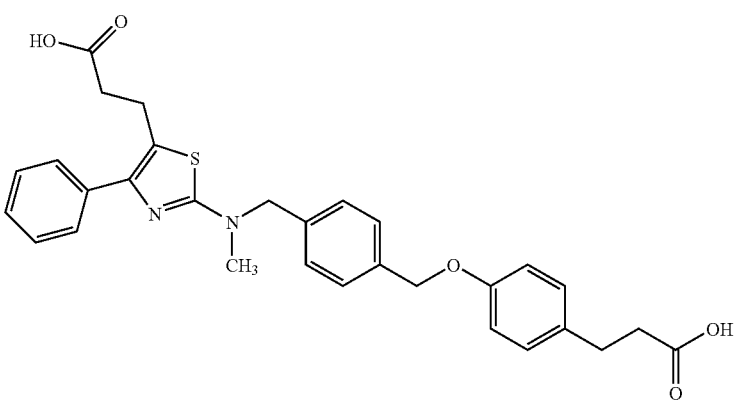 |
| 338 | 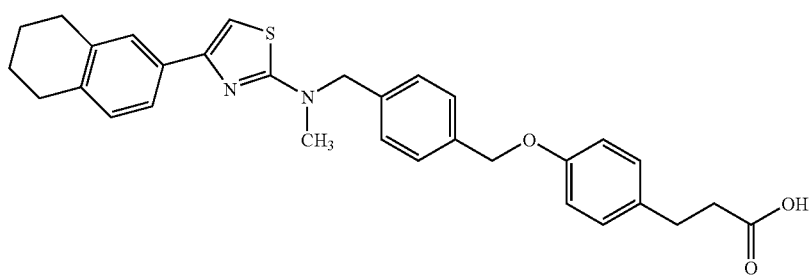 |
| 339 | 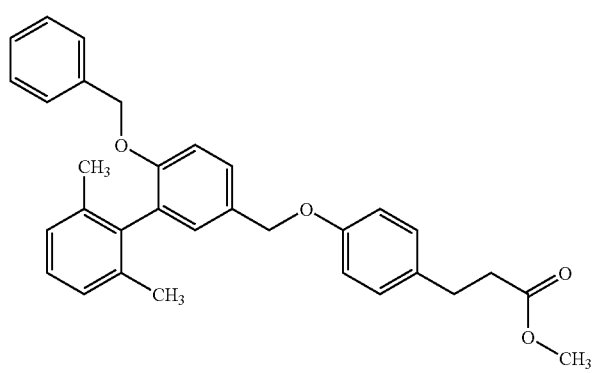 |

US 7,960,369 B2
331                                                                 332
-continued
| Ex.No. | structural formula |
|---|---|
| 340 | 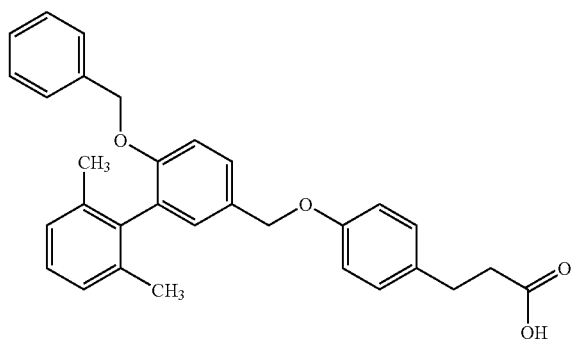 |
| 341 | 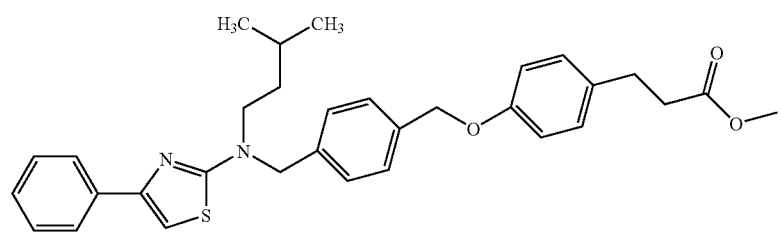 |
| 342 | 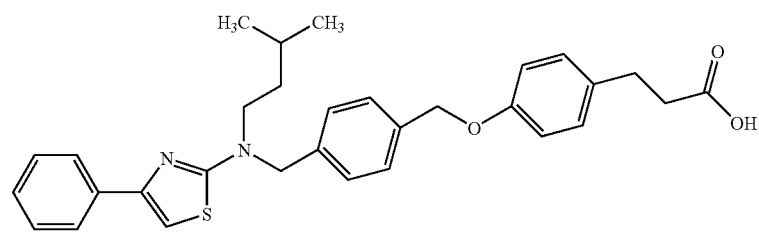 |
| 343 | 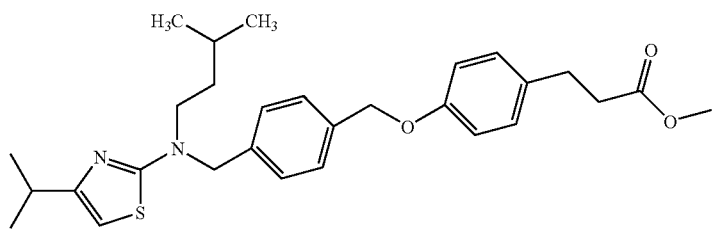 |
| 344 | 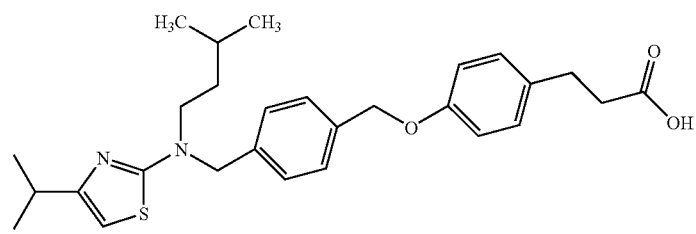 |
| 345 | 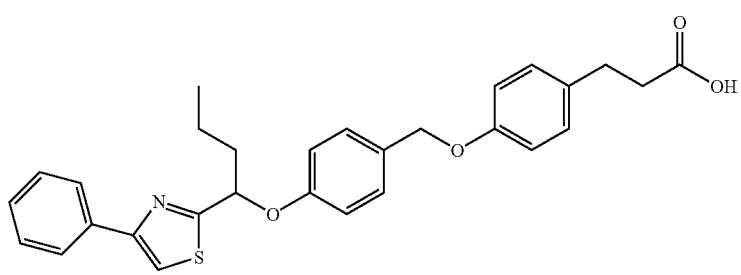 |

INDUSTRIAL APPLICABILITY

The compound and a prodrug thereof of the present invention have superior GPR40 receptor function regulating action and can be used as agents for the prophylaxis or treatment of diabetes and the like.

Moreover, by using the compound and a prodrug thereof of the present invention as a surrogate ligand, GPR40 agonists and GPR40 antagonists can be screened efficiently.

Free Text of Sequence Listing

SEQ ID NO:13
Designed oligonucleotide primer to amplify DNA encoding mGPR40
SEQ ID NO:14
Designed oligonucleotide primer to amplify DNA encoding mGPR40
SEQ ID NO:15
Designed oligonucleotide primer to amplify DNA encoding rGPR40
SEQ ID NO:16
Designed oligonucleotide primer to amplify DNA encoding rGPR40
SEQ ID NO:17
Designed oligonucleotide primer to amplify DNA encoding monkey GPR40
SEQ ID NO:18
Designed oligonucleotide primer to amplify DNA encoding monkey GPR40
SEQ ID NO:19
Designed oligonucleotide primer to amplify DNA encoding monkey GPR40
SEQ ID NO:20
Designed oligonucleotide primer to amplify DNA encoding monkey GPR40
SEQ ID NO:21
Designed oligonucleotide primer to amplify DNA encoding hamster GPR40
SEQ ID NO:22
Designed oligonucleotide primer to amplify DNA encoding hamster GPR40

The invention claimed is:

1. A compound represented by the formula

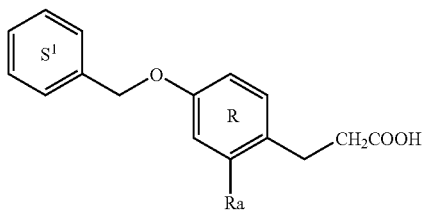

(I-2)

wherein ring S1 is a benzene ring having a substituent represented by the formula: $R^{11}$-$E^2$-, wherein $R^{11}$ is a phenyl group, an indanyl group or a naphthyl group, each optionally having substituent(s), and $E^2$ is a bond or a spacer, and the spacer represented by —$(CH_2)_m{}^1$—$W^1$—$(CH_2)_m{}^2$— wherein $m^1$ and $m^2$ are each an integer of 0 to 3, $W^1$ is —O—, —N(R2)-, —S—, —CO— or —CO—N($R^3$)—, and $R^2$ and $R^3$ are each a hydrogen atom or a $C_{1-6}$ alkyl group-), or $R^{11}$ forms, together with $E^2$ and ring $S^1$,

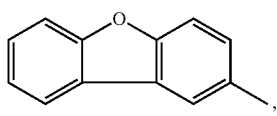

and ring $S^1$ optionally has additional substituent(s) in addition to $R^{11}$-$E^2$-, said additional substituent(s) selected from the group consisting of an optionally substituted $C_{1-6}$ alkyl group, an optionally substituted $C_{1-6}$ alkoxy group, a halogen atom and a $C_{7-16}$ aralkyloxy group; ring R is a phenylene group optionally having substituent(s) selected from the group consisting of a $C_{1-6}$ alkyl group, a halogen atom, a $C_{1-6}$ alkoxy group and a hydroxy group; and Ra is a hydrogen atom, a halogen atom, a $C_{1-6}$ alkyl group or a $C_{1-6}$ alkoxy group or a salt thereof.

2. A compound represented by the formula

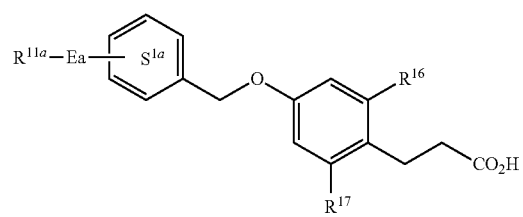

(I-2A)

wherein $R^{11a}$ is a phenyl group having 1 or 2 substituents, Ea is a bond, an oxygen atom or an optionally substituted methylene, ring $S^1$ is a benzene ring optionally having substituent(s) selected from an optionally substituted $C_{1-6}$ alkyl group, an optionally substituted $C_{1-6}$ alkoxy group and a halogen atom, and $R^{16}$ and $R^{17}$ are the same or different and each is a hydrogen atom, a halogen atom, a $C_{1-6}$ alkyl group or a $C_{1-6}$ alkoxy group; or a salt thereof.

3. The compound or salt of claim 2, wherein $R^{11a}$ is a phenyl group having two substituents selected from an optionally substituted $C_{1-6}$ alkyl group, an optionally substituted $C_{1-6}$ alkoxy group and a halogen atom; Ea is a bond, an oxygen atom or a methylene; and $R^{16}$ and $R^{17}$ are the same or different and each is a hydrogen atom or a halogen atom.

4. The compound or salt of claim 3, wherein Ea is a bond.

5. The compound or salt of claim 3, wherein $R^{16}$ is a hydrogen atom, and $R^{17}$ is a fluorine atom.

6. The compound or salt of claim 2, wherein the partial structural formula

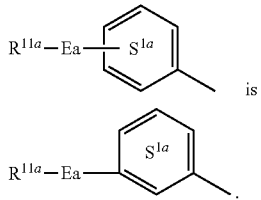

is

7. The compound or salt of claim 6, wherein $R^{11a}$ is a phenyl group having two substituents selected from an optionally substituted $C_{1-6}$ alkyl group, an optionally substituted $C_{1-6}$ alkoxy group and a halogen atom; Ea is a bond; and ring $S^{1a}$ is a benzene ring without additional substituent.

8. The compound or salt of claim 1, wherein ring $S^1$ optionally has a $C_{1-6}$ alkyl group, where the optional substituent of ring $S^1$ is a $C_{1-6}$ alkyl group.

9. The compound or salt of claim 1, wherein R11 is a phenyl group or an indanyl group, each optionally having substituent(s) selected from the group consisting of a halogen atom, a nitro, a carboxy, an optionally halogenated $C_{1-6}$ alkyl, a hydroxy- $C_{1-6}$ alkyl, a carboxy- $C_{1-6}$ alkyl-carbonylamino- $C_{1-6}$ alkyl, an optionally halogenated $C_{1-6}$ alkoxy, a $C_{6-14}$ aryl, a $C_{6-14}$ aryloxy and a $C_{7-16}$ aralkyloxy, $E^2$ is a bond, -0-, —$CH_2$—O—, —CO—, —CONH—, —N($CH_3$)$CH_2$—, —S—$CH_2$— or —C=C—, ring $S^1$ optionally has an additional substituent a $C_{1-6}$ alkyl group, or $R^{11}$ forms together with $E^2$ and ring $S^1$,

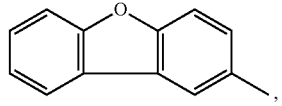

ring R is a phenylene group optionally further having a $C_{1-6}$ alkyl group, and $R_a$ is a hydrogen atom.

10. A pharmaceutical agent comprising the compound or salt of claim 1 or 2.

11. A method of regulating a GPR40 receptor function, which comprises administering an effective amount of the compound or salt of claim 1 or 2 to a mammal.

12. The compound or salt of claim 1, wherein $R^{11}$ is a phenyl group or an indanyl group, each optionally having substituent(s) selected from the group consisting of a halogen atom, a nitro, a carboxy, an optionally halogenated C1-6 alkyl, a hydroxy- $C_{1-6}$ alkyl, a carboxy- $C_{1-6}$ alkyl-carbonylamino- $C_{1-6}$ alkyl, an optionally halogenated $C_{1-6}$ alkoxy, a $C_{6-14}$ aryl, a $C_{6-14}$ aryloxy and a $C_{7-16}$ aralkyloxy; $E^2$ is a bond, —O—, or —$CH_2$—O; ring $S^1$ optionally has a $C_{1-6}$ alkyl group; or $R^{11}$ forms, together with $E^2$ and ring $S^1$,

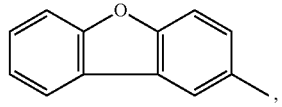

Ring R is a phenylene group optionally having a $C_{1-6}$ alkyl group; and $R_a$ is a hydrogen atom.

* * * * *

UNITED STATES PATENT AND TRADEMARK OFFICE
CERTIFICATE OF CORRECTION

PATENT NO.       : 7,960,369 B2
APPLICATION NO.  : 10/534081
DATED            : June 14, 2011
INVENTOR(S)      : Kohji Fukatsu et al.

Page 1 of 1

It is certified that error appears in the above-identified patent and that said Letters Patent is hereby corrected as shown below:

In the Claims:

At Column 351, line 53 (in claim 1), replace "S1" with -- $S^1$ --.

At Column 351, line 57 (in claim 1), after the word "spacer", insert -- is --.

At Column 351, line 59 (in claim 1), replace "NR2" with -- $NR^2$ --.

At Column 353, line 3 (in claim 2), replace "$S^1$" with -- $S^{1a}$ --.

At Column 353, line 39 (in claim 9), replace "R11" with -- $R^{11}$ --.

At Column 354, line 3 (in claim 9), replace "-0-" with -- -O- --.

At Column 354, line 26 (in claim 12), replace "C1-6" with -- $C_{1-6}$ --.

At Column 354, lines 27-28 (in claim 12), replace "carbony-lamino" with -- carbonylamino --.

Signed and Sealed this
Twenty-sixth Day of June, 2012

David J. Kappos
*Director of the United States Patent and Trademark Office*

SEQUENCE LISTING

```
<160> NUMBER OF SEQ ID NOS: 26

<210> SEQ ID NO 1
<211> LENGTH: 300
<212> TYPE: PRT
<213> ORGANISM: Mus musculus

<400> SEQUENCE: 1

Met Asp Leu Pro Pro Gln Leu Ser Phe Ala Leu Tyr Val Ser Ala Phe
  1               5                  10                  15

Ala Leu Gly Phe Pro Leu Asn Leu Leu Ala Ile Arg Gly Ala Val Ser
                 20                  25                  30

His Ala Lys Leu Arg Leu Thr Pro Ser Leu Val Tyr Thr Leu His Leu
             35                  40                  45

Gly Cys Ser Asp Leu Leu Leu Ala Ile Thr Leu Pro Leu Lys Ala Val
     50                  55                  60

Glu Ala Leu Ala Ser Gly Ala Trp Pro Leu Pro Leu Pro Phe Cys Pro
 65                  70                  75                  80

Val Phe Ala Leu Ala His Phe Ala Pro Leu Tyr Ala Gly Gly Gly Phe
                 85                  90                  95

Leu Ala Ala Leu Ser Ala Gly Arg Tyr Leu Gly Ala Ala Phe Pro Phe
                100                 105                 110

Gly Tyr Gln Ala Ile Arg Arg Pro Arg Tyr Ser Trp Gly Val Cys Val
            115                 120                 125

Ala Ile Trp Ala Leu Val Leu Cys His Leu Gly Leu Ala Leu Gly Leu
        130                 135                 140

Glu Thr Ser Gly Ser Trp Leu Asp Asn Ser Thr Ser Ser Leu Gly Ile
145                 150                 155                 160

Asn Ile Pro Val Asn Gly Ser Pro Val Cys Leu Glu Ala Trp Asp Pro
                165                 170                 175

Asp Ser Ala Arg Pro Ala Arg Leu Ser Phe Ser Ile Leu Leu Phe Phe
            180                 185                 190

Leu Pro Leu Val Ile Thr Ala Phe Cys Tyr Val Gly Cys Leu Arg Ala
        195                 200                 205

Leu Val Arg Ser Gly Leu Ser His Lys Arg Lys Leu Arg Ala Ala Trp
    210                 215                 220
```

```
Val Ala Gly Gly Ala Leu Leu Thr Leu Leu Leu Cys Leu Gly Pro Tyr
225                 230                 235                 240

Asn Ala Ser Asn Val Ala Ser Phe Ile Asn Pro Asp Leu Gly Ser
            245                 250                 255

Trp Arg Lys Leu Gly Leu Ile Thr Gly Ala Trp Ser Val Val Leu Asn
        260                 265                 270

Pro Leu Val Thr Gly Tyr Leu Gly Thr Gly Pro Gly Arg Gly Thr Ile
    275                 280                 285

Cys Val Thr Arg Thr Gln Arg Gly Thr Ile Gln Lys
    290                 295                 300

<210> SEQ ID NO 2
<211> LENGTH: 900
<212> TYPE: DNA
<213> ORGANISM: Mus musculus

<400> SEQUENCE: 2
atggacctgc ccccacagct ctccttcgct ctctatgtat ctgcctttgc gctgggcttt    60
ccattgaact tgttagccat ccgaggcgca gtgtcccacg ctaaactgcg actcactccc   120
agcttggtct acactctcca tctgggctgc tctgatctcc tactggccat cactctgccc   180
ctgaaggctg tggaggccct ggcttctgga gcctggcccc tgccgctccc cttctgccca   240
gtctttgcct tggcccactt tgctcccctc tacgcaggcg gaggcttcct agctgctctc   300
agcgctggcc gctacctggg gctgccttc cccttcgggt accaagccat ccggaggccc   360
cgctattcct ggggtgtgtg tgtggctata tgggcccttg tcctctgcca cctggggctg   420
gcccttggct tggagacttc cggaagctgg ctggacaaca gtaccagttc cctgggcatc   480 aacataccg tgaatggctc cccggtctgc ctggaagcct gggatcccga ctctgcccgc   540
cctgcccgtc tcagtttctc cattctgctc ttctttctgc ccttggtcat cactgccttc   600
tgctatgtgg gctgcctccg ggccctggtg cgctcaggcc tgagccacaa acggaagctc   660
agggcagctt gggtggccgg aggcgctctc ctcacactcc tgctctgcct ggggccctat   720
aatgcctcca atgtggctag tttcataaac ccggacctag gaggctcctg gaggaagttg   780
ggactcatca caggggcctg gagtgtggta ctcaacccac tggtcactgg ctacttggga   840
acaggtcctg gacggggaac aatatgtgtg acgaggactc aaagaggaac aattcagaag   900

<210> SEQ ID NO 3
<211> LENGTH: 300
<212> TYPE: PRT
<213> ORGANISM: Rattus norvegicus

<400> SEQUENCE: 3

Met Asp Leu Pro Pro Gln Leu Ser Phe Ala Leu Tyr Val Ser Ala Phe
1               5                   10                  15

Ala Leu Gly Phe Pro Leu Asn Leu Leu Ala Ile Arg Gly Ala Val Ser
            20                  25                  30

His Ala Lys Leu Arg Leu Thr Pro Ser Leu Val Tyr Thr Leu His Leu
        35                  40                  45

Ala Cys Ser Asp Leu Leu Leu Ala Ile Thr Leu Pro Leu Lys Ala Val
    50                  55                  60

Glu Ala Leu Ala Ser Gly Val Trp Pro Leu Pro Leu Pro Phe Cys Pro
65                  70                  75                  80

Val Phe Ala Leu Ala His Phe Ala Pro Leu Tyr Ala Gly Gly Gly Phe
                85                  90                  95

Leu Ala Ala Leu Ser Ala Gly Arg Tyr Leu Gly Ala Ala Phe Pro Phe
```

100                 105                 110
Gly Tyr Gln Ala Ile Arg Arg Pro Cys Tyr Ser Trp Gly Val Cys Val
            115                 120                 125

Ala Ile Trp Ala Leu Val Leu Cys His Leu Gly Leu Ala Leu Gly Leu
        130                 135                 140

Glu Ala Pro Arg Gly Trp Val Asp Asn Thr Thr Ser Ser Leu Gly Ile
145                 150                 155                 160

Asn Ile Pro Val Asn Gly Ser Pro Val Cys Leu Glu Ala Trp Asp Pro
                165                 170                 175

Asp Ser Ala Arg Pro Ala Arg Leu Ser Phe Ser Ile Leu Leu Phe Phe
            180                 185                 190

Leu Pro Leu Val Ile Thr Ala Phe Cys Tyr Val Gly Cys Leu Arg Ala
        195                 200                 205

Leu Val His Ser Gly Leu Ser His Lys Arg Lys Leu Arg Ala Ala Trp
    210                 215                 220

Val Ala Gly Gly Ala Leu Leu Thr Leu Leu Cys Leu Gly Pro Tyr
225                 230                 235                 240

Asn Ala Ser Asn Val Ala Ser Phe Ile Asn Pro Asp Leu Glu Gly Ser
                245                 250                 255

Trp Arg Lys Leu Gly Leu Ile Thr Gly Ala Trp Ser Val Val Leu Asn
            260                 265                 270

Pro Leu Val Thr Gly Tyr Leu Gly Thr Gly Pro Gly Gln Gly Thr Ile
        275                 280                 285

Cys Val Thr Arg Thr Pro Arg Gly Thr Ile Gln Lys
    290                 295                 300

<210> SEQ ID NO 4
<211> LENGTH: 900
<212> TYPE: DNA
<213> ORGANISM: Rattus norvegicus

<400> SEQUENCE: 4
atggacctgc cccacagct ctccttcgct ctctatgtat cagcctttgc actaggcttt      60
ccattgaact tgttagccat ccgaggtgca gtgtcccacg cgaaactgcg actcaccccc    120
agcttggtct acactctcca tttggcctgc tctgacctcc tactggccat caccctgccc    180
ctgaaggctg tggaggccct ggcttctggg gtctggcccc tgccactccc cttctgccca    240
gtctttgcct tggcccactt tgcgcccctc tatgcaggtg gaggcttcct ggctgctctc    300
agtgctggcc gctacctggg agctgccttc ccctttggat accaagccat ccggaggccc    360
tgctattcct ggggtgtgtg tgtggctata tgggcccttg tccttttgcca cctgggactg    420
gctcttggct tggaggctcc cagaggctgg gtggataaca ccaccagttc cctgggcatc    480
aacataccg tgaatggctc cccggtctgc ctggaagcgt gggatcctga ctctgcccgc    540
cctgcccgac tcagtttctc gattctgctc ttctttctgc ccttggttat cactgctttc    600
tgctatgtgg gctgcctccg ggccctggtg cactcgggcc tgagccacaa acggaagctc    660
agggcagctt gggtggctgg aggagcactt ctcacactcc tgctctgcct ggggccctat    720
aatgcttcca atgtggctag tttcataaac ccggacttag aaggctcctg gaggaagttg    780
gggctcatca caggagcctg gagtgtggtg ctcaacccac tggtcactgg ctacttggga    840
acaggtcctg gacaggggac aatatgtgtg tccaggactc aagagggac aattcagaag    900

<210> SEQ ID NO 5
<211> LENGTH: 300
<212> TYPE: PRT

<213> ORGANISM: Homo sapiens

<400> SEQUENCE: 5

```
Met Asp Leu Pro Pro Gln Leu Ser Phe Gly Leu Tyr Val Ala Ala Phe
  1               5                  10                  15
Ala Leu Gly Phe Pro Leu Asn Val Leu Ala Ile Arg Gly Ala Thr Ala
             20                  25                  30
His Ala Arg Leu Arg Leu Thr Pro Ser Leu Val Tyr Ala Leu Asn Leu
         35                  40                  45
Gly Cys Ser Asp Leu Leu Leu Thr Val Ser Leu Pro Leu Lys Ala Val
     50                  55                  60
Glu Ala Leu Ala Ser Gly Ala Trp Pro Leu Pro Ala Ser Leu Cys Pro
 65                  70                  75                  80
Val Phe Ala Val Ala His Phe Phe Pro Leu Tyr Ala Gly Gly Gly Phe
                 85                  90                  95
Leu Ala Ala Leu Ser Ala Gly Arg Tyr Leu Gly Ala Ala Phe Pro Leu
            100                 105                 110
Gly Tyr Gln Ala Phe Arg Arg Pro Cys Tyr Ser Trp Gly Val Cys Ala
        115                 120                 125
Ala Ile Trp Ala Leu Val Leu Cys His Leu Gly Leu Val Phe Gly Leu
    130                 135                 140
Glu Ala Pro Gly Gly Trp Leu Asp His Ser Asn Thr Ser Leu Gly Ile
145                 150                 155                 160
Asn Thr Pro Val Asn Gly Ser Pro Val Cys Leu Glu Ala Trp Asp Pro
                165                 170                 175
Ala Ser Ala Gly Pro Ala Arg Phe Ser Leu Ser Leu Leu Leu Phe Phe
            180                 185                 190
Leu Pro Leu Ala Ile Thr Ala Phe Cys Tyr Val Gly Cys Leu Arg Ala
        195                 200                 205
Leu Ala Arg Ser Gly Leu Thr His Arg Arg Lys Leu Arg Ala Ala Trp
    210                 215                 220
Val Ala Gly Gly Ala Leu Leu Thr Leu Leu Leu Cys Val Gly Pro Tyr
225                 230                 235                 240
Asn Ala Ser Asn Val Ala Ser Phe Leu Tyr Pro Asn Leu Gly Gly Ser
                245                 250                 255
Trp Arg Lys Leu Gly Leu Ile Thr Gly Ala Trp Ser Val Val Leu Asn
            260                 265                 270
Pro Leu Val Thr Gly Tyr Leu Gly Arg Gly Pro Gly Leu Lys Thr Val
        275                 280                 285
Cys Ala Ala Arg Thr Gln Gly Gly Lys Ser Gln Lys
    290                 295                 300
```

<210> SEQ ID NO 6
<211> LENGTH: 900
<212> TYPE: DNA
<213> ORGANISM: Homo sapiens

<400> SEQUENCE: 6

```
atggacctgc ccccgcagct ctccttcggc ctctatgtgg ccgcctttgc gctgggcttc      60
ccgctcaacg tcctggccat ccgaggcgcg acggcccacg cccggctccg tctcacccct     120
agcctggtct acgccctgaa cctgggctgc tccgacctgc tgctgacagt ctctctgccc     180
ctgaaggcgg tggaggcgct agcctccggg gcctggcctc tgccggcctc gctgtgcccc     240
gtcttcgcgg tggcccactt cttcccactc tatgccggcg ggggcttcct ggccgccctg     300
agtgcaggcc gctacctggg agcagccttc cccttgggct accaagcctt ccggaggccg     360
```

-continued

```
tgctattcct gggggggtgtg cgcggccatc tgggccctcg tcctgtgtca cctgggtctg    420
gtctttgggt tggaggctcc aggaggctgg ctggaccaca gcaacacctc cctgggcatc    480
aacacaccgg tcaacggctc tccggtctgc ctggaggcct gggacccggc ctctgccggc    540
ccggcccgct tcagcctctc tctcctgctc ttttttctgc ccttggccat cacagccttc    600
tgctacgtgg gctgcctccg ggcactggcc cgctccggcc tgacgcacag gcggaagctg    660
cgggccgcct gggtggccgg cggggccctc ctcacgctgc tgctctgcgt aggaccctac    720
aacgcctcca acgtgccagc ttcctgtac cccaatctag gaggctcctg gcggaagctg    780
gggctcatca cgggtgcctg gagtgtggtg cttaatccgc tggtgaccgg ttacttggga    840
aggggtcctg gcctgaagac agtgtgtgcg gcaagaacgc aaggggggcaa gtcccagaag    900
```

<210> SEQ ID NO 7
<211> LENGTH: 300
<212> TYPE: PRT
<213> ORGANISM: Macaca fascicularis

<400> SEQUENCE: 7

```
Met Asp Leu Pro Pro Gln Leu Ser Phe Ala Leu Tyr Val Ala Ala Phe
 1               5                  10                  15

Ala Leu Gly Phe Pro Leu Asn Val Leu Ala Ile Arg Gly Ala Arg Ala
                20                  25                  30

His Ala Arg Arg Arg Leu Thr Pro Ser Leu Val Tyr Ala Leu Asn Leu
            35                  40                  45

Gly Cys Ser Asp Leu Leu Thr Val Ser Leu Pro Leu Lys Ala Val
        50                  55                  60

Glu Ala Leu Ala Ser Gly Ala Trp Pro Leu Pro Ala Ser Leu Cys Pro
 65                  70                  75                  80

Val Phe Gly Val Ala His Phe Ala Pro Leu Tyr Ala Gly Gly Phe
                85                  90                  95

Leu Ala Ala Leu Ser Ala Gly Arg Tyr Leu Gly Ala Ala Phe Pro Leu
            100                 105                 110

Gly Tyr Gln Ala Phe Arg Arg Pro Cys Tyr Ser Trp Gly Val Cys Ala
        115                 120                 125

Ala Ile Trp Ala Leu Val Leu Cys His Leu Gly Leu Val Phe Val Leu
    130                 135                 140

Glu Ala Pro Gly Gly Trp Leu Asp His Ser Asn Thr Ser Leu Gly Ile
145                 150                 155                 160

Asn Thr Pro Val Asn Gly Ser Pro Val Cys Leu Glu Ala Trp Asp Pro
                165                 170                 175

Ala Ser Ala Gly Pro Ala Arg Phe Ser Leu Ser Leu Leu Phe Phe
            180                 185                 190

Leu Pro Leu Ala Ile Thr Ala Phe Cys Tyr Val Gly Cys Leu Arg Ala
        195                 200                 205

Leu Ala His Ser Gly Leu Thr His Arg Arg Lys Leu Arg Ala Ala Trp
    210                 215                 220

Val Ala Gly Gly Ala Leu Leu Thr Leu Leu Cys Val Gly Pro Tyr
225                 230                 235                 240

Asn Ala Ser Asn Val Ala Ser Phe Leu Asn Pro Asn Leu Gly Ser
                245                 250                 255

Trp Arg Lys Leu Gly Leu Ile Thr Gly Ala Trp Ser Val Val Leu Asn
            260                 265                 270

Pro Leu Val Thr Gly Tyr Leu Gly Arg Gly Pro Gly Leu Lys Thr Val
        275                 280                 285
```

Cys Ala Ala Arg Thr Gln Gly Ser Thr Ser Gln Lys
    290                 295                 300

<210> SEQ ID NO 8
<211> LENGTH: 900
<212> TYPE: DNA
<213> ORGANISM: Macaca fascicularis

<400> SEQUENCE: 8

```
atggacctgc ccccgcagct ctcctttgcc ctctatgtgg cggcctttgc gctgggcttc    60
ccgctcaacg tcctggccat ccagggggcg agggcccacg cccggcgccg tctcaccccc   120
agcctggtct acgccctgaa cctgggctgc tccgacctgt tgctgacagt ctccctgccc   180
ctgaaggcgg tggaggcgct ggcctccggg gcctggcctc tgccggcctc actgtgccct   240
gtcttcgggg tggcccactt tgctccactc tatgccggcg ggggcttcct ggccgccctg   300
agtgcaggcc gctacctggg agcggccttc cccttgggct accaagcctt ccggaggccg   360
tgctattcct gggggtgtg tgcggccatc tgggccctcg tcctgtgtca cctgggtctg   420
gtctttgtgt tggaggctcc gggaggctgg ctggaccaca gcaacacctc actgggcatc   480
aacacaccgg tcaacggctc tcccgtctgc ctggaggcct gggacccggc tctgccggc    540
ccggcccgct tcagcctctc tctcctgctt tttttcctgc ccttggccat cacagccttc   600
tgctacgtgg gctgcctccg ggcactggcc cactccggcc tgacccacag gcggaagctg   660
agggccgcct gggtagccgg cggggccctc ctcacgctgc tgctctgcgt aggaccctac   720
aacgcctcca atgtggccag ctttctgaac cccaatctgg gaggctcctg gcggaagctg   780
gggctcatca cggtgcctg gagtgtggtg ctcaacccgc tggtgaccgg ttacttggga   840
aggggtcctg gcctgaagac agtgtgtgcg gcaagaacgc aagggagcac gtcccagaag   900
```

<210> SEQ ID NO 9
<211> LENGTH: 300
<212> TYPE: PRT
<213> ORGANISM: Mesocricetus auratus

<400> SEQUENCE: 9

Met Ala Leu Ser Pro Gln Leu Phe Phe Ala Leu Tyr Val Ser Ala Phe
  1               5                  10                  15

Ala Leu Gly Phe Pro Leu Asn Leu Leu Ala Ile Arg Gly Ala Val Ala
                 20                  25                  30

Arg Ala Arg Leu Arg Leu Thr Pro Asn Leu Val Tyr Thr Leu His Leu
             35                  40                  45

Ala Cys Ser Asp Leu Leu Leu Ala Ile Thr Leu Pro Val Lys Ala Val
         50                  55                  60

Glu Ala Leu Ala Ser Gly Ala Trp Pro Leu Pro Leu Pro Leu Cys Pro
 65                  70                  75                  80

Val Phe Val Leu Val His Phe Ala Pro Leu Tyr Ala Gly Gly Gly Phe
                 85                  90                  95

Leu Ala Ala Leu Ser Ala Gly Arg Tyr Leu Gly Ala Ala Phe Pro Phe
                100                 105                 110

Gly Tyr Gln Ala Val Arg Arg Pro Arg Tyr Ser Trp Gly Val Cys Val
            115                 120                 125

Ala Ile Trp Ala Leu Val Leu Cys His Met Gly Leu Val Leu Gly Leu
        130                 135                 140

Glu Ala Pro Gly Gly Trp Leu Asn Thr Thr Ser Ser Ser Leu Gly Ile
145                 150                 155                 160

```
Asn Thr Pro Val Asn Gly Ser Pro Val Cys Leu Glu Ala Trp Asp Pro
            165                 170                 175

Asn Ser Ala Arg Pro Ala Arg Leu Ser Phe Ser Ile Leu Leu Phe Phe
        180                 185                 190

Val Pro Leu Val Ile Thr Ala Phe Cys Tyr Val Gly Cys Leu Arg Ala
    195                 200                 205

Leu Ala His Ser Gly Leu Ser His Lys Arg Lys Leu Arg Ala Ala Trp
    210                 215                 220

Ala Ala Gly Gly Ala Phe Leu Thr Leu Leu Leu Cys Leu Gly Pro Tyr
225                 230                 235                 240

Asn Ala Ser Asn Val Ala Ser Phe Val Asn Pro Asp Leu Gly Gly Ser
                245                 250                 255

Trp Arg Lys Leu Gly Leu Ile Thr Gly Ser Trp Ser Val Val Leu Asn
            260                 265                 270

Pro Leu Val Thr Gly Tyr Leu Gly Ala Ser Pro Gly Arg Gly Thr Val
        275                 280                 285

Cys Thr Thr Arg Thr Gln Gly Gly Thr Ile Gln Lys
    290                 295                 300

<210> SEQ ID NO 10
<211> LENGTH: 900
<212> TYPE: DNA
<213> ORGANISM: Mesocricetus auratus

<400> SEQUENCE: 10
atggccctgt ctccccaact cttcttcgcc ctctatgtgt ctgccttcgc gctgggcttc      60
ccgctgaacc tgttggccat ccgaggcgcc gtggcccgtg caaggctgcg gctcaccccc     120
aacctggtct atacactcca cctggcctgc tctgacctgc tcctggccat cacgctaccc     180
gtgaaggccg tggaggccct ggcttctggg gcctggcccc tgccgctccc cttgtgccct     240
gtctttgtct tggtgcactt cgccccactc tatgcgggcg aggcttcct ggcggctctc     300 agtgctggcc gctacctggg ggctgccttc cccttcgggt accaagccgt tcggcggccc     360
cgctactcct ggggcgtgtg tgtggctata tgggcccttg tcctctgcca catggggctg     420
gtcctcggct tggaggctcc cggaggctgg ctgaacacca ccagcagctc cctgggaatc     480
aacacaccgg tgaatggttc cccggtgtgc ctggaagcct gggatcccaa ctctgcccgg     540
cctgcccgcc tcagtttctc catcctgctc ttcttcgtgc ccctggtcat caccgccttc     600
tgctacgtgg gctgcctgcg gctctggcc cactcgggcc tgagccacaa acggaagctc     660
agggcagcct gggcggccgg aggggccttt ctcacactcc tgctctgctt ggggccctac     720
aatgcctcca atgtggcgag tttcgtaaac ccggacctgg gaggctcctg aggaagctg     780 gggctcatca cagggtcctg gagtgtggta ctcaacccgc tggtcaccgg ttacttggga     840
gcaagtcctg gccgagggac agtatgtacg acaaggactc aaggaggaac aattcagaag     900

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgtcgacccg gcggccccat ggacctgccc ccg                                   33

<210> SEQ ID NO 12
```

```
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
catcgattag cagtggcgtt acttctggga ctt                                    33

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtcgaccacc atggacctgc ccccacagct ctccttcgct c                           41

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
actagtctac ttctgaattg ttcctctttg agtcctcg                               38

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtcgaccacc atggacctgc ccccacagct ctccttcgct c                           41

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
actagtctac ttctgaattg tccctcttgg agtcctgg                               38

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tttctctgtg ggcctcgttt cctc                                              24

<210> SEQ ID NO 18
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 18
cgtgctctgg ctcggtgctc ctc                                         23

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggcctcgttt cctccctgat                                             20

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gccctcctgc cccatgctcc ttcc                                        24

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtcgacgacg agaggcaccc actcggcccc atg                              33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gctagcctac ttctgaattg ttcctccttg agt                              33

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic primer
<220> FEATURE:
<223> OTHER INFORMATION: Description of Artificial Sequence: Synthetic
      primer

<400> SEQUENCE: 23
cgccaguugu gacauucuut t                                           21

<210> SEQ ID NO 24
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic primer
<220> FEATURE:
<223> OTHER INFORMATION: Description of Artificial Sequence: Synthetic
      primer

<400> SEQUENCE: 24
ttgcggucaa cacuguaaga a                                            21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic primer
<220> FEATURE:
<223> OTHER INFORMATION: Description of Artificial Sequence: Synthetic
      primer

<400> SEQUENCE: 25
cuuguuagcc auccgaggct t                                            21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic primer
<220> FEATURE:
<223> OTHER INFORMATION: Description of Artificial Sequence: Synthetic
      primer

<400> SEQUENCE: 26
ttgaacaatc ggtaggctcc g                                            21
```